US009566290B2

(12) United States Patent
Baker et al.

(10) Patent No.: US 9,566,290 B2
(45) Date of Patent: *Feb. 14, 2017

(54) BORON-CONTAINING SMALL MOLECULES

(71) Applicant: Anacor Pharmaceuticals, Inc., Palo Alto, CA (US)

(72) Inventors: Stephen J. Baker, Collegeville, PA (US); Tsutomu Akama, Sunnyvale, CA (US); Vincent S. Hernandez, Watsonville, CA (US); Karin M. Hold, Belmont, CA (US); Kirk Maples, San Jose, CA (US); Jacob J. Plattner, Berkeley, CA (US); Virginia Sanders, San Francisco, CA (US); Yong-Kang Zhang, San Jose, CA (US); Gregory T. Fieldson, Morgantown, WV (US); James J. Leyden, Malvern, CA (US)

(73) Assignee: Anacor Pharmaceuticals, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/134,286

(22) Filed: Apr. 20, 2016

(65) Prior Publication Data

US 2016/0228463 A1    Aug. 11, 2016

Related U.S. Application Data

(60) Continuation of application No. 15/091,394, filed on Apr. 5, 2016, which is a continuation of application No. 15/068,352, filed on Mar. 11, 2016, which is a continuation of application No. 15/046,322, filed on Feb. 17, 2016, which is a continuation of application No. 14/537,771, filed on Nov. 10, 2014, now abandoned, which is a continuation of application No. 14/201,459, filed on Mar. 7, 2014, now Pat. No. 9,353,133, which is a continuation of application No. 13/356,488, filed on Jan. 23, 2012, now Pat. No. 8,722,917, which is a continuation of application No. 12/629,753, filed on Dec. 2, 2009, now Pat. No. 8,115,026, which is a division of application No. 11/505,591, filed on Aug. 16, 2006, now Pat. No. 7,767,657, and a continuation-in-part of application No. 11/357,687, filed on Feb. 16, 2006, now Pat. No. 7,582,621, said application No. 14/537,771 is a continuation-in-part of application No. 13/874,329, filed on Apr. 30, 2013, now Pat. No. 8,889,656, which is a continuation of application No. 13/224,252, filed on Sep. 1, 2011, now Pat. No. 8,440,642, which is a continuation of application No. 12/507,010, filed on Jul. 21, 2009, now Pat. No. 8,039,451, which is a

(60) Provisional application No. 60/755,227, filed on Dec. 30, 2005, provisional application No. 60/746,361, filed on May 3, 2006, provisional application No.

(Continued)

(51) Int. Cl.
| | |
|---|---|
| A61K 31/69 | (2006.01) |
| C07F 5/02 | (2006.01) |
| C07F 5/04 | (2006.01) |
| C07H 19/06 | (2006.01) |
| C07H 19/16 | (2006.01) |
| C07H 21/00 | (2006.01) |
| C07H 23/00 | (2006.01) |
| A61K 31/70 | (2006.01) |
| A61K 31/7076 | (2006.01) |
| A61K 9/00 | (2006.01) |
| A61K 47/10 | (2006.01) |
| A61K 9/08 | (2006.01) |

(52) U.S. Cl.
CPC ............ *A61K 31/69* (2013.01); *A61K 9/0012* (2013.01); *A61K 9/08* (2013.01); *A61K 31/70* (2013.01); *A61K 31/7076* (2013.01); *A61K 47/10* (2013.01); *C07F 5/025* (2013.01); *C07F 5/04* (2013.01); *C07H 19/06* (2013.01); *C07H 19/16* (2013.01); *C07H 21/00* (2013.01); *C07H 23/00* (2013.01)

(58) Field of Classification Search
USPC ........................................................ 514/64
See application file for complete search history.

(56) References Cited

U.S. PATENT DOCUMENTS

| | | |
|---|---|---|
| 2,260,336 A | 10/1941 | Prescott et al. |
| 2,741,548 A | 4/1956 | Darling et al. |

(Continued)

FOREIGN PATENT DOCUMENTS

| | | |
|---|---|---|
| EP | 0969531 | 1/2000 |
| EP | 0765331 B1 | 8/2000 |

(Continued)

OTHER PUBLICATIONS

U.S. Appl. No. 13/861,846, filed Apr. 12, 2013, now abandoned.
U.S. Appl. No. 13/673,860, filed Nov. 9, 2012, now abandoned.
U.S. Appl. No. 13/607,321, filed Sep. 7, 2012, now abandoned.
U.S. Appl. No. 13/607,405, filed Sep. 7, 2012, now abandoned.
U.S. Appl. No. 13/607,250, filed Sep. 7,2012, now abandoned.
U.S. Appl. No. 15/091,394, filed Apr. 5, 2016.
U.S. Appl. No. 15/068,352, filed Mar. 11, 2016.
U.S. Appl. No. 15/046,322, filed Feb. 17, 2016.
U.S. Appl. No. 14/977,052, filed Dec. 21, 2015.
U.S. Appl. No. 14/537,771, filed Nov. 10, 2014.
U.S. Appl. No. 14/537,694, filed Nov. 10, 2014, now abandoned.
U.S. Appl. No. 14/165,428, filed Mar. 7, 2014, now abandoned.
U.S. Appl. No. 14/688,581, filed Apr. 16, 2015.

(Continued)

*Primary Examiner* — Rei-Tsang Shiao
(74) *Attorney, Agent, or Firm* — Morgan, Lewis & Bockius LLP

(57) ABSTRACT

This invention relates to compounds useful for treating fungal infections, more specifically topical treatment of onychomycosis and/or cutaneous fungal infections. This invention is directed to compounds that are active against fungi and have properties that allow the compound, when placed in contact with a patient, to reach the particular part of the skin, nail, hair, claw or hoof infected by the fungus. In particular the present compounds have physiochemical properties that facilitate penetration of the nail plate.

12 Claims, 63 Drawing Sheets

Related U.S. Application Data continuation of application No. 11/357,687, filed on Feb. 16, 2006, now Pat. No. 7,582,621.60/654,060, filed on Feb. 16, 2005, provisional application No. 60/654,060, filed on Feb. 16, 2005.

(56) References Cited

U.S. PATENT DOCUMENTS

| | | | |
|---|---|---|---|
| 2,831,866 | A | 4/1958 | Freeman et al. |
| 3,093,659 | A | 6/1963 | Bell et al. |
| 3,104,255 | A | 9/1963 | Emrick et al. |
| 3,297,525 | A | 1/1967 | Grier |
| 3,370,957 | A | 2/1968 | Wagner et al. |
| 3,686,398 | A | 8/1972 | Kohn et al. |
| 3,816,472 | A | 6/1974 | Shapiro et al. |
| 3,873,279 | A | 3/1975 | Singer |
| 4,202,894 | A | 5/1980 | Pfiffner |
| 4,602,011 | A | 7/1986 | West et al. |
| 4,716,035 | A | 12/1987 | Sampathkamar |
| 4,766,113 | A | 8/1988 | West et al. |
| 4,822,822 | A | 4/1989 | Arita et al. |
| 4,894,220 | A | 1/1990 | Nabi et al. |
| 4,919,934 | A | 4/1990 | Deckner et al. |
| 4,977,268 | A | 12/1990 | McPhail et al. |
| 5,264,206 | A | 11/1993 | Bohn et al. |
| 5,348,947 | A | 9/1994 | Patel et al. |
| 5,348,948 | A | 9/1994 | Patel et al. |
| 5,498,407 | A | 3/1996 | Atlas |
| 5,591,731 | A | 1/1997 | Kennedy et al. |
| 5,668,258 | A | 9/1997 | Stolowitz |
| 5,688,928 | A | 11/1997 | Stolowitz |
| 5,831,045 | A | 11/1998 | Stolowitz et al. |
| 5,880,188 | A | 3/1999 | Austin et al. |
| 5,962,498 | A | 10/1999 | Driedger et al. |
| 6,042,845 | A | 3/2000 | Sun et al. |
| 6,080,774 | A | 6/2000 | Murugesan et al. |
| 6,083,903 | A | 7/2000 | Adams et al. |
| 6,143,794 | A | 11/2000 | Chaudhuri et al. |
| 6,221,640 | B1 | 4/2001 | Tao et al. |
| 6,224,887 | B1 | 5/2001 | Samour et al. |
| 6,306,628 | B1 | 10/2001 | Rothschild et al. |
| 6,369,098 | B1 | 4/2002 | Pershadsingh et al. |
| 6,521,619 | B2 | 2/2003 | Link et al. |
| 6,699,994 | B1 | 3/2004 | Babu et al. |
| 6,800,645 | B1 | 10/2004 | Cox et al. |
| 6,855,848 | B2 | 2/2005 | Scherer et al. |
| 7,074,392 | B1 | 7/2006 | Friedman et al. |
| 7,169,603 | B2 | 1/2007 | Hedley et al. |
| 7,205,425 | B2 | 4/2007 | Shibasaki et al. |
| 7,217,701 | B2 | 5/2007 | Mikoshiba et al. |
| 7,390,806 | B2 | 6/2008 | Lee et al. |
| 7,446,236 | B2 | 11/2008 | Naud et al. |
| 7,465,836 | B2 | 12/2008 | Lee et al. |
| 7,582,621 | B2 * | 9/2009 | Baker ............ C07F 5/02 514/64 |
| 7,767,657 | B2 | 8/2010 | Baker et al. |
| 7,816,344 | B2 | 10/2010 | Baker et al. |
| 8,039,450 | B2 | 10/2011 | Akama et al. |
| 8,039,451 | B2 | 10/2011 | Baker et al. |
| 8,115,026 | B2 | 2/2012 | Baker et al. |
| 8,168,614 | B2 | 5/2012 | Baker et al. |
| 8,343,944 | B2 | 1/2013 | Xia et al. |
| 8,440,642 | B2 | 5/2013 | Baker et al. |
| 8,461,134 | B2 | 6/2013 | Hernandez et al. |
| 8,461,135 | B2 | 6/2013 | Akama et al. |
| 8,461,336 | B2 | 6/2013 | Zhou et al. |
| 8,461,364 | B2 | 6/2013 | Wheeler et al. |
| 8,470,803 | B2 | 6/2013 | Akama et al. |
| 8,501,712 | B2 | 8/2013 | Baker et al. |
| 8,546,357 | B2 | 10/2013 | Akama et al. |
| 8,703,742 | B2 | 4/2014 | Hernandez et al. |
| 8,716,478 | B2 | 5/2014 | Jarnagin et al. |
| 8,722,917 | B2 | 5/2014 | Baker et al. |
| 8,853,186 | B2 | 10/2014 | Akama et al. |
| 8,889,656 | B2 * | 11/2014 | Baker ............ C07F 5/02 514/64 |
| 8,895,534 | B2 | 11/2014 | Baker et al. |
| 9,012,431 | B2 | 4/2015 | Akama |
| 9,029,353 | B2 | 5/2015 | Baker et al. |
| 9,145,429 | B2 | 9/2015 | Jarnagin et al. |
| 9,156,860 | B2 | 10/2015 | Akama et al. |
| 9,243,003 | B2 | 1/2016 | Conde et al. |
| 9,353,133 | B2 | 5/2016 | Baker et al. |
| 2002/0010332 | A1 | 1/2002 | Vollmuller et al. |
| 2002/0028831 | A1 | 3/2002 | Manley |
| 2002/0161230 | A1 | 10/2002 | Meudt et al. |
| 2002/0165121 | A1 | 11/2002 | Brehove |
| 2002/0193672 | A1 | 12/2002 | Walsh et al. |
| 2003/0032673 | A1 | 2/2003 | Nagy |
| 2003/0181766 | A1 | 9/2003 | Satoh et al. |
| 2004/0077601 | A1 | 4/2004 | Adams et al. |
| 2004/0224923 | A1 | 11/2004 | Lee et al. |
| 2004/0259833 | A1 | 12/2004 | Benkovic et al. |
| 2004/0259842 | A1 | 12/2004 | Mikoshiba et al. |
| 2005/0054644 | A1 | 3/2005 | Lee et al. |
| 2005/0125852 | A1 | 6/2005 | Caenepeel et al. |
| 2006/0009386 | A1 | 1/2006 | Stossel et al. |
| 2006/0222671 | A1 | 10/2006 | Weidner |
| 2006/0234981 | A1 | 10/2006 | Baker et al. |
| 2007/0155699 | A1 | 7/2007 | Baker et al. |
| 2007/0286822 | A1 | 12/2007 | Sanders et al. |
| 2007/0293457 | A1 | 12/2007 | Baker et al. |
| 2009/0227541 | A1 | 9/2009 | Baker et al. |
| 2010/0048570 | A1 | 2/2010 | Kim et al. |
| 2010/0256092 | A1 | 10/2010 | Xia et al. |
| 2013/0059802 | A1 | 3/2013 | Baker et al. |
| 2013/0059803 | A1 | 3/2013 | Baker et al. |
| 2013/0064783 | A1 | 3/2013 | Baker et al. |
| 2013/0210770 | A1 | 8/2013 | Baker et al. |
| 2014/0142064 | A1 | 5/2014 | Baker et al. |
| 2014/0221631 | A1 | 8/2014 | Baker et al. |
| 2015/0065459 | A1 | 3/2015 | Baker et al. |
| 2015/0119364 | A1 | 4/2015 | Baker et al. |

FOREIGN PATENT DOCUMENTS

| | | |
|---|---|---|
| EP | 1155698 A1 | 11/2001 |
| EP | 1 444 981 A1 | 8/2004 |
| JP | 2002-53583 A | 2/2002 |
| JP | 2002-508359 A | 3/2002 |
| JP | 2003-212837 A | 7/2003 |
| JP | 2004-514669 A | 5/2004 |
| JP | 2005-022986 A | 1/2005 |
| WO | WO 9533754 | 5/1995 |
| WO | WO 9622023 A1 | 7/1996 |
| WO | WO 9812206 A1 | 3/1998 |
| WO | WO 0027822 | 5/2000 |
| WO | WO 0044387 A1 | 8/2000 |
| WO | WO 0075142 A2 | 12/2000 |
| WO | WO 0114578 A1 | 3/2001 |
| WO | WO 0149303 A1 | 7/2001 |
| WO | WO 0187846 A2 | 11/2001 |
| WO | WO 0244184 | 6/2002 |
| WO | WO 03/009689 A1 | 2/2003 |
| WO | WO 03033002 A1 | 4/2003 |
| WO | WO 03059916 A2 | 7/2003 |
| WO | WO 2004/043925 A2 | 5/2004 |
| WO | WO 2004056322 A2 | 7/2004 |
| WO | WO 2004081008 A1 | 9/2004 |
| WO | WO 2005002577 A1 | 1/2005 |
| WO | WO 2005013892 A3 | 2/2005 |
| WO | WO 2005/066172 | 7/2005 |
| WO | WO 2005/110410 A2 | 11/2005 |
| WO | WO 2005/123054 | 12/2005 |
| WO | WO 2005123094 A2 | 12/2005 |
| WO | WO 2006007384 | 1/2006 |
| WO | WO 2006062731 A1 | 6/2006 |
| WO | WO 2006079843 A1 | 8/2006 |
| WO | WO 2006089067 A2 | 8/2006 |
| WO | WO 2006096131 A1 | 9/2006 |
| WO | WO 2007022437 A2 | 2/2007 |
| WO | WO 2007078340 A2 | 7/2007 |
| WO | WO 2007095638 A2 | 8/2007 |
| WO | WO 2007146965 A2 | 12/2007 |
| WO | WO 2008157726 A1 | 12/2008 |

(56) References Cited

FOREIGN PATENT DOCUMENTS

| WO | WO 2009111676 A2 | 9/2009 |
|---|---|---|
| WO | WO 2009140309 A2 | 11/2009 |
| WO | WO 2010028005 A1 | 3/2010 |
| WO | WO 2010045503 A | 4/2010 |
| WO | WO 2010045505 A1 | 4/2010 |
| WO | WO 2015/171186 | 11/2015 |

OTHER PUBLICATIONS

U.S. Appl. No. 11/762,038, filed Jun. 12, 2007, now abandoned.
U.S. Appl. No. 11/865,725, filed Oct. 1, 2007, now abandoned.
U.S. Appl. No. 12/752,789, filed Apr. 1, 2010, now abandoned.
U.S. Appl. No. 14/536,483, filed Nov. 7, 2014.
U.S. Appl. No. 14/666,075, filed Mar. 23, 2015.
U.S. Appl. No. 13/062,450, filed Mar. 4, 2011.
U.S. Appl. No. 12/464,829, filed May 12, 2009, now abandoned.
U.S. Appl. No. 12/873,036, filed Aug. 31, 2010, now abandoned.
U.S. Appl. No. 13/503,016, filed Jun. 25, 2012, now allowed.
U.S. Appl. No. 12/857,305, filed Aug. 16, 2010, now abandoned.
U.S. Appl. No. 12/852,351, filed Aug. 6, 2010.
U.S. Appl. No. 14/852,122, filed Sep. 11, 2015.
U.S. Appl. No. 12/944,699, filed Nov. 11, 2010, now abandoned.
U.S. Appl. No. 14/969,467, filed Dec. 15, 2015.
U.S. Appl. No. 14/221,637, filed Mar. 21, 2014.
U.S. Appl. No. 14/852,220, filed Sep. 11, 2015.
U.S. Appl. No. 14/760,208, filed Jul. 10, 2015.
U.S. Appl. No. 14/394,427, filed Oct. 14, 2014.
U.S. Appl. No. 14/765,152, filed Jul. 31, 2015.
U.S. Appl. No. 14/906,849, filed Jan. 21, 2016.
U.S. Appl. No. 14/910,996, filed Feb. 8, 2016.
Patent Owner's Response Pursuant to 37 C.F.R. § 42.120, 74 pages, IPR2015-01776, Jun. 6, 2016.
Patent Owner's Exhibit List, 22 pages, IPR2015-01776, Jun. 6, 2016.
Curriculum Vitae of Mahmoud A. Ghannoum, IPR2015-01776, Jun. 6, 2016 [Exhibit 2029].
Curriculum Vitae of Paul J. Reider, Ph.D., IPR2015-01776, Jun. 6, 2016 [Exhibit 2030].
Curriculum Vitae of Howard Ira Maibach, M.D., (Honorary) Ph.D., IPR2015-01776, Jun. 6, 2016 [Exhibit 2031].
Deposition of Narasimha Murthy, Ph.D., vol. 1 of 3, Case No. IPR2015-01776 U.S. Pat. No. 7,582,621, Case No. IPR2015-01780 U.S. Pat. No. 7,767,657, Case No. IPR2015-01785 U.S. Pat. No. 7,767,567, May 4, 5, 6, and 12, 2016, 638 pages, Jun. 6, 2016 [Exhibit 2032].
Deposition of Stephen B. Kahl, Ph.D., vol. 1, Case No. IPR2015-01776 U.S. Pat. No. 7,582,621, Case No. IPR2015-01780 U.S. Pat. No. 7,767,657, Case No. IPR2015-01785 U.S. Pat. No. 7,767,567, Apr. 7 and 8, 2016, 583 pages, Jun. 6, 2016 [Exhibit 2033].
Declaration of Paul J. Reider, Ph.D. in Support of Patent Owner Response, 96 pages, IPR2015-01776, Jun. 6, 2016 [Exhibit 2034].
Declaration of Mahmoud A. Ghannoum, Ph.D. E.M.B.A., in Support of Patent Owner Response, Pursuant to 37 C.F.R. § 42.120, 85 pages, IPR2015-01776, Jun. 6,2016 [Exhibit 2035].
Declaration of Majella Lane, Ph.D., in Support of Patent Owner Response, Pursuant to 37 C.F.R. § 42.120, 28 pages, IPR2015-01776, Jun. 6, 2016 [Exhibit 2036].
Declaration of Howard I. Maibach, Ph.D., in Support of Patent Owner Response, Pursuant to 37 C.F.R. § 42.120, 33 pages, IPR2015-01776, Jun. 6, 2016 [Exhibit 2037].
Fletcher et al., Onychomycosis: The Development of a Clinical Diagnostic Aid for Toenail Disease, Part I. Establishing Discriminating Historical and Clinical Features, Brit. J. Dermatol., vol. 150, No. 4, pp. 701-705 (2004), IPR2015-01776, Jun. 6, 2016 [Exhibit 2038].
Kemna & Elewski, A U.S. Epidemiologic Survey of Superficial Fungal Diseases, J. Am. Acad. of Dermatol., vol. 35, No. 4, pp. 539-542, (1996), IPR2015-01776, Jun. 6, 2016 [Exhibit 2039].
Shivakumar, Repka, & Murthy, Transungual Drug Delivery: an Update, J. Drug Del. Sci. Tech., vol. 24, No. 3, pp. 301-310 (2014) (Ex. 3 from Murthy Deposition), IPR2015-01776, Jun. 6, 2016 [Exhibit 2040].
Topical Nail Products and Ungual Drug Delivery (S. Narasimha Murthy & Howard I. Maibach eds., 2013) (Ex. 4 from Murthy Deposition), 300 pages, IPR2015-01776, Jun. 6, 2016 [Exhibit 2041].
Koo et al., Synthesis and Comparative Toxicology of a Series of Polyhedral Borane Anion-Substituted Tetraphenyl Porphyrins, J.Med. Chem., vol. 50, pp. 820-827 (2007), IPR2015-01776, Jun. 6, 2016 [Exhibit 2042].
Office of Toxic Substances, Environmental Protection Agency, "Preliminary Investigation of Effects on the Environment of Boron, Indium, Nickel, Selenium, Vanadium and Their Compounds," EPA-56/2-75-005A (Aug. 1975) available at http://nepis.epa.gov/Exe/ZyPDF.cgi/9101277V.PDF?Dockey=9101277V.PDF, 118 pages, IPR2015-01776, Jun. 6, 2016 [Exhibit 2043].
Van Proosdij-Hartzema, Boriumverbindingen: Verleden, Heden en Toekomst, Ned. T. Geneesk., vol. 110, No. 51, pp. 2260-2269 (1966) with certified English translation, IPR2015-01776, Jun. 6, 2016 [Exhibit 2044].
Elewski et al., Efficacy, Safety and Tolerability of Topical Terbinafine Nail Solution in Patients with Mild-to-Moderate Toenail Onychomycosis: Results from Three Randomized Studies using Double-Blind Vehicle-Controlled and Open-Label Active-Controlled Designs, J. Eur. Acad. Derm. & Vener., vol. 27, No. 3, pp. 287-294 (2013), IPR2015-01776, Jun. 6, 2016 [Exhibit 2045].
Cecil Textbook of Medicine, (J. Claude Bennett & Fred Plum ed., 1996), 6 pages, IPR2015-01776, Jun. 6, 2016 [Exhibit 2046].
Hay et al., Fungal (onychomycosis) and other Infections Involving the Nail Apparatus in Baran and Dawber's Diseases of the Nails and their Management, (R. Baran et al., eds., 2001), 51 pages, IPR2015-01776, Jun. 6, 2016 [Exhibit 2047].
EPA Correspondence, 1992 Labeling Rev., Amended Biobor Label available at https://www3.epa.gov/pesticides/chem_search/ppls/065217-00001-19920403.pdf, 5 pages, IPR2015-01776, Jun. 6, 2016 [Exhibit 2048].
Ghannoum et al., A Large-Scale North American Study of Fungal Isolates From Nails: The Frequency of Onychomycosis, Fungal Distribution, and Antifungal Susceptibility Patterns, J. Am. Acad. Dermatol., vol. 43, No. 4, pp. 641-648 (2000), IPR2015-01776, Jun. 6, 2016 [Exhibit 2049].
Segal et al., Treatment of Candida Nail Infection with Terbinafine, J. Am. Acad. Dermatol., vol. 35, No. 6, pp. 958-961 (1996), IPR2015-01776, Jun. 6, 2016 [Exhibit 2050].
Rock et al., Antifungal Agent Inhibits an Aminoacyl-tRNA Synthetase by Trapping tRNA in the Editing Site, Science, vol. 316, pp. 1759-1761 (2007), IPR2015-01776, Jun. 6, 2016 [Exhibit 2051].
Soloway et al., Penetration of Brain and Brain Tumor by Aromatic Compounds as a Function of Molecular Substituents, J. Pharmacol. & Exp. Therapeutics, vol. 129, pp. 310-314 (1960), IPR2015-01776, Jun. 6, 2016 [Exhibit 2052].
Baran et al., Onychomycosis: The Current Approach to Diagnosis and Therapy, Martin Dunitz Publishers, London, U.K. (1999), IPR2015-01776, Jun. 6, 2016 [Exhibit 2053].
Gupchup & Zatz, Structural Characteristics and Permeability Properties of the Human Nail: A Review, 50 J. Cosmet. Sci. 363, 363-85 (Nov./Dec. 1999), IPR2015-01776, Jun. 6, 2016 [Exhibit 2054].
Elkeeb et al., Tranungual Drug Delivery: Current Status, 384 Internat. J. Pharm. 1-8 (2010), IPR2015-01776, Jun. 6, 2016 [Exhibit 2055].

(56) References Cited

OTHER PUBLICATIONS

Scher, Onychomycosis: Therapeutic Update, J. Am. Acad. Derm., vol. 40, No. 6 (part 2), pp. S21-S26 (1999), IPR2015-01776, Jun. 6, 2016 [Exhibit 2056].

Baeza et al., cDNA Representational Difference Analysis Used in the Identification of Genes Expressed by Trichophyton rubrum During Contact with Keratin, Microbes & Infection, vol. 9, pp. 1415-1421 (2007), IPR2015-01776, Jun. 6, 2016 [Exhibit 2057].

Hamaguchi et al., Characterization of an Extracellular Keratinase from Microsporum canis, Jpn. J. Med. Mycol., vol. 41, No. 4, pp. 257-262, (2000), IPR2015-01776, Jun. 6, 2016 [Exhibit 2058].

Foster et al., Epidemiologic Surveillance of Cutaneous Fungal Infection in the United States from 1999 to 2002, Am. Acad. Dermatol., vol. 50, No. 5, pp. 748-752 (2004), IPR2015-01776, Jun. 6, 2016 [Exhibit 2059].

Jinna & Finch, Spotlight on Tavaborole for the Treatment of Onychomycosis, Drug Des. Devel. Ther., vol. 5, No. 9, pp. 6185-6190, (Nov. 20, 2015), IPR2015-01776, Jun. 6, 2016 [Exhibit 2060].

Childs-Kean & Jourjy, Antifungal Penetration into the Nail and New Topicals for Onychomycosis, Curr. Fungal Infect. Rep., vol. 10, pp. 24-29 (2016), IPR2015-01776, Jun. 6, 2016 [Exhibit 2061].

Rosen & Stein Gold, Antifungal Drugs for Onychomycosis: Efficacy, Safety, and Mechanisms of Action, Semin. Cutan. Med. Surg., vol. 35, No. 3S, pp. S51-S55 (Mar. 2016), IPR2015-01776, Jun. 6, 2016 [Exhibit 2062].

Poulakos et al., Efinaconazole and Tavaborole: Emerging Antifungal Alternatives for the Topical Treatment of Onychomycosis, J. Pharm. Pract., advance online publication, doi: 10.1177/0897190016630904, pp. 1-11 (2016), IPR2015-01776, Jun. 6, 2016 [Exhibit 2063].

Drake et al., Effect of Onychomycosis on Quality of Life, J. Am. Acad. Dermatol., vol. 38, No. 5, Part 1, pp. 702-704 (1998), IPR2015-01776, Jun. 6, 2016 [Exhibit 2064].

Scher et al., Onychomycosis: Diagnosis and Definition of Cure, J. Am. Acad. Dermatol., vol. 56, No. 6, pp. 939-944 (2007), IPR2015-01776, Jun. 6, 2016 [Exhibit 2065].

Summerbell et al., Onychomycosis, Tinea Pedis and Tinea Manuum Caused by Non-Dermatophytic Filamentous Fungi, Mycoses, vol. 32, No. 12, pp. 609-619 (1989), IPR2015-01776, Jun. 6, 2016 [Exhibit 2066].

Ellis et al., Non-Dermatophytes in Onychomycosis of the Toenails, Brit. J. Dermatol., vol. 136, pp. 490-493 (1997), IPR2015-01776, Jun. 6,2016 [Exhibit 2067].

McGinley et al., Composition and Density of Microflora in the Subungual Space of the Hand, J. Clin. Microbiol., vol. 26, No. 5, pp. 950-953 (1988), IPR2015-01776, Jun. 6, 2016 [Exhibit 2068].

Strausbaugh et al., High Frequency of Yeast Carriage on Hands of Hospital Personnel, J. Clin. Microbiol., vol. 32, No. 9, pp. 2299-2300 (1994), IPR2015-01776, Jun. 6, 2016 [Exhibit 2069].

Elewski, Onychomycosis: Pathogenesis, Diagnosis, and Management, Clin. Microbiol. Rev., vol. 11, No. 3, pp. 415-429(1998), IPR2015-01776, Jun. 6, 2016 [Exhibit 2070].

Summerbell, Nondermatophytic Molds Causing Dermatophytosis-Like Nail and Skin Infection, in Laboratory Handbook of Dermatophytes, Chap. 8, pp. 213-256 (Kane et at. eds. 1997), IPR2015-01776, Jun. 6, 2016 [Exhibit 2071].

Weitzman & Summerbell, the Dermatophytes, Clin. Microbio. Rev., vol. 8, No. 2, pp. 240-259 (1995), IPR2015-01776, Jun. 6, 2016 [Exhibit 2072].

Gupta et al., Pulse ltraconazole vs. Continuous Terbinafine for the Treatment of Dermatophyte Toenail Onychomycosis in Patients with Diabetes Mellitus, J. Euro. Acad. Dermatol. & Venerol., vol. 20, pp. 1188-1193 (2006), IPR2015-01776, Jun. 6, 2016 [Exhibit 2073].

FDA Approved Label for Sporanox® (Supplement 034, Action Date Jul. 14, 2004) available at http://www.accessdata.fda.gov/drugsatfda_docs/appletter/2004/200 83s034,035ltr.pdf (letter) and http://www.accessdata.fda.gov/drugsatfda_docs/label/2004/20083s 034,035lbl.pdf (label), IPR2015-01776, Jun. 6, 2016 [Exhibit 2074].

FDA Approved Label for Lamisil® (Supplement 012, Action Date Jan. 21, 2004) available at http://www.accessdata.fda.gov/drugsatfda_docs/appletter/2004/205 39slr012ltr.pdf (letter) and http://www.accessdata.fda.gov/drugsatfda_docs/label/2004/20539sl r012_lamisil_lbl.pdf (label), IPR2015-01776, Jun. 6, 2016 [Exhibit 2075].

FDA Approved Label for Gris-PEG® (Supplement 046, Action Date Mar. 26, 2003) available at http://www.accessdata.fda.gov/drugsatfda_docs/appletter/2003/504 75slr046ltr.pdf (letter) and http://www.accessdata.fda.gov/drugsatfda_docs/label/2003/50475sl r046_gris-peg_lbl.pdf (label), IPR2015-01776, Jun. 6, 2016 [Exhibit 2076].

FDA Approved Label for Penlac®, (Supplement 004, Action Date Dec. 3, 2004) available at http://www.accessdata.fda.gov/drugsatfda_docs/appletter/2004/210 22s004ltr.pdf (letter) and http://www.accessdata.fda.gov/drugsatfda_docs/label/2004/21022s 004lbl.pdf (label), IPR2015-01776, Jun. 6, 2016 [Exhibit 2077].

Naglik et al., Candida albicans Secreted Aspartyl Proteinases in Virulence and Pathogenesis, Microbio. & Molecular Bio. Revs., vol. 67, No. 3, pp. 400-428 (2003), IPR2015-01776, Jun. 6, 2016 [Exhibit 2078].

Hattori et al., Keratinolytic Proteinase Produced by Candida albicans, Sabouraudia: J. Med. Vet. Mycology, vol. 22, No. 3, pp. 175-183 (1984), IPR2015-01776, Jun. 6, 2016 [Exhibit 2079].

Weary & Canby, Absence of Keratinolytic Activity in Three Strains of Candida albicans, J. Invest. Derm., vol. 46, No. 5, pp. 464-734 (1966), IPR2015-01776, Jun. 6, 2016 [Exhibit 2080].

Nenoff et al., Mycology—An Update. Part 1: Dermatomycoses: Causative Agents, Epidemiology and Pathogenesis, J. Dtsch. Derm. Ges., vol. 12, No. 3, pp. 188-210 (2014) (including English online version on Wiley Online Library), IPR2015-01776, Jun. 6, 2016 [Exhibit 2081].

Balkis et al., Mechanisms of Fungal Resistance, Drugs, vol. 62(7), pp. 1025-1040 (2002), IPR2015-01776, Jun. 6, 2016 [Exhibit 2082].

CLSI, Reference Method for Broth Dilution Antifungal Susceptibility Testing of Filamentous Fungi; Approved Standard-Second Edition, CLSI document M38-A2 (2008), IPR2015-01776, Jun. 6, 2016 [Exhibit 2083].

Ghannoum et al., Intra- and Interlaboratory Study for Testing the Antifungal Susceptibilities of Dermatophytes, J. Clin. Microbiol., vol. 42, No. 7, pp. 2977-2979 (2004), IPR2015-01776, Jun. 6, 2016 [Exhibit 2084].

Norris et al., Optimal Growth Conditions for the Determination of the Antifungal Susceptibility of Three Species of Dermatophytes with the Use of a Microdilution Method, J. Am. Acad. Dermatol., vol. 40, No. 6, pp. S9-S13, (1999), IPR2015-01776, Jun. 6, 2016 [Exhibit 2085].

Jessup et al., Antifungal Susceptibility Testing of Dermatophytes: Establishing a Medium for Inducing Conidial Growth and Evaluation of Susceptibility of Clinical Isolates, J. Clin. Microbiol., vol. 38, No. 1, pp. 341-344 (2000), IPR2015-01776, Jun. 6, 2016 [Exhibit 2086].

Kokjohn et al., Evaluation of in vitro Activity of Ciclopirox Olamine, Butenafine HCl and Econazole Nitrate Against Dermatophytes, Yeasts and Bacteria, Int'l J. Dermatol., vol. 42, suppl. 1, pp. 11-17 (2003), IPR2015-01776, Jun. 6, 2016 [Exhibit 2087].

NCCLS (now CLSI), Reference Method for Broth Dilution Antifungal Susceptibility Testing of Yeasts; Approved Standard—Second Edition, NCCLS document M27-A2 (2002), IPR2015-01776, Jun. 6, 2016 [Exhibit 2088].

Mukherjee et al., Combination Treatment of Invasive Fungal Infections, Clin. Microbiol. Rev., vol. 18, No. 1, pp. 163-194 (2005), IPR2015-01776, Jun. 6, 2016 [Exhibit 2089].

Ghannoum & Rice, Antifungal Agents: Mode of Action, Mechanisms of Resistance, and Correlation of These Mechanisms with Bacterial Resistance, Clin. Microbiol. Rev., vol. 12, No. 4, pp. 501-517 (1999), IPR2015-01776, Jun. 6, 2016 [Exhibit 2090].

(56) References Cited

OTHER PUBLICATIONS

Gupta et al., Drug Interactions with Itraconazole, Fluconazole, and Terbinafine and their Management, J. Am. Acad. Dermatol., vol. 41, No. 2, pp. 237-249 (1999), IPR2015-01776, Jun. 6, 2016 [Exhibit 2091].
Gupta & Lyons, The Rise and Fall of Oral Ketoconazole, J. Cutaneous Med. & Surgery, vol. 19, No. 4, pp. 352-357 (2015), IPR2015-01776, Jun. 6, 2016 [Exhibit 2092].
Gull & Trinci, Griseofulvin Inhibits Fungal Mitosis, Nature, vol. 244, pp. 292-294 (1973), IPR2015-01776, Jun. 6, 2016 [Exhibit 2093].
Ku et al., Mutation of a Major Keratin Phosphorylation Site Predisposes to Hepatotoxic Injury in Transgenic Mice, J. Cell Biol., vol. 143, No. 7, pp. 2023-2032 (1998), IPR2015-01776, Jun. 6,2016 [Exhibit 2094].
Katz, Possible Drug Interactions in Oral Treatment of Onychomycosis, J. Am. Podiatr. Med. Ass'n, vol. 87, No. 12, pp. 571-574 (1997), IPR2015-01776, Jun. 6, 2016 [Exhibit 2095].
Nguyen & Yu, Voriconazole Against Fluconazole-Susceptible and Resistant Candida Isolates: in-vitro Efficacy Compared with that of Itraconazole and Ketoconazole, J. Antimicrobial Chemotherapy, vol. 42, pp. 253-256 (1998), IPR2015-01776, Jun. 6, 2016 [Exhibit 2096].
Johnson & Kauffman, Voriconazole: A New Triazole Antifungal Agent, Clin. Infect. Dis., vol. 36, No. 5, pp. 630-637 (2003), IPR2015-01776, Jun. 6, 2016 [Exhibit 2097].
Elewski & Tavakkol, Safety and Tolerability of Oral Antifungal Agents in the Treatment of Fungal Nail Disease: a Proven Reality, Ther. Clin. Risk Manag., vol. 1, No. 4, pp. 299-306 (2005), IPR2015-01776, Jun. 6, 2016 [Exhibit 2098].
Center for Drug Evaluation and Research, Guidance for Industry: Clinical Development and Labeling of Anti-Infective Drug Products (1992) available at http://www.fda.gov/downloads/Drugs/GuidanceComplianceRegulatoryInformation/Guidances/UCM070975.pdf, IPR2015-01776, Jun. 6, 2016 [Exhibit 2099].
Rodgers & Bassler, Treating Onychomycosis, Am. Fam. Physician, vol. 63, No. 4, pp. 663-672 (2001), IPR2015-01776, Jun. 6, 2016 [Exhibit 2100].
Ghannoum et al., Amorolfine 5% Nail Lacquer Exhibits Potent Antifungal Activity Compared to Three Acid-Based Devices Indicated for the Treatment of Onychomycosis An In Vitro Nail Penetration Assay, Derm. & Therapy, vol. 6, No. 1, pp. 69-75 (2016), IPR2015-01776, Jun. 6, 2016 [Exhibit 2101].
Declaration of Jennifer Augsburger in Support of Patent Owner's Response, IPR2015-01776, Jun. 6, 2016 [Exhibit 2102].
Fukuoka et al., Genetic Basis for Differential Activities of Fluconazole and Voriconazole against Candida krusei, Antimicrob. Agents Chemother., vol. 47, No. 4, pp. 1213-1219 (2003), IPR2015-01776, Jun. 6, 2016 [Exhibit 2103].
Orozco et al., Mechanism of Fluconazole Resistance in Candida krusei, Antimicrob. Agents Chemother., vol. 42, No. 10, pp. 2645-2649 (1998), IPR2015-01776, Jun. 6, 2016 [Exhibit 2104].
Nimura et al., Comparison of In Vitro Antifungal Activities of Topical Antimycotics Launched in 1990s in Japan, Int'l J. Antimicrob. Agents, vol. 18, pp. 173-178 (2001), IPR2015-01776, Jun. 6, 2016 [Exhibit 2105].
Ghannoum et al., Terbinafine HCl Nail Solution With and Without Nail Penetration Enhancer: Evaluation of Minimum Inhibitory Concentration and Minimum Fungicidal Concentrations, (abstract) J. Am. Acad. Dermatol., vol. 58, No. 2, suppl. 2, p. AB12 (2008), IPR2015-01776, Jun. 6, 2016 [Exhibit 2106].
Ghannoum et al., Determination of the Efficacy of Terbinafine Hydrochloride Nail Solution in the Topical Treatment of Dermatophytosis in a Guinea Pig Model, Mycoses, vol. 52, No. 1, pp. 35-43 (2009), IPR2015-01776, Jun. 6, 2016 [Exhibit 2107].
Rex et al., Antifungal Susceptibility Testing, Clin. Microbio. Revs., vol. 6, No. 4, pp. 367-381 (1993), IPR2015-01776, Jun. 6, 2016 [Exhibit 2108].
EPA Correspondence, 1997 Labeling Rev., Amended Biobor Label available at www3.epa.gov/pesticides/chem_search/ppls/065217-000001-19970327.pdf, IPR2015-01776, Jun. 6, 2016 [Exhibit 2109].
Ferrari et al., Occurrence of Heterotrophic Bacteria and Fungi in an Aviation Fuel Handling System and its Relationship with Fuel Fouling, Revista Argentina de Microbiologia, vol. 30, No. 3, pp. 105-114 (1998), IPR2015-01776, Jun. 6, 2016 [Exhibit 2110].
Aly, Ecology and Epidemiology of Dermatophyte Infections, J. Am. Acad. Derm., vol. 31, No. 3, pp. S21-S25 (1994), IPR2015-01776, Jun. 6,2016 [Exhibit 2111].
Crane & Sanders, Evaluation of a Biocidal Turbine-Fuel Additive, Aviation Medical Report—AM 67-21, pp. 1-10 (Federal Aviation Administration, Office of Aviation Medicine 1967) available at http://www.faa.gov/data_research/research/med_humanfacs/oamtechreports/1960s/media/am67-21.pdf, IPR2015-01776, Jun. 6, 2016 [Exhibit 2112].
Alley et al., Recent Progress on the Topical Therapy of Onychomycosis, Expert Opin. Investig. Drugs, vol. 16, No. 2, pp. 157-167 (2007), IPR2015-01776, Jun. 6, 2016 [Exhibit 2113].
Smith & March, March's Advanced Organic Chemistry: Reactions, Mechanism, and Structure, John Wiley & Sons, New York, NY (5th ed., 2001), IPR2015-01776, Jun. 6, 2016 [Exhibit 2114].
Batsanov, Van der Weals Radii of Elements, Inorg. Materials, vol. 37, pp. 871-885 (2001), IPR2015-01776, Jun. 6, 2016 [Exhibit 2115].
Henman et al., Effects of Decaborane on Gastric Secretion in the Shay Rat, Br. J. Pharmacol., vol. 40, No. 1, p. 164P (1970), IPR2015-01776, Jun. 6, 2016 [Exhibit 2116].
Steiner et al., Diphenylborinic Acid Is a Strong Inhibitor of Serine Proteases, Bioorg. & Med. Chem. Lett., vol. 4, pp. 2417-2420 (1994), IPR2015-01776, Jun. 6, 2016 [Exhibit 2117].
Hall, Boronic Acids, Prep. and App. in Organic Synthesis and Med., pp. 123-131(Wiley-VCH, 2005), IPR2015-01776, Jun. 6, 2016 [Exhibit 2118].
Hall, Boronic Acids, Prep. and App. in Organic Synthesis and Med., pp. 28-49 (Wiley-VCH, 2005), IPR2015-01776, Jun. 6, 2016 [Exhibit 2119].
Iliev et al., Skin Roughness is Negatively Correlated to Irritation with DMSO, but not with NaOH and SLS, Exp. Dermatol., vol. 6, No. 4, pp. 157-160 (1997), IPR2015-01776, Jun. 6, 2016 [Exhibit 2120].
DiMasi et al., Innovation in the Pharmaceutical Industry: New Estimates of R&D Costs, J. Health. Econ., vol. 47, pp. 20-33 (2016), IPR2015-01776, Jun. 6, 2016 [Exhibit 2121].
Endo, The Discovery and Development of HMG-CoA Reductase Inhibitors, J. Lipid Res., vol. 33, pp. 1569-1582 (1992), IPR2015-01776, Jun. 6, 2016 [Exhibit 2122].
O'Driscoll et al., Simvastatin, an Hmg-Coenzyme A Reductase Inhibitor, Improves Endothelial Function Within 1 Month, Circulation, vol. 95, pp. 1126-1131 (1997), IPR2015-01776, Jun. 6, 2016 [Exhibit 2123].
Tenjarla et al., Preparation, Characterization, and Evaluation of Miconazole-Cyclodextrin Complexes for Improved Oral and Topical Delivery, J. Pharm. Sci., vol. 87, No. 4, pp. 425-429 (1998), IPR2015-01776, Jun. 6, 2016 [Exhibit 2124].
Dixon & Villar, Bioactive Diversity and Screening Library Selection Via Affinity Fingerprinting, J. Chem. Info. & Comp. Sci., vol. 38, pp. 1192-1203 (1998), IPR2015-01776, Jun. 6, 2016 [Exhibit 2125].
Silverman, The Organic Chemistry of Drug Design and Drug Action, Elsevier Academic Press, Evanston, Il. (2d Ed., 2004), IPR2015-01776, Jun. 6, 2016 [Exhibit 2126].
Cursiefen & Bergua, Acute Bilateral Blindness Caused by Accidental Methanol Intoxication During Fire "Eating," Br. J. Ophthamol., vol. 86, pp. 1064-1065 (2002), IPR2015-01776, Jun. 6, 2016 [Exhibit 2127].
DeCamp & Kahl et al., Specific Inhibition of HIV-1 Protease by Boronated Porphyrins, J. Med. Chem., vol. 35, pp. 3426-3428 (1992), IPR2015-01776, Jun. 6, 2016 [Exhibit 2128].
Soloway, Correlation of Drug penetration of Brain and Chemical Structure, Science, vol. 128, pp. 1572-1574 (1958), IPR2015-01776, Jun. 6, 2016 [Exhibit 2129].

(56) References Cited

OTHER PUBLICATIONS

Soloway et al., Evaluation of Boron Compounds for Use in Neutron Capture Therapy of Brain Tumors. I. Animal Investigations, J. Pharmacol. & Exp. Therapeutics, vol. 134, pp. 117-122 (1961), IPR2015-01776, Jun. 6, 2016 [Exhibit 2130].
Soloway et al., Penetration of Brain and Brain Tumor by Aromatic Compounds as a Function of Molecular Substituents. III, J. Med. Chem., vol. 5, pp. 191-196 (1962), IPR2015-01776, Jun. 6, 2016 [Exhibit 2131].
Dominguez et al., S1 Heterocyclic Thrombin Inhibitors, Bioorg. & Med. Chem. Lett., vol. 7, pp. 79-94 (1997), IPR2015-01776, Jun. 6, 2016 [Exhibit 2133].
Fevig et al., Rational Design of Boropeptide Thrombin Inhibitors: β,β-Dialkylphenethylglycine P2 Analogs of Dup 714 With Greater Selectivity over Complement Factor I and an Improved Safety Profile, Bioorg. & Med. Chem. Lett., vol. 8, pp. 301-306 (1998), IPR2015-01776, Jun. 6, 2016 [Exhibit 2134].
Lewis, Sax's Dangerous Properties of Industrial Materials, John Wiley & Sons, New York, NY, (10th ed., 2000), IPR2015-01776, Jun. 6, 2016 [Exhibit 2135].
Vyakaranam et al., New Boron Analogues of Pyrophosphates and Deoxynucleoside Boranophosphates, Metal Based Drugs, vol. 8, pp. 145-148 (2001), IPR2015-01776, Jun. 6, 2016 [Exhibit 2136].
Philipp & Bender, Inhibition of Serine Proteases by Arylboronic Acids, PNAS USA, vol. 68, pp. 478-480 (1971), IPR2015-01776, Jun. 6, 2016 [Exhibit 2137].
Kettner & Shenvi, Inhibition of the Serine Proteases Leukocyte Elastase, Pancreatic Elastase, Cathepsin G, and Chymotrypsin by Peptide Boronic Acids, J. Biol. Chem., vol. 259, pp. 15106-15114 (1984), IPR2015-01776, Jun. 6, 2016 [Exhibit 2138].
Whyte et al., Molecular Recognition With Boronic Acids—Applications in Chemical Biology, J. Chem. Biol., vol. 6, pp. 161-174 (2013), IPR2015-01776, Jun. 6, 2016 [Exhibit 2139].
Biobor Label (Kahl Dep. Ex. 77), IPR2015-01776, Jun. 6, 2016 [Exhibit 2140].
Truhaut et al., Effects of Repeated Injections of Low Doses of Boron Derivatives on Reproductive Function in Rats, C. R. Acad. Sc. Paris, pp. 5099-5102 (May 20, 1964) with certified English translation, IPR2015-01776, Jun. 6, 2016 [Exhibit 2141].
Truhaut & Nguyen, Study of the Distribution of Three Boron Derivatives in Organisms and the Rate of Unbinding Over the Course of Various Forms of Experimental Intoxication in Animals, Ann. Biol. Clin., vol. 23, pp. 84-105 (1965) with certified English translation, IPR2015-01776, Jun. 6, 2016 [Exhibit 2142].
FDA Approved Label for Velcade® (Action Date May 13, 2003) available at http://www.accessdata.fda.gov/drugsatfda_docs/appletter/2003/216 02ltr.pdf (letter) and http://www.accessdata.fda.gov/drugsatfda_docs/label/2003/021602 lbl.pdf (label), IPR2015-01776, Jun. 6, 2016 [Exhibit 2143].
Austin Prosecution History, Amendment & Remarks (Jul. 7, 1998), IPR2015-01776, Jun. 6, 2016 [Exhibit 2145].
Caujolle, Recherches Pharmacologiques Sur Les Derives Organiques Du Bore, Therapie, No. XV, pp. 791-802 (1960) with certified English translation, IPR2015-01776, Jun. 6, 2016 [Exhibit 2147].
Article 4(a) of Council Directive, Official Journal of the European Communities, No. L 262/169-200 (Jul. 27, 1976), IPR2015-01776, Jun. 6, 2016 [Exhibit 2148].
The Ministry for Public Health and the National Health Insurance Program, J. Off. Rep. Fr., pp. 483-485 (1972) with certified English translation, IPR2015-01776, Jun. 6, 2016 [Exhibit 2149].
Dictionnaire Vidal (Office de Vulgarisation Pharmaceutique, Paris, 1964) with certified English translation, IPR2015-01776, Jun. 6, 2016 [Exhibit 2150].
Dictionnaire Vidal (Office de Vulgarisation Pharmaceutique, Paris, 1964) with certified English translation, IPR2015-01776, Jun. 6, 2016 [Exhibit 2151].
Vidal, Le Dictionnaire (80th ed., France, 2004) with certified English translation, IPR2015-01776, Jun. 6, 2016 [Exhibit 2152].
Boislambert & Wangen, Respecting a New Tranquilizer (Critical Study), Nanterre Departmental Center (1960) with certified English translation, IPR2015-01776, Jun. 6, 2016 [Exhibit 2153].
Biobor JF Service Bulletin No. 982, Biobor JF Aviation Fuel Additive (1992), IPR2015-01776, Jun. 6, 2016 [Exhibit 2154].
Wu et al., Cell Immobilization Using PVA Crosslinked with Boric Acid, Biotech. & Bioeng., vol. 39, pp. 447-449 (1992), IPR2015-01776, Jun. 6, 2016 [Exhibit 2155].
Freeman Prosecution History, Amendment & Remarks (Aug. 5, 2009), IPR2015-01776, Jun. 6, 2016 [Exhibit 2156].
Roberts, Onychomycosis: Current Treatment and Future Challenges, 141 (Suppl. 56) Brit. J. of Derm. 1, 1-4 (1999), IPR2015-01776, Jun. 6, 2016 [Exhibit 2158].
Vlahovic at al., Evaluation of the Appearance of Nail Polish Following Daily Treatment of Ex Vivo Human Fingernails with Topical Soliutionss of Tavaborole or Efinaconazole, J. of Drugs in Derm. (2016), IPR2015-01776, Jun. 6, 2016 [Exhibit 2159].
Freedberg et al., Fitzpatrick's Dermatology in General Medicine, McGraw-Hill Co. (6th ed. 2003), IPR2015-01776, Jun. 6, 2016 [Exhibit 2160].
Rosen et al., Onychomycosis: Epidemiology, Diagnosis, and Treatment in a Changing Lanscape, J. of Drugs in Derm., vol. 14, No. 3, pp. 223-228 (2015), IPR2015-01776, Jun. 6, 2016 [Exhibit 2161].
Tom & Kane, Management of Toenail Onychomycosis, Am. J. Health-Syst. Pharm,, vol. 56, No. 9, pp. 865-871 (1999), IPR2015-01776, Jun. 6, 2016 [Exhibit 2162].
Stier et al., Patient Satisfaction with Oral versus Nonoral Therapeutic Approaches in Onychomycosis, J. of the Am. Pod. Med. Assoc., vol. 91, No. 10, pp. 521-527 (Nov./Dec. 2001), IPR2015-01776, Jun. 6, 2016 [Exhibit 2163].
Del Rosso, The Role of Topical Antifungal Therapy for Onychomycosis and the Emergence of Newer Agents, J. of Clin. and Aesth. Derm., vol. 7, No. 7, pp. 10-18 (2014), IPR2015-01776, Jun. 6, 2016 [Exhibit 2164].
Wang & Sun, Human Nail and Its Topical Treatment: Brief Review of Current Research and Development of Topical Antifungal Drug Delivery for Onychomycosis Treatment, J. of Cosm. Sci., vol. 50, No. 1, pp. 71-74 (1999), IPR2015-01776, Jun. 6, 2016 [Exhibit 2165].
Ameen et al., British Association of Dermatologists' Guidelines for the Management of Onychomycosis 2014, British J. Dermatol., vol. 171, No. 5, pp. 937-958 (2014), IPR2015-01776, Jun. 6, 2016 [Exhibit 2166].
Vlahovic et al., Diagnosis and Management of Onychomycosis: Perspectives from a Joint Podiatric Medicine-Dermatology Roundtable, J. of the Am. Pod. Med. Assoc., vol. 106, No. 2, pp. 155-162 (Mar./Apr. 2016), IPR2015-01776, Jun. 6, 2016 [Exhibit 2167].
Gupta & Paquet, Improved Efficacy in Onychomycosis Therapy, Clinics in Derm., vol. 31, No. 5, pp. 555-563 (2013), IPR2015-01776, Jun. 6, 2016 [Exhibit 2168].
Daly et al., Antifungals, in Handbook of Systemic Drug Treatment in Dermatology (Wakelin et al. eds. 2015), IPR2015-01776, Jun. 6, 2016 [Exhibit 2169].
U.S. Dept. of Health & Human Services, Health, United States, 2015 (May 2016), IPR2015-01776, Jun. 6, 2016 [Exhibit 2170].
Effendy, Therapeutic Strategies in Onychomycosis, J. of the Euro. Acad. of Derm. and Venereol., vol. 4, suppl. 1, pp. S3-S10 (1995), IPR2015-01776, Jun. 6, 2016 [Exhibit 2171].
Bodman et al., Topical Treatments for Onychomycosis: A Historical Perspective, J. Am. Podiatr. Med. Assoc., vol. 93, No. 2, pp. 136-141 (2003), IPR2015-01776, Jun. 6, 2016 [Exhibit 2172].
FDA Center for Drug Evaluation and Research, Dermatologic and Ophthalmic Drugs Advisory Committee Meeting, Nov. 4, 1999 (Transcript) available at http://www.fda.gov/ohrms/dockets/ac/99/transcpt/3564t1.pdf, IPR2015-01776, Jun. 6, 2016 [Exhibit 2173].
NexMed Mar. 31, 2009 Form 10-Q, http://www.sec.gov/Archives/edgar/data/1017491/0001144204090 25204/v148508_10q.htm, IPR2015-01776, Jun. 6, 2016 [Exhibit 2174].
PRWeb, MediQuest Announces Sale of Late Stage Onychomycosis Program to EFFELL LLC, First in a Series of Asset Sales, Sep. 19, 2012, http://www.prweb.com/releases/2012/9/prweb9911525.htm, IPR2015-01776, Jun. 6, 2016 [Exhibit 2175].

(56) References Cited

OTHER PUBLICATIONS

SEC, Watson Pharmaceuticals Reports Earnings Per Share of $0.48 for Fourth Quarter 2003, Feb. 5, 2004, https://www.sec.gov/Archives/edgar/data/884629/00011046590400 2780/a04-1963_1ex99d1.htm, IPR2015-01776, Jun. 6, 2016 [Exhibit 2176].

SEC, Macrochem Discontinues Research and Product Development Activities, Terminates Substantially All Non-Management Personnel, Will Seek Buyer for Company or Its Assets, Sep. 1, 2005, http://www.sec.gov/Archives/edgar/data/743884/000074388405000054/exhibit991.txt, IPR2015-01776, Jun. 6, 2016 [Exhibit 2177].

PR Newswire, Celtic Pharma Announces Presentation of Preclinical Data at the 69th Annual Meeting of the AAD in New Orleans, Feb. 7, 2011, http://www.prnewswire.com/news-releases/celtic-pharma-announces-presentation-of-preclinical-data-at-the-69th-annual-meeting-of-the-aad-in-new-orleans- 115474199.html, IPR2015-01776, Jun. 6, 2016 [Exhibit 2178].

Song & Deresinski, Hepatoxicity of Antifungal Agents, Investigational Drugs, vol. 6, No. 2, pp. 170-177 (2005), IPR2015-01776, Jun. 6, 2016 [Exhibit 2179].

Vlahovic, Onychomycosis Evaluation, Treatment Options, Managing Recurrence, and Patient Outcomes, Clin. Podiatr. Med. Surg. (2016) (article in press), IPR2015-01776, Jun. 6, 2016 [Exhibit 2180].

Comments of Vivian Liu, NexMed President and CEO, NexMed Investor Update Conference Call (Jul. 8, 2009), IPR2015-01776, Jun. 6, 2016 [Exhibit 2181].

ProQuest LLC, Terbinafine Gel—MediQuest Therapeutics, Adis R&D Insight (Mar. 2016), IPR2015-01776, Jun. 6, 2016 [Exhibit 2182].

ProQuest LLC, Fluconazole Transdermal—Watson Pharmaceuticals, Adis R&D Insight (Dec. 2015), IPR2015-01776, Jun. 6, 2016 [Exhibit 2183].

ProQuest LLC, Terbinafine Topical—Celtic Pharma, Adis R&D Insight (May 2015), IPR2015-01776, Jun. 6, 2016 [Exhibit 2184].

Gupta & Studholme, Novel Investigational Therapies for Onychomycosis: an Update, Expert Opin. Investig. Drugs, vol. 25, No. 3, pp. 297-305 (2016), IPR2015-01776, Jun. 6, 2016 [Exhibit 2185].

Summerbell, Epidemiology and Ecology of Onychomycosis, Dermatology, vol. 194, suppl. 1, pp. 32-36 (1997), IPR2015-01776, Jun. 6, 2016 [Exhibit 2186].

Curriculum vitae of Majella Lane, Ph.D., IPR2015-01776, Jun. 6, 2016 [Exhibit 2187].

Walters et al., Physiochemical Characterization of the Human Nail: Permeation Pattern for Water and the Homologous Alcohols and Differences with Respect to the Stratum Corneum, J. Pharm. Pharmacol. 1983, vol. 35, No. 1, pp. 28-33 (1983), IPR2015-01776, Jun. 6, 2016 [Exhibit 2188].

Forslind, Biophysical Studies of the Normal Nail, Acta Dermatovener, vol. 50, pp. 161-168 (1970), IPR2015-01776, Jun. 6, 2016 [Exhibit 2189].

Kobayashi et al., Drug Permeation Through the Three Layers of the Human Nail Plate, J. Pharm. Pharmacol., vol. 51, No. 3, pp. 271-278 (1999), IPR2015-01776, Jun. 6, 2016 [Exhibit 2190].

Runne & Orfanos, The Human Nail: Structure, Growth and Pathological Changes, Curr. Probl. Derm., vol. 9, pp. 102-149 (1981), IPR2015-01776, Jun. 6, 2016 [Exhibit 2191].

Mertin & Lippold, In-vitro Permeability of the Human Nail and of a Keratin Membrane from Bovine Hooves: Influence of the Partition Coefficient Octanol/Water and the Water Solubility of Drugs on their Permeability and Maximum Flux, J. Pharm. Pharmacol., vol. 49, No. 1, pp. 30-34 (1997), IPR2015-01776, Jun. 6, 2016 [Exhibit 2192].

European Commission Scientific Committee on Consumer Products, Opinion on Toluene (Apr. 15, 2008), IPR2015-01776, Jun. 6, 2016 [Exhibit 2193].

Mertin & Lippold, In Vitro Permeability of the Human Nail and of a Keratin Membrane from Bovine Hooves: Penetration of Chloramphenicol from Lipophilic Vehicles and from a Nail Lacquer, J. Pharm. Pharmacol., vol. 49, No. 3, pp. 241-245 (1997), IPR2015-01776, Jun. 6, 2016 [Exhibit 2194].

Murthy et al., Iontophoretic Drug Delivery across Human Nail, J. Pharm. Sciences, vol. 96, No. 2, pp. 305-311 (2007), IPR2015-01776, Jun. 6, 2016 [Exhibit 2195].

Marty, Amorolfine Nail Lacquer: a Novel Formulation, J. Eur. Acad. Dermatol. & Venerol., vol. 4, suppl. 1, pp. S17-S21 (1995), IPR2015-01776, Jun. 6, 2016 [Exhibit 2196].

Baran, Nail Damage Caused by Weed Killers and Insecticides, Arch. Dermatol., vol. 110, No. 1, p. 467 (1974), IPR2015-01776, Jun. 6, 2016 [Exhibit 2197].

Little & Gordon, Survival of Fungus Cultures Maintained under Mineral Oil for Twelve Years, Mycologia, vol. 59, pp. 733-736 (1967), IPR2015-01776, Jun. 6, 2016 [Exhibit 2198].

Comaish & Greener, The Inhibiting Effect of Soft Paraffin on the Köbner Response in Psoriasis, British J. of Dermatol., vol. 94, pp. 195-200 (1976), IPR2015-01776, Jun. 6, 2016 [Exhibit 2199].

Williams & Barry, Penetration Enhancers, Advanced Drug Delivery Revs., vol. 56, p. 603-18 (2004), IPR2015-01776, Jun. 6, 2016 [Exhibit 2200].

Jungbauer et al., Toxic Hygroscopic Contact Reaction to N-methyl-2-pyrrolidone, Contact Dermatitis, vol. 45, No. 5, pp. 303-304 (2001), IPR2015-01776, Jun. 6, 2016 [Exhibit 2201].

Structural Diagrams in Kahl Deposition, IPR2015-01776, Jun. 6, 2016 [Exhibit 2202].

Patent Owner's Response Pursuant to 37 C.F.R. § 42.120, U.S. Pat. No. 7,767,657, 74 pages, IPR2015-01780, Jun. 6, 2016.

Patent Owner's Exhibit List, U.S. Pat. No. 7,767,657, 21 pages, IPR2015-01780, Jun. 6, 2016.

Declaration of Paul J. Reider, Ph.D., IPR2015-01780, Jun. 6, 2016 [Exhibit 2034].

Declaration of Mahmoud A. Ghannoum, Ph.D., E.M.B.A., IPR2015-01780, Jun. 6, 2016 [Exhibit 2035].

Declaration of Majella Lane, Ph.D., IPR2015-01780, Jun. 6, 2016 [Exhibit 2036].

Declaration of Howard I. Maibach, M.D., Ph.D., IPR2015-01780, Jun. 6, 2016 [Exhibit 2037].

Declaration of Jennifer Augsburger in Support of Patent Owner's Response, IPR2015-01780, Jun. 6, 2016 [Exhibit 2102].

The Merck Index: An Encyclopedia of Chemicals, Drugs, and Biologicals (Merck Research Laboratories, 13th ed., 2001), IPR2015-01780, Jun. 6, 2016 [Exhibit 2157].

Barnett & Scher, Nail Cosmetics, Int'l J. of Dermatol., vol. 31, No. 10, pp. 675-681 (1992), IPR2015-01780, Jun. 6, 2016 [Exhibit 2202].

Patent Owner's Response Pursuant to 37 C.F.R. § 42.120, U.S. Pat. No. 7,767,657, 68 pages, IPR2015-01785, Jun. 6, 2016.

Patent Owner's Exhibit List, U.S. Pat. No. 7,767,657, 19 pages, IPR2015-01785, Jun. 6, 2016.

Declaration of Paul J. Reider, Ph.D., IPR2015-01785, Jun. 6, 2016 [Exhibit 2034].

Declaration of Mahmoud A. Ghannoum, Ph.D., E.M.B.A., IPR2015-01785, Jun. 6, 2016 [Exhibit 2035].

Declaration of Majella Lane, Ph.D., IPR2015-01785, Jun. 6, 2016 [Exhibit 2036].

Declaration of Howard I. Maibach, M.D., Ph.D., IPR2015-01785, Jun. 6, 2016 [Exhibit 2037].

Declaration of Jennifer Augsburger in Support of Patent Owner's Response, IPR2015-01785, Jun. 6, 2016 [Exhibit 2102].

Petitioner's Updated Exhibit List, U.S. Pat. No. 7,582,621, 3 pages, IPR2015-01776.

Patent Owner Anacor Pharmaceuticals, Inc.'s Mandatory Notices Under 37 C.F.R. § 42.8, 4 pages, IPR2015-01776, Sep. 2, 2015.

Patent Owner Anacor Pharmaceuticals, Inc.'s Updated Mandatory Notices Under 37 C.F.R. § 42.8, 3 pages, IPR2015-01776, Oct. 26, 2015.

Petitioner's Updated Mandatory Notice Pursuant to 37 C.F.R. § 42.8, 5 pages, IPR2015-01776, Jan. 20, 2016.

Patent Owner's Objections to Petitioner's Evidence Under 37 C.F.R. § 42.64(b)(1), 8 pages, IPR2015-01776, Mar. 8, 2016.

Patent Owner Anacor Pharmaceuticals, Inc.'s Updated Mandatory Notice, 4 pages, IPR2015-01776, Mar. 17, 2016.

(56) References Cited

OTHER PUBLICATIONS

Petitioner's Updated Exhibit List, U.S. Pat. No. 7,767,657, 5 pages, IPR2015-01780.
Patent Owner Anacor Pharmaceuticals, Inc.'s Mandatory Notices Under 37 C.F.R. § 42.8, 4 pages, IPR2015-01780, Sep. 2, 2015.
Patent Owner Anacor Pharmaceuticals, Inc.'s Updated Mandatory Notices Under 37 C.F.R. § 42.8, 3 pages, IPR2015-01780, Oct. 26, 2015.
Petitioner's Updated Mandatory Notice Pursuant to 37 C.F.R. § 42.8, 5 pages, IPR2015-01780, Jan. 20, 2016.
Patent Owner Anacor Pharmaceuticals, Inc.'s Updated Mandatory Notice, 4 pages, IPR2015-01780, Mar. 17, 2016.
Patent Owner's Objections to Petitioner's Evidence Under 37 C.F.R. §42.64(b)(1), 19 pages, IPR2015-01780, Mar. 8, 2016.
Patent Owner Anacor Pharmaceuticals, Inc.'s Mandatory Notices Under 37 C.F.R. § 42.8, 4 pages, IPR2015-01785, Sep. 2, 2015.
Patent Owner Anacor Pharmaceuticals, Inc.'s Updated Mandatory Notices Under 37 C.F.R. § 42.8, 3 pages, IPR2015-01785, Oct. 26, 2015.
Petitioner's Updated Mandatory Notice Pursuant to 37 C.F.R. § 42.8, 5 pages, IPR2015-01785, Jan. 20, 2016.
Patent Owner Anacor Pharmaceuticals, Inc.'s Updated Mandatory Notice, 4 pages, IPR2015-01785, Mar. 17, 2016.
Baudoin, Olivier, et al. "A Novel 1,3-Central-to-Axial Chirality Induction Approach to Cyclooctadiene Lignans", Synlett, Oct. 16, 2003, No. 13, pp. 2009-2012.
Cummings, William M., et al. "Arylboronic Acids. A Medium-Size Ring Containing Boronic Ester Groups", The Journal of Organic Chemistry, vol. 34, No. 6, Jun. 1969.
U.S. Appl. No. 14/977,052, filed Dec. 22, 2015.
U.S. Appl. No. 14/201,459, filed Mar. 7, 2014, now allowed.
U.S. Appl. No. 13/673,860, filed Nov. 9, 2012, Anacor Pharmaceuticals, Inc.
U.S. Appl. No. 14/977,052, filed Dec. 21, 2015, Anacor Pharmaceuticals, Inc.
Adamczyk-Wozniac, et al., "Benzoxaboroles—Old Compounds with new applications", Journal of Organometalic Chemistry 694;3533-3541 (2009).
Akama, et al., "Discovery and structure-activity study of novel benzoxaborole anti-inflammatory agent (AN2728) for the potential topical treatment of psoriasis and atopic dernatitis", Bioorganic & Medicinal Chemistry Letters, (2009) 19: 2129-2132.
Alexander, et al., "Imprinted Polymers as Protecting Groups for Regioselective Modification of Polyfunctional Substrates", J. Am. Chem. Soc. 1999, 121, 6640-6651.
Alley, et al., "Recent Progress on Topical Therapy of Onychomycosis", Expert Opinion Investigate Drugs(Feb. 2007) 16(2): 157-67.
Austin, et al., "Oxaboroles and Salts and their Use of Biocides for Plastics", CAS, vol. 124, pp. 234-024, (1996).
Bailey, et al., "Boron-Containing Antibacterial Agents: Effects on Growth and Morphology of Bacteria Under Various Culture Conditions," Antimicrobial Agents and Chemotherapy, 17(04):549-553, (Apr. 1980).
Baker, et al., "Discovery of New Boron-Containing Antifungal Agent, 5-Fluoro-1,3-dihydro-1-hydroxy-2, 1-benzoxaborole (AN2690) for Potential Treatment of Onychomoycosis", Journal of Medicinal Chemistry, vol. 49, No. 15; pp. 4447-4450, (Jul. 27, 2006).
Baker, et al., "Identification of a Novel Boron-Containing Antibacterial Agent (AN0128) with Anti-inflammatory activity, for the Potential Treatment of Cutaneous Diseases", Bioorganic & Medicinal Chemistry Letters (2006) 16: 5963-5937.
Baker, et al., "Progress on New Therapeutics for Fungal Nail Infections", Annual Reports in Medicinal Chemistry, vol. 40: pp. 323-335, (2005).
Bell, et al., "Design, synthesis and evaluation of a novel series of spiroketals based on the structure of the antibacterial gyrase inhibitor novobiocin", J. Chem. Soc., Perkin Trans., 1997 vol. 18, No. 1, pp. 2789-2801.

Bessis, N., "Gene Therapy for Rheumatoid Arthritis," J. Gene Med, vol. 4; pp. 581-591 (2002).
Brown, et al., "Chiral Synthesis Via Organoboranes. 35. Simple Procedures for the Efficient Recycling of the Terpenyl Chiral Auxiliaries and Convenient Isolation of the Homoallylic Alcohols in Asymmetric Allyl- and Crotylboration of Aldehydes," J. Org. Chem., vol. 57, No. 24; pp. 6608-6614, (1992).
Cairns, et al., "Derivatives of 1,4-Xylene-2,5-diboronic acid and 1,4-xylene-2-boronic acid", J. Org. Chem. vol. 29; pp. 2810-2812, (1964).
Chander, et al. "Prevalence of Fungal Corneal Ulcers in Northern India", Infections, vol. 22, No. 3; pp. 207-209, (1994).
Chemical Abstracts Registry No. 159752-29-1, Entered STN Dec. 23, 1994.
Chemical Abstracts Registry No. 71889-05-9, Entered STN Nov. 16, 1984.
Chemical Abstracts Registry No. 845302-09-2, Entered STN Mar. 11, 2005.
Chemical Abstracts Registry No. 849062-11-9, Entered STN Apr. 22, 2005.
Chemical Abstracts Registry No. 849062-10-8, Entered STN Apr. 22, 2005.
*Coalition for Affordable Drugs X LLC*, v. *Anacor Pharmaceuticals, Inc.*, Case No. IPR2015-01776, U.S. Pat. No. 7,582,621 B2, Decision entered: Feb. 23, 2016, Paper No. 24, 16 pages.
*Coalition for Affordable Drugs X LLC*, v. *Anacor Pharmaceuticals, Inc.*, Case No. IPR2015-01780, U.S. Pat. No. 7,767,657 B2, Decision filed: Feb. 23, 2016, Paper No. 24, 28 pages.
*Coalition for Affordable Drugs X LLC*, v. *Anacor Pharmaceuticals, Inc.*, Case No. IPR2015-01785, U.S. Pat. No. 7,767,657 B2, Decision filed: Feb. 23, 2016, Paper No. 24, 26 pages.
Cody et al. CAS: 142: 168379, 2004.
Cui, et al., "Organoboron Compounds with an 8-Hydroxyquinolato Chelate and Its Derivatives: Substituent Effects on Structures and Luminescence," Inorganic Chemistry, vol. 44, No. 03; pp. 601-609, (Feb. 7, 2005).
Cusack, S., et al., "The 2 A Crystal Structure of leucyl-tRNA Synthetase and its Complex with a Leucyl-Adenylate Analogue." EMBO Journal, vol. 19; pp. 2351-2361, (2000).
Dale, et al., "Substituted Styrenes VII. Syntheses and some Reactions of the Vinylbenzeneboronic Acids" J. Org. Chem. vol. 27; pp. 2598-2603, (Jan. 1, 1962).
Demir et al., "Generation of Aryl Radicals from Arylboronic Acids by Manganese(III) Acetate: Synthesis of Biaryls and Heterobiaryls", J. Org. Chem. 2003, 68, 578-580.
Denis, "Pharmacology 1104 Lecture: Drug Classifications & Characteristics of Antimicrobials" (2003).
Dian, "International Nomenclature of Organics", China Petrochemical Press, 1st Edition; 50-51 (Jan. 21, 2004).
Falck, et al., "Bromo-Boronolactonization of Olefins", J. Org. Chem. 2001, 66. 7148-7150.
Farfan, et al., "Through-Bond Modulation on N—B Ring Formation Shown by NMR and X-Ray Diffraction Studies of Borate Derivatives of Pyridyl Alcohols," J. Chem. Soc. Perkin Trans., vol. 2; pp. 527-532 (1992).
Ferrer, "Targeting Aminoacyl-tRNA Synthetases for the Treatment of Fungal Infections", Drug News Perspective, vol. 19, No. 6; pp. 347-348, (Jul./Aug. 2006).
Fevig et al. CAS: 137: 125150, 2002.
Fungicide: Definition from Answer.com, (1998).
Goodman, et al., "Goodman & Gilman's Manual of Pharmacology and Therapeutics" Chapter 40;681-694 (2008).
Grassberger, et al., "Degradation of 1,2-dihydro-1-hydroxy-2-(organosulfonyl)2,3,1-benzodiasaborines and -thieno[3,2-d][1,,3]diazaborines in Alkaline Aqueous Solutions", Liebigs Annalen Der Chemie, vol. 4; pp. 683-688, (1985).
Guo-Zheng, et al., "Single Site Transarylation of 2,2'-Dimetalized-1,1'-Binaphthyl to Aminocloroborates and Synthesis of 2-Binaphthyl Boron Compounds," Youji Huaxue/Organic Chemistry, Science Press, vol. 16, No. 02; pp. 139-144, (1996) (English Abstract).

(56) References Cited

OTHER PUBLICATIONS

Haynes, et al., "Arylboronic Acids VIII. Reactions of boronphthalide" J. Org. Chem. vol. 29, No. 11; pp. 3229-3233, (1964).
Hauck, et al., "Preparation and Anticonvulsant Activity of Some Aryldialkylsuccinimides" Research Lab of Parke Davis Co. (1967).
He, et al., "Small-Molecule Inhibition of TNF-alpha", Science, vol. 310, No. 5750; pp. 1022-1025, (Nov. 11, 2005).
Hui, et al., "In Vitro Penetration of a Novel Oxaborole Antifungal (AN2690) into the Human Nail Plate", Journal of Pharmaceutical Sciences (2007) 96(10): 2622-2631.
Ishihara et at. CAS: 141: 388701, 2004.
Kamikawa, et al., "Stereoselective Synthesis of Both Enantiomers of Axially Chiral Biaryls Utilizing Planar Chiral Tricarbonyl(arene)chromium Complexes", pp. 1375-1384, J. Org. Chem. vol. 61, 1996.
Lampe, et al., "Synthesis and Protein Kinase Inhibitory Activity of Balanol Analogues with Modified Benzophenone Subunits", J. Med. Chem., vol. 45(12); pp. 2624-2643, (2002).
Lee, K., et al., "Molecular Study of the Editing Active Site of *Escherichia coli* Leucyl-tRNA Synthetase: Two Amino Acid Binding Site in the Editing Domain", vol. 54; pp. 693-704, (2004).
Lennarz, et al., "Arylboronic Acids. IV. Reactions of Boronophthalide" J. Am. Chem. Soc. vol. 82; pp. 2172-2175, (1960).
Li, et al., "An Improved Protocol for Preparation of 3-Pyridyl- and Some Arylboronic Acids", J. Org. Chem., vol. 67; pp. 5394-5397, (2002).
Luan, et al., "Inhibition of Experimental Periodontitis by a topical boron-base antimicrobial" J Dent. Res, 87(2):148-152 (2008).
Koster, et al., "Cyclisierugen von Bor-Stickstoff-Verbindugen in der Hietz" Liebigs Ann. Chem., vol. 720; pp. 23-31, (1968).
Koster, et al., "Boron Compounds, XXXIX. Alkenoxy(diorgany)boranes Substituted at the Alkeonxy Group from 2-methylacrolein and triorganylboranes," Justus Liebigs Annalen Der Chemie, No. 06; pp. 1116-1134, (1976).
McMillin, et al., "Systemic Aspects of Psoriasis: An Integrative Model Based on Intestinal Etiology", Int. Med. vol. 2, Issue 2/3, (1999).
Mikami et at. CAS: 122: 314944, 1995.
Moeder, et al., "Kinetic Analysis of the Asymmetric Amplification exhibited by B-chlorodiisopinocampheylborane," Journal of Physical Organic Chemistry, vol. 17, No. 4; pp. 317-324, (Apr. 2004).
Monovich, et al., "Total Synthesis of (--)-Steganone Utilizing a Samarium(II) Iodide Promoted 8-Endo Ketyl-Olefin Cyclization", J. Am. Chem. Soc. 2000, 122, 52-57.
Morissette, et al., "High-throughput Crystallization: Polymorphs, Salts, Co-Crystals and Solvates of Pharmaceutical Solids", Advanced Drug Delivery Reviews, vol. 56; pp. 273-300, (2004).
Motokazu, et al., "Stereoselective induction of an axial chirality by Suzuki cross coupling of tricaronyl (arene) chromium complexes with arylboronic acids", J. Chem. Soc., Chem. Commun., 1994, vol. 23, pp. 2697-2698.
Murdan, "Drug Delivery to the Nail Following Topical Application", International Journal of Pharmaceutics, vol. 236: pp. 1-26, (2002).
N. Miyaura, "Product subclass 7: hydroxyboranes", Science of Synthesis 2004, 6, 257-300.
Oshima, et al., "Regiospecific Glycosidation of Unprotected Sugars via Arylboronic Activation", J. Am. Chem. Soc. 1999, 121, 2315-2316.
Patani, et al., "Bioisosterism: A Rational Approach to Drug Design", Chem. Rev., vol. 96; pp. 3147-3176 (1996).
Perola, E., et al., "Successful Virtual Screening of a Chemical Database for Farnesltransferase Inhibitor Leads." vol. 43; pp. 401-4008, (2000).
Qin, et al., "Luminescent Organoboron Quinolate Polymers," Journal of the American Chemical Society, vol. 126, No. 22; pp. 7015-7018, (Jun. 9, 2004).
Qin, Clinical Mycology, Fudan Press, Shanghai Medical University Press, pp. 92, 111, 340-341, 365, 437 and 487 (2001) With English Translation.
Rau, et al., "Pd-catalyzed synthesis, characterization and modification of poly(p-phenylene)s bearing butoxymethyl side chains", pp. 2225-2238, Makromol. Chem. 194, 1993.
Resnick, et al., "Chemoenzymatic Synthesis of Chiral Boronates for the $^1$H NMR Determination of the Absolute Configuration and Enantiomeric Excess of Bacterial and Synthetic cis-Diols", pp. 3546-3549, J. Org. Chem., 1995, vol. 60.
Robinson et al. CAS: 132: 43141, 1999.
Rock, et al., "An Antifungal Agents Inhibits Aminoacyl-tRNA Synthetase by Trapping tRNA in the Editing Site", Science, vol. 316, No. 5832; pp. 1759-1761, (Jun. 22, 2007).
Silverman, "The Organic Chemistry of Drug Design and Drug Action", 2nd Edition, Northwestern University, Department of Chemistry, Evanston, Illinois, Section 2: 29-32 (2004).
Snyder, et al. "Common Bacteria Whose Susceptibility to Antimicrobials in no longer Predictable" J. Med. Liban, vol. 48 No. 4; pp. 208-214, (2000).
Stones et al. CAS: 141: 271084, 2004.
Sugar, et al., "Comparison of Three Methods of Antifungal Susceptibility Testing with the Proposed NCCLS Standard Broth Macrodilution Assay: Lack of Effect of Phenol Red" Diagn. Microbiol. Infect. Dis. vol. 21; pp. 129-133, (1995).
Tabuchi, et al., "Anticoccidial Activity of some Azacyclo Organoborinates," Heterocycles, vol. 60, No. 01; pp. 177-182, (2003).
Tan, Y-L, et al., "Dilithiation of arenetricarbonylchromium(0) complexes with enantioselective quench: application to chiral biaryl synthesis", Department of Chemestry, London, pp. 3269-3280, vol. 24, 2001.
Tatsumi, et al., "Therapeutic Efficacy of Topically applied KP-103 against Experimental Tinea Uguium in Guinea Pigs in Comparison with Amorolfine and Terbinafine", Antimicrobial Agents and Chemotherapy, vol. 46, No. 12; pp. 3797-3801 (2002).
Toporcer, et al., "Preparation and Properties of some Tetracoordinate Boron Compounds. The Pseudo-metal Ion Concept," Inorganic Chemistry, vol. 4, No. 11; pp. 649-1655, (Nov. 1965).
Torssell, "Zur Kenntnis der Arylborasauren III*, Bromierung der Tolyborsauren nach Wohl-Ziegler", Arkiv for Kemi, Band 10 nr 36, Sep. 12, 1956.
Toyota, et al., "Intramolecular C=O•••B Interactions in o-Boron Substituted Benzaldehyde, Acetophenone, and Benzophenone", Bull.Chem. Soc. Jpn., 75, 2667-2671 (2002).
Trujillo, et al., "X-Ray Crystallographic Study of Boroxazolidones, Obtained from L,ornithine, L-methionine, Kainic acid and 2,6-pyridinedicarboxylic acid", Journal of Organometallic Chemistry, vol. 571; pp. 21-29, (1998).
Tschampel, et al., "Arylboronic Acids. VII. Some Reactions to o-Formybenzeneboronic Acids", J. Org. Chem. vol. 29, No. 8; pp. 2168-2172, (1964).
Turner, et al., Current Pharmaceutical Design, vol. 2; pp. 209-224 (1996).
Uemura, et al., "Stereoselective induction of an axial chirality by Suzuki cross coupling of tricaronyl (arene) chromium complexes with arylboronic acids", J. Chem. Soc., Chem. Commun., 1994, vol. 23, pp. 2697-2698.
Vippagunta, "Crystalline Solids", Advanced Drug Delivery Reviews, vol. 48; pp. 3-26, (2001).
Wang, et al. "Synthetic Strategies Based on Aromatic Metalation—Cross Coupling Links. A Concise Formal Synthesis of the Azaphenanthrene Alkaloid Eupolauramine", pp. 4883-4884, Tetrahedron Letters, vol. 32, No. 37, 1991, Great Britain.
Wang, et al., "Expression, Purification and Characterization of Human cAMP-Specific Phosphodiesterase (PDE4) Subtypes A, B, C, and D", Biochemical and Biophysical Research Communications, vol. 234; pp. 320-324, (1997).
Williams, et al., "Foye's Principles of Medicinal Chemistry", 5th Edition, 2002, Lippincoot Williams & Wilkins, p. 59.

(56) References Cited

OTHER PUBLICATIONS

Wulff, et al., "On the chemistry of binding sites VII, Enantioselective binding using chiral boronic acids", pp. 216-221, Recl. Trav. Chim. Pays-Bas 109, 1990.
Ye, et al., "Convenient and Versatile Syntheis of formyl-substituted Benzoxaboroles", Tetrahedron, vol. 65; pp. 8738-8744, (2009).
Zhdankin, et al., "Synthesis and Structure of Benzoboroxoles: Novel Organboron Heterocycles," Tetrahedron Letters, vol. 40; pp. 6705-6708, (1999).
Zhou, et al., "Hemodextrin: a Self-assembled Cyclodextrin-Porphyrin Construct That Binds Dioxygen," Biophysical Chemistry, 105:639-648 (2003).
Zhou, et al., "Structure-activity Studies on a Library of Potent Calix[4]arene-based PDGF Antagonists that Inhibit PDGF-stimulated PDGFR Tyrosine Phosphorylation," Org. Biomol. Chem., 4:2376-2386 (2006).
Zhou, et al., "Pattern Recognition of Proteins Based on an Array of Functionalized Porphyrins," J. Am. Chem. Soc., 128:2421-2425 (2006).
Zixing, et al., "Synthesis of Aromatic Nitrogen-containing Heterocyclic Derivatives of Asymmetric Diarylborinic Acids," Wuhan Daxue Xuebo-Wuhan University Journal, vol. 3; pp. 67-71, (1990), (English Abstract).
"Structure-Activity Studies led to the Discovery of AN2898 in Development for Topical Treatment of Psoriasis and Atopic Dermatitis", Scientific Presentation at the American Academy of Dermatology Annual Meeting, San Francisco, CA Mar. 6-10, 2009.
"AN2898 Inhibits Cytokines Relevant to Topical Treatment of Psoriasis and Atopic Dermatitis", Scientific Presentation at the American Academy of Dermatology Annual Meeting, San Francisco, CA Mar. 6-10, 2009.
"AN2718 has Broad Spectrum Antifungal Activity Necessary for the Topical Treatment of Skin and Nail Fungal Infections", Scientific Presentation at the American Academy of Dermatology Annual Meeting, San Francisco, CA Mar. 6-10, 2009.
"AN2718 Demonstrates Significant Efficacy in Three Phase Ib Psoriasis Microplaque Trials" Scientific Presentation at the American Academy of Dermatology Annual Meeting, San Francisco, CA Mar. 6-10, 2009.
"AN2728 Demonstrates Significant Safety and Efficacy in Phase IIa Double Blind Trial in Plaque Type Psoriasis", Scientific Presentation at the American Academy of Dermatology Annual Meeting, San Francisco, CA Mar. 6-10, 2009.
"AN2728 Preclinical Studies Demonstrate an Acceptable Safety Profile for the Topical Treatment of Psoriasis and Atopic Dermatitis", Scientific Presentation at the American Academy of Dermatology Annual Meeting, San Francisco, CA May 6-10, 2009.
"A New Class of Benzoxaborole-based Potent Antitrypanosomal Agents: Probing Effect of Different Linkage Groups in *Trypanosoma brucei* Growth Inhibition", Scientific Presentation at the American Society of Tropical Medicine and Hygiene Conference, New Orleans, LA Dec. 7-11, 2008.
"AN2920, a Novel Oxaborole, Shows In Vitro and In Vivo Activity Against *Trypanosomal brucei*", Scientific Presentation at the American Society of Tropical Medicine and Hygiene Conference, New Orleans, LA Dec. 7-11, 2008.
"A Novel Oxaborole, AN3520, Show Efficacy against Human African Trypanosomiasis In Vitro and In Vivo, Including Promise in a Murine CNS Model of T. brucei Infection", Scientific Presentation at the American Society of Tropical Medicine and Hygiene Conference, New Orleans, LA Dec. 7-11, 2008.
"Antifungal Activity and Mechanism of Action of a Benzoxaborole, AN2718, which is in Development for the Treatment of Tinea Pedis", Scientific Presentation at the 48th Interscience Conference on Antimicrobial Agents and Chemotherapy, Washington, D.C. Oct. 25-28, 2008.
"AN2728 Ointment, a Novel Oxaborole with Anti-Inflammatory Activity, Demonstrates Safety and Significant Efficacy in a Phase Ib Psoriasis Plaque Test", Scientific Presentation at Montagna Symposium on Biology of Skin, Gleneden Beach, OR, Oct. 2-6, 2008.
"Preclinical Toxicology of AN2728, a Novel Oxaborole in Development for the Topical Treatment of Psoriasis", Scientific Presentation at the International Investigative Dermatology Conference, Kyoto, Japan, May 14-18, 2008.
"AN2898, a Novel Oxaborole Compound with Anti-Inflammatory Activity: Mechanism of Action and in vitro Cytokine Inhibition", Scientific Presentation at the International Investigative Dermatology Conference, Kyoto, Japan, May 14-18, 2008.
"Structure-Activity Studies of AN2728 and AN2898, Novel Oxaborole Compounds with Anti-Inflammatory Activity", Scientific Presentation at the International Investigative Dermatology Conference, Kyoto, Japan, May 14-18, 2008.
"In Vitro Activity and Mechanism of Action of AN2728, a Novel Oxaborole in Development for Treatment of Psoriasis", Scientific Presentation at the International Investigative Dermatology Conference, Kyoto, Japan, May 14-18, 2008.
"AN2898, a Novel Oxaborole Compound with Anti-Inflammatory Activity: Results of In Vivo Efficacy and Preclinical Safety Studies", Scientific Presentation at the International Investigative Dermatology Conference, Kyoto, Japan, May 14-18, 2008.
"AN2728, a Novel Oxaborole in Development for Treatment of Psoriasis, Demonstrates Significant Activity in a Micro Plaque Study", Scientific Presentation at the International Investigative Dermatology Conference, Kyoto, Japan, May 14-18, 2008.
"Preclinical Toxicology of AN2728, a Novel Borinic Acid Ester with Anti-Inflammatory Activity", American Academy of Dermatology, 65th Annual Meeting, Washington, DC, Feb. 2-6, 2007.
"AN2728, a Novel Oxaborole with Broad-Spectrum In Vitro Anti-Inflammatory Activity", American Academy of Dermatology, 65th Annual Meeting, Washington, DC, Feb. 2-6, 2007.
"In Vitro Nail Penetration of AN2690, Effect of Vehicle and Co-Efficient of Efficacy", American Academy of Dermatology, 65th Annual Meeting, Washington, DC, Feb. 2-6, 2007.
"Interim Results of a Multi-Center Study to Evaluate the Safety and Efficacy of Topically Applied AN2690 5.0% and 7.5% Solutions for the Treatment of Onychomycosis of the Great Toenail", American Academy of Dermatology, 65th Annual Meeting, Washington, DC, Feb. 2-6, 2007.
"In vivo Nail Residence Time of AN2690, a Novel Broad-Spectrum Antifungal Agent in Development for the Topical Treatment of Onychomycosis", American Academy of Dermatology, 65th Annual Meeting, Washington, DC, Feb. 2-6, 2007.
"An Open-Label, Multi-dose Study of Absorption and Systemic Pharmacokinetics of AN2690 Applied as a 7.5% Solution to All Toenails of Adult Patients with Moderate to Severe Onychomycosis", American Academy of Dermatology, 65th Annual Meeting, Washington, DC, Feb. 2-6, 2007.
"Medicinal Chemistry Development of AN2728, a Novel Oxaborole in Development for the Topical Treatment of Psoriasis", American Academy of Dermatology, 65th Annual Meeting, Washington, DC, Feb. 2-6, 2007.
"Skin Penetration and Anti-Inflammatory Activity of AN2728, a Novel Oxaborole", American Academy of Dermatology, 65th Annual Meeting, Washington, DC, Feb. 2-6, 2007.
"Nail Penetration and Nail Concentration of AN2690, a Novel Broad-Spectrum Antifungal Agent in Development for the Topical Treatment of Onychomycosis", Scientific Presentation at the American Associate of Pharmaceutical Scientist, Annual Meeting, San Antonio, TX, Oct. 29-Nov. 2, 2006.
Aswell et al. CAS: 141: 296025, 2004.
Naumov, et al. "Polyfunctionalized Aryllead Triacetates in a Cascade Synthesis of Tetracyclic Isochromanocoumarin-Type Compounds", Synthesis 2005, pp. 1178-1182.
Mikami, et al., "Synthesis of Sugar-containing Polymers by Self-condensation with Diboronic Acid", J.Chem. Soc., Chem. Commun., 1995, pp. 153-154.
Stones, et al. "Modular Solid-Phase Synthetic Approach to Optimize Structural and Electronic Properties of Oligoboronic Acid Receptors and Sensors for the Aqueous Recognition of Oligosaccharides", Chem.Eur. J. 2004, 10, pp. 92-100.
Linnane, et al. "The Synthesis and Properties of a Calixarene-based 'Sugar Bowl'", J. chem. Soc., Chem. Commun., 1995, pp. 1997-1998.

(56) References Cited

OTHER PUBLICATIONS

*Coalition for Affordable Drugs X LLC,* v. *Anacor Pharmaceuticals, Inc.,* Case No. Unassigned, U.S. Pat. No. 7,582,621, Petition for Inter Partes Review of U.S. Pat. No. 7,582,621, 66 pages. [IPR2015-01776].
*Coalition for Affordable Drugs X LLC,* v. *Anacor Pharmaceuticals, Inc.,* Case No. Unassigned, U.S. Pat. No. 7,582,621, Power of Attorney in Inter Partes Review, 3 pages. [IPR2015-01776].
*Coalition for Affordable Drugs X LLC,* v. *Anacor Pharmaceuticals, Inc.,* Case No. Unassigned, U.S. Pat. No. 7,582,621, Appendix of Exhibits, 3 pages. [IPR2015-01776].
Declaration of Stephen Kahl, Ph.D. [Exhibit 1006].
Curriculum Vitae of Stephen B. Kahl, Ph.D. [Exhibit 1007].
Declaration of S. Narasimha Murthy, Ph.D. [Exhibit 1008].
Curriculum Vitae of S. Narasimha Murthy, Ph.D. [Exhibit 1009].
BioborJF® Specification Sheet (2015) [Exhibit 1024].
BioborJF® Material Safety Data Sheet (2004) [Exhibit 1025].
Michael P. Groziak, Boron Therapeutics on the Horizon, 8 Am. J. of Therapeutics 321-28 (2001) [Exhibit 1027].
Declaration of Ryan J. Fletcher [Exhibit 1030].
Kerydin® Prices, available at http://www.goodrx.com/kerydin (last visited Aug. 6, 2015) [Exhibit 1031].
Q1Group LLC, 2015 Medicare Part D Plan's Negotiated Retail Drug Price, Kerydin 5% Topical Solution (Jul. 2015), available at http://www.q1medicare.com/PartD-2015MedicarePlan RetailDrugPriceprint.php?stateReg-13MI&ndc-55724011121&formulary-00015191&contractId—H2322&planId—008&segmentId=0&zipCountyCode=26115&cplanType—M&cletter—K&cmode—state [Exhibit 1032].
Declaration of Stephen Kahl, Ph.D. [Exhibit 1009].
Curriculum Vitae of Stephen Kahl, Ph.D. [Exhibit 1010].
Declaration of S. Narasimha Murthy, Ph.D. [Exhibit 1011].
Curriculum Vitae of S. Narasimha Murthy, Ph.D. [Exhibit 1012].
Dirk Mertin & Bernhard C. Lippold, In-vitro Permeability of the Human Nail and of a Keratin Membrane from Bovine Hooves: Penetration of Chloramphenicol from Lipophilic Vehicles and a Nail Lacquer, 49 J. Pharmacy & Pharmacology 241 (1997) [Exhibit 1030].
National Center for Biotechnology Information (NCBI), PubChem Compound Database, CID=6440876, available at https://pubchem.ncbi.nlm.nih.gov/compound/6440876 (last visited Jul. 31, 2015) [Exhibit 1035].
National Center for Biotechnology Information (NCBI), PubChem Compound Database, SID=24898472, available at https://pubchem.ncbi.nlm.nih.gov/substance/24898472 (last visited Jul. 31, 2015) [Exhibit 1036].
Remington: The Science and Practice of Pharmacy (Lippincott Williams & Wilkins, 21st ed. 2005) [Exhibit 1037].
Hawley's Condensed Chemical Dictionary (John Wiley & Sons, Inc., 13th ed. 1997) [Exhibit 1038].
Aldrich Handbook of Fine Chemicals and Laboratory Equipment (2003-2004) [Exhibit 1039].
National Center for Biotechnology Information (NCBI), PubChem Compound Database, CID-2484, available at https://ubchem.ncbi.nlm.nih..ov/compound/2484 (last visited Aug. 11, 2015) [Exhibit 1040].
National Center for Biotechnology Information (NCBI), PubChem Compound Database, CID=3198, available at htlps://pubchem.ncbi.nlm.nih.gov/compound/3198 (last visited Aug. 2, 2015) [Exhibit 1041].
National Center for Biotechnology Information (NCBI), PubChem Compound Database, CID-68553, available at https://pubchem.ncbi.nlm.nih.gov/compound/68553 (last visited Aug. 2, 2015) [Exhibit 1042].
National Center for Biotechnology Information (NCBI), PubChem Compound Database, CID=2812, available at https://pubchem.ncbi.nlm.nih.gov/compound/2812 (last visited Aug. 2, 2015) [Exhibit 1043].
National Center for Biotechnology Information (NCBI), PubChem Compound Database, CID-11499245, available at https://pubchem.ncbi.nlm.nih.gov/compound/11499245 (last visited Aug. 2, 2015) [Exhibit 1044].
Meds. & Healthcare Prods. Regulatory Agency, Curanail 5% Nail Lacquer (Amorolfine Hydrochloride) PL 10590/0049, UK Public Assessment Report (approved Jul. 4, 2006) [Exhibit 1045].
National Center for Biotechnology Information (NCBI), PubChem Compound Database, CID=22497760, available at https://pubchem.ncbi.nlm.nih.gov/compound/22497760 (last visited Aug. 4, 2015) [Exhibit 1046].
National Center for Biotechnology Information (NCBI), PubChem Compound Database, CID-61764, available at https://pubchem.ncbi.nlm.nih.gov/compound/61764 (last visited Aug. 4, 2015) [Exhibit 1047].
Declaration of Kathleen E. Ott [Exhibit 1050].
*Coalition for Affordable Drugs X LLC,* v. *Anacor Pharmaceuticals, Inc.,* Case No. Unassigned, U.S. Pat. No. 7,767,657, Second Petition for Inter Partes Review of U.S. Pat. No. 7,767,657, 70 pages. [IPR2015-01785].
*Coalition for Affordable Drugs X LLC,* v. *Anacor Pharmaceuticals, Inc.,* Case No. Unassigned, U.S. Pat. No. 7,767,657, Power of Attorney in Second Petition for Inter Partes Review of U.S. Pat. No. 7,767,657, 3 pages. [IPR2015-01785].
*Coalition for Affordable Drugs X LLC,* v. *Anacor Pharmaceuticals, Inc.,* Case No. Unassigned, U.S. Pat. No. 7,767,657, Appendix of Exhibits for Second Petition for Inter Partes Review of U.S. Pat. No. 7,767,657, 5 pages. [IPR2015-01785].
National Center for Biotechnology Information (NCBI), PubChem Compound Database, CID-66827, available at https://pubchem.ncbi.nlm.nih.gov/compound/66827 (last visited Aug. 4, 2015) [Exhibit 1046].
National Center for Biotechnology Information (NCBI), PubChem Compound Database, CID-2775922, available at https://pubchem.ncbi.nlm.nih.gov/compound/2775922 (last visited Aug. 4, 2015) [Exhibit 1047].
Declaration of Kathleen E. Ott. [Exhibit 1050].
*Coalition for Affordable Drugs X LLC,* v. *Anacor Pharmaceuticals, Inc.,* Case No. IPR2015-01776, U.S. Pat. No. 7,582,621, Patent Owner Preliminary Response, 70 pages.
FDA Approved Label for Kerydin® (Rev. Mar. 2015) [Exhibit 2001].
Fairchild et al., In Vitro Determination of Uptake, Retention, Distribution, Biological Efficacy, and Toxicity of Boronated Compounds for Neutron Capture Therapy: A Comparison of Porphyrins with Sulfhydryl Boron Hydrides, Cancer Res., vol. 50, pp. 4860-4865 (1990) [Exhibit 2002].
Charif et al., A Historical Perspective on Onychomycosis, Dermatol. Ther. vol. 3, pp. 43-45 (1997) [Exhibit 2003].
Heath et al., Fatty Acid Biosynthesis as a Target for Novel Antibacterials, Curr. Opin. Invest. Drugs, vol. 5, pp. 146-153 (2004) [Exhibit 2004].
Baldock et al., A Mechanism of Drug Action Revealed by Structural Studies of Enoyl Reductase, Science, vol. 274, pp. 2107-2110 (1996) [Exhibit 2005].
Biobor, R.E.D. Facts, EPA-738-R-93-004 (Jun. 1993), http://nepis.epa.gov/Exe/ZyPDF.cgi?Dockey=200009P5.PDF [Exhibit 2006].
Lefkovits et al., Direct Thrombin Inhibitors in Cardiovascular Medicine, Circulation, vol. 90, pp. 1522-1536 (1994) [Exhibit 2007].
Grassberger et al., Preparation and Antibacterial Activities of New 1,2,3-Diazaborine Derivatives and Analogs, J. Med. Chem., vol. 27, No. 8, pp. 947-953 (1984).
Baldock et al., Mechanism of Action of Diazaborines, Biochem. Pharm., vol. 55, pp. 1541-1549 (1998).
Heindel et al., The Developmental Toxicity of Boric Acid in Mice, Rats, and Rabbits, Environ. Health Perspect., vol. 102, suppl. 7, pp. 107-112 (1994) [Exhibit 2010].
Richardson, Clinical Update: Proteasome Inhibitors in Hematologic Malignancies, Cancer Treatment Rev., vol. 29, suppl. 1, pp. 33-39 (2003) [Exhibit 2011].

(56) References Cited

OTHER PUBLICATIONS

Bross et al., Approval Summary for Bortezomib for injection in the Treatment of Multiple Myeloma, Clin. Cancer Res., vol. 10, pp. 3954-3964 (2004) [Exhibit 2012].
Adams, Proteasome Inhibitors as Therapeutic Agents, Expert Opin. Ther. Patents, vol. 13, No. 1, pp. 45-57 (2003) [Exhibit 2013].
Dorland's Illustrated Medical Dictionary, p. 211 (29th ed. 2000) [Exhibit 2014].
Stedman's Medical Dictionary, p. 204 (27th ed. 2000) [Exhibit 2015].
Random House Webster's Unabridged Dictionary, p. 209 (2nd ed. 2001) [Exhibit 2016].
Jordon et al., Boric Acid Poisoning: A Report of a Fatal Adult Case from Cutaneous Use. A Critical Evaluation of the Use of This Drug in Dermatologic Practice, JAMA Derm, vol. 75, pp. 720-728 (1957) [Exhibit 2017].
Triggle, Pharmacological Receptors: A Century of Discovery—and More, Pharm. Acta Helvetiae, vol. 74, pp. 79-84 (2000) [Exhibit 2019].
Larsen et al., The Prevalence of Onychomycosis in Patients with Psoriasis and Other Skin Diseases, Acta Derm. Venereol., vol. 83, pp. 206-209 (2003) [Exhibit 2020].
Osborne et al., Antifungal Drug Response in an In Vitro Model of Dermatophyte Nail Infection, Med. Mycol., vol. 42, pp. 159-163 (2004) [Exhibit 2022].
Favre et al., Comparison of In Vitro Activities of 17 Antifungal Drugs Against a Panel of 20 Dermatophytes by Using a Microdilution Assay, J. Clin. Microbiol., vol. 41, No. 10, pp. 4817-4819 (2003) [Exhibit 2023].
Sangster, Octanol-Water Partition Coefficients of Simple Organic Compounds, J. Phys. Chem. Ref. Data, vol. 18, pp. 1111-1227 (1989) [Exhibit 2024].
Powers et al., Structure-Based Approach for Binding Site Identification on AmpC β-Lactamase, J. Med. Chem., vol. 45, pp. 3222-3234 (2002) [Exhibit 2025].
Boric Acid, R.E.D. Facts, EPA-738-F-93-006 (Sep. 1993), http://archive.epa.gov/pesticides/reregistration/web/pdf/0024fact.pdf [Exhibit 2026].
Vander Straten et al., Cutaneous Infections: Dermatophytosis, Onychomycosis, and Tinea Versicolor, Infect. Dis. Clinics N. Am., vol. 17, pp. 87-112 (2003) [Exhibit 2027].
*Coalition for Affordable Drugs X LLC*, v. *Anacor Pharmaceuticals, Inc.*, Case No. IPR2015-01780, U.S. Pat. No. 7,767,657, Patent Owner Preliminary Response, 69 pages.
*Coalition for Affordable Drugs X LLC*, v. *Anacor Pharmaceuticals, Inc.*, Case No. IPR2015-01785, U.S. Pat. No. 7,767,657, Patent Owner Preliminary Response, 70 pages.
Handbook of Aqueous Solubility Data (Samuel H. Yalkowsky & Yan He eds., CRC Press, 2003) [Exhibit 2027].
Patent Owner's Updated Exhibit List, Sep. 27, 2016, 22 pages, IPR2015-01776.
Declaration of Michael N. Kennedy in Support of Patent Owner's Motion for Admission Pro Hac Vice of Michael N. Kennedy Under C.F.R. 37 C.F.R. § 42.10, 4 pages, IPR2015-01776 [Exhibit 2203].
Declaration of Jeffrey B. Elikan in Support of Patent Owner's Motion for Admission Pro Hac Vice, Jun. 15, 2016, IPR2015-01776 [Exhibit 2204].
Declaration of George F. Pappas in Support of Patent Owner's Motion for Admission Pro Hac Vice of George F. Pappas Under C.F.R. 37 C.F.R. § 42.10, 4 pages, IPR2015-01776 [Exhibit 2205].
Transcript, Deposition of Stephen B. Kahl, Ph.D., Sep. 14, 2016, 75 pages, IPR2015-01776 [Exhibit 2206].
Transcript, Deposition of Narashimha Murthy, Ph.D., Sep. 17, 2016, 125 pages, IPR2015-01776 [Exhibit 2207].
Signature Pages and Errata to Majella Lane, Ph.D., Deposition Transcript, 4 pages, IPR2015-01776 [Exhibit 2208].
Signature Pages and Errata to Mahmoud Ghannoum, Ph.D., E.M.B.A. Deposition Transcript, 5 pages, IPR2015-01776 [Exhibit 2209].
Signature Page to Howard Maibach, M.D., Ph.D., Deposition Transcript, 1 page, IPR2015-01776 [Exhibit 2210].
Signature Pages and Errata to Paul J. Reider, Ph.D., Deposition Transcript, 3 pages, IPR2015-01776 [Exhibit 2211].
Patent Owner's Exhibit List, Sep. 27, 2016, 22 pages, IPR2015-01780.
Declaration of Michael N. Kennedy in Support of Patent Owner's Motion for Admission Pro Hac Vice of Michael N. Kennedy Under 37 C.F.R. § 42.10, Jun. 10, 2016, 4 pages, IPR2015-01780 [Exhibit 2205].
Declaration of Jeffrey B. Elikan in Support of Patent Owner's Motion for Admission Pro Hac Vice of Jeffrey B. Elikan Under 37 C.F.R. § 42.10, 4 pages, IPR2015-01780 [Exhibit 2206].
Declaration of George F. Pappas in Support of Patent Owner's Motion for Admission Pro Hac Vice of George F. Pappas Under 37 C.F.R. § 42.10, Jun. 27, 2016, 4 pages, IPR2015-01780 [Exhibit 2207].
Transcript, Deposition of Stephen B. Kahl, Ph.D., Sep. 14, 2016, 75 pages, IPR2015-01780 [Exhibit 2208].
Transcript, Deposition of Narashimha Murthy, Ph.D., Sep. 17, 2016, 125 pages, IPR2015-01780 [Exhibit 2209].
Signature Pages and Errata to Majella Lane, Ph.D., Deposition Transcript, 4 pages, IPR2015-01780 [Exhibit 2210].
Signature Pages and Errata to Mahmoud A. Ghannoum, Ph.D., E.M.B.A. Deposition Transcript, 5 pages, IPR2015-01780 [Exhibit 2211].
Signature Page to Howard Maibach, M.D., Ph.D., Deposition Transcript, 1 page, IPR2015-01780 [Exhibit 2212].
Signature Pages and Errata to Paul J. Reider, Ph.D. Deposition Transcript, 3 pages, IPR2015-01780 [Exhibit 2213].
Patent Owner's Exhibit List, Sep. 27, 2016, 20 pages, IPR2015-01785.
Declaration of Michael N. Kennedy in Support of Patent Owner's Motion for Admission Pro Hac Vice of Michael N. Kennedy Under 37 C.F.R. § 42.10, Jun. 10, 2016, 4 pages, IPR2015-01785 [Exhibit 2187].
Declaration of Jeffrey B. Elikan in Support of Patent Owner's Motion for Admission Pro Hac Vice of Jeffrey B. Elikan Under 37 C.F.R. § 42.10, Jun. 15, 2016, 4 pages, IPR2015-01785 [Exhibit 2188].
Declaration of George F. Pappas in Support of Patent Owner's Motion for Admission Pro Hac Vice of George F. Pappas Under 37 C.F.R. § 42.10, Jun. 27, 2016, 4 pages, IPR2015-01785 [Exhibit 2189].
Transcript, Deposition of Stephen B. Kahl, Ph.D., Sep. 14, 2016, 75 pages, IPR2015-01785 [Exhibit 2190].
Transcript, Deposition of Narashimha Murthy, Ph.D., Sep. 17, 2016, 125 pages, IPR2015-01785 [Exhibit 2191].
Signature Pages and Errata to Majella Lane, Ph.D. Deposition Transcript, 4 pages, IPR2015-01785 [Exhibit 2192].
Signature Pages and Errata to Mahmoud A. Ghannoum, Ph.D., Deposition Transcript, 5 pages, IPR2015-01785 [Exhibit 2193].
Signature Page to Howard Maibach, M.D., Ph.D., Deposition Transcript, 1 page, IPR2015-01785 [Exhibit 2194].
Signature Pages and Errata to Paul J. Reider, Ph.D., Deposition Transcript, 3 pages, IPR2015-01785 [Exhibit 2195].
Petitioner's Updated Exhibit List, 8 pages, IPR2015-01776.
Petitioner's Updated Exhibit List, 7 pages, IPR2015-01776.
Supplemental Declaration of Ryan J. Fletcher in Support of Petitioner's Supplemental Evidence and Response to Patent Owner's Objections to the Petition Evidence Pursuant to 37 C.F.R. § 42.54, 4 pages, IPR2015-01776 [Exhibit 1036].
Biobor, R.E.D. Facts, EPA-738-R-93-004 (Jun. 1993), http://nepis.epa.gov/Exe/ZyPDF.cgi?Dockey=200009P5.PDF, 4 pages, IPR2015-01776 [Exhibit 1037].
Excerpts from the Certified Prosecution History for U.S. Pat. No. 6,878,365, Including the MSDS Sheet for BioborJF®, 12 pages, IPR2015-01776 [Exhibit 1038].
Supplemental Declaration of Stephen Kahl, Ph.D., 4 pages, IPR2015-01776 [Exhibit 1039].
Supplemental Kerydin Prices, 28 pages, available at http://www.goodrx.com/kerydin; http://www.goodrx.com/how-goodrx-works; http://www.goodrx.com/press; IPR2015-01776 [Exhibit 1040].

(56) References Cited

OTHER PUBLICATIONS

Q1 Medicare 2015 Kerydin Price, 14 pages, available at https://q1mediacare.com/PartD-2016MedicarePlan-RetailDrugPrice.php?ndc=10337090544&letter=K&formulary=00016286&stateReg=13MI&contractId=H2322&planId=008&segmentId=0#History; IPR2015-01776 [Exhibit 1041].
Supplemental Declaration of S. Narashimha Murthy, Ph.D. in Support of Petitioner's Supplemental Evidence and Response to Patent Owner's Objections to the Petition Evidence Pursuant to 37 C.F.R. § 42.64, 5 pages, IPR2015-01776 [Exhibit 1042].
Declaration of Stephen Kahl, Ph.D. in Support of Petition for Inter Partes Review of U.S. Pat. No. 7,582,621, 18 pages, IPR2015-01776 [Exhibit 1043].
Deposition of Narashimha Murthy, Ph.D. in Support of Petitioner's Reply to Patent Owner's Response, 65 pages, IPR2015-01776 [Exhibit 1044].
Deposition Transcripts of Dr. Majella Lane, Jul. 7-8, 2016, 319 pages, IPR2015-01776 [Exhibit 1045].
Deposition of Transcripts Dr. Mahmoud A. Ghannoum, Jul. 18-19, 2016, 352 pages, IPR2015-01776 [Exhibit 1046].
Deposition Transcript of Dr. Howard Maibach, Jul. 13, 2016, 193 pages, IPR2015-01776 [Exhibit 1047].
Deposition of Transcripts of Dr. Paul J. Reider, Jul. 21-22, 2016, 368 pages, IPR2015-01776 [Exhibit 1048].
Progress in Heterocyclic Chemistry, ch. 1, 1-21 (G.W. Gribble & T.L. Gilchrist eds., 1st ed., 2000) (Reider Dep. Ex. 5) IPR2015-01776 [Exhibit 1049].
Wester, et. al, "In Vivo Percutaneous Absorption of Boric Acid, Borax, and Disodium Octraborate Tetrahydrate in Humans Compared to in Vitro Absorption in Human Skin from Infinite and Finite Doses", 45 Toxicological Sciences, pp. 42-51 (1998), (Maibach Dep. Ex. 9) IPR2015-01776 [Exhibit 1050].
Press Release, Anacor, *Anacor Co-Founders Recognized for Scientific Achievements*, Jun. 10, 2009, 2 pages, available at http://investor.anacor.com/releasedetail.cfm?releaseid+527603, IPR2015-01776 [Exhibit 1051].
Hubbard, S. A., "Comparative Toxicology of Borates", 66 Biological Trace Element Research, Proceedings of the Second Int'l Symposium on the Health Effect of Boron and Its Compounds, 343-57 (Humana Press, 1998) ("Hubbard"), IPR2015-01776 [Exhibit 1054].
Baker, et al., "Therapeutic potential of boron-containing compounds", Future Med. Chem (2009) 1(7), pp. 1275-1288, IPR2015-01776 [Exhibit 1056].
Li, et al. "An Improved Protocol for the Preparation of 3-Pyridyl- and Some Arylboronic Acids", 67 J. Org. Chem (2002), pp. 5394-5397, IPR2015-01776 [Exhibit 1057].
Donald E. Garrett, Borates Handbook of Deposits, Processing, Properties, and Use, 333-429 (Academic Press, 1998), IPR2015-01776 [Exhibit 1058].
Baker, et al., "Boron-containing inhibitors of synthetases", Chem. Soc. Rev., 2011, 40, pp. 4279-4285, IPR2015-01776 [Exhibit 1059].
Yang, et al. "Boronic Acid Compounds as Potential Pharmaceutical Agents", 23 Medicinal Research Reviews, No. 3, 2003, pp. 346-368, IPR2015-01776 [Exhibit 1060].
Wester, et al. "In Vivo Percutaneous Absorption of Boron as Boric Acid, Borax, and Disodium Octaborate Tetrahydrate in Humans", Biological Trace Element Research, 66 Biological Trace Element Research, Proceedings of the Second Int'l Symposium on the Health Effect of Boron and Its Compounds 101-09 (Humana Press, 1998) IPR2015-01776 [Exhibit 1061].
Certified U.S. Appl. No. 60/654,060, 43 pages, IPR2015-01776 [Exhibit 1064].
Mertin, et al. "In-vitro Permeability of the Human Nail and of a Keratin Membrane from Bovine Hooves: Prediction of the Penetration Rate of Antimycotics through the Nail Plate and their Efficacy", J. Pharm. Pharmacol., 1997, 49, pp. 866-872, IPR2015-01776 [Exhibit 1065].

Baker, et al., "Progress on New Therapeutics for Fungal Nail Infections", Annual Reports in Medicinal Chemistry (2005), vol. 40, 13 pages, IPR2015-01776 [Exhibit 1066].
ASTM® D5134 Qualitative Reference Naphtha Standard, Safety Data Sheet, Version 3.10, available at http://www.sigmaaldrich.com/MSDS/MSDS/DisplayMSDSPage.do?country=US&language=en&productNumber=48265-U&brand=SUPELCO&PageToGoToURL=http%3A%2F%2Fwww.sigmaaldrich.com%2Fcatalog%2Fproduct%2Fsupelco%2F48265u%3Flang%3Den (Reider Deposition Ex. No. 12), IPR2015-01776 [Exhibit 1067].
Tavaborole, Material Safety Data Sheet, available at http://www.syninnova.com/generatemsdspdf.php?pid=SL-264, IPR2015-01776 [Exhibit 1068].
Center for Drug Evaluation and Research Approval Package for Jublia® topical solution, 10%, available at http://www.accessdata.fda.gov/drugsatfda_docs/nda/2014/203567Orig1s000ApLtr.pdf, IPR2015-01776 [Exhibit 1069].
Prosecution History for U.S. Pat. No. 7,582,621, 558 pages, IPR2015-01776 [Exhibit 1070].
Center for Drug Evaluation and Research Approval Package for Kerydin® topical solution, 5%, available at http://www.accessdata.fda.gov/drugsatfda_docs/nda/2014/204427Orig1s000Approv.pdf, 9 pages, IPR2015-01776 [Exhibit 1071].
Hideghéty, et al. "Tissue uptake of BSH in patients with glioblastoma in the EORTC 11961 phase I BNCT trial", Journal of Neuro-Oncology, 62, 2003, pp. 145-156, IPR2015-01776 [Exhibit 1072].
Joensuu, et al. "Boron neutron capture therapy of brain tumors: clinical trials at the Finnish facility using boronophenylalanine", Journal of Neuro-Oncology, 62, 2003, pp. 123-134, IPR2015-01776 [Exhibit 1073].
Henriksson, et al. "Boron neutron capture therapy (BNCT) for glioblastoma multiforme: A phase II study evaluating a prolonged high-dose of boronophenylalanine (BPA)", Radiotherapy and Oncology 88 (2008), pp. 183-191, IPR2015-01776 [Exhibit 1074].
Kushwaha, et al. "Trans-ungual Delivery of AR-12, a Novel Antifungal Drug" Poster Presentation, (Oct. 29, 2015) (Murthy Dep. Ex. 1) 1 page, IPR2015-01776 [Exhibit 1075].
Kobayashi, et al. "In vitro permeation of several drugs through the human nail plate: relationship between physicochemical properties and nail permeability of drugs", European Journal of Pharmaceutical Sciences, 21 (2004), pp. 471-477, IPR2015-01776 [Exhibit 1076].
Greer, D., "Evolving Role of Nondermatophytes in Onychomycosis", International Journal of Dermatology, vol. 34, No. 8, Aug. 1995, (Ghannoum Dep. Ex. 5), 5 pages, IPR2015-01776 [Exhibit 1077].
Galimberti, et al. "The Activity of Ketoconazole in the Treatment of Onychomycosis", Oxford Journals, Aug. 1980, pp. 596-598, IPR2015-01776 [Exhibit 1078].
Gupta, et al. "Ciclopirox nail lacquer topical solution 8% in the treatment of toenail onychomycosis", American Academy of Dermatology, Inc.,vol. 43, No. 4, 12 pages, (Ghannoum Dep. Ex. 4) IPR2015-01776 [Exhibit 1079].
Declaration of Ryan J. Fletcher in Support of Petition for Inter Partes Review of U.S. Pat. No. 7,582,621, 4 pages, IPR2015-01776 [Exhibit 1080].
Signature Pages & Errata Sheets to Stephen B. Kahl, Ph.D. dated Apr. 7-8, 2016 Deposition Transcript, 9 pages, IPR2015-01776 [Exhibit 1081].
Signature Pages & Errata Sheet to Stephen B. Kahl, Ph.D. dated Sep. 14, 2016 Deposition Transcript, 2 pages, IPR2015-01776 [Exhibit 1082].
Signature Pages & Errata Sheet to Narasimha Murthy, Ph.D. dated May 4-6, 2016, Deposition Transcript, 8 pages, IPR2015-01776 [Exhibit 1083].
Signature Page & Errata Sheet to Narasimha Murthy, Ph.D. dated Sep. 17, 2016, Deposition Transcript, 1 page, IPR2015-01776 [Exhibit 1084].
Email from Ryan James Fletcher to Counsel for Patent Owner dated Apr. 5, 2016 regarding Petitioner Response to PO Evidence Objections, 1 page, IPR2015-01776 [Exhibit 1085].

(56) References Cited

OTHER PUBLICATIONS

Petitioner's Updated Exhibit List, Oct. 11,2016, 10 pages, IPR2015-01780.
Petitioner's Updated Exhibit List, Aug. 24, 2016, 10 pages, IPR2015-01780.
Supplemental Declaration of Kathleen E. Ott in Support in Support of Petitioner's Supplemental Evidence and Response to Patent Owner's Objections to the Petition Evidence Pursuant to 37 C.F.R. § 42.54, 5 pages, IPR2015-01780 [Exhibit 1054].
Supplemental Declaration of S. Narashimha Murthy, Ph.D. in Support of Petitioner's Supplemental Evidence and Response to Patent Owner's Objections to the Petition Evidence Pursuant to 37 C.F.R. § 42.64, 9 pages, IPR2015-01780 [Exhibit 1059].
Gantrez® Copolymers, Technical Profile (International Specialty Products (Copyright 1999) with affidavit from Archive.org, 19 pages, IPR2015-01780 [Exhibit 1060].
Aldrich Handbook of Fine Chemicals and Laboratory Equipment (2003-2004), 7 pages, IPR2015-01780 [Exhibit 1061].
Remington: The Science and Practice of Pharmacy (Lippincott Williams & Wilkins, 19th ed. 1995), 9 pages, IPR2015-01780 [Exhibit 1062].
Hawley's Condensed Chemical Dictionary (John Wiley & Sons, Inc., 12th ed. 1993), 7 pages, IPR2015-01780 [Exhibit 1063].
Department of Health and Human Services Letter (1999) Regarding Clotrimazole (Mycelex®), 16 pages, IPR2015-01780 [Exhibit 1065].
Supplemental Declaration of Stephen Kahl, Ph.D., 4 pages, IPR2015-01780 [Exhibit 1066].
Pittrof et al, Loceryl® Nail Lacquer—Realization of a New Galenical Approach to Onychomycosis Therapy, Clinical and Experimental Dermatology, 17 (Suppl. 1):26-28 (1992), 3pages, IPR2015-01780 [Exhibit 1067].
Declaration of Stephen Kahl, Ph.D. in Support of First Petition for Inter Partes Review of U.S. Pat. No. 7,767,657, 18 pages, IPR2015-01780 [Exhibit 1069].
Deposition of S. Narashimha Murthy, Ph.D. in Support of Petitioner's Reply to Patent Owner's Response, 72 pages, IPR2015-01780 [Exhibit 1070].
Deposition of Majella Lane, Ph.D., 319 pages, IPR2015-01780 [Exhibit 1071].
Deposition of Mahmoud A. Ghannoum, Ph.D., 352 pages, IPR2015-01780 [Exhibit 1072].
Deposition of Howard Maibach, M.D., Ph.D., 193 pages, IPR2015-01780 [Exhibit 1073].
Deposition of Paul J. Reider, Ph.D., 368 pages, IPR2015-01780 [Exhibit 1074].
Prosecution History(Response to Restriction Requirement) for U.S. Pat. No. 7,767,657, 8 pages, IPR2015-01780 [Exhibit 1105].
Declaration of Ryan J. Fletcher in Support of Petition for Inter Partes Review of U.S. Pat. No. 7,767,657, 4 pages, IPR2015-01780 [Exhibit 1107].
Signature Pages & Errata Sheets to Stephen B. Kahl, Ph.D. dated Apr. 7-8, 2016, 9 pages, IPR2015-01780 [Exhibit 1108].
Signature Pages & Errata Sheet to Stephen B. Kahl, Ph.D. dated Sep. 14, 2016, 2 pages, IPR2015-01780 [Exhibit 1109].
Signature Pages & Errata Sheet to Narasimha Murthy, Ph.D. dated May 4-6, 2016, 8 pages, IPR2015-01780 [Exhibit 1110].
Signature Page & Errata Sheet to Narasimha Murthy, Ph.D. dated Sep. 17, 2016, 1 page, IPR2015-01780 [Exhibit 1111].
Email from Ryan James Fletcher to Counsel for Patent Owner dated Apr. 5, 2016 regarding Petitioner Response to PO Evidence Objections, 1 page, IPR2015-01780 [Exhibit 1112].
Petitioner's Updated Exhibit List, Oct. 11,2016, 10 pages, IPR2015-01785.
Petitioner's Updated Exhibit List, Aug. 24, 2016, 10 pages, IPR2015-01785.
Supplemental Declaration of Kathleen E. Ott in Support in Support of Petitioner's Supplemental Evidence and Response to Patent Owner's Objections to the Petition Evidence Pursuant to 37 C.F.R. § 42.54, 5 pages, IPR2015-01785 [Exhibit 1054].
Supplemental Declaration of S. Narashimha Murthy, Ph.D. in Support of Petitioner's Supplemental Evidence and Response to Patent Owner's Objections to the Petition Evidence Pursuant to 37 C.F.R. § 42.64, 8 pages, IPR2015-01785 [Exhibit 1059].
Supplemental Declaration of Stephen Kahl, Ph.D., 4 pages, IPR2015-01785 [Exhibit 1066].
Declaration of Stephen Kahl, Ph.D. in Support of Second Petition for Inter Partes Review of U.S. Pat. No. 7,767,657, 18 pages, IPR2015-01785 [Exhibit 1069].
Declaration of S. Narasimha Murthy, Ph.D. in Support of Petitioner's Reply to Patent Owner's Response, 70 pages, IPR2015-01785 [Exhibit 1070].
Deposition of Majella Lane, Ph.D., 319 pages, IPR2015-01785 [Exhibit 1071].
Deposition of Mahmoud A. Ghannoum, Ph.D., 352 pages, IPR2015-01785 [Exhibit 1072].
Deposition of Howard Maibach, M.D., Ph.D., 193 pages, IPR2015-01785 [Exhibit 1073].
Deposition of Paul J. Reider, Ph.D., 368 pages, IPR2015-01785 [Exhibit 1074].
Declaration of Ryan J. Fletcher in Support of Petition for Inter Partes Review of U.S. Pat. No. 7,767,657, 4 pages, IPR2015-01785 [Exhibit 1107].
Signature Pages & Errata Sheets to Stephen B. Kahl, Ph.D. dated Apr. 7-8, 2016, 9 pages, IPR2015-01785 [Exhibit 1108].
Signature Pages & Errata Sheet to Stephen B. Kahl, Ph.D. dated Sep. 14, 2016, 2 pages, IPR2015-01785 [Exhibit 1109].
Signature Pages & Errata Sheet to Narasimha Murthy, Ph.D. dated May 4-6, 2016, 8 pages, IPR2015-01785 [Exhibit 1110].
Signature Page & Errata Sheet to Narasimha Murthy, Ph.D. dated Sep. 17, 2016, 1 page, IPR2015-01785 [Exhibit 1111].
Email from Ryan James Fletcher to Counsel for Patent Owner dated Apr. 5, 2016 regarding Petitioner Response to PO Evidence Objections, 1 page, IPR2015-01785 [Exhibit 1112].
Patent Owner, Case No. IPR2015-01776, U.S. Pat. No. 7,582,621, Petitioner's Objections to Patent Owner's Evidence Under 37 C.F.R. § 42.64(B)(1), Jun. 13, 2016, 188 pages.
Petitioner Coalition for Affordable Drugs X LLC's Notice of Deposition of Mahmoud A. Ghannoum, Ph.D., Jun. 24, 2016, 4 pages, IPR2015-01776.
Petitioner Coalition for Affordable Drugs X LLC's Notice of Deposition of Majella Lane, Ph.D., Jun. 24, 2016, 4 pages, IPR2015-01776.
Petitioner Coalition for Affordable Drugs X LLC's Notice of Deposition of Paul J. Reider, Ph.D., Jun. 24, 2016, 4 pages, IPR2015-01776.
Petitioner Coalition for Affordable Drugs X LLC's Notice of Deposition of Howard Maibach, Ph.D., Jul. 1, 2016, 4 pages, IPR2015-01776.
Petitioner's Reply to Patent Owner's Response, Aug. 24, 2016, 36 pages, IPR2015-01776.
Petitioner's Request for Oral Argument, Sep. 27, 2016, 4 pages, IPR2015-01776.
Petitioner's Response to Patent Owner's Identification of new Arguments and Evidence in Petitioner's Reply, Oct. 4, 2016, 6 pages, IPR2015-01776.
Patent Owner's Identification of New Arguments and Evidence in Petitioner's Reply, Sep. 27, 2016, 6 pages, IPR2015-01776.
Patent Owner's Motion for Observations Regarding the Cross-Examination Testimony of Stephen B. Kahl, Ph.D., Sep. 27, 2016, 5 pages, IPR2015-01776.
Patent Owner's Motion to Exclude Evidence Pursuant to 37 C.F.R. § 42.64, Sep. 27, 2016, 18 pages, IPR2015-01776.
Patent Owner's Motion for Observations Regarding the Cross-Examination Testimony of S. Narasimha Murthy, Ph.D., Sep. 27, 2016, 10 pages, IPR2015-01776.
Patent Owner's Request for Oral Argument Under C.F.R. § 42.70, Sep. 27, 2016, 4 pages, IPR2015-01776.
Trial Hearing Order Regarding IPR2015-01776, 01780, and 01785, Entered Oct. 4, 2016, 5 pages.
Patent Owner Anacor Pharmaceuticals, Inc.'s Notice of Deposition of Stephen B. Kahl, Ph.D., Sep. 7, 2016, 4 pages, IPR2015-01776.

(56) References Cited

OTHER PUBLICATIONS

Patent Owner's Motion for Admission Pro Hac Vice of Michael N. Kennedy Under C.F.R. § 42.10, Jun. 13, 2016, 6 pages, IPR2015-01776.
Patent Owner Anacor Pharmaceuticals, Inc.'s Notice of Deposition of S. Narasimha Murthy, Ph.D., Sep. 7, 2016, 4 pages, IPR2015-01776.
Patent Owner's Objections to Evidence Under 37 C.F.R. § 42.64(b)(1), Aug. 31, 2016, 8 pages, IPR2015-01776.
Patent Owner's Motions for Pro Hac Vice Admission of Michael N. Kennedy and Jeffrey B. Elikan Under 37 C.F.R. § 42.10, Entered Jun. 29, 2016, 3 pages, IPR2015-01776.
Patent Owner's Motion for Pro Hac Vice Admission of George F. Pappas Under 37 C.F.R. § 42.10, Entered Jul. 8, 2016, 3 pages, IPR2015-01776.
Patent Owner's Motion for Admission Pro Hac Vice of Jeffrey B. Elikan Under 37 C.F.R. § 42.10, Jun. 20, 2016, 6 pages, IPR2015-01776.
Patent Owner's Motion for Admission Pro Hac Vice of George F. Pappas Under 37 C.F.R. § 42.10, Jun. 30, 2016, 6 pages, IPR2015-01776.
Petitioner's Response to Patent Owner's Motion to Exclude Evidence Pursuant to 37 C.F.R. § 42.64, Oct. 11, 2016, 18 pages, IPR2015-01776.
Petitioner's Response to Patent Owner's Motion for Observations Regarding the Cross Examination Testimony of Stephen B. Kahl, Ph.D., Oct. 11, 2016, 5 pages, IPR2015-01776.
Petitioner's Response to Patent Owner's Motion for Observations Regarding the Cross-Examination Testimony of S. Narasimha Murthy, Ph.D., Oct. 11, 2016, 14 pages, IPR2015-01776.
Petitioner's Objections to Patent Owner's Evidence Under 37 C.F.R. § 42.64(B)(1), Jun. 13, 2016, 186 pages, IPR2015-01780.
Petitioner Coalition for Affordable Drugs X LLC's Notice of Deposition of Mahmoud A. Ghannoum, Ph.D., Jun. 24, 2016, 4 pages, IPR2015-01780.
Petitioner Coalition for Affordable Drugs X LLC's Notice of Deposition of Majella Lane, Ph.D., Jun. 24, 2016, 4 pages, IPR2015-01780.
Petitioner Coalition for Affordable Drugs X LLC's Notice of Deposition of Paul J. Reider, Ph.D., Jun. 24, 2016, 4 pages, IPR2015-01780.
Petitioner Coalition for Affordable Drugs X LLC's Notice of Deposition of Howard Maibach, Ph.D., Jul. 1, 2016, 4 pages, IPR2015-01780.
Petitioner's Reply to Patent Owner's Response IPR2015-01780, Aug. 24, 2016, 36 pages.
Petitioner's Request for Oral Argument, Sep. 27, 2016, 5 pages, IPR2015-01780.
Petitioner's Response to Patent Owner's Identification of new Arguments and Evidence in Petitioner's Reply, Oct. 4, 2016, 6 pages, IPR2015-01780.
Trial Hearing Order Regarding, Entered Oct. 4, 2016, 5 pages, IPR2015-01780.
Patent Owner's Motions for Pro Hac Vice Admission of Michael N. Kennedy and Jeffrey B. Elikan Under 37 C.F.R. § 42.10, Entered Jun. 29, 2016, 3 pages, IPR2015-01780.
Patent Owner's Motion for Pro Hac Vice Admission of George F. Pappas Under 37 C.F.R. § 42.10, Entered Jul. 8, 2016, 3 pages, IPR2015-01780.
Patent Owner's Motion for Admission Pro Hac Vice of Jeffrey B. Elikan Under 37 C.F.R. § 42.10, Jun. 20, 2016, 6 pages, IPR2015-01780.
Patent Owner's Identification of New Arguments and Evidence in Petitioner's Reply, Sep. 27, 2016, 6 pages, IPR2015-01780.
Patent Owner Anacor Pharmaceuticals, Inc.'s Notice of Deposition of Stephen B. Kahl, Ph.D., Sep. 7, 2016, 4 pages, IPR2015-01780.
Patent Owner's Motion for Observations Regarding the Cross-Examination Testimony of Stephen B. Kahl, Ph.D., Sep. 27, 2016, 5 pages, IPR2015-01780.

Patent Owner's Motion for Admission Pro Hac Vice of Michael N. Kennedy Under C.F.R. § 42.10, Jun. 13, 2016, 6 pages, IPR2015-01780.
Patent Owner's Motion to Exclude Evidence Pursuant to 37 C.F.R. § 42.64, Sep. 27, 2016, 18 pages, IPR2015-01780.
Patent Owner Anacor Pharmaceuticals, Inc.'s Notice of Deposition of S. Narasimha Murthy, Ph.D., Sep. 7, 2016, 4 pages, IPR2015-01780.
Patent Owner's Motion for Observations Regarding the Cross-Examination Testimony of S. Narasimha Murthy, Ph.D., Sep. 27, 2016, 10 pages, IPR2015-01780.
Patent Owner's Motion for Admission Pro Hac Vice of George F. Pappas Under 37 C.F.R. § 42.10, Jun. 30, 2016, 6 pages, IPR2015-01780.
Patent Owner's Objections to Evidence Under 37 C.F.R. §42.64(b)(1), Aug. 31, 2016, 8 pages, IPR2015-01780.
Patent Owner's Request for Oral Argument Under 37 C.F.R. § 42.70, Sep. 27, 2016, 5 pages, IPR2015-01780.
Petitioner's Response to Patent Owner's Motion to Exclude Evidence Pursuant to 37 C.F.R. § 42.64, Oct. 11, 2016, 18 pages, IPR2015-01780.
Petitioner's Response to Patent Owner's Motion for Observations Regarding the Cross-Examination Testimony of Stephen B. Kahl, Ph.D., Oct. 11, 2016, 5 pages, IPR2015-01780.
Petitioner's Response to Patent Owner's Motion for Observations Regarding the Cross-Examination Testimony of S. Narasimha Murthy, Ph.D., Oct. 11, 2016, 14 pages, IPR2015-01780.
Petitioner's Objections to Patent Owner's Evidence Under 37 C.F.R. § 42.64(B)(1), Jun. 13, 2016, 168 pages, IPR2015-01785.
Petitioner Coalition for Affordable Drugs X LLC's Notice of Deposition of Mahmoud A. Ghannoum, Ph.D., Jun. 24, 2016, 4 pages, IPR2015-01785.
Petitioner Coalition for Affordable Drugs X LLC's Notice of Deposition of Majella Lane, Ph.D., Jun. 24, 2016, 4 pages, IPR2015-01785.
Petitioner Coalition for Affordable Drugs X LLC's Notice of Deposition of Paul J. Reider, Ph.D., Jun. 24, 2016, 4 pages, IPR2015-01785.
Petitioner Coalition for Affordable Drugs X LLC's Notice of Deposition of Howard Maibach, Ph.D., Jul. 1, 2016, 4 pages, IPR2015-01785.
Petitioner's Reply to Patent Owner's Response, Aug. 24, 2016, 36 pages, IPR2015-01785.
Petitioner's Request for Oral Argument, Sep. 27, 2016, 5 pages, IPR2015-01785.
Petitioner's Response to Patent Owner's Identification of new Arguments and Evidence in Petitioner's Reply, Oct. 4, 2016, 6 pages, IPR2015-01785.
Petitioner's Response to Patent Owner's Motion to Exclude Evidence Pursuant to 37 C.F.R. § 42.64, Oct. 11, 2016, 12 pages, IPR2015-01785.
Petitioner's Response to Patent Owner's Motion for Observations Regarding the Cross-Examination Testimony of Stephen B. Kahl, Ph.D., Oct. 11, 2016, 5 pages, IPR2015-01785.
Petitioner's Response to Patent Owner's Motion for Observations Regarding the Cross-Examination Testimony of S. Narasimha Murthy, Ph.D., Oct. 11, 2016, 14 pages, IPR2015-01785.
Trial Hearing Order, Entered Oct. 4, 2016, 5 pages, IPR2015-01785.
Patent Owner's Motions for Pro Hac Vice Admission of Michael N. Kennedy and Jeffrey B. Elikan Under 37 C.F.R. § 42.10, Entered Jun. 29, 2016, 3 pages, IPR2015-01785.
Patent Owner's Motion for Pro Hac Vice Admission of George F. Pappas Under 37 C.F.R. § 42.10, Entered Jul. 8, 2016, 3 pages, IPR2015-01785.
Patent Owner's Identification of New Arguments and Evidence in Petitioner's Reply, Sep. 27, 2016, 6 pages, IPR2015-01785.
Patent Owner's Motion for Observations Regarding the Cross-Examination Testimony of Stephen B. Kahl, Ph.D., Sep. 27, 2016, 5 pages, IPR2015-01785.
Patent Owner's Motion for Observations Regarding the Cross-Examination Testimony of S. Narasinnha Murthy, Ph.D., Sep. 27, 2016, 10 pages, IPR2015-01785.

(56) References Cited

OTHER PUBLICATIONS

Patent Owner's Motion to Exclude Evidence Pursuant to 37 C.F.R. § 42.64, Sep. 27, 2016, 12 pages, IPR2015-01785.
Patent Owner's Request for Oral Argument Under 37 C.F.R. § 42.70, Sep. 27, 2016, 5 pages, IPR2015-01785.
Patent Owner Anacor Pharmaceuticals, Inc.'s Notice of Deposition of Stephen B. Kahl, Ph.D., Sep. 7, 2016, 4 pages, IPR2015-01785.
Patent Owner Anacor Pharmaceuticals, Inc.'s Notice of Deposition of S. Narasimha Murthy, Ph.D., Sep. 7, 2016, 4 pages, IPR2015-01785.
Patent Owner's Objections to Evidence Under 37 C.F.R. §42.64(b)(1), Aug. 31, 2016, 8 pages, IPR2015-01785.

\* cited by examiner

FIGURE 1A

| | MIC (ug/mL) | | | | | | | |
|---|---|---|---|---|---|---|---|---|
| | C. albicans ATCC 90028 | C. albicans F56 | C. neoformans F285 | A. fumigatus ATCC 13073 | T. mentagrophytes F311 | S. cerevisiae ANA309 | T. rubrum F296 | T. rubrum F296 w/ 5% keratin |
| C1 | 1 | 2 | 2 | 1 | 2 | 0.5 | 1 | 1 |
| C2 | 2 | 0.5 | 1 | 2 | 4 | | 8 | 8 |
| C3 | 16 | 32 | 32 | 16 | 16 | 4 | 32 | |
| C4 | 64 | 64 | > 64 | 32 | 32 | 8 | 32 | |
| C5 | 4 | 8 | 2 | 2 | 4 | 0.25 | 4 | |
| C6 | 8 | 16 | 8 | 16 | 16 | 64 | 16 | |
| C7 | > 64 | > 64 | > 64 | > 64 | 32 | 4 | 64 | |
| C8 | 2 | 2 | 8 | 2 | 4 | 2 | 8 | |
| C9 | > 64 | > 64 | > 64 | > 64 | 64 | >64 | 64 | |

FIGURE 1B

| | | | | | | | | |
|---|---|---|---|---|---|---|---|---|
| C10 | 0.5 | 0.5 | 0.25 | 0.25 | ≤0.5 | <0.06 | 1 | 2 |
| C11 | 32 | 32 | 32 | 32 | 2 | 2 | 4 | |
| C12 | 256 | | | | | >64 | | |
| C13 | 16 | | | | | 2 | 16 | |
| C16 | 32 | | | | | 8 | 16 | |
| C17 | 64 | 64 | 64 | 16 | 4 | 16 | 8 | |
| C18 | | | | | | 2 | | |
| C19 | | | | | | 0.5 | 8 | |
| C20 | | | | | | 8 | | |
| C21 | | | | | | 4 | | |
| C22 | | | | | | >64 | | |
| C23 | | | | | | >64 | | |

FIGURE 1C

| | | | | | | | | |
|---|---|---|---|---|---|---|---|---|
| C24 | | | | | | 16 | | |
| C25 | | | | | | >64 | | |
| C26 | | | | | | >64 | | |
| C27 | | | | | | >64 | | |
| C28 | | | | | | <0.06 | 4 | |
| C31 | | | | | | 8 | | |

FIGURE 2A

EXAMPLE 2A

| Fungus | Broth used | MIC (µg/mL) | | | | |
| --- | --- | --- | --- | --- | --- | --- |
| | | (C10) | Ciclopirox | Terbinafine | Fluconazole | Itraconazole |
| *A. fumigatus* ATCC 13073 | RPMI | 0.25 | nt | nt | >64 | 0.25 |
| *C. albicans* ATCC 90028 | RPMI | 1 | 0.5 | nt | 0.25 | ≤0.12 |
| *C. albicans* F56 | RPMI | 0.5 | nt | nt | >64 | 0.25 |
| *C. glabrata* ATCC 90030 | RPMI + MOPs | ≤0.5 | ≤0.5 | 64 | nt | ≤0.5 |
| *C. krusei* ATCC 44507 | RPMI + MOPs | 1 | ≤0.5 | 64 | nt | ≤0.5 |
| *C. neoformans* F285 | RPMI | 0.25 | nt | nt | 2 | ≤0.12 |
| *C. parapsilosis* ATCC 22019 | RPMI + MOPs | ≤0.5 | ≤0.5 | ≤0.5 | nt | ≤0.5 |
| *C. tropicalis* ATCC 13803 | RPMI + MOPs | ≤0.5 | ≤0.5 | 256 | nt | 1 |
| *E. floccosum* ATCC 52066 | RPMI + MOPs | ≤0.5 | ≤0.5 | ≤0.5 | nt | ≤0.5 |
| *F. solani* ATCC 36031 | RPMI + MOPs | ≤0.5 | 4 | 64 | nt | >256 |
| *M. furfur* ATCC 44344 | Urea | 1 | ≤0.5 | 2 | nt | ≤0.5 |
| *M. pachydermatis* ATCC 96746 | Urea | 1 | ≤0.5 | ≤0.5 | nt | ≤0.5 |
| *M. sympodialis* ATCC 44031 | Urea | 1 | ≤0.5 | ≤0.5 | nt | ≤0.5 |
| *M. audouinii* ATCC 42558 | RPMI + MOPs | 2 | 1 | ≤0.5 | nt | ≤0.5 |
| *M. canis* ATCC 10214 | RPMI + MOPs | 2 | ≤0.5 | ≤0.5 | nt | ≤0.5 |
| *M. gypseum* ATCC 24103 | RPMI + MOPs | 2 | ≤0.5 | ≤0.5 | nt | ≤0.5 |
| *T. mentagrophytes* F311 | RPMI + MOPs | 1 | 0.5 | ≤0.5 | 32 | ≤0.12 |
| *T. rubrum* F296 | RPMI + MOPs | 1 | 1 | ≤0.5 | 1 | ≤0.12 |
| *T. rubrum* F296 | RPMI + MOPS + 5% keratin powder | 2 | 1 | nt | 1 | nt |
| *T. tonsurans* ATCC 28942 | RPMI + MOPs | 2 | ≤0.5 | ≤0.5 | nt | ≤0.5 | nt = not tested

FIGURE 2B

EXAMPLE 2B

| Fungus | Broth used* | MFC (μg/mL) | | | |
|---|---|---|---|---|---|
| | | (C10) | Ciclopirox | Terbinafine | Itraconazole |
| T. mentagrophytes F311 | RPMI + MOPs | 16 | 1 | ≤ 0.5 | 4 |
| T. rubrum F296 | RPMI + MOPs | 8 | 2 | ≤ 0.5 | 4 |

FIGURE 3

| Nail Samples | Radioactivity as mg Equivalent/g Nail Samples | | P value (t-test) |
|---|---|---|---|
| | Group A (C10) | Group C (Ciclopirox) | |
| Dorsal/intermediate center | 25.65 ± 8.80 | 7.40 ± 3.47 | 0.0008 |
| Ventral/intermediate center | 20.46 ± 4.72 | 3.09 ± 2.07 | 0.0001 |
| Remainder nail | 26.06 ± 12.41 | 4.38 ± 2.73 | 0.0022 |

* The data represents the mean ± S.D. of each group (n = 6).

FIGURE 4

| Sampling day | Radioactivity as mg Equivalent/Samples* | | P-value (t-test) |
| --- | --- | --- | --- |
| | Group A (C10) | Group C (Ciclopirox) | |
| Day 3 | 0.0609 ± 0.0605 | 0.0011 ± 0.0020 | 0.0043 |
| Day 6 | 0.1551 ± 0.1314 | 0.0013 ± 0.0027 | 0.0022 |
| Day 9 | 0.3892 ± 0.3714 | 0.0018 ± 0.0030 | 0.0022 |
| Day 12 | 0.6775 ± 0.6663 | 0.0014 ± 0.0019 | 0.0022 |
| Day 15 | 0.9578 ± 0.6106 | 0.0033 ± 0.0041 | 0.0022 |
| Total | 2.2405 ± 1.7325 | 0.0089 ± 0.0131 | 0.0022 |

* The data represents the mean ± S.D. of each group (n = 6).

Figure 10(1)

SUMMARY:
SEQ ID NO: 1–15    amino acid sequences of leucyl-tRNA synthetase editing domain SEQ ID NO: 1       amino acid sequences of leucyl-tRNA synthetase editing domain from *S. cerivisiae*.

SEQ ID NO: 2       amino acid sequences of leucyl-tRNA synthetase editing domain from *S. cerivisiae* – overexpressed version SEQ ID NO: 16–17   genomic sequences for tRNA-leu and tRNA-ile from *S. cerivisiae*.

SEQ ID NO: 18-62   tRNA sequences for tRNA-leu

A.
SEQ ID NO: 1
TPQEYIGVKIEALEFADDAAKIIDSSSDLDKSKKFYFVAATLRPETMYGQTCCFVSPTI
EYGIFDAGDSYFITTERAFKNMSYQKLTPKRGFYKPIVTVPGKAFIGTKIHAPQSVYPE
LRILPMETVIATKGTGVVTCVPSNSPDDYITTKDLLHKPEYYGIKPEWIDHEIVPIMHTE
KYGDLTAKAIVEEKKIQSPKDKNLLAEAKKIAYKEDYYTGTMIYGPYKGEKVEQAKNK
VKADMIAAGEAFVYNEPESQDP

SEQ ID NO: 2
MTPQEYIGVKIEALEFADDAAKIIDSSSDLDKSKKFYFVAATLRPETMYGQTCCFVSPTI
EYGIFDAGDSYFITTERAFKNMSYQKLTPKRGFYKPIVTVPGKAFIGTKIHAPQSVYPE
LRILPMETVIATKGTGVVTCVPSNSPDDYITTKDLLHKPEYYGIKPEWIDHEIVPIMHTE
KYGDLTAKAIVEEKKIQSPKDKNLLAEAKKIAYKEDYYTGTMIYGPYKGEKVEQAKNK
VKADMIAAGEAFVYNEPESQDPQDPNSSSVDKLAAALEHHHHH

B.
SEQ ID NO: 3 G- E.coli crystal structure (185 amino acids) – tRNA synthetase editing domain
EGVEITFNVNDYDNTLTVYTTRPDTFMGCTYLAVAAGHPLAQKAAENNPELAAFIDECR
NTKVAEAEMATMEKKGVDTGFKAVHPLTGEEIPVWAANFVLMEYGTGAVMAVPGHD
QRDYEFASKYGLNIKPVILAADGSEPDLSQQALTEKGVLFNSGEFNGLDHEAAFNAIAD
KLTAMGVGERK

SEQ ID NO: 4 G+ Propionibacter acnes (185 aa) – tRNA synthetase editing domain
EGAYVDFTIDGHKEPVRVFTTRPDTLYGATFMVVAPDSALAQEIVSDEARPAFETYLDE
VKKKSEIERQATDHEKTGVPLGVEATNPVNGAKVPVWAGDYVLADYGTGAVMAVPA
HDQRDLDFARTYGIDVIPVIDTGEADPRESGVATTGDGVYQNSGFLNGIATKAEAIAKM
CEFLDEKGIGE

Figure 10(2)

SEQ ID NO: 5 from G- Pseudomonas aeruginosa (194 aa) – tRNA synthetase editing domain GMEIGFPYDQASIGHAGQLKVFTTRPDTLMGATYVAVAAEHPLATQAAQNDPQLQAFI
DECKRGGVAEADIATQEKKGMATSLFVEHPLTGDKLPVWVANYVLMNYGEGAVMAV
PGHDERDFEFANKYGLPIRQVIAKVEGDDDFESSVWKEWYGAKDESVLTVNSGKYDNL
GYQAAFDAIGADLEAKGLGQAR

SEQ ID NO: 6 G+ Bacillus anthracis (183 aa) – tRNA synthetase editing domain
EGAEVHFNIDGTDEKFTVFTTRPDTLFGASYCVLAPEHALVADITTADQKEAVEAYINSV
KMKSDLERTELAKEKTGVFTGAYAVNPVNGEKLPIWIADYVLATYGTGAVMAVPAHD
ERDYEFASTFNLPMKEVVKGGDITKEAYTGDGAHVNSAFLDGLNKEEAIAKMIEWLEV
TSAGNQKV

SEQ ID NO: 7 from G+ Staphylococcus aureus (183 aa) – tRNA synthetase editing domain
EGAKVTFKIEQSDQNIEVFTTRPDTIYGTSFLVLSPEHPLVNEITTSDKEQEVKLYQNEA
SKKSDLERTDLAKEKTGVFTGTFAINPLSGDKLPIWIADYVLSTYGTGAVMAVPGHDER
DHEFATKFNLPIIEVIEGGEVQKYAYTGEGKHINSGELDGLENEAAISKAIELLESKGAGE
KKV

SEQ ID NO: 8 G+ Streptococcus pyogens (182 aa) – tRNA synthetase editing domain
GANVTFKVKDTDKNFTVFTTRPDTLFGATYAVLAPEHALVDAITTADQAEAVADYKRQ
ASLKSDLARTDLAKEKTGVWTGSYAINPVNGKEIPVWIADYVLASYGTGAIMAVPAHD
ERDWEFAKQFNLDIIPVLEGGNVEEAAFTEDGLHINSGFLDGLDKASAIAKMVEWLEAE
GVGNEKV

SEQ ID NO: 9 G+ Thermus thermophilus (187 aa) – tRNA synthetase editing domain
EGAEILFPVEGKEVRIPVFTTRPDTLFGATFLVLAPEHPLTLELAAPEKREEVLAYVEAA
KRKTEIERQAEGREKTGVFLGAYALNPATGERIPIWTADYVLFGYGTGAIMAVPAHDQR
DYEFARKFGLPIKKVIERPGEPLPEPLERAYEEPGIMVNSGPFDGTESEEGKRKVIAWLEE
KGLGKGR

SEQ ID NO: 10 Mycobacterium tuberculosis (186 aa) – tRNA synthetase editing domain
FEVDIEVFTTRPDTLFGATYLVLAPEHDLVDELVAASWPAGVNPLWTYGGGTPGEAIAA
YRRAMAAKSDLERQESREKTGVFVGSYAINPANGEPVPIFIADYVLAGYGTGAIMAVPG
HDQRDWDFARAFGLPIVEVIAGGNISESAYTGDGILVNSDYLNGMSVPAAKRAIVDRLE
SAGRGRARI

SEQ ID NO: 11 Candida albicans (251 aa) – tRNA synthetase editing domain
YVGIKIRLTDVAPQAQELFKKESLDVKENKVYLVAATLRPETMYGQTCCFVSPKIDYGV
FDAGNGDYFITTERAFKNMSFQNLTPKRGYYKPLFTINGKTLIGSRIDAPYAVNKNLRVL
PMETVLATKGTGVVTCVPSDSPDDFVTTRDLANKPEYYGIEKDWVQTDIVPIVHTEKYG
DKCAEFLVNDLKIQSPKDSVQLANAKELAYKEGFYNGTMLIGKYKGDKVEDAKPKVK
QDLIDEGLAFVYNEPE

Figure 10(3)

SEQ ID NO: 12 Aspergillus fumigatus (256 aa) – tRNA synthetase editing domain
YTAMKLQVKEWAPEIAELVKGKIEDDAKVYFVPATLRPETMYGQTCCFLGPKIKYGIFR
VKEKEYYIVTKRAAWNMAFQGIFFDSEHFPKTQDELPLVLEAPGSAFVGTLVNAPLSFH
TEGVRILPMEGVSATKGTGVVTSVPSDSPDDYATLVDLAKKPEYYGIKKEWAELEIFPLI
ETPTYGNLTAPTLVKKLKINSPKDVNQLAQAKELAYGEAYYKGTMLVGEFKGEPVSAA
KEKIRKSLYESGDAFPFADP

SEQ ID NO: 13 Trichophyton rubrum CP1 (256 aa) – tRNA synthetase editing domain
YTAMKLKVKEWSPKAKEIIQGKIEKDANVYFVPATLRPETMYGQTCCFVGPAISYGIFK
VKEKEYYVVTKRAAWNMAFQGIFFDVNNLPKSQDELPPVVEAPGSALIGTLVNAPLSFH
KEGVRILPMETVSANKGTGVVSCVPSDSPDDFATISDLAKKADYYGIQKEWAELEIHPLI
ETPTYGNLTAPALVKQLKINSPKDTVQLAQAKDLAYTEGFYKGKMLVGEFKGEPVQTA
KEKVRNSLIKSGDAFPFADP

SEQ ID NO: 14 Homo sapiens (253 aa) – tRNA synthetase editing domain
VGPQEYTLLKLKVLEPYPSKLSGLKGKNIFLVAATLRPETMFGQTNCWVRPDMKYIGFE
TVNGDIFICTQKAARNMSYQGFTKDNGVVPVVKELMGEEILGASLSAPLTSYKVIYVLP
MLTIKEDKGTGVVTSVPSDSPDDIAALRDLKKKQALRAKYGIRDDMVLPFEPVPVIEIPG
FGNLSAVTICDELKIQSQNDREKLAEAKEKIYLKGFYEGIMLVDGFKGQKVQDVKKTIQ
KKMIDAGDALIYMEPE

SEQ ID NO: 15 Trypanosoma brucei (259 aa) – tRNA synthetase editing domain
YTVVKLKVKNPLEQPALAPFSEIIGNRSVILPGATLRPETVIGQTNCWVSPNFSYMAYSIL
NGTGEEEIYIMTSRAARNLAYQNFTVNGKTGVDPSPLFEVDGAKLIGLPLSAPLCPYDTI
YTLPMQSIIETKGTGVVMSVPADSPDDYINYVQLVNKPDYRAKLGLKDEWVANKIVSLI
EVPGEMGRESAKYMCEKLKINGPNATDLLEEAKKVIYQAGFYQGVMIAGPFAGEKVSA
AKVKTVKLLEEQNAAIRYYEP

C.

SEQ ID NO: 16 *Saccharomyces cerevisiae* tRNA-Leu (genomic)
gggagtttgg ccgagtggtt taaggcgtca gatttaggct ctgatatctt cggatgcaag ggttcgaatc ccttagctct cacca

SEQ ID NO: 17 *Saccharomyces cerevisiae* tRNA-Ile (genomic)
gaaactataa ttcaattggt tagaatagta ttttgataag gtacaaatat aggttcaatccctgttagtt tcat

D.

SEQ ID NO: 18 *Saccharomyces cerevisiae* tRNA-Leu
G G U U G U U U G m$^2$G C ac$^4$C G A G C Gm G D C D A A G G C m$_2^2$G C C U G A Ψ U
m$^5$C A A m$^1$G C Ψ C A G G U A U C G U A A G A U G m$^5$C A A G A G T Ψ C G A A U C U
C U U A G C A A C C A C C A

Figure 10(4)

SEQ ID NO: 19 Haloferax Volcanii tRNA-Leu
G C G A G G G U A G C U A A fa$^7$d$^7$G U C A G G A A A A A G C m$_2^2$G G C G G A C U C A
A m$^1$G A Ψ C C G C U C C C G U A G G G G U Cm$^5$C G U G G G m$^1$Ψ Ψ Cm m$^1$I A A U C C
C U C C C C U C G C A C C A

SEQ ID NO: 20 Phage T4 tRNA-Leu
G C G A G A A s$^4$U G G U C A A A D U m$^2$G G D A A A G G C A C A G C A C U unkU A A
ms$^2$i$^6$A A Ψ G C U G C G G A A UGA U U U C C U U G U G G G T Ψ C G A G U C C C A C
U U C U C G C A C C A

SEQ ID NO: 21 Phage T5 tRNA-Leu
G G GG C U A U G C U G G A A C D Gm G D A G A C A A U A C G G C C U U A Gm$^6$A U
Ψ C C G U A G C U U A A A U G C G U G G G A G T Ψ C G A G U C U C C C U A G C C C
C A C C A

SEQ ID NO: 22 Bacillus Subtilis tRNA-Leu
GCGGG U G U G C G G G A A U D GG D A G A C C G G C U A G A U U C A Gm$^1$G A Ψ
C U A G G G U C U U U A U G G A C C U G A G G G T Ψ C A m$^1$A G U C C C U U C A C
C C G C A C C A

SEQ ID NO: 23 E.Coli tRNA-Leu
G C C C G G A s$^4$U G G U G GA A DC GmGD A G A CAC A AGGGA Ψ U unkA A A ms$^2$i$^6$A
A Ψ C C C U C G G C G U U C G C G C U G U G C G G G T Ψ C A A G U C C C G C U C C
G G G U A C C A

SEQ ID NO: 22 E.Coli tRNA-Leu2
GCGAA G G U G G C G G A A D D Gm G D A G A C G C G C U A G C U U C A G unkG Ψ
G Ψ U A G U G U C C U U A C G G A C G U G G G G G T Ψ C A A G U C C C C C C C U
C G C A C C A

SEQ ID NO: 23 E.Coli tRNA-Leu3
GCCGA G G U G G U G G A A D D Gm G D A G A C A C G C U A C C U U G A G unkG Ψ
G G U A G U G C C C A A U A G G G C U U A C G G G T Ψ C A A G U C C C G U C C U C
G G U A C C A

SEQ ID NO: 24 Salmonella Typhi tRNA-Leu
GCGAA G G U G G C G G A A D D Gm G D A G A C G C G C U A G C U U C A G unkG Ψ
G Ψ U A G U G U C C U U A C G G A C G U G G G G G T Ψ C A A G U C C C C C C C U
C G C A C C A

Figure 10(5)

SEQ ID NO: 25 Rhodospiril.Rub tRNA-Leu
G C C U U U G U A G C G G A A D G G D A A C G C G G C A G A C U C A A unkA A Ψ C U
G C U U U G G U A A C C C A G G U G G U A G T Ψ C G A C U C U C C C A A A G G C
A C C A

SEQ ID NO: 26 Anacystis Nidulans tRNA-Leu
G G G C A A G U G G C G G A A U D G G D A G A C G C A G C A G A C U C A A unkA A Ψ
C U G C C G C U A G C G A U A G U G U G U G G G T Ψ C G A G U C C C A C C U U G C
C C A C C A

SEQ ID NO: 27 Anacystis Nidulans tRNA-Leu2
G C G G A A C U G G C G G A A U D G G D A G A C G C G C U A G A U U C A Gm$^1$G Ψ Ψ
C U A G U G G U U U C A C G A C U G U C C G G G T Ψ C A A G U C C C G G G U U C C
G C A C C A

SEQ ID NO: 28 Bacillus Stearo tRNA-Leu
G C C G A U G s$^4$U G G C G G A A U D G G C A Gm$^1$A C G C G C A C G A C U Cm A A
ms$^2$i$^6$A A Ψ C G U G U G G G C U U U G C C C G U G U G G G T Ψ C G A C U C C C A C
C A U C G G C A C C A

SEQ ID NO: 29 Glycine Max tRNA-Leu
G C C U U G G U G G U G A A A U Gm G D A G C C A C G C G A G A C U Cm A A unkA A
Ψ C U C G U G C U A C A G A G C G U G G A G G T Ψ C G A G U C C U C U U C A A G G
C A C C A

SEQ ID NO: 30 Glycine Max tRNA-Leu2
G G G G A U A U G G C G A A A U U Gm G D A G A C G C Ψ A C G G A C U Um A A
unkA A Ψ C C G U C G A C U U A A G A A A U C A U G A G G G T Ψ C A A G U C C C U
C U A U C C C C A C C A

SEQ ID NO: 31 Glycine Max tRNA-Leu3
G C C G C U A U G G U G A A A U U Gm GD A G A C A C G C U G C U C U U Am$^7$G m$^1$G A
A G C A G U G C U A G A G C A U C U C G G T Ψ C G A G U C C G A G U A G C G G C A
C C A

SEQ ID NO: 32 Phaseolus Vulgaris tRNA-Leu1
G G C U U G A U G G U G A A A U U Gm G D A G A C A C G C G A G A C U Cm A A unkA
A U C U C G U G C U A A A G A G C G U G G A G G T Ψ C G A G U C C U C U U C A A
G U C A C C A

Figure 10(6)

SEQ ID NO: 33 Phaseolus Vulgaris tRNA-Leu2
G G GG A U A U G G C G A A A U U Gm G D A G A C G C Ψ A C G G A C U unkU A A
unkA A Ψ C C G U C G A C U U A A U A A A U C A U G A G G G T Ψ C A A G U C C C U
C U A U C C C C A C C A

SEQ ID NO: 34 Phaseolus Vulgaris tRNA-Leu3
GCCGC U A U G G U G A A A U U Gm GD A G A C A C G C U G C U C U U Am$^7$G m$^1$G A
A G C A G U G C U A G A G C A U C U C G G T Ψ C G A G U C C G A G U A G C G G C A
C C A

SEQ ID NO: 35 Spinacia Oleracea tRNA-Leu
GCCGC U A U G G U G A A A U U Gm GD A G A C A C G C U G C U C U U Am$^7$G m$^1$G A
A G C A G U G C G A G A G C A U C U C G G T Ψ C G A G U C C G A G U A G C G G C A
C C A

SEQ ID NO: 36 Neurospora Crassa tRNA-Leu1
AUCCG A G U G A U G G A A D G G D A G A C A U A A C A U G C U unkU A A A A C A
U G U G G G C U U C A A G C U G U G A A G G T Ψ C A A G U C C U U C U U C G G A
U A C C A

SEQ ID NO: 37 Neurospora Crassa tRNA-Leu2
AUAGG U G U G C U G G A A D U G G D A G A C A G G U U C C G Ψ U U A Gm$^1$G C C
G G A A U G G U U U A A A A A C U G U A C A A G T Ψ C A A G U C U U G U C A U C
U A U A C C A

SEQ ID NO: 38 Saccharomyces Cer. tRNA-Leu
GCUAU U U U G G U G G A A D U G G D A G A C A Cm$_2^2$G A U A C Ψ C U cmnm$^5$U A A
m$^1$G A Ψ G U A U U A C U U U A C A G U A U G A A G G T Ψ C A A G U C C U U U A A
A U A G C A C C A

SEQ ID NO: 39 Solanum Tuberosum tRNA-Leu
G U C A G G A U G G C ac$^4$C G A G D Gm G D C acp$^3$U A A G G C m$_2^2$G C C A G A C U
unk A A m$^1$G U Ψ C U G G Um C U U C G U A A G A G G G m$^5$C G U G G G T Ψ C A m$^1$A
A U C C C A C U U C U G A C A C C A

SEQ ID NO: 40 Phaseolus Vulgaris tRNA-Leu1
G U C A G G A U G m$^2$G C ac$^4$C G A G D Gm G D C acp$^3$U A A G G C m$_2^2$G C C A G A C U
unk A A m$^1$G Ψ Ψ C U G G Um C U U C G A G A G A G G G m$^5$C G U G G G T Ψ C A m1A
A U C C C A C U U C U G A C A C C A

Figure 10(7)

SEQ ID NO: 41 Phaseolus Vulgaris tRNA-Leu2
G U C A G G A U G m$^2$G C ac$^4$C G A G D Gm G D C acp3U A A G G C m$_2^2$G C C A G A C U
unk A A m$^1$G Ψ Ψ C U G G Um C U U C G A A A G A G G G m$^5$C G U G G G T Ψ C A m$^1$A
A U C C C A C U U C U G A C A C C A

SEQ ID NO: 42 Phaseolus Vulgaris tRNA-Leu3
G A U A G U U U G m$^2$G C ac$^4$C G A G D Gm G D C acp3U A A G G C m$_2^2$G C C A G A Ψ U
unk A G m$^1$G C Ψ C U G G Um C C G A A A unk G G G m$^5$C G U G G G T Ψ C A m$^1$A A U C
C C A C A G C U G U C A C C A

SEQ ID NO: 43 Phaseolus Vulgaris tRNA-Leu4
G C U G G U U U G G C ac$^4$C G A G A Gm G D D A A G G C m$_2^2$G G A A G A C U unk A A
m$^1$G A Ψ C U U C Um G C A G U C A A C U G C G m$^5$C A U G G G T Ψ C G m$^1$A A C C C
C A U A G C C A G C A C C A

SEQ ID NO: 44 Rat Liver A tRNA-Leu1
C U U U U A U m$^1$A m$^2$G G A U A G A A G D A A U C C A Ψ U G G U C U U A Gm$^1$G A A
C C A A A A A C m$^5$C U U G G U G C A A C U C C A A A U A A A A G U A C C A

SEQ ID NO: 45 Candida Albicans tRNA-Leu
G A U A C G A U G G C ac$^4$C G A G D Gm G D D A A G G C m$_2^2$G A A G G A U G C A
Gm$^1$G Ψ Ψ C C U U U G G G C AUU G C C C G m$^5$C G C A G G T Ψ C G m$^1$A A C C C U G
C U C G U G U C G C C A

SEQ ID NO: 46 Saccharomyces Cer. tRNA-Leu1
G G U U G U U U G m$^2$G C ac$^4$C G A G C Gm G D C D A A G G C m$_2^2$G C C U G A Ψ U
m$^5$C A A m$^1$G C Ψ C A G G U A U C G U A A G A U G m$^5$C A A G A G T Ψ C G A A U C U
C U U A G C A A C C A C C A

SEQ ID NO: 47 Saccharomyces Cer. tRNA-Leu2
G G G A G U U U G m$^2$G C ac$^4$C G A G D Gm G D D D A A G G C m$_2^2$G Ψ C A G A Ψ U U A
Gm$^1$G C Ψ C U G A U A U C U U C G G A U G m$^5$C A A G G G T Ψ C G m$^1$A A U C C C U
U A G C U C U C A C C A

SEQ ID NO: 44 Saccharomyces Cer. tRNA-Leu3
G G A G G G U U G m$^2$G C ac$^4$C G A G D Gm G D C D A A G G C m$_2^2$G G C A G A Cm U U
A A m$^1$G A Ψ C U G U U G G A C G G U U G U C C Gm$^5$C G C G A G T Ψ C G m$^1$A A C C U
C G C A U C C U U C A C C A

SEQ ID NO: 45 Torulopsis Utilis tRNA-Leu
GGAUC U U U G m$^2$G C ac$^4$C G A G C Gm G D D U A A G G C m$_2^2$G C U C G A Cm U Cm
A A m$^1$G A Ψ C G A G U A U C G U A A G A U G m$^5$C A U G A G T Ψ C G m$^1$A A U C U C
A U A G G A U C C A C C A

Figure 10(8)

SEQ ID NO: 46 Candida Cylindra. tRNA-Leu
G G C C G U U U G m$_2^2$G C ac4C G A G D Gm G D C D A A G G C m$_2^2$G U C U G A Cm U Cm A A m$^1$G A Ψ C A G A Um C U C G U A A G A G G m$^5$C G U G U G T Ψ C G m$^1$A A C C A C A C A G C G G U C A C C A

SEQ ID NO: 47 Candida Cylindra. tRNA-Leu2
GGUUC U C U G G C ac$^4$C G A G D G G D C D A A G G C m$_2^2$G C A U G G Ψ U I A Gm$^1$G Ψ C C A U G U C U C U U C G G A G G m$^5$C G C G A G T Ψ C G m$^1$A A C C U C G C G G G A A U C A C C A

SEQ ID NO: 48 Candida Cylindra. tRNA-Leu3
GGCUC U C U G G C ac$^4$C G A G D G G D C D A A G G C m$_2^2$G C U A G G G U I A Gm$^1$G Ψ C C U A G U C U C U U C G G A G G m$^5$C G C G A G T Ψ C G m$^1$A A C C U C G C G G G A G U C A C C A

SEQ ID NO: 49 Phaseolus Vulgaris tRNA-Leu1
G U C A G G A U G m$_2^2$G C ac$^4$C G A G D G G D C $^{acp3U}$ A A G G C m$_2^2$G C C A G A C U unk A A $^{m1G}$ Ψ Ψ C U G G Um C U U C G A G A G A G G G m$^5$C G U G G G T Ψ C A m$^1$A A U C C C A C U U C U G A C A C C A

SEQ ID NO: 50 Phaseolus Vulgaris tRNA-Leu2
G U C A G G A U G m$_2^2$G C ac$^4$C G A G D G G D C acp3U A A G G C m$_2^2$G C C A G A C U unk A A m$^1$G Ψ Ψ C U G G Um C U U C G A A A G A G G G m$^5$C G U G G G T Ψ C A m$^1$A A U C C C A C U U C U G A C A C C A

SEQ ID NO: 51 Phaseolus Vulgaris tRNA-Leu3
G A U A G U U U G m$_2^2$G C ac$^4$C G A G D G G D C acp$^3$U A A G G C m$_2^2$G C C A G A Ψ U unk A G m$^1$G C Ψ C U G G Um C C G A A A unk G G G m$^5$C G U G G G U Ψ C A m$^1$A A U C C C A C A G C U G U C A C C A

SEQ ID NO: 52 Phaseolus Vulgaris tRNA-Leu4
G C U GG U U U G G C ac$^4$C G A G A G G D D A A G G C m$_2^2$G G A A G A C U unk A A m$^1$G A Ψ C U U C Um G C A G U C A A C U G C G m$^5$C A U G G G T Ψ C G m$^1$A A C C C C A U A G C C A G C A C C A

SEQ ID NO: 53 Solanum Tuberosum tRNA-Leu
G U C A G G A U G G C ac$^4$C G A G D G G D C acp$^3$U A A G G C m$_2^2$G C C A G A C U unk A A m$^1$G U Ψ C U G G Um C U U C G U A A G A G G G m$^5$C G U G G G T Ψ C A m$^1$A A U C C C A C U U C U G A C A C C A

Figure 10(9)

SEQ ID NO: 54 Cucumis Sativus tRNA-Leu
G U C A G G A U G m$^2$G C m$^5$C G A G D G G D C acp$^3$U A A G G C m$_2^2$G C C A G A C U unkU A A m1G Ψ Ψ C U G G Um C C U C U A A G G A G G G m$^5$C G U G G G T Ψ C A m$^1$A A U C C C A C U U C U G A C A C C A

SEQ ID NO: 55 Caenorhabdi.Eleg. tRNA-Leu
G G A G A G A U G G C ac$^4$C G A G C G G D C U A A G G C G C U G G U U U I A G G C A C C A G U C C C U U C G G G G G C G U G G G T U C G A A U C C C A C U C U C U U C A C C A

SEQ ID NO: 56 Mycoplasma Capric. tRNA-Leu2
C C C C A A G unkU G G C G G A A U A G G D A G m$^1$A C G C A U U G G A C U cmnm$^5$Um A A m$^6$A A Ψ C C A A C G G G C U U A A U A U C C U G U G C C G G U Ψ C A A G U C C G G C C U U G G G G A C C A

SEQ ID NO: 57 Mycoplasma Capric. tRNA-Leu1
G C C U U U U U G G C G G A A U D G G C A Gm1A C G C A U U A G A C U Cm A A m$^6$A A Ψ C U A A C G A A G A A A U U C G U A U C G G U Ψ C G A A U C C G A U A A A G G G C A C C A

SEQ ID NO: 58 Haloferax Volcanii YX tRNA-Leu5
G C G C G G G U A G C C A A fa7d7GU G G C C A A A GGCm$_2^2$G C A G C G C U mo$^5$U A G m$^1$G A C G C U G U G G U G U A G A C C U U m$^5$C G C A G G m$^1$Ψ Ψ Cm G A A C C C U G U C C C G C G C A C C A

SEQ ID NO: 59 Haloferax Volcanii YX tRNA-Leu4
GCGGG G G U G G C U G A fa$^7$d$^7$G C C A G G C C A A A A G C m$^2$G G C G G A C U U A Am$^1$G A Ψ C C G C U C C C G U A G G G G U U C G C G A Gm$^1$Ψ Ψ Cm G A A U C U C G U C C C C C G C A C C A

SEQ ID NO: 60 Haloferax Volcanii tRNA-Leu3
G C G U G G G U A G C C A A fa$^7$d$^7$G C C A G G C C A A C G G C m$_2^2$G C A G C G U U G A Gm$^1$G G m$^5$CG C U G U C C U G U A G A G G U Cm$^5$C G C C G G m$^1$Ψ Ψ Cm m$^1$I A A U C C G G U C C C A C G C A C C A

SEQ ID NO: 61 Haloferax Volcanii tRNA-Leu2
GCAGG G A U A G C C A Afa$^7$d$^7$G U C U G G C C A A C G G C m$_2^2$G C A G C G U U C A Gm$^1$G G C G C U G U C U C A U A G G A G U Cm$^5$C G C A G G m$^1$Ψ Ψ Cm m$^1$I A A U C C U G C U C C C U G C A C C A

SEQ ID NO: 62 Haloferax Volcanii tRNA-Leu1
G C G A G G G U A G C U A A fa$^7$d$^7$G U C A G G A A A A A G C m$_2^2$G G C G G A C U C A Am$^1$G A Ψ C C G C U C C C G U A G G G G U Cm5C G U G G G m$^1$Ψ Ψ Cm m$^1$I A A U C C C U C C C C U C G C A C C A

FIGURE 13

Percent cdc60 Bound with C10 at Equilibrium

| Additive | Free [C10], µM | % cdc60 Occupied |
|---|---|---|
| 20 mM ATP | 27.5 | 44.0 |
| 5 mM ATP | 30.1 | 29.9 |
| 2.5 mM ATP | 39.1 | 7.7 |
| 0.5 mM ATP | 34.8 | 7.4 |
| 0.1 mM ATP | 36.8 | -2.9 |
| 20 mM AMP | 33.3 | 59.0 |
| Nothing | 42.6 | -6.6 |

Assay conditions: 31 uM cdc60, 1 mM DTT, 0 mM Leucine, 0 mM tRNA, initial [C10] are 72 – 79 uM, pre-equilibrium. 1x AARS buffer C10 Inhibits LeuRS Aminoacylation of tRNA$^{leu}$

FIGURE 18A

5-chlorobenzo[c][1,2]oxaborol-1(3H)-ol, benzo[c][1,2]oxaborol-1(3H)-ol, 5-chloro-3-methylbenzo[c][1,2]oxaborol-1(3H)-ol, 6-fluoro-3,4-dihydrobenzo[c][1,2]oxaborinin-1-ol, 5,6-difluorobenzo[c][1,2]oxaborol-1(3H)-ol, 1-hydroxy-1,3-dihydrobenzo[c][1,2]oxaborole-5-carbonitrile, 5-methoxybenzo[c][1,2]oxaborol-1(3H)-ol, 5-methylbenzo[c][1,2]oxaborol-1(3H)-ol, 5-(hydroxymethyl)benzo[c][1,2]oxaborol-1(3H)-ol, 5-fluorobenzo[c][1,2]oxaborol-1(3H)-ol, naphtho[1,2-c][1,2]oxaborol-1(3H)-ol, 6-fluorobenzo[c][1,2]oxaborol-1(3H)-ol, 3-benzyl-3-methylbenzo[c][1,2]oxaborol-1(3H)-ol, 3-benzylbenzo[c][1,2]oxaborol-1(3H)-ol, 4-fluorobenzo[c][1,2]oxaborol-1(3H)-ol, *4-(1-hydroxy-1,3-dihydrobenzo[c][1,2]oxaborol-5-yloxy)benzonitril*, 4-(1-hydroxy-1,3-dihydrobenzo[c][1,2]oxaborol-6-yloxy)benzonitrile, 3-(1-hydroxy-1,3-dihydrobenzo[c][1,2]oxaborol-6-yloxy)benzonitrile, 6-(4-chlorophenoxy)benzo[c][1,2]oxaborol-1(3H)-ol, 6-phenoxybenzo[c][1,2]oxaborol-1(3H)-ol, 4-((1-hydroxy-1,3-dihydrobenzo[c][1,2]oxaborol-5-yloxy)methyl)benzonitrile, 2-(1-hydroxy-1,3-dihydrobenzo[c][1,2]oxaborol-5-yloxy)benzonitrile, 5-phenoxybenzo[c][1,2]oxaborol-1(3H)-ol, N,N-diethyl-4-(1-hydroxy-1,3-dihydrobenzo[c][1,2]oxaborol-5-yloxy)benzamide, (4-(1-hydroxy-1,3-dihydrobenzo[c][1,2]oxaborol-5-yloxy)phenyl)(morpholino)methanone, 4-(1-hydroxy-1,3-dihydrobenzo[c][1,2]oxaborol-5-yloxy)phthalonitrile, 6-(phenylthio)benzo[c][1,2]oxaborol-1(3H)-ol, 6-(4-(trifluoromethoxy)phenoxy)benzo[c][1,2]oxaborol-1(3H)-ol, N-(1-hydroxy-1,3-dihydrobenzo[c][1,2]oxaborol-5-yl)-N-methylbenzenesulfonamide, 6-(4-methoxyphenoxy)benzo[c][1,2]oxaborol-1(3H)-ol, 6-(4-methoxyphenylthio)benzo[c][1,2]oxaborol-1(3H)-ol, 6-(4-methoxyphenylsulfonyl)benzo[c][1,2]oxaborol-1(3H)-ol, 6-(4-methoxyphenylsulfinyl)benzo[c][1,2]oxaborol-1(3H)-ol, 5-(trifluoromethyl)benzo[c][1,2]oxaborol-1(3H)-ol, 4-(1-hydroxy-1,3-dihydrobenzo[c][1,2]oxaborol-4-yloxy)benzonitrile, 3-(1-hydroxy-1,3-dihydrobenzo[c][1,2]oxaborol-5-yloxy)benzonitrile, 4-(1-hydroxy-1,3-dihydrobenzo[c][1,2]oxaborol-5-yloxy)benzoic acid, 5-(4-(1H-tetrazol-5-yl)phenoxy)benzo[c][1,2]oxaborol-1(3H)-ol, 7-Hydroxy-2,1-oxaborolano[5,4-c]pyridine [[1,2]oxaborolo[3,4-c]pyridin-1(3H)-ol], Ethyl 2-(1-hydroxy-1,3-

FIGURE 18B dihydrobenzo[c][1,2]oxaborol-5-yloxy)acetate, 2-(1-hydroxy-1,3-dihydrobenzo[c][1,2]oxaborol-5-yloxy)acetic acid, 6-(thiophen-2-ylthio)benzo[c][1,2]oxaborol-1(3H)-ol, 6-(4-fluorophenylthio)benzo[c][1,2]oxaborol-1(3H)-ol, 1-(3-((1-hydroxy-1,3-dihydrobenzo[c][1,2]oxaborol-5-yloxy)methyl)phenyl)pentan-1-one, 2-(1-hydroxy-1,3-dihydrobenzo[c][1,2]oxaborol-5-yloxy)-1-(piperidin-1-yl)ethanone, 2-(1-hydroxy-1,3-dihydrobenzo[c][1,2]oxaborol-5-yloxy)-1-(4-(pyrimidin-2-yl)piperazin-1-yl)ethanone, 6-(4-(pyridin-2-yl)piperazin-1-yl)benzo[c][1,2]oxaborol-1(3H)-ol, 6-nitrobenzo[c][1,2]oxaborol-1(3H)-ol, 6-aminobenzo[c][1,2]oxaborol-1(3H)-ol, 6-(dimethylamino)benzo[c][1,2]oxaborol-1(3H)-ol, N-(1-hydroxy-1,3-dihydrobenzo[c][1,2]oxaborol-6-yl)benzamide, 6-(4-phenylpiperazin-1-yl)benzo[c][1,2]oxaborol-1(3H)-ol, 6-(1H-indol-1-yl)benzo[c][1,2]oxaborol-1(3H)-ol, 6-morpholinobenzo[c][1,2]oxaborol-1(3H)-ol, 6-(1-hydroxy-1,3-dihydrobenzo[c][1,2]oxaborol-5-yloxy)nicotinonitrile, 5-fluoro-6-nitrobenzo[c][1,2]oxaborol-1(3H)-ol, 5-bromo-6-(hydroxymethyl)benzo[c][1,2]oxaborol-1(3H)-ol, 3,7-dihydro-1,5-dihydroxy-1H,3H-benzo[1,2-c:4,5-c']bis[1,2]oxaborole, 1-(1-hydroxy-1,3-dihydrobenzo[c][1,2]oxaborol-6-yl)-3-phenylurea, N-(1-hydroxy-1,3-dihydrobenzo[c][1,2]oxaborol-6-yl)benzenesulfonamide, N-(1-hydroxy-1,3-dihydrobenzo[c][1,2]oxaborol-6-yl)acetamide, 7-(hydroxymethyl)benzo[c][1,2]oxaborol-1(3H)-ol, 7-methylbenzo[c][1,2]oxaborol-1(3H)-ol, 6-(3-(phenylthio)-1H-indol-1-yl)benzo[c][1,2]oxaborol-1(3H)-ol, 3-(1-(1-hydroxy-1,3-dihydrobenzo[c][1,2]oxaborol-6-yl)-1H-indol-3-ylthio)propanenitrile, 6-(5-methoxy-1H-indol-1-yl)benzo[c][1,2]oxaborol-1(3H)-ol, 6-amino-5-fluorobenzo[c][1,2]oxaborol-1(3H)-ol, 6-(benzylamino)-5-fluorobenzo[c][1,2]oxaborol-1(3H)-ol, 6-(5-methoxy-3-(phenylthio)-1H-indol-1-yl)benzo[c][1,2]oxaborol-1(3H)-ol, 3-(1-(1-hydroxy-1,3-dihydrobenzo[c][1,2]oxaborol-6-yl)-5-methoxy-1H-indol-3-ylthio)propanenitrile, 4-(1-hydroxy-1,3-dihydrobenzo[c][1,2]oxaborol-7-yloxy)benzonitrile, 6-(5-chloro-1H-indol-1-yl)benzo[c][1,2]oxaborol-1(3H)-ol, 3-(5-chloro-1-(1-hydroxy-1,3-dihydrobenzo[c][1,2]oxaborol-6-yl)-1H-indol-3-ylthio)propanenitrile, 6-(benzylamino)benzo[c][1,2]oxaborol-1(3H)-ol, 6-(dibenzylamino)benzo[c][1,2]oxaborol-1(3H)-ol, 7-(4-(1H-tetrazol-5-

FIGURE 18C yl)phenoxy)benzo[c][1,2]oxaborol-1(3H)-ol, 6-(5-chloro-3-(phenylthio)-1H-indol-1-yl)benzo[c][1,2]oxaborol-1(3H)-ol, 3,4-dihydro-1H-thieno[3,2-c][1,2]oxaborinin-1-ol, 6-(4-(pyrimidin-2-yl)piperazin-1-yl)benzo[c][1,2]oxaborol-1(3H)-ol, 7-(benzyloxy)benzo[c][1,2]oxaborol-1(3H)-ol, 4-(1-hydroxy-1,3-dihydrobenzo[c][1,2]oxaborol-6-ylthio)pyridinium chloride, 6-(pyridin-2-ylthio)benzo[c][1,2]oxaborol-1(3H)-ol, 6-(pyridin-2-ylthio)benzo[c][1,2]oxaborol-1(3H)-ol, 7-fluorobenzo[c][1,2]oxaborol-1(3H)-ol, 6-(4-(trifluoromethyl)phenoxybenzo[c][1,2]oxaborol-1(3H)-ol, 6-(4-chlorophenylthio)benzo[c][1,2]oxaborol-1(3H)-ol, 6-(4-chlorophenylsulfinyl)benzo[c][1,2]oxaborol-1(3H)-ol, 6-(4-chlorophenylsulfonyl)benzo[c][1,2]oxaborol-1(3H)-ol, N-(1-hydroxy-1,3-dihydrobenzo[c][1,2]oxaborol-5-yl)-N-(phenylsulfonyl)benzenesulfonamide, 6-(4-(trifluoromethyl)phenylthio)benzo[c][1,2]oxaborol-1(3H)-ol, 6-(4-(trifluoromethyl)phenylsulfinyl)benzo[c][1,2]oxaborol-1(3H)-ol, 6-(4-(methylthio)phenylthio)benzo[c][1,2]oxaborol-1(3H)-ol, 6-(p-tolylthio)benzo[c][1,2]oxaborol-1(3H)-ol, and 3-((1-hydroxy-1,3-dihydrobenzo[c][1,2]oxaborol-5-yloxy)methyl)benzonitrile.

| No. | $R^{9a}$ | $R^{10a}$ | $R^{11a}$ | $R^{12a}$ |
|---|---|---|---|---|
| 1 | F | H | H | H |
| 2 | H | F | H | H |
| 3 | H | H | F | H |
| 4 | H | H | H | F |
| 5 | F | F | H | H |
| 6 | H | F | F | H |
| 7 | H | H | F | F |
| 8 | F | H | F | H |
| 9 | H | F | H | F |
| 10 | F | H | H | F |
| 11 | H | F | F | F |
| 12 | F | H | F | F |
| 13 | F | F | H | F |
| 14 | F | F | F | H |
| 15 | F | F | F | F |
| 16 | Cl | H | H | H |
| 17 | H | Cl | H | H |
| 18 | H | H | Cl | H |
| 19 | H | H | H | Cl |
| 20 | Cl | Cl | H | H |
| 21 | H | Cl | Cl | H |
| 22 | H | H | Cl | Cl |
| 23 | Cl | H | Cl | H |
| 24 | H | Cl | H | Cl |
| 25 | Cl | H | H | Cl |
| 26 | H | Cl | Cl | Cl |
| 27 | Cl | H | Cl | Cl |
| 28 | Cl | Cl | H | Cl |
| 29 | Cl | Cl | Cl | H |
| 30 | Cl | Cl | Cl | Cl |
| 31 | Br | H | H | H |

FIGURE 19B

| No. | $R^{9a}$ | $R^{10a}$ | $R^{11a}$ | $R^{12a}$ |
|---|---|---|---|---|
| 32 | H | Br | H | H |
| 33 | H | H | Br | H |
| 34 | H | H | H | Br |
| 35 | Br | Br | H | H |
| 36 | H | Br | Br | H |
| 37 | H | H | Br | Br |
| 38 | Br | H | Br | H |
| 39 | H | Br | H | Br |
| 40 | Br | H | H | Br |
| 41 | H | Br | Br | Br |
| 42 | Br | H | Br | Br |
| 43 | Br | Br | H | Br |
| 44 | Br | Br | Br | H |
| 45 | Br | Br | Br | Br |
| 46 | -CN | H | H | H |
| 47 | H | -CN | H | H |
| 48 | H | H | -CN | H |
| 49 | H | H | H | -CN |
| 50 | -CN | -CN | H | H |
| 51 | H | -CN | -CN | H |
| 52 | H | H | -CN | -CN |
| 53 | -CN | H | -CN | H |
| 54 | H | -CN | H | -CN |
| 55 | -CN | H | H | -CN |
| 56 | H | -CN | -CN | -CN |
| 57 | -CN | H | -CN | -CN |
| 58 | -CN | -CN | H | -CN |
| 59 | -CN | -CN | -CN | H |
| 60 | -CN | -CN | -CN | -CN |
| 61 | -Me | H | H | H |
| 62 | H | -Me | H | H |
| 63 | H | H | -Me | H |
| 64 | H | H | H | -Me |
| 65 | -Me | -Me | H | H |
| 66 | H | -Me | -Me | H |
| 67 | H | H | -Me | -Me |
| 68 | -Me | H | -Me | H |
| 69 | H | -Me | H | -Me |
| 70 | -Me | H | H | -Me |
| 71 | H | -Me | -Me | -Me |
| 72 | -Me | H | -Me | -Me |

FIGURE 19C

| No. | $R^{9a}$ | $R^{10a}$ | $R^{11a}$ | $R^{12a}$ |
|---|---|---|---|---|
| 73 | -Me | -Me | H | -Me |
| 74 | -Me | -Me | -Me | H |
| 75 | -Me | -Me | -Me | -Me |
| 76 | -CH$_2$OH | H | H | H |
| 77 | H | -CH$_2$OH | H | H |
| 78 | H | H | -CH$_2$OH | H |
| 79 | H | H | H | -CH$_2$OH |
| 80 | -CH$_2$OH | -CH$_2$OH | H | H |
| 81 | H | -CH$_2$OH | -CH$_2$OH | H |
| 82 | H | H | -CH$_2$OH | -CH$_2$OH |
| 83 | -CH$_2$OH | H | -CH$_2$OH | H |
| 84 | H | -CH$_2$OH | H | -CH$_2$OH |
| 85 | -CH$_2$OH | H | H | -CH$_2$OH |
| 86 | H | -CH$_2$OH | -CH$_2$OH | -CH$_2$OH |
| 87 | -CH$_2$OH | H | -CH$_2$OH | -CH$_2$OH |
| 88 | -CH$_2$OH | -CH$_2$OH | H | -CH$_2$OH |
| 89 | -CH$_2$OH | -CH$_2$OH | -CH$_2$OH | H |
| 90 | -CH$_2$OH | -CH$_2$OH | -CH$_2$OH | -CH$_2$OH |
| 91 | -benzyl | H | H | H |
| 92 | H | -benzyl | H | H |
| 93 | H | H | -benzyl | H |
| 94 | H | H | H | -benzyl |
| 95 | -benzyl | -benzyl | H | H |
| 96 | H | -benzyl | -benzyl | H |
| 97 | H | H | -benzyl | -benzyl |
| 98 | -benzyl | H | -benzyl | H |
| 99 | H | -benzyl | H | -benzyl |
| 100 | -benzyl | H | H | -benzyl |
| 101 | H | -benzyl | -benzyl | -benzyl |
| 102 | -benzyl | H | -benzyl | -benzyl |
| 103 | -benzyl | -benzyl | H | -benzyl |
| 104 | -benzyl | -benzyl | -benzyl | H |
| 105 | -benzyl | -benzyl | -benzyl | -benzyl |
| 106 | -OMe | H | H | H |
| 107 | H | -OMe | H | H |
| 108 | H | H | -OMe | H |
| 109 | H | H | H | -OMe |
| 110 | -OMe | -OMe | H | H |
| 111 | H | -OMe | -OMe | H |
| 112 | H | H | -OMe | -OMe |
| 113 | -OMe | H | -OMe | H |

FIGURE 19D

| No. | $R^{9a}$ | $R^{10a}$ | $R^{11a}$ | $R^{12a}$ |
|---|---|---|---|---|
| 114 | -OMe | H | H | -OMe |
| 115 | H | -OMe | -OMe | -OMe |
| 116 | -OMe | H | -OMe | -OMe |
| 117 | -OMe | -OMe | H | -OMe |
| 118 | -OMe | -OMe | -OMe | H |
| 119 | -OMe | -OMe | -OMe | -OMe |
| 120 | -4-cyanophenoxy | H | H | H |
| 121 | H | -4-cyanophenoxy | H | H |
| 122 | H | H | -4-cyanophenoxy | H |
| 123 | H | H | H | -4-cyanophenoxy |
| 124 | -4-cyanophenoxy | -4-cyanophenoxy | H | H |
| 125 | H | -4-cyanophenoxy | -4-cyanophenoxy | H |
| 126 | H | H | -4-cyanophenoxy | -4-cyanophenoxy |
| 127 | -4-cyanophenoxy | H | -4-cyanophenoxy | H |
| 128 | H | -4-cyanophenoxy | H | -4-cyanophenoxy |
| 129 | -4-cyanophenoxy | H | H | -4-cyanophenoxy |
| 130 | H | -4-cyanophenoxy | -4-cyanophenoxy | -4-cyanophenoxy |
| 131 | -4-cyanophenoxy | H | -4-cyanophenoxy | -4-cyanophenoxy |
| 132 | -4-cyanophenoxy | -4-cyanophenoxy | H | -4-cyanophenoxy |
| 133 | -4-cyanophenoxy | -4-cyanophenoxy | -4-cyanophenoxy | H |
| 134 | -4-cyanophenoxy | -4-cyanophenoxy | -4-cyanophenoxy | -4-cyanophenoxy |
| 135 | -3-cyanophenoxy | H | H | H |
| 136 | H | -3-cyanophenoxy | H | H |
| 137 | H | H | -3-cyanophenoxy | H |
| 138 | H | H | H | -3-cyanophenoxy |
| 139 | -3-cyanophenoxy | -3-cyanophenoxy | H | H |
| 140 | H | -3-cyanophenoxy | -3-cyanophenoxy | H |
| 141 | H | H | -3-cyanophenoxy | -3-cyanophenoxy |
| 142 | -3-cyanophenoxy | H | -3-cyanophenoxy | H |
| 143 | H | -3-cyanophenoxy | H | -3-cyanophenoxy |
| 144 | -3-cyanophenoxy | H | H | -3-cyanophenoxy |
| 145 | H | -3-cyanophenoxy | -3-cyanophenoxy | -3-cyanophenoxy |
| 146 | -3-cyanophenoxy | H | -3-cyanophenoxy | -3-cyanophenoxy |
| 147 | -3-cyanophenoxy | -3-cyanophenoxy | H | -3-cyanophenoxy |
| 148 | -3-cyanophenoxy | -3-cyanophenoxy | -3-cyanophenoxy | H |
| 149 | -3-cyanophenoxy | -3-cyanophenoxy | -3-cyanophenoxy | -3-cyanophenoxy |
| 150 | -2-cyanophenoxy | H | H | H |
| 151 | H | -2-cyanophenoxy | H | H |
| 152 | H | H | -2-cyanophenoxy | H |
| 153 | H | H | H | -2-cyanophenoxy |

FIGURE 19E

| No. | $R^{9a}$ | $R^{10a}$ | $R^{11a}$ | $R^{12a}$ |
|---|---|---|---|---|
| 154 | -2-cyanophenoxy | -2-cyanophenoxy | H | H |
| 155 | H | -2-cyanophenoxy | -2-cyanophenoxy | H |
| 156 | H | H | -2-cyanophenoxy | -2-cyanophenoxy |
| 157 | -2-cyanophenoxy | H | -2-cyanophenoxy | H |
| 158 | H | -2-cyanophenoxy | H | -2-cyanophenoxy |
| 159 | -2-cyanophenoxy | H | H | -2-cyanophenoxy |
| 160 | H | -2-cyanophenoxy | -2-cyanophenoxy | -2-cyanophenoxy |
| 161 | -2-cyanophenoxy | H | -2-cyanophenoxy | -2-cyanophenoxy |
| 162 | -2-cyanophenoxy | -2-cyanophenoxy | H | -2-cyanophenoxy |
| 163 | -2-cyanophenoxy | -2-cyanophenoxy | -2-cyanophenoxy | H |
| 164 | -2-cyanophenoxy | -2-cyanophenoxy | -2-cyanophenoxy | -2-cyanophenoxy |
| 165 | -4-chlorophenoxy | H | H | H |
| 166 | H | -4-chlorophenoxy | H | H |
| 167 | H | H | -4-chlorophenoxy | H |
| 168 | H | H | H | -4-chlorophenoxy |
| 169 | -4-chlorophenoxy | -4-chlorophenoxy | H | H |
| 170 | H | -4-chlorophenoxy | -4-chlorophenoxy | H |
| 171 | H | H | -4-chlorophenoxy | -4-chlorophenoxy |
| 172 | -4-chlorophenoxy | H | -4-chlorophenoxy | H |
| 173 | H | -4-chlorophenoxy | H | -4-chlorophenoxy |
| 174 | -4-chlorophenoxy | H | H | -4-chlorophenoxy |
| 175 | H | -4-chlorophenoxy | -4-chlorophenoxy | -4-chlorophenoxy |
| 176 | -4-chlorophenoxy | H | -4-chlorophenoxy | -4-chlorophenoxy |
| 177 | -4-chlorophenoxy | -4-chlorophenoxy | H | -4-chlorophenoxy |
| 178 | -4-chlorophenoxy | -4-chlorophenoxy | -4-chlorophenoxy | H |
| 179 | -4-chlorophenoxy | -4-chlorophenoxy | -4-chlorophenoxy | -4-chlorophenoxy |
| 180 | -3-chlorophenoxy | H | H | H |
| 181 | H | -3-chlorophenoxy | H | H |
| 182 | H | H | -3-chlorophenoxy | H |
| 183 | H | H | H | -3-chlorophenoxy |
| 184 | -3-chlorophenoxy | -3-chlorophenoxy | H | H |
| 185 | H | -3-chlorophenoxy | -3-chlorophenoxy | H |
| 186 | H | H | -3-chlorophenoxy | -3-chlorophenoxy |
| 187 | -3-chlorophenoxy | H | -3-chlorophenoxy | H |
| 188 | H | -3-chlorophenoxy | H | -3-chlorophenoxy |
| 189 | -3-chlorophenoxy | H | H | -3-chlorophenoxy |
| 190 | H | -3-chlorophenoxy | -3-chlorophenoxy | -3-chlorophenoxy |
| 191 | -3-chlorophenoxy | H | -3-chlorophenoxy | -3-chlorophenoxy |
| 192 | -3-chlorophenoxy | -3-chlorophenoxy | H | -3-chlorophenoxy |
| 193 | -3-chlorophenoxy | -3-chlorophenoxy | -3-chlorophenoxy | H |
| 194 | -3-chlorophenoxy | -3-chlorophenoxy | -3-chlorophenoxy | -3-chlorophenoxy |

FIGURE 19F

| No. | $R^{9a}$ | $R^{10a}$ | $R^{11a}$ | $R^{12a}$ |
|---|---|---|---|---|
| 195 | -2-chlorophenoxy | H | H | H |
| 196 | H | -2-chlorophenoxy | H | H |
| 197 | H | H | -2-chlorophenoxy | H |
| 198 | H | H | H | -2-chlorophenoxy |
| 199 | -2-chlorophenoxy | -2-chlorophenoxy | H | H |
| 200 | H | -2-chlorophenoxy | -2-chlorophenoxy | H |
| 201 | H | H | -2-chlorophenoxy | -2-chlorophenoxy |
| 202 | -2-chlorophenoxy | H | -2-chlorophenoxy | H |
| 203 | H | -2-chlorophenoxy | H | -2-chlorophenoxy |
| 204 | -2-chlorophenoxy | H | H | -2-chlorophenoxy |
| 205 | H | -2-chlorophenoxy | -2-chlorophenoxy | -2-chlorophenoxy |
| 206 | -2-chlorophenoxy | H | -2-chlorophenoxy | -2-chlorophenoxy |
| 207 | -2-chlorophenoxy | -2-chlorophenoxy | H | -2-chlorophenoxy |
| 208 | -2-chlorophenoxy | -2-chlorophenoxy | -2-chlorophenoxy | H |
| 209 | -2-chlorophenoxy | -2-chlorophenoxy | -2-chlorophenoxy | -2-chlorophenoxy |
| 210 | -phenoxy | H | H | H |
| 211 | H | -phenoxy | H | H |
| 212 | H | H | -phenoxy | H |
| 213 | H | H | H | -phenoxy |
| 214 | -phenoxy | -phenoxy | H | H |
| 215 | H | -phenoxy | -phenoxy | H |
| 216 | H | H | -phenoxy | -phenoxy |
| 217 | -phenoxy | H | -phenoxy | H |
| 218 | H | -phenoxy | H | -phenoxy |
| 219 | -phenoxy | H | H | -phenoxy |
| 220 | H | -phenoxy | -phenoxy | -phenoxy |
| 221 | -phenoxy | H | -phenoxy | -phenoxy |
| 222 | -phenoxy | -phenoxy | H | -phenoxy |
| 223 | -phenoxy | -phenoxy | -phenoxy | H |
| 224 | -phenoxy | -phenoxy | -phenoxy | -phenoxy |
| 225 | -4-cyanophenylthio | H | H | H |
| 226 | H | -4-cyanophenylthio | H | H |
| 227 | H | H | -4-cyanophenylthio | H |
| 228 | H | H | H | -4-cyanophenylthio |
| 229 | -4-cyanophenylthio | -4-cyanophenylthio | H | H |
| 230 | H | -4-cyanophenylthio | -4-cyanophenylthio | H |
| 231 | H | H | -4-cyanophenylthio | -4-cyanophenylthio |
| 232 | -4-cyanophenylthio | H | -4-cyanophenylthio | H |
| 233 | H | -4-cyanophenylthio | H | -4-cyanophenylthio |
| 234 | -4-cyanophenylthio | H | H | -4-cyanophenylthio |
| 235 | H | -4-cyanophenylthio | -4-cyanophenylthio | -4-cyanophenylthio |

FIGURE 19G

| No. | $R^{9a}$ | $R^{10a}$ | $R^{11a}$ | $R^{12a}$ |
|---|---|---|---|---|
| 236 | -4-cyanophenylthio | H | -4-cyanophenylthio | -4-cyanophenylthio |
| 237 | -4-cyanophenylthio | -4-cyanophenylthio | H | -4-cyanophenylthio |
| 238 | -4-cyanophenylthio | -4-cyanophenylthio | -4-cyanophenylthio | H |
| 239 | -4-cyanophenylthio | -4-cyanophenylthio | -4-cyanophenylthio | -4-cyanophenylthio |
| 240 | -3-cyanophenylthio | H | H | H |
| 241 | H | 3-cyanophenylthio | H | H |
| 242 | H | H | -3-cyanophenylthio | H |
| 243 | H | H | H | -3-cyanophenylthio |
| 244 | -3-cyanophenylthio | -3-cyanophenylthio | H | H |
| 245 | H | -3-cyanophenylthio | -3-cyanophenylthio | H |
| 246 | H | H | -3-cyanophenylthio | -3-cyanophenylthio |
| 247 | -3-cyanophenylthio | H | -3-cyanophenylthio | H |
| 248 | H | -3-cyanophenylthio | H | -3-cyanophenylthio |
| 249 | -3-cyanophenylthio | H | H | -3-cyanophenylthio |
| 250 | H | -3-cyanophenylthio | -3-cyanophenylthio | -3-cyanophenylthio |
| 251 | -3-cyanophenylthio | H | -3-cyanophenylthio | -3-cyanophenylthio |
| 252 | -3-cyanophenylthio | -3-cyanophenylthio | H | -3-cyanophenylthio |
| 253 | -3-cyanophenylthio | -3-cyanophenylthio | -3-cyanophenylthio | H |
| 254 | -3-cyanophenylthio | -3-cyanophenylthio | -3-cyanophenylthio | -3-cyanophenylthio |
| 255 | -2-cyanophenylthio | H | H | H |
| 256 | H | -2-cyanophenylthio | H | H |
| 257 | H | H | -2-cyanophenylthio | H |
| 258 | H | H | H | -2-cyanophenylthio |
| 259 | -2-cyanophenylthio | -2-cyanophenylthio | H | H |
| 260 | H | -2-cyanophenylthio | -2-cyanophenylthio | H |
| 261 | H | H | -2-cyanophenylthio | -2-cyanophenylthio |
| 262 | -2-cyanophenylthio | H | -2-cyanophenylthio | H |
| 263 | H | -2-cyanophenylthio | H | -2-cyanophenylthio |
| 264 | -2-cyanophenylthio | H | H | -2-cyanophenylthio |
| 265 | H | -2-cyanophenylthio | -2-cyanophenylthio | -2-cyanophenylthio |
| 266 | 2-cyanophenylthio | H | -2-cyanophenylthio | -2-cyanophenylthio |
| 267 | 2-cyanophenylthio | -2-cyanophenylthio | H | -2-cyanophenylthio |
| 268 | 2-cyanophenylthio | -2-cyanophenylthio | -2-cyanophenylthio | H |
| 269 | 2-cyanophenylthio | -2-cyanophenylthio | -2-cyanophenylthio | -2-cyanophenylthio |
| 270 | -OCH$_2$C(O)OH | H | H | H |
| 271 | H | -OCH$_2$C(O)OH | H | H |
| 272 | H | H | -OCH$_2$C(O)OH | H |
| 273 | H | H | H | -OCH$_2$C(O)OH |
| 274 | F | -OCH$_2$C(O)OH | H | H |
| 275 | H | -OCH$_2$C(O)OH | F | H |

FIGURE 19H

| No. | $R^{9a}$ | $R^{10a}$ | $R^{11a}$ | $R^{12a}$ |
|---|---|---|---|---|
| 276 | H | -OCH$_2$C(O)OH | H | F |
| 277 | F | -OCH$_2$C(O)OH | F | H |
| 278 | H | -OCH$_2$C(O)OH | F | F |
| 279 | F | -OCH$_2$C(O)OH | F | F |
| 280 | -NMeS(O)$_2$Ph | H | H | H |
| 281 | H | -NMeS(O)$_2$Ph | H | H |
| 282 | H | H | -NMeS(O)$_2$Ph | H |
| 283 | H | H | H | -NMeS(O)$_2$Ph |
| 284 | F | -NMeS(O)$_2$Ph | H | H |
| 285 | H | -NMeS(O)$_2$Ph | F | H |
| 286 | H | -NMeS(O)$_2$Ph | H | F |
| 287 | F | -NMeS(O)$_2$Ph | F | H |
| 288 | H | -NMeS(O)$_2$Ph | F | F |
| 289 | F | -NMeS(O)$_2$Ph | F | F |
| 290 | -CH$_2$OH | H | H | H |
| 291 | H | -CH$_2$OH | H | H |
| 292 | H | H | -CH$_2$OH | H |
| 293 | H | H | H | -CH$_2$OH |
| 294 | -CH$_2$OH | F | H | H |
| 295 | -CH$_2$OH | H | F | H |
| 296 | -CH$_2$OH | H | H | F |
| 297 | -CH$_2$OH | Cl | H | H |
| 298 | -CH$_2$OH | H | Cl | H |
| 299 | -CH$_2$OH | H | H | Cl |
| 300 | F | -CH$_2$OH | H | H |
| 301 | H | -CH$_2$OH | F | H |
| 302 | H | -CH$_2$OH | H | F |
| 303 | Cl | -CH$_2$OH | H | H |
| 304 | H | -CH$_2$OH | Cl | H |
| 305 | H | -CH$_2$OH | H | Cl |
| 306 | F | H | -CH$_2$OH | H |
| 307 | H | F | -CH$_2$OH | H |
| 308 | H | H | -CH$_2$OH | F |
| 309 | Cl | H | -CH$_2$OH | H |
| 310 | H | Cl | -CH$_2$OH | H |
| 311 | H | H | -CH$_2$OH | Cl |
| 312 | F | H | H | -CH$_2$OH |
| 313 | H | F | H | -CH$_2$OH |
| 314 | H | H | F | -CH$_2$OH |
| 315 | Cl | H | H | -CH$_2$OH |
| 316 | H | Cl | H | -CH$_2$OH |

FIGURE 19I

| No. | $R^{9a}$ | $R^{10a}$ | $R^{11a}$ | $R^{12a}$ |
|---|---|---|---|---|
| 317 | H | H | Cl | -CH$_2$OH |
| 318 | F | -CH$_2$OH | F | H |
| 319 | H | -CH$_2$OH | F | F |
| 320 | F | -CH$_2$OH | F | F |
| 321 | H | -NH$_2$ | H | H |
| 322 | H | H | -NH$_2$ | H |
| 323 | H | H | H | -NH$_2$ |
| 324 | -NH$_2$ | F | H | H |
| 325 | -NH$_2$ | H | F | H |
| 326 | -NH$_2$ | H | H | F |
| 327 | -NH$_2$ | Cl | H | H |
| 328 | -NH$_2$ | H | Cl | H |
| 329 | -NH$_2$ | H | H | Cl |
| 330 | F | -NH$_2$ | H | H |
| 331 | H | -NH$_2$ | F | H |
| 332 | H | -NH$_2$ | H | F |
| 333 | Cl | -NH$_2$ | H | H |
| 334 | H | -NH$_2$ | Cl | H |
| 335 | H | -NH$_2$ | H | Cl |
| 336 | F | H | -NH$_2$ | H |
| 337 | H | F | -NH$_2$ | H |
| 338 | H | H | -NH$_2$ | F |
| 339 | Cl | H | -NH$_2$ | H |
| 340 | H | Cl | -NH$_2$ | H |
| 341 | H | H | -NH$_2$ | Cl |
| 342 | F | H | H | -NH$_2$ |
| 343 | H | F | H | -NH$_2$ |
| 344 | H | H | F | -NH$_2$ |
| 345 | Cl | H | H | -NH$_2$ |
| 346 | H | Cl | H | -NH$_2$ |
| 347 | H | H | Cl | -NH$_2$ |
| 348 | F | -NH$_2$ | F | H |
| 349 | H | -NH$_2$ | F | F |
| 350 | F | -NH$_2$ | F | F |
| 351 | -O(4-CN-Ph) | H | H | H |
| 352 | H | -O(4-CN-Ph) | H | H |
| 353 | H | H | -O(4-CN-Ph) | H |
| 354 | H | H | H | -O(4-CN-Ph) |
| 355 | F | -O(4-CN-Ph) | H | H |
| 356 | H | -O(4-CN-Ph) | F | H |
| 357 | H | -O(4-CN-Ph) | H | F |

FIGURE 19J

| No. | $R^{9a}$ | $R^{10a}$ | $R^{11a}$ | $R^{12a}$ |
|---|---|---|---|---|
| 358 | F | -O(4-CN-Ph) | F | H |
| 359 | H | -O(4-CN-Ph) | F | F |
| 360 | F | -O(4-CN-Ph) | F | F |
| 361 | 3-(phenylthio)-1H-indol-1-yl | H | H | H |
| 362 | H | 3-(phenylthio)-1H-indol-1-yl | H | H |
| 363 | H | H | 3-(phenylthio)-1H-indol-1-yl | H |
| 364 | H | H | H | 3-(phenylthio)-1H-indol-1-yl |
| 365 | F | 3-(phenylthio)-1H-indol-1-yl | H | H |
| 366 | H | 3-(phenylthio)-1H-indol-1-yl | F | H |
| 367 | H | 3-(phenylthio)-1H-indol-1-yl | H | F |
| 368 | F | 3-(phenylthio)-1H-indol-1-yl | F | H |
| 369 | H | 3-(phenylthio)-1H-indol-1-yl | F | F |
| 370 | F | 3-(phenylthio)-1H-indol-1-yl | F | F |
| 371 | dibenzylamino | H | H | H |
| 372 | H | dibenzylamino | H | H |
| 373 | H | H | dibenzylamino | H |
| 374 | H | H | H | dibenzylamino |
| 375 | F | dibenzylamino | H | H |
| 376 | H | dibenzylamino | F | H |
| 377 | H | dibenzylamino | H | F |
| 378 | F | dibenzylamino | F | H |
| 379 | H | dibenzylamino | F | F |
| 380 | F | dibenzylamino | F | F |
| 381 | -S(O)$_2$(4-Cl-Ph) | H | H | H |
| 382 | H | -S(O)$_2$(4-Cl-Ph) | H | H |
| 383 | H | H | -S(O)$_2$(4-Cl-Ph) | H |
| 384 | H | H | H | -S(O)$_2$(4-Cl-Ph) |
| 385 | F | -S(O)$_2$(4-Cl-Ph) | H | H |
| 386 | H | -S(O)$_2$(4-Cl-Ph) | F | H |
| 387 | H | -S(O)$_2$(4-Cl-Ph) | H | F |
| 388 | F | -S(O)$_2$(4-Cl-Ph) | F | H |
| 389 | H | -S(O)$_2$(4-Cl-Ph) | F | F |
| 390 | F | -S(O)$_2$(4-Cl-Ph) | F | F |
| 391 | -S(4-pyridyl) | H | H | H |
| 392 | H | -S(4-pyridyl) | H | H |
| 393 | H | H | -S(4-pyridyl) | H |

FIGURE 19K

| No. | $R^{9a}$ | $R^{10a}$ | $R^{11a}$ | $R^{12a}$ |
|---|---|---|---|---|
| 394 | H | H | H | -S(4-pyridyl) |
| 395 | F | -S(4-pyridyl) | H | H |
| 396 | H | -S(4-pyridyl) | F | H |
| 397 | H | -S(4-pyridyl) | H | F |
| 398 | F | -S(4-pyridyl) | F | H |
| 399 | H | -S(4-pyridyl) | F | F |
| 400 | F | -S(4-pyridyl) | F | F |
| 401 | -NHCH$_2$Ph | H | H | H |
| 402 | H | -NHCH$_2$Ph | H | H |
| 403 | H | H | -NHCH$_2$Ph | H |
| 404 | H | H | H | -NHCH$_2$Ph |
| 405 | F | -NHCH$_2$Ph | H | H |
| 406 | H | -NHCH$_2$Ph | F | H |
| 407 | H | -NHCH$_2$Ph | H | F |
| 408 | F | -NHCH$_2$Ph | F | H |
| 409 | H | -NHCH$_2$Ph | F | F |
| 410 | F | -NHCH$_2$Ph | F | F |

FIGURE 20A

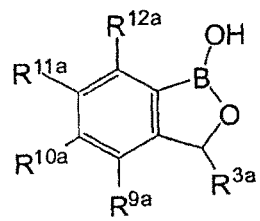

| No. | R³ᵃ | R⁹ᵃ | R¹⁰ᵃ | R¹¹ᵃ | R¹²ᵃ |
|---|---|---|---|---|---|
| 1 | -CH₂Ph | F | H | H | H |
| 2 | -CH₂Ph | H | F | H | H |
| 3 | -CH₂Ph | H | H | F | H |
| 4 | -CH₂Ph | H | H | H | F |
| 5 | -CH₂Ph | F | F | H | H |
| 6 | -CH₂Ph | H | F | F | H |
| 7 | -CH₂Ph | H | H | F | F |
| 8 | -CH₂Ph | F | H | F | H |
| 9 | -CH₂Ph | H | F | H | F |
| 10 | -CH₂Ph | F | H | H | F |
| 11 | -CH₂Ph | H | F | F | F |
| 12 | -CH₂Ph | F | H | F | F |
| 13 | -CH₂Ph | F | F | H | F |
| 14 | -CH₂Ph | F | F | F | H |
| 15 | -CH₂Ph | F | F | F | F |
| 16 | -CH₂Ph | -OCH₂C(O)OH | H | H | H |
| 17 | -CH₂Ph | H | -OCH₂C(O)OH | H | H |
| 18 | -CH₂Ph | H | H | -OCH₂C(O)OH | H |
| 19 | -CH₂Ph | H | H | H | -OCH₂C(O)OH |
| 20 | -CH₂Ph | F | -OCH₂C(O)OH | H | H |
| 21 | -CH₂Ph | H | -OCH₂C(O)OH | F | H |
| 22 | -CH₂Ph | H | -OCH₂C(O)OH | H | F |
| 23 | -CH₂Ph | F | -OCH₂C(O)OH | F | H |
| 24 | -CH₂Ph | H | -OCH₂C(O)OH | F | F |
| 25 | -CH₂Ph | F | -OCH₂C(O)OH | F | F |
| 26 | -CH₂Ph | -NMeS(O)₂Ph | H | H | H |
| 27 | -CH₂Ph | H | -NMeS(O)₂Ph | H | H |
| 28 | -CH₂Ph | H | H | -NMeS(O)₂Ph | H |
| 29 | -CH₂Ph | H | H | H | -NMeS(O)₂Ph |
| 30 | -CH₂Ph | F | -NMeS(O)₂Ph | H | H |
| 31 | -CH₂Ph | H | -NMeS(O)₂Ph | F | H |
| 32 | -CH₂Ph | H | -NMeS(O)₂Ph | H | F |
| 33 | -CH₂Ph | F | -NMeS(O)₂Ph | F | H |

FIGURE 20B

| No. | $R^{3a}$ | $R^{9a}$ | $R^{10a}$ | $R^{11a}$ | $R^{12a}$ |
|---|---|---|---|---|---|
| 34 | -CH$_2$Ph | H | -NMeS(O)$_2$Ph | F | F |
| 35 | -CH$_2$Ph | F | -NMeS(O)$_2$Ph | F | F |
| 36 | -CH$_2$Ph | H | -CH$_2$OH | H | H |
| 37 | -CH$_2$Ph | H | H | -CH$_2$OH | H |
| 38 | -CH$_2$Ph | H | H | H | -CH$_2$OH |
| 39 | -CH$_2$Ph | -CH$_2$OH | F | H | H |
| 40 | -CH$_2$Ph | -CH$_2$OH | H | F | H |
| 41 | -CH$_2$Ph | -CH$_2$OH | H | H | F |
| 42 | -CH$_2$Ph | -CH$_2$OH | Cl | H | H |
| 43 | -CH$_2$Ph | -CH$_2$OH | H | Cl | H |
| 44 | -CH$_2$Ph | -CH$_2$OH | H | H | Cl |
| 45 | -CH$_2$Ph | F | -CH$_2$OH | H | H |
| 46 | -CH$_2$Ph | H | -CH$_2$OH | F | H |
| 47 | -CH$_2$Ph | H | -CH$_2$OH | H | F |
| 48 | -CH$_2$Ph | Cl | -CH$_2$OH | H | H |
| 49 | -CH$_2$Ph | H | -CH$_2$OH | Cl | H |
| 50 | -CH$_2$Ph | H | -CH$_2$OH | H | Cl |
| 51 | -CH$_2$Ph | F | H | -CH$_2$OH | H |
| 52 | -CH$_2$Ph | H | F | -CH$_2$OH | H |
| 53 | -CH$_2$Ph | H | H | -CH$_2$OH | F |
| 54 | -CH$_2$Ph | Cl | H | -CH$_2$OH | H |
| 55 | -CH$_2$Ph | H | Cl | -CH$_2$OH | H |
| 56 | -CH$_2$Ph | H | H | -CH$_2$OH | Cl |
| 57 | -CH$_2$Ph | F | H | H | -CH$_2$OH |
| 58 | -CH$_2$Ph | H | F | H | -CH$_2$OH |
| 59 | -CH$_2$Ph | H | H | F | -CH$_2$OH |
| 60 | -CH$_2$Ph | Cl | H | H | -CH$_2$OH |
| 61 | -CH$_2$Ph | H | Cl | H | -CH$_2$OH |
| 62 | -CH$_2$Ph | H | H | Cl | -CH$_2$OH |
| 63 | -CH$_2$Ph | F | -CH$_2$OH | F | H |
| 64 | -CH$_2$Ph | H | -CH$_2$OH | F | F |
| 65 | -CH$_2$Ph | F | -CH$_2$OH | F | F |
| 66 | -CH$_2$Ph | H | -NH$_2$ | H | H |
| 67 | -CH$_2$Ph | H | H | -NH$_2$ | H |
| 68 | -CH$_2$Ph | H | H | H | -NH$_2$ |
| 69 | -CH$_2$Ph | -NH$_2$ | F | H | H |
| 70 | -CH$_2$Ph | -NH$_2$ | H | F | H |
| 71 | -CH$_2$Ph | -NH$_2$ | H | H | F |
| 72 | -CH$_2$Ph | -NH$_2$ | Cl | H | H |
| 73 | -CH$_2$Ph | -NH$_2$ | H | Cl | H |
| 74 | -CH$_2$Ph | -NH$_2$ | H | H | Cl |
| 75 | -CH$_2$Ph | F | -NH$_2$ | H | H |

FIGURE 20C

| No. | $R^{3a}$ | $R^{9a}$ | $R^{10a}$ | $R^{11a}$ | $R^{12a}$ |
|---|---|---|---|---|---|
| 76 | -CH$_2$Ph | H | -NH$_2$ | F | H |
| 77 | -CH$_2$Ph | H | -NH$_2$ | H | F |
| 78 | -CH$_2$Ph | Cl | -NH$_2$ | H | H |
| 79 | -CH$_2$Ph | H | -NH$_2$ | Cl | H |
| 80 | -CH$_2$Ph | H | -NH$_2$ | H | Cl |
| 81 | -CH$_2$Ph | F | H | -NH$_2$ | H |
| 82 | -CH$_2$Ph | H | F | -NH$_2$ | H |
| 83 | -CH$_2$Ph | H | H | -NH$_2$ | F |
| 84 | -CH$_2$Ph | Cl | H | -NH$_2$ | H |
| 85 | -CH$_2$Ph | H | Cl | -NH$_2$ | H |
| 86 | -CH$_2$Ph | H | H | -NH$_2$ | Cl |
| 87 | -CH$_2$Ph | F | H | H | -NH$_2$ |
| 88 | -CH$_2$Ph | H | F | H | -NH$_2$ |
| 89 | -CH$_2$Ph | H | H | F | -NH$_2$ |
| 90 | -CH$_2$Ph | Cl | H | H | -NH$_2$ |
| 91 | -CH$_2$Ph | H | Cl | H | -NH$_2$ |
| 92 | -CH$_2$Ph | H | H | Cl | -NH$_2$ |
| 93 | -CH$_2$Ph | F | -NH$_2$ | F | H |
| 94 | -CH$_2$Ph | H | -NH$_2$ | F | F |
| 95 | -CH$_2$Ph | F | -NH$_2$ | F | F |
| 96 | -CH$_2$Ph | -O(4-CN-Ph) | H | H | H |
| 97 | -CH$_2$Ph | H | -O(4-CN-Ph) | H | H |
| 98 | -CH$_2$Ph | H | H | -O(4-CN-Ph) | H |
| 99 | -CH$_2$Ph | H | H | H | -O(4-CN-Ph) |
| 100 | -CH$_2$Ph | F | -O(4-CN-Ph) | H | H |
| 101 | -CH$_2$Ph | H | -O(4-CN-Ph) | F | H |
| 102 | -CH$_2$Ph | H | -O(4-CN-Ph) | H | F |
| 103 | -CH$_2$Ph | F | -O(4-CN-Ph) | F | H |
| 104 | -CH$_2$Ph | H | -O(4-CN-Ph) | F | F |
| 105 | -CH$_2$Ph | F | -O(4-CN-Ph) | F | F |
| 106 | -CH$_2$Ph | 3-(phenylthio)-1H-indol-1-yl | H | H | H |
| 107 | -CH$_2$Ph | H | 3-(phenylthio)-1H-indol-1-yl | H | H |
| 108 | -CH$_2$Ph | H | H | 3-(phenylthio)-1H-indol-1-yl | H |
| 109 | -CH$_2$Ph | H | H | H | 3-(phenylthio)-1H-indol-1-yl |
| 110 | -CH$_2$Ph | F | 3-(phenylthio)-1H-indol-1-yl | H | H |
| 111 | -CH$_2$Ph | H | 3-(phenylthio)-1H-indol-1-yl | F | H |
| 112 | -CH$_2$Ph | H | 3-(phenylthio)-1H-indol-1-yl | H | F |
| 113 | -CH$_2$Ph | F | 3-(phenylthio)-1H-indol-1-yl | F | H |

FIGURE 20D

| No. | $R^{3a}$ | $R^{9a}$ | $R^{10a}$ | $R^{11a}$ | $R^{12a}$ |
| --- | --- | --- | --- | --- | --- |
| 114 | -CH$_2$Ph | H | 3-(phenylthio)-1H-indol-1-yl | F | F |
| 115 | -CH$_2$Ph | F | 3-(phenylthio)-1H-indol-1-yl | F | F |
| 116 | -CH$_2$Ph | dibenzylamino | H | H | H |
| 117 | -CH$_2$Ph | H | dibenzylamino | H | H |
| 118 | -CH$_2$Ph | H | H | dibenzylamino | H |
| 119 | -CH$_2$Ph | H | H | H | dibenzylamino |
| 120 | -CH$_2$Ph | F | dibenzylamino | H | H |
| 121 | -CH$_2$Ph | H | dibenzylamino | F | H |
| 122 | -CH$_2$Ph | H | dibenzylamino | H | F |
| 123 | -CH$_2$Ph | F | dibenzylamino | F | H |
| 124 | -CH$_2$Ph | H | dibenzylamino | F | F |
| 125 | -CH$_2$Ph | F | dibenzylamino | F | F |
| 126 | -CH$_2$Ph | -S(O)$_2$(4-Cl-Ph) | H | H | H |
| 127 | -CH$_2$Ph | H | -S(O)$_2$(4-Cl-Ph) | H | H |
| 128 | -CH$_2$Ph | H | H | -S(O)$_2$(4-Cl-Ph) | H |
| 129 | -CH$_2$Ph | H | H | H | -S(O)$_2$(4-Cl-Ph) |
| 130 | -CH$_2$Ph | F | -S(O)$_2$(4-Cl-Ph) | H | H |
| 131 | -CH$_2$Ph | H | -S(O)$_2$(4-Cl-Ph) | F | H |
| 132 | -CH$_2$Ph | H | -S(O)$_2$(4-Cl-Ph) | H | F |
| 133 | -CH$_2$Ph | F | -S(O)$_2$(4-Cl-Ph) | F | H |
| 134 | -CH$_2$Ph | H | -S(O)$_2$(4-Cl-Ph) | F | F |
| 135 | -CH$_2$Ph | F | -S(O)$_2$(4-Cl-Ph) | F | F |
| 136 | -CH$_2$Ph | -S(4-pyridyl) | H | H | H |
| 137 | -CH$_2$Ph | H | -S(4-pyridyl) | H | H |
| 138 | -CH$_2$Ph | H | H | -S(4-pyridyl) | H |
| 139 | -CH$_2$Ph | H | H | H | -S(4-pyridyl) |
| 140 | -CH$_2$Ph | F | -S(4-pyridyl) | H | H |
| 141 | -CH$_2$Ph | H | -S(4-pyridyl) | F | H |
| 142 | -CH$_2$Ph | H | -S(4-pyridyl) | H | F |
| 143 | -CH$_2$Ph | F | -S(4-pyridyl) | F | H |
| 144 | -CH$_2$Ph | H | -S(4-pyridyl) | F | F |
| 145 | -CH$_2$Ph | F | -S(4-pyridyl) | F | F |
| 146 | -CH$_2$Ph | -NHCH$_2$Ph | H | H | H |
| 147 | -CH$_2$Ph | H | -NHCH$_2$Ph | H | H |
| 148 | -CH$_2$Ph | H | H | -NHCH$_2$Ph | H |
| 149 | -CH$_2$Ph | H | H | H | -NHCH$_2$Ph |
| 150 | -CH$_2$Ph | F | -NHCH$_2$Ph | H | H |
| 151 | -CH$_2$Ph | H | -NHCH$_2$Ph | F | H |
| 152 | -CH$_2$Ph | H | -NHCH$_2$Ph | H | F |
| 153 | -CH$_2$Ph | F | -NHCH$_2$Ph | F | H |
| 154 | -CH$_2$Ph | H | -NHCH$_2$Ph | F | F |

FIGURE 20E

| No. | $R^{3a}$ | $R^{9a}$ | $R^{10a}$ | $R^{11a}$ | $R^{12a}$ |
|---|---|---|---|---|---|
| 155 | -CH$_2$Ph | F | -NHCH$_2$Ph | F | F |
| 156 | Me | F | H | H | H |
| 157 | Me | H | F | H | H |
| 158 | Me | H | H | F | H |
| 159 | Me | H | H | H | F |
| 160 | Me | F | F | H | H |
| 161 | Me | H | F | F | H |
| 162 | Me | H | H | F | F |
| 163 | Me | F | H | F | H |
| 164 | Me | H | F | H | F |
| 165 | Me | F | H | H | F |
| 166 | Me | H | F | F | F |
| 167 | Me | F | H | F | F |
| 168 | Me | F | F | H | F |
| 169 | Me | F | F | F | H |
| 170 | Me | F | F | F | F |
| 171 | Me | -OCH$_2$C(O)OH | H | H | H |
| 172 | Me | H | -OCH$_2$C(O)OH | H | H |
| 173 | Me | H | H | -OCH$_2$C(O)OH | H |
| 174 | Me | H | H | H | -OCH$_2$C(O)OH |
| 175 | Me | F | -OCH$_2$C(O)OH | H | H |
| 176 | Me | H | -OCH$_2$C(O)OH | F | H |
| 177 | Me | H | -OCH$_2$C(O)OH | H | F |
| 178 | Me | F | -OCH$_2$C(O)OH | F | H |
| 179 | Me | H | -OCH$_2$C(O)OH | F | F |
| 180 | Me | F | -OCH$_2$C(O)OH | F | F |
| 181 | Me | -NMeS(O)$_2$Ph | H | H | H |
| 182 | Me | H | -NMeS(O)$_2$Ph | H | H |
| 183 | Me | H | H | -NMeS(O)$_2$Ph | H |
| 184 | Me | H | H | H | -NMeS(O)$_2$Ph |
| 185 | Me | F | -NMeS(O)$_2$Ph | H | H |
| 186 | Me | H | -NMeS(O)$_2$Ph | F | H |
| 187 | Me | H | -NMeS(O)$_2$Ph | H | F |
| 188 | Me | F | -NMeS(O)$_2$Ph | F | H |
| 189 | Me | H | -NMeS(O)$_2$Ph | F | F |
| 190 | Me | F | -NMeS(O)$_2$Ph | F | F |
| 191 | Me | H | -CH$_2$OH | H | H |
| 192 | Me | H | H | -CH$_2$OH | H |
| 193 | Me | H | H | H | -CH$_2$OH |
| 194 | Me | -CH$_2$OH | F | H | H |
| 195 | Me | -CH$_2$OH | H | F | H |

FIGURE 20F

| No. | $R^{3a}$ | $R^{9a}$ | $R^{10a}$ | $R^{11a}$ | $R^{12a}$ |
|---|---|---|---|---|---|
| 196 | Me | -CH$_2$OH | H | H | F |
| 197 | Me | -CH$_2$OH | Cl | H | H |
| 198 | Me | -CH$_2$OH | H | Cl | H |
| 199 | Me | -CH$_2$OH | H | H | Cl |
| 200 | Me | F | -CH$_2$OH | H | H |
| 201 | Me | H | -CH$_2$OH | F | H |
| 202 | Me | H | -CH$_2$OH | H | F |
| 203 | Me | Cl | -CH$_2$OH | H | H |
| 204 | Me | H | -CH$_2$OH | Cl | H |
| 205 | Me | H | -CH$_2$OH | H | Cl |
| 206 | Me | F | H | -CH$_2$OH | H |
| 207 | Me | H | F | -CH$_2$OH | H |
| 208 | Me | H | H | -CH$_2$OH | F |
| 209 | Me | Cl | H | -CH$_2$OH | H |
| 210 | Me | H | Cl | -CH$_2$OH | H |
| 211 | Me | H | H | -CH$_2$OH | Cl |
| 212 | Me | F | H | H | -CH$_2$OH |
| 213 | Me | H | F | H | -CH$_2$OH |
| 214 | Me | H | H | F | -CH$_2$OH |
| 215 | Me | Cl | H | H | -CH$_2$OH |
| 216 | Me | H | Cl | H | -CH$_2$OH |
| 217 | Me | H | H | Cl | -CH$_2$OH |
| 218 | Me | F | -CH$_2$OH | F | H |
| 219 | Me | H | -CH$_2$OH | F | F |
| 220 | Me | F | -CH$_2$OH | F | F |
| 221 | Me | H | -NH$_2$ | H | H |
| 222 | Me | H | H | -NH$_2$ | H |
| 223 | Me | H | H | H | -NH$_2$ |
| 224 | Me | -NH$_2$ | F | H | H |
| 225 | Me | -NH$_2$ | H | F | H |
| 226 | Me | -NH$_2$ | H | H | F |
| 227 | Me | -NH$_2$ | Cl | H | H |
| 228 | Me | -NH$_2$ | H | Cl | H |
| 229 | Me | -NH$_2$ | H | H | Cl |
| 230 | Me | F | -NH$_2$ | H | H |
| 231 | Me | H | -NH$_2$ | F | H |
| 232 | Me | H | -NH$_2$ | H | F |
| 233 | Me | Cl | -NH$_2$ | H | H |
| 234 | Me | H | -NH$_2$ | Cl | H |
| 235 | Me | H | -NH$_2$ | H | Cl |
| 236 | Me | F | H | -NH$_2$ | H |
| 237 | Me | H | F | -NH$_2$ | H |

FIGURE 20G

| No. | $R^{3a}$ | $R^{9a}$ | $R^{10a}$ | $R^{11a}$ | $R^{12a}$ |
|---|---|---|---|---|---|
| 238 | Me | H | H | -NH$_2$ | F |
| 239 | Me | Cl | H | -NH$_2$ | H |
| 240 | Me | H | Cl | -NH$_2$ | H |
| 241 | Me | H | H | -NH$_2$ | Cl |
| 242 | Me | F | H | H | -NH$_2$ |
| 243 | Me | H | F | H | -NH$_2$ |
| 244 | Me | H | H | F | -NH$_2$ |
| 245 | Me | Cl | H | H | -NH$_2$ |
| 246 | Me | H | Cl | H | -NH$_2$ |
| 247 | Me | H | H | Cl | -NH$_2$ |
| 248 | Me | F | -NH$_2$ | F | H |
| 249 | Me | H | -NH$_2$ | F | F |
| 250 | Me | F | -NH$_2$ | F | F |
| 251 | Me | -O(4-CN-Ph) | H | H | H |
| 252 | Me | H | -O(4-CN-Ph) | H | H |
| 253 | Me | H | H | -O(4-CN-Ph) | H |
| 254 | Me | H | H | H | -O(4-CN-Ph) |
| 255 | Me | F | -O(4-CN-Ph) | H | H |
| 256 | Me | H | -O(4-CN-Ph) | F | H |
| 257 | Me | H | -O(4-CN-Ph) | H | F |
| 258 | Me | F | -O(4-CN-Ph) | F | H |
| 259 | Me | H | -O(4-CN-Ph) | F | F |
| 260 | Me | F | -O(4-CN-Ph) | F | F |
| 261 | Me | 3-(phenylthio)-1H-indol-1-yl | H | H | H |
| 262 | Me | H | 3-(phenylthio)-1H-indol-1-yl | H | H |
| 263 | Me | H | H | 3-(phenylthio)-1H-indol-1-yl | H |
| 264 | Me | H | H | H | 3-(phenylthio)-1H-indol-1-yl |
| 265 | Me | F | 3-(phenylthio)-1H-indol-1-yl | H | H |
| 266 | Me | H | 3-(phenylthio)-1H-indol-1-yl | F | H |
| 267 | Me | H | 3-(phenylthio)-1H-indol-1-yl | H | F |
| 268 | Me | F | 3-(phenylthio)-1H-indol-1-yl | F | H |
| 269 | Me | H | 3-(phenylthio)-1H-indol-1-yl | F | F |
| 270 | Me | F | 3-(phenylthio)-1H-indol-1-yl | F | F |
| 271 | Me | dibenzylamino | H | H | H |
| 272 | Me | H | dibenzylamino | H | H |
| 273 | Me | H | H | dibenzylamino | H |
| 274 | Me | H | H | H | dibenzylamino |

FIGURE 20H

| No. | $R^{3a}$ | $R^{9a}$ | $R^{10a}$ | $R^{11a}$ | $R^{12a}$ |
|---|---|---|---|---|---|
| 275 | Me | F | dibenzylamino | H | H |
| 276 | Me | H | dibenzylamino | F | H |
| 277 | Me | H | dibenzylamino | H | F |
| 278 | Me | F | dibenzylamino | F | H |
| 279 | Me | H | dibenzylamino | F | F |
| 280 | Me | F | dibenzylamino | F | F |
| 281 | Me | -S(O)$_2$(4-Cl-Ph) | H | H | H |
| 282 | Me | H | -S(O)$_2$(4-Cl-Ph) | H | H |
| 283 | Me | H | H | -S(O)$_2$(4-Cl-Ph) | H |
| 284 | Me | H | H | H | -S(O)$_2$(4-Cl-Ph) |
| 285 | Me | F | -S(O)$_2$(4-Cl-Ph) | H | H |
| 286 | Me | H | -S(O)$_2$(4-Cl-Ph) | F | H |
| 287 | Me | H | -S(O)$_2$(4-Cl-Ph) | H | F |
| 288 | Me | F | -S(O)$_2$(4-Cl-Ph) | F | H |
| 289 | Me | H | -S(O)$_2$(4-Cl-Ph) | F | F |
| 290 | Me | F | -S(O)$_2$(4-Cl-Ph) | F | F |
| 291 | Me | -S(4-pyridyl) | H | H | H |
| 292 | Me | H | -S(4-pyridyl) | H | H |
| 293 | Me | H | H | -S(4-pyridyl) | H |
| 294 | Me | H | H | H | -S(4-pyridyl) |
| 295 | Me | F | -S(4-pyridyl) | H | H |
| 296 | Me | H | -S(4-pyridyl) | F | H |
| 297 | Me | H | -S(4-pyridyl) | H | F |
| 298 | Me | F | -S(4-pyridyl) | F | H |
| 299 | Me | H | -S(4-pyridyl) | F | F |
| 300 | Me | F | -S(4-pyridyl) | F | F |
| 301 | Me | -NHCH$_2$Ph | H | H | H |
| 302 | Me | H | -NHCH$_2$Ph | H | H |
| 303 | Me | H | H | -NHCH$_2$Ph | H |
| 304 | Me | H | H | H | -NHCH$_2$Ph |
| 305 | Me | F | -NHCH$_2$Ph | H | H |
| 306 | Me | H | -NHCH$_2$Ph | F | H |
| 307 | Me | H | -NHCH$_2$Ph | H | F |
| 308 | Me | F | -NHCH$_2$Ph | F | H |
| 309 | Me | H | -NHCH$_2$Ph | F | F |
| 310 | Me | F | -NHCH$_2$Ph | F | F |

BORON-CONTAINING SMALL MOLECULES

CROSS-REFERENCE TO RELATED APPLICATIONS

The present application is a continuation of U.S. patent application Ser. No. 15/091,394, filed Apr. 5, 2016, which is a continuation of U.S. patent application Ser. No. 15/068,352, filed Mar. 11, 2016, which is a continuation of U.S. patent application Ser. No. 15/046,322, filed on Feb. 17, 2016, which is a continuation of U.S. patent application Ser. No. 14/537,771, filed Nov. 10, 2014, which is a continuation of U.S. patent application Ser. No. 14/201,459, filed Mar. 7, 2014, now U.S. Pat. No. 9,353,133, which is a continuation of U.S. patent application Ser. No. 13/356,488, filed Jan. 23, 2012, now U.S. Pat. No. 8,722,917, which is a continuation of U.S. patent application Ser. No. 12/629,753, filed Dec. 2, 2009, now U.S. Pat. No. 8,115,026, which is a divisional of U.S. patent application Ser. No. 11/505,591, filed Aug. 16, 2006, now U.S. Pat. No. 7,767,657, which claims the benefit of U.S. Provisional Patent Application No. 60/755,227, filed Dec. 30, 2005, and the benefit of U.S. Provisional Patent Application No. 60/746,361, filed May 3, 2006, all of which are incorporated by reference in their entirety for all purposes. U.S. patent application Ser. No. 11/505,591 is also a continuation-in-part of U.S. patent application Ser. No. 11/357,687, filed Feb. 16, 2006, now U.S. Pat. No. 7,582,621, which claims the benefit of U.S. Provisional Patent Application No. 60/654,060, filed Feb. 16, 2005, all of which are incorporated by reference in their entirety for all purposes. U.S. patent application Ser. No. 14/537,771 is also a continuation-in-part of U.S. patent application Ser. No. 13/874,329, filed Apr. 30, 2013, now U.S. Pat. No. 8,889,656, which is a continuation of U.S. patent application Ser. No. 13/224,252, filed Sep. 1, 2011, now U.S. Pat. No. 8,440,642, which is a continuation of U.S. patent application Ser. No. 12/507,010, filed Jul. 21, 2009, now U.S. Pat. No. 8,039,451, which is a continuation of U.S. patent application Ser. No. 11/357,687, filed Feb. 16, 2006, now U.S. Pat. No. 7,582,621, which claims the benefit of 60/654,060, filed Feb. 16, 2005, all of which are incorporated by reference in their entirety for all purposes.

BACKGROUND FOR THE INVENTION

Infections of the nail and hoof, known as ungual and/or periungual infections, pose serious problems in dermatology. These ungual and/or periungual can be caused by sources such as fungi, viruses, yeast, bacteria and parasites. Onychomycosis is an example of these serious ungual and/or periungual infections and is caused by at least one fungus. Current treatment for ungual and/or periungual infections generally falls into three categories: systemic administration of medicine; surgical removal of all or part of the nail or hoof followed by topical treatment of the exposed tissue; or topical application of conventional creams, lotions, gels or solutions, frequently including the use of bandages to keep these dosage forms in place on the nail or hoof. All of these approaches have major drawbacks. The following discussion is particularly directed to drawbacks associated with current treatment of ungual and/or periungual antifungal infections.

Long term systemic (oral) administration of an antifungal agent for the treatment of onychomycosis is often required to produce a therapeutic effect in the nail bed. For example, oral treatment with the antifungal compound terbinafine typically requires administration of 200 to 400 mg/day for 12 weeks before any significant therapeutic benefit is realized. Such long term, high dose systemic therapy can have significant adverse effects. For example, terbinafine has been reported to have liver toxicity effects and reduces testosterone levels in blood due to adverse effects on the testes. Patient compliance is a problem with such long term therapies especially those which involve serious adverse effects. Moreover, this type of long term oral therapy is inconvenient in the treatment of a horse or other ruminants afflicted with fungal infections of the hoof. Accordingly, the risks associated with parenteral treatments generate significant disincentive against their use and considerable patient noncompliance.

Surgical removal of all or part of the nail followed by topical treatment also has severe drawbacks. The pain and discomfort associated with the surgery and the undesirable cosmetic appearance of the nail or nail bed represent significant problems, particularly for patients more sensitive to physical appearance. Generally, this type of treatment is not realistic for ruminants such as horses.

Topical therapy has significant problems too. Topical dosage forms such as creams, lotions, gels etc., can not keep the drug in intimate contact with the infected area for therapeutically effective periods of time. Bandages have been used to hold drug reservoirs in place in an attempt to enhance absorption of the pharmaceutical agent. However the bandages are thick, awkward, troublesome and generally lead to poor patient compliance.

Hydrophilic and hydrophobic film forming topical antifungal solutions have also been developed. These dosage forms provide improved contact between the drug and the nail. Topical formulations for fungal infection treatment have largely tried to deliver the drug to the target site (an infected nail bed) by diffusion across or through the nail.

Nail is more like hair than stratum corneum with respect to chemical composition and permeability. Nitrogen is the major component of the nail attesting to the nail's proteinaceous nature. The total lipid content of mature nail is 0.1-1.0%, while the stratum corneum lipid is about 10% w/w. The nail is 100-200 times thicker than the stratum corneum and has a very high affinity and capacity for binding and retaining antifungal drugs. Consequently little if any drug penetrates through the nail to reach the target site. Because of these reasons topical therapy for fungal infections have generally been ineffective.

Compounds known as penetration or permeation enhancers are well known in the art to produce an increase in the permeability of skin or other body membranes to a pharmacologically active agent. The increased permeability allows an increase in the rate at which the drug permeates through the skin and enters the blood stream. Penetration enhancers have been successful in overcoming the impermeability of pharmaceutical agents through the skin. However, the thin stratum corneum layer of the skin, which is about 10 to 15 cells thick and is formed naturally by cells migrating toward the skin surface from the basal layer, has been easier to penetrate than nails. Moreover, known penetration enhancers have not proven to be useful in facilitating drug migration through the nail tissue.

Antimicrobial compositions for controlling bacterial and fungal infections comprising a metal chelate of 8-hydroxyquinoline and an alkyl benzene sulfonic acid have been shown to be efficacious due to the increased ability of the oleophilic group to penetrate the lipid layers of micro-cells. The compounds however, do not effectively increase the ability to carry the pharmaceutically active antifungal through the cornified layer or stratum corneum of the skin.

U.S. Pat. No. 4,602,011, West et al., Jul. 22, 1986; U.S. Pat. No. 4,766,113, West et al., Aug. 23, 1988.

Therefore, there is a need in the art for compounds which can effectively penetrate the nail. There is also need in the art for compounds which can effectively treat ungual and/or periungual infections. These and other needs are addressed by the current invention.

Aminoacyl-tRNA synthetases (ARS) are a family of essential enzymes that attach amino acids to the 3' terminal adenosine end of tRNAs, the charged tRNAs are then used by the translation machinery to synthesis proteins from mRNA. Although there are few exceptions, for example in Gram-positive bacteria and archaea, most organisms have at least one ARS for each amino acid. In the case of eukaryotes, they have two ARS, one is localized to the cytoplasm while the other ARS is located in the organelle(s). The ARS catalyzes two reactions, as outlined below, the first reaction adenylates the amino acid with ATP followed by its transfer to the 2'- or 3'-hydroxyl of the terminal adenosine of tRNA.

Amino acid (AA)+ATP→AA-AMP+PPi;

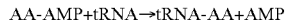
AA-AMP+tRNA→tRNA-AA+AMP

The family of 20 ARS fall into two distinct structural classes as determined by their crystal structure. Class I, which have a Rossman like fold, include the ARS for the following amino acids-arginine, cysteine, glutamate, glutamine, isolelucine, leucine, lysine (in archaea and some bacteria), valine, methionine, tryptophan and tyrosine. Class II ARS include the enzymes for the amino acids, alanine, asparagine, aspartate, glycine, histidine, lysine, phenylalanine, proline, serine and threonine. The ARS mediated reaction is the major checkpoint of specificity that ensures the correct amino acid is charged to its cognate tRNA. Since some amino acids only differ by a single methylene group, for example valine and isoleucine, it has been postulated that the specificity of the synthetic reaction alone can't explain the observed in vivo accuracy of tRNA charging. The synthetic active site should be able to exclude amino acids that are not close analogs of the cognate amino acid, but analogous amino acids pose a bigger problem. Therefore to increase specificity, proof-reading and editing must occur. So far nine ARS have been shown to have an editing mechanism that significantly reduces the frequency of mischarged tRNAs. The enzymes for the following amino acids have been shown to have editing activity-alanine, isoleucine, leucine, methionine, lysine, phenylalanine, proline, threonine and valine. These ARS can hydrolyse the incorrectly adenylated amino acid AA-AMP (pre-transfer editing) or the incorrectly charged tRNA (post-transfer editing). To date the isoleucyl, leucyl and valyl-tRNA synthetases have the best-characterized editing mechanisms; an additional structural domain called the connective polypeptide I (CP1) inserted in the synthetic domain has been shown to contain the editing active site. This is located more than 25 Å away from the synthetic active site, which suggests that both the adenylated amino acid intermediate and amino acid tethered to the 3'end of the tRNA must be moved from the active site in the synthetic domain to the editing site for the reaction to be proof-read. It has been postulated that the 3'end of the charged tRNA is translocated in a similar manner to that of the proof-reading mechanism of DNA polymerases. Much less is known about the translocation of the adenylated amino acid. A similar CP1 domain is also present in the methionine and cysteine ARS enzymes, but it is much smaller than that found in the valine, isoleucine and leucine enzymes. Despite the absence of a direct homolog to the CP1-like domain in class II ARS, separate editing domains have been found in the enzymes for proline and threonine. Although editing is important to ensure the correct charging of tRNAs, it is not essential for viability and is not required for the synthesis of charged tRNAs. For example, in Escherichia coli, in which 10 amino acids in the editing domain of isoleucyl-tRNA synthetase were changed to alanine, the resulting mutant was still viable, although it did have many pleiotropic effects, including a noticeable cell growth defect.

In spite of significant homologies between human, bacterial and fungal ARS there are a number of compounds that have been developed as anti-infectives. The most notable example of an ARS inhibitor is the commercial antibiotic mupirocin (pseudomonic acid), which is sold under the label Bactroban. Mupirocin specifically inhibits bacterial isoleucyl-tRNA synthetases, while its activity against the human homolog is more than 1,000 times less active. Mupirocin binds specifically to the synthetic active site and mutants that are resistant to this drug have mutations in the synthetic domain of leucyl-tRNA synthetase. Likewise, reveromycin A inhibits the eukaryotic isoleucyl-tRNA synthetases: Saccharomyces cerevisiae resistance mutants have mutations in the synthetic domain. So far all attempts to develop better ARS inhibitors than mupirocin, an isoleucine-adenylate analogue, have relied on inhibiting the synthetic reactions.

Since it has been previously thought not to be essential for the synthesis of charged tRNAs, the editing domain of tRNA synthetases has not been thought a promising target for drug development. Data from mutational analysis of the ARS editing domains tend to suggest that inhibition of the editing mechanism leads only to an increase in mischarged tRNAs and does not lead to cell death. Compounds that are active against, and specific for, the editing domain of the tRNA synthetase would provide access to a new class of antimicrobial therapeutics to augment the arsenal of agents currently in use. Quite surprisingly, the present invention provides such compounds and methods of using these compounds.

SUMMARY OF THE INVENTION

In one aspect, the invention provides a structure according to the following formula:

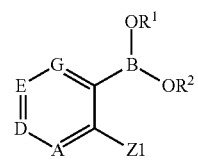

in which $R^1$ and $R^2$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^1$ and $R^2$, together with the atoms to which they are attached, can be optionally joined to form a 4- to 7-membered ring. Z1 is a member selected from

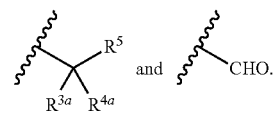

$R^{3a}$ and $R^{4a}$ are members independently selected from H, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^5$ is a member selected from halogen and $OR^g$. $R^g$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. A is a member selected from $CR^{9a}$ and N. D is a member selected from $CR^{10a}$ and N. E is a member selected from $CR^{11a}$ and N. G is a member selected from $CR^{12a}$ and N. $R^{9a}$, $R^{10a}$, $R^{11a}$ and $R^{12a}$ are members independently selected from H, $OR^*$, $NR^*R^{**}$, $SR^*$, $-S(O)R^*$, $-S(O)_2R^*$, $-S(O)_2NR^*R^{**}$, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. Each $R^*$ and $R^{**}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{9a}$ and $R^{10a}$, along with the atoms to which they are attached, are optionally joined to form a ring. $R^{10a}$ and $R^{11a}$, along with the atoms to which they are attached, are optionally joined to form a ring. $R^{11a}$ and $R^{12a}$, along with the atoms to which they are attached, are optionally joined to form a ring. The combination of nitrogens (A+D+E+G) is an integer selected from 0 to 3.

BRIEF DESCRIPTION OF THE DRAWINGS

FIG. 1A, FIG. 1B, FIG. 1C are a table of minimum inhibitory concentration (MIC) data of cyclic boronic esters against various fungi.

FIG. 2A displays minimum inhibitory concentration (MIC) for C10, ciclopirox, terbinafine, fluconazole and itraconazole (comparator drugs) against 19 test strains of fungi.

FIG. 2B displays minimum fungicidal concentration (MFC) for C10, ciclopirox, terbinafine and itraconazole (comparator drugs) against 2 test strains of fungi.

FIG. 3 displays a comparison of Normalized C10 and Ciclopirox Equivalent in Each Part of Nail Plate Samples after 14-day Treatment.

FIG. 4 displays a comparison of C10 and Ciclopirox Equivalent in Cotton Ball Supporting Bed Samples after 14-day Treatment.

FIG. 10(1), FIG. 10(2), FIG. 10(3), FIG. 10(4), FIG. 10(5), FIG. 10(6), FIG. 10(7), FIG. 10(8), FIG. 10(9) are Amino acid sequences for leucyl-tRNA synthetase editing domains and nucleotide sequences for tRNA-Leu and tRNA-Ile. (A) Amino acid sequences for leucyl-tRNA synthetase editing domain from S. cerivisiae in wild type (SEQ ID NO: 1) and over-expressing form (SEQ ID NO: 2); (B) Amino acid sequences for leucyl-tRNA synthetase editing domains from indicated species; (C) Genomic nucleotide sequence for tRNA-leu and tRNA-ile from S. cerivisiae; in one embodiment of the invention, an aminoacyl tRNA synthetase will bind to the transcribed and methylated products for which these sequences serve as a template; (D) tRNA-Leu nucleotide sequences from indicated species.

FIG. 13 Effect of ATP on binding of C10 to cdc60. The binding assay was conducted with an initial [C10] concentration of approximately 72-79 μM (pre-equilibrium).

FIG. 18A, FIG. 18B, FIG. 18C display the names of exemplary compounds of the invention.

FIG. 19A, FIG. 19B, FIG. 19C, FIG. 19D, FIG. 19E, FIG. 19F, FIG. 19G, FIG. 19H, FIG. 19I, FIG. 19J, FIG. 19K display exemplary compounds of the invention.

FIG. 20A, FIG. 20B, FIG. 20C, FIG. 20D, FIG. 20E, FIG. 20F, FIG. 20G, FIG. 20H display exemplary compounds of the invention.

DETAILED DESCRIPTION OF THE INVENTION

I. Definitions and Abbreviations

Figure 5:
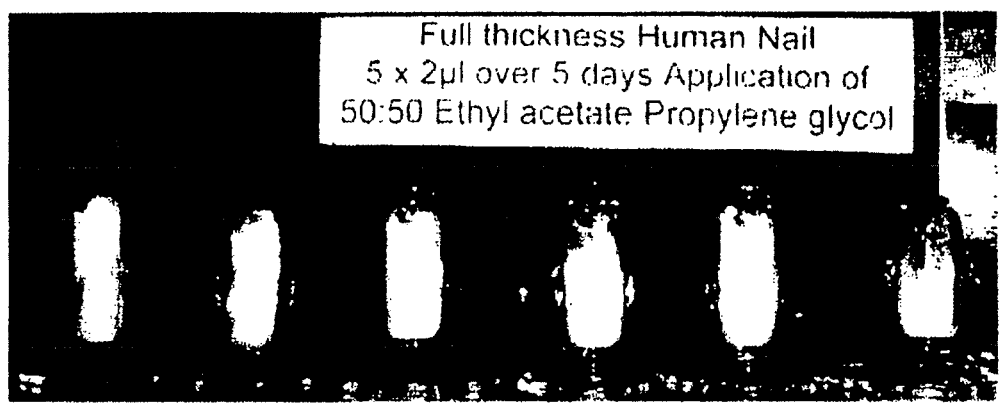
FIG. 5 displays the results of a placebo for C10 (50:50 propylene glycol and ethyl acetate) applied per day over five days. Full carpet growth of the organism T. rubrum was observed.
Figure 6:
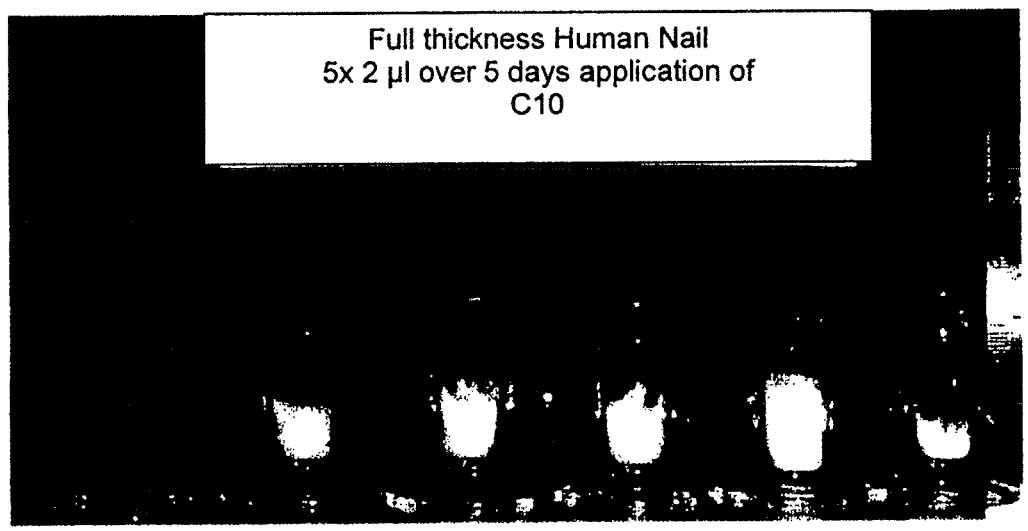
FIG. 6 displays the results of a 40 μL/cm² aliquot of C10 10% w/v solution applied per day over five days. Zones of inhibition (in the order of the cells shown in the figure) of 100%, 67%, 46%, 57%, 38% and 71% were observed for the growth of T. rubrum. Green arrow indicates the measurement of zone of inhibition.
Figure 7:
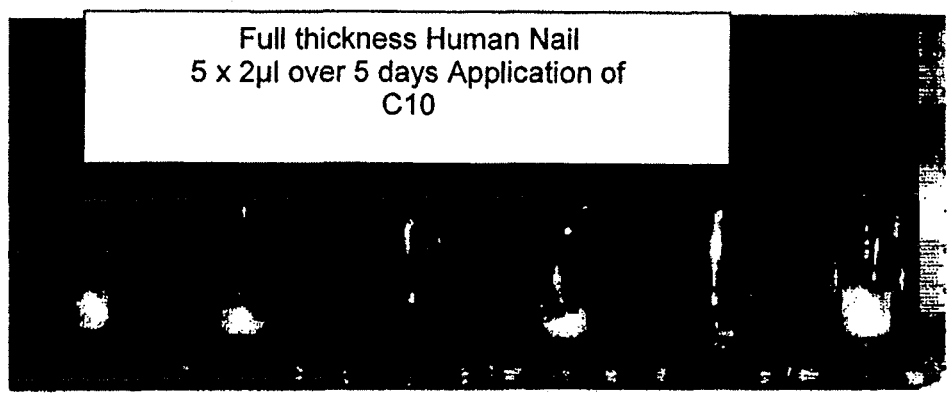
FIG. 7 displays the results of a 40 μL/cm² aliquot of C10 10% w/v solution applied per day over five days. Zones of inhibition (in the order of the cells shown in the figure) of 74%, 86%, 100%, 82%, 100% and 84% were observed for the growth of T. rubrum.
Figure 8:
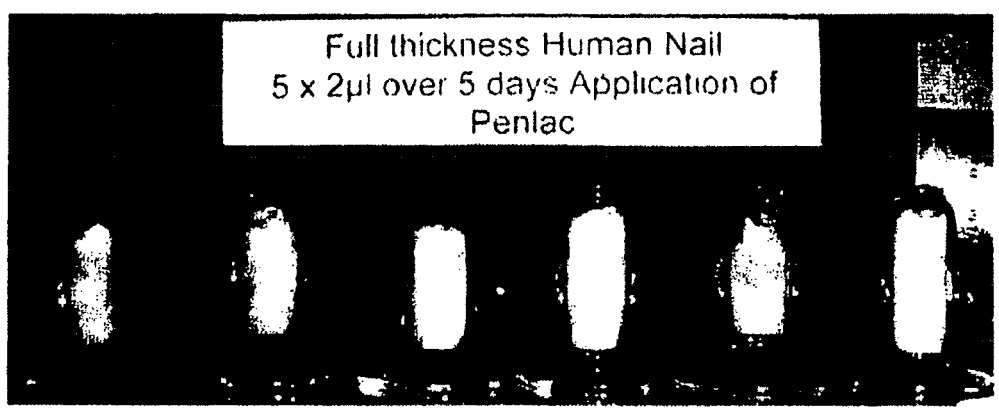
FIG. 8 displays the results of a 40 μL/cm² aliquot of 8% ciclopirox in w/w commercial lacquer applied per day over five days. No zone of inhibition observed; full carpet growth of T. rubrum.
Figure 9:
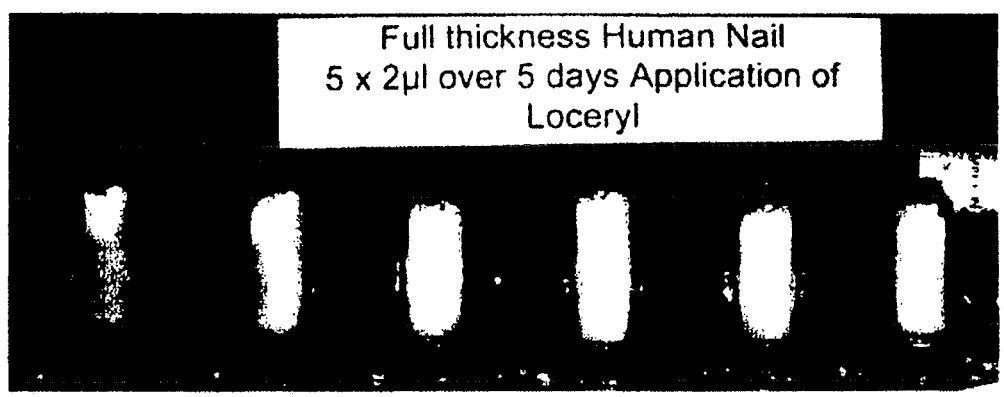
FIG. 9 displays the results of a 40 μL/cm² aliquot of 5% amorolfine w/v in commercial lacquer applied per day over five days. No zone of inhibition observed; full carpet growth of T. rubrum.
Figure 11A:
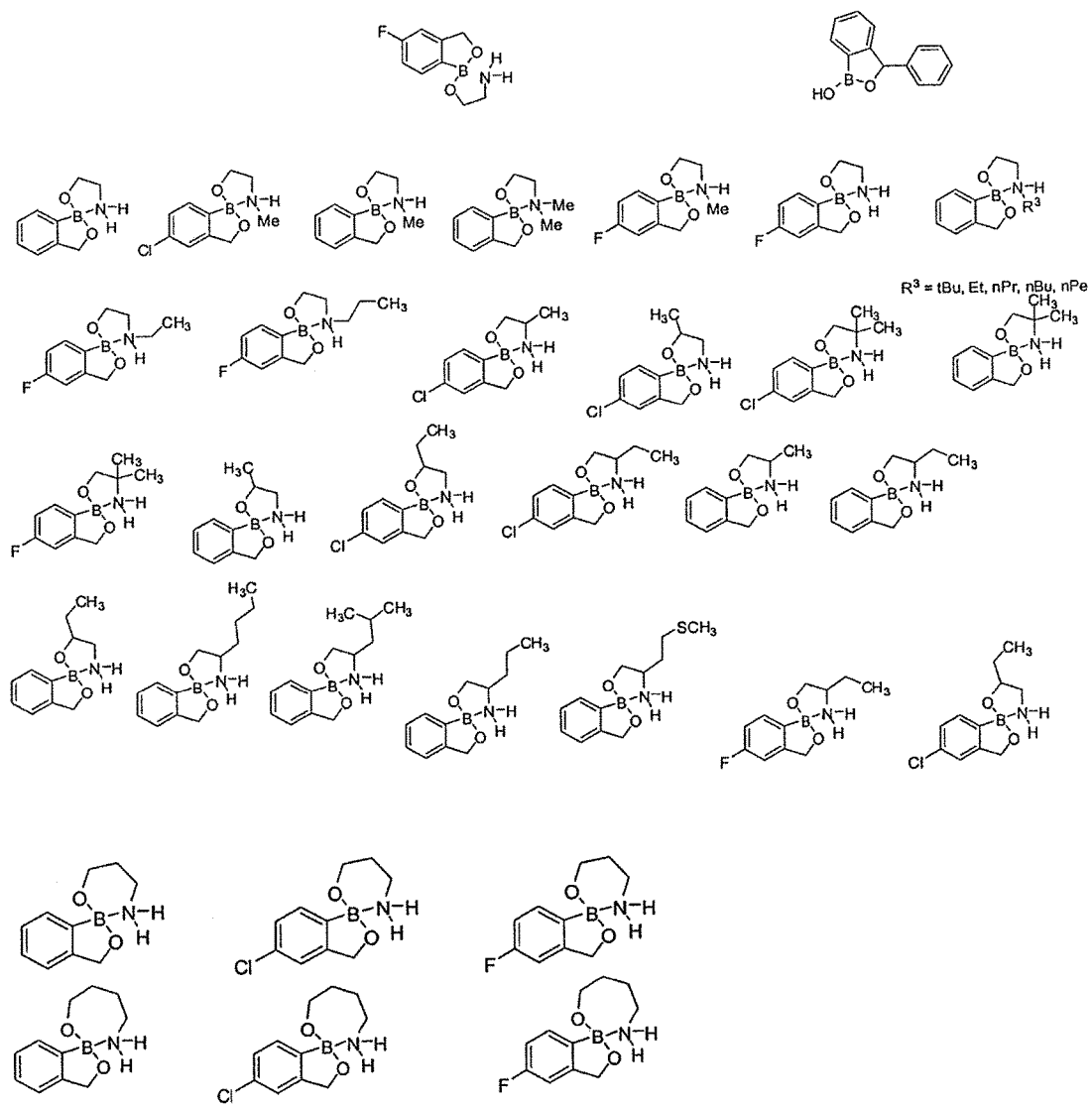
FIG. 11A, FIG. 11B, FIG. 11C, FIG. 11D, FIG. 11E, FIG. 11F display structures of cyclic boronic esters.
Figure 11B:
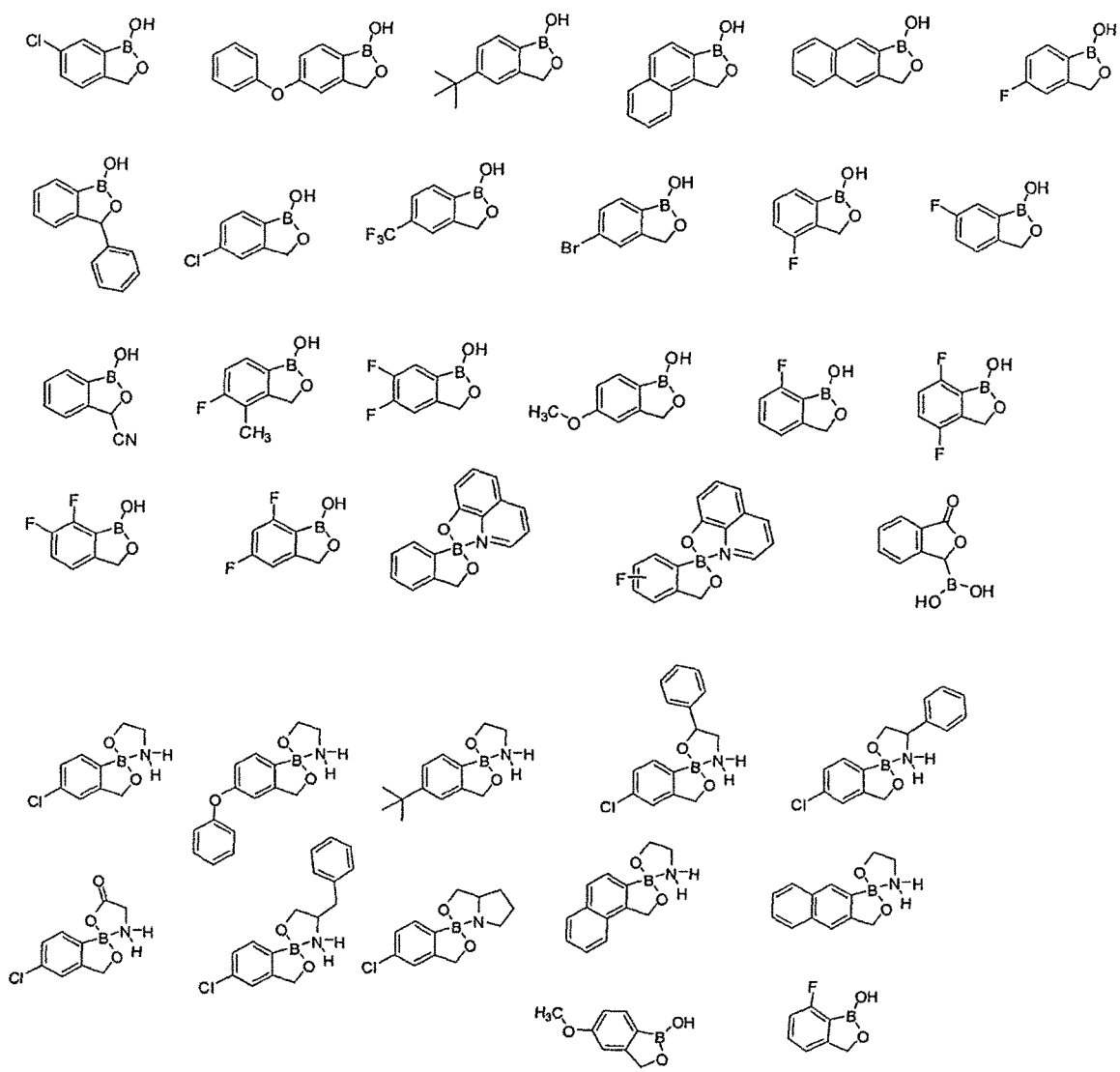
Figure 11C:
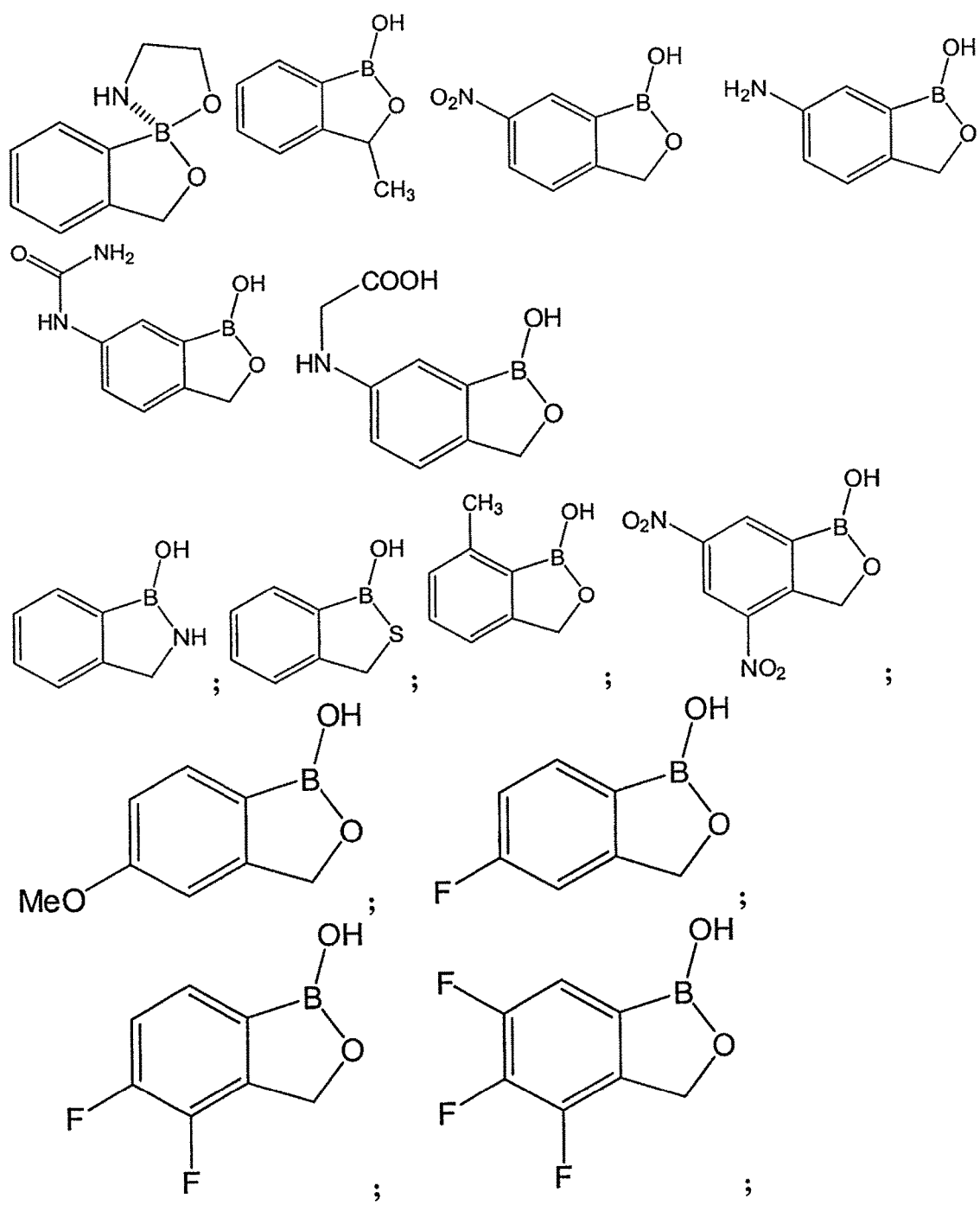
Figure 11D:
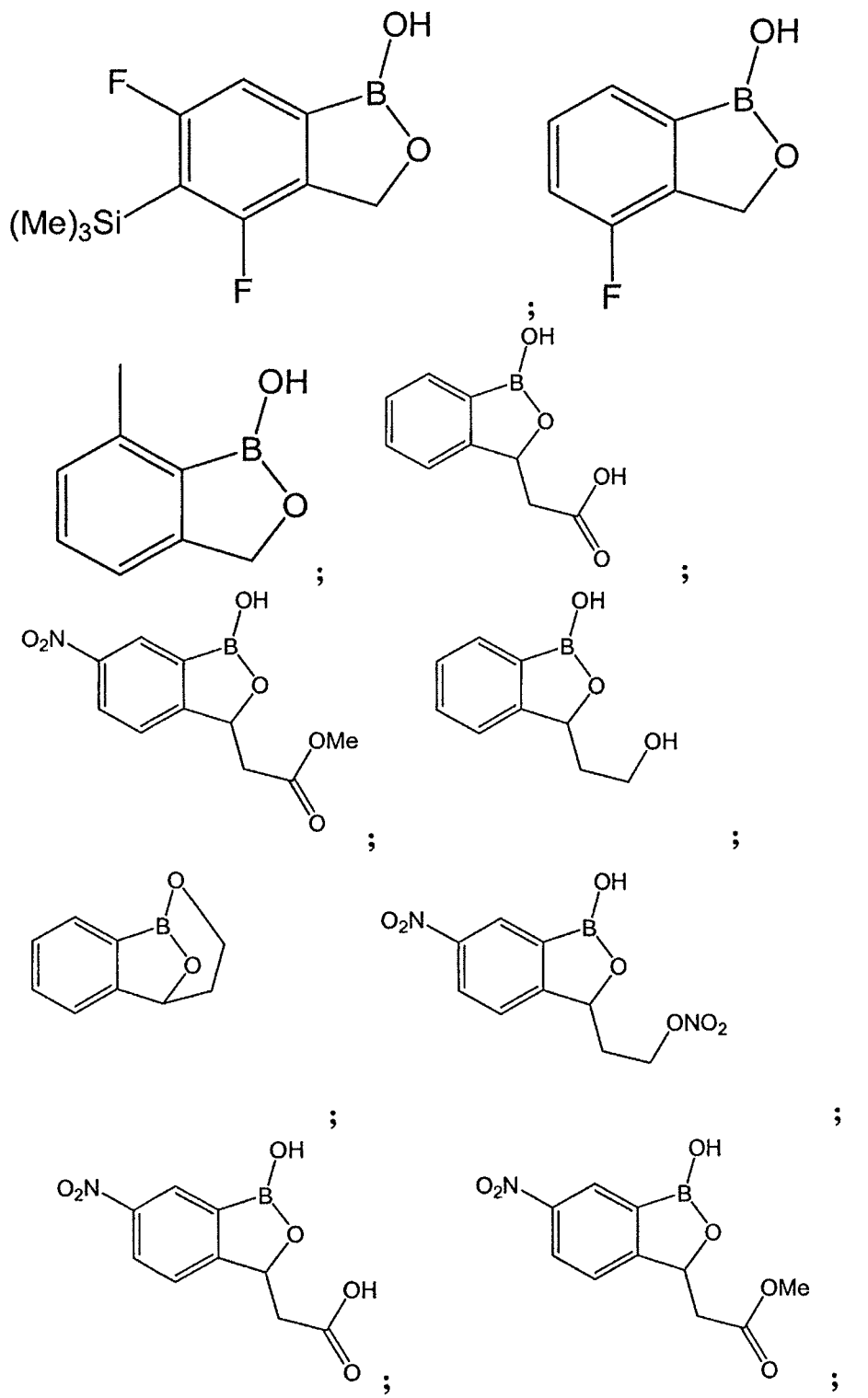
Figure 11E:
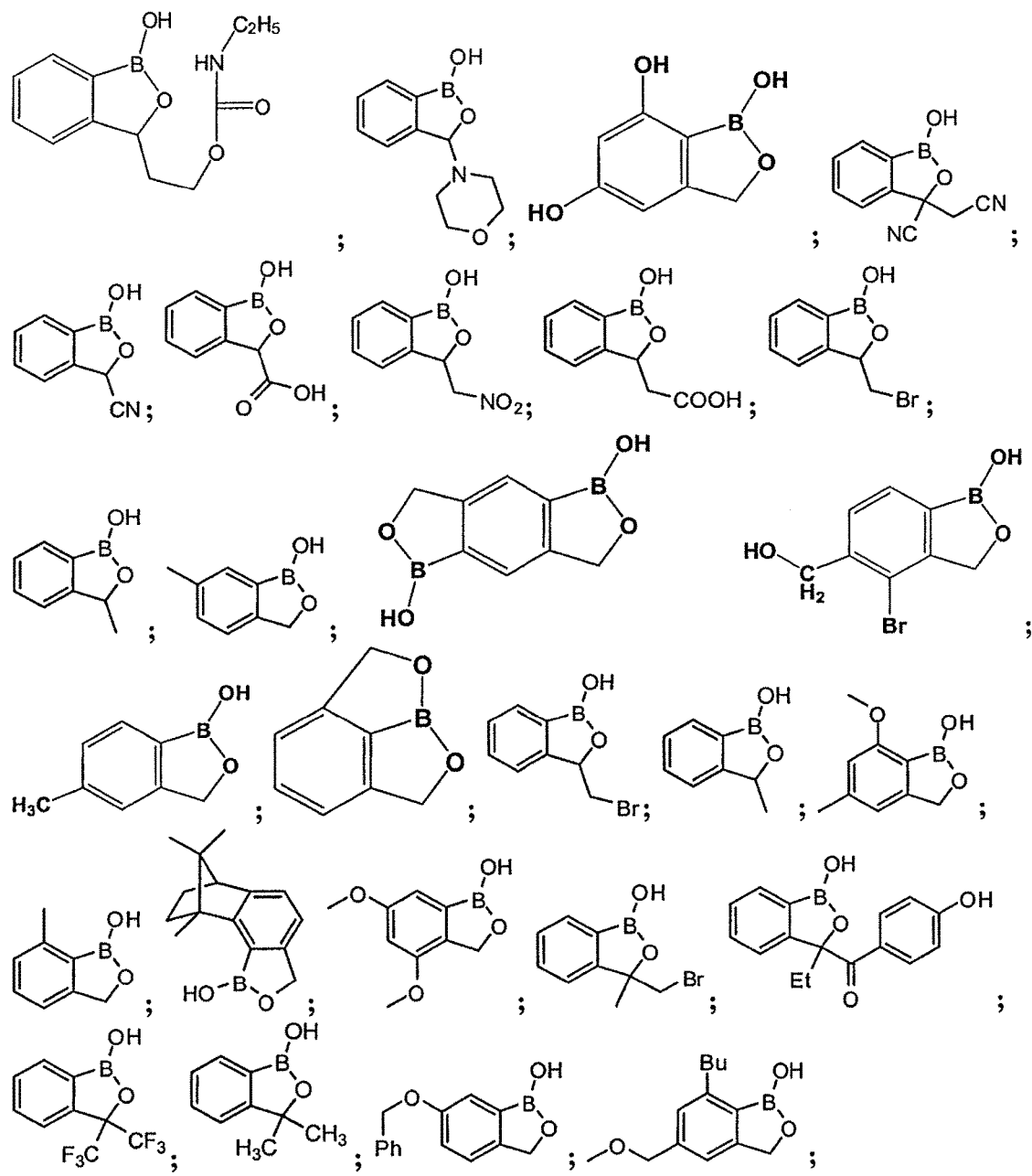
Figure 11F:
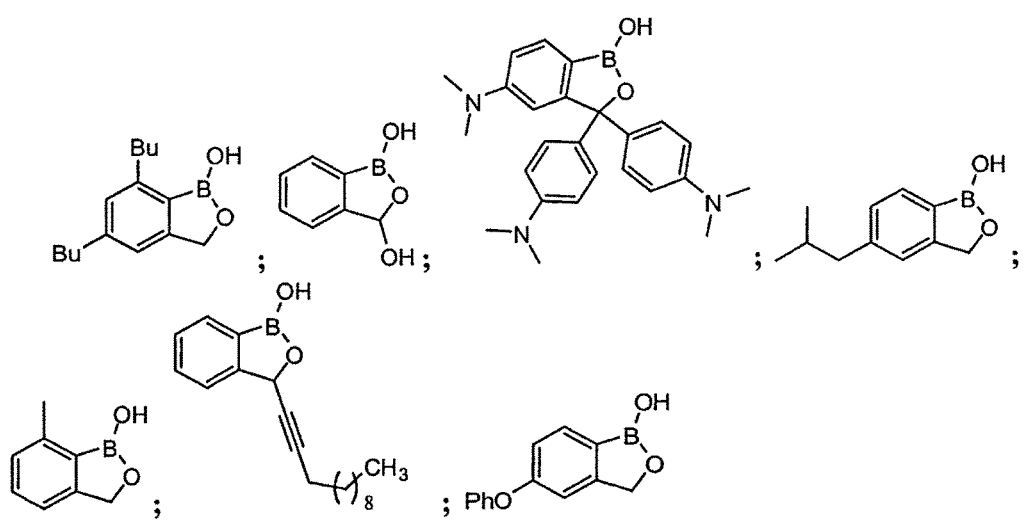
Figure 12A:
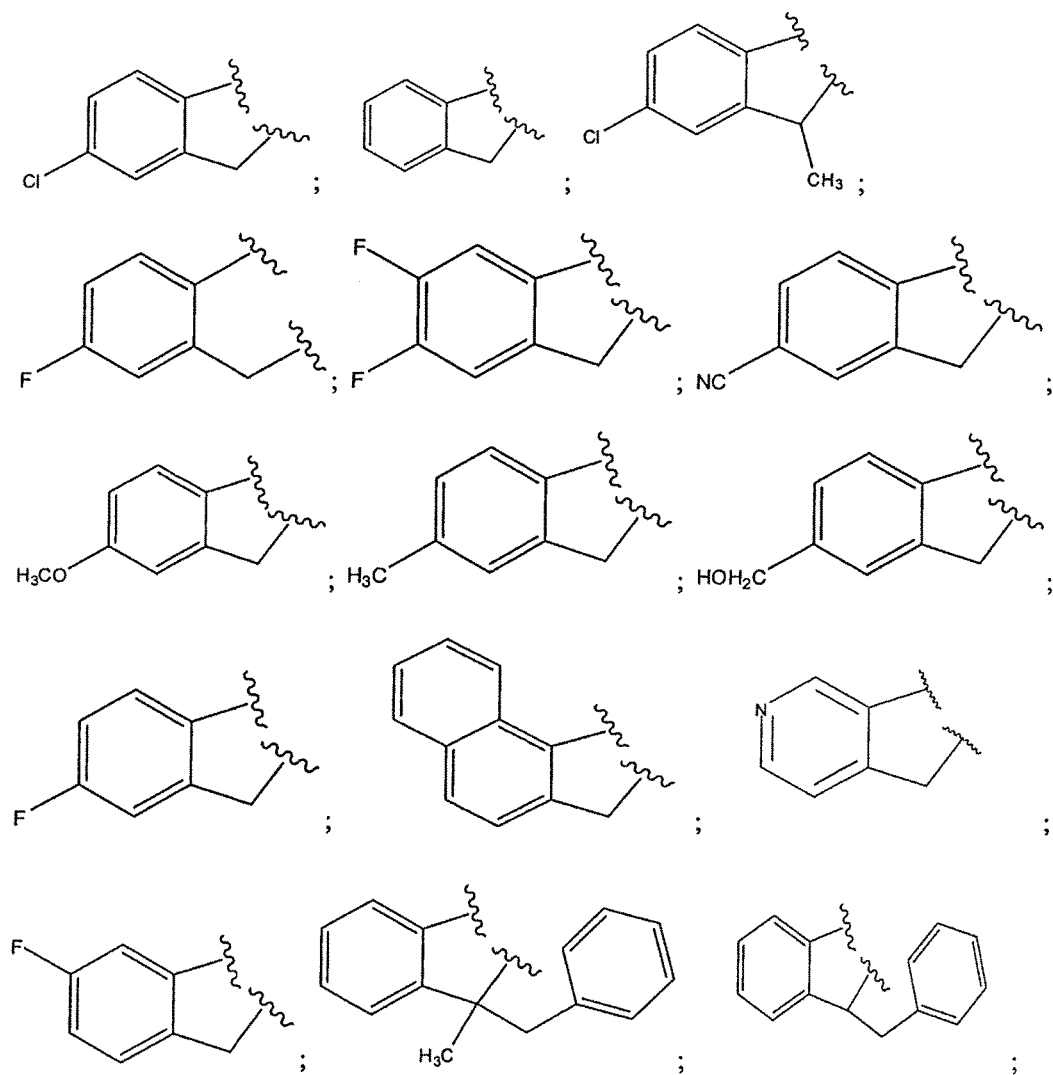
FIG. 12A, FIG. 12B, FIG. 12C, FIG. 12D, FIG. 12E, FIG. 12F, FIG. 12G, FIG. 12H, FIG. 12I display different structures for portions of the compounds of the invention.
Figure 12B:
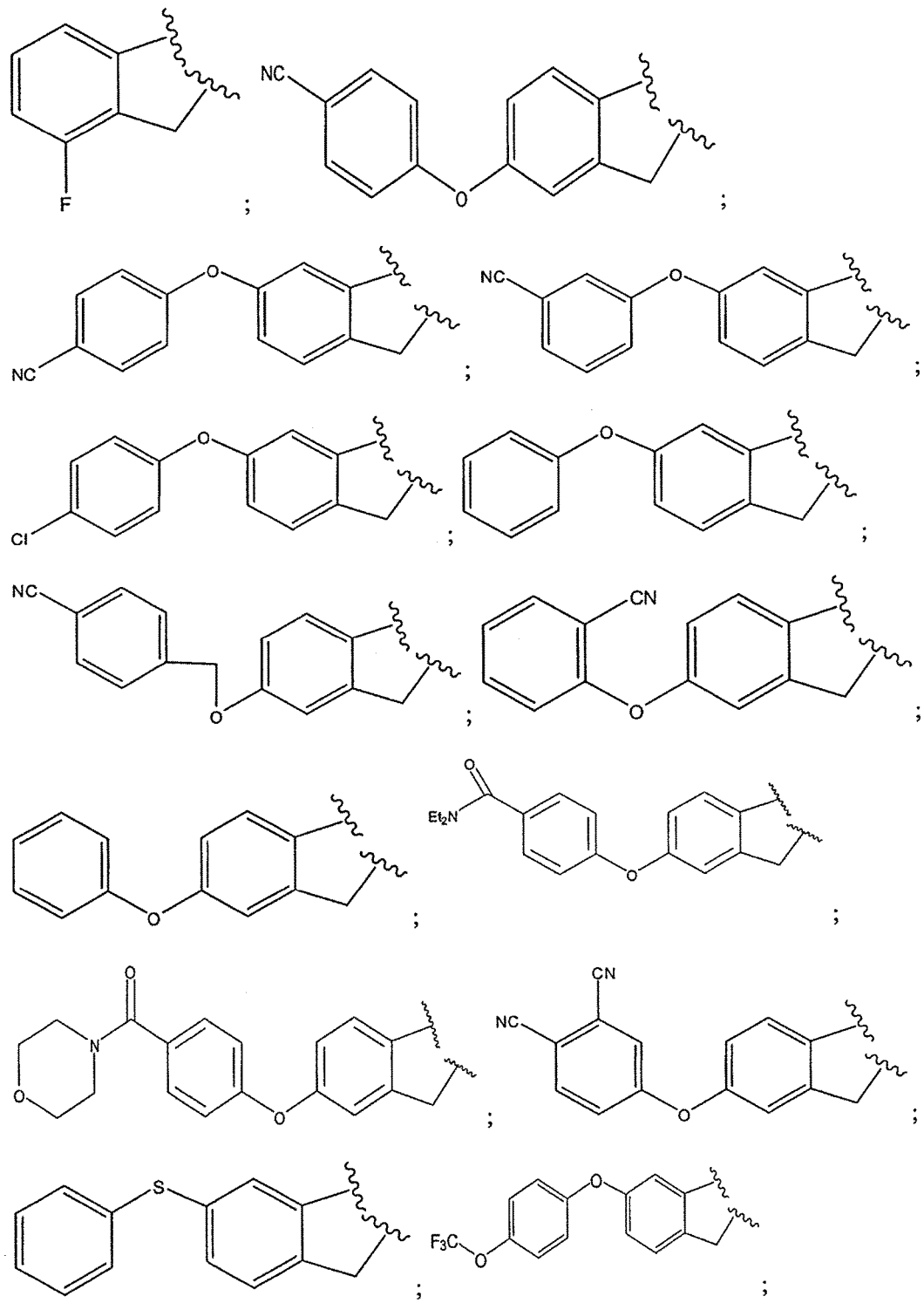
Figure 12C:
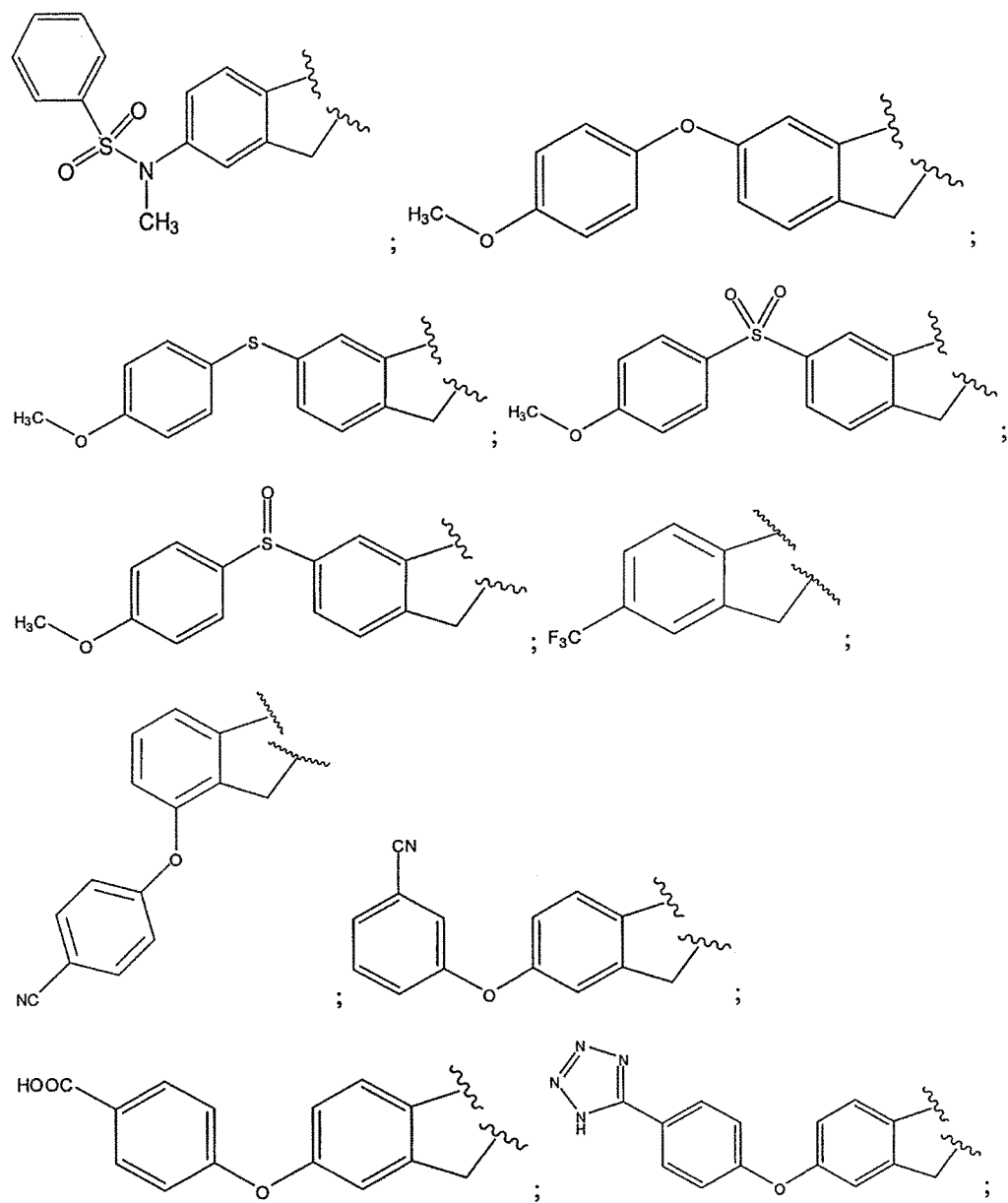
Figure 12D:
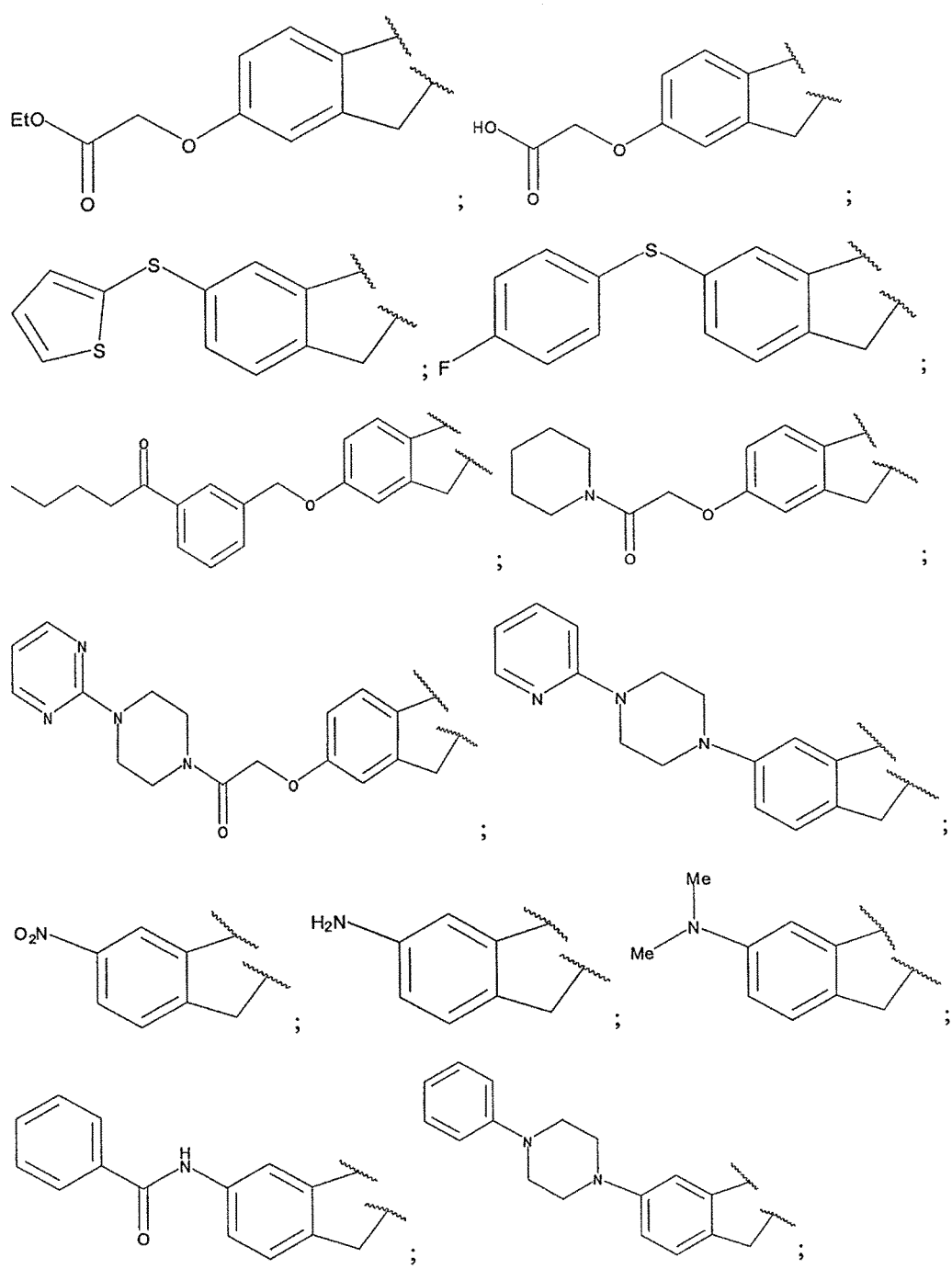
Figure 12E:
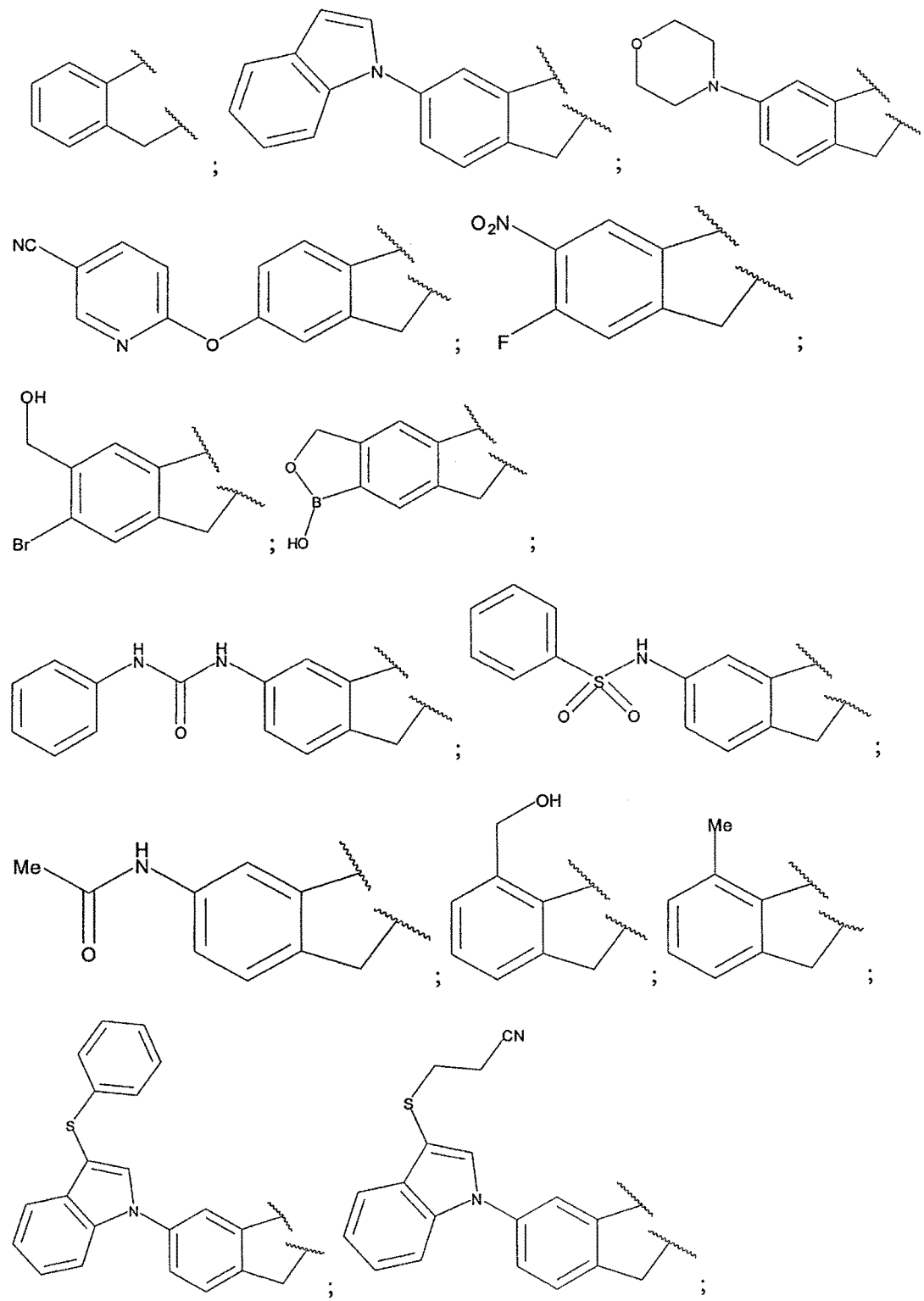
Figure 12F:
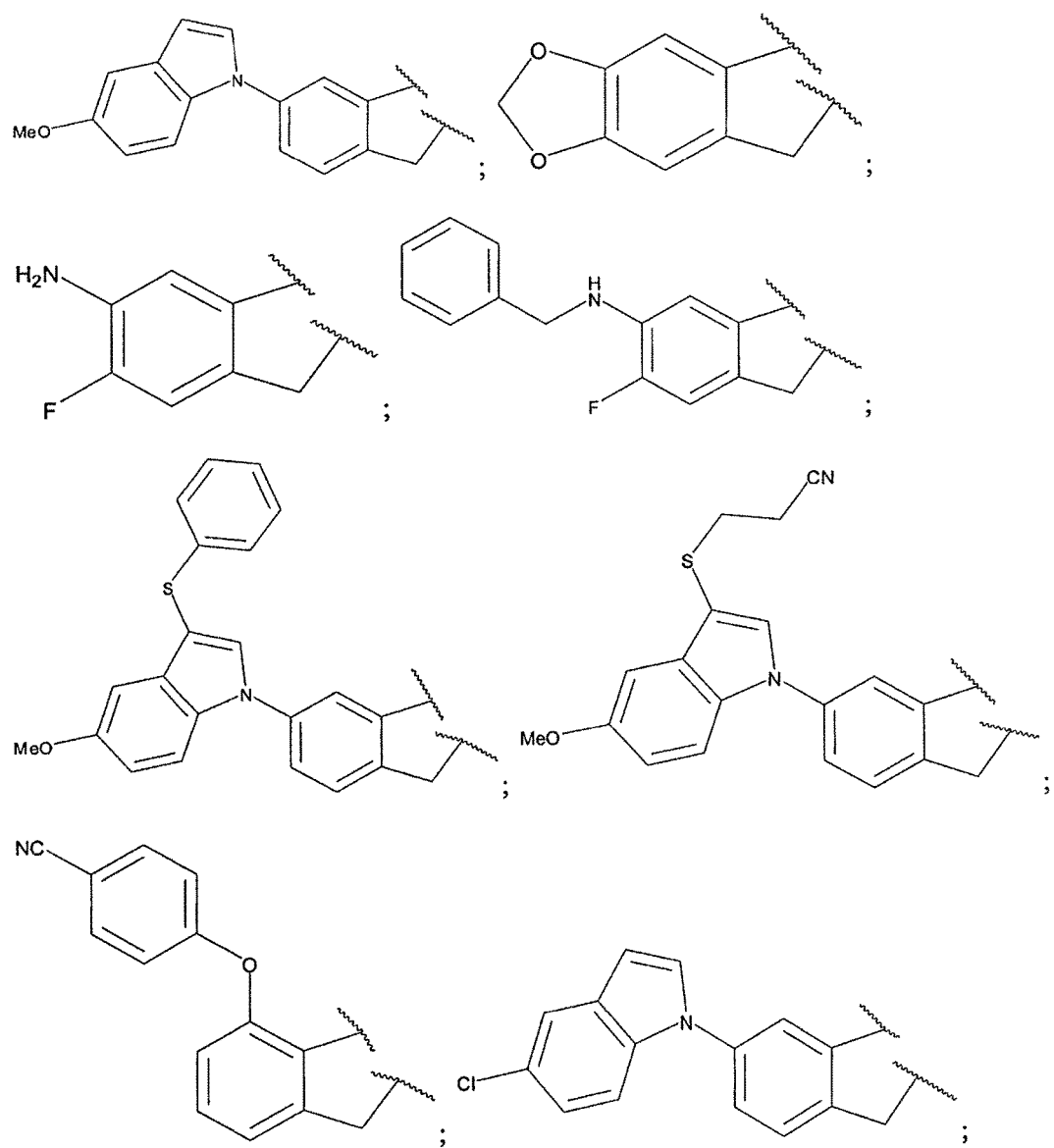
Figure 12G:
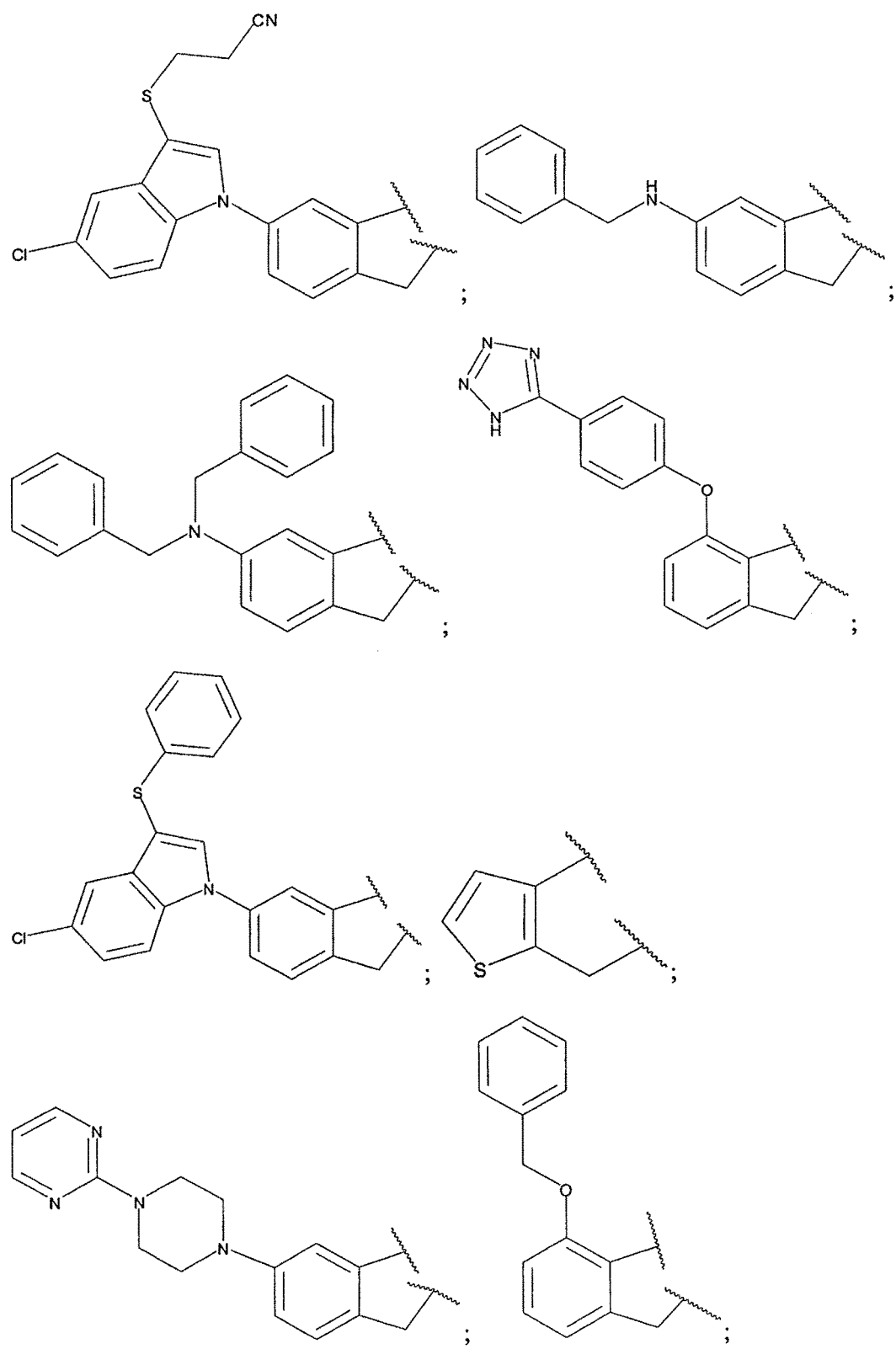
Figure 12H:
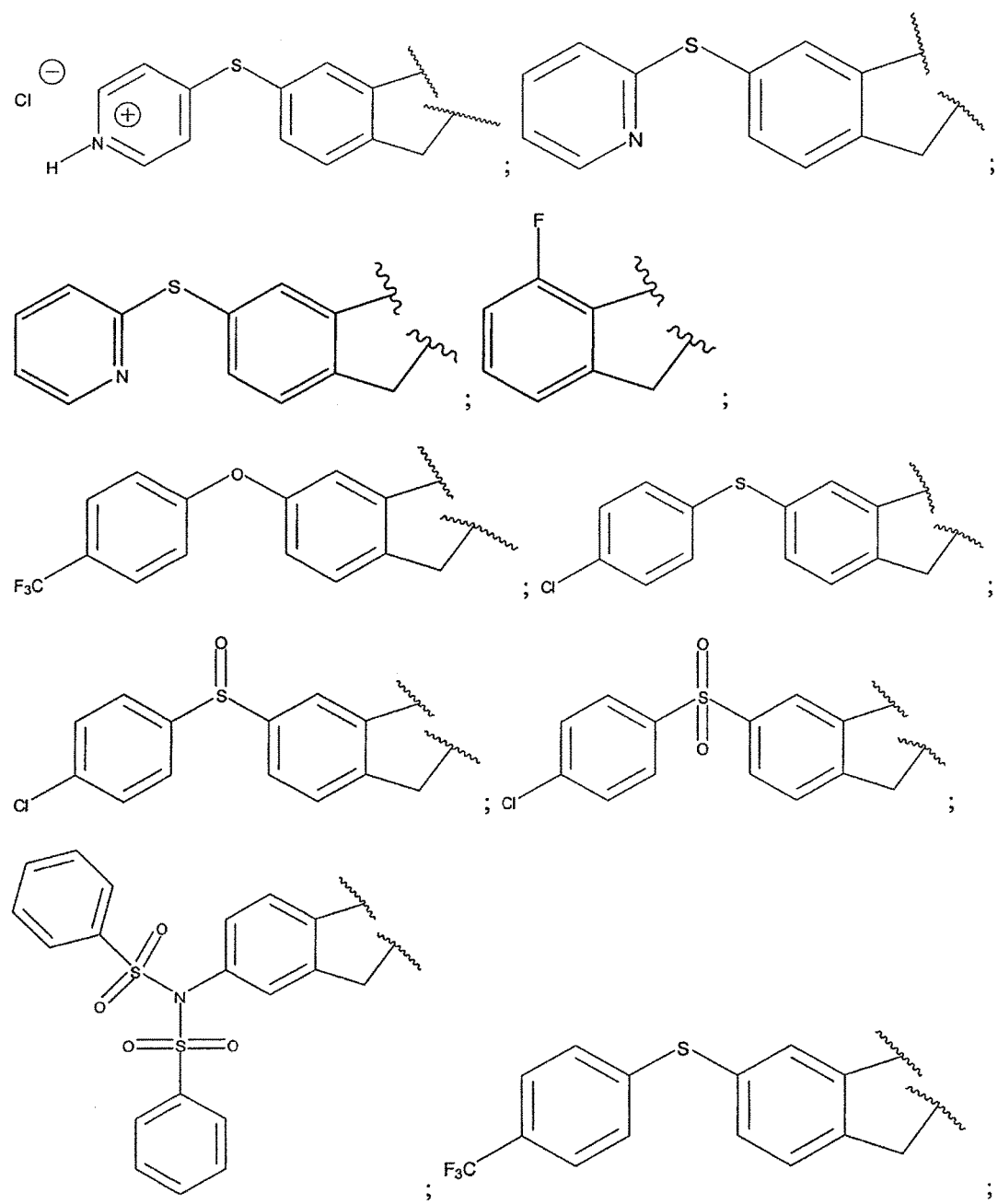
Figure 12I:
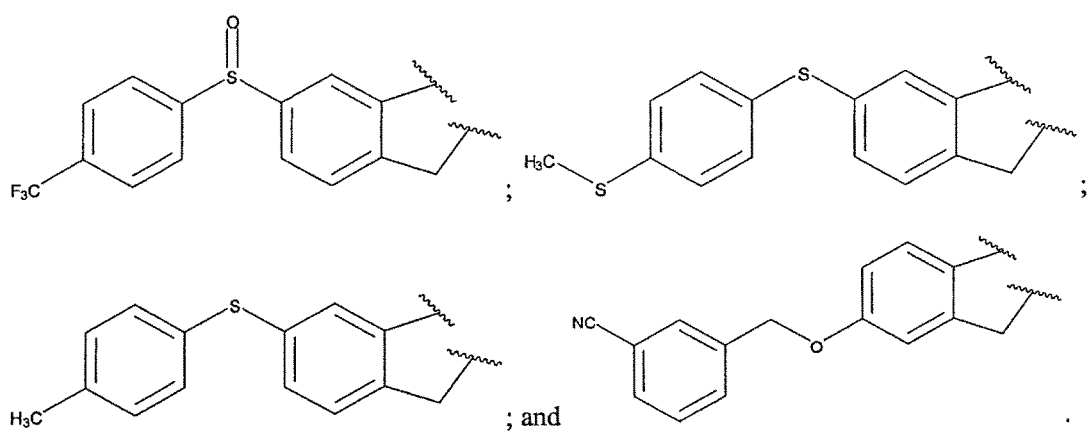
Figure 14:
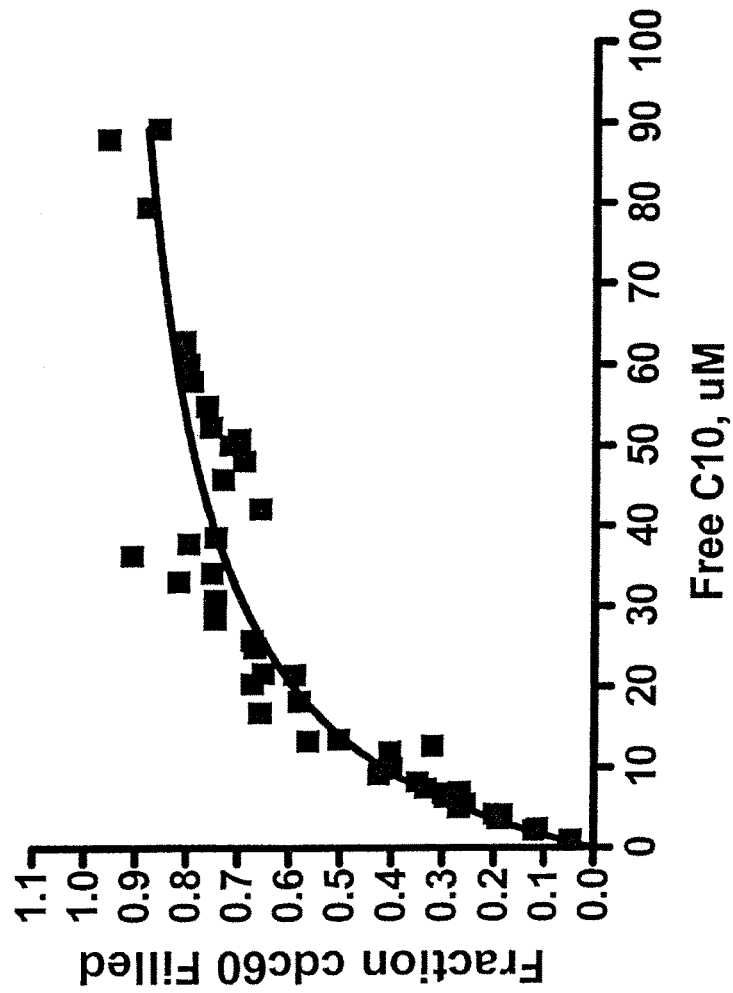
FIG. 14 Binding curve of cdc60 against concentration of free [C10].
Figure 15:
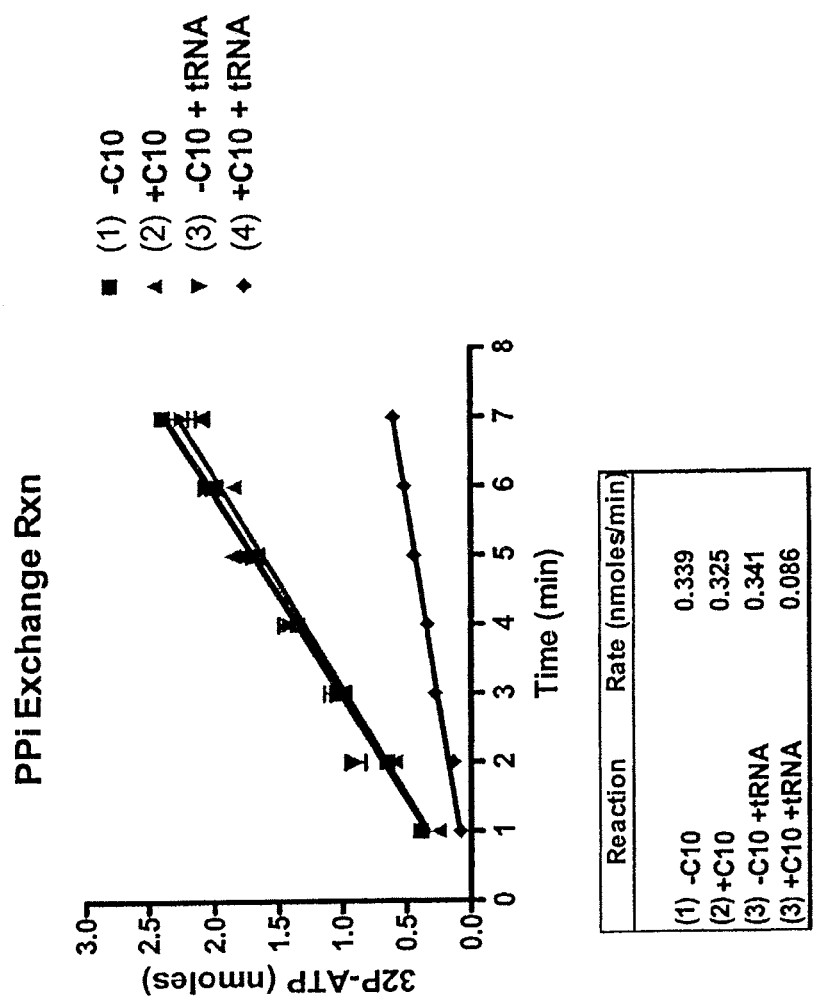
FIG. 15 Data from PPi exchange reaction experiment to determine rate of editing in the presence and absence of C10.
Figure 16:
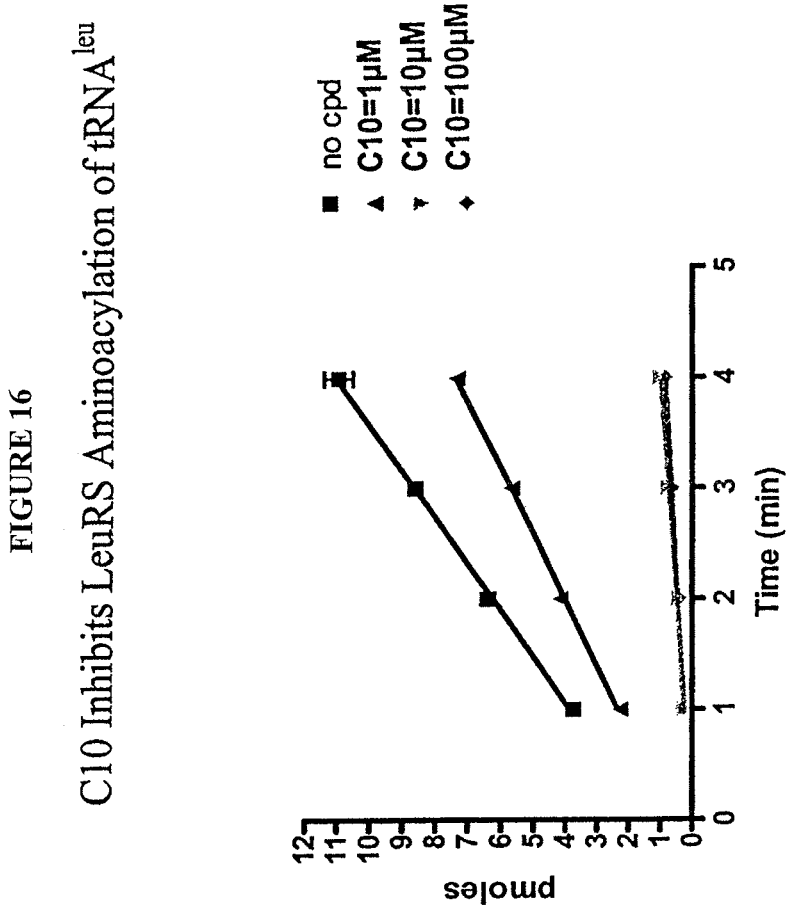
FIG. 16 Data from an aminoacylation experiment showing the effect of C10 at different concentrations on the aminoacylation of $tRNA^{leu}$.
Figure 17:
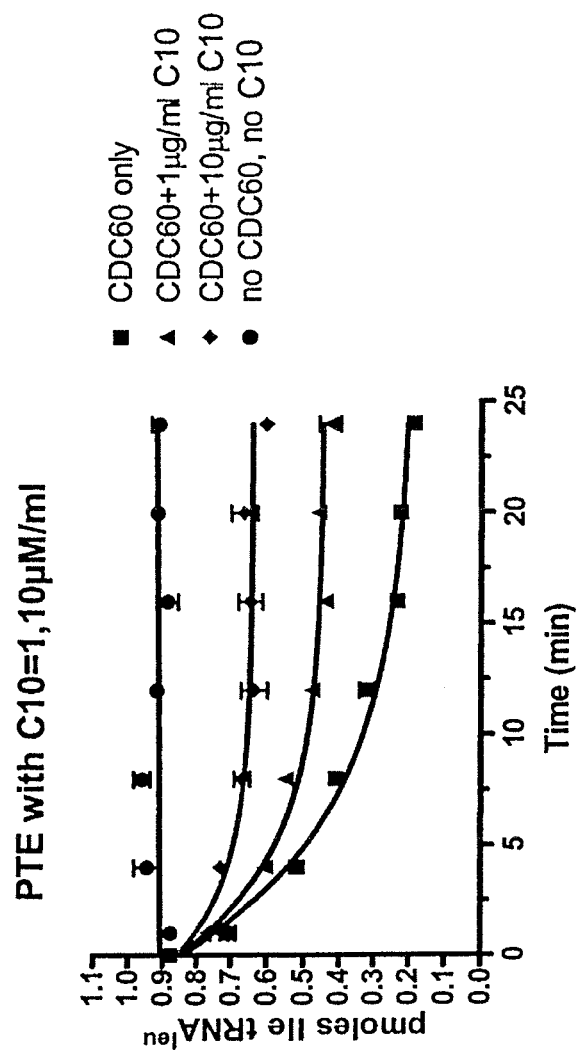
FIG. 17 Results from post transfer editing assay conducted in S. cerevisiae at differing concentrations of C10 across a range of time points.

The abbreviations used herein generally have their conventional meaning within the chemical and biological arts.

"Compound of the invention," as used herein refers to the compounds discussed herein, pharmaceutically acceptable salts and prodrugs of these compounds.

"Boron containing compounds", as used herein, refers to the compounds of the invention that contain boron as part of their chemical formula.

MIC, or minimum inhibitory concentration, is the point where the compound stops more than 50% of cell growth, preferably 60% of cell growth, preferably 70% of cell growth, preferably 80% of cell growth, preferably 90% of cell growth, relative to an untreated control.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "poly" as used herein means at least 2. For example, a polyvalent metal ion is a metal ion having a valency of at least 2.

"Moiety" refers to the radical of a molecule that is attached to another moiety.

The symbol $\sim\!\!\sim$, whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, 6-quinolyl, dioxaborolane, dioxaborinane and dioxaborepane. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''' and R'''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''' and R'''' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

"Ring" as used herein, means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 to 7 atoms in the encircling arrangement. The ring optionally included a heteroatom. Thus, the term "5- to 7-membered ring" includes, for example pyridinyl and piperidinyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), germanium (Ge), aluminum (Al) and boron (B).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

The term "derived from" includes its plain language meaning and also refers to a molecule that is 99%, 98%, 97%, 96%, 95%, 94%, 93%, 92%, 91%, 90%, 89%, 88%, 87%, 86%, 85%, 84%, 83%, 82%, 81%, 80%, 75%, 70%, 65%, or 60% homologous to a referenced molecule. The molecules referred to in this definition include chains of RNA or DNA, oligonucleotides, polypeptides, or proteins of any length and composition.

The term "immunological marker" includes oligonucleotides, proteins, antibodies, peptides, polypeptides, enzymes, or any other molecule able to induce an immune response in appropriate animals or cells or to bind with specific antibodies.

The term "noncognate" is meant to encompass both the singular and plural forms of the word, i.e. the phrase "noncognate amino acid" comprises one or more amino acids.

By "effective" amount of a drug, formulation, or permeant is meant a sufficient amount of a active agent to provide the desired local or systemic effect. A "Topically effective," "Cosmetically effective," "pharmaceutically effective," or "therapeutically effective" amount refers to the amount of drug needed to effect the desired therapeutic result.

"Topically effective" refers to a material that, when applied to the skin, nail, hair, claw or hoof produces a desired pharmacological result either locally at the place of application or systemically as a result of transdermal passage of an active ingredient in the material.

"Cosmetically effective" refers to a material that, when applied to the skin, nail, hair, claw or hoof, produces a desired cosmetic result locally at the place of application of an active ingredient in the material.

The term "pharmaceutically acceptable salts" is meant to include salts of the compounds of the invention which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the present invention provides compounds which are in a prodrug form. Prodrugs of the compounds or complexes described herein readily undergo chemical changes under physiological conditions to provide the compounds of the present invention. Additionally, prodrugs can be converted to the compounds of the present invention by chemical or biochemical methods in an ex vivo environment.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The term "pharmaceutically acceptable carrier" or "pharmaceutically acceptable vehicle" refers to any formulation or carrier medium that provides the appropriate delivery of an effective amount of a active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in *Remington: The Science and Practice of Pharmacy,* 21st Ed., Lippincott, Williams & Wilkins (2005) which is incorporated herein by reference.

"Pharmaceutically acceptable topical carrier" and equivalent terms refer to pharmaceutically acceptable carriers, as described herein above, suitable for topical application. An inactive liquid or cream vehicle capable of suspending or dissolving the active agent(s), and having the properties of being nontoxic and non-inflammatory when applied to the skin, nail, hair, claw or hoof is an example of a pharmaceutically-acceptable topical carrier. This term is specifically intended to encompass carrier materials approved for use in topical cosmetics as well.

The term "pharmaceutically acceptable additive" refers to preservatives, antioxidants, fragrances, emulsifiers, dyes and excipients known or used in the field of drug formulation and that do not unduly interfere with the effectiveness of the biological activity of the active agent, and that is sufficiently non-toxic to the host or patient. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, other permeation enhancers, and other conventional components of topical or transdermal delivery formulations as are known in the art.

The terms "enhancement," "penetration enhancement" or "permeation enhancement" relate to an increase in the permeability of the skin, nail, hair, claw or hoof to a drug, so as to increase the rate at which the drug permeates through the skin, nail, hair, claw or hoof. The enhanced permeation effected through the use of such enhancers can be observed, for example, by measuring the rate of diffusion of the drug through animal or human skin, nail, hair, claw or hoof using a diffusion cell apparatus. A diffusion cell is described by Merritt et al. Diffusion Apparatus for Skin Penetration, *J of Controlled Release,* 1 (1984) pp. 161-162. The term "permeation enhancer" or "penetration enhancer" intends an agent or a mixture of agents, which, alone or in combination, act to increase the permeability of the skin, nail, hair or hoof to a drug.

The term "excipients" is conventionally known to mean carriers, diluents and/or vehicles used in formulating drug compositions effective for the desired use.

The term "topical administration" refers to the application of a pharmaceutical agent to the external surface of the skin, nail, hair, claw or hoof, such that the agent crosses the external surface of the skin, nail, hair, claw or hoof and enters the underlying tissues. Topical administration includes application of the composition to intact skin, nail, hair, claw or hoof, or to an broken, raw or open wound of skin, nail, hair, claw or hoof. Topical administration of a pharmaceutical agent can result in a limited distribution of the agent to the skin and surrounding tissues or, when the agent is removed from the treatment area by the bloodstream, can result in systemic distribution of the agent.

The term "transdermal delivery" refers to the diffusion of an agent across the barrier of the skin, nail, hair, claw or hoof resulting from topical administration or other application of a composition. The stratum corneum acts as a barrier and few pharmaceutical agents are able to penetrate intact skin. In contrast, the epidermis and dermis are permeable to many solutes and absorption of drugs therefore occurs more readily through skin, nail, hair, claw or hoof that is abraded or otherwise stripped of the stratum corneum to expose the epidermis. Transdermal delivery includes injection or other delivery through any portion of the skin, nail, hair, claw or hoof or mucous membrane and absorption or permeation through the remaining portion. Absorption through intact skin, nail, hair, claw or hoof can be enhanced by placing the active agent in an appropriate pharmaceutically acceptable vehicle before application to the skin, nail, hair, claw or hoof. Passive topical administration may consist of applying the active agent directly to the treatment site in combination with emollients or penetration enhancers. As used herein, transdermal delivery is intended to include delivery by permeation through or past the integument, i.e. skin, nail, hair, claw or hoof.

The term "microbial infection" refers to any infection of a host tissue by an infectious agent including, but not limited to, viruses, bacteria, mycobacteria, fungus and parasites (see, e.g., Harrison's Principles of Internal Medicine, pp. 93-98 (Wilson et al., eds., 12th ed. 1991); Williams et al., *J. of Medicinal Chem.* 42:1481-1485 (1999), herein each incorporated by reference in their entirety).

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Inhibiting" and "blocking," are used interchangeably herein to refer to the partial or full blockade of an editing domain of a tRNA synthetase.

"Ventral/intermediate center" as used herein refers to powdered nail samples drilled from the center of the inner surface (facing the nail bed) approximately 0.3-0.5 mm in depth to the surface. The area is beneath the dosed site of the nail place but does not include dosed surface (dorsal nail surface).

"Ventral/intermediate center" as used herein refers to the immediate area of dosed site.

"Remainder nail" as used herein refers to the remaining part of the nail that has not been dosed.

"Supporting bed" as used herein refers to the cotton ball placed within the Teflon chamber of the diffusion cell to provide moisture to the nail plate and also to receive chemicals penetrating through the nail plate.

"Surfacing washing" as used herein refers to ethanol (or other organic solvents) and soap/water washing on the surface of the dosed site.

"Cell washing" as used herein, refers to ethanol (or other organic solvents) and soap/water wash of the inside of the diffusion cell.

A "human nail unit", as defined herein, can be the nail plate, the nail bed, proximal nail fold, lateral nail fold and combinations thereof.

The term "leaving group" means a functional group or atom which can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The term "amino-protecting group" means a protecting group suitable for preventing undesired reactions at an amino nitrogen. Representative amino-protecting groups include, but are not limited to, formyl; acyl groups, for example alkanoyl groups, such as acetyl, trichloroacetyl or trifluoroacetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBS); and the like.

The term "hydroxy-protecting group" means a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

Boron is able to form dative bonds with oxygen, sulfur or nitrogen under some circumstances in this invention. Dative bonds are usually weaker than covalent bonds. In situations where a boron is covalently bonded to at least one oxygen, sulfur or nitrogen, and is at the same time datively bonded to an oxygen, sulfur or nitrogen, respectively, the dative bond and covalent bond between the boron and the two identical heteroatoms can interconvert or be in the form of a resonance hybrid. There is potential uncertainty surrounding the exact nature and extent of electron sharing in these situations. The structures supplied are not intended to include any and all possible bonding scenarios between boron and the atom to which it is bound. Non limiting examples of these bonds are as follows:

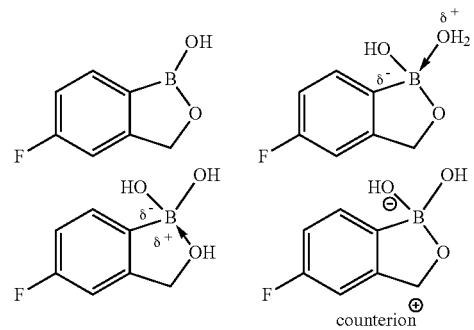

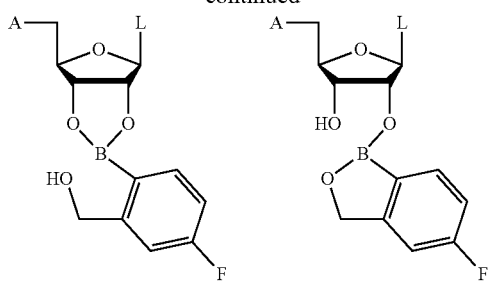

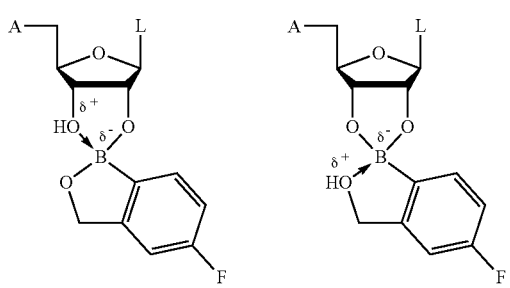

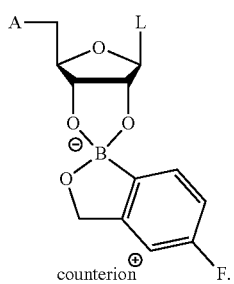

"Salt counterion", as used herein, refers to positively charged ions that associate with a compound of the invention when the boron is fully negatively or partially negatively charged. Examples of salt counterions include H⁺, $H_3O^+$, ammonium, potassium, calcium, magnesium and sodium.

The compounds comprising a boron bonded to a carbon and three heteroatoms (such as three oxygens described in this section) can optionally contain a fully negatively charged boron or partially negatively charged boron, due to the nature of the dative bond between the boron and one of the oxygens. Due to the negative charge, a positively charged counterion may associate with this compound, thus forming a salt. Examples of positively charged counterions include H⁺, $H_3O^+$, calcium, sodium, ammonium, potassium. The salts of these compounds are implicitly contained in descriptions of these compounds.

The present invention also encompasses compounds that are poly- or multi-valent species, including, for example, species such as dimers, trimers, tetramers and higher homologs of the compounds of use in the invention or reactive analogues thereof. For example, dimers of C10 can form under the following conditions:

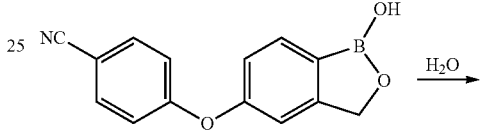

In another example, dimers of C17 can form under the following conditions:

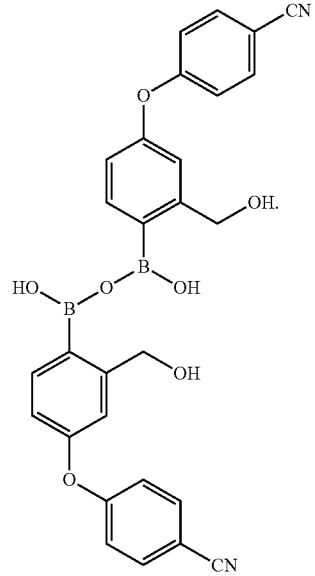

The present invention also encompasses compounds that are anhydrides of the cyclic boronic esters are synthesized by subjecting these compounds to dehydrating conditions. Examples of these anhydrides are provided below:

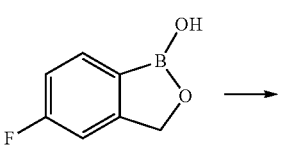

-continued
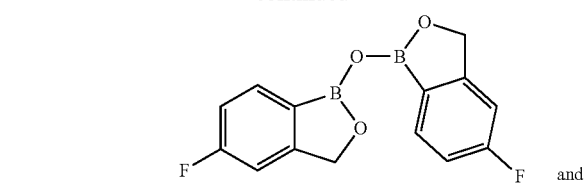
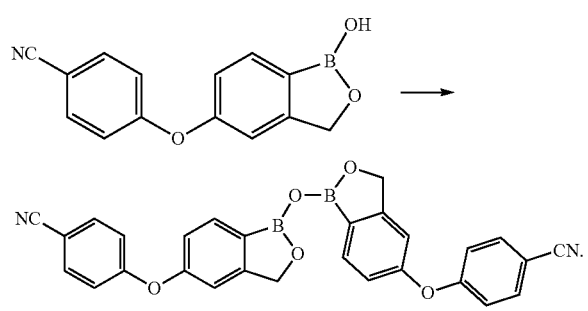
Trimers of the compounds of the invention are also produced. For example, trimers of acyclic boronic esters can be formed as follows:
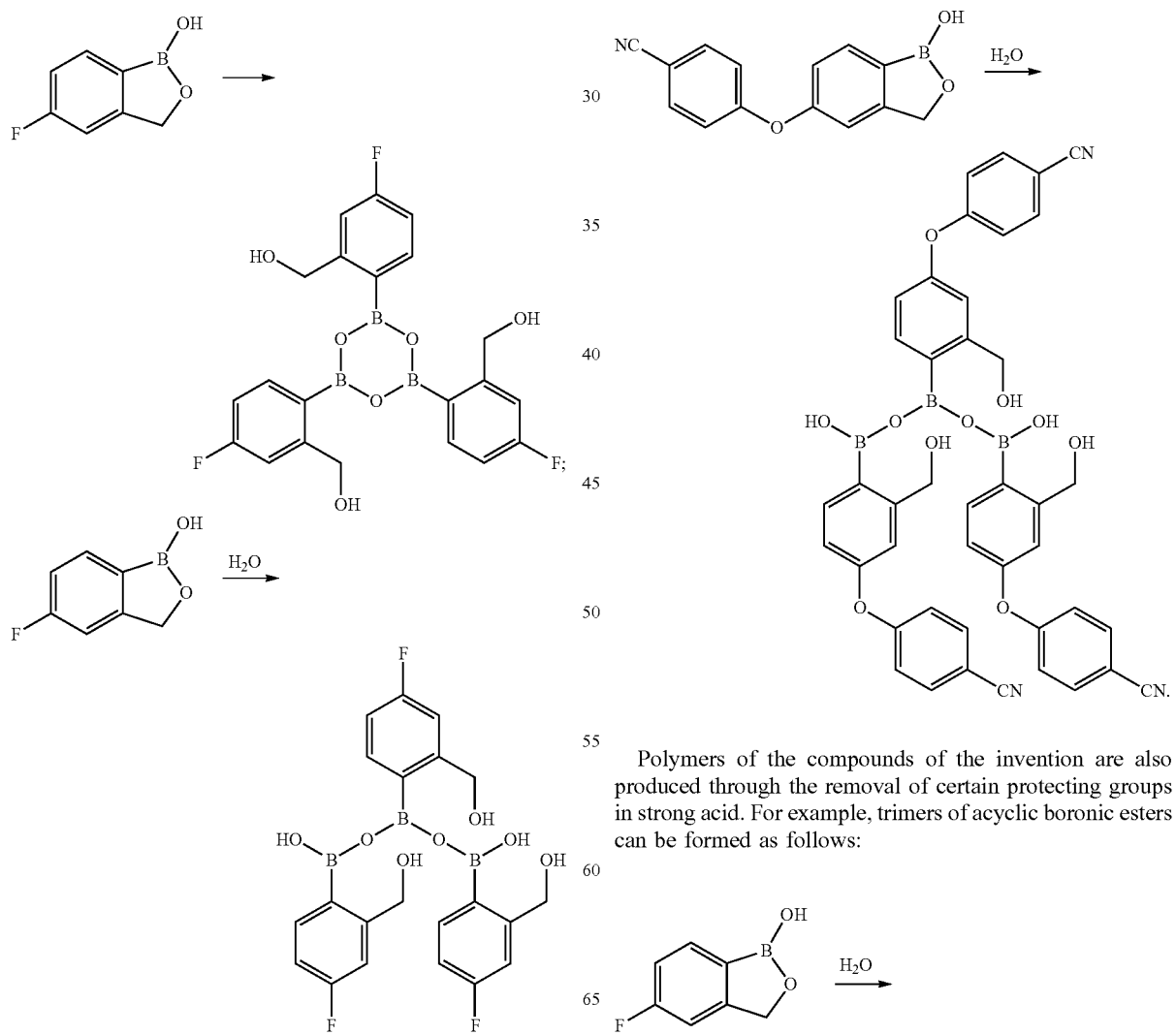
-continued
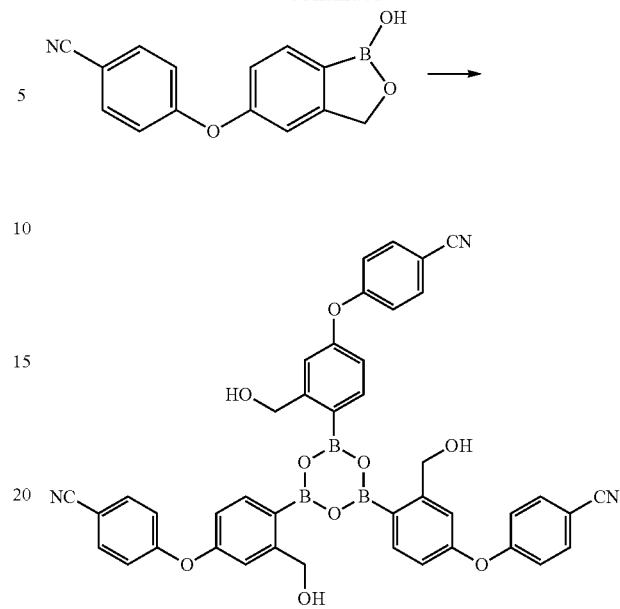
Polymers of the compounds of the invention are also produced through the removal of certain protecting groups in strong acid. For example, trimers of acyclic boronic esters can be formed as follows:

-continued

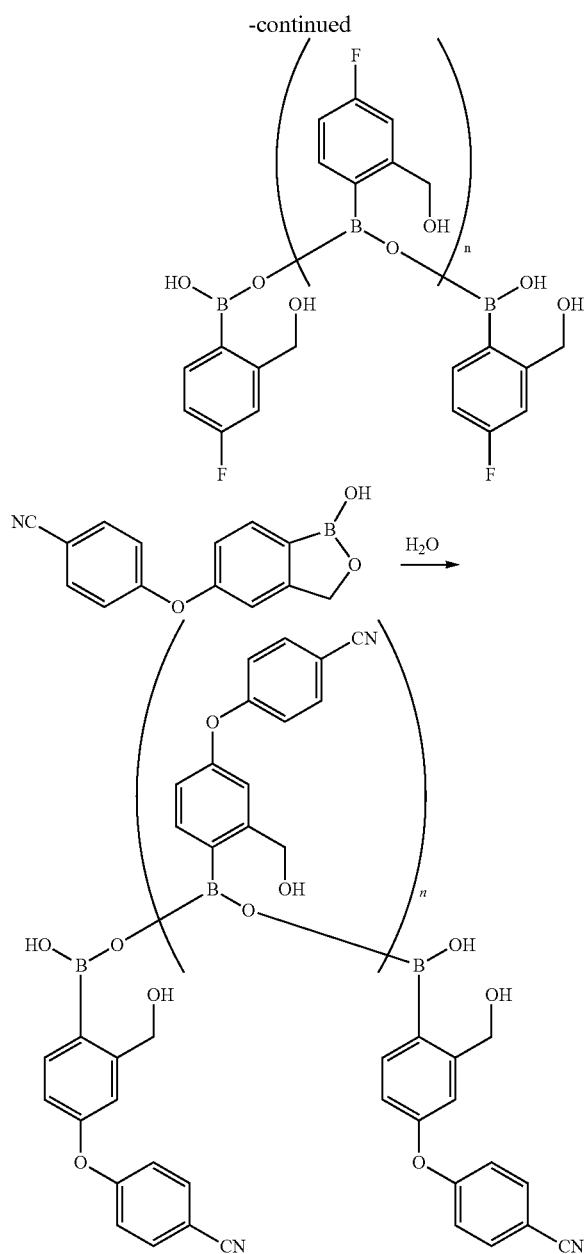

Also of use in the present invention are compounds that are poly- or multi-valent species, including, for example, species such as dimers, trimers, tetramers and higher homologs of the compounds of use in the invention or reactive analogues thereof. The poly- and multi-valent species can be assembled from a single species or more than one species of the invention. For example, a dimeric construct can be "homo-dimeric" or "heterodimeric." Moreover, poly- and multi-valent constructs in which a compound of the invention or a reactive analogue thereof, is attached to an oligomeric or polymeric framework (e.g., polylysine, dextran, hydroxyethyl starch and the like) are within the scope of the present invention. The framework is preferably polyfunctional (i.e. having an array of reactive sites for attaching compounds of use in the invention). Moreover, the framework can be derivatized with a single species of the invention or more than one species of the invention.

Moreover, the present invention includes the use of compounds within the motif set forth in the formulae contained herein, which are functionalized to afford compounds having water-solubility that is enhanced relative to analogous compounds that are not similarly functionalized. Thus, any of the substituents set forth herein can be replaced with analogous radicals that have enhanced water solubility. For example, it is within the scope of the invention to replace a hydroxyl group with a diol, or an amine with a quaternary amine, hydroxy amine or similar more water-soluble moiety. In a preferred embodiment, additional water solubility is imparted by substitution at a site not essential for the activity towards the editing domain of the compounds set forth herein with a moiety that enhances the water solubility of the parent compounds. Methods of enhancing the water-solubility of organic compounds are known in the art. Such methods include, but are not limited to, functionalizing an organic nucleus with a permanently charged moiety, e.g., quaternary ammonium, or a group that is charged at a physiologically relevant pH, e.g. carboxylic acid, amine. Other methods include, appending to the organic nucleus hydroxyl- or amine-containing groups, e.g. alcohols, polyols, polyethers, and the like. Representative examples include, but are not limited to, polylysine, polyethyleneimine, poly(ethyleneglycol) and poly(propyleneglycol). Suitable functionalization chemistries and strategies for these compounds are known in the art. See, for example, Dunn, R. L., et al., Eds. POLYMERIC DRUGS AND DRUG DELIVERY SYSTEMS, ACS Symposium Series Vol. 469, American Chemical Society, Washington, D.C. 1991.

II. Introduction

The present invention provides novel boron compounds and methods for the preparation of these molecules. The invention further provides boron compounds as analogs comprising a functional moiety, such as a drug moiety and methods of use for said analogs.

III. The Compounds

III.a) Cyclic Boronic Esters

In a first aspect, the invention provides a compound having a structure according to Formula I:

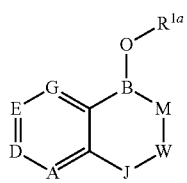

(I)

wherein B is boron. $R^{1a}$ is a member selected from a negative charge, a salt counterion, H, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. M is a member selected from oxygen, sulfur and $NR^{2a}$. $R^{2a}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. J is a member selected from $(CR^{3a}R^{4a})_{n1}$ and $CR^{5a}$. $R^{3a}$, $R^{4a}$, and $R^{5a}$ are members independently selected from H, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The index n1 is an integer selected from 0 to 2. W is a member selected from C=O (carbonyl), $(CR^{6a}R^{7a})_{m1}$ and $CR^{8a}$. $R^{6a}$, $R^{7a}$, and $R^{8a}$ are members independently selected from H, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The index m1 is an integer selected from 0 and 1. A is a member selected from $CR^{9a}$ and N. D is a member selected from $CR^{10a}$ and N. E is a member selected from $CR^{11a}$ and N. G is a member selected from $CR^{12a}$ and N. $R^{9a}$, $R^{10a}$, $R^{11a}$ and $R^{12a}$ are members independently selected from H, OR*, NR*R**, SR*, —S(O)R*, —S(O)$_2$R*, —S(O)$_2$NR*R**, —C(O)R*, —C(O)OR*, —C(O)NR*R**, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. Each R* and R** are members independently selected from H, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The combination of nitrogens (A+D+E+G) is an integer selected from 0 to 3. A member selected from $R^{3a}$, $R^{4a}$ and $R^{5a}$ and a member selected from $R^{6a}$, $R^{7a}$ and $R^{8a}$, together with the atoms to which they are attached, are optionally joined to form a 4 to 7 membered ring. $R^{3a}$ and $R^{4a}$, together with the atoms to which they are attached, are optionally joined to form a 4 to 7 membered ring. $R^{6a}$ and $R^{7a}$, together with the atoms to which they are attached, are optionally joined to form a 4 to 7 membered ring. $R^{9a}$ and $R^{10a}$, together with the atoms to which they are attached, are optionally joined to form a 4 to 7 membered ring. $R^{10a}$ and $R^{11a}$ together with the atoms to which they are attached, are optionally joined to form a 4 to 7 membered ring. $R^{11a}$ and $R^{12a}$, together with the atoms to which they are attached, are optionally joined to form a 4 to 7 membered ring.

In an exemplary embodiment, the compound has a structure according to Formula (Ia):

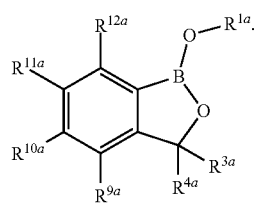

(Ia)

In another exemplary embodiment, each $R^{3a}$ and $R^{4a}$ is a member independently selected from H, cyano, substituted or unsubstituted methyl, substituted or unsubstituted ethyl, trifluoromethyl, substituted or unsubstituted hydroxymethyl, substituted or unsubstituted hydroxyalkyl, substituted or unsubstituted benzyl, substituted or unsubstituted phenyl, substituted or unsubstituted mercaptomethyl, substituted or unsubstituted mercaptoalkyl, substituted or unsubstituted aminomethyl, substituted or unsubstituted alkylaminomethyl, substituted or unsubstituted dialkylaminomethyl, substituted or unsubstituted arylaminomethyl, substituted or unsubstituted indolyl and substituted or unsubstituted amido. In another exemplary embodiment, each $R^{3a}$ and $R^{4a}$ is a member independently selected from cyano, substituted or unsubstituted methyl, substituted or unsubstituted ethyl, trifluoromethyl, substituted or unsubstituted hydroxymethyl, substituted or unsubstituted hydroxyalkyl, substituted or unsubstituted benzyl, substituted or unsubstituted phenyl, substituted or unsubstituted mercaptomethyl, substituted or unsubstituted mercaptoalkyl, substituted or unsubstituted aminomethyl, substituted or unsubstituted alkylaminomethyl, substituted or unsubstituted dialkylaminomethyl, substituted or unsubstituted arylaminomethyl, substituted or unsubstituted indolyl, substituted or unsubstituted amido.

In another exemplary embodiment, each $R^{3a}$ and $R^{4a}$ is a member selected from H, substituted or unsubstituted methyl, substituted or unsubstituted ethyl, substituted or unsubstituted propyl, substituted or unsubstituted isopropyl, substituted or unsubstituted butyl, substituted or unsubstituted t-butyl, substituted or unsubstituted phenyl and substituted or unsubstituted benzyl. In another exemplary embodiment, $R^{3a}$ and $R^{4a}$ is a member selected from methyl, ethyl, propyl, isopropyl, butyl, t-butyl, phenyl and benzyl. In another exemplary embodiment, $R^{3a}$ is H and $R^{4a}$ is a member selected from methyl, ethyl, propyl, isopropyl, butyl, t-butyl, phenyl and benzyl. In another exemplary embodiment, $R^{3a}$ is H and $R^{4a}$ H.

In another exemplary embodiment, each $R^{9a}$, $R^{10a}$, $R^{11a}$ and $R^{12a}$ is a member independently selected from H, OR*, NR*R**, SR*, —S(O)R*, —S(O)$_2$R*, —S(O)$_2$NR*R**, —C(O)R*, —C(O)OR*, —C(O)NR*R**, halogen, cyano, nitro, substituted or unsubstituted methoxy, substituted or unsubstituted methyl, substituted or unsubstituted ethoxy, substituted or unsubstituted ethyl, trifluoromethyl, substituted or unsubstituted hydroxymethyl, substituted or unsubstituted hydroxyalkyl, substituted or unsubstituted benzyl, substituted or unsubstituted phenyl, substituted or unsubstituted phenyloxy, substituted or unsubstituted phenyl methoxy, substituted or unsubstituted thiophenyloxy, substituted or unsubstituted pyridinyloxy, substituted or unsubstituted pyrimidinyloxy, substituted or unsubstituted benzylfuran, substituted or unsubstituted methylthio, substituted or unsubstituted mercaptomethyl, substituted or unsubstituted mercaptoalkyl, substituted or unsubstituted phenylthio, substituted or unsubstituted thiophenylthio, substituted or unsubstituted phenyl methylthio, substituted or unsubstituted pyridinylthio, substituted or unsubstituted pyrimidinylthio, substituted or unsubstituted benzylthiofuranyl, substituted or unsubstituted phenylsulfonyl, substituted or unsubstituted benzylsulfonyl, substituted or unsubstituted phenylmethylsulfonyl, substituted or unsubstituted thiophenylsulfonyl, substituted or unsubstituted pyridinylsulfonyl, substituted or unsubstituted pyrimidinylsulfonyl, substituted or unsubstituted sulfonamidyl, substituted or unsubstituted phenylsulfinyl, substituted or unsubstituted benzylsulfinyl, substituted or unsubstituted phenylmethylsulfinyl, substituted or unsubstituted thiophenylsulfinyl, substituted or unsubstituted pyridinylsulfinyl, substituted or unsubstituted pyrimidinylsulfinyl, substituted or unsubstituted amino, substituted or unsubstituted alkylamino, substituted or unsubstituted dialkylamino, substituted or unsubstituted trifluoromethylamino, substituted or unsubstituted aminomethyl, substituted or unsubstituted alkylaminomethyl, substituted or unsubstituted dialkylaminomethyl, substituted or unsubstituted arylaminomethyl, substituted or unsubstituted benzylamino, substituted or unsubstituted phenylamino, substituted or unsubstituted thiophenylamino, substituted or unsubstituted pyridinylamino, substituted or unsubstituted pyrimidinylamino, substituted or unsubstituted indolyl, substituted or unsubstituted morpholino, substituted or unsubstituted alkylamido, substituted or unsubstituted arylamido, substituted or unsubstituted ureido, substituted or unsubstituted carbamoyl, and substituted or unsubstituted piperizinyl. In an exemplary embodiment, $R^{9a}$, $R^{10a}$, $R^{11a}$ and $R^{12a}$ are selected from the previous list of substituents with the exception of —C(O)R*, —C(O)OR*, —C(O)NR*R**.

In another exemplary embodiment, $R^{9a}$, $R^{10a}$, $R^{11a}$ and $R^{12a}$ are members independently selected from fluoro, chloro, bromo, nitro, cyano, amino, methyl, hydroxylmethyl, trifluoromethyl, methoxy, trifluoromethyoxy, ethyl, diethylcarbamoyl, pyridin-2-yl, pyridin-3-yl, pyridin-4-yl, pyrimidinyl, piperizino, piperizinyl, piperizinocarbonyl, piperizinylcarbonyl, carboxyl, 1-tetrazolyl, 1-ethoxycarbonylmethoxy, carboxymethoxy, thiophenyl, 3-(butylcarbonyl) phenylmethoxy, 1H-tetrazol-5-yl, 1-ethoxycarbonylmethyloxy-, 1-ethoxycarbonylmethyl-, 1-ethoxycarbonyl-, carboxymethoxy-, thiophen-2-yl, thiophen-2-ylthio-, thiophen-3-yl, thiophen-3-ylthio, 4-fluorophenylthio, butylcarbonylphenylmethoxy, butylcarbonylphenylmethyl, butylcarbonylmethyl, 1-(piperidin-1-yl)carbonyl)methyl, 1-(piperidin-1-yl)carbonyl)methoxy, 1-(piperidin-2-yl)carbonyl)methoxy, 1-(piperidin-3-yl)carbonyl)methoxy, 1-(4-(pyrimidin-2-yl)piperazin-1-yl)carbonyl)methoxy, 1-(4-(pyrimidin-2-yl)piperazin-1-yl)carbonyl)methyl, 1-(4-(pyrimidin-2-yl)piperazin-1-yl)carbonyl, 1-4-(pyrimidin-2-yl)piperazin-1-yl, 1-(4-(pyridin-2-yl)piperazin-1-yl) carbonyl), 1-(4-(pyridin-2-yl)piperazin-1-yl) carbonylmethyl, (1-(4-(pyridin-2-yl)piperazin-1-yl) carbonyl)-methoxy), 1-(4-(pyridin-2-yl)piperazin-1-yl, 1H-indol-1-yl, morpholino-, morpholinyl, morpholinocarbonyl, morpholinylcarbonyl, phenylureido, phenylcarbamoyl, acetamido, 3-(phenylthio)-1H-indol-1-yl, 3-(2-cyanoethylthio)-1H-indol-1-yl, benzylamino, 5-methoxy-3-(phenylthio)-1H-indol-1-yl, 5-methoxy-3-(2-cyanoethylthio)-1H-indol-1-yl)), 5-chloro-1H-indol-1-yl, 5-chloro-3-(2-cyanoethylthio)-1H-indol-1-yl)), dibenzylamino, benzylamino, 5-chloro-3-(phenylthio)-1H-indol-1-yl)), 4-(1H-tetrazol-5-yl)phenoxy, 4-(1H-tetrazol-5-yl)phenyl, 4-(1H-tetrazol-5-yl)phenylthio, 2-cyanophenoxy, 3-cyanophenoxy, 4-cyanophenoxy, 2-cyanophenylthio, 3-cyanophenylthio, 4-cyanophenylthio, 2-chlorophenoxy, 3-chlorophenoxy, 4-chlorophenoxy, 2-fluorophenoxy, 3-fluorophenoxy, 4-fluorophenoxy, 2-cyanobenzyloxy, 3-cyanobenzyloxy, 4-cyanobenzyloxy, 2-chlorobenzyloxy, 3-chlorobenzyloxy, 4-chlorobenzyloxy, 2-fluorobenzyloxy, 3-fluorobenzyloxy, 4-fluorobenzyloxy, unsubstituted phenyl, unsubstituted benzyl. In an exemplary embodiment, $R^{9a}$ is H and $R^{12a}$ is H.

In an exemplary embodiment, the compound according to Formula (I) or Formula (Ia) is a member selected from:

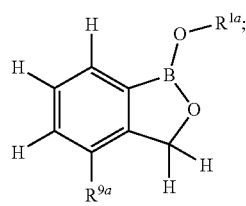
(Ib)

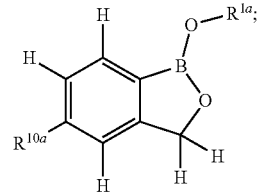
(Ic)

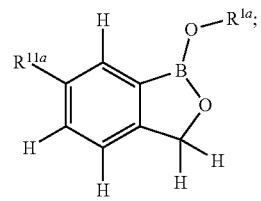
(Id)

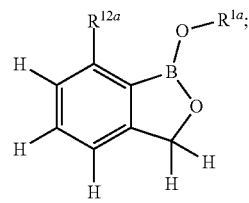
(Ie)

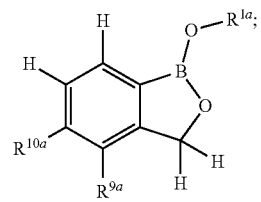
(If)

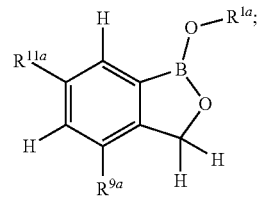
(Ig)

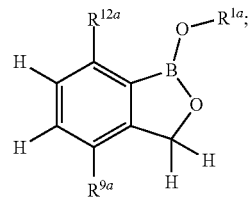
(Ih)

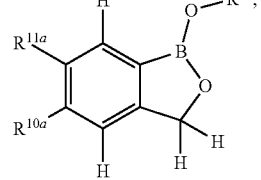
(Ii)

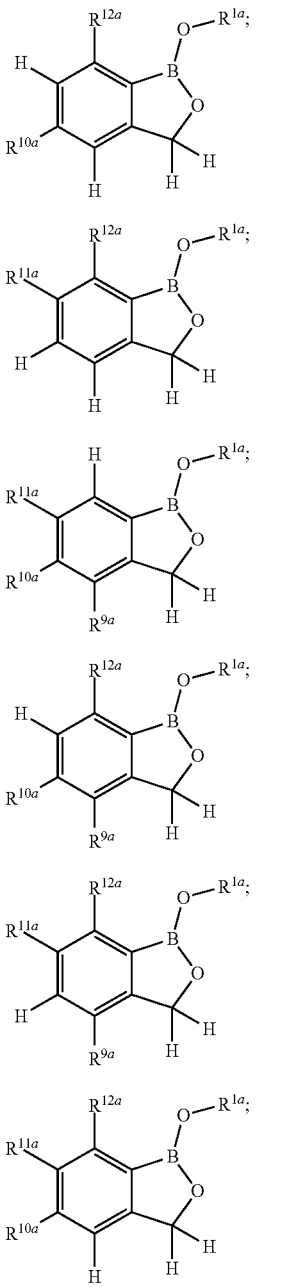

In an exemplary embodiment, the compound has a structure according to one of Formulae I-Io with substituent selections for $R^{9a}$, $R^{10a}$, $R^{11a}$ and $R^{12a}$ including all the possibilities contained in paragraph 106 except for H. In an exemplary embodiment, the compound has a structure according to one of Formulae Ib-Io with substituent selections for $R^{9a}$, $R^{10a}$, $R^{11a}$ and $R^{12a}$ including all the possibilities contained in paragraph 107 except for H.

In an exemplary embodiment, the compound has a formula according to Formulae (Ib)-(Ie) wherein $R^{1a}$ is a member selected from H, a negative charge and a salt counterion and the remaining R group ($R^{9a}$ in Ib, $R^{10a}$ in Ic, $R^{11a}$ in Id, and $R^{12a}$ in Ie) is a member selected from fluoro, chloro, bromo, nitro, cyano, amino, methyl, hydroxylmethyl, trifluoromethyl, methoxy, trifluoromethyoxy, ethyl, diethylcarbamoyl, pyridin-2-yl, pyridin-3-yl, pyridin-4-yl, pyrimidinyl, piperizino, piperizinyl, piperizinocarbonyl, piperizinylcarbonyl, carboxyl, 1-tetrazolyl, 1-ethoxycarbonylmethoxy, carboxymethoxy, thiophenyl, 3-(butylcarbonyl) phenylmethoxy, 1H-tetrazol-5-yl, 1-ethoxycarbonylmethyloxy-, 1-ethoxycarbonylmethyl-, 1-ethoxycarbonyl-, carboxymethoxy-, thiophen-2-yl, thiophen-2-ylthio-, thiophen-3-yl, thiophen-3-ylthio, 4-fluorophenylthio, butylcarbonylphenylmethoxy, butylcarbonylphenylmethyl, butylcarbonylmethyl, 1-(piperidin-1-yl)carbonyl)methyl, 1-(piperidin-1-yl)carbonyl)methoxy, 1-(piperidin-2-yl)carbonyl)methoxy, 1-(piperidin-3-yl)carbonyl)methoxy, 1-(4-(pyrimidin-2-yl)piperazin-1-yl)carbonyl)methoxy, 1-(4-(pyrimidin-2-yl)piperazin-1-yl)carbonyl)methyl, 1-(4-(pyrimidin-2-yl)piperazin-1-yl)carbonyl, 1-4-(pyrimidin-2-yl)piperazin-1-yl, 1-(4-(pyridin-2-yl)piperazin-1-yl) carbonyl), 1-(4-(pyridin-2-yl)piperazin-1-yl) carbonylmethyl, (1-(4-(pyridin-2-yl)piperazin-1-yl) carbonyl)-methoxy), 1-(4-(pyridin-2-yl)piperazin-1-yl, 1H-indol-1-yl, morpholino-, morpholinyl, morpholinocarbonyl, morpholinylcarbonyl, phenylureido, phenylcarbamoyl, acetamido, 3-(phenylthio)-1H-indol-1-yl, 3-(2-cyanoethylthio)-1H-indol-1-yl, benzylamino, 5-methoxy-3-(phenylthio)-1H-indol-1-yl, 5-methoxy-3-(2-cyanoethylthio)-1H-indol-1-yl)), 5-chloro-1H-indol-1-yl, 5-chloro-3-(2-cyanoethylthio)-1H-indol-1-yl)), dibenzylamino, benzylamino, 5-chloro-3-(phenylthio)-1H-indol-1-yl)), 4-(1H-tetrazol-5-yl)phenoxy, 4-(1H-tetrazol-5-yl)phenyl, 4-(1H-tetrazol-5-yl)phenylthio, 2-cyanophenoxy, 3-cyanophenoxy, 4-cyanophenoxy, 2-cyanophenylthio, 3-cyanophenylthio, 4-cyanophenylthio, 2-chlorophenoxy, 3-chlorophenoxy, 4-chlorophenoxy, 2-fluorophenoxy, 3-fluorophenoxy, 4-fluorophenoxy, 2-cyanobenzyloxy, 3-cyanobenzyloxy, 4-cyanobenzyloxy, 2-chlorobenzyloxy, 3-chlorobenzyloxy, 4-chlorobenzyloxy, 2-fluorobenzyloxy, 3-fluorobenzyloxy and 4-fluorobenzyloxy.

In an exemplary embodiment, the compound has a formula according to Formulae (If)-(Ik) wherein $R^{1a}$ is a member selected from H, a negative charge and a salt counterion and each of the remaining two R groups ($R^{9a}$ and $R^{10a}$ in If, $R^{9a}$ and $R^{11a}$ in Ig, $R^{9a}$ and $R^{12a}$ in Ih, $R^{10a}$ and $R^{11a}$ in Ii, $R^{10a}$ and $R^{12a}$ in Ij, $R^{11a}$ and $R^{12a}$ in Ik) is a member independently selected from fluoro, chloro, bromo, nitro, cyano, amino, methyl, hydroxylmethyl, trifluoromethyl, methoxy, trifluoromethyoxy, ethyl, diethylcarbamoyl, pyridin-2-yl, pyridin-3-yl, pyridin-4-yl, pyrimidinyl, piperizino, piperizinyl, piperizinocarbonyl, piperizinylcarbonyl, carboxyl, 1-tetrazolyl, 1-ethoxycarbonylmethoxy, carboxymethoxy, thiophenyl, 3-(butylcarbonyl) phenylmethoxy, 1H-tetrazol-5-yl, 1-ethoxycarbonylmethyloxy-, 1-ethoxycarbonylmethyl-, 1-ethoxycarbonyl-, carboxymethoxy-, thiophen-2-yl, thiophen-2-ylthio-, thiophen-3-yl, thiophen-3-ylthio, 4-fluorophenylthio, butylcarbonylphenylmethoxy, butylcarbonylphenylmethyl, butylcarbonylmethyl, 1-(piperidin-1-yl)carbonyl)methyl, 1-(piperidin-1-yl)carbonyl)methoxy, 1-(piperidin-2-yl)carbonyl)methoxy, 1-(piperidin-3-yl)carbonyl)methoxy, 1-(4-(pyrimidin-2-yl)piperazin-1-yl)carbonyl)methoxy, 1-(4-(pyrimidin-2-yl)piperazin-1-yl)carbonyl)methyl, 1-(4-(pyrimidin-2-yl)piperazin-1-yl)carbonyl, 1-4-(pyrimidin-2-yl)piperazin-1-yl, 1-(4-(pyridin-2-yl)piperazin-1-yl) carbonyl), 1-(4-(pyridin-2-yl)piperazin-1-yl) carbonylmethyl, (1-(4-(pyridin-2-yl)piperazin-1-yl) carbonyl)-methoxy), 1-(4-(pyridin-2-yl)piperazin-1-yl, 1H-indol-1-yl, morpholino-, morpholinyl, morpholinocarbonyl, morpholinylcarbonyl, phenylureido, phenylcarbamoyl, acetamido, 3-(phenylthio)-1H-indol-1-yl, 3-(2-cyanoethylthio)-1H-indol-1-yl, benzylamino, 5-methoxy-3-(phenylthio)-1H-indol-1-yl, 5-methoxy-3-(2-cyanoethylthio)-1H-indol-1-yl)), 5-chloro-1H-indol-1-yl, 5-chloro-3-(2-cyanoethylthio)-1H-indol-1-yl)), dibenzylamino, benzylamino, 5-chloro-3-(phenylthio)-1H-indol-1-yl)), 4-(1H-tetrazol-5-yl)phenoxy, 4-(1H-tetrazol-5-yl)phenyl, 4-(1H-tetrazol-5-yl)phenylthio, 2-cyanophenoxy, 3-cyanophenoxy, 4-cyanophenoxy, 2-cyanophenylthio, 3-cyanophenylthio, 4-cyanophenylthio, 2-chlorophenoxy, 3-chlorophenoxy, 4-chlorophenoxy, 2-fluorophenoxy, 3-fluorophenoxy, 4-fluorophenoxy, 2-cyanobenzyloxy, 3-cyanobenzyloxy, 4-cyanobenzyloxy, 2-chlorobenzyloxy, 3-chlorobenzyloxy, 4-chlorobenzyloxy, 2-fluorobenzyloxy, 3-fluorobenzyloxy, and 4-fluorobenzyloxy.

In an exemplary embodiment, the compound has a formula according to Formulae (Il)-(Io) wherein $R^{1a}$ is a member selected from H, a negative charge and a salt counterion and each of the remaining three R groups ($R^{9a}$, $R^{10a}$, $R^{11a}$ in (Il), $R^{9a}$, $R^{10a}$, $R^{12a}$ in (Im), $R^{9a}$, $R^{11a}$, $R^{12a}$ in (In), $R^{10a}$, $R^{11a}$, $R^{12a}$ in (Io)) is a member independently selected from fluoro, chloro, bromo, nitro, cyano, amino, methyl, hydroxylmethyl, trifluoromethyl, methoxy, trifluoromethyoxy, ethyl, diethylcarbamoyl, pyridin-2-yl, pyridin-3-yl, pyridin-4-yl, pyrimidinyl, piperizino, piperizinyl, piperizinocarbonyl, piperizinylcarbonyl, carboxyl, 1-tetrazolyl, 1-ethoxycarbonylmethoxy, carboxymethoxy, thiophenyl, 3-(butylcarbonyl) phenylmethoxy, 1H-tetrazol-5-yl, 1-ethoxycarbonylmethyloxy-, 1-ethoxycarbonylmethyl-, 1-ethoxycarbonyl-, carboxymethoxy-, thiophen-2-yl, thiophen-2-ylthio-, thiophen-3-yl, thiophen-3-ylthio, 4-fluorophenylthio, butylcarbonylphenylmethoxy, butylcarbonylphenylmethyl, butylcarbonylmethyl, 1-(piperidin-1-yl)carbonyl)methyl, 1-(piperidin-1-yl)carbonyl)methoxy, 1-(piperidin-2-yl)carbonyl)methoxy, 1-(piperidin-3-yl)carbonyl)methoxy, 1-(4-(pyrimidin-2-yl)piperazin-1-yl)carbonyl)methoxy, 1-(4-(pyrimidin-2-yl)piperazin-1-yl)carbonyl)methyl, 1-(4-(pyrimidin-2-yl)piperazin-1-yl)carbonyl, 1-4-(pyrimidin-2-yl)piperazin-1-yl, 1-(4-(pyridin-2-yl)piperazin-1-yl)carbonyl), 1-(4-(pyridin-2-yl)piperazin-1-yl)carbonylmethyl, (1-(4-(pyridin-2-yl)piperazin-1-yl)carbonyl)-methoxy), 1-(4-(pyridin-2-yl)piperazin-1-yl, 1H-indol-1-yl, morpholino-, morpholinyl, morpholinocarbonyl, morpholinylcarbonyl, phenylureido, phenylcarbamoyl, acetamido, 3-(phenylthio)-1H-indol-1-yl, 3-(2-cyanoethylthio)-1H-indol-1-yl, benzylamino, 5-methoxy-3-(phenylthio)-1H-indol-1-yl, 5-methoxy-3-(2-cyanoethylthio)-1H-indol-1-yl)), 5-chloro-1H-indol-1-yl, 5-chloro-3-(2-cyanoethylthio)-1H-indol-1-yl)), dibenzylamino, benzylamino, 5-chloro-3-(phenylthio)-1H-indol-1-yl)), 4-(1H-tetrazol-5-yl)phenoxy, 4-(1H-tetrazol-5-yl)phenyl, 4-(1H-tetrazol-5-yl)phenylthio, 2-cyanophenoxy, 3-cyanophenoxy, 4-cyanophenoxy, 2-cyanophenylthio, 3-cyanophenylthio, 4-cyanophenylthio, 2-chlorophenoxy, 3-chlorophenoxy, 4-chlorophenoxy, 2-fluorophenoxy, 3-fluorophenoxy, 4-fluorophenoxy, 2-cyanobenzyloxy, 3-cyanobenzyloxy, 4-cyanobenzyloxy, 2-chlorobenzyloxy, 3-chlorobenzyloxy, 4-chlorobenzyloxy, 2-fluorobenzyloxy, 3-fluorobenzyloxy, and 4-fluorobenzyloxy.

In an exemplary embodiment, there is a proviso that the compound cannot be a member selected from FIG. 11. In another exemplary embodiment, there is a proviso that the compound cannot be a member selected from C1-C40.

In another exemplary embodiment, there is a proviso that the compound cannot have a structure according to Formula (Ix):

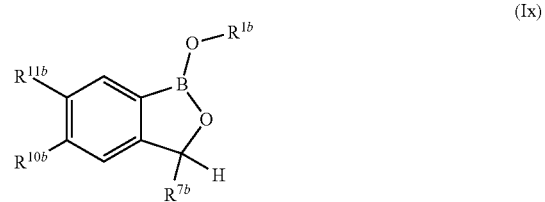

wherein $R^{7b}$ is a member selected from H, methyl, ethyl and phenyl. $R^{10b}$ is a member selected from H, OH, $NH_2$, SH, halogen, substituted or unsubstituted phenoxy, substituted or unsubstituted phenylalkyloxy, substituted or unsubstituted phenylthio and substituted or unsubstituted phenylalkylthio. $R^{11b}$ is a member selected from H, OH, $NH_2$, SH, methyl, substituted or unsubstituted phenoxy, substituted or unsubstituted phenylalkyloxy, substituted or unsubstituted phenylthio and substituted or unsubstituted phenylalkylthio. In another exemplary embodiment, there is a proviso that the compound cannot have a structure according to Formula (Ix) wherein $R^{1b}$ is a member selected from a negative charge, H and a salt counterion. In another exemplary embodiment, there is a proviso that the compound cannot have a structure according to Formula (Ix) wherein $R^{10b}$ and $R^{11b}$ are H. In another exemplary embodiment, there is a proviso that the compound cannot have a structure according to Formula (Ix) wherein one member selected from $R^{10b}$ and $R^{11b}$ is H and the other member selected from $R^{10b}$ and $R^{11b}$ is a member selected from halo, methyl, cyano, methoxy, hydroxymethyl and p-cyanophenyloxy. In another exemplary embodiment, there is a proviso that the compound cannot have a structure according to Formula (Ix) wherein $R^{10b}$ and $R^{11b}$ are members independently selected from fluoro, chloro, methyl, cyano, methoxy, hydroxymethyl, and p-cyanophenyl. In another exemplary embodiment, there is a proviso that the compound cannot have a structure according to Formula (Ix) wherein $R^{1b}$ is a member selected from a negative charge, H and a salt counterion; $R^{7b}$ is H; $R^{10b}$ is F and $R^{11b}$ is H. In another exemplary embodiment, there is a proviso that the compound cannot have a structure according to Formula (Ix) wherein $R^{11b}$ and $R^{12b}$, along with the atoms to which they are attached, are joined to form a phenyl group. In another exemplary embodiment, there is a proviso that the compound cannot have a structure according to Formula (Ix) wherein $R^{1b}$ is a member selected from a negative charge, H and a salt counterion; $R^{7b}$ is H; $R^{10b}$ is 4-cyanophenoxy; and $R^{11b}$ is H.

In another exemplary embodiment, there is a proviso that the compound cannot have a structure according to Formula (Iy)

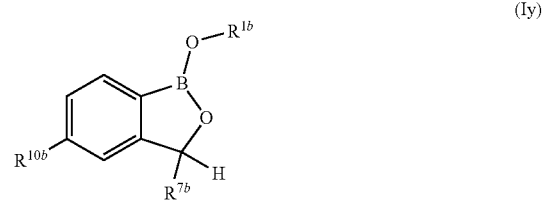

wherein $R^{10b}$ is a member selected from H, halogen, CN and substituted or unsubstituted $C_{1-4}$ alkyl.

In another exemplary embodiment, there is a proviso that a structure does not have the which is a member selected from Formulae (I) to (Io) at least one member selected from $R^{3a}$, $R^{4a}$, $R^{5a}$, $R^{6a}$, $R^{7a}$, $R^{8a}$, $R^{9a}$, $R^{10a}$, $R^{11a}$ and $R^{12a}$ is nitro, cyano or halogen. In another exemplary embodiment, there is a proviso that when M is oxygen, W is a member selected from $(CR^{3a}R^{4a})_{n1}$, wherein n1 is 0, J is a member selected from $(CR^{6a}R^{7a})_{m1}$, wherein m1 is 1, A is $CR^{9a}$, D is $CR^{10a}$, E is $CR^{11a}$, G is $CR^{12a}$, the $R^{9a}$ is not halogen, methyl, ethyl, or optionally joined with $R^{10a}$ to form a phenyl ring; $R^{10a}$ is not unsubstituted phenoxy, $C(CH_3)_3$, halogen, $CF_3$, methoxy, ethoxy, or optionally joined with $R^{9a}$ to form a phenyl ring; $R^{11a}$ is not halogen or optionally joined with $R^{10a}$ to form a phenyl ring; and $R^{12a}$ is not halogen. In another exemplary embodiment, there is a proviso that when M is oxygen, W is a member selected from $(CR^{3a}R^{4a})_{n1}$, wherein n1 is 0, J is a member selected from $(CR^{6a}R^{7a})_{m1}$, wherein m1 is 1, A is $CR^{9a}$, D is $CR^{10a}$, E is $CR^{11a}$, G1 is $CR^{12a}$, then neither $R^{6a}$ nor $R^{7a}$ are halophenyl. In another exemplary embodiment, there is a proviso that when M is oxygen, W is a member selected from $(CR^{3a}R^{4a})_{n1}$, wherein n1 is 0, J is a member selected from $(CR^{6a}R^{7a})_{m1}$, wherein m1 is 1, A is $CR^{9a}$, D is $CR^{10a}$, E is $CR^{11a}$, G is $CR^{12a}$, and $R^{9a}$, $R^{10a}$ and $R^{11a}$ are H, then $R^{6a}$, $R^{7a}$ and $R^{12a}$ are not H. In another exemplary embodiment, there is a proviso that when M is oxygen wherein n1 is 1, J is a member selected from $(CR^{6a}R^{7a})_{m1}$, wherein m1 is 0, A is $CR^{9a}$, D is $CR^{10a}$, E is $CR^{11a}$, G is $CR^{12a}$, $R^{9a}$ is H, $R^{10a}$ is H, $R^{11a}$ is H, $R^{6a}$ is H, $R^{7a}$ is H, $R^{12a}$ is H, then W is not C=O (carbonyl). In another exemplary embodiment, there is a proviso that when M is oxygen, W is $CR^{5a}$, J is $CR^{8a}$, A is $CR^{9a}$, D is $CR^{10a}$, E is $CR^{11a}$, G is $CR^{12a}$, $R^{6a}$, $R^{7a}$, $R^{9a}$, $R^{10a}$, $R^{11a}$ and $R^{12a}$ are H, then $R^{5a}$ and $R^{8a}$, together with the atoms to which they are attached, do not form a phenyl ring.

In an exemplary embodiment, the compound of the invention has a structure which is a member selected from:

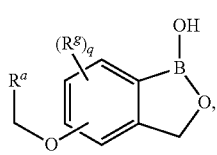
(Iab)

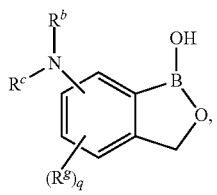
(Iac)

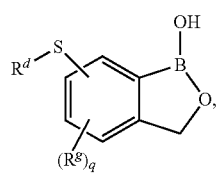
(Iad)

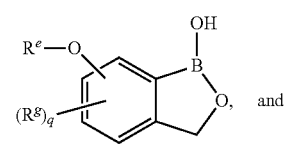
(Ia) and

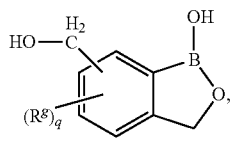
(Iaf)

in which q is a number between 0 and 1. $R^g$ is halogen. $R^a$, $R^b$, $R^c$, $R^d$ and $R^e$ are members independently selected from a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, there is a proviso that the compound is not a member selected from

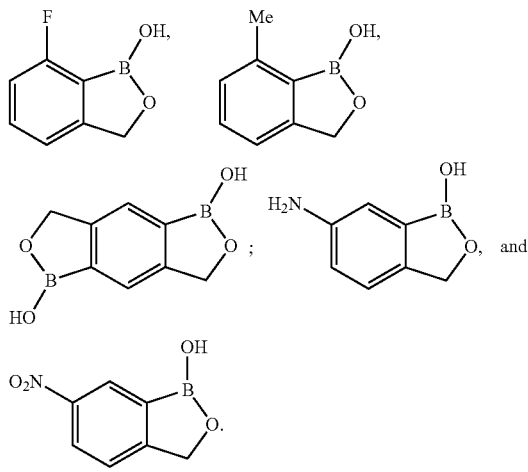

In an exemplary embodiment, the compound has a structure is a member selected from:

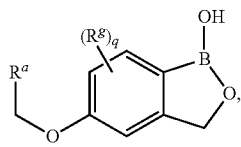
(Iag)

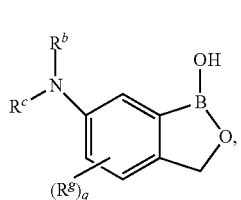
(Iah)

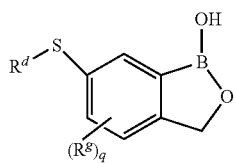
(Iai)

-continued (Iaj)

(Iak)

In an exemplary embodiment, $R^a$, $R^d$ and $R^e$ are each members independently selected from:

In an exemplary embodiment, $R^b$ and $R^c$ are members independently selected from H, methyl, In another exemplary embodiment, $R^b$ is H and $R^c$ is a member selected from H, methyl,
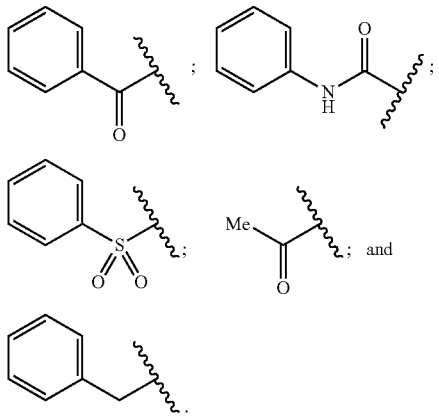
In another exemplary embodiment, $R^b$ and $R^c$ are, together with the nitrogen to which they are attached, optionally joined to form a member selected from
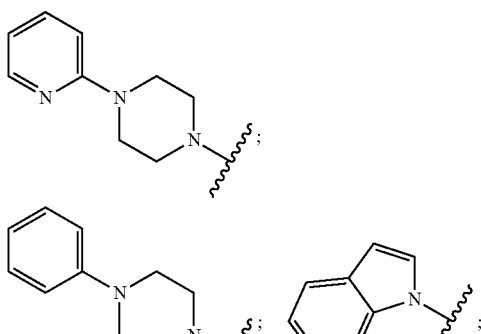
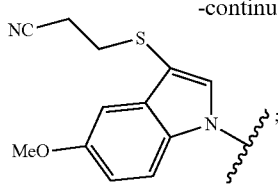
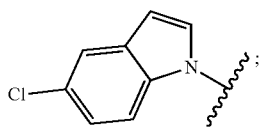
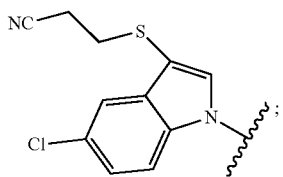
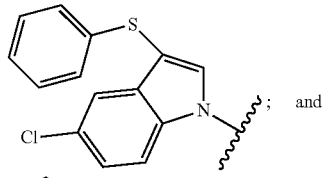
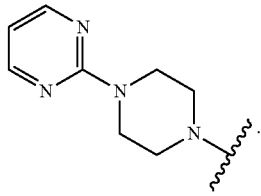
In an exemplary embodiment, $R^a$ is a member selected from
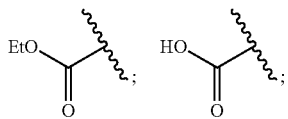
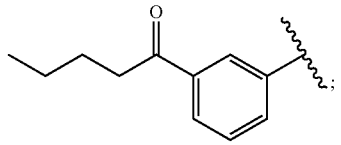
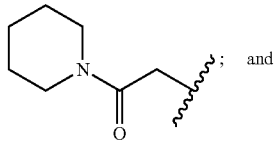
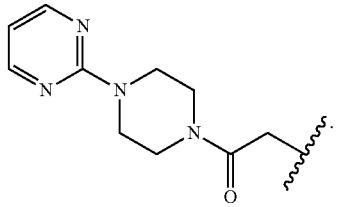

In an exemplary embodiment, $R^d$ is a member selected from
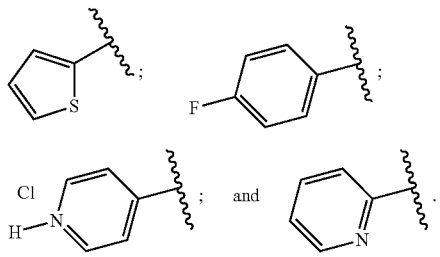
In an exemplary embodiment, $R^e$ is a member selected from
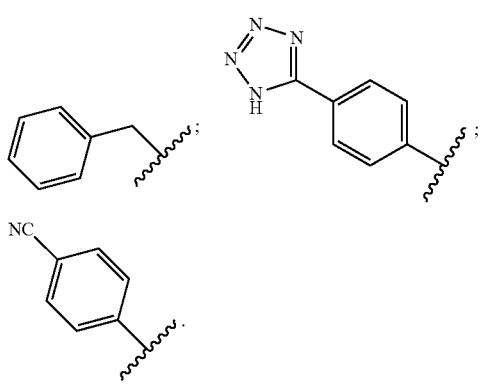
In an exemplary embodiment, the compound is a member selected from
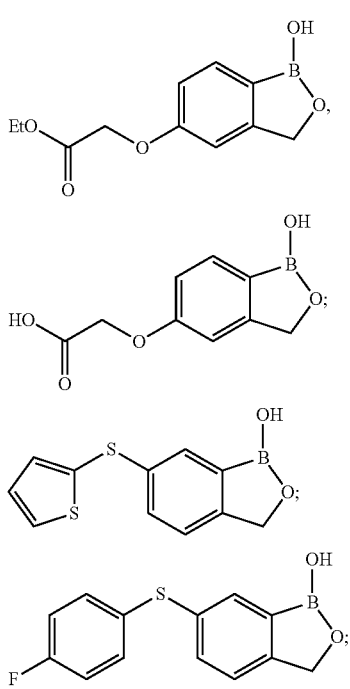
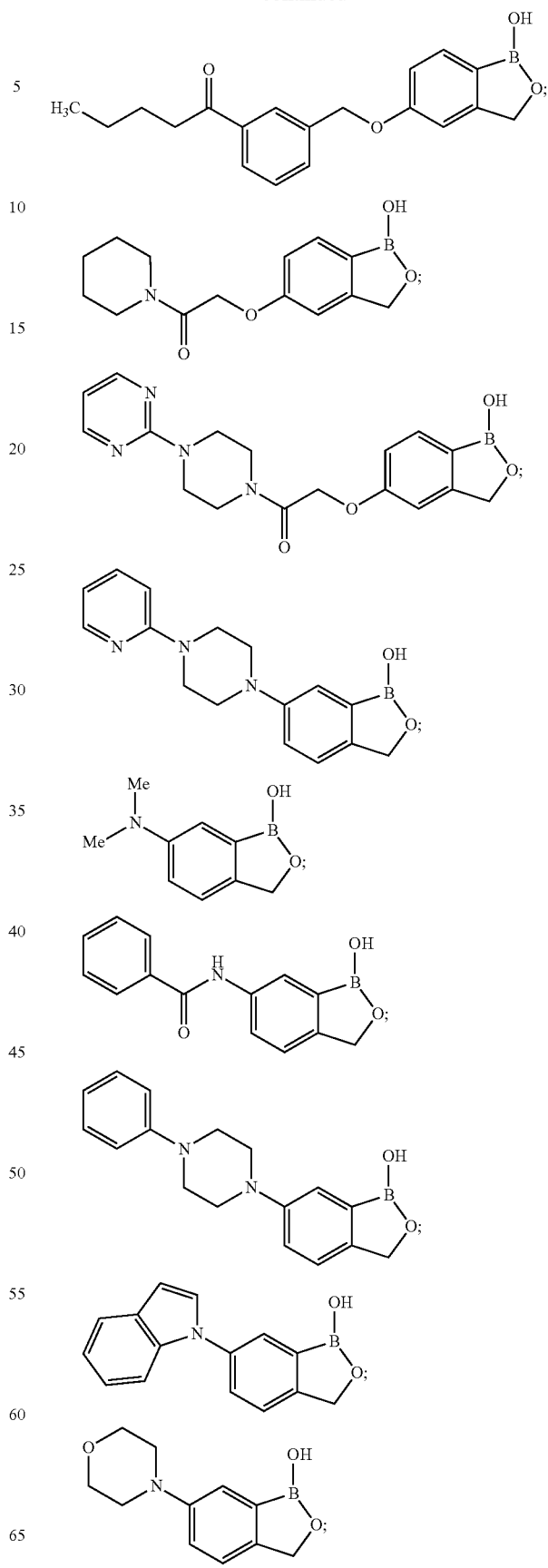

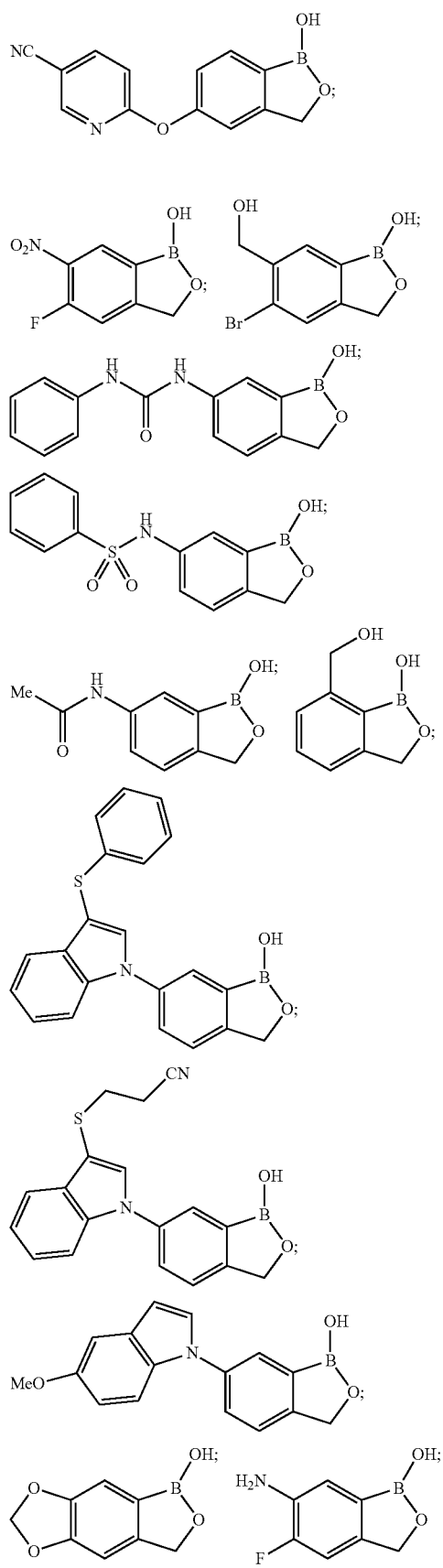
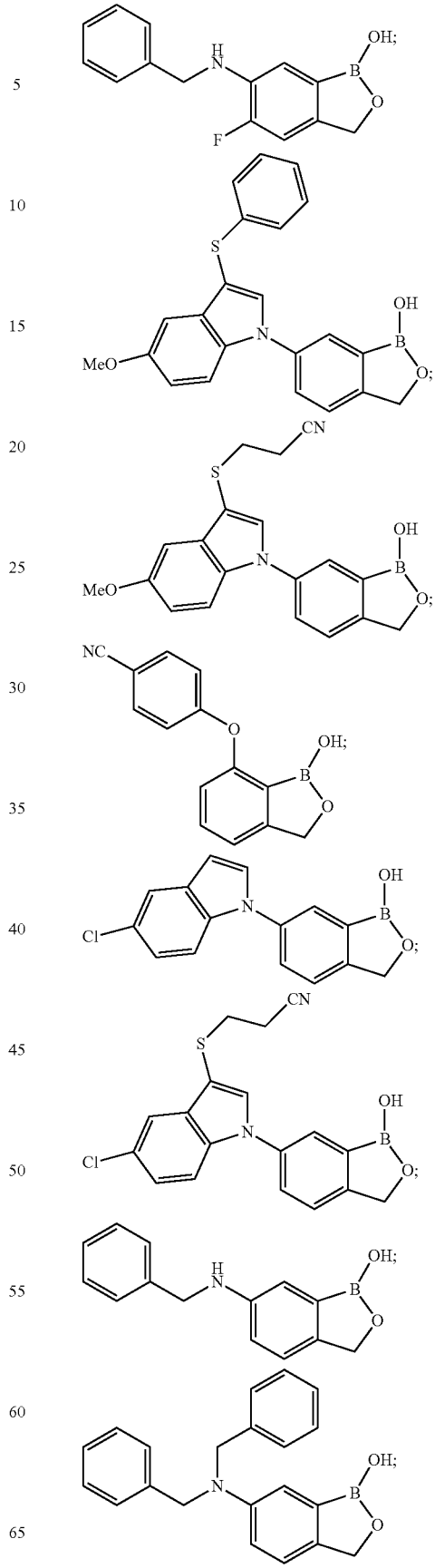

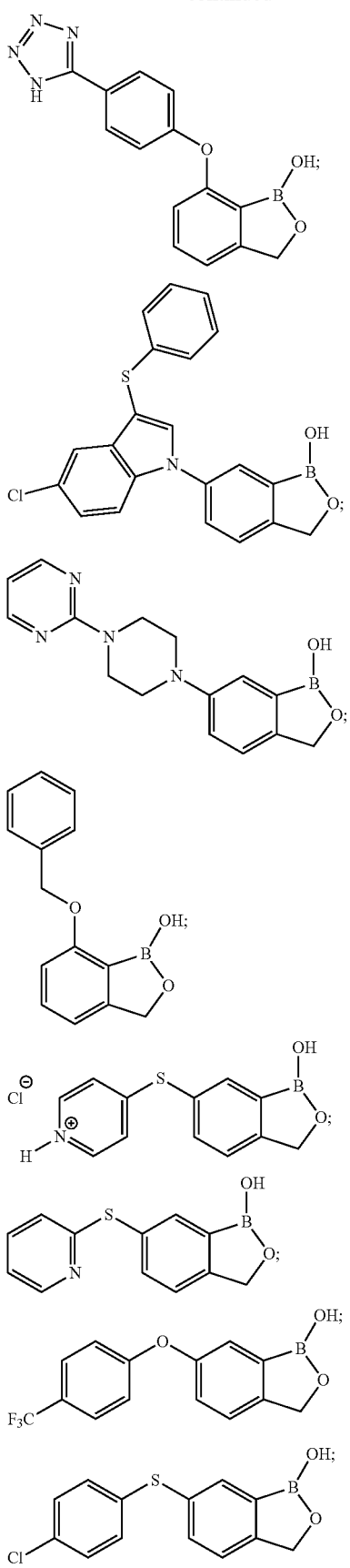
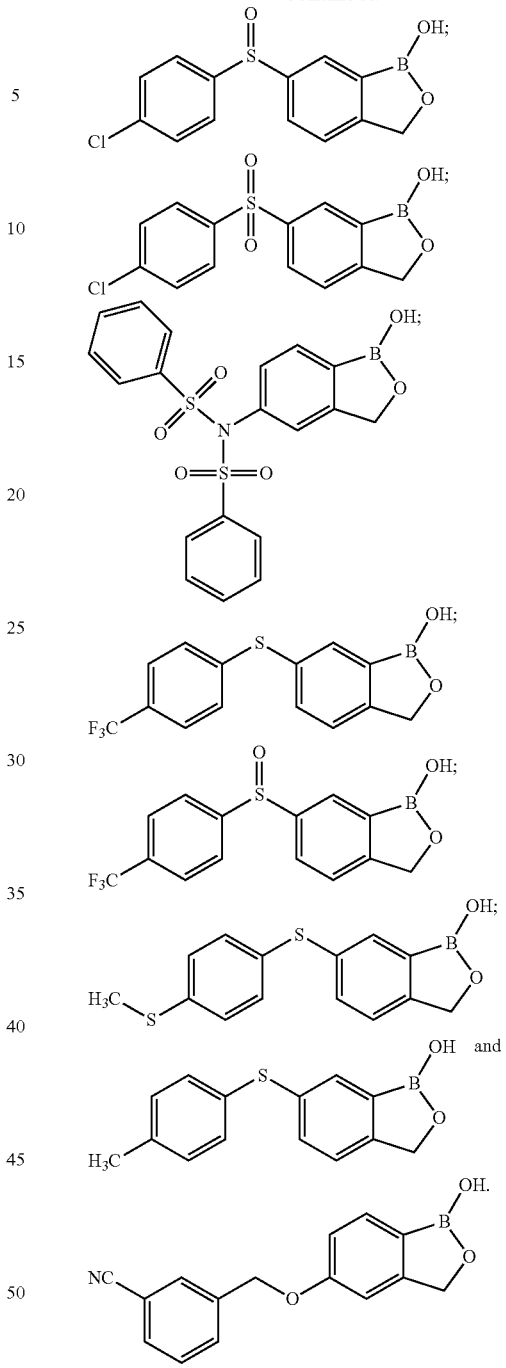

Figure 19A:
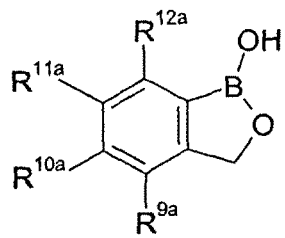

In an exemplary embodiment, the compound has a structure which is described in FIG. 19. In an exemplary embodiment, the compound has a structure which is described in FIG. 20.

In an exemplary embodiment, the compound has a structure according to a member selected from Formulae I(b), I(c), I(d), and I(e) wherein said remaining R group ($R^{9a}$ for I(b), $R^{10a}$ for I(c), $R^{11a}$ for I(d) and $R^{12a}$ for I(e)) is carboxymethoxy.

In an exemplary embodiment, the compound has a structure which is a member selected from Formulae (If)-(Ik), wherein either $R^{9a}$ or $R^{10a}$ for Formula (If), either $R^{9a}$ or $R^{11a}$ for Formula (Ig), either $R^{9a}$ or $R^{12a}$ for Formula (Ih), either $R^{10a}$ or $R^{11a}$ for Formula (Ii), either $R^{10a}$ or $R^{12a}$ for Formula (Ij), either $R^{11a}$ or $R^{12a}$ for Formula (Ik) is halogen, and the other substituent in the pairing (ex. if $R^{9a}$ is F in Formula (If), then $R^{10a}$ is selected from the following substituent listing), is a member selected from $NH_2$, $N(CH_3)$ H, and $N(CH_3)_2$.

In another exemplary embodiment, the compound has a structure which is a member selected from:

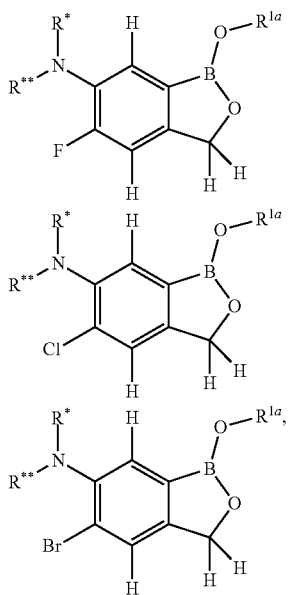

in which R* and R** are members selected from: H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, the compound is a member selected from

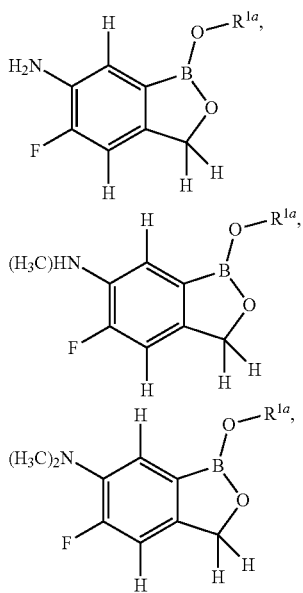

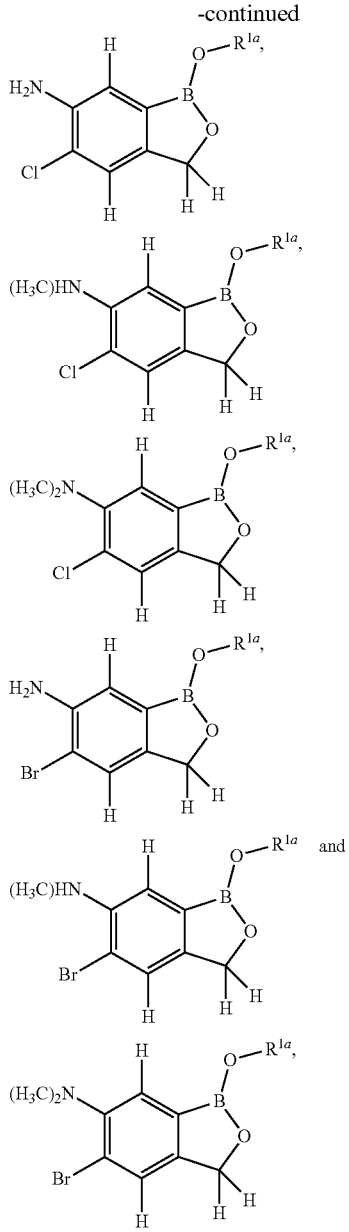

wherein $R^{1a}$ is a member selected from a negative charge, H and a salt counterion.

In another exemplary embodiment, the compound has a structure which is a member selected from:

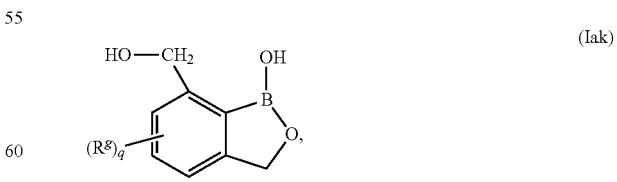

(Iak)

wherein q is 1 and $R^g$ is a member selected from fluoro, chloro and bromo.

In another exemplary embodiment, the compounds and embodiments described above in Formulae (I)-(Io) can form a hydrate with water, a solvate with an alcohol (e.g. methanol, ethanol, propanol); an adduct with an amino compound (e.g. ammonia, methylamine, ethylamine); an adduct with an acid (e.g. formic acid, acetic acid); complexes with ethanolamine, quinoline, amino acids, and the like.

In another exemplary embodiment, the compound has a structure according to Formula (Ip):

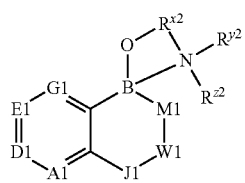
(Ip)

in which $R^{x2}$ is a member selected from substituted or unsubstituted $C_1$-$C_5$ alkyl and substituted or unsubstituted $C_1$-$C_5$ heteroalkyl. $R^{y2}$ and $R^{z2}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In another exemplary embodiment, the compound has a structure according to Formula (Iq):

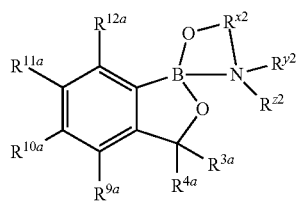
(Iq)

wherein B is boron. $R^{x2}$ is a member selected from substituted or unsubstituted $C_1$-$C_5$ alkyl and substituted or unsubstituted $C_1$-$C_5$ heteroalkyl. $R^{y2}$ and $R^{z2}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In another exemplary embodiment, at least one member selected from $R^{3a}$, $R^{4a}$, $R^{5a}$, $R^{6a}$, $R^{7a}$, $R^{8a}$, $R^{9a}$, $R^{10a}$, $R^{11a}$ and $R^{12a}$ is a member selected from nitro, cyano and halogen.

In another exemplary embodiment, the compound has a structure which is a member selected from the following Formulae:

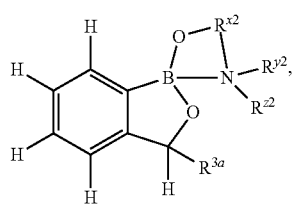
(Ir)

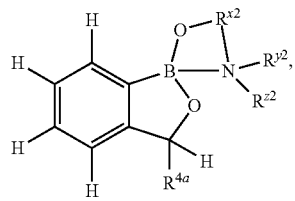
(Is)

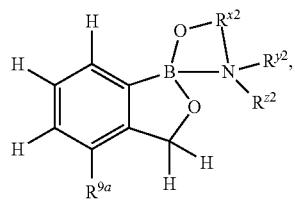
(It)

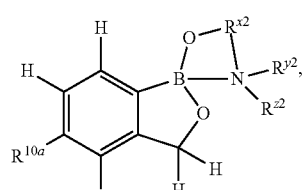
(Iu)

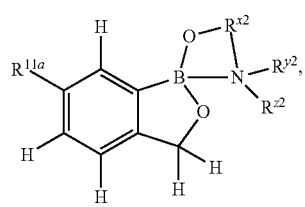
(Iv)

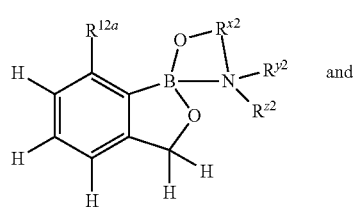
(Iw) and

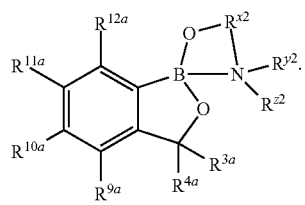
(Iz)

In another exemplary embodiment, the compound has a formula according to Formulae (Ib)-(Ie) wherein at least one member selected from $R^{3a}$, $R^{4a}$, $R^{5a}$, $R^{6a}$, $R^{7a}$, $R^{8a}$, $R^{9a}$, $R^{10a}$, $R^{11a}$ and $R^{12a}$ is a member selected from nitro, cyano, fluro, chloro, bromo and cyanophenoxy. In another exemplary embodiment, the compound is a member selected from

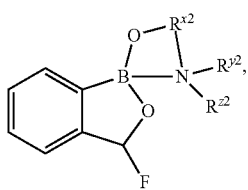

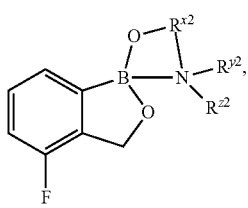

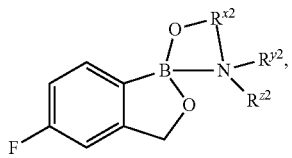

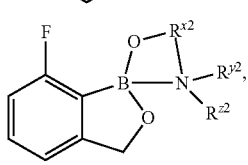

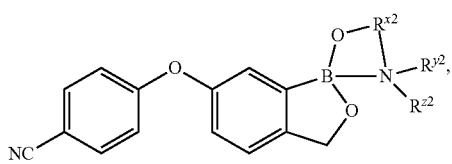

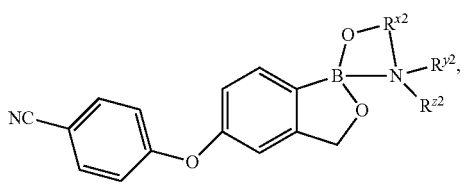

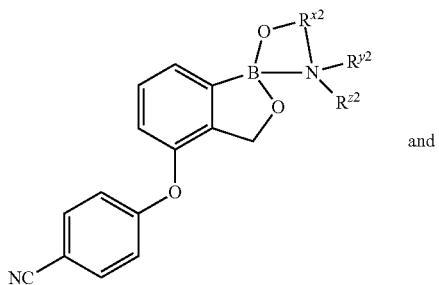

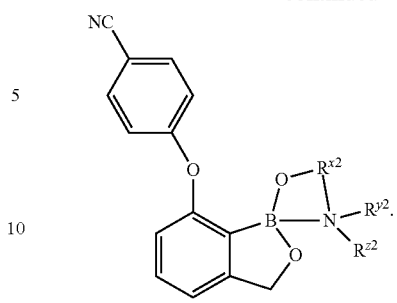

In another exemplary embodiment, the compound is a member selected from

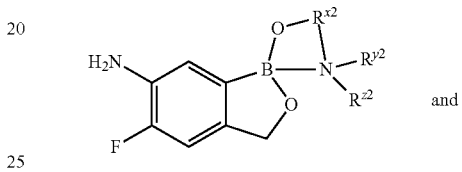 and

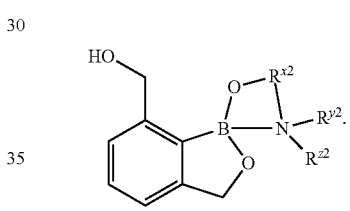

In another exemplary embodiment, there is a proviso that the compound cannot have a structure according to Formula (Iaa):

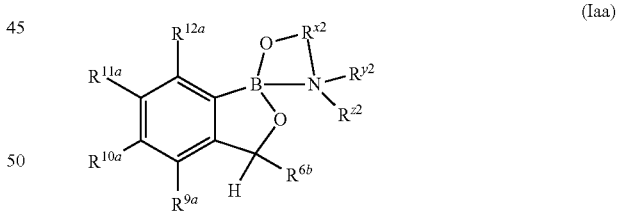

(Iaa)

wherein $R^{6b}$, $R^{9b}$, $R^{10b}$, $R^{11b}$ and $R^{12b}$ have the same substituent listings as described for Formulae (Ix) and (Iy) above.

In another exemplary embodiment, the invention provides poly- or mutli-valent species of the compounds of the invention. In an exemplary embodiment, the invention provides a dimer of the compounds described herein. In an exemplary embodiment, the invention provides a dimer of the compounds described herein. In an exemplary embodiment, the invention provides a dimer of a compound which is a member selected from C1-C96. In an exemplary embodiment the dimer is a member selected from

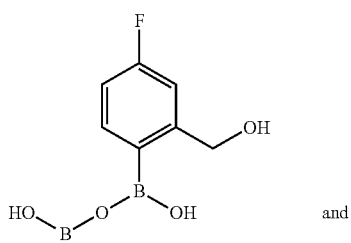

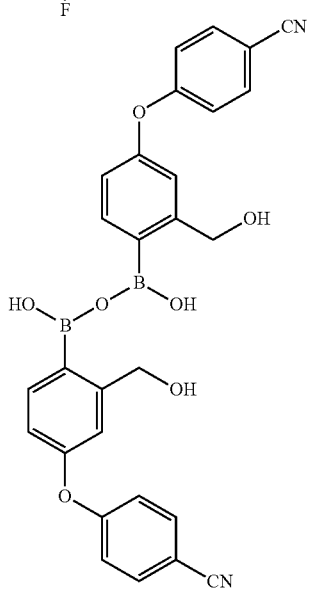

In an exemplary embodiment, the invention provides an anhydride of the compounds described herein. In an exemplary embodiment, the invention provides an anhydride of the compounds described herein. In an exemplary embodiment, the invention provides an anhydride of a compound which is a member selected from C1-C96. In an exemplary embodiment the anhydride is a member selected from

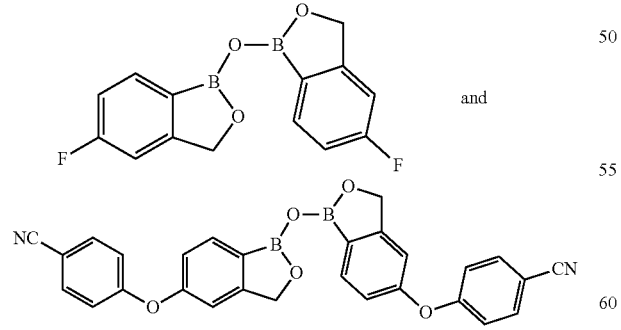

In an exemplary embodiment, the invention provides a trimer of the compounds described herein. In an exemplary embodiment, the invention provides a trimer of the compounds described herein. In an exemplary embodiment, the invention provides a trimer of a compound which is a member selected from C1-C96. In an exemplary embodiment the trimer is a member selected from

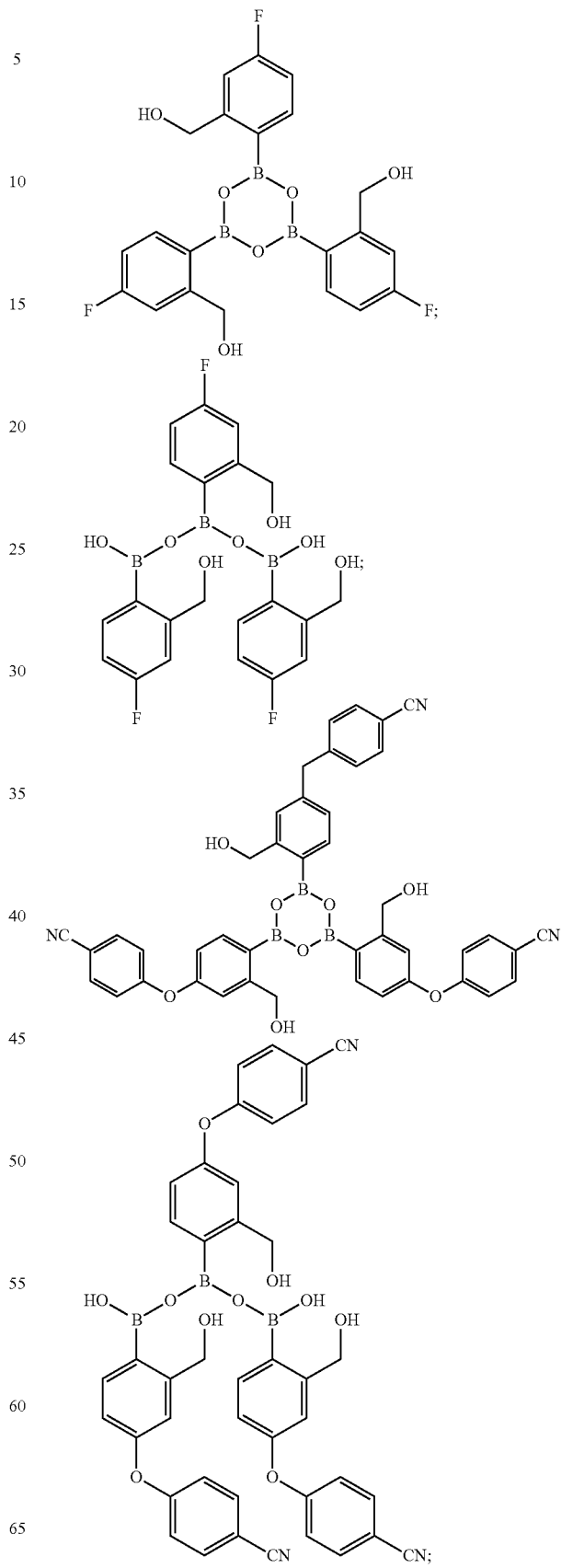

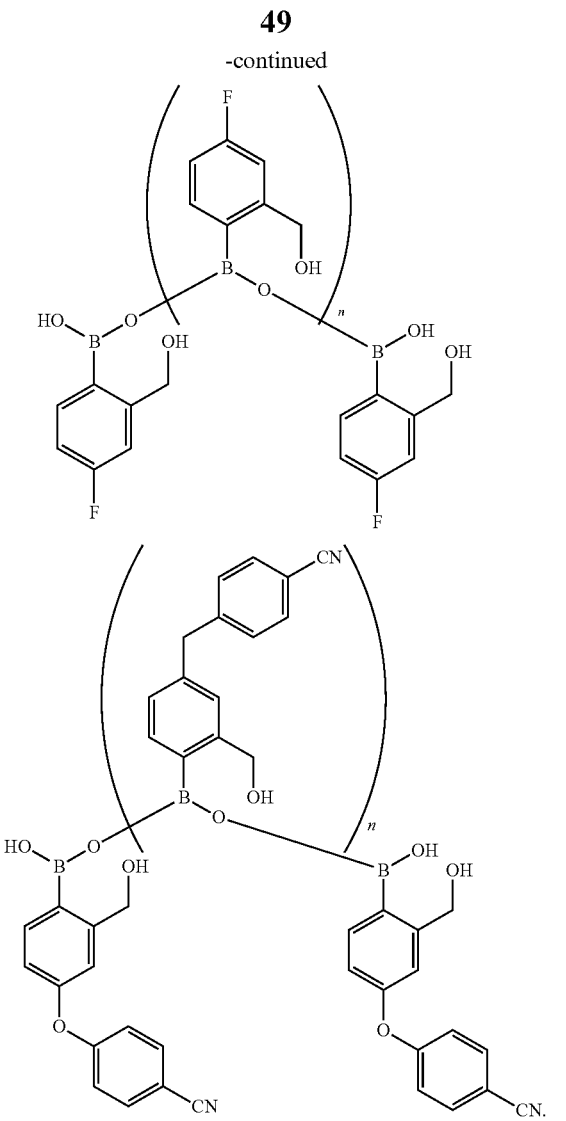

Pyridinyloxaboroles

In an exemplary embodiment, the compound has a structure which is a member selected from Formulae (IIa) (IIb) (IIc) and (IId).

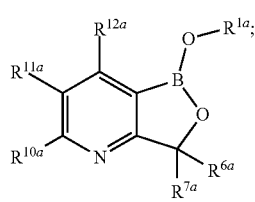

(IIa)

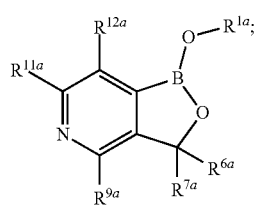

(IIb)

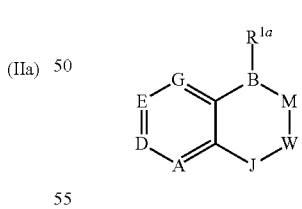

(IIc)

(IId)

Oxaborines

In an exemplary embodiment, the compound has a structure according to Formula (III):

(III)

I. b.) Cyclic Borinic Esters

In one aspect, the invention provides compounds useful in the methods which have a structure according to Formula VII:

(VII)

wherein the variables $R^{1a}$, A, D, E, G, J, W and M are described elsewhere herein.

In an exemplary embodiment of Formula (VII), $R^1$ is substituted or unsubstituted alkyl ($C_1$-$C_4$). In an exemplary embodiment of Formula (VII), $R^1$ is substituted or unsubstituted alkyloxy. In an exemplary embodiment of Formula (VII), $R^1$ is substituted or unsubstituted cycloalkyl ($C_3$-$C_7$). In an exemplary embodiment of Formula (VII), $R^1$ is substituted or unsubstituted alkenyl. In a further exemplary embodiment thereof, the substituted alkenyl has the structure

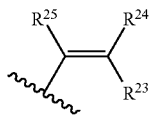
(VIIa)

wherein $R^{23}$, $R^{24}$, and $R^{25}$ are each members independently selected from H, haloalkyl, aralkyl, substituted aralkyl, $(CH_2)_rOH$ (where r=1 to 3), $CH_2NR^{26}R^{27}$ (wherein $R^{26}$ and $R^{27}$ are independently selected from hydrogen and alkyl), $CO_2H$, $CO_2$alkyl, $CONH_2$, S-alkyl, S-aryl, $SO_2$alkyl, $SO_3H$, $SCF_3$, CN, halogen, $CF_3$, $NO_2$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In another exemplary embodiment of Formula (VII), $R^1$ is a substituted or unsubstituted alkynyl. In a further exemplary embodiment thereof, the substituted alkynyl has the structure

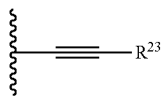
(VIIb)

wherein $R^{23}$ is defined as before.

In an exemplary embodiment of Formula (VII), $R^1$ is substituted or unsubstituted aryl. In a further exemplary embodiment thereof the substituted aryl has the structure

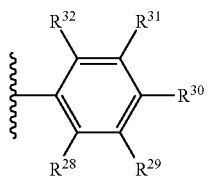
(VIIc)

wherein $R^{28}$, $R^{29}$, $R^3$, $R^{31}$ and $R^{32}$ are each members independently selected from H, aralkyl, substituted aralkyl, $(CH_2)_sOH$ (where s=1 to 3), $CO_2H$, $CO_2$alkyl, $CONH_2$, CONHalkyl, $CON(alkyl)_2$, OH, alkoxy, aryloxy, SH, S-alkyl, S-aryl, $SO_2$alkyl, $SO_3H$, $SCF_3$, CN, halogen, $CF_3$, $NO_2$, $(CH_2)_tNR^{26}R^{27}$ (wherein $R^{26}$ and $R^{27}$ are independently selected from hydrogen, alkyl, and alkanoyl)(t=0 to 2), $SO_2NH_2$, $OCH_2CH_2NH_2$, $OCH_2CH_2NH$alkyl, $OCH_2CH_2N(alkyl)_2$, oxazolidin-2-yl, alkyl substituted oxazolidin-2-yl, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment of Formula (VII), $R^1$ is a substituted or unsubstituted aralkyl. In a further exemplary embodiment thereof the substituted aralkyl has the structure

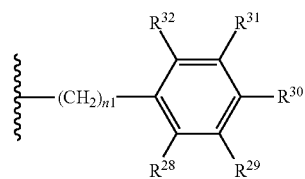
(VIId)

wherein $R^{28}$, $R^{29}$, $R^3$, $R^{31}$ and $R^{32}$ are defined as before, and n1 is an integer selected from 1 to 15.

In an exemplary embodiment of Formula (VII), $R^1$ is a substituted or unsubstituted heteroaryl. In a further exemplary embodiment thereof, heteroaryl has the structure

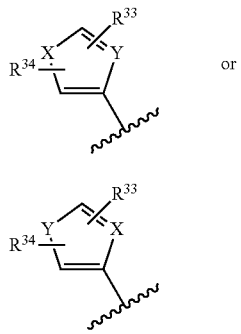
(VIIe)

or (VIIf)

wherein X is a member selected from CH=CH, N=CH, $NR^{35}$ (wherein $R^{35}$=H, alkyl, aryl or benzyl), O, or S. Y=CH or N. $R^{33}$ and $R^{34}$ are each members independently selected from H, haloalkyl, aralkyl, substituted aralkyl, $(CH_2)_uOH$ (where u=1, 2 or 3), $(CH_2)_vNR^{26}R^{27}$ (wherein $R^{26}$ and $R^{27}$ are independently selected from hydrogen, alkyl and alkanoyl)(v=0 to 3), $CO_2H$, $CO_2$alkyl, $CONH_2$, S-alkyl, S-aryl, $SO_2$alkyl, $SO_3H$, $SCF_3$, CN, halogen, $CF_3$, $NO_2$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

The structures of the invention also permit solvent interactions that may afford structures (Formula VIIg) that include atoms derived from the solvent encountered by the compounds of the invention during synthetic manipulations and therapeutic uses. Structure VIIg arises from the formation of a dative bond between the solvent(s) with the Lewis acidic boron center. Thus, such solvent complexes could be stable entities with comparative bioactivities. Such structures are expressly contemplated by the present invention where R*** is H or alkyl.

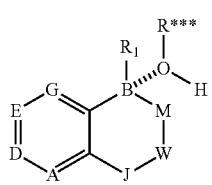
Formula (VIIg)

In an exemplary embodiment, the compound has a structure which is a member selected from 2-(3-Chlorophenyl)-

[1,3,2]-dioxaborolane, (3-Chlorophenyl)(4'-fluoro-(2'-(methoxymethoxy)-methyl)-phenyl)-borinic acid, 1-(3-Chlorophenyl)-5-fluoro-1,3-dihydrobenzo[c][1,2] oxaborole, 1-(3-Chlorophenyl)-6-fluoro-1,3-dihydrobenzo [c][1,2]oxaborole, 1-(3-Chlorophenyl)-1,3-dihydrobenzo[c][1,2]oxaborole, 5-Chloro-1-(3-Fluorophenyl)-1,3-dihydrobenzo[c][1,2]oxaborole, 2-(3-fluorophenyl)-[1,3,2]-dioxaborolane, 3-(Benzo[c][1,2]oxaborol-1(3H)-yl)benzonitrile, 2-(3-cyanophenyl)-[1,3,2]-dioxaborolane, (3-Chlorophenyl)(5'-fluoro-(2'-(methoxymethoxy)methyl)-phenyl)-borinic acid, 1-(3-Chlorophenyl)-1,3-dihydro-3,3dimethylbenzo[c][1,2]oxaborole, (3-Chlorophenyl)(2-(2-(methoxymethoxy)propan-2yl)phenylborinic acid, 1-(3-Chlorophenyl)-1,3-dihydro-3,3-dimethylbenzo[c][1,2] oxaborole, 1-(4-Chlorophenyl)-1,3-dihydrobenzo[c][1,2] oxaborole, 2-(4-chlorophenyl)-[1,3,2]-dioxaborolane, 4-(Benzo[c][1,2]oxaborol-1(3H)-yl)benzonitrile, 2-(4-cyanophenyl)-[1,3,2]-dioxaborolane, 4-(5-Fluorobenzo[c][1,2] oxaborol-1(3H)-yl)benzonitrile, 2-(4-cyanophenyl)-[1,3,2]-dioxaborolane, 3-(5-Fluorobenzo[c][1,2]oxaborol-1(3H)-yl) benzonitrile, 2-(3-cyanophenyl)-[1,3,2]-dioxaborolane, 3-(6-Fluorobenzo[c][1,2]oxaborol-1(3H)-yl)benzonitrile, 2-(3-cyanophenyl)-[1,3,2]-dioxaborolane, 1-(3-Cyanophenyl)-5,6-dimethoxy-1,3-dihydrobenzo[c][1,2]-oxaborole, 2-(3-chlorophenyl)-[1,3,2]-dioxaborolane, (4-(5-(Fluorobenzo[c][1,2]oxaborol-1(3H)-yl)phenylmethanamine, 5-Fluoro-2-(methoxymethoxymethyl)phenyl]-[1,3,2]-dioxaborolane, 4-(5-(Fluorobenzo[c][1,2]oxaborol-1(3H)-yl) phenylmethanamine, (3-(5-(Fluorobenzo[c][1,2]oxaborol-1 (3H)-yl)-phenylmethanamine, (4-(5-(Fluorobenzo[c][1,2] oxaborol-1(3H)-yl)phenyl)methanol, (3-(5-(Fluorobenzo[c] [1,2]oxaborol-1(3H)-yl)phenyl)methanol, 3-(6-Fluorobenzo [c][1,2]oxaborol-1(3H)-yl)phenol, 3-(5-Fluorobenzo[c][1,2] oxaborol-1(3H)-yl)pyridine, (2-(Benzo[c][1,2]oxaborol-1 (3H)-yl)phenyl)methanol, 2-[(Methoxymethoxy)methyl] phenyl boronic acid, 2-[(Methoxymethoxymethyl)pheny]-[1,3,2]-dioxaborolane, Bis [2-(methoxymethoxymethyl) phenyl]borinic acid, (2-(Benzo[c][1,2]oxaborol-1(3H)-yl) phenyl)methanol, (2-(Benzo[c][1,2]oxaborol-1(3H)-yl) phenyl)-N,N-dimethylmethanamine, (2-(Benzo[c][1,2] oxaborol-1(3H)-yl)-5-chlorophenyl)-N,N-dimethylmethanamine, (2-(Benzo[c][1,2]oxaborol-1(3H)-yl)-5-chlorophenyl)methanol, (2-(Benzo[c][1,2]oxaborol-1 (3H)-yl)-5-chlorophenyl)methanol, (5-Chloro-2-(5-chlorobenzo[c][1,2]oxaborol-1(3H)-yl)phenyl)methanol, Bis[4-chloro-2-(methoxymethoxymethyl)phenyl]borinic acid, (5-Chloro-2-(5-chlorobenzo[c][1,2]oxaborol-1(3H)-yl)phenyl)methanol, (5-Chloro-2-(5-chlorobenzo[c][1,2] oxaborol-1(3H)-yl)phenyl-N,N-dimethylmethanamine, 1-(4-chloro-2-methoxyphenyl)-1,3-dihydrobenzo[c][1,2] benzoxaborole, 4-Chloro-2-methoxyphenylboronic acid ethylene glycol ester, 1-(4-chloro-2-methoxyphenyl)-1,3-dihydrobenzo[c][1,2]benzoxaborole, 2-(Benzo[c][1,2]oxaboral-1(3H)-yl)-5-chlorophenol, 2-(3-(Benzo[c][1.2]oxaborol-1(3H)-yl)phenoxy)-5-chlorophenol, 2-(3-(Benzo[c][1,2] oxaborol-1(3H)-yl)Phenoxy)-5-chlorophenol 4-((3-(5-Fluorobenzo[c][1,2]oxaborol-1(3H)-yl)phenyl)methyl) morpholine, 3-(5-Fluorobenzo[c][1,2]oxaborol-1(3H)-yl] phenyl)-methyl 8-hydroxy-quinoline-2-carboxylate, 1-(3-Chlorophenyl)-2,3-dihydro-2-(methoxymethy)-1H-benzo [c][1,2]azaborole, 3-Chlorophenyl 2-[N,N-bis (methoxymethyl)aminomethyl]phenylborinic acid, 1-(3-Chlorophenyl)-2,3-dihydro-2-(methoxymethy)-1H-benzo [c][1,2]azaborole, 1-(3-Chlorophenyl)-1,3,4,5-tetrahydrobenzo-[c][1,2]-oxaborepine, 1-(3-Chlorophenyl)-1,3,4,5-tetrahydrobenzo[c][1,2]oxaborepine, 1-(3-Chlorophenyl)-3,4-dihydro-1H-benzo[c][1,2]-oxaborinine, 2-(3-Chlorophenyl)-[1,3,2]dioxaborolane, (3-Chlorophenyl) (2'-(2-(methoxymethoxy)ethyl)phenyl)borinic acid, and 1-(3-Chlorophenyl)-3,4-dihydro-1H-benzo[c][1,2]oxaborinine.

I. c.) 2'-amino ribofuranoses

In another aspect, the invention provides compounds useful in the methods which is a 2'-amino ribofuranose. In an exemplary embodiment, the 1'-position of the ribofuranose is substituted with a member selected from substituted or unsubstituted aryl and substituted or unsubstituted heteroaryl. In another exemplary embodiment, the 1'-position of the ribofuranose is substituted with a member selected from substituted or unsubstituted purine, substituted or unsubstituted pyrimidine, substituted or unsubstituted pyridine and substituted or unsubstituted imidazole. In another exemplary embodiment, the 1'-position of the ribofuranose is substituted with a member selected from substituted or unsubstituted nicotinic acid, substituted or unsubstituted nicotinamide, substituted or unsubstituted nucleic acid base, substituted or unsubstituted adenine,

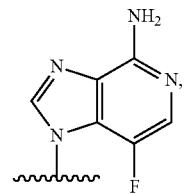 [SMILES: *n1cnc2c(N)ncc(F)c21]

substituted or unsubstituted cytosine, substituted or unsubstituted guanine, substituted or unsubstituted thymine, substituted or unsubstituted uracil, substituted or unsubstituted N,N-dimethyl guanine, substituted or unsubstituted dihydrouracil, substituted or unsubstituted 4-thiouridine and substituted or unsubstituted inosine. In another exemplary embodiment, the compound has a structure according to Formula (VIII):

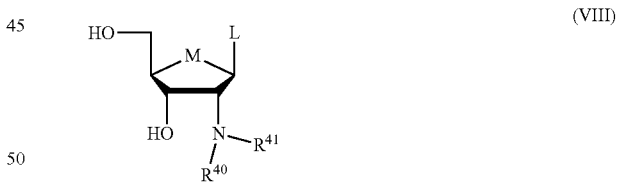

wherein L is a member selected from substituted or unsubstituted purine, substituted or unsubstituted pyrimidine, substituted or unsubstituted pyridine and substituted or unsubstituted imidazole. M, as defined herein earlier, is a member selected from O, S, and $NR^2$. $R^{40}$ and $R^{41}$ are each members independently selected from H, aralkyl, substituted aralkyl, $(CH_2)_sOH$ (where s=1 to 3), $CO_2H$, $CO_2alkyl$, $C(O)NH_2$, $C(O)NHalkyl$, $CON(alkyl)_2$, $C(O)R^{23}$, OH, alkoxy, aryloxy, SH, S-alkyl, S-aryl, $SO_2alkyl$, $SO_3H$, $SCF_3$, CN, halogen, $CF_3$, $NO_2$, $(CH_2)_tNR^{26}R^{27}$ (wherein $R^{26}$ and $R^{27}$ are independently selected from hydrogen, alkyl, and alkanoyl)(t=0 to 2), $SO_2NH_2$, $OCH_2CH_2NH_2$, $OCH_2CH_2NHalkyl$, $OCH_2CH_2N(alkyl)_2$, oxazolidin-2-yl, alkyl substituted oxazolidin-2-yl, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl,

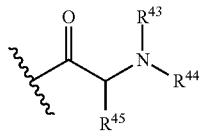 and 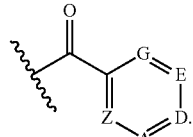

$R^{43}$, $R^{44}$, and $R^{45}$ are each members independently selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{43}$ and $R^{44}$, together with the atoms to which they are attached, are optionally joined to form a 4 to 7 membered ring. $R^{43}$ and $R^{45}$, together with the atoms to which they are attached, are optionally joined to form a 4 to 7 membered ring. $R^{44}$ and $R^{45}$, together with the atoms to which they are attached, are optionally joined to form a 4 to 7 membered ring. A, D, E and G are all defined elsewhere herein. Z is a member selected from $CR^{46}$ and N. The combinations of nitrogens (A+D+E+G+Z) is an integer selected from 0 to 4. At least two members selected from $R^9$, $R^{10}$, $R^{11}$, $R^{12}$ and $R^{46}$, together with the atoms to which they are attached, are optionally joined to form a 4 to 7 membered ring.

In an exemplary embodiment,

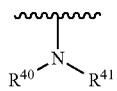

is a member selected from:

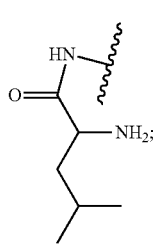 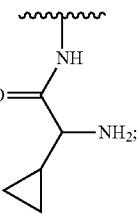 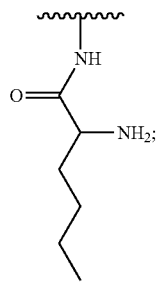

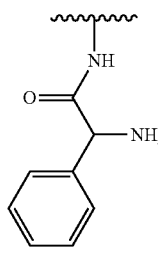 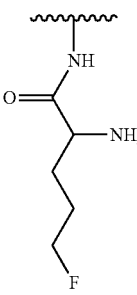 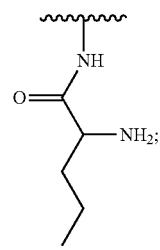

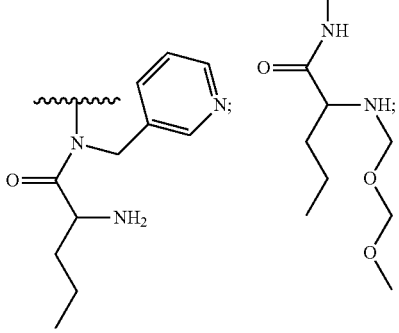

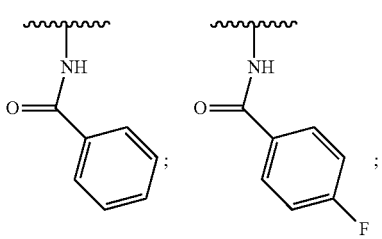

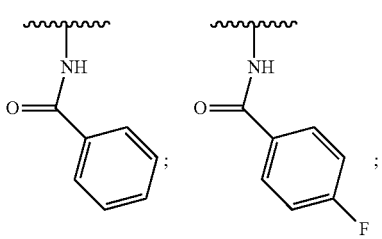

In another exemplary embodiment, the compound has a formula according to the following formulae:

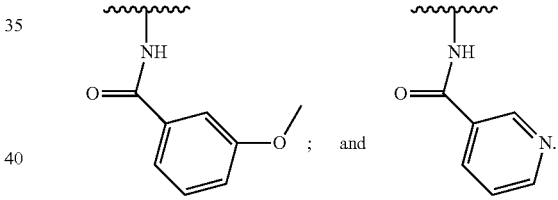

(VIIIa)

and

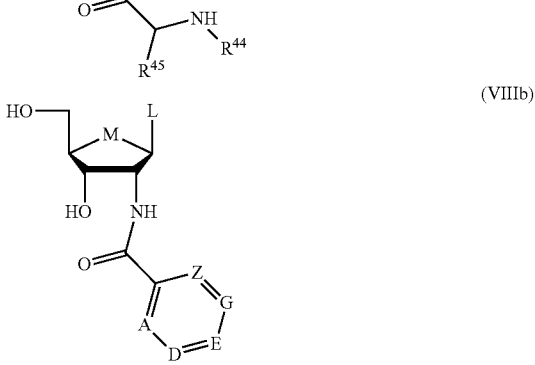

(VIIIb)

In an exemplary embodiment, the compound is a member selected from:
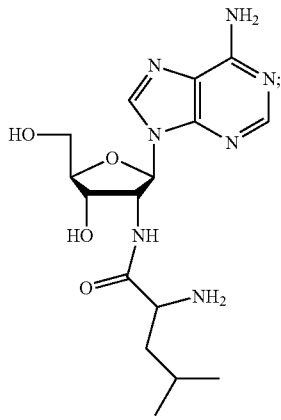
(D1)
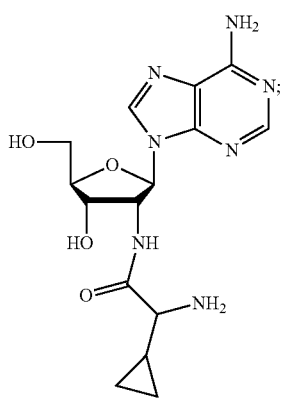
(D2)
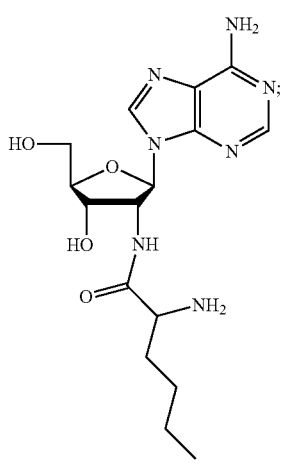
(D3)
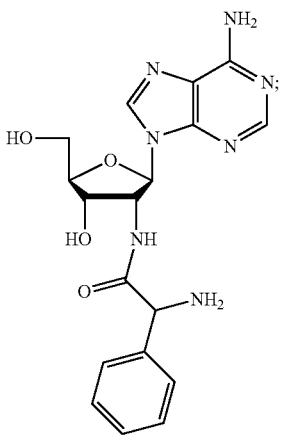
(D4)
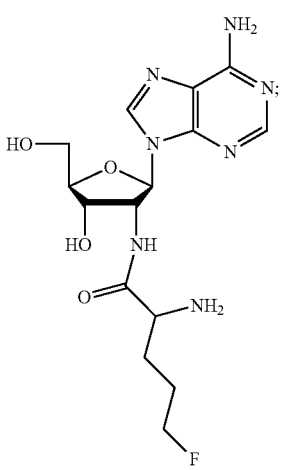
(D5)
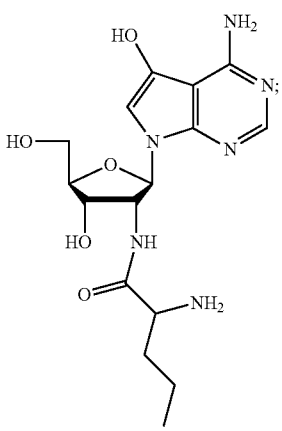
(D6)

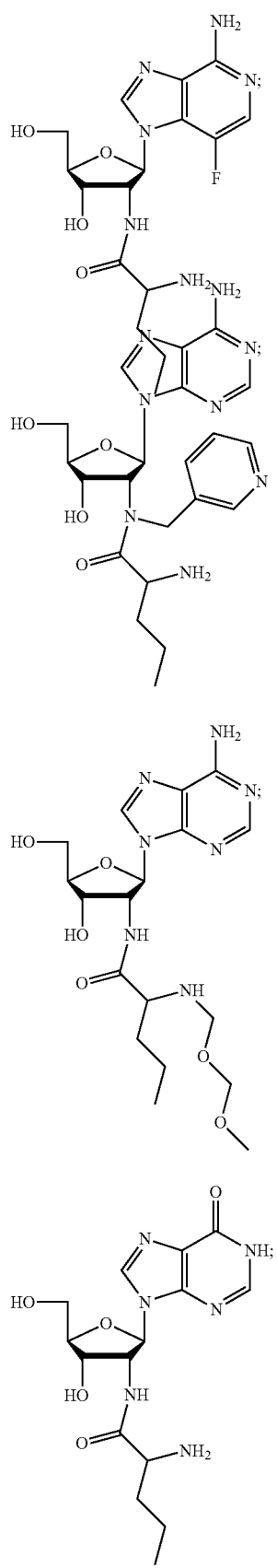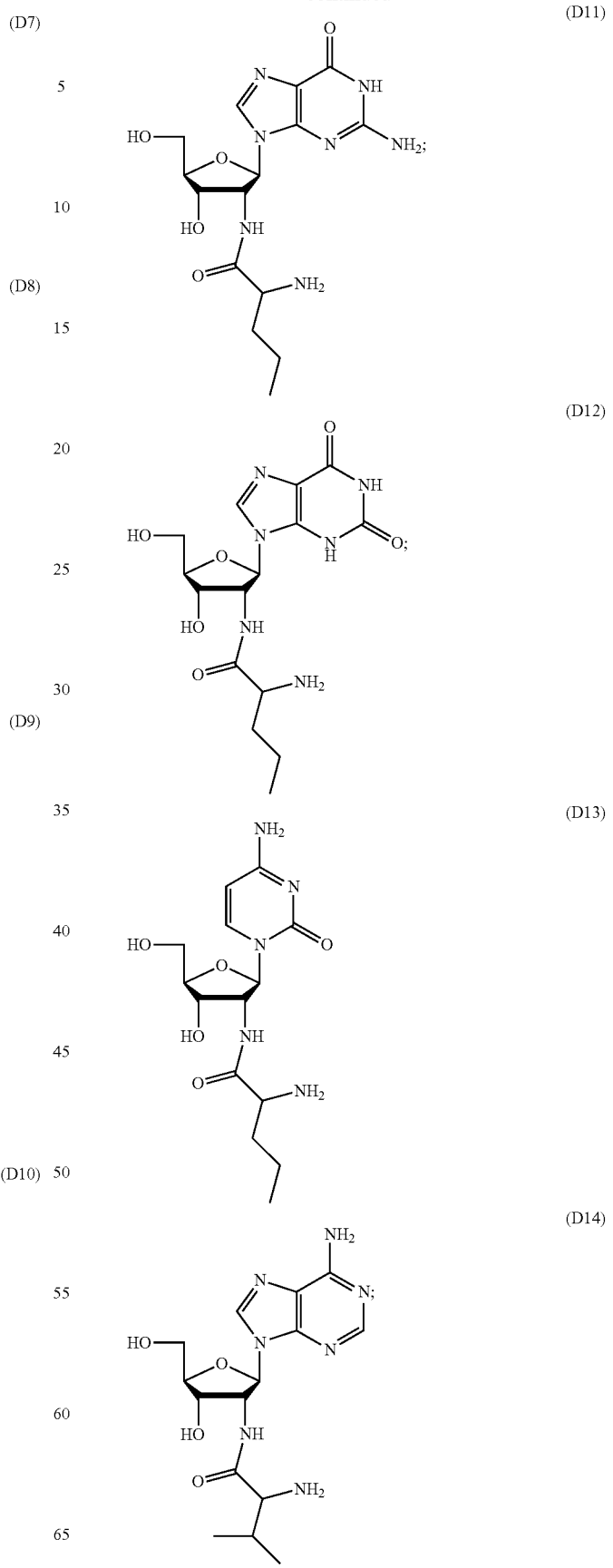

-continued

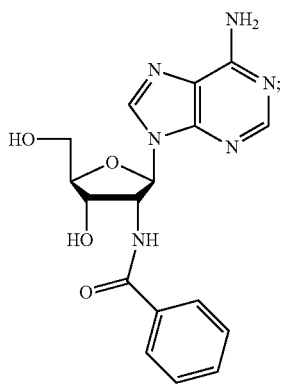
(D15)

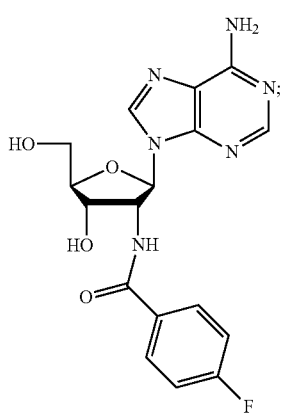
(D16)

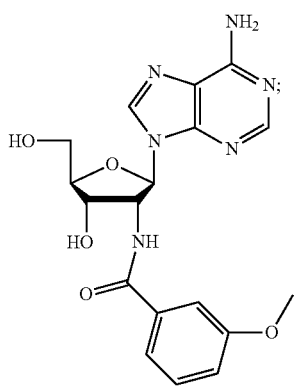
(D17)

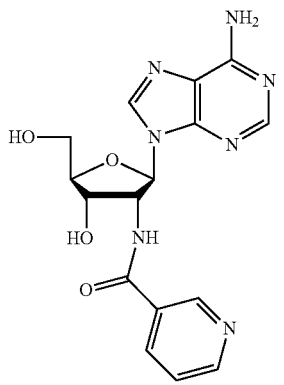
(D18)

and

-continued

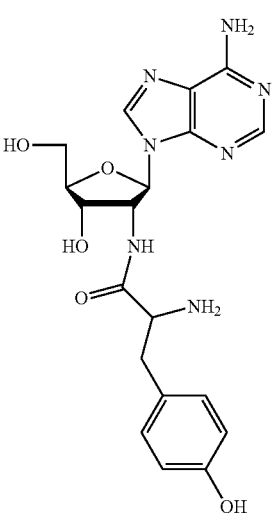
(D19)

I. d.) 3'-amino ribofuranoses

In another aspect, the invention provides compounds useful in the methods which is a 3'-amino ribofuranose. In an exemplary embodiment, the 1'-position of the ribofuranose is substituted with a member selected from substituted or unsubstituted aryl and substituted or unsubstituted heteroaryl. In another exemplary embodiment, the 1'-position of the ribofuranose is substituted with a member selected from substituted or unsubstituted purine, substituted or unsubstituted pyrimidine, substituted or unsubstituted pyridine, and substituted or unsubstituted imidazole. In another exemplary embodiment, the 1'-position of the ribofuranose is substituted with a member selected from substituted or unsubstituted nicotinic acid, substituted or unsubstituted nicotinamide, substituted or unsubstituted nucleic acid base, substituted or unsubstituted adenine,

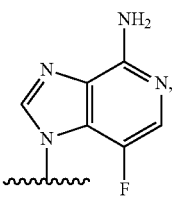 [SMILES: *n1cnc2c(N)ncc(F)c21]

substituted or unsubstituted cytosine, substituted or unsubstituted guanine, substituted or unsubstituted thymine, substituted or unsubstituted uracil, substituted or unsubstituted N,N-dimethyl guanine, substituted or unsubstituted dihydrouracil, substituted or unsubstituted 4-thiouridine and substituted or unsubstituted inosine. In another exemplary embodiment, the compound has a structure according to Formula (VIIIc):

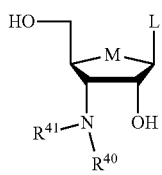

(VIIIc)

wherein L is a member selected from substituted or unsubstituted purine, substituted or unsubstituted pyrimidine, substituted or unsubstituted pyridine and substituted or unsubstituted imidazole. M, as defined herein earlier, is a member selected from O, S, and $NR^2$. $R^{40}$ and $R^{41}$ are each members independently selected from H, aralkyl, substituted aralkyl, $(CH_2)_sOH$ (where s=1 to 3), $CO_2H$, $CO_2$alkyl, $C(O)NH_2$, C(O)NHalkyl, CON(alkyl)$_2$, $C(O)R^{23}$, OH, alkoxy, aryloxy, SH, S-alkyl, S-aryl, $SO_2$alkyl, $SO_3H$, $SCF_3$, CN, halogen, $CF_3$, $NO_2$, $(CH_2)_tNR^{26}R^{27}$ (wherein $R^{26}$ and $R^{27}$ are independently selected from hydrogen, alkyl, and alkanoyl)(t=0 to 2), $SO_2NH_2$, $OCH_2CH_2NH_2$, $OCH_2CH_2NH$alkyl, $OCH_2CH_2N$(alkyl)$_2$, oxazolidin-2-yl, alkyl substituted oxazolidin-2-yl, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl,

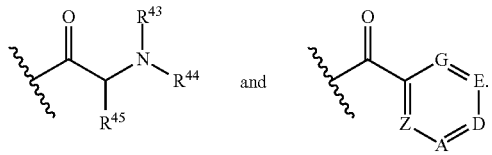

$R^{43}$, $R^{44}$, and $R^{45}$ are each members independently selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{43}$ and $R^{44}$, together with the atoms to which they are attached, are optionally joined to form a 4 to 7 membered ring. $R^{43}$ and $R^{45}$, together with the atoms to which they are attached, are optionally joined to form a 4 to 7 membered ring. $R^{44}$ and $R^{45}$, together with the atoms to which they are attached, are optionally joined to form a 4 to 7 membered ring. A, D, E and G are all defined elsewhere herein. Z is a member selected from $CR^{46}$ and N. The combinations of nitrogens (A+D+E+G+Z) is an integer selected from 0 to 4. At least two members selected from $R^9$, $R^{10}$, $R^{11}$, $R^{12}$ and $R^{46}$, together with the atoms to which they are attached, are optionally joined to form a 4 to 7 membered ring.

In an exemplary embodiment,

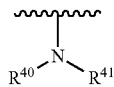

is a member selected from:

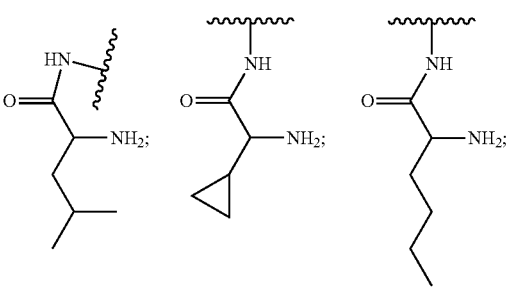

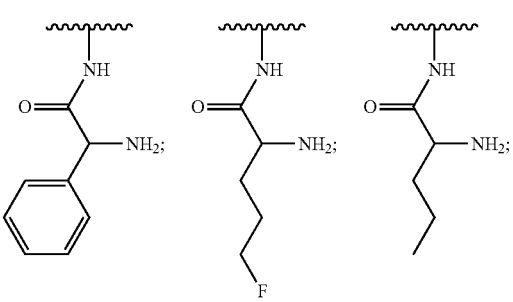

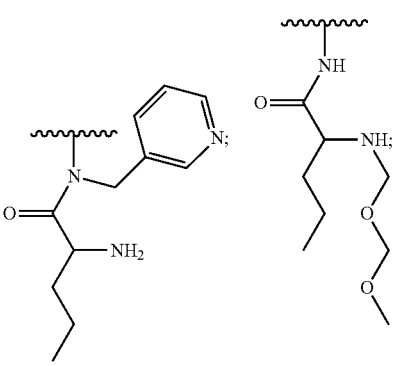

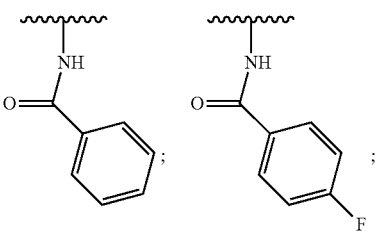

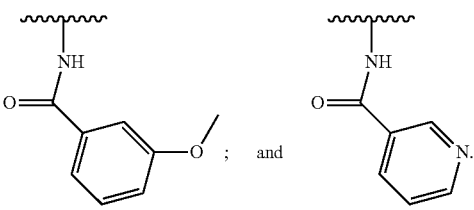

In another exemplary embodiment, the compound has a formula according to the following formulae:
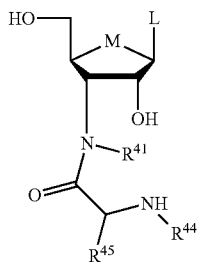 (VIIId)
and
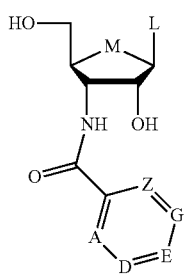 (VIIIe)
In an exemplary embodiment, the compound is a member selected from:
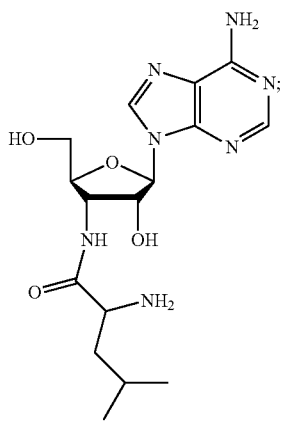 (E1)
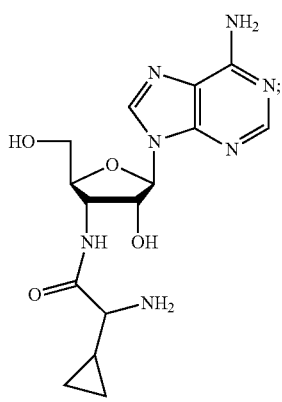 (E2)
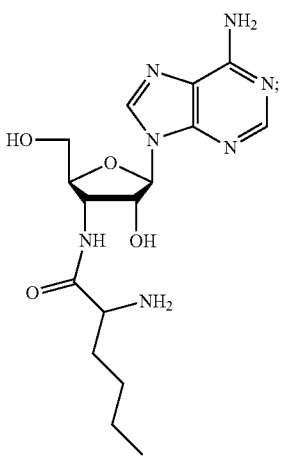 (E3)
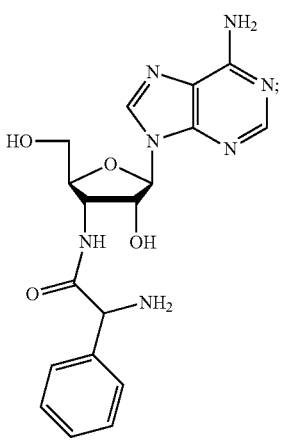 (E4)
(E5)

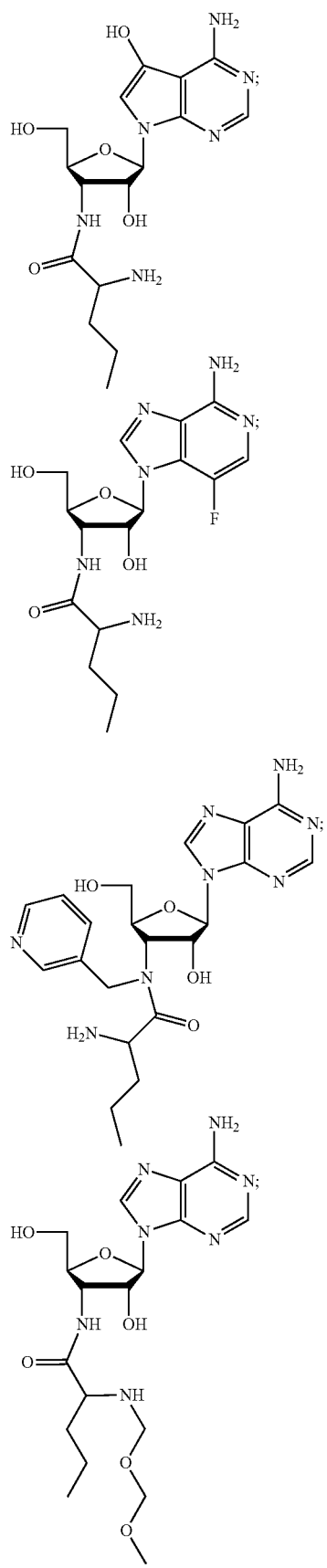
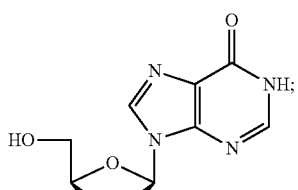
(E10)
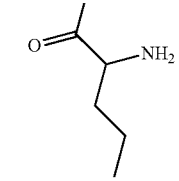
(E11)
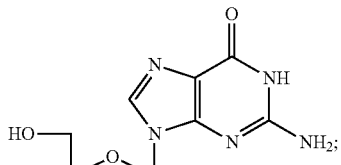
(E12)
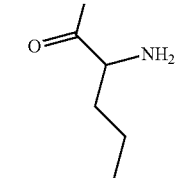
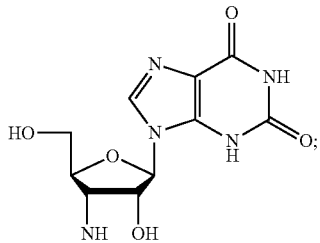
(E13)
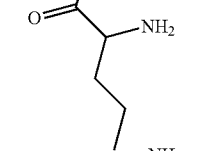
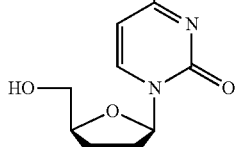
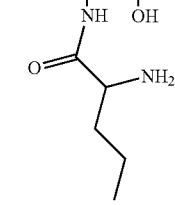

(E14)
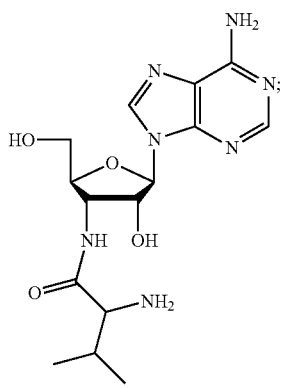

(E15)
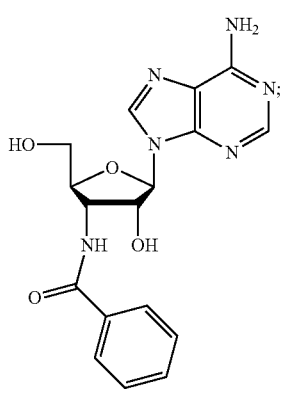

(E16)
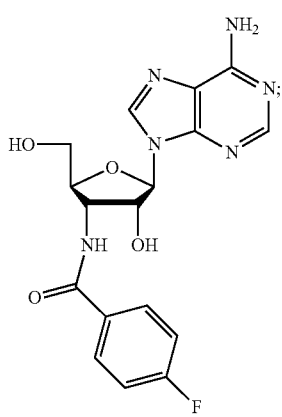

(E17)
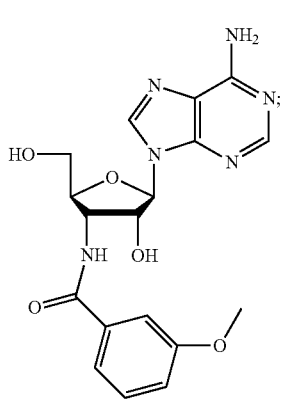

(E18)
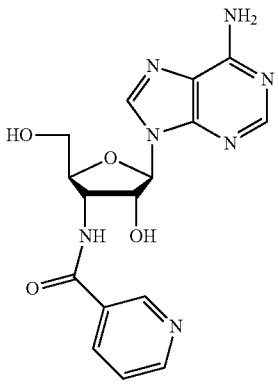
and (E19)
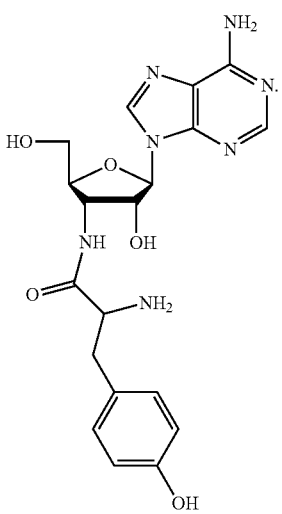

I. e.) Acyclic Boronic Acids and Esters, Part I

Acyclic boronic acids and esters such as those described in this section can also be utilized in the invention. These compounds can be used to kill or inhibit the growth of the microorganisms described herein, as well as treat the diseases described herein. In addition, these compounds can be used as synthetic intermediates in the generation of the compounds described herein.

In another aspect, the compound has a structure according to the following formula:

(IX)
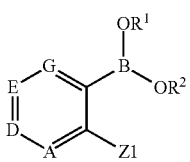

in which $R^1$ and $R^2$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^1$ and $R^2$, together with the atoms to which they are attached, can be optionally joined to form a 4- to 7-membered ring. Z1 is a member selected from

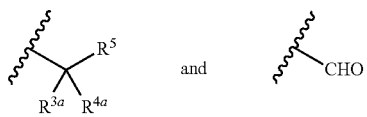 and wherein each $R^{3a}$ and $R^{4a}$ is a member independently selected from H, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^5$ is a member selected from halogen and $OR^6$. $R^6$ is a member selected from H, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. A is a member selected from $CR^{9a}$ and N. D is a member selected from $CR^{10a}$ and N. E is a member selected from $CR^{11a}$ and N. G is a member selected from $CR^{12a}$ and N. $R^{9a}$, $R^{10a}$, $R^{11a}$ and $R^{12a}$ are members independently selected from H, OR*, NR*R**, SR*, —S(O)R*, —S(O)$_2$R*, —S(O)$_2$NR*R**, —C(O)R*, —C(O)OR*, —C(O)NR*R**, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. Each R* and R** is a member independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{9a}$ and $R^{10a}$, along with the atoms to which they are attached, are optionally joined to form a ring. $R^{10a}$ and $R^{11a}$, along with the atoms to which they are attached, are optionally joined to form a ring. $R^{11a}$ and $R^{12a}$, along with the atoms to which they are attached, are optionally joined to form a ring. The combination of nitrogens (A+D+E+G) is an integer selected from 0 to 3.

In an exemplary embodiment, there is a proviso that the compound is not a member selected from:

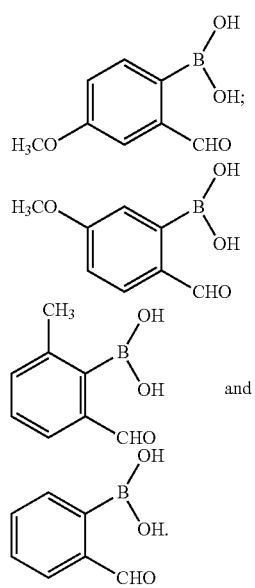

In an exemplary embodiment, the compound has a structure according to Formula IXa

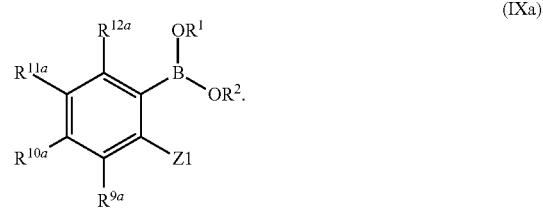

(IXa)

In another exemplary embodiment, each $R^{3a}$ and $R^{4a}$ is a member independently selected from H, cyano, substituted or unsubstituted methyl, substituted or unsubstituted ethyl, trifluoromethyl, substituted or unsubstituted hydroxymethyl, substituted or unsubstituted hydroxyalkyl, substituted or unsubstituted benzyl, substituted or unsubstituted phenyl, substituted or unsubstituted mercaptomethyl, substituted or unsubstituted mercaptoalkyl, substituted or unsubstituted aminomethyl, substituted or unsubstituted alkylaminomethyl, substituted or unsubstituted dialkylaminomethyl, substituted or unsubstituted arylaminomethyl, substituted or unsubstituted indolyl and substituted or unsubstituted amido. In another exemplary embodiment, each $R^{3a}$ and $R^{4a}$ is a member independently selected from cyano, substituted or unsubstituted methyl, substituted or unsubstituted ethyl, trifluoromethyl, substituted or unsubstituted hydroxymethyl, substituted or unsubstituted hydroxyalkyl, substituted or unsubstituted benzyl, substituted or unsubstituted phenyl, substituted or unsubstituted mercaptomethyl, substituted or unsubstituted mercaptoalkyl, substituted or unsubstituted aminomethyl, substituted or unsubstituted alkylaminomethyl, substituted or unsubstituted dialkylaminomethyl, substituted or unsubstituted arylaminomethyl, substituted or unsubstituted indolyl, substituted or unsubstituted amido.

In another exemplary embodiment, each $R^{3a}$ and $R^{4a}$ is a member selected from H, substituted or unsubstituted methyl, substituted or unsubstituted ethyl, substituted or unsubstituted propyl, substituted or unsubstituted isopropyl, substituted or unsubstituted butyl, substituted or unsubstituted t-butyl, substituted or unsubstituted phenyl and substituted or unsubstituted benzyl. In another exemplary embodiment, $R^{3a}$ and $R^{4a}$ is a member selected from methyl, ethyl, propyl, isopropyl, butyl, t-butyl, phenyl and benzyl. In another exemplary embodiment, $R^{3a}$ is H and $R^{4a}$ is a member selected from methyl, ethyl, propyl, isopropyl, butyl, t-butyl, phenyl and benzyl. In another exemplary embodiment, $R^{3a}$ is H and $R^{4a}$ H.

In another exemplary embodiment, Z1 is CHO. In another exemplary embodiment, Z1 is

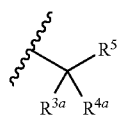

wherein $R^5$ is a member selected from OH, substituted or unsubstituted methoxy, substituted or unsubstituted ethoxy, substituted or unsubstituted methoxymethoxy, substituted or unsubstituted ethoxyethoxy, substituted or unsubstituted trialkylsialyl, and substituted or unsubstituted tetrahydro-2H-pyran-2yloxy. In another exemplary embodiment, $R^5$ is substituted or unsubstituted trialkylsialyl, wherein said trialkylsialyl is a member selected from substituted or unsubstituted trimethylsilyl, substituted or unsubstituted tert-butyldimethylsilyl, and substituted or unsubstituted tributylsilyl. In another exemplary embodiment, $R^5$ is substituted or unsubstituted methoxy, substituted or unsubstituted ethoxy, substituted or unsubstituted methoxymethoxy, substituted or unsubstituted ethoxyethoxy, and substituted or unsubstituted tetrahydro-2H-pyran-2yloxy. In another exemplary embodiment, $R^5$ is a member selected from methoxy, ethoxy, methoxymethoxy, ethoxyethoxy and tetrahydro-2H-pyran-2yloxy. In another exemplary embodiment, Z1 is

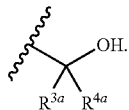

In an exemplary embodiment, $R^{9a}$, $R^{10a}$, $R^{11a}$ and $R^{12a}$ is a member independently selected from H, OR*, NR*R**, SR*, —S(O)R*, —S(O)$_2$R*, —S(O)$_2$NR*R**, —C(O)R*, —C(O)OR*, —C(O)NR*R**, halogen, cyano, nitro, substituted or unsubstituted methoxy, substituted or unsubstituted methyl, substituted or unsubstituted ethoxy, substituted or unsubstituted ethyl, trifluoromethyl, substituted or unsubstituted hydroxymethyl, substituted or unsubstituted hydroxyalkyl, substituted or unsubstituted benzyl, substituted or unsubstituted phenyl, substituted or unsubstituted phenyloxy, substituted or unsubstituted phenyl methoxy, substituted or unsubstituted thiophenyloxy, substituted or unsubstituted pyridinyloxy, substituted or unsubstituted pyrimidinyloxy, substituted or unsubstituted benzylfuran, substituted or unsubstituted methylthio, substituted or unsubstituted mercaptomethyl, substituted or unsubstituted mercaptoalkyl, substituted or unsubstituted phenylthio, substituted or unsubstituted thiophenylthio, substituted or unsubstituted phenyl methylthio, substituted or unsubstituted pyridinylthio, substituted or unsubstituted pyrimidinylthio, substituted or unsubstituted benzylthiofuranyl, substituted or unsubstituted phenylsulfonyl, substituted or unsubstituted benzylsulfonyl, substituted or unsubstituted phenylmethylsulfonyl, substituted or unsubstituted thiophenylsulfonyl, substituted or unsubstituted pyridinylsulfonyl, substituted or unsubstituted pyrimidinylsulfonyl, substituted or unsubstituted sulfonamidyl, substituted or unsubstituted phenylsulfinyl, substituted or unsubstituted benzylsulfinyl, substituted or unsubstituted phenylmethylsulfinyl, substituted or unsubstituted thiophenylsulfinyl, substituted or unsubstituted pyridinylsulfinyl, substituted or unsubstituted pyrimidinylsulfinyl, substituted or unsubstituted amino, substituted or unsubstituted alkylamino, substituted or unsubstituted dialkylamino, substituted or unsubstituted trifluoromethylamino, substituted or unsubstituted aminomethyl, substituted or unsubstituted alkylaminomethyl, substituted or unsubstituted dialkylaminomethyl, substituted or unsubstituted arylaminomethyl, substituted or unsubstituted benzylamino, substituted or unsubstituted phenylamino, substituted or unsubstituted thiophenylamino, substituted or unsubstituted pyridinylamino, substituted or unsubstituted pyrimidinylamino, substituted or unsubstituted indolyl, substituted or unsubstituted morpholino, substituted or unsubstituted alkylamido, substituted or unsubstituted arylamido, substituted or unsubstituted ureido, substituted or unsubstituted carbamoyl, and substituted or unsubstituted piperizinyl. In an exemplary embodiment, $R^{9a}$, $R^{10a}$, $R^{11a}$ and $R^{12a}$ are selected from the previous list of substituents with the exception of —C(O)R*, —C(O)OR*, —C(O)NR*R**.

In another exemplary embodiment, $R^{9a}$, $R^{10a}$, $R^{11a}$ and $R^{12a}$ are members independently selected from fluoro, chloro, bromo, nitro, cyano, amino, methyl, hydroxylmethyl, trifluoromethyl, methoxy, trifluoromethyoxy, ethyl, diethylcarbamoyl, pyridin-2-yl, pyridin-3-yl, pyridin-4-yl, pyrimidinyl, piperizino, piperizinyl, piperizinocarbonyl, piperizinylcarbonyl, carboxyl, 1-tetrazolyl, 1-ethoxycarbonylmethoxy, carboxymethoxy, thiophenyl, 3-(butylcarbonyl) phenylmethoxy, 1H-tetrazol-5-yl, 1-ethoxycarbonylmethyloxy-, 1-ethoxycarbonylmethyl-, 1-ethoxycarbonyl-, carboxymethoxy-, thiophen-2-yl, thiophen-2-ylthio-, thiophen-3-yl, thiophen-3-ylthio, 4-fluorophenylthio, butylcarbonylphenylmethoxy, butylcarbonylphenylmethyl, butylcarbonylmethyl, 1-(piperidin-1-yl)carbonyl)methyl, 1-(piperidin-1-yl)carbonyl)methoxy, 1-(piperidin-2-yl)carbonyl)methoxy, 1-(piperidin-3-yl)carbonyl)methoxy, 1-(4-(pyrimidin-2-yl)piperazin-1-yl)carbonyl)methoxy, 1-(4-(pyrimidin-2-yl)piperazin-1-yl)carbonyl)methyl, 1-(4-(pyrimidin-2-yl)piperazin-1-yl)carbonyl, 1-4-(pyrimidin-2-yl)piperazin-1-yl, 1-(4-(pyridin-2-yl)piperazin-1-yl) carbonyl), 1-(4-(pyridin-2-yl)piperazin-1-yl) carbonylmethyl, (1-(4-(pyridin-2-yl)piperazin-1-yl) carbonyl)-methoxy), 1-(4-(pyridin-2-yl)piperazin-1-yl, 1H-indol-1-yl, morpholino-, morpholinyl, morpholinocarbonyl, morpholinylcarbonyl, phenylureido, phenylcarbamoyl, acetamido, 3-(phenylthio)-1H-indol-1-yl, 3-(2-cyanoethylthio)-1H-indol-1-yl, benzylamino, 5-methoxy-3-(phenylthio)-1H-indol-1-yl, 5-methoxy-3-(2-cyanoethylthio)-1H-indol-1-yl)), 5-chloro-1H-indol-1-yl, 5-chloro-3-(2-cyanoethylthio)-1H-indol-1-yl)), dibenzylamino, benzylamino, 5-chloro-3-(phenylthio)-1H-indol-1-yl)), 4-(1H-tetrazol-5-yl)phenoxy, 4-(1H-tetrazol-5-yl)phenyl, 4-(1H-tetrazol-5-yl)phenylthio, 2-cyanophenoxy, 3-cyanophenoxy, 4-cyanophenoxy, 2-cyanophenylthio, 3-cyanophenylthio, 4-cyanophenylthio, 2-chlorophenoxy, 3-chlorophenoxy, 4-chlorophenoxy, 2-fluorophenoxy, 3-fluorophenoxy, 4-fluorophenoxy, 2-cyanobenzyloxy, 3-cyanobenzyloxy, 4-cyanobenzyloxy, 2-chlorobenzyloxy, 3-chlorobenzyloxy, 4-chlorobenzyloxy, 2-fluorobenzyloxy, 3-fluorobenzyloxy, 4-fluorobenzyloxy, unsubstituted phenyl, unsubstituted benzyl. In an exemplary embodiment, $R^{9a}$ is H and $R^{12a}$ is H. In an exemplary embodiment, the compound has a subsitutent combination for $R^{9a}$, $R^{10a}$, $R^{11a}$, and $R^{12a}$ which is a member selected from those described in Formulae (I), (Ia) (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Iz), (Iaa), (Iab), (Iac), (Iad), (Iae), (Iaf), (Iag), (Iah), (Iai), (Iaj), (Iak), above, and/or the subsequent paragraphs describing Formulae (I), (Ia) (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Iz), (Iaa), (Iab), (Iac), (Iad), (Iae), (Iaf), (Iag), (Iah), (Iai), (Iaj), (Iak).

In an exemplary embodiment, the compound is an acyclic boronic acid or ester in which a portion of the acyclic boronic acid or ester as in Figure (IXb) below (IXb)

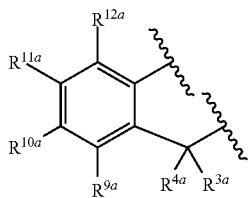

is a member selected from a structure in FIG. 12. In another exemplary embodiment, the compound is a dimer, anhydride or trimer of an acyclic boronic acid or ester described herein. In another exemplary embodiment, the compound is a dimer, anhydride or trimer of an acyclic boronic acid or ester in which a portion of the acyclic boronic acid or ester as in Figure (IXb) is a member selected a structure in FIG. 12.

In an exemplary embodiment, $R^1$ and $R^2$ are each members independently selected from H, substituted or unsubstituted methyl, substituted or unsubstituted ethyl, substituted or unsubstituted propyl, substituted or unsubstituted isopropyl, substituted or unsubstituted butyl, substituted or unsubstituted t-butyl, substituted or unsubstituted phenyl and substituted or unsubstituted benzyl. $R^1$ and $R^2$, together with the atoms to which they are joined, can optionally form a member selected from substituted or unsubstituted dioxaborolane, substituted or unsubstituted dioxaborinane, substituted or unsubstituted dioxaborepane.

In an exemplary embodiment, $R^1$ and $R^2$ are each members independently selected from H, methyl, ethyl, propyl, isopropyl, butyl, t-butyl, phenyl and benzyl. In an exemplary embodiment, $R^1$ and $R^2$ are each members independently selected from H, methyl, isopropyl, and phenyl. In an exemplary embodiment, $R^1$ and $R^2$ are methyl. In an exemplary embodiment, $R^1$ and $R^2$ are isopropyl. In an exemplary embodiment, $R^1$ and $R^2$ are H.

In another exemplary embodiment, $R^1$ and $R^2$, together with the atoms to which they are joined, form a member selected from substituted or unsubstituted dioxaborolane, substituted or unsubstituted dioxaborinane, substituted or unsubstituted dioxaborepane. In another exemplary embodiment, $R^1$ and $R^2$, together with the atoms to which they are joined, form a member selected from dioxaborolane, substituted or unsubstituted tetramethyldioxaborolane, substituted or unsubstituted phenyldioxaborolane, dioxaborinane, dimethyldioxaborinane and dioxaborepane.

In an exemplary embodiment, the compound is a member selected from (IXc)

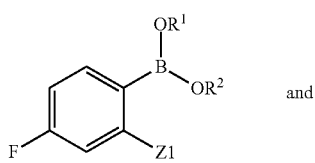 and (IXd)

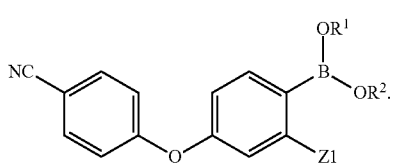

In an exemplary embodiment, the compound is a member selected from:

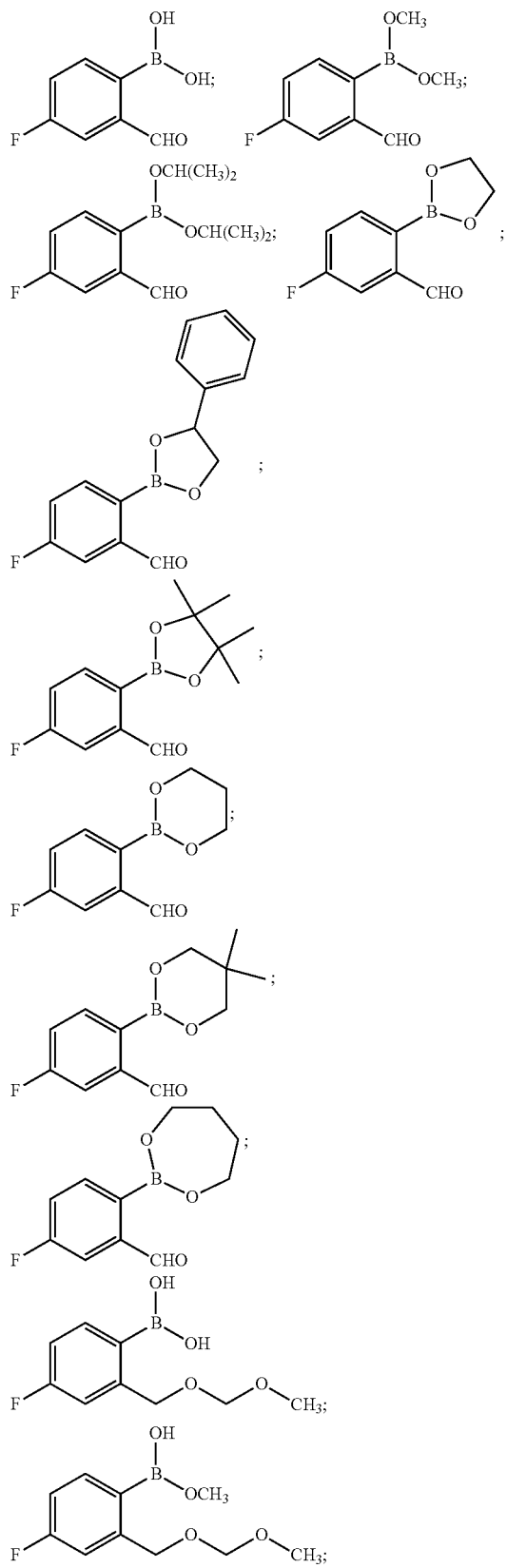

77
-continued
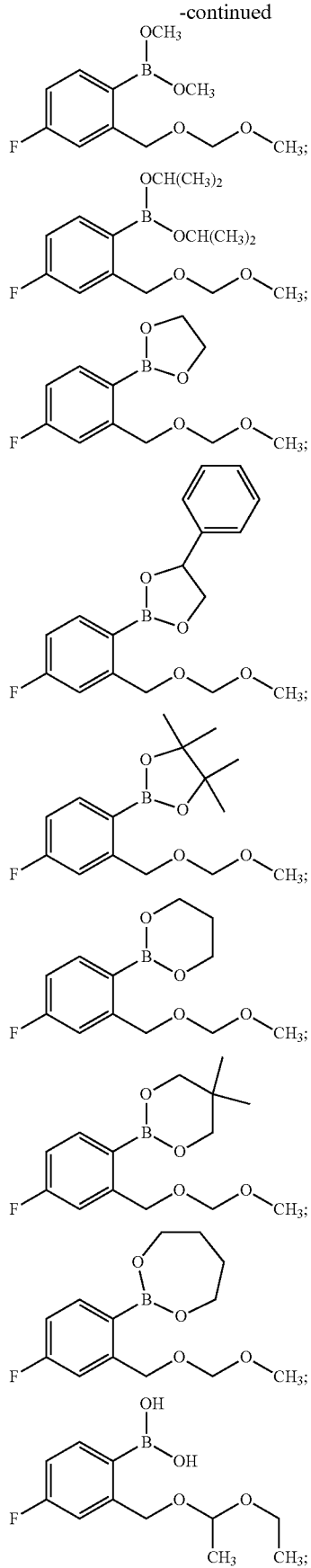
78
-continued
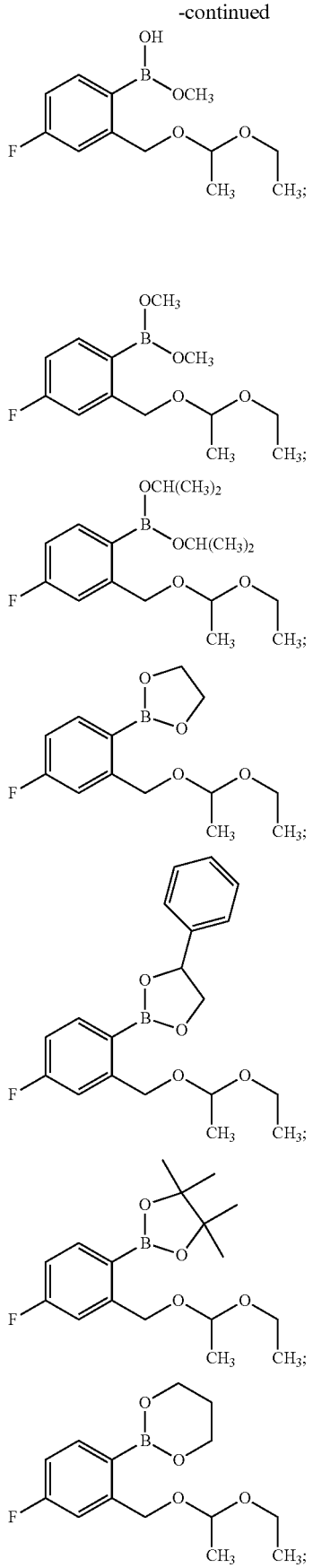

-continued
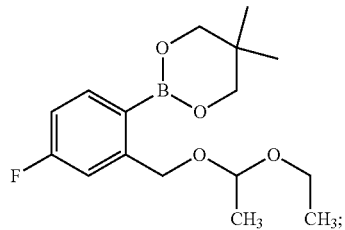
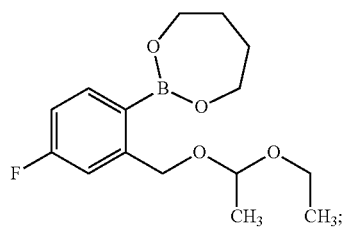
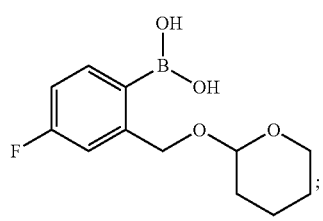
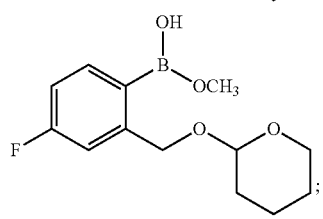
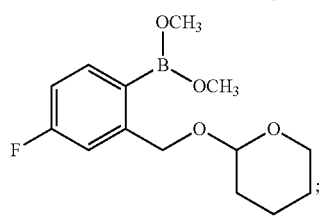
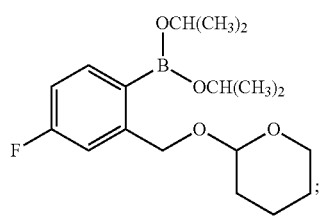
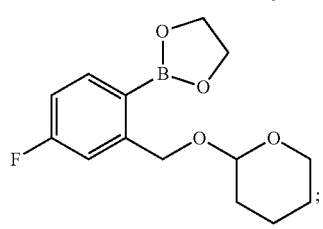
-continued
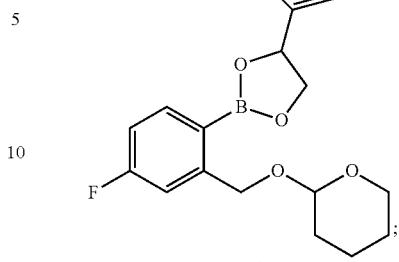
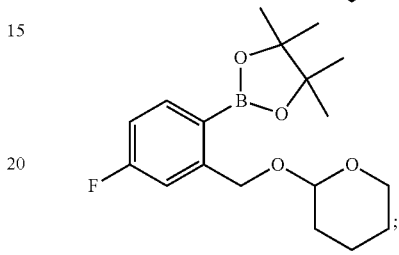
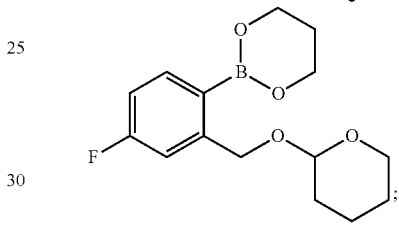
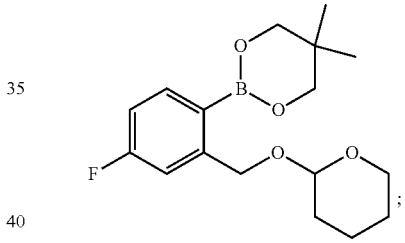
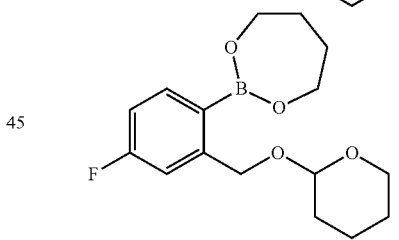
In an exemplary embodiment, the compound is a member selected from
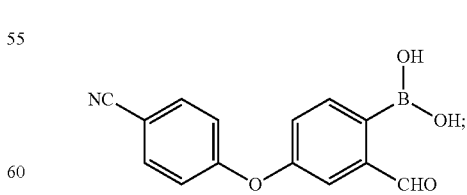
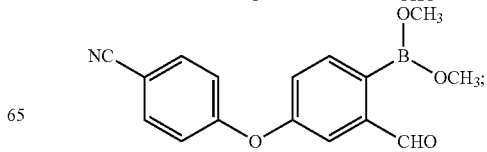

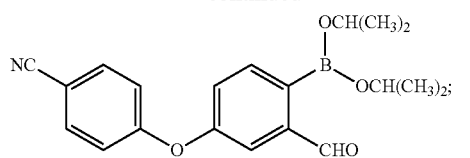
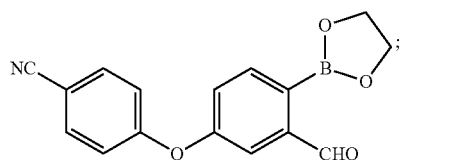
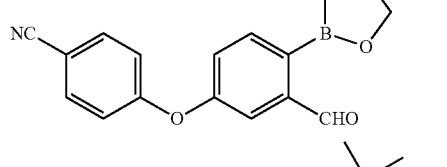
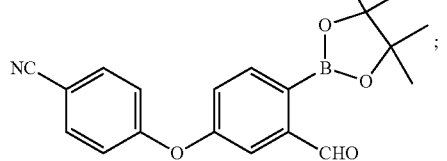
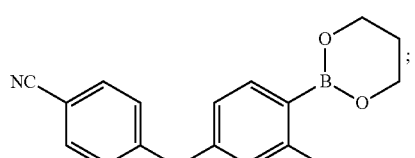
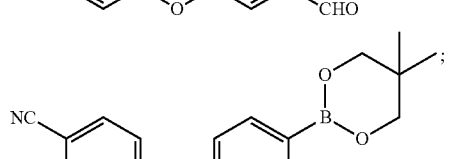
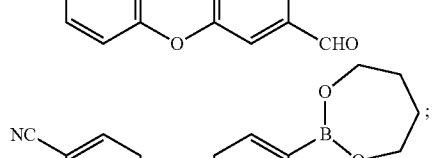
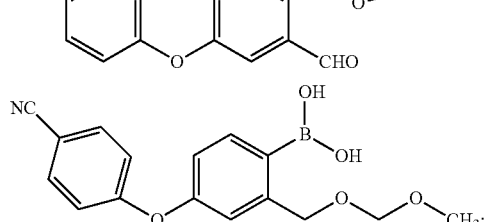
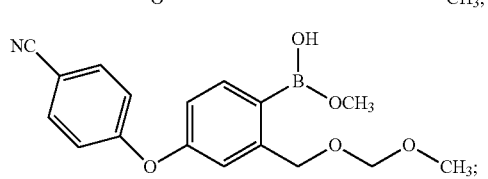
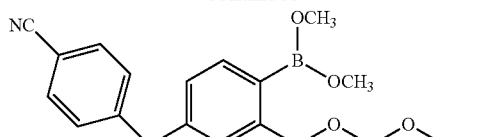
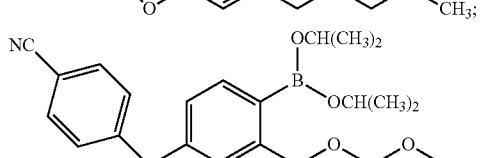
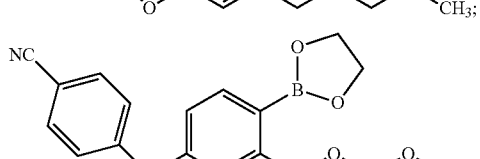
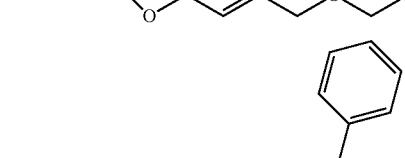
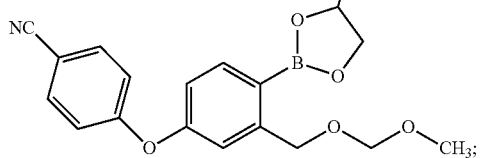
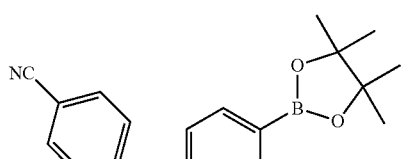
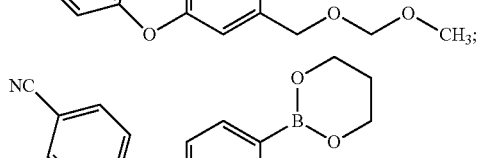
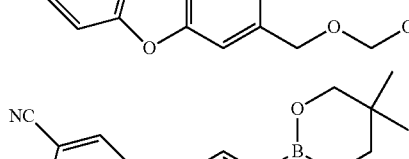
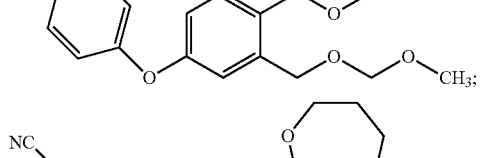
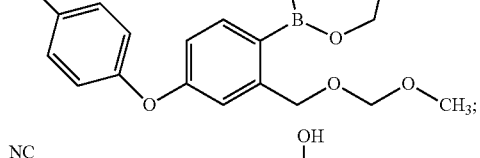
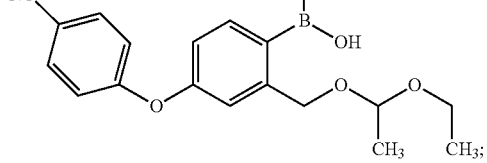

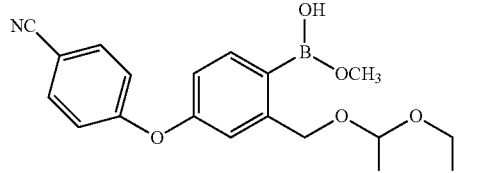
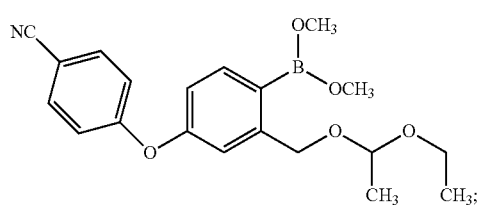
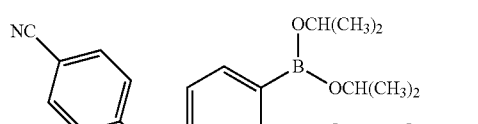
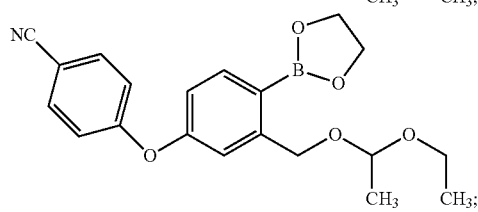
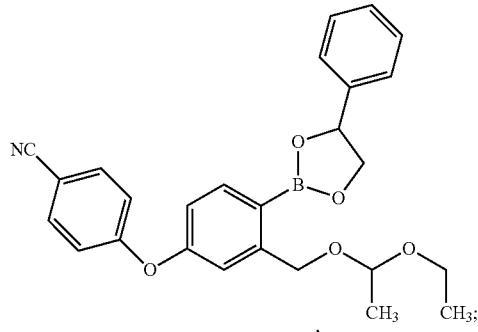
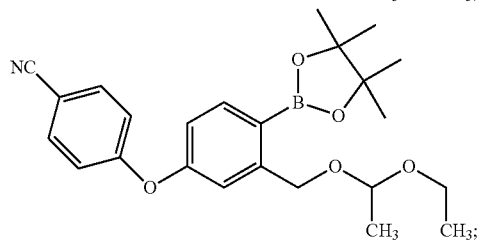
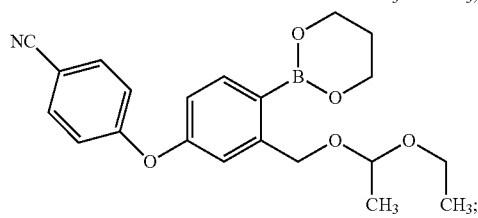
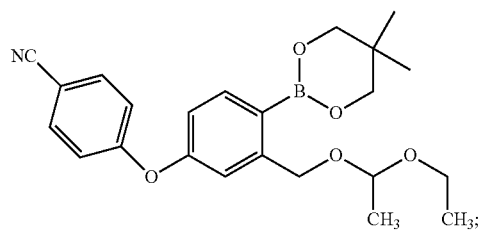
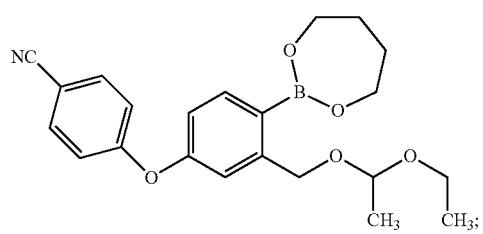
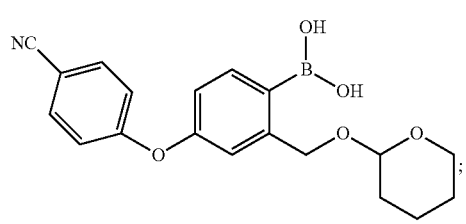
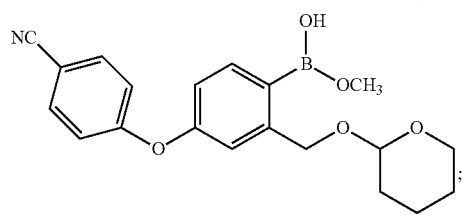
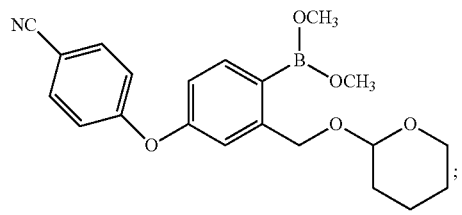
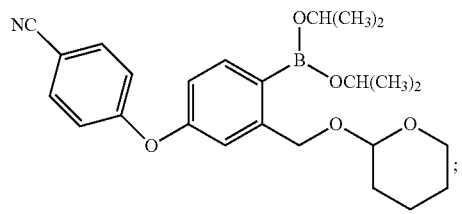
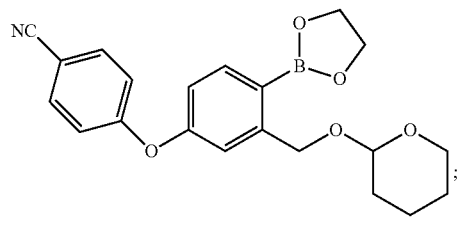

-continued

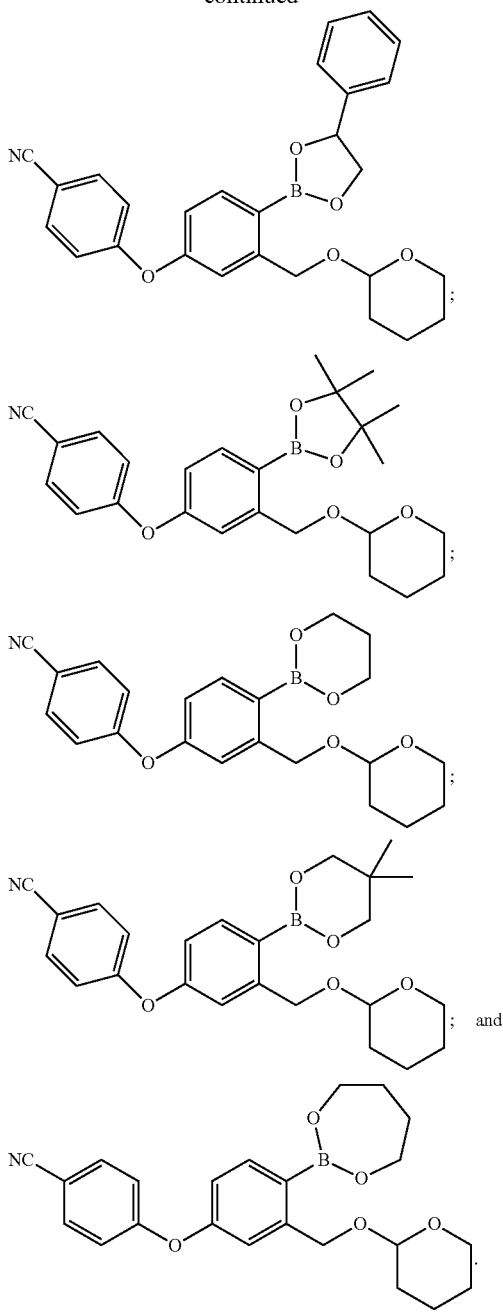

In another exemplary embodiment, the compounds and embodiments described herein can form a hydrate with water, a solvate with an alcohol (e.g. methanol, ethanol, propanol); an adduct with an amino compound (e.g. ammonia, methylamine, ethylamine); an adduct with an acid (e.g. formic acid, acetic acid); complexes with ethanolamine, quinoline, amino acids, and the like.

In an exemplary embodiment, acyclic boronic esters described herein can be used as intermediates in the synthesis of the compounds described herein. In another exemplary embodiment, the acyclic boronic esters described herein can be used as intermediates in the synthesis of a compound which is a member selected from Formulae (I), (Ia) (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Iz), (Iaa), (Iab), (Iac), (Iad), (Iae), (Iaf), (Iag), (Iah), (Iai), (Iaj), (Iak).

I. f.) Acyclic Boronic Acids and Esters, Part II

Acyclic boronic acids and esters described herein can also be utilized in the invention. These compounds can be used to kill or inhibit the growth of the microorganisms described herein, as well as treat the diseases described herein. In addition, these compounds can be used as synthetic intermediates in the generation of other compounds described herein. In an exemplary embodiment, these other compounds are the cyclic boronic esters and cyclic borinic esters described herein.

In another aspect, the compound has a structure according to the following formula:

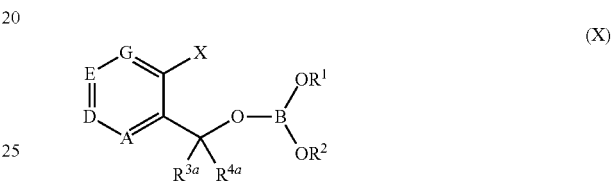

(X)

in which $R^1$ and $R^2$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^1$ and $R^2$, together with the atoms to which they are attached, can be optionally joined to form a 4- to 7-membered ring. X is a member selected from substituted or unsubstituted triflate, halogen, substituted or unsubstituted sulfonic esters and substituted or unsubstituted acyloxy groups, and substituted or unsubstituted diazo. $R^{3a}$ and $R^{4a}$ are members independently selected from H, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. A is a member selected from $CR^{9a}$ and N. D is a member selected from $CR^{10a}$ and N. E is a member selected from $CR^{11a}$ and N. G is a member selected from $CR^{12a}$ and N. $R^{9a}$, $R^{10a}$, $R^{11a}$ and $R^{12a}$ are members independently selected from H, OR*, NR*R**, SR*, —S(O)R*, —S(O)$_2$R*, —S(O)$_2$NR*R**, —C(O)R*, —C(O)OR*, —C(O)NR*R**, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. Each R* and R** is a member independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{9a}$ and $R^{10a}$, along with the atoms to which they are attached, are optionally joined to form a ring. $R^{10a}$ and $R^{11a}$, along with the atoms to which they are attached, are optionally joined to form a ring. $R^{11a}$ and $R^{12a}$, along with the atoms to which they are attached, are optionally joined to form a ring. The combination of nitrogens (A+D+E+G) is an integer selected from 0 to 3.

In an exemplary embodiment, this aspect has the proviso that the compound is not:

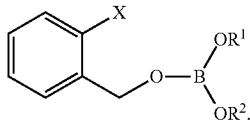

In an exemplary embodiment, the compound has a structure according to Formula (Xa)

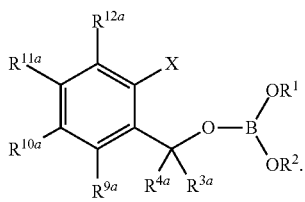

(Xa)

In another exemplary embodiment, each $R^{3a}$ and $R^{4a}$ is a member independently selected from H, cyano, substituted or unsubstituted methyl, substituted or unsubstituted ethyl, trifluoromethyl, substituted or unsubstituted hydroxymethyl, substituted or unsubstituted hydroxyalkyl, substituted or unsubstituted benzyl, substituted or unsubstituted phenyl, substituted or unsubstituted mercaptomethyl, substituted or unsubstituted mercaptoalkyl, substituted or unsubstituted aminomethyl, substituted or unsubstituted alkylaminomethyl, substituted or unsubstituted dialkylaminomethyl, substituted or unsubstituted arylaminomethyl, substituted or unsubstituted indolyl and substituted or unsubstituted amido. In another exemplary embodiment, each $R^{3a}$ and $R^{4a}$ is a member independently selected from cyano, substituted or unsubstituted methyl, substituted or unsubstituted ethyl, trifluoromethyl, substituted or unsubstituted hydroxymethyl, substituted or unsubstituted hydroxyalkyl, substituted or unsubstituted benzyl, substituted or unsubstituted phenyl, substituted or unsubstituted mercaptomethyl, substituted or unsubstituted mercaptoalkyl, substituted or unsubstituted aminomethyl, substituted or unsubstituted alkylaminomethyl, substituted or unsubstituted dialkylaminomethyl, substituted or unsubstituted arylaminomethyl, substituted or unsubstituted indolyl, substituted or unsubstituted amido.

In another exemplary embodiment, each $R^{3a}$ and $R^{4a}$ is a member selected from H, substituted or unsubstituted methyl, substituted or unsubstituted ethyl, substituted or unsubstituted propyl, substituted or unsubstituted isopropyl, substituted or unsubstituted butyl, substituted or unsubstituted t-butyl, substituted or unsubstituted phenyl and substituted or unsubstituted benzyl. In another exemplary embodiment, $R^{3a}$ and $R^{4a}$ is a member selected from methyl, ethyl, propyl, isopropyl, butyl, t-butyl, phenyl and benzyl. In another exemplary embodiment, $R^{3a}$ is H and $R^{4a}$ is a member selected from methyl, ethyl, propyl, isopropyl, butyl, t-butyl, phenyl and benzyl. In another exemplary embodiment, $R^{3a}$ is H and $R^{4a}$ H.

In another exemplary embodiment, $R^{9a}$, $R^{10a}$, $R^{11a}$ and $R^{12a}$ is a member selected from H, OR*, NR*R**, SR*, —S(O)R*, —S(O)$_2$R*, —S(O)$_2$NR*R**, —C(O)R*, —C(O)OR*, —C(O)NR*R**, halogen, cyano, nitro, substituted or unsubstituted methoxy, substituted or unsubstituted methyl, substituted or unsubstituted ethoxy, substituted or unsubstituted ethyl, trifluoromethyl, substituted or unsubstituted hydroxymethyl, substituted or unsubstituted hydroxyalkyl, substituted or unsubstituted benzyl, substituted or unsubstituted phenyl, substituted or unsubstituted phenyloxy, substituted or unsubstituted phenyl methoxy, substituted or unsubstituted thiophenyloxy, substituted or unsubstituted pyridinyloxy, substituted or unsubstituted pyrimidinyloxy, substituted or unsubstituted benzylfuran, substituted or unsubstituted methylthio, substituted or unsubstituted mercaptomethyl, substituted or unsubstituted mercaptoalkyl, substituted or unsubstituted phenylthio, substituted or unsubstituted thiophenylthio, substituted or unsubstituted phenyl methylthio, substituted or unsubstituted pyridinylthio, substituted or unsubstituted pyrimidinylthio, substituted or unsubstituted benzylthiofuranyl, substituted or unsubstituted phenylsulfonyl, substituted or unsubstituted benzylsulfonyl, substituted or unsubstituted phenylmethylsulfonyl, substituted or unsubstituted thiophenylsulfonyl, substituted or unsubstituted pyridinylsulfonyl, substituted or unsubstituted pyrimidinylsulfonyl, substituted or unsubstituted sulfonamidyl, substituted or unsubstituted phenylsulfinyl, substituted or unsubstituted benzylsulfinyl, substituted or unsubstituted phenylmethylsulfinyl, substituted or unsubstituted thiophenylsulfinyl, substituted or unsubstituted pyridinylsulfinyl, substituted or unsubstituted pyrimidinylsulfinyl, substituted or unsubstituted amino, substituted or unsubstituted alkylamino, substituted or unsubstituted dialkylamino, substituted or unsubstituted trifluoromethylamino, substituted or unsubstituted aminomethyl, substituted or unsubstituted alkylaminomethyl, substituted or unsubstituted dialkylaminomethyl, substituted or unsubstituted arylaminomethyl, substituted or unsubstituted benzylamino, substituted or unsubstituted phenylamino, substituted or unsubstituted thiophenylamino, substituted or unsubstituted pyridinylamino, substituted or unsubstituted pyrimidinylamino, substituted or unsubstituted indolyl, substituted or unsubstituted morpholino, substituted or unsubstituted alkylamido, substituted or unsubstituted arylamido, substituted or unsubstituted ureido, substituted or unsubstituted carbamoyl, and substituted or unsubstituted piperizinyl. In an exemplary embodiment, $R^{9a}$, $R^{10a}$, $R^{11a}$ and $R^{12a}$ are selected from the previous list of substituents with the exception of —C(O)R*, —C(O)OR*, —C(O)NR*R**.

In another exemplary embodiment, $R^{9a}$, $R^{10a}$, $R^{11a}$ and $R^{12a}$ are members independently selected from fluoro, chloro, bromo, nitro, cyano, amino, methyl, hydroxylmethyl, trifluoromethyl, methoxy, trifluoromethyoxy, ethyl, diethylcarbamoyl, pyridin-2-yl, pyridin-3-yl, pyridin-4-yl, pyrimidinyl, piperizino, piperizinyl, piperizinocarbonyl, piperizinylcarbonyl, carboxyl, 1-tetrazolyl, 1-ethoxycarbonylmethoxy, carboxymethoxy, thiophenyl, 3-(butylcarbonyl) phenylmethoxy, 1H-tetrazol-5-yl, 1-ethoxycarbonylmethyloxy-, 1-ethoxycarbonylmethyl-, 1-ethoxycarbonyl-, carboxymethoxy-, thiophen-2-yl, thiophen-2-ylthio-, thiophen-3-yl, thiophen-3-ylthio, 4-fluorophenylthio, butylcarbonylphenylmethoxy, butylcarbonylphenylmethyl, butylcarbonylmethyl, 1-(piperidin-1-yl)carbonyl)methyl, 1-(piperidin-1-yl)carbonyl)methoxy, 1-(piperidin-2-yl)carbonyl)methoxy, 1-(piperidin-3-yl)carbonyl)methoxy, 1-(4-(pyrimidin-2-yl)piperazin-1-yl)carbonyl)methoxy, 1-(4-(pyrimidin-2-yl)piperazin-1-yl)carbonyl)methyl, 1-(4-(pyrimidin-2-yl)piperazin-1-yl)carbonyl, 1-4-(pyrimidin-2-yl)piperazin-1-yl, 1-(4-(pyridin-2-yl)piperazin-1-yl) carbonyl), 1-(4-(pyridin-2-yl)piperazin-1-yl) carbonylmethyl, (1-(4-(pyridin-2-yl)piperazin-1-yl) carbonyl)-methoxy), 1-(4-(pyridin-2-yl)piperazin-1-yl, 1H-indol-1-yl, morpholino-, morpholinyl, morpholinocarbonyl, morpholinylcarbonyl, phenylureido, phenylcarbamoyl, acetamido, 3-(phenylthio)-1H-indol-1-yl, 3-(2-cyanoethylthio)-1H-indol-1-yl, benzylamino, 5-methoxy-3-(phenylthio)-1H-indol-1-yl, 5-methoxy-3-(2-cyanoethylthio)-1H-indol-1-yl)), 5-chloro-1H-indol-1-yl, 5-chloro-3-(2-cyanoethylthio)-1H-indol-1-yl)), dibenzylamino, benzylamino, 5-chloro-3-(phenylthio)-1H-indol-1-yl)), 4-(1H-tetrazol-5-yl)phenoxy, 4-(1H-tetrazol-5-yl)phenyl, 4-(1H-tetrazol-5-yl)phenylthio, 2-cyanophenoxy, 3-cyanophenoxy, 4-cyanophenoxy, 2-cyanophenylthio, 3-cyanophenylthio, 4-cyanophenylthio, 2-chlorophenoxy, 3-chlorophenoxy, 4-chlorophenoxy, 2-fluorophenoxy, 3-fluorophenoxy, 4-fluorophenoxy, 2-cyanobenzyloxy, 3-cyanobenzyloxy, 4-cyanobenzyloxy, 2-chlorobenzyloxy, 3-chlorobenzyloxy, 4-chlorobenzyloxy, 2-fluorobenzyloxy, 3-fluorobenzyloxy, 4-fluorobenzyloxy, unsubstituted phenyl, unsubstituted benzyl. In an exemplary embodiment, $R^{9a}$ is H and $R^{12a}$ is H. In an exemplary embodiment, the compound has a subsitutent combination for $R^{9a}$, $R^{10a}$, $R^{11a}$, and $R^{12a}$ which is a member selected from those described in Formulae (I), (Ia) (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Iz), (Iaa), (Iab), (Iac), (Iad), (Iae), (Iaf), (Iag), (Iah), (Iai), (Iaj), (Iak), above, and/or the subsequent paragraphs describing Formulae (I), (Ia) (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Iz), (Iaa), (Iab), (Iac), (Iad), (Iae), (Iaf), (Iag), (Iah), (Iai), (Iaj), (Iak).

In an exemplary embodiment, the compound is an acyclic boronic acid or ester in which a portion of the acyclic boronic acid or ester is as in Figure (IXb) below

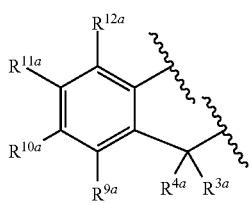
(IXb)

is a member selected from a structure in FIG. 12. In another exemplary embodiment, the compound is a dimer, anhydride or trimer of an acyclic boronic acid or ester described herein. In another exemplary embodiment, the compound is a dimer, anhydride or trimer of an acyclic boronic acid or ester in which a portion of the acyclic boronic acid or ester as in Figure (IXb) is a member selected a structure in FIG. 12.

In an exemplary embodiment, $R^1$ and $R^2$ are each members independently selected from H, substituted or unsubstituted methyl, substituted or unsubstituted ethyl, substituted or unsubstituted propyl, substituted or unsubstituted isopropyl, substituted or unsubstituted butyl, substituted or unsubstituted t-butyl, substituted or unsubstituted phenyl and substituted or unsubstituted benzyl. $R^1$ and $R^2$, together with the atoms to which they are joined, can optionally form a member selected from substituted or unsubstituted dioxaborolane, substituted or unsubstituted dioxaborinane, substituted or unsubstituted dioxaborepane.

In an exemplary embodiment, X is a member selected from triflate, chloro, bromo, iodo, substituted or unsubstituted sulfonic esters, substituted or unsubstituted acyloxy groups, and substituted or unsubstituted diazo. In an exemplary embodiment, X is a sulfonic ester group, which is a member selected from substituted or unsubstituted mesylate, substituted or unsubstituted tosylate, substituted or unsubstituted brosylate and substituted or unsubstituted nosylate. In an exemplary embodiment, X is an acyloxy group, which is a member selected from substituted or unsubstituted acetoxy and substituted or unsubstituted trifluoroacetoxy. In another exemplary embodiment, X is a member selected from bromo, iodo, mesylate and diazo. In another exemplary embodiment, X is a member selected from bromo and iodo.

In another exemplary embodiment, $R^1$ and $R^2$, together with the atoms to which they are joined, form a member selected from dioxaborolane, substituted or unsubstituted tetramethyldioxaborolane, substituted or unsubstituted phenyldioxaborolane, dioxaborinane, dimethyldioxaborinane and dioxaborepane.

In another exemplary embodiment, $R^{3a}$ and $R^{4a}$ are each members independently selected from H, methyl, ethyl, propyl, butyl, phenyl, benzyl, cyano, halogen and nitro.

In an exemplary embodiment, the compound is a member selected from

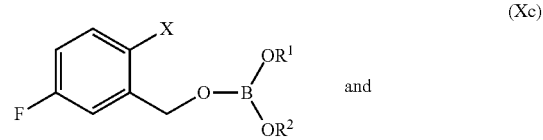
(Xc)

and

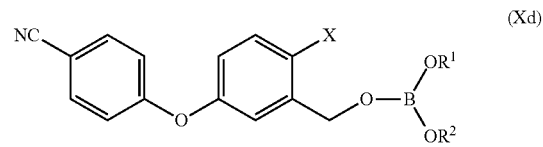
(Xd)

In an exemplary embodiment, the compound is a member selected from

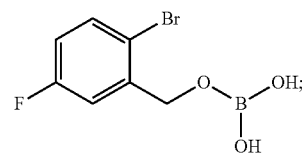

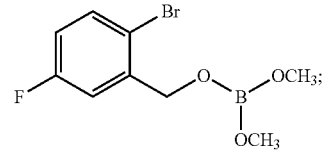

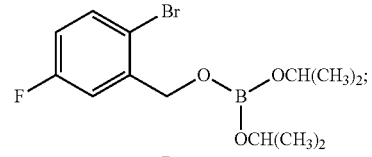

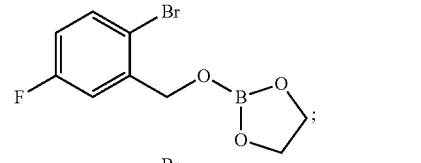

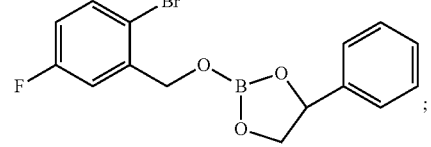

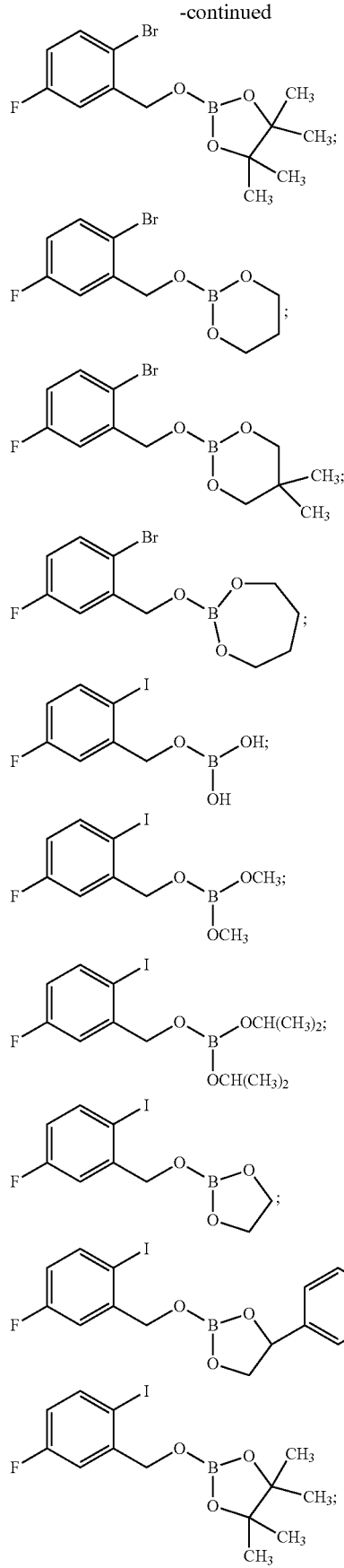
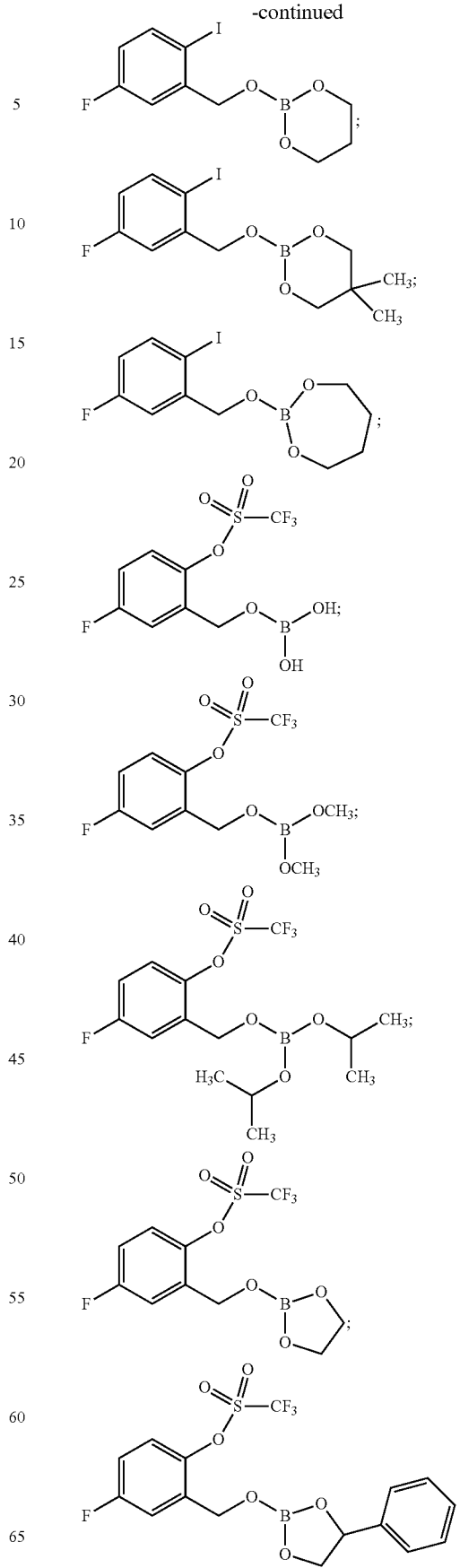

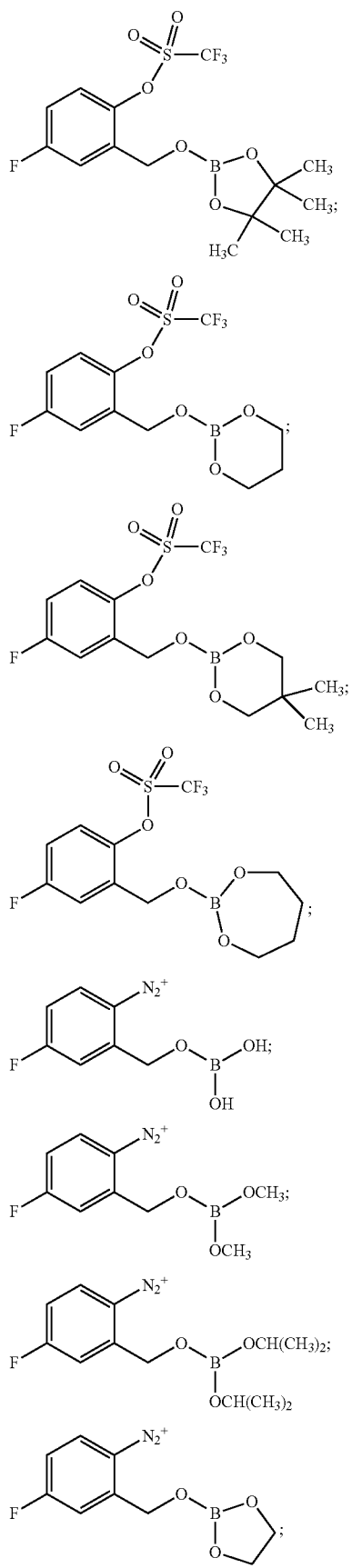
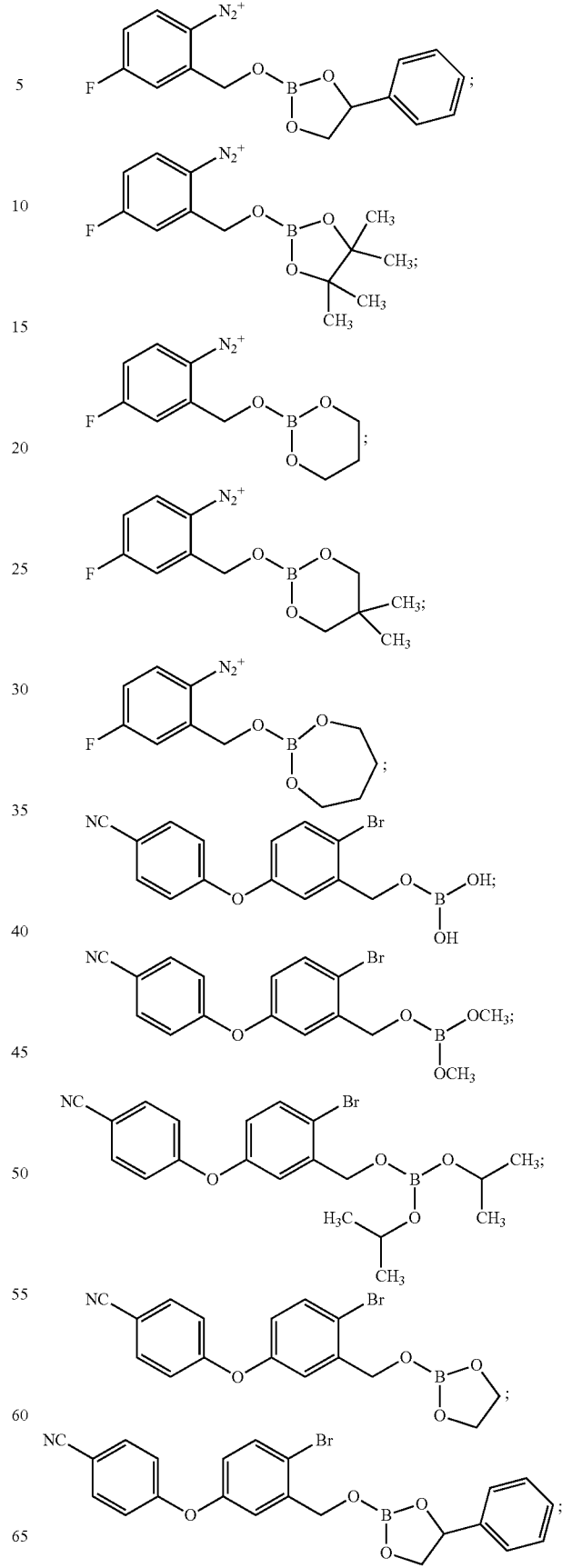

95
-continued
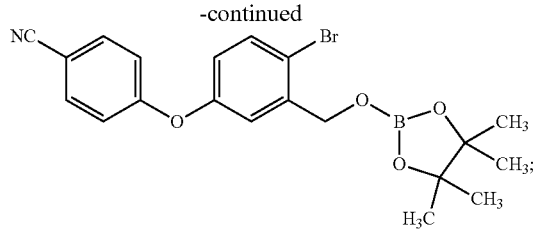
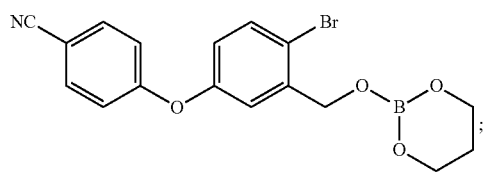
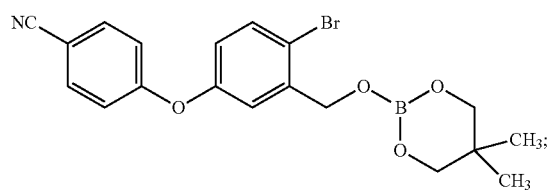
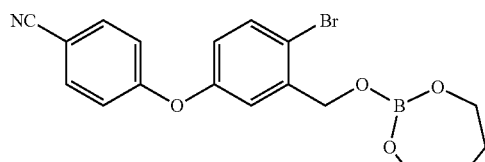
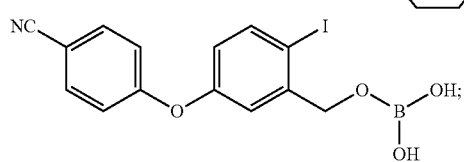
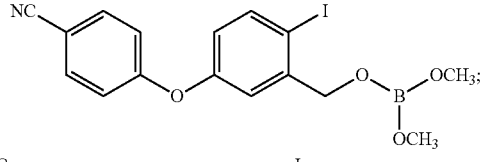
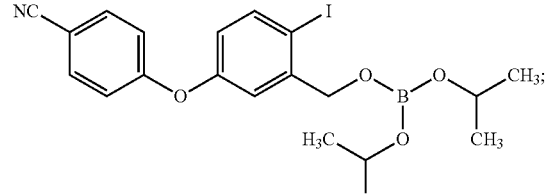
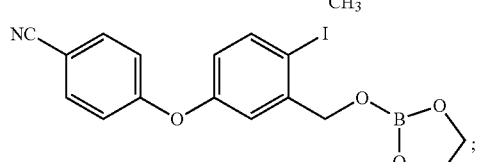
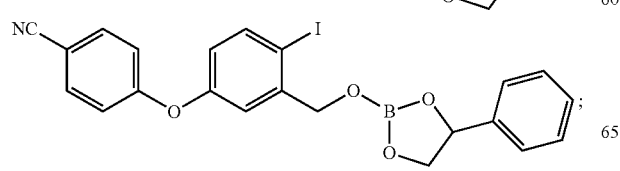
96
-continued
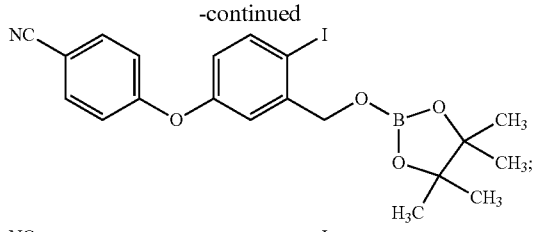
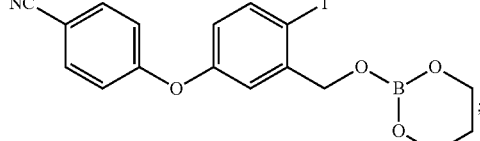
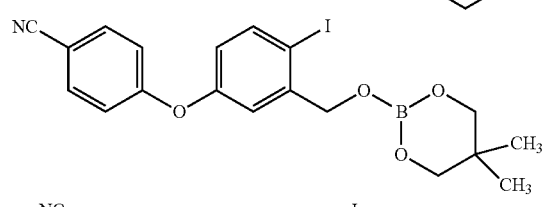
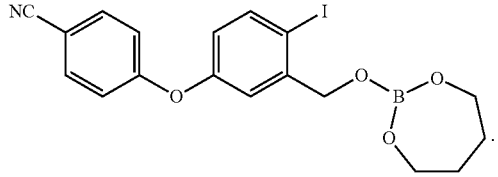
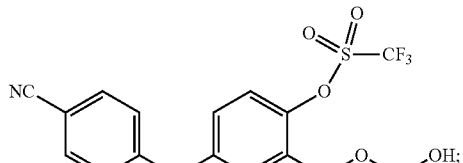
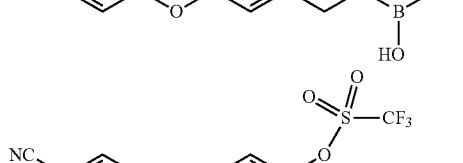
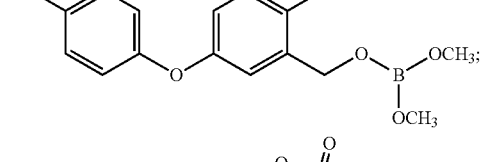
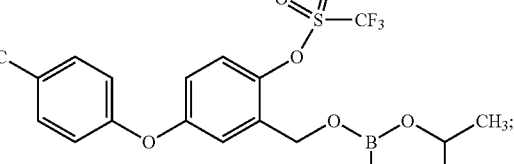
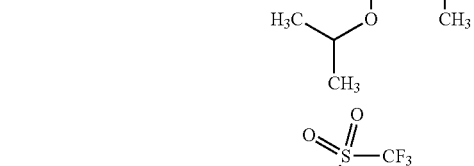
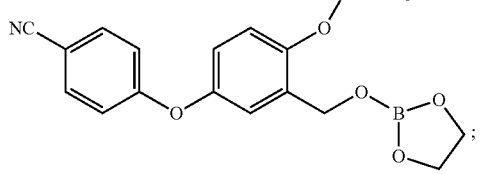

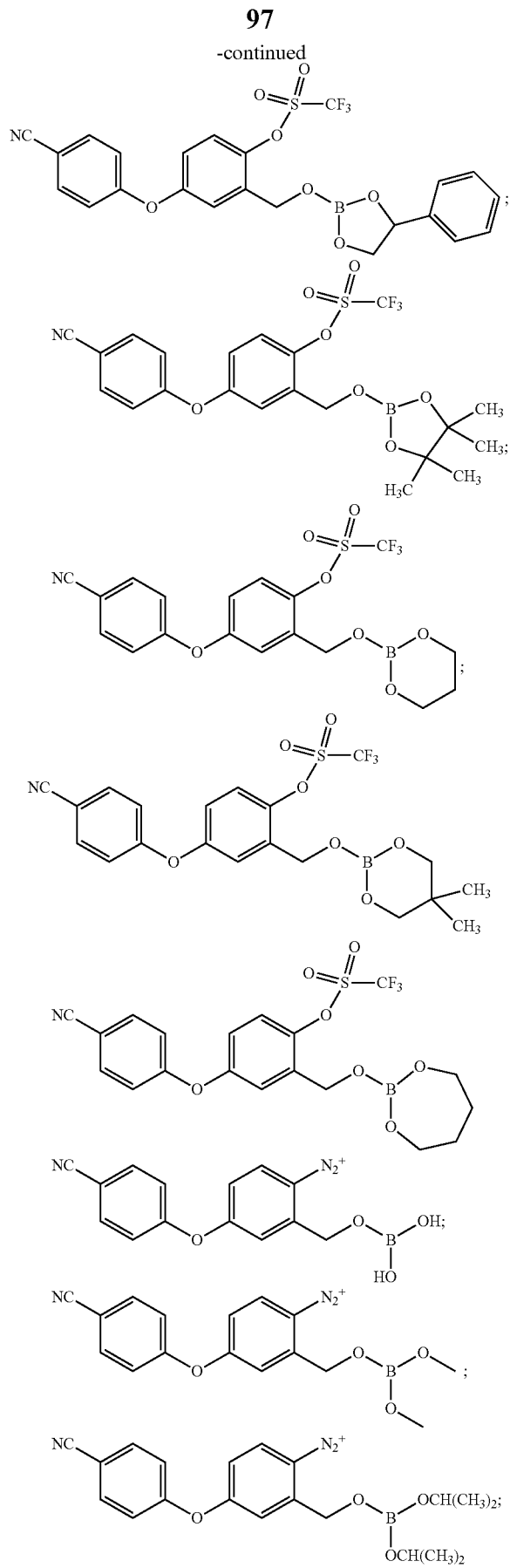

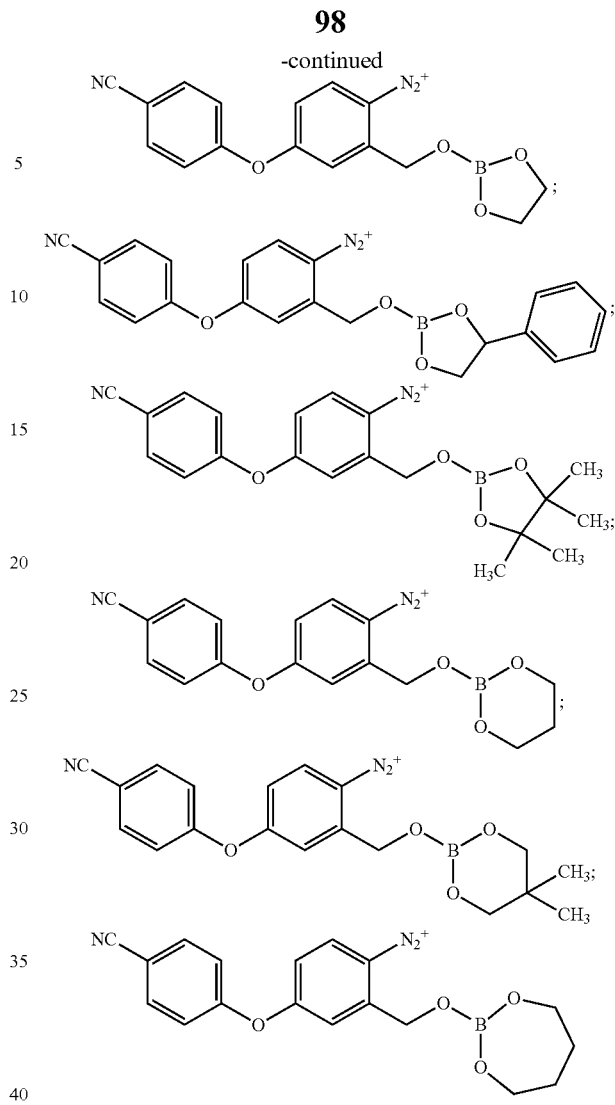

In an exemplary embodiment, acyclic boronic esters described herein can be used as intermediates in the synthesis of the compounds described herein. In another exemplary embodiment, the acyclic boronic esters described herein can be used as intermediates in the synthesis of a compound which is a member selected from Formulae (I), (Ia) (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Iz), (Iaa), (Iab), (Iac), (Iad), (Iae), (Iaf), (Iag), (Iah), (Iai), (Iaj), (Iak).

I. e.) Additional Compounds

Compounds such as those described herein can also be utilized in the invention. The compounds of the invention can form between the 2',3' diol of the ribose ring of a nucleic acid, nucleoside or nucleotide, and a cyclic or acyclic boronic ester such as those described herein. These compounds can be used in a human or in an animal to kill or inhibit the growth of the microorganisms described herein, as well as to treat the diseases described herein. These compounds can be formed in vitro as well as in vivo. Methods of making these compounds are provided in the Examples section.

In another aspect, the invention provides a compound having a structure according to the following formula:

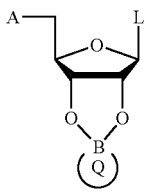

(XII)

wherein B is boron. L is a member selected from OR$^7$, substituted or unsubstituted purine, substituted or unsubstituted pyrimidine, substituted or unsubstituted pyridine and substituted or unsubstituted imidazole. R$^7$ is a member selected from H, substituted or unsubstituted alkyl, substituted or unsubstituted heteroalkyl, substituted or unsubstituted cycloalkyl, substituted or unsubstituted aryl and substituted or unsubstituted heteroaryl. A is a member selected from OH, substituted or unsubstituted monophosphate, substituted or unsubstituted diphosphate, substituted or unsubstituted triphosphate,

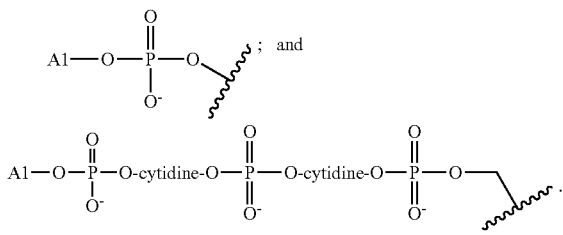

A1 is a nucleic acid sequence which comprises between 1 and 100 nucleotides. Q is a member selected from substituted or unsubstituted heterocycloalkyl and substituted or unsubstituted heteroaryl. Q comprises said boron and at least one oxygen.

In an exemplary embodiment, the aspect has the proviso that the compound cannot comprise a member selected from C1-C40.

In an exemplary embodiment, the aspect has a proviso that the compound cannot comprise a member which is described in FIG. 11. In an exemplary embodiment, the aspect has a proviso that the compound cannot involve a compound which is described in expired U.S. Pat. No. 5,880,188.

In an exemplary embodiment, the compound has a structure according to the following formula (XIIa):

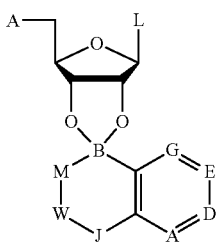

(XIIa)

wherein M is a member selected from O and S. J is a member selected from (CR$^{3a}$R$^{4a}$)$_{n1}$ and CR$^{5a}$. R$^{3a}$, R$^{4a}$, and R$^{5a}$ are members independently selected from H, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. n1 is an integer selected from 0 to 2. W is a member selected from C=O (carbonyl), (CR$^{6a}$R$^{7a}$)$_m$ and CR$^{8a}$. R$^{6a}$, R$^{7a}$, and R$^{8a}$ are members independently selected from H, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The index m1 is an integer selected from 0 and 1. A is a member selected from CR$^{9a}$ and N. D is a member selected from CR$^{10a}$ and N. E is a member selected from CR$^{11a}$ and N. G is a member selected from CR$^{12a}$ and N. R$^{9a}$, R$^{10a}$, R$^{11a}$ and R$^{12a}$ are members independently selected from H, OR*, NR*R**, SR*, —S(O)R*, —S(O)$_2$R*, —S(O)$_2$NR*R**, —C(O)R*, —C(O)OR*, —C(O)NR*R**, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. Each R* and R** are members independently selected from H, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The combination of nitrogens (A+D+E+G) is an integer selected from 0 to 3. A member selected from R$^{3a}$, R$^{4a}$ and R$^{5a}$ and a member selected from R$^{6a}$, R$^{7a}$ and R$^{8a}$, together with the atoms to which they are attached, are optionally joined to form a 4 to 7 membered ring. R$^{3a}$ and R$^{4a}$, together with the atoms to which they are attached, are optionally joined to form a 4 to 7 membered ring. R$^{6a}$ and R$^{7a}$, together with the atoms to which they are attached, are optionally joined to form a 4 to 7 membered ring. R$^{9a}$ and R$^{10a}$, together with the atoms to which they are attached, are optionally joined to form a 4 to 7 membered ring. R$^{10a}$ and R$^{11a}$, together with the atoms to which they are attached, are optionally joined to form a 4 to 7 membered ring. R$^{11a}$ and R$^{12a}$, together with the atoms to which they are attached, are optionally joined to form a 4 to 7 membered ring.

In another exemplary embodiment, each R$^{3a}$ and R$^{4a}$ is a member independently selected from H, cyano, substituted or unsubstituted methyl, substituted or unsubstituted ethyl, trifluoromethyl, substituted or unsubstituted hydroxymethyl, substituted or unsubstituted hydroxyalkyl, substituted or unsubstituted benzyl, substituted or unsubstituted phenyl, substituted or unsubstituted mercaptomethyl, substituted or unsubstituted mercaptoalkyl, substituted or unsubstituted aminomethyl, substituted or unsubstituted alkylaminomethyl, substituted or unsubstituted dialkylaminomethyl, substituted or unsubstituted arylaminomethyl, substituted or unsubstituted indolyl and substituted or unsubstituted amido. In another exemplary embodiment, each R$^{3a}$ and R$^{4a}$ is a member independently selected from cyano, substituted or unsubstituted methyl, substituted or unsubstituted ethyl, trifluoromethyl, substituted or unsubstituted hydroxymethyl, substituted or unsubstituted hydroxyalkyl, substituted or unsubstituted benzyl, substituted or unsubstituted phenyl, substituted or unsubstituted mercaptomethyl, substituted or unsubstituted mercaptoalkyl, substituted or unsubstituted aminomethyl, substituted or unsubstituted alkylaminomethyl, substituted or unsubstituted dialkylaminomethyl, substituted or unsubstituted arylaminomethyl, substituted or unsubstituted indolyl, substituted or unsubstituted amido.

In another exemplary embodiment, each $R^{3a}$ and $R^{4a}$ is a member selected from H, substituted or unsubstituted methyl, substituted or unsubstituted ethyl, substituted or unsubstituted propyl, substituted or unsubstituted isopropyl, substituted or unsubstituted butyl, substituted or unsubstituted t-butyl, substituted or unsubstituted phenyl and substituted or unsubstituted benzyl. In another exemplary embodiment, $R^{3a}$ and $R^{4a}$ is a member selected from methyl, ethyl, propyl, isopropyl, butyl, t-butyl, phenyl and benzyl. In another exemplary embodiment, $R^{3a}$ is H and $R^{4a}$ is a member selected from methyl, ethyl, propyl, isopropyl, butyl, t-butyl, phenyl and benzyl. In another exemplary embodiment, $R^{3a}$ is H and $R^{4a}$ H.

In another exemplary embodiment, each $R^{9a}$, $R^{10a}$, $R^{11a}$ and $R^{12a}$ is a member independently selected from H, OR*, NR*R**, SR*, —S(O)R*, —S(O)$_2$R*, —S(O)$_2$NR*R**, —C(O)R*, —C(O)OR*, —C(O)NR*R**, halogen, cyano, nitro, substituted or unsubstituted methoxy, substituted or unsubstituted methyl, substituted or unsubstituted ethoxy, substituted or unsubstituted ethyl, trifluoromethyl, substituted or unsubstituted hydroxymethyl, substituted or unsubstituted hydroxyalkyl, substituted or unsubstituted benzyl, substituted or unsubstituted phenyl, substituted or unsubstituted phenyloxy, substituted or unsubstituted phenyl methoxy, substituted or unsubstituted thiophenyloxy, substituted or unsubstituted pyridinyloxy, substituted or unsubstituted pyrimidinyloxy, substituted or unsubstituted benzylfuran, substituted or unsubstituted methylthio, substituted or unsubstituted mercaptomethyl, substituted or unsubstituted mercaptoalkyl, substituted or unsubstituted phenylthio, substituted or unsubstituted thiophenylthio, substituted or unsubstituted phenyl methylthio, substituted or unsubstituted pyridinylthio, substituted or unsubstituted pyrimidinylthio, substituted or unsubstituted benzylthiofuranyl, substituted or unsubstituted phenylsulfonyl, substituted or unsubstituted benzylsulfonyl, substituted or unsubstituted phenylmethylsulfonyl, substituted or unsubstituted thiophenylsulfonyl, substituted or unsubstituted pyridinylsulfonyl, substituted or unsubstituted pyrimidinylsulfonyl, substituted or unsubstituted sulfonamidyl, substituted or unsubstituted phenylsulfinyl, substituted or unsubstituted benzylsulfinyl, substituted or unsubstituted phenylmethylsulfinyl, substituted or unsubstituted thiophenylsulfinyl, substituted or unsubstituted pyridinylsulfinyl, substituted or unsubstituted pyrimidinylsulfinyl, substituted or unsubstituted amino, substituted or unsubstituted alkylamino, substituted or unsubstituted dialkylamino, substituted or unsubstituted trifluoromethylamino, substituted or unsubstituted aminomethyl, substituted or unsubstituted alkylaminomethyl, substituted or unsubstituted dialkylaminomethyl, substituted or unsubstituted arylaminomethyl, substituted or unsubstituted benzylamino, substituted or unsubstituted phenylamino, substituted or unsubstituted thiophenylamino, substituted or unsubstituted pyridinylamino, substituted or unsubstituted pyrimidinylamino, substituted or unsubstituted indolyl, substituted or unsubstituted morpholino, substituted or unsubstituted alkylamido, substituted or unsubstituted arylamido, substituted or unsubstituted ureido, substituted or unsubstituted carbamoyl, and substituted or unsubstituted piperizinyl. In an exemplary embodiment, $R^{9a}$, $R^{10a}$, $R^{11a}$ and $R^{12a}$ are selected from the previous list of substituents with the exception of —C(O)R*, —C(O)OR*, —C(O)NR*R**.

In another exemplary embodiment, $R^{9a}$, $R^{10a}$, $R^{11a}$ and $R^{12a}$ are members independently selected from fluoro, chloro, bromo, nitro, cyano, amino, methyl, hydroxylmethyl, trifluoromethyl, methoxy, trifluoromethyoxy, ethyl, diethylcarbamoyl, pyridin-2-yl, pyridin-3-yl, pyridin-4-yl, pyrimidinyl, piperizino, piperizinyl, piperizinocarbonyl, piperizinylcarbonyl, carboxyl, 1-tetrazolyl, 1-ethoxycarbonylmethoxy, carboxymethoxy, thiophenyl, 3-(butylcarbonyl) phenylmethoxy, 1H-tetrazol-5-yl, 1-ethoxycarbonylmethyloxy-, 1-ethoxycarbonylmethyl-, 1-ethoxycarbonyl-, carboxymethoxy-, thiophen-2-yl, thiophen-2-ylthio-, thiophen-3-yl, thiophen-3-ylthio, 4-fluorophenylthio, butylcarbonylphenylmethoxy, butylcarbonylphenylmethyl, butylcarbonylmethyl, 1-(piperidin-1-yl)carbonyl)methyl, 1-(piperidin-1-yl)carbonyl)methoxy, 1-(piperidin-2-yl)carbonyl)methoxy, 1-(piperidin-3-yl)carbonyl)methoxy, 1-(4-(pyrimidin-2-yl)piperazin-1-yl)carbonyl)methoxy, 1-(4-(pyrimidin-2-yl)piperazin-1-yl)carbonyl)methyl, 1-(4-(pyrimidin-2-yl)piperazin-1-yl)carbonyl, 1-4-(pyrimidin-2-yl)piperazin-1-yl, 1-(4-(pyridin-2-yl)piperazin-1-yl) carbonyl), 1-(4-(pyridin-2-yl)piperazin-1-yl) carbonylmethyl, (1-(4-(pyridin-2-yl)piperazin-1-yl) carbonyl)-methoxy), 1-(4-(pyridin-2-yl)piperazin-1-yl, 1H-indol-1-yl, morpholino-, morpholinyl, morpholinocarbonyl, morpholinylcarbonyl, phenylureido, phenylcarbamoyl, acetamido, 3-(phenylthio)-1H-indol-1-yl, 3-(2-cyanoethylthio)-1H-indol-1-yl, benzylamino, 5-methoxy-3-(phenylthio)-1H-indol-1-yl, 5-methoxy-3-(2-cyanoethylthio)-1H-indol-1-yl)), 5-chloro-1H-indol-1-yl, 5-chloro-3-(2-cyanoethylthio)-1H-indol-1-yl)), dibenzylamino, benzylamino, 5-chloro-3-(phenylthio)-1H-indol-1-yl)), 4-(1H-tetrazol-5-yl)phenoxy, 4-(1H-tetrazol-5-yl)phenyl, 4-(1H-tetrazol-5-yl)phenylthio, 2-cyanophenoxy, 3-cyanophenoxy, 4-cyanophenoxy, 2-cyanophenylthio, 3-cyanophenylthio, 4-cyanophenylthio, 2-chlorophenoxy, 3-chlorophenoxy, 4-chlorophenoxy, 2-fluorophenoxy, 3-fluorophenoxy, 4-fluorophenoxy, 2-cyanobenzyloxy, 3-cyanobenzyloxy, 4-cyanobenzyloxy, 2-chlorobenzyloxy, 3-chlorobenzyloxy, 4-chlorobenzyloxy, 2-fluorobenzyloxy, 3-fluorobenzyloxy, 4-fluorobenzyloxy, unsubstituted phenyl, unsubstituted benzyl.

In an exemplary embodiment, the compound has a structure according to the following formula:

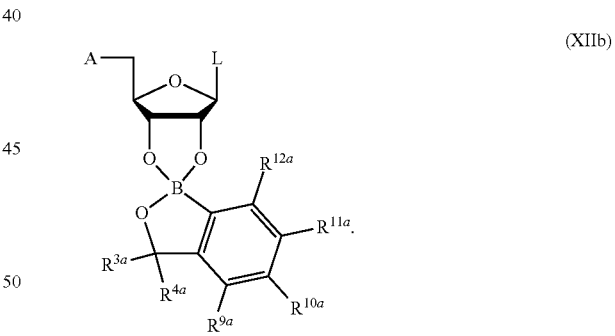

(XIIb)

In another exemplary embodiment, $R^{9a}$, $R^{10a}$, $R^{11a}$ and $R^{12a}$ are members independently selected from H, halogen, cyano, nitro, substituted or unsubstituted methoxy, substituted or unsubstituted methyl, substituted or unsubstituted ethoxy, substituted or unsubstituted ethyl, trifluoromethyl, substituted or unsubstituted hydroxymethyl, substituted or unsubstituted hydroxyalkyl, substituted or unsubstituted benzyl, substituted or unsubstituted phenyl, substituted or unsubstituted phenyloxy, substituted or unsubstituted phenyl methoxy, substituted or unsubstituted thiophenyloxy, substituted or unsubstituted pyridinyloxy, substituted or unsubstituted pyrimidinyloxy, substituted or unsubstituted benzylfuran, substituted or unsubstituted methylthio, substituted or unsubstituted mercaptomethyl, substituted or unsubstituted mercaptoalkyl, substituted or unsubstituted phenylthio, substituted or unsubstituted thiophenylthio, substituted or unsubstituted phenyl methylthio, substituted or unsubstituted pyridinylthio, substituted or unsubstituted pyrimidinylthio, substituted or unsubstituted benzylthiofuranyl, substituted or unsubstituted phenylsulfonyl, substituted or unsubstituted benzylsulfonyl, substituted or unsubstituted phenylmethylsulfonyl, substituted or unsubstituted thiophenylsulfonyl, substituted or unsubstituted pyridinylsulfonyl, substituted or unsubstituted pyrimidinylsulfonyl, substituted or unsubstituted sulfonamidyl, substituted or unsubstituted phenylsulfinyl, substituted or unsubstituted benzylsulfinyl, substituted or unsubstituted phenylmethylsulfinyl, substituted or unsubstituted thiophenylsulfinyl, substituted or unsubstituted pyridinylsulfinyl, substituted or unsubstituted pyrimidinylsulfinyl, substituted or unsubstituted amino, substituted or unsubstituted alkylamino, substituted or unsubstituted dialkylamino, substituted or unsubstituted trifluoromethylamino, substituted or unsubstituted aminomethyl, substituted or unsubstituted alkylaminomethyl, substituted or unsubstituted dialkylaminomethyl, substituted or unsubstituted arylaminomethyl, substituted or unsubstituted benzylamino, substituted or unsubstituted phenylamino, substituted or unsubstituted thiophenylamino, substituted or unsubstituted pyridinylamino, substituted or unsubstituted pyrimidinylamino, substituted or unsubstituted indolyl, substituted or unsubstituted morpholino, substituted or unsubstituted alkylamido, substituted or unsubstituted arylamido, substituted or unsubstituted ureido, substituted or unsubstituted carbamoyl, and substituted or unsubstituted piperizinyl.

In another exemplary embodiment, $R^{9a}$, $R^{10a}$, $R^{11a}$ and $R^{12a}$ are members independently selected from H, fluoro, chloro, bromo, nitro, cyano, amino, methyl, hydroxylmethyl, trifluoromethyl, methoxy, trifluoromethyoxy, ethyl, diethylcarbamoyl, pyridin-2-yl, pyridin-3-yl, pyridin-4-yl, pyrimidinyl, piperizino, piperizinyl, piperizinocarbonyl, piperizinylcarbonyl, carboxyl, 1-tetrazolyl, 1-ethoxycarbonylmethoxy, carboxymethoxy, thiophenyl, 3-(butylcarbonyl) phenylmethoxy, 1H-tetrazol-5-yl, 1-ethoxycarbonylmethyloxy-, 1-ethoxycarbonylmethyl-, 1-ethoxycarbonyl-, carboxymethoxy-, thiophen-2-yl, thiophen-2-ylthio-, thiophen-3-yl, thiophen-3-ylthio, 4-fluorophenylthio, butylcarbonylphenylmethoxy, butylcarbonylphenylmethyl, butylcarbonylmethyl, 1-(piperidin-1-yl)carbonyl)methyl, 1-(piperidin-1-yl)carbonyl)methoxy, 1-(piperidin-2-yl)carbonyl)methoxy, 1-(piperidin-3-yl)carbonyl)methoxy, 1-(4-(pyrimidin-2-yl)piperazin-1-yl)carbonyl)methoxy, 1-(4-(pyrimidin-2-yl)piperazin-1-yl)carbonyl)methyl, 1-(4-(pyrimidin-2-yl)piperazin-1-yl)carbonyl, 1-4-(pyrimidin-2-yl)piperazin-1-yl, 1-(4-(pyridin-2-yl)piperazin-1-yl) carbonyl), 1-(4-(pyridin-2-yl)piperazin-1-yl) carbonylmethyl, (1-(4-(pyridin-2-yl)piperazin-1-yl) carbonyl)-methoxy), 1-(4-(pyridin-2-yl)piperazin-1-yl, 1H-indol-1-yl, morpholino-, morpholinyl, morpholinocarbonyl, morpholinylcarbonyl, phenylureido, phenylcarbamoyl, acetamido, 3-(phenylthio)-1H-indol-1-yl, 3-(2-cyanoethylthio)-1H-indol-1-yl, benzylamino, 5-methoxy-3-(phenylthio)-1H-indol-1-yl, 5-methoxy-3-(2-cyanoethylthio)-1H-indol-1-yl)), 5-chloro-1H-indol-1-yl, 5-chloro-3-(2-cyanoethylthio)-1H-indol-1-yl)), dibenzylamino, benzylamino, 5-chloro-3-(phenylthio)-1H-indol-1-yl)), 4-(1H-tetrazol-5-yl)phenoxy, 4-(1H-tetrazol-5-yl)phenyl, 4-(1H-tetrazol-5-yl)phenylthio, 2-cyanophenoxy, 3-cyanophenoxy, 4-cyanophenoxy, 2-cyanophenylthio, 3-cyanophenylthio, 4-cyanophenylthio, 2-chlorophenoxy, 3-chlorophenoxy, 4-chlorophenoxy, 2-fluorophenoxy, 3-fluorophenoxy, 4-fluorophenoxy, 2-cyanobenzyloxy, 3-cyanobenzyloxy, 4-cyanobenzyloxy, 2-chlorobenzyloxy, 3-chlorobenzyloxy, 4-chlorobenzyloxy, 2-fluorobenzyloxy, 3-fluorobenzyloxy, and 4-fluorobenzyloxy. In an exemplary embodiment, $R^{9a}$ is H and $R^{12a}$ is H. In an exemplary embodiment, the compound has a subsitutent combination for $R^{9a}$, $R^{10a}$, $R^{11a}$, and $R^{12a}$ which is a member selected from those described in Formulae (I), (Ia) (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Iz), (Iaa), (Iab), (Iac), (Iad), (Iae), (Iaf), (Iag), (Iah), (Iai), (Iaj), (Iak) above, and/or the subsequent paragraphs describing Formulae (I), (Ia) (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Iz), (Iaa), (Iab), (Iac), (Iad), (Iae), (Iaf), (Iag), (Iah), (Iai), (Iaj), (Iak).

In an exemplary embodiment, the portion of the cyclic boronic ester as in the figure below

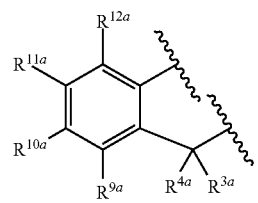

is a member selected from a structure in FIG. 12.

In an exemplary embodiment, the compound has a structure according to the following formula:

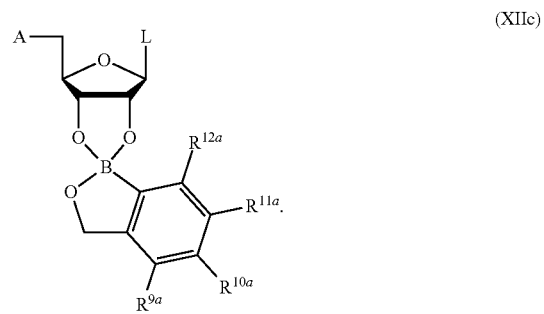

(XIIc)

In an exemplary embodiment, the compound has a structure according to the following formula:

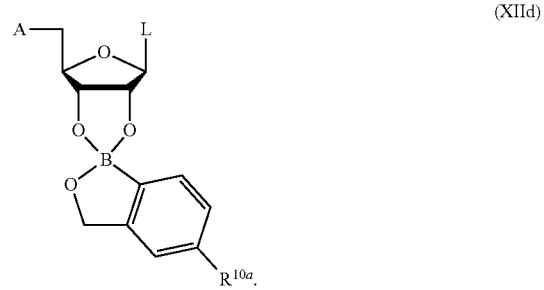

(XIId)

In an exemplary embodiment, the compound has a structure according to the following formula:

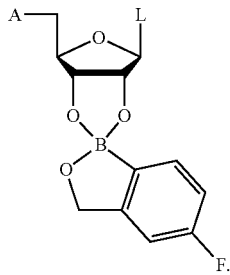

In another exemplary embodiment, the compound has a structure which is a member selected from Formulae (XII), (XIIa), (XIIb), (XIIc), (XIId) and (XIIe) wherein L is a member selected from substituted or unsubstituted adenine, substituted or unsubstituted guanine, substituted or unsubstituted cytidine, substituted or unsubstituted uracil, and substituted or unsubstituted thymine. In another exemplary embodiment, L is OH. In another exemplary embodiment, L is adenine.

In another exemplary embodiment, the compound has a structure which is a member selected from

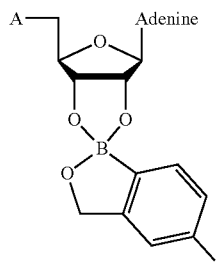 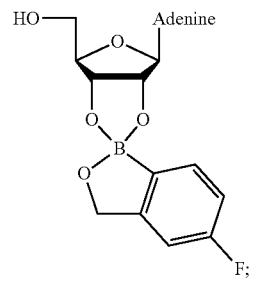

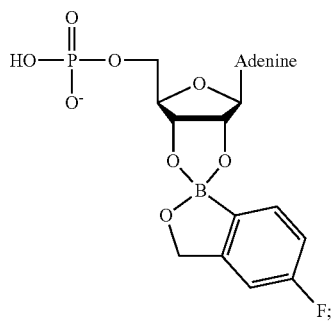 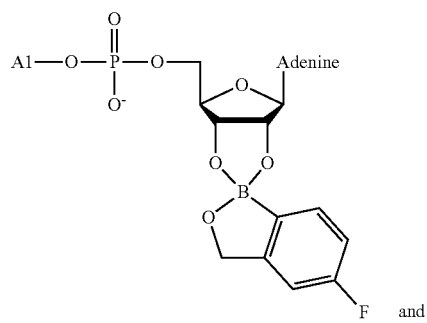 and

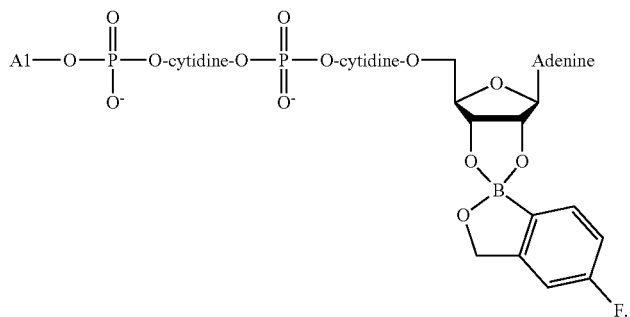

In another exemplary embodiment, A1 is a nucleic acid sequence between 72 and 90 nucleotides. In another exemplary embodiment, A1 is a nucleic acid sequence between 35 and 150 nucleotides. In another exemplary embodiment, A1 is a nucleic acid sequence between 50 and 100 nucleotides. In another exemplary embodiment, A1 is a nucleic acid sequence between 75 and 85 nucleotides. In another exemplary embodiment, A1 is a nucleic acid sequence which is a tRNA or a portion of a tRNA. In another exemplary embodiment, said tRNA or the portion of said tRNA is a member selected from alanyl tRNA, isoleucyl tRNA, leucyl tRNA, methionyl tRNA, lysyl tRNA, phenylalanyl tRNA, prolyl tRNA, threonyl tRNA and valyl tRNA. In another exemplary embodiment, said tRNA or the portion of said tRNA is leucyl tRNA. In another exemplary embodiment, said tRNA or the portion of said tRNA has a sequence which is a member selected from SEQ ID NOS: 18-62. In another exemplary embodiment, A1 is a nucleic acid sequence wherein two final nucleotides are each cytidine.

In another exemplary embodiment, the compound further comprises a tRNA synthetase or a portion of a tRNA synthetase which comprises the editing domain, wherein said compound is noncovalently attached to the editing domain of said tRNA synthetase. In another exemplary embodiment, the tRNA synthetase is a member selected from a mitochondrial tRNA synthetase and a cytoplasmic tRNA synthetase. In another exemplary embodiment, the tRNA synthetase is a member selected from alanyl tRNA synthetase, isoleucyl tRNA synthetase, leucyl tRNA synthetase, methionyl tRNA synthetase, lysyl tRNA synthetase, phenylalanyl tRNA synthetase, prolyl tRNA synthetase, threonyl tRNA synthetase and valyl tRNA synthetase.

In an exemplary embodiment, the compound described herein is present in a microorganism described in this application.

In another exemplary embodiment, there is a proviso that the compound is not present in a microorganism that is a member selected from *Saccharomyces cerevisiae, Aspergillus niger, Pseudomonas aeruginosa, Staphylococcus aureus, Aureobasidium pullulans, Fusarium solani, Penicillium pinophilum, Scopulariopsis brevicaulis, Streptoverticillium waksmanii, Alternaria alternata, Cladosporium herbarum, Phoma violacea, Stemphylium dentriticum, Candida albicans, Escherichia coli,* and *Glioclasium roseum*. In another exemplary embodiment, there is a proviso that when the compound is present in a fungus, the fungus is not a member selected from *Saccharomyces cerevisiae, Aspergillus niger, Fusarium solani, Penicillium pinophilum, Scopulariopsis brevicaulis, Streptoverticillium waksmanii, Alternaria alternata, Cladosporium herbarum, Phoma violacea, Stemphylium dentriticum, Candida albicans,* and *Glioclasium roseum*.

In an exemplary embodiment, the compound is present in a microorganism which is a member selected from a dermatophyte, *Trichophyton, Microsporum, Epidermophyton* and yeast-like fungi. In an exemplary embodiment, there is a proviso that when the compound is present in a yeast-like fungus, that yeast-like fungus is not a member selected from *Aspergillus niger* and *Candida albicans*. In another exemplary embodiment, the microorganism is a member selected from a dermatophyte, *Trichophyton, Microsporum, Epidermophyton* and yeast-like fungi. In an exemplary embodiment, the microorganism is a dermatophyte. In another exemplary embodiment, the microorganism is a member selected from *Trichophyton* species. In an exemplary embodiment, the microorganism is a member selected from is a member selected from *T. rubrum* and *T. menagrophytes*.

In an exemplary embodiment, the microorganism is a dermatophyte and said dermatophyte is a member selected from *T. rubrum* and *T. menagrophytes*.

In another exemplary embodiment, the compound is present in a human or an animal. In another exemplary embodiment, the compound is present in a microorganism which is in, or on the surface of, a human or an animal. In another exemplary embodiment, the compound is present in a microorganism which is present in a human nail unit of a human or a nail, hoof, or horn component of an animal. In another exemplary embodiment, the compound is present in a microoganism which is present in a member selected from a human nail plate, human nail bed, proximal nail fold, lateral nail fold and combinations thereof. In another exemplary embodiment, the compound is present in a microoganism which is present in a member selected from a human nail plate and a human nail bed. In another exemplary embodiment, the compound is present in a microoganism which is present in a member selected from a proximal nail fold and a lateral nail fold. In another exemplary embodiment, the microorganism is a member selected from dermatophyte, *Trichophyton, Microsporum, Epidermophyton* and yeast-like fungi. In another exemplary embodiment, wherein said compound is a dermatophyte. In another exemplary embodiment, the dermatophyte is a member selected from *T. rubrum* and *T. menagrophytes*.

I. f) Formulations with Keratin

When a compound of the invention described herein is applied to a nail component of a human, the compound absorbs or penetrates into the nail. The human nail is primarily composed of keratin (i.e. hair keratin or α-keratin) as well as trace amounts of lipid components. Therefore, in the process of treating a disease of the nail or killing or inhibiting the growth of a microorganism, a formulation comprising a human nail unit and a compound of the invention is formed.

In another aspect, the invention provides a formulation comprising: (a) a compound which is a member selected from a boron-containing compound, a 2'-amino ribofuranose-containing compound, a 3'-amino ribofuranose-containing compound, and combinations thereof; and (b) a keratin containing component which is a member selected from a human nail unit, skin and hair. In an exemplary embodiment, the compound of part (a) contacts the component of part (b). In an exemplary embodiment, the keratin containing component is a nail plate of the human nail unit. In an exemplary embodiment, the keratin containing component is a nail bed of the human nail unit. In an exemplary embodiment, the keratin containing component is a proximal nail fold of the human nail unit. In an exemplary embodiment, the keratin containing component is a lateral nail fold of the human nail unit. In another exemplary embodiment, the human nail unit comprises a member selected from keratin and lipid. In another exemplary embodiment, keratin is a member selected from skin keratin and nail/hair keratin. In another exemplary embodiment, lipid is a member selected from cholesterol sulfate, cerebroside, ceramide, free sterol, free fatty acids, triglycerides, sterol esters, wax esters, and squalene.

In an exemplary embodiment, the compound is present in the formulation at a concentration which is a member selected from about 0.001%, about 0.01%, about 0.05%, about 0.1%, about 0.5%, about 1%, about 1.5%, about 2%, about 2.5%, about 3%. In another exemplary embodiment, the keratin is present in said formulation at a concentration which is a member selected from about 99.99%, about 99.95%, about 99.90%, about 99.5%, about 99.0%, about 98.5%, about 98.0%, about 97.5% and about 97%. In another exemplary embodiment, the compound is a compound described herein. In another exemplary embodiment, the compound is as described in Formulae (I), (Ia) (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Iz), (Iaa), (Iab), (Iac), (Iad), (Iae), (Iaf), (Iag), (Iah), (Iai), (Iaj), (Iak), (Il), (IIa), (IIb), (IIc), (IId), and (III). In another exemplary embodiment, the compound is an acyclic boronic ester as described herein. In another exemplary embodiment, the compound is a member selected from C1-C96 described herein. In another exemplary embodiment, the compound is a member selected from a compound appearing in FIG. 19. In another exemplary embodiment, the compound is a member selected from a compound appearing in FIG. 20. In another exemplary embodiment, the compound is 1,3-dihydro-5-fluoro-1-hydroxy-2,1-benzoxaborole. In another exemplary embodiment, 1,3-dihydro-5-fluoro-1-hydroxy-2,1-benzoxaborole is present is said formulation at a concentration which is a member selected from about 0.001%, about 0.01%, about 0.05%, about 0.1%, about 0.5%, about 1%, and about 1.5%.

In another aspect, the invention provides a method of forming this formulation, wherein said method comprises applying said compound to a formulation comprising keratin, thereby forming said formulation. In an exemplary embodiment, the formulation comprising keratin is a human nail unit. In an exemplary embodiment, the formulation comprising keratin is a member selected from a nail plate, nail bed, proximal nail fold, and lateral nail fold. Methods of making these formulations are described in the Examples section.

I. g.) Preparation of Boron-Containing Editing Domain Inhibitors

Compounds of use in the present invention can be prepared using commercially available starting materials, known intermediates, or by using the synthetic methods published in references described and incorporated by reference herein.

I. h.) Boronic Esters

The following exemplary schemes illustrate methods of preparing boron-containing molecules of the present invention. These methods are not limited to producing the compounds shown, but can be used to prepare a variety of molecules such as the compounds and complexes described herein. The compounds of the present invention can also be synthesized by methods not explicitly illustrated in the schemes but are well within the skill of one in the art. The compounds can be prepared using readily available materials of known intermediates.

In the following schemes, the symbol X represents bromo or iodo. The symbol Y is selected from H, lower alkyl, and arylalkyl. The symbol Z is selected from H, alkyl, and aryl. The symbol PG represents protecting group. The symbols A, D, E, G, $R^x$, $R^y$, $R^z$, $R^{1a}$, $R^{2a}$, $R^{3a}$, $R^{4a}$, $R^{5a}$, $R^{6a}$, $R^{7a}$, $R^{8a}$, $R^{9a}$, $R^{10a}$, $R^{11a}$, and $R^{12a}$ can be used to refer to the corresponding symbols in the compounds described herein.

Boronic Acid Preparation Strategy #1

In Scheme 1, Step 1 and 2, compounds 1 or 2 are converted into alcohol 3. In step 1, compound 1 is treated with a reducing agent in an appropriate solvent. Suitable reducing agents include borane complexes, such as borane-tetrahydrofuran, borane-dimethylsulfide, combinations thereof and the like. Lithium aluminum hydride, or sodium borohydride can also be used as reducing agents. The reducing agents can be used in quantities ranging from 0.5 to 5 equivalents, relative to compound 1 or 2. Suitable solvents include diethyl ether, tetrahydrofuran, 1,4-dioxane, 1,2-dimethoxyethane, combinations thereof and the like. Reaction temperatures range from 0° C. to the boiling point of the solvent used; reaction completion times range from 1 to 24 h.

In Step 2, the carbonyl group of compound 2 is treated with a reducing agent in an appropriate solvent. Suitable reducing agents include borane complexes, such as borane-tetrahydrofuran, borane-dimethylsulfide, combinations thereof and the like. Lithium aluminum hydride, or sodium borohydride can also be used as reducing agents. The reducing agents can be used in quantities ranging from 0.5 to 5 equivalents, relative to compound 2. Suitable solvents include lower alcohol, such as methanol, ethanol, and propanol, diethyl ether, tetrahydrofuran, 1,4-dioxane and 1,2-dimethoxyethane, combinations thereof and the like. Reaction temperatures range from 0° C. to the boiling point of the solvent used; reaction completion times range from 1 to 24 h.

In Step 3, the hydroxyl group of compound 3 is protected with a protecting group which is stable under neutral or basic conditions. The protecting group is typically selected from methoxymethyl, ethoxyethyl, tetrahydropyran-2-yl, trimethylsilyl, tert-butyldimethylsilyl, tributylsilyl, combinations thereof and the like. In the case of methoxymethyl, compound 3 is treated with 1 to 3 equivalents of chloromethyl methyl ether in the presence of a base. Suitable bases include sodium hydride, potassium tert-butoxide, tertiary amines, such as diisopropylethylamine, triethylamine, 1,8-diazabicyclo[5,4,0]undec-7-ene, and inorganic bases, such as sodium hydroxide, sodium carbonate, potassium hydroxide, potassium carbonate, combinations thereof and the like. The bases can be used in quantities ranging from 1 to 3 equivalents, relative to compound 3. Reaction temperatures range from 0° C. to the boiling point of the solvent used; preferably between 0 and 40° C.; reaction completion times range from 1 h to 5 days.

In the case of tetrahydropyran-2-yl, compound 3 is treated with 1 to 3 equivalents of 3,4-dihydro-2H-pyran in the presence of 1 to 10 mol % of acid catalyst. Suitable acid catalysts include pyridinium p-toluenesulfonic acid, p-toluenesulfonic acid, camphorsulfonic acid, methanesulfonic acid, hydrogen chloride, sulfuric acid, combinations thereof and the like. Suitable solvents include dichloromethane, chloroform, tetrahydrofuran, 1,4-dioxane, 1,2-dimethoxyethane, toluene, benzene, and acetonitrile combinations thereof and the like. Reaction temperatures range from 0° C. to the boiling point of the solvent used; preferably between 0 and 60° C., and is complete in 1 h to 5 days.

In the case of trialkylsilyl, compound 3 is treated with 1 to 3 equivalents of chlorotrialkylsilyane in the presence of 1 to 3 equivalents of base. Suitable bases include tertiary amines, such as imidazole, diisopropylethylamine, triethylamine, 1,8-diazabicyclo[5,4,0]undec-7-ene, combinations thereof and the like. Reaction temperatures range from 0° C. to the boiling point of the solvent used; preferably between 0 and 40° C.; reaction completion times range from 1 to 48 h.

In Step 4, compound 4 is converted into boronic acid (5) through halogen metal exchange reaction. Compound 4 is treated with 1 to 3 equivalents of alkylmetal reagent relative to compound 4, such as n-butyllithium, sec-butyllithium, tert-butyllithium, isopropylmagnesium chloride or Mg turnings with or without an initiator such as diisobutylaluminum hydride (DiBA1), followed by the addition of 1 to 3 equivalents of trialkyl borate relative to compound 4, such as trimethyl borate, triisopropyl borate, or tributyl borate. Suitable solvents include tetrahydrofuran, ether, 1,4-dioxane, 1,2-dimethoxyethane, toluene, hexanes, combinations thereof and the like. Alkylmetal reagent may also be added in the presence of trialkyl borate. The addition of butyllithium is carried out at between –100 and 0° C., preferably at between –80 and –40° C. The addition of isopropylmagnesium chloride is carried out at between –80 and 40° C., preferably at between –20 and 30° C. The addition of Mg turnings, with or without the addition of DiBA1, is carried out at between –80 and 40° C., preferably at between –35 and 30° C. The addition of the trialkyl borate is carried out at between –100 and 20° C. After the addition of trialkyl borate, the reaction is allowed to warm to room temperature, which is typically between –30 and 30° C. When alkylmetal reagent is added in the presence of trialkyl borate, the reaction mixture is allowed to warm to room temperature after the addition. Reaction completion times range from 1 to 12 h. Compound 5 may not be isolated and may be used for the next step without purification or in one pot.

In Step 5, the protecting group of compound 5 is removed under acidic conditions to give compound of the invention. Suitable acids include acetic acid, trifluoroacetic acid, hydrochloric acid, hydrobromic acid, sulfuric acid, p-toluenesulfonic acid and the like. The acids can be used in quantities ranging from 0.1 to 20 equivalents, relative to compound 5. When the protecting group is trialkylsilyl, basic reagents, such as tetrabutylammonium fluoride, can also be used. Suitable solvents include tetrahydrofuran, 1,4-dioxane, 1,2-dimethoxyethane, methanol, ethanol, propanol, acetonitrile, acetone, combination thereof and the like. Reaction temperatures range from 0° C. to the boiling point of the solvent used; preferably between 10° C. and reflux temperature of the solvent; reaction completion times range from 0.5 to 48 h. The product can be purified by methods known to those of skill in the art.

Scheme 1

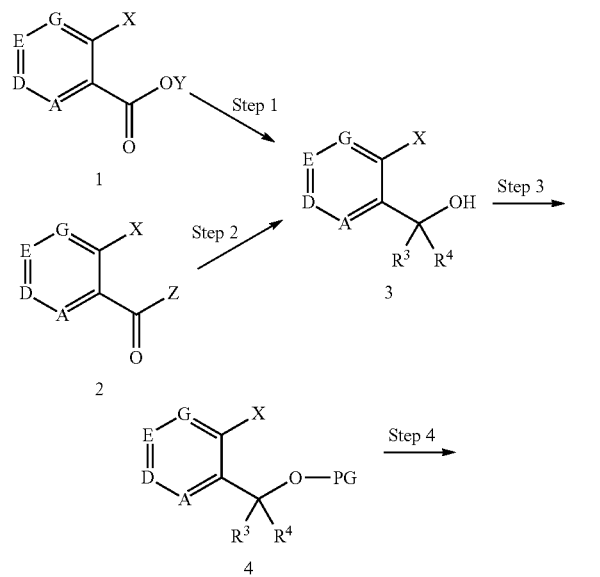

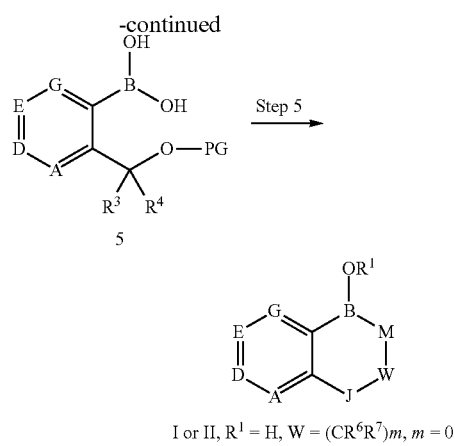

I or II, $R^1$ = H, W = $(CR^6R^7)m$, $m = 0$

In another aspect, the invention provides a method of making a tetrahydropyran-containing boronic ester, said ester having a structure according to the following formula:

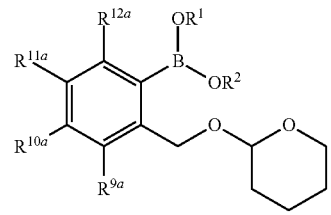

wherein $R^1$ and $R_2$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^1$ and $R^2$, together with the atoms to which they are attached, can be optionally joined to form a 4- to 7-membered ring. $R^{9a}$, $R^{10a}$, $R^{11a}$ and $R^{12a}$ are members independently selected from H, OR*, NR*R**, SR*, —S(O)R*, —S(O)$_2$R*, —S(O)$_2$NR*R**, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. R* and R** is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The method comprises: a) subjecting a first compound to Grignard or organolithium conditions, said first compound having a structure according to the following formula:

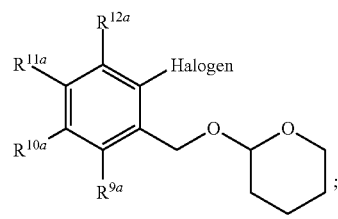

b) contacting the product of step a) with a borate ester, thereby forming said tetrahydropyran-containing boronic ester. In an exemplary embodiment, halogen is a member selected from iodo and bromo. In another exemplary embodiment, the borate ester is a member selected from B(OR$^1$)$_2$(OR$^2$), wherein R$^1$ and R$^2$ are each members independently selected from H, substituted or unsubstituted methyl, substituted or unsubstituted ethyl, substituted or unsubstituted propyl, substituted or unsubstituted isopropyl, substituted or unsubstituted butyl, substituted or unsubstituted t-butyl, substituted or unsubstituted phenyl and substituted or unsubstituted benzyl. R$^1$ and R$^2$, together with the atoms to which they are joined, can optionally form a member selected from substituted or unsubstituted dioxaborolane, substituted or unsubstituted dioxaborinane and substituted or unsubstituted dioxaborepane. In another exemplary embodiment, the borate ester is a member selected from B(OR$^1$)$_2$(OR$^2$), wherein R$^1$ and R$^2$, together with the atoms to which they are joined, form a member selected from dioxaborolane, substituted or unsubstituted tetramethyldioxaborolane, substituted or unsubstituted phenyldioxaborolane, dioxaborinane, dimethyldioxaborinane and dioxaborepane. In another exemplary embodiment, the Grignard or organolithium conditions further comprise diisobutyl aluminum hydride. In another exemplary embodiment, the temperature of the Grignard reaction does not exceed about 35° C. In another exemplary embodiment, the temperature of the Grignard reaction does not exceed about 40° C. In another exemplary embodiment, the temperature of the Grignard reaction does not exceed about 45° C. In an exemplary embodiment, step (b) is performed at a temperature of from about −30° C. to about −20° C. In another exemplary embodiment, step (b) is performed at a temperature of from about −35° C. to about −25° C. In another exemplary embodiment, step (b) is performed at a temperature of from about −50° C. to about −0° C. In another exemplary embodiment, step (b) is performed at a temperature of from about −40° C. to about −20° C. In another exemplary embodiment, the tetrahydropyran-containing boronic ester is

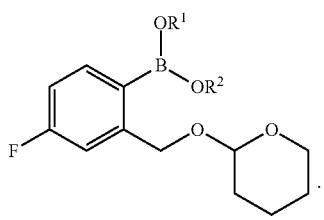

In another aspect, the invention provides a method of making a compound having a structure according to the following formula

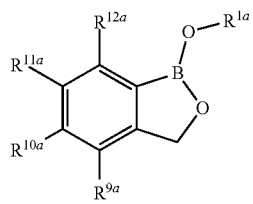

said method comprising: a) subjecting a first compound to Grignard or organolithium conditions, said first compound having a structure according to the following formula:

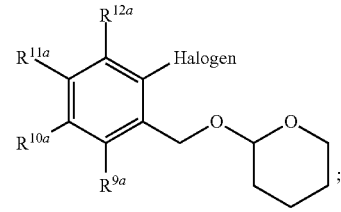

b) quenching said subjecting reaction with water and a organic acid, thereby forming said compound. In an exemplary embodiment, wherein said organic acid is a member selected from acetic acid. In another exemplary embodiment, the quenching step is essentially not contacted with a strong acid. In another exemplary embodiment, the compound is 1,3-dihydro-5-fluoro-1-hydroxy-2,1-benzoxaborole. In another exemplary embodiment, the compound is purified by recrystallization from a recrystallization solvent, wherein said recrystallization solvent essentially does not contain acetonitrile. In an exemplary embodiment, the recrystallization solvent contains less than 2% acetonitrile. In an exemplary embodiment, the recrystallization solvent contains less than 1% acetonitrile. In an exemplary embodiment, the recrystallization solvent contains less than 0.5% acetonitrile. In an exemplary embodiment, the recrystallization solvent contains less than 0.1% acetonitrile. In an exemplary embodiment, the recrystallization solvent contains toluene and a hydrocarbon solvent. In an exemplary embodiment, the recrystallization solvent contains about 1:1 toluene:hydrocarbon solvent. In an exemplary embodiment, the recrystallization solvent contains about 2:1 toluene:hydrocarbon solvent. In an exemplary embodiment, the recrystallization solvent contains about 3:1 toluene:hydrocarbon solvent. In an exemplary embodiment, the recrystallization solvent contains about 4:1 toluene:hydrocarbon solvent. In an exemplary embodiment, the hydrocarbon solvent is a member selected from heptane, octane, hexane, pentane and nonane. In an exemplary embodiment, the recrystallization solvent is 3:1 toluene:heptane.

Boronic Acid Preparation Strategy #2

In Scheme 2, Step 6, compound 2 is converted into boronic acid (6) via a transition metal catalyzed cross-coupling reaction. Compound 2 is treated with 1 to 3 equivalents of bis(pinacolato)diboron or 4,4,5,5-tetramethyl-1,3,2-dioxaborolane in the presence of transition metal catalyst, with the use of appropriate ligand and base as necessary. Suitable transition metal catalysts include palladium(II) acetate, palladium(II) acetoacetonate, tetrakis(triphenylphosphine)palladium, dichlorobis(triphenylphosphine)palladium, [1,1'-bis(diphenylphosphino)ferrocen] dichloropalladium(II), combinations thereof and the like. The catalyst can be used in quantities ranging from 1 to 5 mol % relative to compound 2. Suitable ligands include triphenylphosphine, tri(o-tolyl)phosphine, tricyclohexylphosphine, combinations thereof and the like. The ligand can be used in quantities ranging from 1 to 5 equivalents relative to compound 2. Suitable bases include sodium carbonate, potassium carbonate, potassium phenoxide, triethylamine, combinations thereof and the like. The base can be used in quantities ranging from 1 to 5 equivalents relative to compound 2. Suitable solvents include N,N-dimethylformamide, dimethylsufoxide, tetrahydrofuran, 1,4-dioxane, toluene, combinations thereof and the like. Reaction temperatures range from 20° C. to the boiling point of the solvent used; preferably between 50 and 150° C.; reaction completion times range from 1 to 72 h.

Pinacol ester is then oxidatively cleaved to give compound 6. Pinacol ester is treated with sodium periodate followed by acid. Sodium periodate can be used in quantities ranging from 2 to 5 equivalents relative to compound 6. Suitable solvents include tetrahydrofuran, 1,4-dioxane, acetonitrile, methanol, ethanol, combinations thereof and the like. Suitable acids include hydrochloric acid, hydrobromic acid, sulfuric acid combinations thereof and the like. Reaction temperatures range from 0° C. to the boiling point of the solvent used; preferably between 0 and 50° C.; reaction completion times range from 1 to 72 h.

In Step 7, the carbonyl group of compound 6 is treated with a reducing agent in an appropriate solvent to give a compound of the invention. Suitable reducing agents include borane complexes, such as borane-tetrahydrofuran, borane-dimethylsulfide, combinations thereof and the like. Lithium aluminum hydride, or sodium borohydride can also be used as reducing agents. The reducing agents can be used in quantities ranging from 0.5 to 5 equivalents, relative to compound 6. Suitable solvents include lower alcohol, such as methanol, ethanol, and propanol, diethyl ether, tetrahydrofuran, 1,4-dioxane and 1,2-dimethoxyethane, combinations thereof and the like. Reaction temperatures range from 0° C. to the boiling point of the solvent used; reaction completion times range from 1 to 24 h.

Scheme 2

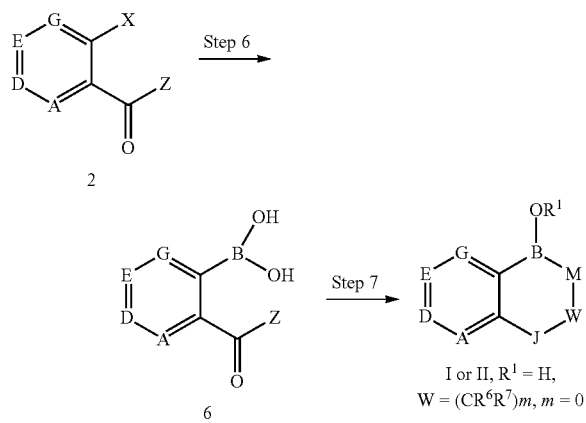

Boronic Acid Preparation Strategy #3

In Scheme 3, Step 8, compounds of the invention can be prepared in one step from compound 3. Compound 3 is mixed with trialkyl borate then treated with alkylmetal reagent. Suitable alkylmetal reagents include n-butyllithium, sec-butyllithium, tert-butyllithium combinations thereof and the like. Suitable trialkyl borates include trimethyl borate, triisopropyl borate, tributyl borate, combinations thereof and the like. The addition of butyllithium is carried out at between −100 and 0° C., preferably at between −80 and −40° C. The reaction mixture is allowed to warm to room temperature after the addition. Reaction completion times range from 1 to 12 h. The trialkyl borate can be used in quantities ranging from 1 to 5 equivalents relative to compound 3. The alkylmetal reagent can be used in quantities ranging from 1 to 2 equivalents relative to compound 3. Suitable solvents include tetrahydrofuran, ether, 1,4-dioxane, 1,2-dimethoxyethane, toluene, hexanes, combinations thereof and the like. Reaction completion times range from 1 to 12 h. Alternatively, a mixture of compound 3 and trialkyl borate can be refluxed for 1 to 3 h and the alcohol molecule formed upon the ester exchange can be distilled out before the addition of alkylmetal reagent.

Scheme 3

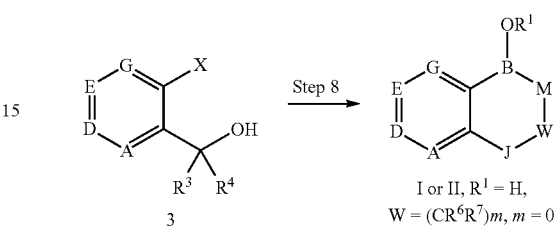

Boronic Acid Preparation Strategy #4

In Scheme 4, Step 10, the methyl group of compound 7 is brominated using N-bromosuccinimide. N-bromosuccinimide can be used in quantities ranging from 0.9 to 1.2 equivalents relative to compound 7. Suitable solvents include carbon tetrachloride, tetrahydrofuran, 1,4-dioxane, chlorobenzene, combinations thereof and the like. Reaction temperatures range from 20° C. to the boiling point of the solvent used; preferably between 50 and 150° C.; reaction completion times range from 1 to 12 h.

In Step 11, the bromomethylene group of compound 8 is converted to the benzyl alcohol 3. Compound 8 is treated with sodium acetate or potassium acetate. These acetates can be used in quantities ranging from 1 to 10 equivalents relative to compound 8. Suitable solvents include tetrahydrofuran, 1,4-dioxane, N,N-dimethylformamide, N,N-dimethylacetamide, N-methylpyrrolidone, dimethylsulfoxide, combinations thereof and the like. Reaction temperatures range from 20° C. to the boiling point of the solvent used; preferably between 50 and 100° C.; reaction completion times range from 1 to 12 h. The resulting acetate is hydrolyzed to compound 3 under basic conditions. Suitable bases include sodium hydroxide, lithium hydroxide, potassium hydroxide, combinations thereof and the like. The base can be used in quantities ranging from 1 to 5 equivalents relative to compound 8. Suitable solvents include methanol, ethanol, tetrahydrofuran, water, combinations thereof and the like. Reaction temperatures range from 20° C. to the boiling point of the solvent used; preferably between 50 and 100° C.; reaction completion times range from 1 to 12 h. Alternatively, compound 8 can be directly converted into compound 3 under the similar condition above.

Steps 3 through 5 convert compound 3 into a compound of the invention.

Scheme 4

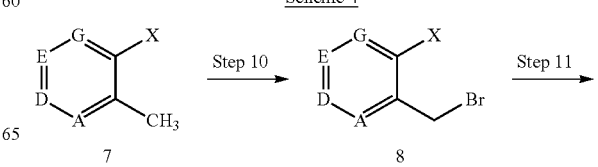

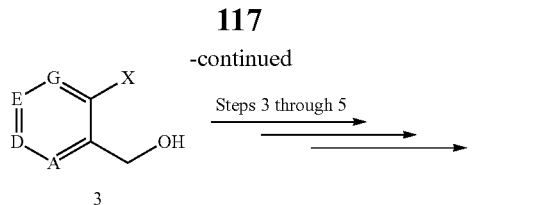

Steps 3 through 5

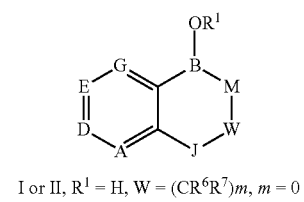

I or II, R$^1$ = H, W = (CR$^6$R$^7$)$_m$, m = 0

Boronic Acid Preparation Strategy #5

In Scheme 5, Step 12, compound 2 is treated with (methoxymethyl) triphenylphosphonium chloride or (methoxymethyl)triphenylphosphonium bromide in the presence of base followed by acid hydrolysis to give compound 9. Suitable bases include sodium hydride, potassium tert-butoxide, lithium diisopropylamide, butyllithium, lithium hexamethyldisilazane, combinations thereof and the like. The (methoxymethyl)triphenylphosphonium salt can be used in quantities ranging from 1 to 5 equivalents relative to compound 2. The base can be used in quantities ranging from 1 to 5 equivalents relative to compound 2. Suitable solvents include tetrahydrofuran, 1,2-dimethoxyethane, 1,4-dioxane, ether, toluene, hexane, N,N-dimethylformamide, combinations thereof and the like. Reaction temperatures range from 0° C. to the boiling point of the solvent used; preferably between 0 and 30° C.; reaction completion times range from 1 to 12 h. The enolether formed is hydrolyzed under acidic conditions. Suitable acids include hydrochloric acid, hydrobromic acid, sulfuric acid, and the like. Suitable solvents include tetrahydrofuran, 1,2-dimethoxyethane, 1,4-dioxane, methanol, ethanol, combination thereof and the like. Reaction temperatures range from 20° C. to the boiling point of the solvent used; preferably between 50 and 100° C.; reaction completion times range from 1 to 12 h.

Steps 2 through 5 convert compound 9 into a compound of the invention.

Scheme 5

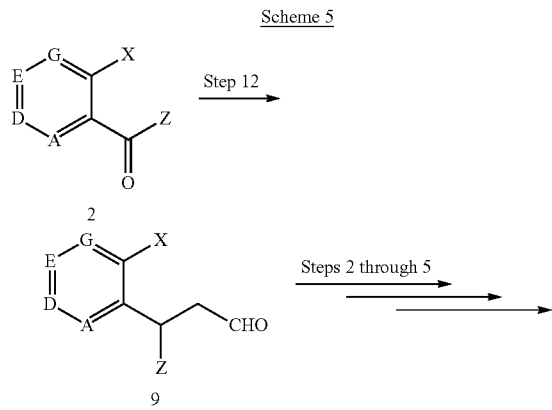

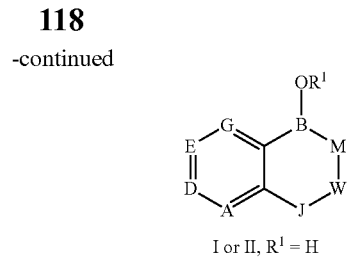

I or II, R$^1$ = H

Boronic Acid Preparation Strategy #6

In Scheme 6, compound (I) wherein R$^1$ is H is converted into compound (I) wherein R$^1$ is alkyl by mixing with the corresponding alcohol, R$^1$OH. The suitable solvents include tetrahydrofuran, 1,2-dimethoxyethane, 1,4-dioxane, toluene, combinations thereof and the like. The alcohol (R$^1$OH) can be used as the solvent as well. Reaction temperatures range from 20° C. to the boiling point of the solvent used; preferably between 50 and 100° C.; reaction completion times range from 1 to 12 h.

Scheme 6

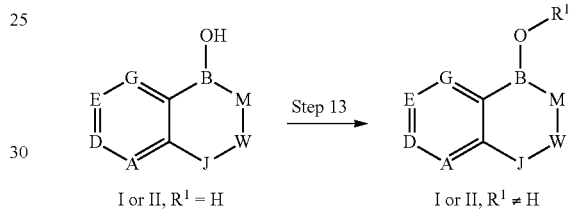

Boronic Acid Preparation Strategy #7

In Scheme 7, compound (Ia) is converted into its aminoalcohol complex (Ib). Compound (Ia) is treated with HOR$^1$NR$^{1a}$R$^{1b}$. The aminoalcohol can be used in quantities ranging from 1 to 10 equivalents relative to compound (Ia). Suitable solvents include methanol, ethanol, propanol, tetrahydrofuran, acetone, acetonitrile, 1,2-dimethoxyethane, 1,4-dioxane, toluene, N,N-dimethylformamide, water, combination thereof and the like. Reaction temperatures range from 20° C. to the boiling point of the solvent used; preferably between 50 and 100° C.; reaction completion times range from 1 to 24 h.

Scheme 7

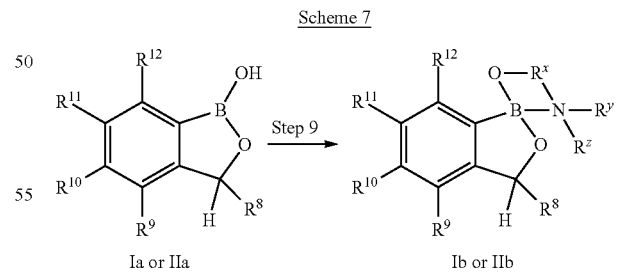

Ia or IIa        Ib or IIb

The compounds of the invention can be converted into hydrates and solvates by methods similar to those described above.

I. h.) Borinic Esters

Methods of making borinic esters are known in the art, and it is within the knowledge of one skilled in the art to use these methods in order to make the boronic esters described herein. Examples include U.S. patent application Ser. No. 10/868,268 and U.S. Prov. Pat. Application No. 60/813,623, filed May 2, 2006 which are herein incorporated by reference.

I. i.) 2'-amino or 3'-amino ribofuranoses

Methods of making 2'-amino ribofuranoses or 3'-amino ribofuranoses are known in the art, and it is within the knowledge of one skilled in the art to use these methods in order to make the 2'-amino ribofuranoses described herein.

Ashton et al. (Can. Pat. App. 2,031,644 (1991)) and Durette, et al. (UK Pat. App. 2,207,678 (1989)) disclose the synthesis of the amino acid starting material for compound D5. Hardee, et al., (PCT Int. App. WO2005020885 (2005)) discloses the synthesis of the nucleoside starting material for compound D6. Sakthivel, (Sakthivel, et al., *Tet. Let.* 46(22): 3883-3887 (2005)) Sartorelli, et al., (U.S. Pat. Appl. Pub. 2004116362); Roberts, et al., (PCT Int. Appl. WO2003093290); Liu, et al., *Nucleosides, Nucleotides & Nucleic Acids*, 20(12): 1975-2000 (2001); Minakawa, et al., *J. Org. Chem.*, 64(19): 7158-7172 (1999); Daelemans, et al., *Molecular Pharmacology*, 52(6): 1157-1163 (1997) all disclose the synthesis of the nucleoside starting material for compound D7.

Examples of how to prepare these compounds is shown below:

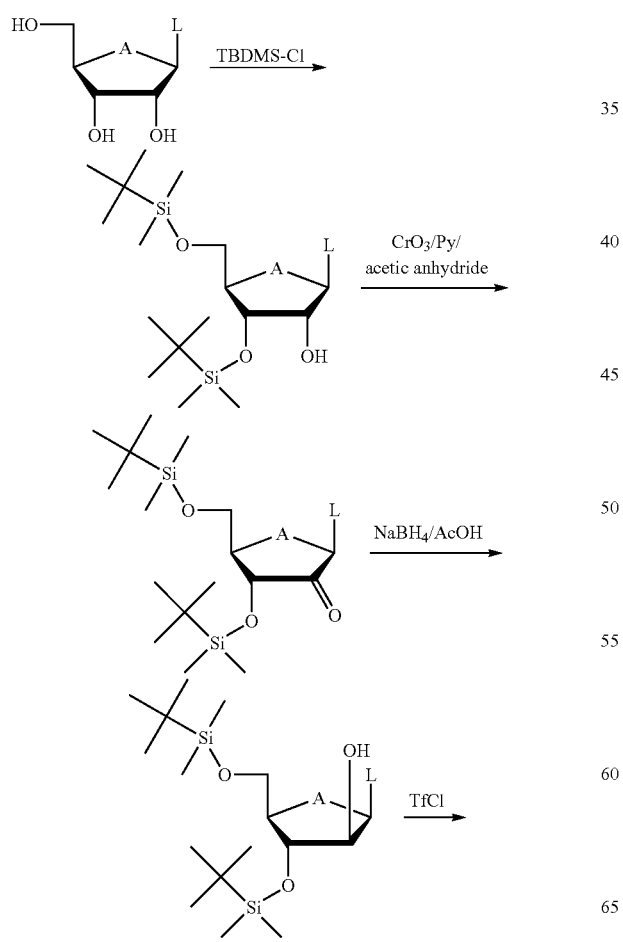

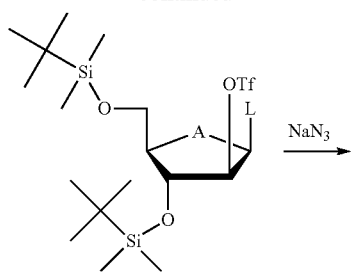

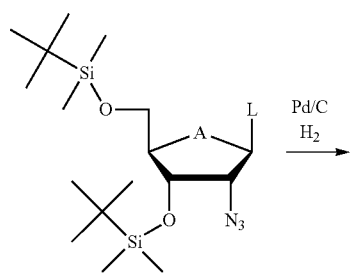

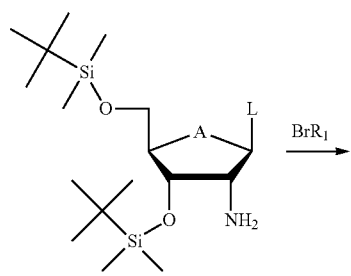

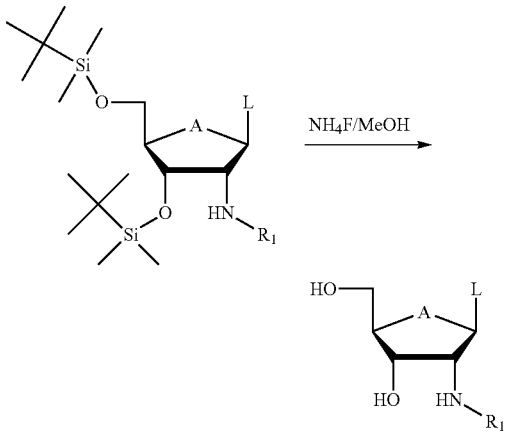

Compounds 1-14 are produced by a final step (Lincecum, T. L. et al., *S. Molecular Cell*, 11: 951-963 (2003); Kim, B.-T. et al., *J. Bull. Korean Chem. Soc.*, 25: 243-248 (2004)):

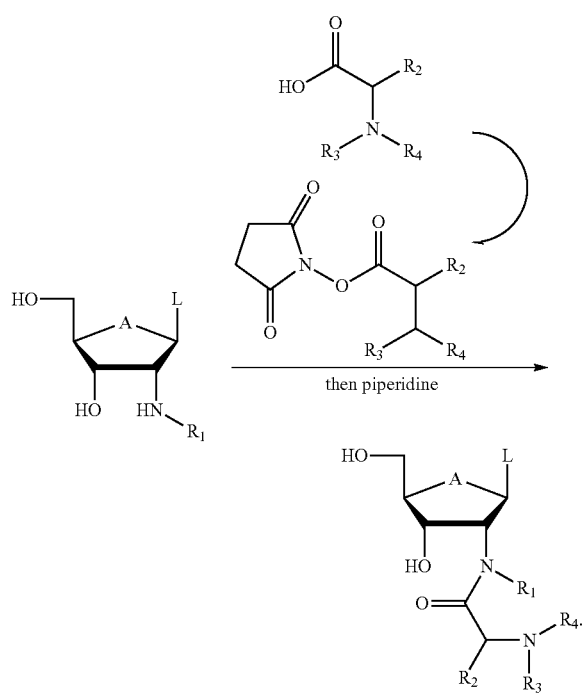

Compounds 15-18 are produced by a final step (See Lincecum):

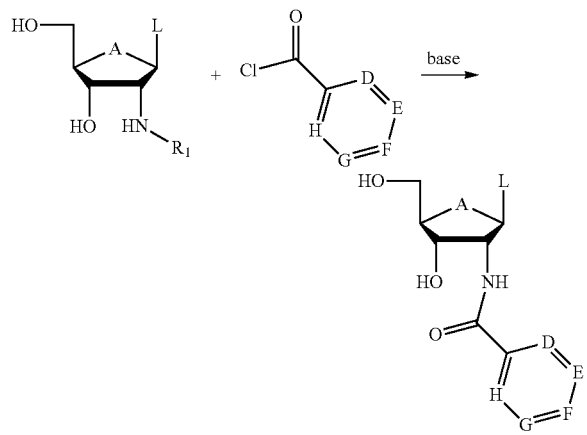

Methods for preparing dimers, trimers and higher homologs of small organic molecules, such as those of use in the present invention, as well as methods of functionalizing a polyfunctional framework molecule are well known to those of skill in the art. For example, an aromatic amine of the invention is converted to the corresponding isothiocyanate by the action of thiophosgene. The resulting isothiocyanate is coupled to an amine of the invention, thereby forming either a homo- or heterodimeric species. Alternatively, the isothiocyanate is coupled with an amine-containing backbone, such as polylysine, thereby forming a conjugate between a polyvalent framework and a compound of the invention. If it is desired to prepare a heterofunctionalized polyvalent species, the polylysine is underlabeled with the first isothiocyanate and subsequently labeled with one or more different isothiocyanates. Alternatively, a mixture of isothiocyanates is added to the backbone. Purification proceeds by, for example, size exclusion chromatography, dialysis, nanofiltration and the like.

II. Assays for Inhibitors of tRNA Synthetase Editing Domains

Art-recognized techniques of genetics and molecular biology are of use to identify compounds that bind to and/or inhibit the editing domain of a tRNA synthetase. Moreover, these techniques are of use to distinguish whether a compound binds to and/or inhibits the synthetic domain, the editing domain, or both the editing and synthetic domains.

In an exemplary assay, activity of a representative compound against the editing domain was confirmed. To identify the target of the novel boron-containing antifungal compound C10, mutants in S. cerevisiae showing resistance to compound C10 were isolated. Characterization of 11 mutants showed that they have an 8-64 fold increase in resistance to C10 over wildtype. The mutants were furthermore shown to be sensitive to various antifungal agents with known modes of action, suggesting that the cellular target of C10 is distinct from the target of the other antifungal agents. Isolation of three different plasmids bearing CDC60 from plasmid libraries generated from three independently isolated mutants implicated CDC60, the gene for the cytoplasmic leucyl-tRNA synthetase in resistance against C10. Sequence analysis of CDC60 from the 11 mutants revealed that the mutations were all located in the editing domain of this enzyme. In a further series of experiments, additional copies of the CDC60 gene were introduced in S. cerevisiae, which gave rise to an eight-fold increase in resistance to C10. These findings confirm a strong link between the editing activity of the enzyme and the inhibition of C10, which entails a novel mechanism of tRNA synthetase inhibition.

Assays to determine whether, and how effectively, a particular compound binds to and/or inhibits the editing domain of a selected tRNA synthetase are also set forth herein, and additional assays are readily available to those of skill in the art. Briefly, in an exemplary assay, an improperly charged tRNA and a tRNA synthetase that is capable of editing the improperly charged tRNA are combined. The resulting mixture is contacted with the putative inhibitor and the degree of editing inhibition is observed.

Another assay uses genetics to show that a drug works via the editing domain. In this assay, the compound is first tested against a strain of cells over-expressing copies of the tRNA synthetase gene. The compound's effect on the over-expressing strain is compared with a control strain to determine whether the compound is active against the synthetase. If the minimum inhibitory concentration (MIC) is 2-fold higher in the strain with extra copies of the synthetase gene than the MIC of the inhibitor against a wild type cell, a further genetic screen is conducted to determine whether the increased resistance is due to mutations in the editing domain. In this second screen, the control strain is challenged against a high concentration of the inhibitor. The colonies surviving the challenge are isolated and DNA from these cells is isolated. The editing domain is amplified using a proof-reading PCR enzyme and the appropriate primers. The PCR product can be purified using standard procedures. The sequence amplified mutant DNA is compared to wildtype. If the mutant DNA bears mutations in the editing domain, such results would suggest that the compound binds to the editing domain and affects the editing function of the molecule through this domain.

The assays set forth above are useful in essentially any microbial system, e.g., bacterial, fungal, parasitic, viral and the like.

Generally, the compounds to be tested are present in the assays in ranges from about 1 pM to about 100 mM, preferably from about 1 pM to about 1 µM. Other compounds range from about 1 nM to about 100 nM, preferably from about 1 nM to about 1 µM.

The effects of the test compounds upon the function of the enzymes can also be measured by any suitable physiological change. When the functional consequences are determined using intact cells or animals, one can also measure a variety of effects such as transmitter release, hormone release, transcriptional changes to both known and uncharacterized genetic markers, changes in cell metabolism such as cell growth or pH changes, and changes in intracellular second messengers such as $Ca^{2+}$, or cyclic nucleotides.

High throughput screening (HTS) is also of use in identifying promising candidates of the invention.

Utilizing the assays set forth herein and others readily available in the art, those of skill in the art will be able to readily and routinely determine other compounds and classes of compounds that operate to bind to and/or inhibit the editing domain of tRNA synthetases.

In another aspect, the invention provides a method for identifying a compound which binds to an editing domain of a tRNA synthetase comprising: a) contacting said editing domain with a test compound under conditions suitable for binding; and b) detecting binding of said test compound to said editing domain. In an exemplary embodiment, detecting binding of said compound comprises use of at least one detectable element, isotope, or chemical label attached to said compound. In an exemplary embodiment, the element, isotope or chemical label is detected by a fluorescent, luminescent, radioactive, or absorbance readout. In an exemplary embodiment, the contacting of said test compound with said editing domain also includes further contacting said test compound and said editing domain with a member selected from AMP and a molecule with a terminal adenosine. In an exemplary embodiment, said tRNA synthetase is derived from a member selected from alanyl tRNA synthetase, isoleucyl tRNA synthetase, leucyl tRNA synthetase, methionyl tRNA synthetase, lysyl tRNA synthetase, phenylalanyl tRNA synthetase, prolyl tRNA synthetase, threonyl tRNA synthetase and valyl tRNA synthetase. In an exemplary embodiment, the tRNA synthetase is derived from leucyl tRNA synthetase. In an exemplary embodiment, the tRNA synthetase is derived from a mutated tRNA synthetase, wherein said mutated tRNA synthetase comprises amino acid mutations in an editing domain. In another exemplary embodiment, the mutated tRNA synthetase comprises amino acid mutations in the editing domain as listed in Table 4. In another exemplary embodiment, wherein said editing domain of a tRNA synthetase comprises the amino acid sequence of SEQ ID NOS: 1-15.

In another aspect, the invention provides a method for identifying a compound which binds to an editing domain of a tRNA synthetase, said assay comprising: a) contacting said editing domain of a tRNA synthetase with said compound under conditions suitable for binding of said compound with said editing domain of a tRNA synthetase; b) comparing a biological activity of said editing domain of a tRNA synthetase contacting said compound to said biological activity when not contacting said compound; and c) identifying said compound as binding to said editing domain of a tRNA synthetase if said biological activity of said editing domain of a tRNA synthetase is reduced when contacting said compound. In an exemplary embodiment, the biological activity is hydrolysis of noncognate amino acid. In another exemplary embodiment, the hydrolysis of said noncognate amino acid is detected through the use of one or more labels. In another exemplary embodiment, the labels include a radiolabel, a fluorescent marker, an antibody, or a combination thereof. In another exemplary embodiment, said labels can be detected using spectroscopy. In another exemplary embodiment, the editing domain of a tRNA synthetase is derived from a member selected from alanyl tRNA synthetase, isoleucyl tRNA synthetase, leucyl tRNA synthetase, methionyl tRNA synthetase, lysyl tRNA synthetase, phenylalanyl tRNA synthetase, prolyl tRNA synthetase, threonyl tRNA synthetase and valyl tRNA synthetase. In another exemplary embodiment, said editing domain of a tRNA synthetase is derived from leucyl tRNA synthetase.

In another aspect, the invention provides a method of generating tRNA molecules with noncognate amino acid comprising: a) creating or isolating a mutated tRNA synthetase with altered amino acid editing domains; and b) contacting a tRNA molecule with said mutated tRNA synthetase and a noncognate amino acid. In another exemplary embodiment, the mutated tRNA synthetase contains one or more amino acid mutations in an editing domain. In another exemplary embodiment, the mutated tRNA synthetase is unable to bind with 1,3-dihydro-5-fluoro-1-hydroxy-2,1-benzoxaborole. In another exemplary embodiment, the mutated tRNA synthetase is able to bind with 1,3-dihydro-5-fluoro-1-hydroxy-2,1-benzoxaborole.

In another aspect, the invention provides a composition that comprises one or more tRNA molecules attached to noncognate amino acids, wherein said tRNA molecules are synthesized using one or more mutated tRNA synthetases isolated from a microorganism or a cell line derived from a microorganism. In an exemplary embodiment, the microorganism is a fungus or a yeast. In an exemplary embodiment, wherein said mutated tRNA synthetases contain amino acid mutations in their editing domains. In an exemplary embodiment, said mutated tRNA synthetases comprise point mutations in the editing domain as listed in Table 4.

III. Amino Acid and Nucleotide Sequences Used in Assays tRNA Sequences that Interact with the tRNA Synthetase-C10-AMP Complex Transfer RNAs (tRNAs) translate mRNA into a protein on a ribosome. Each transfer RNA contains an anti-codon region that hybridizes with mRNA, and an amino acid which may be attached to the growing peptide. The structural gene of tRNA is about 72 to 90 nucleotides long and folds into a cloverleaf structure (Sharp S. J., Schaack J., Coolen L., Burke D. J. and Soll D., "Structure and transcription of eukaryotic tRNA genes", Crit. Rev. Biochem, 19:107 144 (1985); Geiduschek E. O., and Tocchini-Valentini, "Transcription by RNA polymerase III", Annu. Rev. Biochem. 57:873 914 (1988)).

In one embodiment, C10 contacts AMP and a tRNA synthetase, and the tRNA synthetase in turn contacts a tRNA molecule. In another embodiment, C10 contacts AMP from the tRNA molecules and a tRNA synthetase. The nucleotide sequence of the tRNA molecule can be determined by the identity of the tRNA synthetase involved. For example, for leucyl tRNA synthetase, the cognate tRNA molecule bound will be tRNA-leucine (SEQ ID NO: 3), but a noncognate tRNA, such as isoleucine, (SEQ ID NO: 4) may be bound under certain conditions. In this and other embodiments, the term "noncognate" is meant to encompass both the singular and plural forms of the word, i.e. the phrase "noncognate amino acid" comprises one or more amino acids.

SEQ ID NO: 3 corresponds to the nucleotide sequence of the tRNA-Leu gene from *Saccharomyces cerevisiae*: gggagtttgg ccgagtggtt taaggcgtca gatttaggct ctgatatctt cggat-gcaagggttcgaatc ccttagctct cacca SEQ ID NO: 4 corresponds to the nucleotide sequence of the tRNA-Ile gene from *Saccharomyces cerevisiae*: gaaac-tataa ttcaattggt tagaatagta ttttgataag gtacaaatat aggttcaatc cctgttagtt tcatcca Polypeptides Used in Binding and Inhibition Assays In some binding and inhibition assays, it is more effective to use a portion of a tRNA synthetase molecule rather than the whole protein itself. In such assays, polypeptides derived from tRNA synthetases are used in the experiment.

In one preferred embodiment, polypeptide fragments corresponding to the editing domain of a tRNA synthetase molecule are used in assay and binding experiments. Two such fragments are represented by SEQ ID NO: 1 and SEQ ID NO:2.

SEQ ID NO 1:
TPQEYIGVKIEALEFADDAAKIIDSSSDLDKSKKFYFVAATLRPETMYGQ

TCCFVSPTIEYGIFDAGDSYFITTERAFKNMSYQKLTPKRGFYKPIVTVP

GKAFIGTKIHAPQSVYPELRILPMETVIATKGTGVVTCVPSNSPDDYITT

KDLLHKPEYYGIKPEWIDHEIVPIMHTEKYGDLTAKAIVEEKKIQSPKDK

NLLAEAKKIAYKEDYYTGTMIYGPYKGEKVEQAKNKVKADMIAAGEAFVY

NEPESQDP

SEQ ID NO 2:
MTPQEYIGVKIEALEFADDAAKIIDSSSDLDKSKKFYFVAATLRPETMYG

QTCCFVSPTIEYGIFDAGDSYFITTERAFKNMSYQKLTPKRGFYKPIVTV

PGKAFIGTKIHAPQSVYPELRILPMETVIATKGTGVVTCVPSNSPDDYIT

TKDLLHKPEYYGIKPEWIDHEIVPIMHTEKYGDLTAKAIVEEKKIQSPKD

KNLLAEAKKIAYKEDYYTGTMIYGPYKGEKVEQAKNKVKADMIAAGEAFV

YNEPESQDPQDPNSSSVDKLAAALEHHHHH

IV. Methods for Inhibiting the Editing Domain of tRNA Synthetase

According to another aspect of the invention, a method for binding to and/or inhibiting the editing domain of a tRNA synthetase is provided which comprises contacting a tRNA synthetase with a compound that inhibits the editing domain under the conditions in which the tRNA synthetase interacts with its substrate to form an aminoacyl adenylate intermediate and, preferably, to form a charged tRNA. Such conditions are known to those skilled in the art. In an exemplary embodiment, the compound is one described herein. The tRNA synthetase is contacted with an amount of inhibitor sufficient to result in a detectable amount of tRNA synthetase inhibition. This method can be performed on a tRNA synthetase that is contained within an organism or which is outside an organism. In an exemplary embodiment, the method is performed on a tRNA synthetase that is contained within a microorganism or a microbial cell that is in, or on the surface of, a human or an animal. The method results in a decrease in the amount of charged tRNA produced by the tRNA synthetase that has an inhibited editing domain. In an exemplary embodiment, the inhibition takes place in a cell, such as a microbial cell. In another exemplary embodiment, the microbial cell is a bacteria, fungus, yeast or parasite. In another exemplary embodiment, the tRNA synthetase is a mitochondrial tRNA synthetase or a cytoplasmic tRNA synthetase.

In an exemplary embodiment, the invention provides a method of inhibiting conversion of a tRNA molecule into a charged tRNA molecule. The method involves contacting a tRNA synthetase with a compound effective to inhibit activity of an editing domain of said tRNA synthetase, under conditions sufficient to inhibit said activity, thereby inhibiting said conversion wherein the compound is a member selected from those compounds described herein. In an exemplary embodiment, the compound is a member selected from a cyclic boronic ester, cyclic borinic ester, 2'-amino ribofuranose moiety and a 3'-amino ribofuranose moiety. In an exemplary embodiment, the inhibition occurs within a cell, and the cell is a microbial cell. In another exemplary embodiment, the microbial cell is a member selected from a bacteria, fungus, yeast, and parasite. In an exemplary embodiment, the tRNA synthetase is a member selected from a mitochondrial tRNA synthetase and a cytoplasmic tRNA synthetase. In another exemplary embodiment, the tRNA synthetase is a member selected from alanyl tRNA synthetase, isoleucyl tRNA synthetase, leucyl tRNA synthetase, methionyl tRNA synthetase, lysyl tRNA synthetase, phenylalanyl tRNA synthetase, prolyl tRNA synthetase, threonyl tRNA synthetase and valyl tRNA synthetase. In another exemplary embodiment, the compound has a $K_{D,\ synthesis}$ of greater than 100 μM against a synthetic domain of said tRNA synthetase.

In certain embodiments, the mechanism of action of the compound is to inhibit the conversion of a tRNA molecule into a charged tRNA molecule by binding to and/or inhibiting at least the editing domain of the synthetase. The compounds of use in this method may also inhibit or otherwise interact with the synthetic domain (e.g., the active site of the synthetic domain). In a presently preferred embodiment, the editing domain is inhibited selectively in the presence of the synthetic domain. In a preferred embodiment, the synthetic domain is essentially uninhibited, while the editing domain is inhibited at least 50%, preferably at least 60%, more preferably at least 70%, still more preferably, at least 80% and even still more preferably at least 90% of the activity of the tRNA synthetase. In another preferred embodiment, the synthetic domain is inhibited by at most 50%, preferably at most 30%, preferably at most 20%, 10%, preferably at most 8%, more preferably at most 5%, still more preferably, at most 3% and even still more preferably at most 1%. Inhibition of the editing domain produces a decrease in the amount of the properly charged tRNA which results in retardation or cessation of cell growth and division.

In another exemplary embodiment, the ratio of a minimum concentration of said compound inhibiting said editing domain to a minimum concentration of said compound inhibiting said synthetic domain of said tRNA synthetase, represented as $K_{D,\ edit}/K_{D,\ synthesis}$, is less than one. In another exemplary embodiment, the $K_{D,\ edit}/K_{D,\ synthesis}$ of the compound is a member selected from less than 0.5, less than 0.1 and less than 0.05.

V. Methods of Inhibiting Microorganism Growth or Killing Microorganisms

In a further aspect, the invention provides a method for inhibiting the growth, or killing, a microorganism, preferably a bacteria, fungus, virus, yeast or parasite, comprising contacting the microorganism with an inhibitor of a tRNA synthetase, e.g., a compound described by a formula listed herein, under conditions which permit entry of the compound into the organism. In a further aspect, the invention provides a method for inhibiting the growth, or killing, a microorganism, preferably a bacteria, fungus, virus, yeast or parasite, comprising contacting the microorganism with a compound which is a member selected from Formulae (I), (Ia), (Ib), (Ic), (Id) (Ie), (If), (Ig), (Ih) (Ii), (Ij), (Ik), (Il) (Im), (In), (Io), (Ip) (Iq), (Ir), (Is), (It), (Iu), (Iv), (Iw), (Ix) (Iy), (Iz), (Iaa), (Iab), (Iac), (Iad), (Iae), (Iaf), (Iag), (Iah), (Iai), (Iaj), (Iak), (II), (IIa), (IIb), (IIc), (IId), (III), (VIII), (VIIIa), (VIIIb), (VIIIc), (VIIId), (VIIIe), (IX) e.g., a compound described by a formula listed herein, under conditions which permit entry of the compound into the organism. In a further aspect, the invention provides a method for inhibiting the growth, or killing, a microorganism, preferably a bacteria, fungus, virus, yeast or parasite, comprising contacting the microorganism with a compound which is described in either FIG. 19 or FIG. 20 e.g., a compound described by a formula listed herein, under conditions which permit entry of the compound into the organism. In an exemplary embodiment, the compound inhibits the tRNA synthetase through the editing domain of the synthetase. Such conditions are known to one skilled in the art and specific conditions are set forth in the Examples appended hereto. This method involves contacting a microbial cell with a therapeutically-effective amount of an editing domain inhibitor to inhibit tRNA synthetase in vivo or in vitro.

In another aspect, the invention provides a method of inhibiting the growth of a microorganism, or killing a microorganism, or both, comprising contacting the microorganism with a compound described herein. Microorganisms are members selected from fungi, yeast, viruses, bacteria and parasites. In another exemplary embodiment, the microorganism is inside, or on the surface of an animal. In an exemplary embodiment, the animal is a member selected from human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human.

In an exemplary embodiment, the microorganism is a member selected from a fungus and a yeast. In another exemplary embodiment, the fungus or yeast is a member selected from *Candida* species, *Trichophyton* species, *Microsporium* species, *Aspergillus* species, *Cryptococcus* species, *Blastomyces* species, *Cocciodiodes* species, *Histoplasma* species, *Paracoccidioides* species, *Phycomycetes* species, *Malassezia* species, *Fusarium* species, *Epidermophyton* species, *Scytalidium* species, *Scopulariopsis* species, *Alternaria* species, *Penicillium* species, *Phialophora* species, *Rhizopus* species, *Scedosporium* species and *Zygomycetes* class. In another exemplary embodiment, the fungus or yeast is a member selected from *Aspergilus fumigatus* (*A. fumigatus*), *Blastomyces dermatitidis, Candida Albicans* (*C. albicans*, both fluconazole sensitive and resistant strains), *Candida glabrata* (*C. glabrata*), *Candida krusei* (*C. krusei*), *Cryptococcus neoformans* (*C. neoformans*), *Candida parapsilosis* (*C. parapsilosis*), *Candida tropicalis* (*C. tropicalis*), *Cocciodiodes immitis, Epidermophyton floccosum* (*E. floccosum*), *Fusarium solani* (*F. solani*), *Histoplasma capsulatum, Malassezia furfur* (*M. furfur*), *Malassezia pachydermatis* (*M. pachydermatis*), *Malassezia sympodialis* (*M. sympodialis*), *Microsporum audouinii* (*M. audouinii*), *Microsporum canis* (*M. canis*), *Microsporum gypseum* (*M. gypseum*), *Paracoccidioides brasiliensis* and *Phycomycetes* spp, *Trichophyton mentagrophytes* (*T. mentagrophytes*), *Trichophyton rubrum* (*T. rubrum*), *Trichophyton tonsurans* (*T. tonsurans*). In another exemplary embodiment, the fungus or yeast is a member selected from *Trichophyton concentricum, T. violaceum, T. schoenleinii, T. verrucosum, T. soudanense, Microsporum gypseum, M. equinum, Candida guilliermondii, Malassezia globosa, M. obtuse, M. restricta, M. slooffiae*, and *Aspergillus flavus*. In another exemplary embodiment, the fungus or yeast is a member selected from dermatophytes, *Trichophyton, Microsporum, Epidermophyton* and yeast-like fungi.

In an exemplary embodiment, the microorganism is a bacteria. In an exemplary embodiment, the bacteria is a gram-positive bacteria. In another exemplary embodiment, the gram-positive bacteria is a member selected from *Staphylococcus* species, *Streptococcus* species, *Bacillus* species, *Mycobacterium* species, *Corynebacterium* species (*Propionibacterium* species), *Clostridium* species, *Actinomyces* species, *Enterococcus* species and *Streptomyces* species. In another exemplary embodiment, the bacteria is a gram-negative bacteria. In another exemplary embodiment, the gram-negative bacteria is a member selected from *Acinetobacter* species, *Neisseria* species, *Pseudomonas* species, *Brucella* species, *Agrobacterium* species, *Bordetella* species, *Escherichia* species, *Shigella* species, *Yersinia* species, *Salmonella* species, *Klebsiella* species, *Enterobacter* species, *Haemophilus* species, *Pasteurella* species, *Streptobacillus* species, spirochetal species, *Campylobacter* species, *Vibrio* species and *Helicobacter* species. In another exemplary embodiment, the bacterium is a member selected from *Propionibacterium acnes; Staphylococcus aureus; Staphylococcus epidermidis, Staphylococcus saprophyticus; Streptococcus pyogenes; Streptococcus agalactiae; Streptococcus pneumoniae; Enterococcus faecalis; Enterococcus faecium; Bacillus anthracis; Mycobacterium avium-intracellulare; Mycobacterium tuberculosis, Acinetobacter baumanii; Corynebacterium diphtheria; Clostridium perfringens; Clostridium botulinum; Clostridium tetani; Clostridium difficile; Neisseria gonorrhoeae; Neisseria meningitidis; Pseudomonas aeruginosa; Legionella pneumophila; Escherichia coli; Yersinia pestis; Haemophilus influenzae; Helicobacter pylori; Campylobacter fetus; Campylobacter jejuni; Vibrio cholerae; Vibrio parahemolyticus; Treponema pallidum; Actinomyces israelii; Rickettsia prowazekii; Rickettsia rickettsii; Chlamydia trachomatis; Chlamydia psittaci; Brucella abortus; Agrobacterium tumefaciens*; and *Francisella tularensis*.

In an exemplary embodiment, the microorganism is a bacteria, which is a member selected from acid-fast bacterium, including *Mycobacterium* species; bacilli, including *Bacillus* species, *Corynebacterium* species (also *Propionibacterium*) and *Clostridium* species; filamentous bacteria, including *Actinomyces* species and *Streptomyces* species; bacilli, such as *Pseudomonas* species, *Brucella* species, *Agrobacterium* species, *Bordetella* species, *Escherichia* species, *Shigella* species, *Yersinia* species, *Salmonella* species, *Klebsiella* species, *Enterobacter* species, *Haemophilus* species, *Pasteurella* species, and *Streptobacillus* species; spirochetal species, *Campylobacter* species, *Vibrio* species; and intracellular bacteria including *Rickettsiae* species and *Chlamydia* species.

In an exemplary embodiment, the microorganism is a virus. In an exemplary embodiment, the virus is a member selected from hepatitis A-B, human rhinoviruses, Yellow fever virus, human respiratory coronaviruses, Severe acute respiratory syndrome (SARS), respiratory syncytial virus, influenza viruses, parainfluenza viruses 1-4, human immunodeficiency virus 1 (HIV-1), human immunodeficiency virus 2 (HIV-2), Herpes simplex virus 1 (HSV-1), Herpes simplex virus 2 (HSV-2), human cytomegalovirus (HCMV), Varicella zoster virus, Epstein-Barr (EBV), polioviruses, coxsackieviruses, echoviruses, rubella virus, neurodermatropic virus, variola virus, papoviruses, rabies virus, dengue virus, West Nile virus and SARS virus. In another exemplary embodiment, the virus is a member selected from picornaviridae, flaviviridae, coronaviridae, paramyxoviridae, orthomyxoviridae, retroviridae, herpesviridae and hepadnaviridae. In another exemplary embodiment, the virus is a member selected from a virus included in the following table:

TABLE A

Viruses

| Virus Category | Pertinent Human Infections |
|---|---|
| RNA Viruses | |
| Picornaviridae | Polio |
| | Human hepatitis A |
| | Human rhinovirus |
| Togaviridae and Flaviviridae | Rubella - German measles |
| | Yellow fever |
| Coronaviridae | Human respiratory coronavirus (HCV) |
| | Severe acute respiratory syndrome (SAR) |
| Rhabdoviridae | Lyssavirus - Rabies |
| Paramyxoviridae | Paramyxovirus - Mumps |
| | Morbillvirus - measles |
| | Pneumovirus - respiratory syncytial virus |
| Orthomyxoviridae | Influenza A-C |
| Bunyaviridae | Bunyavirus - Bunyamwera (BUN) |
| | Hantavirus - Hantaan (HTN) |
| | Nairevirus - Crimean-Congo hemorrhagic fever (CCHF) |
| | Phlebovirus - Sandfly fever (SFN) |
| | Uukuvirus - Uukuniemi (UUK) |
| | Rift Valley Fever (RVFN) |
| Arenaviridae | Junin - Argentine hemorrhagic fever |
| | Machupo -Bolivian hemorrhagic fever |
| | Lassa - Lassa fever |
| | LCM - aseptic lymphocyctic choriomeningitis |
| Reoviridae | Rotovirus |
| | Reovirus |
| | Orbivirus |
| Retroviridae | Human immunodeficiency virus 1 (HIV-1) |
| | Human immunodeficiency virus 2 (HIV-2) |
| | Simian immunodeficiency virus (SIV) |
| DNA Viruses | |
| Papovaviridae | Pediatric viruses that reside in kidney |
| Adenoviridae | Human respiratory distress and some deep-seated eye infections |
| Parvoviridae | Human gastro-intestinal distress (Norwalk Virus) |
| Herpesviridae | Herpes simplex virus 1 (HSV-1) |
| | Herpes simplex virus 2 (HSV-2) |
| | Human cytomegalovirus (HCMV) |
| | Varicella zoster virus (VZV) |
| | Epstein-Barr virus (EBV) |
| | Human herpes virus 6 (HHV6) |
| Poxviridae | Orthopoxvirus is sub-genus for smallpox |
| Hepadnaviridae | Hepatitis B virus (HBV) |
| | Hepatitis C virus (HCV) |

In another exemplary embodiment, the microorganism is a parasite. In an exemplary embodiment, the parasite is a member selected from *Plasmodium falciparum, P. vivax, P. ovale P. malariae, P. berghei, Leishmania donovani, L. infantum, L. chagasi, L. mexicana, L. amazonensis, L. venezuelensis, L. tropics, L. major, L. minor, L. aethiopica, L. Biana braziliensis, L. (V.) guyanensis, L. (V.) panamensis, L. (V) peruviana, Trypanosoma brucei rhodesiense, T. brucei gambiense, T. cruzi, Giardia intestinalis, G. lambda, Toxoplasma gondii, Entamoeba histolytica, Trichomonas vaginalis, Pneumocystis carinii,* and *Cryptosporidium parvum.*

VI. Methods of Treating or Preventing Infections

In another aspect, the invention provides a method of treating or preventing an infection. The method includes administering to the animal a therapeutically effective amount of the compound of the invention, sufficient to treat or prevent said infection. In an exemplary embodiment, the compound is a compound described herein. In another exemplary embodiment, the compound has a structure according to Formulae (I) to (Iak) and (II) to (XI). In another exemplary embodiment, the compound has a structure which is described in FIG. 19. In another exemplary embodiment, the compound has a structure which is described in FIG. 20. In another exemplary embodiment, the animal is a member selected from human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human. In another exemplary embodiment, the animal is a member selected from a human, cattle, goat, pig, sheep, horse, cow, bull, dog, guinea pig, gerbil, rabbit, cat, chicken and turkey. In another exemplary embodiment, the infection is a member selected from a systemic infection, a cutaneous infection, and an ungual, periungual or subungual infection.

In another exemplary embodiment, the treatment of a disorder or condition occurs through inhibition of an editing domain of an aminoacyl tRNA synthetase.

VI. a) Methods of Treating of Preventing Ungual and/or Periungual Infections

In another aspect, the invention provides a method of treating or preventing an ungual and/or periungual infection. The method includes administering to the animal a therapeutically effective amount of a compound or pharmaceutical formulation of the invention, sufficient to treat or prevent said infection. In another exemplary embodiment, the method includes administering the compound or pharmaceutical formulation of the invention at a site which is a member selected from the skin, nail, hair, hoof, claw and the skin surrounding the nail, hair, hoof and claw.

VI. a) 1) Onychomycosis

Onychomycosis is a disease of the nail caused by yeast, dermatophytes, or other molds, and represents approximately 50% of all nail disorders. Toenail infection accounts for approximately 80% of onychomycosis incidence, while fingernails are affected in about 20% of the cases. Dermatophytes are the most frequent cause of nail plate invasion, particularly in toenail onychomycosis. Onychomycosis caused by a dermatophyte is termed Tinea unguium. *Trichophyton rubrum* is by far the most frequently isolated dermatophyte, followed by *T. mentagrophytes.* Distal subungual onychomycosis is the most common presentation of tinea unguium, with the main site of entry through the hyponychium (the thickened epidermis underneath the free distal end of a nail) progressing in time to involve the nail bed and the nail plate. Discoloration, onycholysis, and accumulation of subungual debris and nail plate dystrophy characterize the disease. The disease adversely affects the quality of life of its victims, with subject complaints ranging from unsightly nails and discomfort with footwear, to more serious complications including secondary bacterial infections.

Many methods are known for the treatment of fungal infections, including the oral and topical use of antibiotics (e.g., nystatin and amphotericin B), imidazole anti-fungal agents such as miconazole, clotrimazole, fluconazole, econazole and sulconazole, and non-imidazole fungal agents such as the allylamine derivatives terbinafine and naftifine, and the benzylamine butenafine.

However, onychomycosis has proven to be resistant to most treatments. Nail fungal infections reside in an area difficult to access by conventional topical treatment and anti-fungal drugs cannot readily penetrate the nail plate to reach the infection sites under the nail. Therefore, onychomycosis has traditionally been treated by oral administration of anti-fungal drugs; however, clearly this is undesirable due to the potential for side effects of such drugs, in particular those caused by the more potent anti-fungal drugs such as itraconazole and ketoconazole. An alternative method of treatment of onychomycosis is by removal of the nail before treating with a topically active anti-fungal agent; such a method of treatment is equally undesirable. Systemic antimycotic agents require prolonged use and have the potential for significant side effects. Topical agents have usually been of little benefit, primarily because of poor penetration of the anti-fungal agents into and through the nail mass.

In an exemplary embodiment, the invention provides a method of treating or preventing onychomycosis. The method includes administering to a human or an animal a therapeutically effective amount of a compound of the invention, or a pharmaceutical formulation of the invention, sufficient to treat or prevent onychomycosis. In another exemplary embodiment, the method includes administering the pharmaceutical formulation of the invention at a site which is a member selected from the skin, nail, hair, hoof, claw and the skin surrounding the nail, hair, hoof and claw. In another exemplary embodiment, the pharmaceutical formulation includes a compound described herein. The method includes administering to a human or an animal a therapeutically effective amount of 1,3-dihydro-5-fluoro-1-hydroxy-2,1-benzoxaborole, sufficient to treat or prevent onychomycosis.

VI. a) 2) Other Unugal and Periungual Infections

In an exemplary embodiment, the invention provides a method of treating or preventing an ungual or periungual infection in a human or an animal. This method comprising administering to the human or the animal a therapeutically effective amount of a compound of the invention, thereby treating or preventing the ungual or periungual infection. In an exemplary embodiment, the ungual or periungual infection is onychomycosis. In an exemplary embodiment, the ungual or periungual infection is a member selected from: onychomycosis, chloronychia, paronychias, erysipeloid, onychorrhexis, gonorrhea, swimming-pool granuloma, larva migrans, leprosy, Orf nodule, milkers' nodules, herpetic whitlow, acute bacterial perionyxis, chronic perionyxis, sporotrichosis, syphilis, tuberculosis *verrucosa* cutis, tularemia, tungiasis, peri- and subungual warts, zona, nail dystrophy (trachyonychia), and dermatological diseases with an effect on the nails, such as psoriasis, pustular psoriasis, alopecia aerata, parakeratosis pustulosa, contact dermatosis, Reiter's syndrome, psoriasiform acral dermatitis, lichen planus, idiopathy atrophy in the nails, lichin nitidus, lichen striatus, inflammatory linear verrucous epidermal naevus (ILVEN), alopecia, pemphigus, bullous pemphigoid, acquired epidermolysis bullosa, Darier's disease, pityriasis rubra pilaris, palmoplantar keratoderma, contact eczema, polymorphic erythema, scabies, Bazex syndrome, systemic scleroderma, systemic lupus erythematosus, chronic lupus erythematosus, dermatomyositus.

The compounds and pharmaceutical formulations of the invention useful for ungual and periungual applications also find application in the cosmetics field, in particular for the treatment of irregularities of the nails, koilonychias, Beau's lines, longitudinal ridging, ingrown nails.

In an exemplary embodiment, the infection is of the skin, nail, hair, claw or hoof, hair, ear and eye and is a member selected from Sporotrichosis, Mycotic keratitis, Extension oculomycosis, Endogenous oculomycosis, Lobomycosis, Mycetoma, Piedra, Pityriasis versicolor, Tinea corporis, Tinea cruris, Tinea pedis, Tinea barbae, Tinea capitis, Tinea nigra, Otomycosis, Tinea favosa, Chromomycosis, and Tinea Imbricata. In an exemplary embodiment, the compound useful for treating these infections is 1,3-dihydro-5-fluoro-1-hydroxy-2,1-benzoxaborole.

VI. b) Methods of Treating Systemic Diseases

In another aspect, the invention provides a method of treating a systemic disease. The method involves contacting an animal with a compound of the invention. The method of delivery for treatment of systemic disesases can be oral, intravenous, transdermal, inhalation, intraperitoneal, and subcutaneous. In an exemplary embodiment, the compound administered is 1,3-dihydro-5-fluoro-1-hydroxy-2,1-benzoxaborole.

In an exemplary embodiment, the infection is systemic and is a member selected from candidiasis, aspergillosis, coccidioidomycosis, cryptococcosis, histoplasmosis, blastomycosis, paracoccidioidomycosis, zygomycosis, phaeohyphomycosis and rhinosporidiosis.

VI. c) Methods of Treating Diseases Involving Viruses

The compounds of the invention are useful for the treatment of diseases of both animals and humans, involving viruses. In an exemplary embodiment, the disease is a member selected from hepatitis A-B-C, yellow fever, respiratory syncytial, influenza, AIDS, herpes simplex, chicken pox, varicella zoster, and Epstein-Barr disease.

VI. d) Methods of Treating Diseases Involving Parasites

The compounds of the invention are useful for the treatment of diseases of both animals and humans, involving parasites. In an exemplary embodiment, the disease is a member selected from malaria, Chagas' disease, Leishmaniasis, African sleeping sickness (African human trypanosomiasis), giardiasis, toxoplasmosis, amebiasis and cryptosporidiosis.

In any of the methods according to the present invention set forth above, it is preferred that the aminoacyl tRNA synthetase is an aminoacyl tRNA synthetase comprising an editing domain. The editing domain is encoded by a portion of the aminoacyl tRNA synthetase involved in proofreading. The editing domain is preferably encoded by a DNA portion having at least conserved residues compared after alignment with the editing site of the leucyl-tRNA synthetase, valyl-tRNA synthetase and isoleucyl-tRNA synthetase. More preferably the synthetase is selected from the group consisting of the valyl-tRNA synthetase, isoleucyl-tRNA synthetase, leucyl-tRNA synthetase, alanyl-tRNA synthetase, prolyl-tRNA synthetase, threonyl-tRNA synthetase, phenyl-tRNA synthetase and lysyl-tRNA synthetase which are known to have an editing site or domain (see for Ile R S Baldwin, A. N. and Berg, P. (1966) J. Biol. Chem. 241, 839-845 and Eldred, E. W. and Schimmel, P. R. (1972) J. Biol. Chem. 247, 2961-2964; for Val R S, Fersht, A. R. and Kaethner, M. M. (1976) Biochemistry. 15 (15), 3342-3346; for Leu R S, English, S. et al., (1986) Nucleic Acids Research. 14 (19), 7529-7539; for Ala R S, Tsui, W. C. and Fersht, A. R. (1981) Nucleic Acids Research. 9, 7529-7539; for Pro R S, Beuning, P. J. and Musier-Forsyth, K. (2000) PNAS. 97 (16), 8916-8920; for Thr R S, Sankaranarayanan, R. et al., (2000) Nat. Struct. Biol. 7, 461-465 and Musier-Foryth, K. and Beuning, P. J. (2000) Nat. Struct. Biol. 7, 435-436; for PheRS, Yarus, M. (1972) PNAS. 69, 1915-1919 and for LysRS, Jakubowski, H. (1997) Biochemistry. 36, 11077-11085.

VII. Methods of Nail Penetration

It is believed that poor penetration of the active agent through the hoof or nail plate and/or excessive binding to keratin, (the major protein in nails and hair) are the reasons for the poor efficacy of 8% ciclopirox w/w in commercial lacquer and other topical treatments that have failed in clinical trials. In mild cases of onychomycosis, the pathogenic fungi reside in the nail plate only. In moderate to severe cases the pathogenic fungi establish a presence in the nail plate and in the nail bed. If the infection is cleared from the nail plate but not from the nail bed, the fungal pathogen can re-infect the nail plate. Therefore, to effectively treat onychomycosis, the infection must be eliminated from the nail plate and the nail bed. To do this, the active agent must penetrate and disseminate substantially throughout the nail plate and nail bed.

It is believed that in order for an active agent to be effective once disseminated throughout the infected area, it must be bioavailable to the fungal pathogen and cannot be so tightly bound to keratin that the drug cannot inhibit growth or kill the infecting fungi.

An understanding of the morphology of the nail plate suggests certain physicochemical properties of an active agent that would facilitate penetration of the nail plate. The desired physicochemical properties are described throughout. The tested compounds of the present invention are able to penetrate the nail plate and were also active against *Trichophyton rubrum* and *mentagrophytes* and other species. In addition, the tested compounds are also active against *Trichophyton rubrum* in the presence of 5% keratin powder.

In an exemplary embodiment, the invention provides a method of killing or inhibiting growth of a microorganism present in a human nail unit, wherein said human nail unit comprises a nail plate. The method comprising contacting a dorsal layer of the nail plate with a compound capable of penetrating the nail plate, traveling through the nail plate to a nail bed underlying said nail plate, and contacting said microorganism, under conditions sufficient for said compound to penetrate said nail plate. In this embodiment, the compound has a molecular weight of between about 100 Da and about 200 Da, a log P value of between about 1.0 and about 2.6, a water solubility greater than about 0.1 mg/mL octanol/saturated water, and an MIC of less than 16 µg/mL against said microorganism, thereby killing or inhibiting the growth of said microorganism.

In an exemplary embodiment, the compound has a structure according to Formula (I) described herein. In another exemplary embodiment, the compound has a structure according to Formula (Ia)-(Iaa) described herein. In another exemplary embodiment, the compound has a structure according to a member selected from Formula (I)-(Iaa), wherein $R^{9a}$, $R^{10a}$, $R^{11a}$ and $R^{12a}$ are members independently selected from members independently selected from H, halogen, cyano, nitro, substituted or unsubstituted methoxy, substituted or unsubstituted methyl, substituted or unsubstituted ethoxy, substituted or unsubstituted ethyl, trifluoromethyl, substituted or unsubstituted hydroxymethyl, substituted or unsubstituted hydroxyalkyl, substituted or unsubstituted benzyl, substituted or unsubstituted phenyl, substituted or unsubstituted phenyloxy, substituted or unsubstituted phenyl methoxy, substituted or unsubstituted thiophenyloxy, substituted or unsubstituted pyridinyloxy, substituted or unsubstituted pyrimidinyloxy, substituted or unsubstituted benzylfuran, substituted or unsubstituted methylthio, substituted or unsubstituted mercaptomethyl, substituted or unsubstituted mercaptoalkyl, substituted or unsubstituted phenylthio, substituted or unsubstituted thiophenylthio, substituted or unsubstituted phenyl methylthio, substituted or unsubstituted pyridinylthio, substituted or unsubstituted pyrimidinylthio, substituted or unsubstituted benzylthiofuranyl, substituted or unsubstituted phenylsulfonyl, substituted or unsubstituted benzylsulfonyl, substituted or unsubstituted phenylmethylsulfonyl, substituted or unsubstituted thiophenylsulfonyl, substituted or unsubstituted pyridinylsulfonyl, substituted or unsubstituted pyrimidinylsulfonyl, substituted or unsubstituted sulfonamidyl, substituted or unsubstituted phenylsulfinyl, substituted or unsubstituted benzylsulfinyl, substituted or unsubstituted phenylmethylsulfinyl, substituted or unsubstituted thiophenylsulfinyl, substituted or unsubstituted pyridinylsulfinyl, substituted or unsubstituted pyrimidinylsulfinyl, substituted or unsubstituted amino, substituted or unsubstituted alkylamino, substituted or unsubstituted dialkylamino, substituted or unsubstituted trifluoromethylamino, substituted or unsubstituted aminomethyl, substituted or unsubstituted alkylaminomethyl, substituted or unsubstituted dialkylaminomethyl, substituted or unsubstituted arylaminomethyl, substituted or unsubstituted benzylamino, substituted or unsubstituted phenylamino, substituted or unsubstituted thiophenylamino, substituted or unsubstituted pyridinylamino, substituted or unsubstituted pyrimidinylamino, substituted or unsubstituted indolyl, substituted or unsubstituted morpholino, substituted or unsubstituted alkylamido, substituted or unsubstituted arylamido, substituted or unsubstituted ureido, substituted or unsubstituted carbamoyl, and substituted or unsubstituted piperizinyl. In another exemplary embodiment, $R^{9a}$, $R^{10a}$, $R^{11a}$ and $R^{12a}$ are members independently selected from H, fluoro, chloro, bromo, nitro, cyano, amino, methyl, hydroxylmethyl, trifluoromethyl, methoxy, trifluoromethyoxy, ethyl, diethylcarbamoyl, pyridin-2-yl, pyridin-3-yl, pyridin-4-yl, pyrimidinyl, piperizino, piperizinyl, piperizinocarbonyl, piperizinylcarbonyl, carboxyl, 1-tetrazolyl, 1-ethoxycarbonylmethoxy, carboxymethoxy, thiophenyl, 3-(butylcarbonyl) phenylmethoxy, 1H-tetrazol-5-yl, 1-ethoxycarbonylmethyloxy-, 1-ethoxycarbonylmethyl-, 1-ethoxycarbonyl-, carboxymethoxy-, thiophen-2-yl, thiophen-2-ylthio-, thiophen-3-yl, thiophen-3-ylthio, 4-fluorophenylthio, butylcarbonylphenylmethoxy, butylcarbonylphenylmethyl, butylcarbonylmethyl, 1-(piperidin-1-yl)carbonyl)methyl, 1-(piperidin-1-yl)carbonyl)methoxy, 1-(piperidin-2-yl)carbonyl)methoxy, 1-(piperidin-3-yl)carbonyl)methoxy, 1-(4-(pyrimidin-2-yl)piperazin-1-yl)carbonyl)methoxy, 1-(4-(pyrimidin-2-yl)piperazin-1-yl)carbonyl)methyl, 1-(4-(pyrimidin-2-yl)piperazin-1-yl)carbonyl, 1-4-(pyrimidin-2-yl)piperazin-1-yl, 1-(4-(pyridin-2-yl)piperazin-1-yl) carbonyl), 1-(4-(pyridin-2-yl)piperazin-1-yl) carbonylmethyl, (1-(4-(pyridin-2-yl)piperazin-1-yl) carbonyl)-methoxy), 1-(4-(pyridin-2-yl)piperazin-1-yl, 1H-indol-1-yl, morpholino-, morpholinyl, morpholinocarbonyl, morpholinylcarbonyl, phenylureido, phenylcarbamoyl, acetamido, 3-(phenylthio)-1H-indol-1-yl, 3-(2-cyanoethylthio)-1H-indol-1-yl, benzylamino, 5-methoxy-3-(phenylthio)-1H-indol-1-yl, 5-methoxy-3-(2-cyanoethylthio)-1H-indol-1-yl)), 5-chloro-1H-indol-1-yl, 5-chloro-3-(2-cyanoethylthio)-1H-indol-1-yl)), dibenzylamino, benzylamino, 5-chloro-3-(phenylthio)-1H-indol-1-yl)), 4-(1H-tetrazol-5-yl)phenoxy, 4-(1H-tetrazol-5-yl)phenyl, 4-(1H-tetrazol-5-yl)phenylthio, 2-cyanophenoxy, 3-cyanophenoxy, 4-cyanophenoxy, 2-cyanophenylthio, 3-cyanophenylthio, 4-cyanophenylthio, 2-chlorophenoxy, 3-chlorophenoxy, 4-chlorophenoxy, 2-fluorophenoxy, 3-fluorophenoxy, 4-fluorophenoxy, 2-cyanobenzyloxy, 3-cyanobenzyloxy, 4-cyanobenzyloxy, 2-chlorobenzyloxy, 3-chlorobenzyloxy, 4-chlorobenzyloxy, 2-fluorobenzyloxy, 3-fluorobenzyloxy, and 4-fluorobenzyloxy. In another exemplary embodiment, wherein $R^{9a}$ is H and $R^{12a}$ is H. In another exemplary embodiment, the compound is 1,3-dihydro-5-fluoro-1-hydroxy-2,1-benzoxaborole.

In another exemplary embodiment, the invention provides a method of treating a disease caused by a microorganism present in a human nail unit, wherein said human nail unit comprises a nail plate, said method comprising: contacting a dorsal layer of the nail plate with a compound capable of penetrating the nail plate, traveling through the nail plate to a nail bed underlying said nail plate, and contacting said microorganism, under conditions sufficient for said compound to penetrate said nail plate and to treat said disease. In this embodiment, the compound has a molecular weight of between about 100 Da and about 200 Da; a log P value of between about 1.0 and about 2.6; a water solubility greater than about 0.1 mg/mL octanol/saturated water, and an MIC of less than 16 μg/mL against said microorganism, thereby treating said disease. In an exemplary embodiment, the compound has a structure according to Formula (I) described herein. In another exemplary embodiment, the compound has a structure which is a member selected from Formula (Ia)-(Iaa) described herein.

In another aspect, the invention provides a method of delivering a compound from the dorsal layer of the nail plate to the nail bed. This method comprises contacting the cell with a compound capable of penetrating the nail plate, under conditions sufficient to penetrate the nail. The compound has a molecular weight of between about 100 and about 200 Da. The compound also has a log P value of between about 1.0 and about 2.6. The compound additionally has a water solubility between about 0.1 mg/mL and 1 g/mL octanol/saturated water, thereby delivering said compound.

In a preferred embodiment, the physicochemical properties of the compound of the invention, described by quantities predictive for migration of the compound through the nail plate, including, but not limited to, molecular weight, log P and solubility in water, and the like, are effective to provide substantial penetration of the nail plate.

Compounds with a molecular weight of less than 200 Da penetrate the nail plate in a manner superior to the commercially available treatment for onychomycosis. In one embodiment of the present invention the compound has a molecular weight of between 130 and 200. In another embodiment of this invention, the compound has a molecular weight of from about 140 to about 200 Da. In another embodiment of this invention, the compound has a molecular weight of from about 170 to about 200 Da. In another embodiment of this invention, the compound has a molecular weight of from about 155 to about 190 Da. In another embodiment of this invention, the compound has a molecular weight of from about 165 to about 185 Da. In another embodiment of this invention, the compound has a molecular weight of from about 145 to about 170 Da. In yet another embodiment the molecular weight is either 151.93 or 168.39 Da.

In one embodiment of the present invention the compound has a log P value of between about −3.5 to about 2.5. In another exemplary embodiment, the compound has a log P value of from about −1.0 to about 2.5. In another exemplary embodiment, the compound has a log P value of from about −1.0 to about 2.0. In another exemplary embodiment, the compound has a log P value of from about −0.5 to about 2.5. In another exemplary embodiment, the compound has a log P value of from about −0.5 to about 1.5. In another exemplary embodiment, the compound has a log P value of from about 0.5 to about 2.5. In another exemplary embodiment, the compound has a log P value of from about 1.0 to about 2.5. In yet another exemplary embodiment, the compound has a log P value of 1.9 or 2.3.

Also contemplated by the present invention is a compound with a log P value less then 2.5, with a molecular weight less than 200 Da, that are still able to penetrate the nail plate.

In one embodiment of the present invention the compound has a water solubility between about 0.1 mg/mL to 1 g/mL in octanol saturated water. In one embodiment of the present invention the compound has a water solubility of between 0.1 mg/mL and 100 mg/mL. In another embodiment of this invention, the compound has a water solubility of from about 0.1 mg/mL and 10 mg/mL. In another embodiment of this invention, the compound has a water solubility of from about 0.1 mg/mL and 1 mg/mL. In another embodiment of this invention, the compound has a water solubility of from about 5 mg/mL and 1 g/mL. In another embodiment of this invention, the compound has a water solubility of from about 10 mg/mL and 500 g/mL. In another embodiment of this invention, the compound has a water solubility of from about 80 mg/mL and 250 mg/mL.

In an exemplary embodiment, the present invention provides a compound with a log P value selected from a range above, with a molecular weight selected from a range above, that are still able to penetrate the nail plate.

In an exemplary embodiment, the present invention provides compounds with a molecular weight selected from a range above, with a water solubility selected from a range above, that are still able to penetrate the nail plate.

In an exemplary embodiment, the present invention provides compounds with a log P selected from a range above, with a water solubility selected from a range above, that are still able to penetrate the nail plate.

In an exemplary embodiment, the present invention provides compounds with a molecular weight selected from a range above, with a log P selected from a range above, and with a water solubility selected from a range above, that are still able to penetrate the nail plate.

Penetration of the nail by the active ingredient may be effected by the polarity of the formulation. However, the polarity of the formulation is not expected have as much influence on nail penetration as some of the other factors, such as the molecular weight or the log P of the active ingredient. The presence of penetration enhancing agents in the formulation is likely to increase penetration of the active agent when compared to similar formulations containing no penetration enhancing agent.

Some examples of molecules with optimal physicochemical properties are given in the table below.

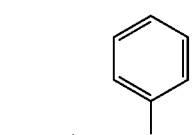

| Structure: | (compound 1) | (compound 2) |
|---|---|---|
| Formula: | $C_7H_6BFO_2$ | $C_7H_6BClO_2$ |
| Molecular weight (Da): | 151.93 | 168.39 |
| Plasma protein binding (%): | 66 | 83 |
| LogP: | 1.9 | 2.3 |
| Water solubility (μg/mL): | >100 | >100 |

Compound 3 below is an example of a compound similar in molecular weight to ciclopirox, and like ciclopirox, penetrates the nail plate poorly.

| Structure: (compound 3) | |
|---|---|
| Formula: | $C_{13}H_{10}BFO$ |
| Molecular weight (Da): | 212.03 |
| Plasma protein binding (%): | 100 |
| cLogP: | 3.55 |
| Water solubility (μg/mL): | not determined |

In a preferred embodiment the topical formulations including a compound described herein has a total molecular weight of less than 200 Da, has a Log P of less than 2.5, and a minimum inhibitory concentration against *Trichophyton rubrum* that is substantially unchanged in the presence of 5% keratin.

The efficacy coefficient (defined as flux over MIC) of a compound also informs one of skill regarding whether the compound may be effective in killing a microorganism, inhibiting the growth of a microorganism, or treating a disease which is caused by a microorganism present in a human nail unit, wherein said human nail unit comprises a nail plate. The method comprises: contacting a dorsal layer of the nail plate with a compound capable of penetrating the nail plate, traveling through the nail plate to a nail bed underlying said nail plate, and contacting said microorganism, under conditions sufficient for said compound to penetrate said nail plate and to treat said disease, wherein the compound has an efficacy coefficient above 10.

In an exemplary embodiment, the compound has an efficacy coefficient between about 10 and about 1000. In an exemplary embodiment, the compound has an efficacy coefficient between about 30 and about 100. In an exemplary embodiment, the compound has an efficacy coefficient between about 100 and about 500. In an exemplary embodiment, the compound has an efficacy coefficient between about 25 and about 200.

This invention is still further directed to methods for treating a fungal infection mediated at least in part by dermatophytes, *Trichophyton, Microsporum* or *Epidermophyton* species, or a yeast-like fungi including *Candida* species, in a human or an animal, which methods comprise administering to a human or an animal, that has been diagnosed with said fungal infection or is at risk of developing said fungal infection, a pharmaceutical composition comprising a pharmaceutically acceptable diluent and a therapeutically effective amount of a compound described herein or mixtures of one or more of such compounds. In one embodiment the infection is onychomycosis.

Compounds contemplated by the present invention may have broad spectrum antifungal activity and as such may be candidates for use against other cutaneous fungal infections.

The methods provided in this aspect of the invention are useful in the penetration of nails and hoofs, as well as the treatment of ungual and periungual conditions.

VIII. Pharmaceutical Formulations

In another aspect, the invention is a pharmaceutical formulation which includes: (a) a pharmaceutically acceptable excipient; and (b) a compound of the invention. In another aspect, the invention is a pharmaceutical formulation which includes: (a) a pharmaceutically acceptable excipient; and (b) a compound having a structure which is a member selected from Formulae (I), (Ia), (Ib), (Ic), (Id) (Ie), (If), (Ig), (Ih) (Ii), (Ij), (Ik), (Il) (Im), (In), (Io), (Ip) (Iq), (Ir), (Is), (It), (Iu), (Iv), (Iw), (Ix) (Iy), (Iz), (Iaa), (Iab), (Iac), (Iad), (Iae), (Iaf), (Iag), (Iah), (Iai), (Iaj), (Iak), (II), (IIa), (IIb), (IIc), (IId), (III). In another aspect, the invention is a pharmaceutical formulation which includes: (a) a pharmaceutically acceptable excipient; and (b) a compound which has a structure according to Formulae (VIII), (VIIIa), (VIIIb), (VIIIc), (VIIId), (VIIIe). In another aspect, the invention is a pharmaceutical formulation which includes: (a) a pharmaceutically acceptable excipient; and (b) a compound which has a structure which is a member selected from D1-D19, E1-E19, (VIII), (VIIIa), (VIIIb), (VIIIc), (VIIId), (VIIIe). In another aspect, the invention is a pharmaceutical formulation which includes: (a) a pharmaceutically acceptable excipient; and (b) a acyclic boronic ester of the invention. In an exemplary embodiment, the compound is described in FIG. 19. In another exemplary embodiment, the compound is described in FIG. 20. In another exemplary embodiment, the invention is a pharmaceutical formulation which includes: (a) a pharmaceutically acceptable excipient; and (b) a acyclic boronic ester of the invention.

In another aspect, the invention is a pharmaceutical formulation comprising: (a) a pharmaceutically acceptable excipient; and (b) a compound having a structure according to Formula I:

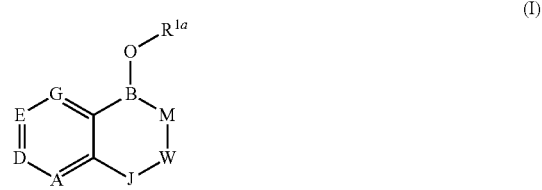

wherein B is boron. $R^{1a}$ is a member selected from a negative charge, a salt counterion, H, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. M is a member selected from oxygen, sulfur and $NR^{2a}$. $R^{2a}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. J is a member selected from $(CR^{3a}R^{4a})_{n1}$ and $CR^{5a}$. $R^{3a}$, $R^{4a}$, and $R^{5a}$ are members independently selected from H, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The index n1 is an integer selected from 0 to 2. W is a member selected from C=O (carbonyl), $(CR^{6a}R^{7a})_{m1}$ and $CR^{8a}$. $R^{6a}$, $R^{7a}$, and $R^{8a}$ are members independently selected from H, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The index m1 is an integer selected from 0 and 1. A is a member selected from $CR^{9a}$ and N. D is a member selected from $CR^{10a}$ and N. E is a member selected from $CR^{11a}$ and N. G is a member selected from $CR^{12a}$ and N. $R^{9a}$, $R^{10a}$, $R^{11a}$ and $R^{12a}$ are members independently selected from H, OR*, NR*R**, SR*, —S(O)R*, —S(O)$_2$R*, —S(O)$_2$NR*R**, —C(O)R*, —C(O)OR*, —C(O)NR*R**, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. Each R* and R** are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The combination of nitrogens (A+D+E+G) is an integer selected from 0 to 3. A member selected from $R^{3a}$, $R^{4a}$ and $R^{5a}$ and a member selected from $R^{6a}$, $R^{7a}$ and $R^{8a}$, together with the atoms to which they are attached, are optionally joined to form a 4 to 7 membered ring. $R^{3a}$ and $R^{4a}$, together with the atoms to which they are attached, are optionally joined to form a 4 to 7 membered ring. $R^{6a}$ and $R^{7a}$, together with the atoms to which they are attached, are optionally joined to form a 4 to 7 membered ring. $R^{9a}$ and $R^{10a}$, together with the atoms to which they are attached, are optionally joined to form a 4 to 7 membered ring. $R^{10a}$ and $R^{11a}$, together with the atoms to which they are attached, are optionally joined to form a 4 to 7 membered ring. $R^{11a}$ and $R^{12a}$, together with the atoms to which they are attached, are optionally joined to form a 4 to 7 membered ring.

In another exemplary embodiment, there is a proviso that the compound cannot have a structure according to Formula (Ix):

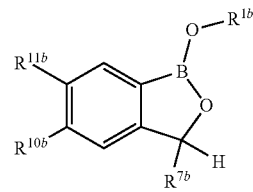

(Ix)

wherein $R^{7b}$ is a member selected from H, methyl, ethyl and phenyl. $R^{10b}$ is a member selected from H, OH, NH$_2$, SH, halogen, substituted or unsubstituted phenoxy, substituted or unsubstituted phenylalkyloxy, substituted or unsubstituted phenylthio and substituted or unsubstituted phenylalkylthio. $R^{11b}$ is a member selected from H, OH, NH$_2$, SH, methyl, substituted or unsubstituted phenoxy, substituted or unsubstituted phenylalkyloxy, substituted or unsubstituted phenylthio and substituted or unsubstituted phenylalkylthio. In another exemplary embodiment, there is a proviso that the compound cannot have a structure according to Formula (Ix) wherein $R^{1b}$ is a member selected from a negative charge, H and a salt counterion. In another exemplary embodiment, there is a proviso that the compound cannot have a structure according to Formula (Ix) wherein $R^{10b}$ and $R^{11b}$ are H. In another exemplary embodiment, there is a proviso that the compound cannot have a structure according to Formula (Ix) wherein one member selected from $R^{10b}$ and $R^{11b}$ is H and the other member selected from $R^{10b}$ and $R^{11b}$ is a member selected from halo, methyl, cyano, methoxy, hydroxymethyl and p-cyanophenyloxy. In another exemplary embodiment, there is a proviso that the compound cannot have a structure according to Formula (Ix) wherein $R^{10b}$ and $R^{11b}$ are members independently selected from fluoro, chloro, methyl, cyano, methoxy, hydroxymethyl, and p-cyanophenyl. In another exemplary embodiment, there is a proviso that the compound cannot have a structure according to Formula (Ix) wherein $R^{1b}$ is a member selected from a negative charge, H and a salt counterion; $R^{7b}$ is H; $R^{10b}$ is F and $R^{11b}$ is H. In another exemplary embodiment, there is a proviso that the compound cannot have a structure according to Formula (Ix) wherein $R^{11b}$ and $R^{12b}$, along with the atoms to which they are attached, are joined to form a phenyl group. In another exemplary embodiment, there is a proviso that the compound cannot have a structure according to Formula (Ix) wherein $R^{1b}$ is a member selected from a negative charge, H and a salt counterion; $R^{7b}$ is H; $R^{10b}$ is 4-cyanophenoxy; and $R^{11b}$ is H.

In another exemplary embodiment, there is a proviso that the compound cannot have a structure according to Formula (Iy)

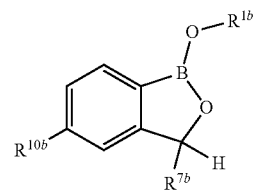

(Iy)

wherein $R^{10b}$ is a member selected from H, halogen, CN and substituted or unsubstituted $C_{1-4}$ alkyl.

In an exemplary embodiment, the pharmaceutical formulation comprises a compound that has a structure according to Formula (Ia):

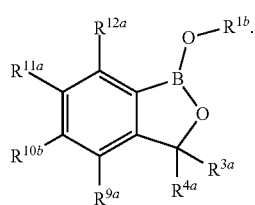

(Ia)

In another exemplary embodiment, each $R^{3a}$ and $R^{4a}$ is a member independently selected from H, cyano, substituted or unsubstituted methyl, substituted or unsubstituted ethyl, trifluoromethyl, substituted or unsubstituted hydroxymethyl, substituted or unsubstituted hydroxyalkyl, substituted or unsubstituted benzyl, substituted or unsubstituted phenyl, substituted or unsubstituted mercaptomethyl, substituted or unsubstituted mercaptoalkyl, substituted or unsubstituted aminomethyl, substituted or unsubstituted alkylaminomethyl, substituted or unsubstituted dialkylaminomethyl, substituted or unsubstituted arylaminomethyl, substituted or unsubstituted indolyl and substituted or unsubstituted amido. In another exemplary embodiment, each $R^{3a}$ and $R^{4a}$ is a member independently selected from cyano, substituted or unsubstituted methyl, substituted or unsubstituted ethyl, trifluoromethyl, substituted or unsubstituted hydroxymethyl, substituted or unsubstituted hydroxyalkyl, substituted or unsubstituted benzyl, substituted or unsubstituted phenyl, substituted or unsubstituted mercaptomethyl, substituted or unsubstituted mercaptoalkyl, substituted or unsubstituted aminomethyl, substituted or unsubstituted alkylaminomethyl, substituted or unsubstituted dialkylaminomethyl, substituted or unsubstituted arylaminomethyl, substituted or unsubstituted indolyl, substituted or unsubstituted amido.

In another exemplary embodiment, each $R^{3a}$ and $R^{4a}$ is a member selected from H, substituted or unsubstituted methyl, substituted or unsubstituted ethyl, substituted or unsubstituted propyl, substituted or unsubstituted isopropyl, substituted or unsubstituted butyl, substituted or unsubstituted t-butyl, substituted or unsubstituted phenyl and substituted or unsubstituted benzyl. In another exemplary embodiment, $R^{3a}$ and $R^{4a}$ is a member selected from methyl, ethyl, propyl, isopropyl, butyl, t-butyl, phenyl and benzyl. In another exemplary embodiment, $R^{3a}$ is H and $R^{4a}$ is a member selected from methyl, ethyl, propyl, isopropyl, butyl, t-butyl, phenyl and benzyl. In another exemplary embodiment, $R^{3a}$ is H and $R^{4a}$ H.

In another exemplary embodiment, $R^{9a}$, $R^{10a}$, $R^{11a}$ and $R^{12a}$ is a member independently selected from H, OR*, NR*R**, SR*, —S(O)R*, —S(O)$_2$R*, —S(O)$_2$NR*R**, —C(O)R*, —C(O)OR*, —C(O)NR*R**, halogen, cyano, nitro, substituted or unsubstituted methoxy, substituted or unsubstituted methyl, substituted or unsubstituted ethoxy, substituted or unsubstituted ethyl, trifluoromethyl, substituted or unsubstituted hydroxymethyl, substituted or unsubstituted hydroxyalkyl, substituted or unsubstituted benzyl, substituted or unsubstituted phenyl, substituted or unsubstituted phenyloxy, substituted or unsubstituted phenyl methoxy, substituted or unsubstituted thiophenyloxy, substituted or unsubstituted pyridinyloxy, substituted or unsubstituted pyrimidinyloxy, substituted or unsubstituted benzylfuran, substituted or unsubstituted methylthio, substituted or unsubstituted mercaptomethyl, substituted or unsubstituted mercaptoalkyl, substituted or unsubstituted phenylthio, substituted or unsubstituted thiophenylthio, substituted or unsubstituted phenyl methylthio, substituted or unsubstituted pyridinylthio, substituted or unsubstituted pyrimidinylthio, substituted or unsubstituted benzylthiofuranyl, substituted or unsubstituted phenylsulfonyl, substituted or unsubstituted benzylsulfonyl, substituted or unsubstituted phenylmethylsulfonyl, substituted or unsubstituted thiophenylsulfonyl, substituted or unsubstituted pyridinylsulfonyl, substituted or unsubstituted pyrimidinylsulfonyl, substituted or unsubstituted sulfonamidyl, substituted or unsubstituted phenylsulfinyl, substituted or unsubstituted benzylsulfinyl, substituted or unsubstituted phenylmethylsulfinyl, substituted or unsubstituted thiophenylsulfinyl, substituted or unsubstituted pyridinylsulfinyl, substituted or unsubstituted pyrimidinylsulfinyl, substituted or unsubstituted amino, substituted or unsubstituted alkylamino, substituted or unsubstituted dialkylamino, substituted or unsubstituted trifluoromethylamino, substituted or unsubstituted aminomethyl, substituted or unsubstituted alkylaminomethyl, substituted or unsubstituted dialkylaminomethyl, substituted or unsubstituted arylaminomethyl, substituted or unsubstituted benzylamino, substituted or unsubstituted phenylamino, substituted or unsubstituted thiophenylamino, substituted or unsubstituted pyridinylamino, substituted or unsubstituted pyrimidinylamino, substituted or unsubstituted indolyl, substituted or unsubstituted morpholino, substituted or unsubstituted alkylamido, substituted or unsubstituted arylamido, substituted or unsubstituted ureido, substituted or unsubstituted carbamoyl, and substituted or unsubstituted piperizinyl. In an exemplary embodiment, $R^{9a}$, $R^{10a}$, $R^{11a}$ and $R^{12a}$ are selected from the previous list of substituents with the exception of —C(O)R*, —C(O)OR*, —C(O)NR*R**.

In another exemplary embodiment, $R^{6a}$, $R^{7a}$, $R^{9a}$, $R^{10a}$, $R^{11a}$ and $R^{12a}$ are members independently selected from fluoro, chloro, bromo, nitro, cyano, amino, methyl, hydroxylmethyl, trifluoromethyl, methoxy, trifluoromethyoxy, ethyl, diethylcarbamoyl, pyridin-2-yl, pyridin-3-yl, pyridin-4-yl, pyrimidinyl, piperizino, piperizinyl, piperizinocarbonyl, piperizinylcarbonyl, carboxyl, 1-tetrazolyl, 1-ethoxycarbonylmethoxy, carboxymethoxy, thiophenyl, 3-(butylcarbonyl) phenylmethoxy, 1H-tetrazol-5-yl, 1-ethoxycarbonylmethyloxy-, 1-ethoxycarbonylmethyl-, 1-ethoxycarbonyl-, carboxymethoxy-, thiophen-2-yl, thiophen-2-ylthio-, thiophen-3-yl, thiophen-3-ylthio, 4-fluorophenylthio, butylcarbonylphenylmethoxy, butylcarbonylphenylmethyl, butylcarbonylmethyl, 1-(piperidin-1-yl)carbonyl)methyl, 1-(piperidin-1-yl)carbonyl)methoxy, 1-(piperidin-2-yl)carbonyl)methoxy, 1-(piperidin-3-yl)carbonyl)methoxy, 1-(4-(pyrimidin-2-yl)piperazin-1-yl)carbonyl)methoxy, 1-(4-(pyrimidin-2-yl)piperazin-1-yl)carbonyl) methyl, 1-(4-(pyrimidin-2-yl)piperazin-1-yl)carbonyl, 1-4-(pyrimidin-2-yl)piperazin-1-yl, 1-(4-(pyridin-2-yl)piperazin-1-yl)carbonyl), 1-(4-(pyridin-2-yl)piperazin-1-yl)carbonylmethyl, (1-(4-(pyridin-2-yl)piperazin-1-yl)carbonyl)-methoxy), 1-(4-(pyridin-2-yl)piperazin-1-yl, 1H-indol-1-yl, morpholino-, morpholinyl, morpholinocarbonyl, morpholinylcarbonyl, phenylureido, phenylcarbamoyl, acetamido, 3-(phenylthio)-1H-indol-1-yl, 3-(2-cyanoethylthio)-1H-indol-1-yl, benzylamino, 5-methoxy-3-(phenylthio)-1H-indol-1-yl, 5-methoxy-3-(2-cyanoethylthio)-1H-indol-1-yl)), 5-chloro-1H-indol-1-yl, 5-chloro-3-(2-cyanoethylthio)-1H-indol-1-yl)), dibenzylamino, benzylamino, 5-chloro-3-(phenylthio)-1H-indol-1- yl)), 4-(1H-tetrazol-5-yl)phenoxy, 4-(1H-tetrazol-5-yl)phenyl, 4-(1H-tetrazol-5-yl)phenylthio, 2-cyanophenoxy, 3-cyanophenoxy, 4-cyanophenoxy, 2-cyanophenylthio, 3-cyanophenylthio, 4-cyanophenylthio, 2-chlorophenoxy, 3-chlorophenoxy, 4-chlorophenoxy, 2-fluorophenoxy, 3-fluorophenoxy, 4-fluorophenoxy, 2-cyanobenzyloxy, 3-cyanobenzyloxy, 4-cyanobenzyloxy, 2-chlorobenzyloxy, 3-chlorobenzyloxy, 4-chlorobenzyloxy, 2-fluorobenzyloxy, 3-fluorobenzyloxy, 4-fluorobenzyloxy, unsubstituted phenyl, unsubstituted benzyl.

In an exemplary embodiment, the pharmaceutical formulation comprises a compound that has a structure which is a member according the following formulas:

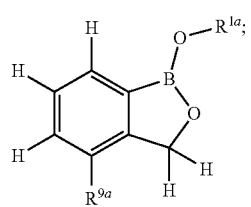
(Ib)

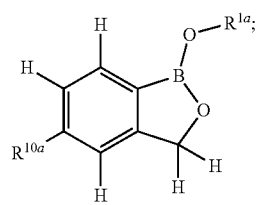
(Ic)

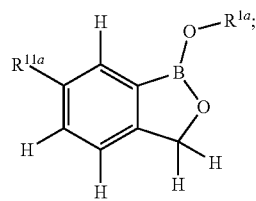
(Id)

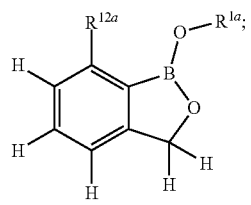
(Ie)

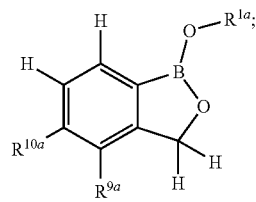
(If)

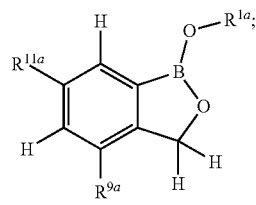
(Ig)

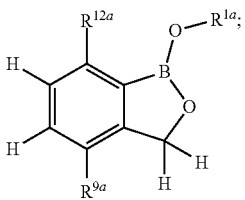
(Ih)

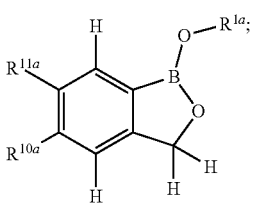
(Ii)

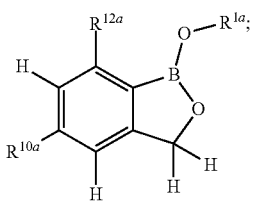
(Ij)

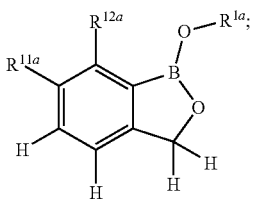
(Ik)

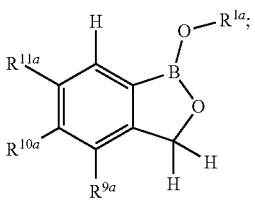
(Il)

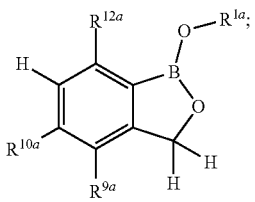
(Im)

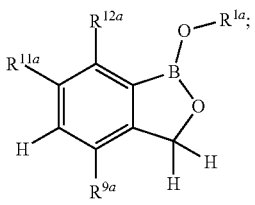
(In)

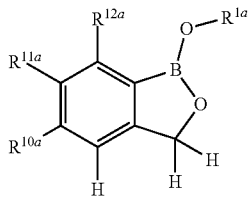

(Io)

In an exemplary embodiment, the pharmaceutical formulation comprises a compound that has a structure according to one of Formulae I-Io with substituent selections for $R^{9a}$, $R^{10a}$, $R^{11a}$ and $R^{12a}$ including all the possibilities contained in paragraph 106 except for H. In an exemplary embodiment, the pharmaceutical formulation comprises a compound that has a structure according to one of Formulae Ib-Io with substituent selections for $R^{9a}$, $R^{10a}$, $R^{11a}$ and $R^{12a}$ including all the possibilities contained in paragraph 107 except for H.

In an exemplary embodiment, the pharmaceutical formulation comprises a compound that has a formula according to Formulae (Ib)-(Ie) wherein Rla is a member selected from H, a negative charge and a salt counterion and the remaining R group ($R^{9a}$ in Ib, $R^{10a}$ in Ic, $R^{11a}$ in Id, and $R^{12a}$ in Ie) is a member selected from fluoro, chloro, bromo, nitro, cyano, amino, methyl, hydroxylmethyl, trifluoromethyl, methoxy, trifluoromethyoxy, ethyl, diethylcarbamoyl, pyridin-2-yl, pyridin-3-yl, pyridin-4-yl, pyrimidinyl, piperizino, piperizinyl, piperizinocarbonyl, piperizinylcarbonyl, carboxyl, 1-tetrazolyl, 1-ethoxycarbonylmethoxy, carboxymethoxy, thiophenyl, 3-(butylcarbonyl) phenylmethoxy, 1H-tetrazol-5-yl, 1-ethoxycarbonylmethyloxy-, 1-ethoxycarbonylmethyl-, 1-ethoxycarbonyl-, carboxymethoxy-, thiophen-2-yl, thiophen-2-ylthio-, thiophen-3-yl, thiophen-3-ylthio, 4-fluorophenylthio, butylcarbonylphenylmethoxy, butylcarbonylphenylmethyl, butylcarbonylmethyl, 1-(piperidin-1-yl)carbonyl)methyl, 1-(piperidin-1-yl)carbonyl)methoxy, 1-(piperidin-2-yl)carbonyl)methoxy, 1-(piperidin-3-yl)carbonyl)methoxy, 1-(4-(pyrimidin-2-yl)piperazin-1-yl)carbonyl)methoxy, 1-(4-(pyrimidin-2-yl)piperazin-1-yl)carbonyl)methyl, 1-(4-(pyrimidin-2-yl)piperazin-1-yl)carbonyl, 1-4-(pyrimidin-2-yl)piperazin-1-yl, 1-(4-(pyridin-2-yl)piperazin-1-yl)carbonyl), 1-(4-(pyridin-2-yl)piperazin-1-yl)carbonylmethyl, (1-(4-(pyridin-2-yl)piperazin-1-yl)carbonyl)-methoxy), 1-(4-(pyridin-2-yl)piperazin-1-yl, 1H-indol-1-yl, morpholino-, morpholinyl, morpholinocarbonyl, morpholinylcarbonyl, phenylureido, phenylcarbamoyl, acetamido, 3-(phenylthio)-1H-indol-1-yl, 3-(2-cyanoethylthio)-1H-indol-1-yl, benzylamino, 5-methoxy-3-(phenylthio)-1H-indol-1-yl, 5-methoxy-3-(2-cyanoethylthio)-1H-indol-1-yl)), 5-chloro-1H-indol-1-yl, 5-chloro-3-(2-cyanoethylthio)-1H-indol-1-yl)), dibenzylamino, benzylamino, 5-chloro-3-(phenylthio)-1H-indol-1-yl)), 4-(1H-tetrazol-5-yl)phenoxy, 4-(1H-tetrazol-5-yl)phenyl, 4-(1H-tetrazol-5-yl)phenylthio, 2-cyanophenoxy, 3-cyanophenoxy, 4-cyanophenoxy, 2-cyanophenylthio, 3-cyanophenylthio, 4-cyanophenylthio, 2-chlorophenoxy, 3-chlorophenoxy, 4-chlorophenoxy, 2-fluorophenoxy, 3-fluorophenoxy, 4-fluorophenoxy, 2-cyanobenzyloxy, 3-cyanobenzyloxy, 4-cyanobenzyloxy, 2-chlorobenzyloxy, 3-chlorobenzyloxy, 4-chlorobenzyloxy, 2-fluorobenzyloxy, 3-fluorobenzyloxy and 4-fluorobenzyloxy.

In an exemplary embodiment, the pharmaceutical formulation comprises a compound that has a formula according to Formulae (If)-(Ik) wherein Rla is a member selected from H, a negative charge and a salt counterion and each of the remaining two R groups ($R^{9a}$ and $R^{10a}$ in If, $R^{9a}$ and $R^{11a}$ in Ig, $R^{9a}$ and $R^{12a}$ in Ih, $R^{10a}$ and $R^{11a}$ in Ii, $R^{10a}$ and $R^{12a}$ in Ij, $R^{11a}$ and $R^{12a}$ in Ik) is a member independently selected from fluoro, chloro, bromo, nitro, cyano, amino, methyl, hydroxylmethyl, trifluoromethyl, methoxy, trifluoromethyoxy, ethyl, diethylcarbamoyl, pyridin-2-yl, pyridin-3-yl, pyridin-4-yl, pyrimidinyl, piperizino, piperizinyl, piperizinocarbonyl, piperizinylcarbonyl, carboxyl, 1-tetrazolyl, 1-ethoxycarbonylmethoxy, carboxymethoxy, thiophenyl, 3-(butylcarbonyl) phenylmethoxy, 1H-tetrazol-5-yl, 1-ethoxycarbonylmethyloxy-, 1-ethoxycarbonylmethyl-, 1-ethoxycarbonyl-, carboxymethoxy-, thiophen-2-yl, thiophen-2-ylthio-, thiophen-3-yl, thiophen-3-ylthio, 4-fluorophenylthio, butylcarbonylphenylmethoxy, butylcarbonylphenylmethyl, butylcarbonylmethyl, 1-(piperidin-1-yl)carbonyl)methyl, 1-(piperidin-1-yl)carbonyl)methoxy, 1-(piperidin-2-yl)carbonyl)methoxy, 1-(piperidin-3-yl)carbonyl)methoxy, 1-(4-(pyrimidin-2-yl)piperazin-1-yl)carbonyl)methoxy, 1-(4-(pyrimidin-2-yl)piperazin-1-yl)carbonyl)methyl, 1-(4-(pyrimidin-2-yl)piperazin-1-yl)carbonyl, 1-4-(pyrimidin-2-yl)piperazin-1-yl, 1-(4-(pyridin-2-yl)piperazin-1-yl)carbonyl), 1-(4-(pyridin-2-yl)piperazin-1-yl)carbonylmethyl, (1-(4-(pyridin-2-yl)piperazin-1-yl)carbonyl)-methoxy), 1-(4-(pyridin-2-yl)piperazin-1-yl, 1H-indol-1-yl, morpholino-, morpholinyl, morpholinocarbonyl, morpholinylcarbonyl, phenylureido, phenylcarbamoyl, acetamido, 3-(phenylthio)-1H-indol-1-yl, 3-(2-cyanoethylthio)-1H-indol-1-yl, benzylamino, 5-methoxy-3-(phenylthio)-1H-indol-1-yl, 5-methoxy-3-(2-cyanoethylthio)-1H-indol-1-yl)), 5-chloro-1H-indol-1-yl, 5-chloro-3-(2-cyanoethylthio)-1H-indol-1-yl)), dibenzylamino, benzylamino, 5-chloro-3-(phenylthio)-1H-indol-1-yl)), 4-(1H-tetrazol-5-yl)phenoxy, 4-(1H-tetrazol-5-yl)phenyl, 4-(1H-tetrazol-5-yl)phenylthio, 2-cyanophenoxy, 3-cyanophenoxy, 4-cyanophenoxy, 2-cyanophenylthio, 3-cyanophenylthio, 4-cyanophenylthio, 2-chlorophenoxy, 3-chlorophenoxy, 4-chlorophenoxy, 2-fluorophenoxy, 3-fluorophenoxy, 4-fluorophenoxy, 2-cyanobenzyloxy, 3-cyanobenzyloxy, 4-cyanobenzyloxy, 2-chlorobenzyloxy, 3-chlorobenzyloxy, 4-chlorobenzyloxy, 2-fluorobenzyloxy, 3-fluorobenzyloxy, and 4-fluorobenzyloxy.

In an exemplary embodiment, the pharmaceutical formulation comprises a compound that has a formula according to Formulae (Il)-(Io) wherein $R^{1a}$ is a member selected from H, a negative charge and a salt counterion and each of the remaining three R groups ($R^{9a}$, $R^{10a}$, $R^{11a}$ in (Il), $R^{9a}$, $R^{10a}$, $R^{12a}$ in (Im), $R^{9a}$, $R^{11a}$, $R^{12a}$ in (In), $R^{10a}$, $R^{11a}$, $R^{12a}$ in (Io)) is a member independently selected from fluoro, chloro, bromo, nitro, cyano, amino, methyl, hydroxylmethyl, trifluoromethyl, methoxy, trifluoromethyoxy, ethyl, diethylcarbamoyl, pyridin-2-yl, pyridin-3-yl, pyridin-4-yl, pyrimidinyl, piperizino, piperizinyl, piperizinocarbonyl, piperizinylcarbonyl, carboxyl, 1-tetrazolyl, 1-ethoxycarbonylmethoxy, carboxymethoxy, thiophenyl, 3-(butylcarbonyl) phenylmethoxy, 1H-tetrazol-5-yl, 1-ethoxycarbonylmethyloxy-, 1-ethoxycarbonylmethyl-, 1-ethoxycarbonyl-, carboxymethoxy-, thiophen-2-yl, thiophen-2-ylthio-, thiophen-3-yl, thiophen-3-ylthio, 4-fluorophenylthio, butylcarbonylphenylmethoxy, butylcarbonylphenylmethyl, butylcarbonylmethyl, 1-(piperidin-1-yl)carbonyl)methyl, 1-(piperidin-1-yl)carbonyl)methoxy, 1-(piperidin-2-yl)carbonyl)methoxy, 1-(piperidin-3-yl)carbonyl)methoxy, 1-(4-(pyrimidin-2-yl)piperazin-1-yl)carbonyl)methoxy, 1-(4-(pyrimidin-2-yl)piperazin-1-yl)carbonyl)methyl, 1-(4-(pyrimidin-2-yl)piperazin-1-yl)carbonyl, 1-4-(pyrimidin-2-yl)piperazin-1-yl, 1-(4-(pyridin-2-yl)piperazin-1-yl)

carbonyl), 1-(4-(pyridin-2-yl)piperazin-1-yl)carbonylmethyl, (1-(4-(pyridin-2-yl)piperazin-1-yl)carbonyl)-methoxy), 1-(4-(pyridin-2-yl)piperazin-1-yl, 1H-indol-1-yl, morpholino-, morpholinyl, morpholinocarbonyl, morpholinylcarbonyl, phenylureido, phenylcarbamoyl, acetamido, 3-(phenylthio)-1H-indol-1-yl, 3-(2-cyanoethylthio)-1H-indol-1-yl, benzylamino, 5-methoxy-3-(phenylthio)-1H-indol-1-yl, 5-methoxy-3-(2-cyanoethylthio)-1H-indol-1-yl)), 5-chloro-1H-indol-1-yl, 5-chloro-3-(2-cyanoethylthio)-1H-indol-1-yl)), dibenzylamino, benzylamino, 5-chloro-3-(phenylthio)-1H-indol-1-yl)), 4-(1H-tetrazol-5-yl)phenoxy, 4-(1H-tetrazol-5-yl)phenyl, 4-(1H-tetrazol-5-yl)phenylthio, 2-cyanophenoxy, 3-cyanophenoxy, 4-cyanophenoxy, 2-cyanophenylthio, 3-cyanophenylthio, 4-cyanophenylthio, 2-chlorophenoxy, 3-chlorophenoxy, 4-chlorophenoxy, 2-fluorophenoxy, 3-fluorophenoxy, 4-fluorophenoxy, 2-cyanobenzyloxy, 3-cyanobenzyloxy, 4-cyanobenzyloxy, 2-chlorobenzyloxy, 3-chlorobenzyloxy, 4-chlorobenzyloxy, 2-fluorobenzyloxy, 3-fluorobenzyloxy, and 4-fluorobenzyloxy.

In an exemplary embodiment, the pharmaceutical formulation comprises a compound that is a member selected from:

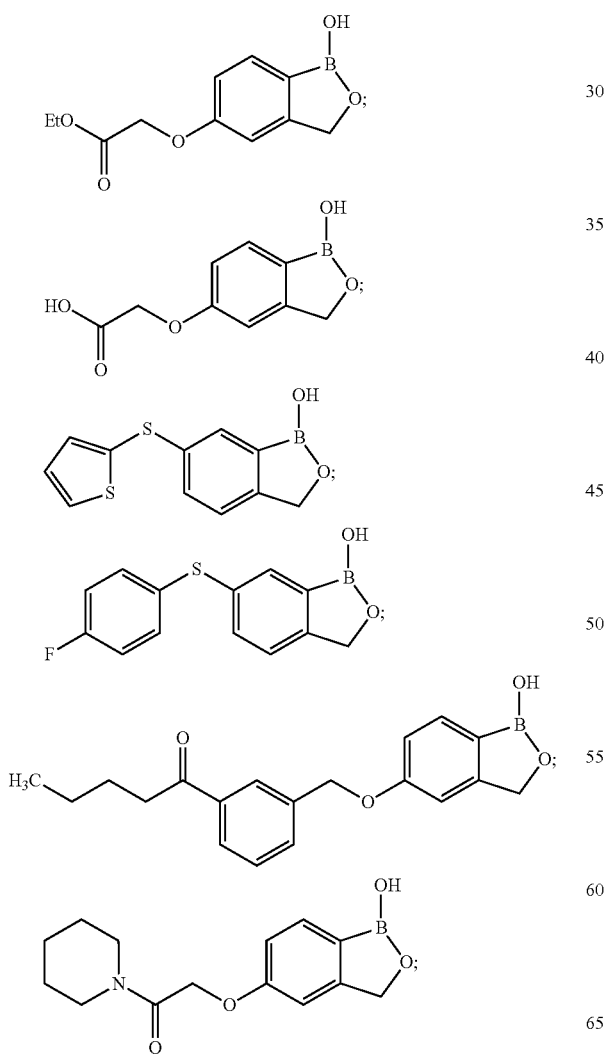

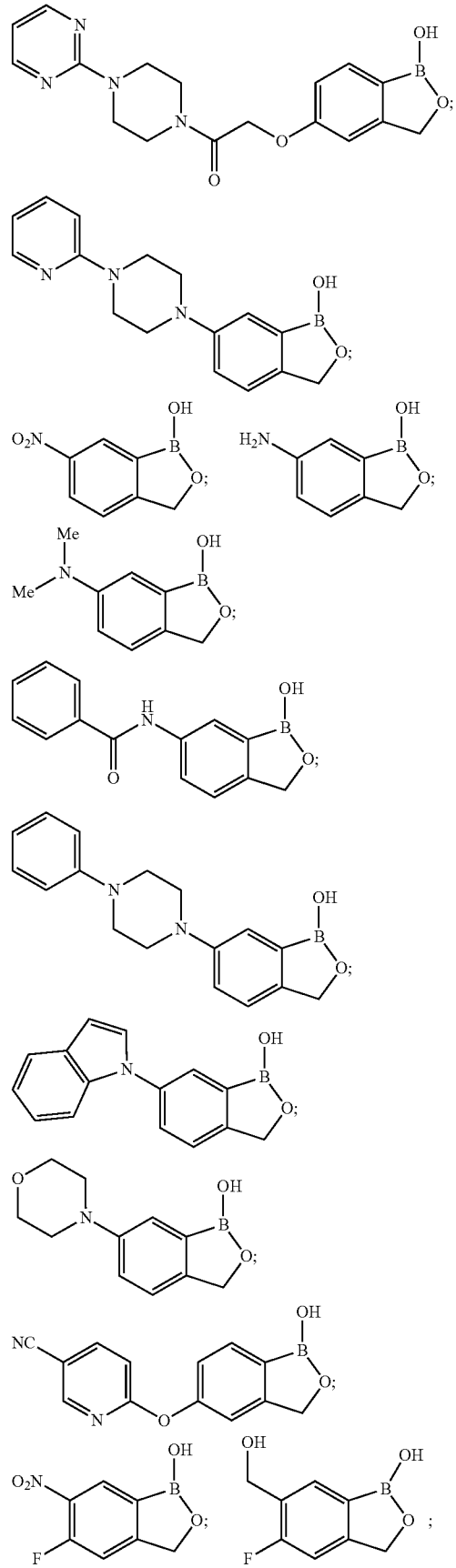

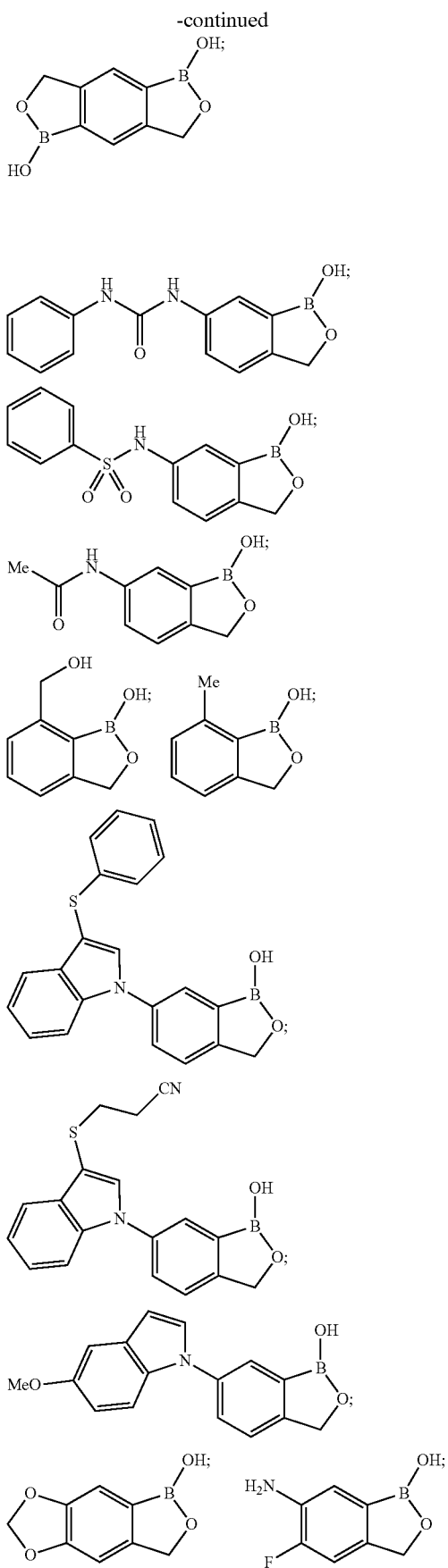
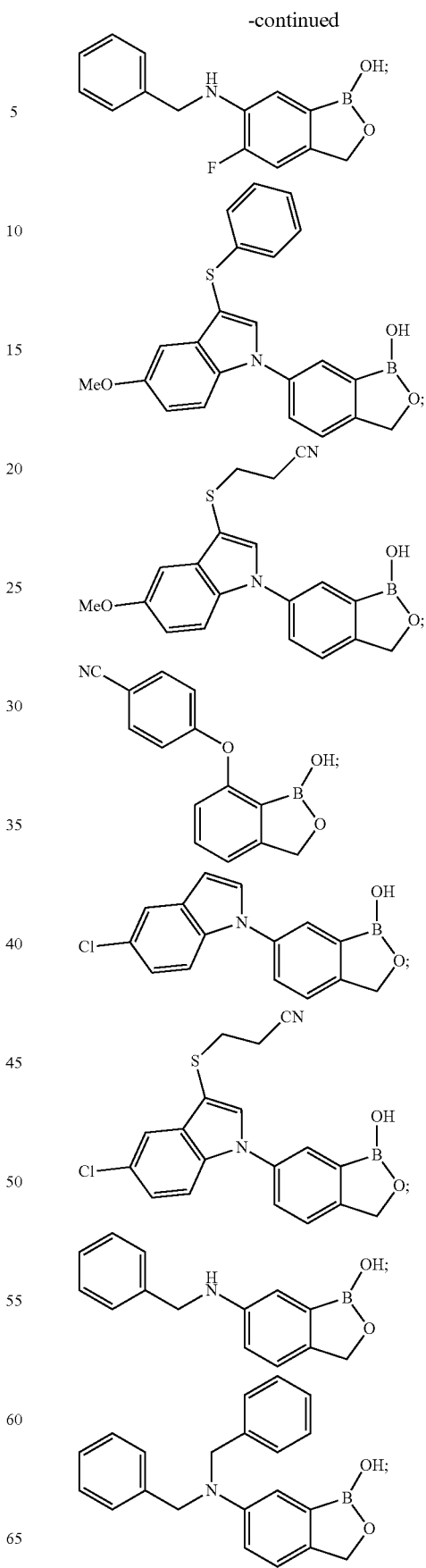

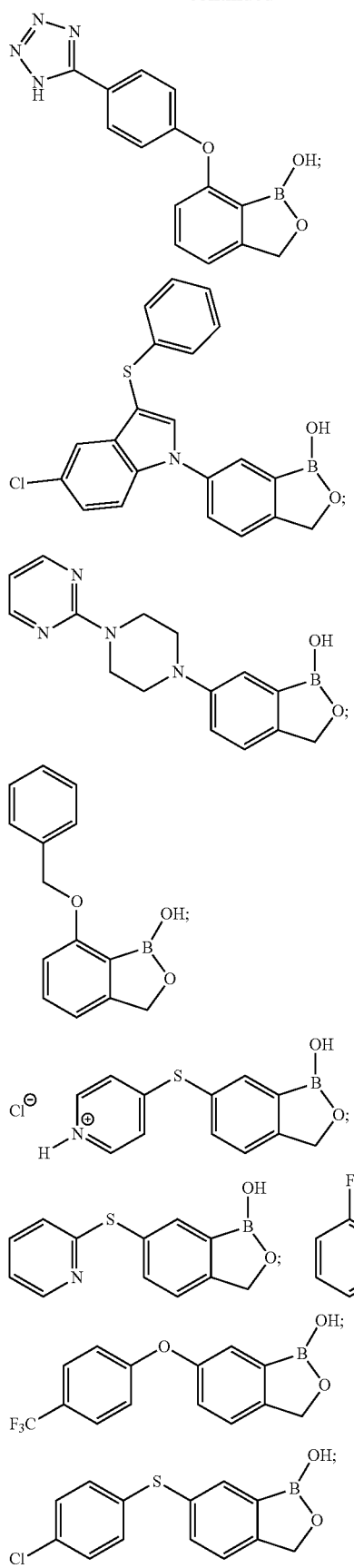
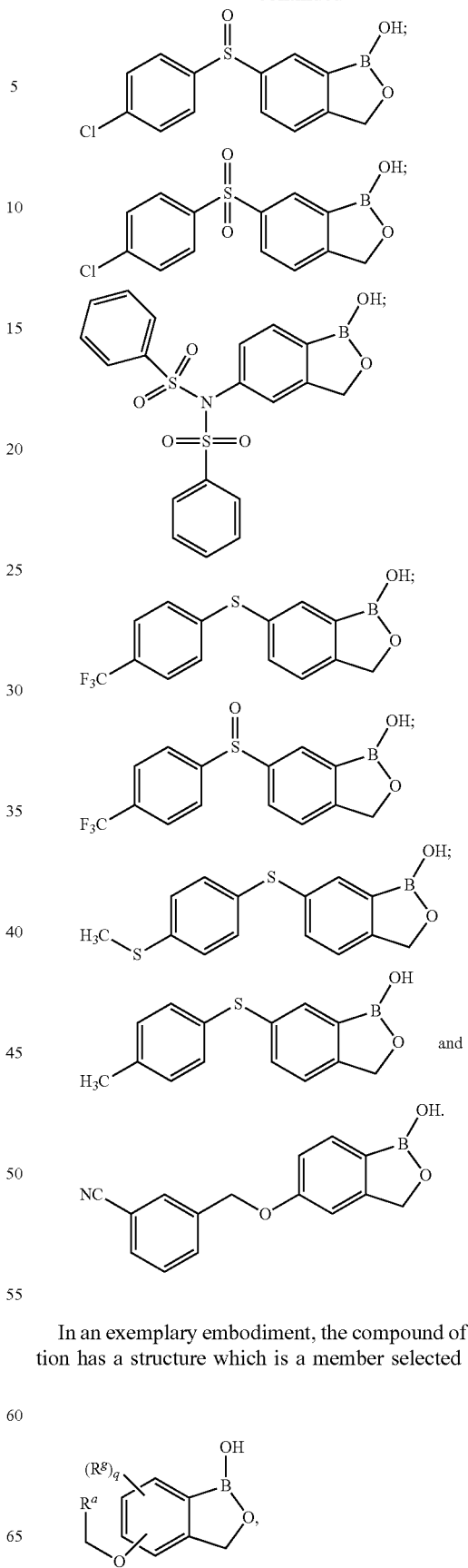
In an exemplary embodiment, the compound of the invention has a structure which is a member selected from:
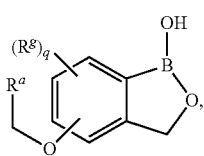
(Iab)

-continued

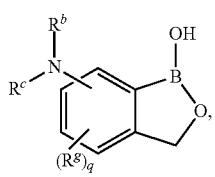 (Iac)

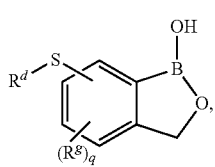 (Iad)

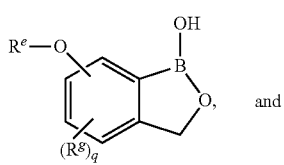 (Ia)

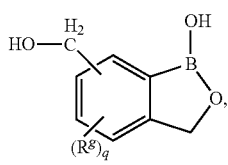 (Iaf)

in which q is a number between 0 and 1. $R^g$ is halogen. $R^a$, $R^b$, $R^c$, $R^d$ and $R^e$ are members independently selected from a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, the compound in the pharmaceutical formulation is a member selected from

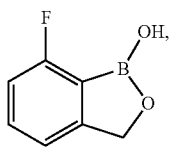

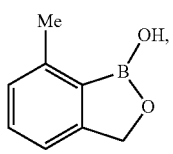

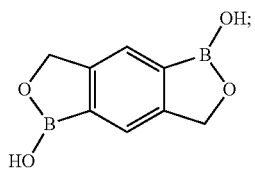

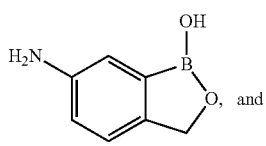 and

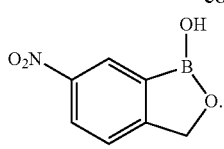 (Iac)

In an exemplary embodiment, the compound has a structure is a member selected from:

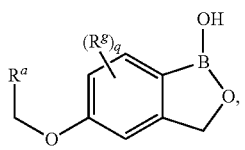 (Iag)

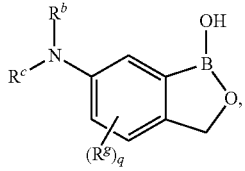 (Iah)

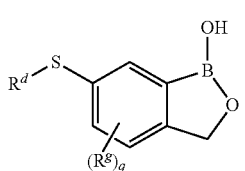 (Iai)

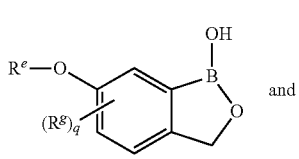 (Iaj) and

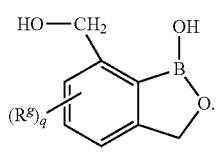 (Iak)

In an exemplary embodiment, $R^a$, $R^d$ and $R^e$ are each members independently selected from:

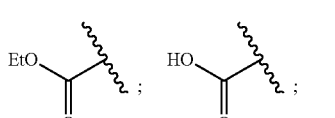

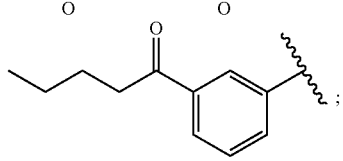

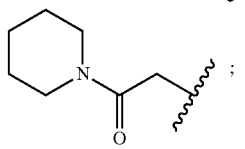

-continued
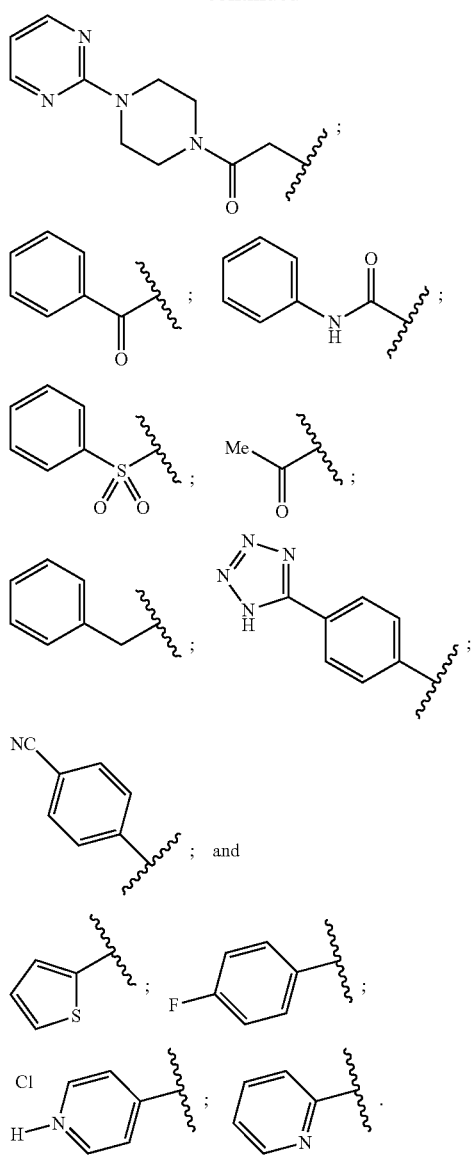
In an exemplary embodiment, $R^b$ and $R^c$ are members independently selected from H, methyl,
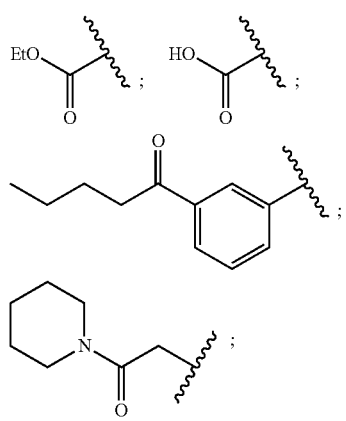
-continued
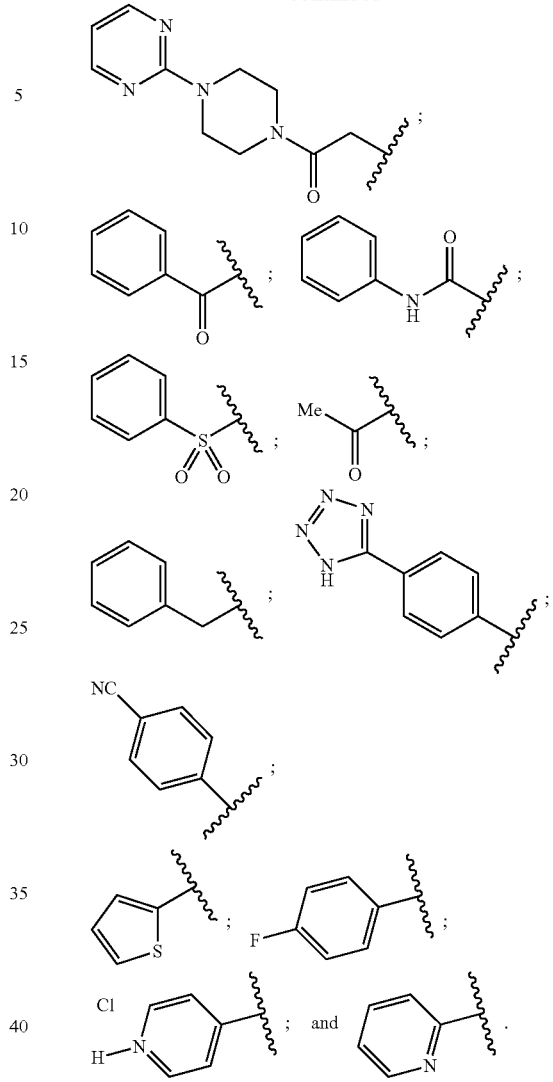
In another exemplary embodiment, $R^b$ is H and $R^c$ is a member selected from H, methyl,
In another exemplary embodiment, $R^b$ and $R^c$ are, together with the nitrogen to which they are attached, optionally joined to form a member selected from

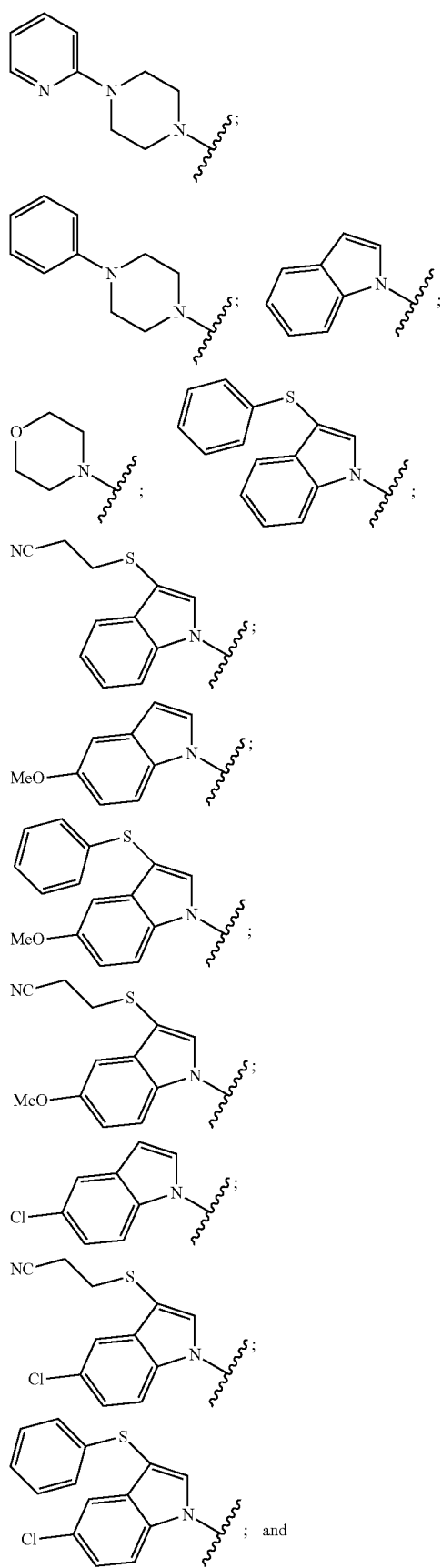
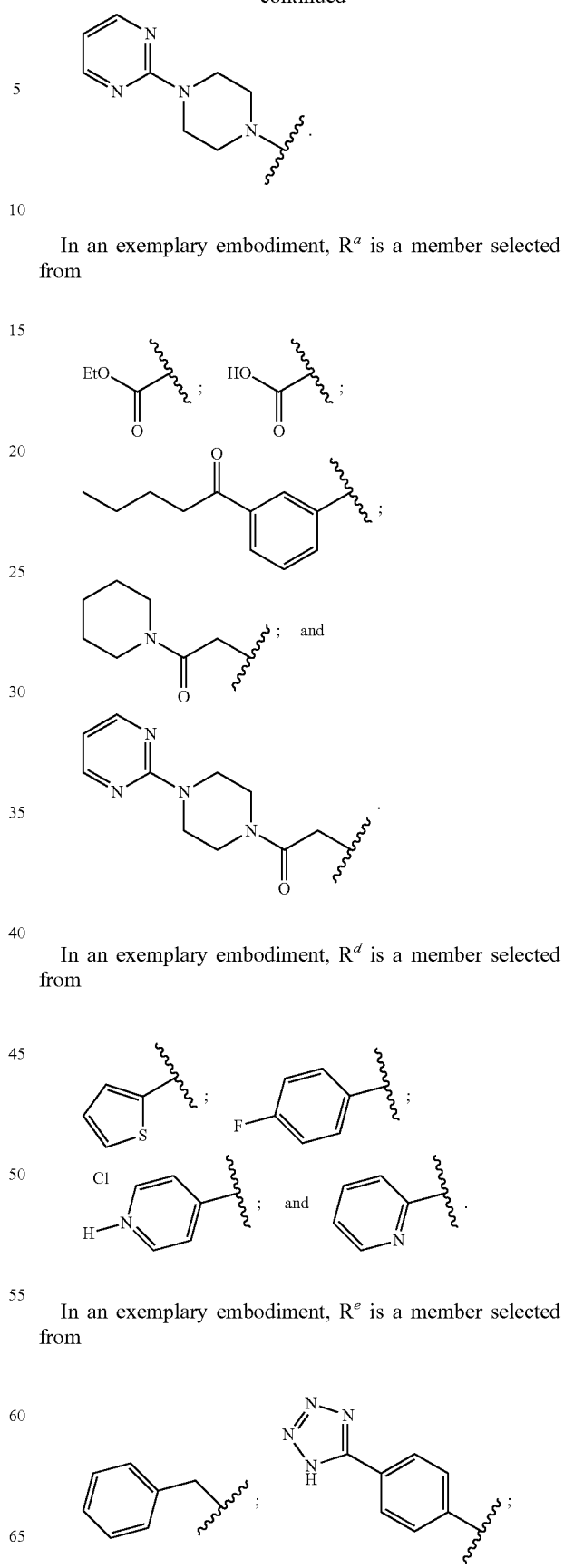
In an exemplary embodiment, $R^a$ is a member selected from
In an exemplary embodiment, $R^d$ is a member selected from
In an exemplary embodiment, $R^e$ is a member selected from -continued

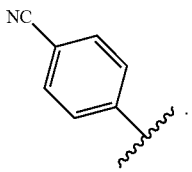

In another exemplary embodiment, the pharmaceutical formulations described herein can form a hydrate with water, a solvate with an alcohol (e.g. methanol, ethanol, propanol); an adduct with an amino compound (e.g. ammonia, methylamine, ethylamine); an adduct with an acid (e.g. formic acid, acetic acid); complexes with ethanolamine, quinoline, amino acids, and the like.

In an exemplary embodiment, the pharmaceutical formulation comprises a compound that has a structure according to Formula (Ip):

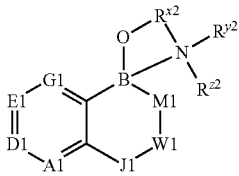

(Ip)

in which $R^{x2}$ is a member selected from substituted or unsubstituted $C_1$-$C_5$ alkyl and substituted or unsubstituted $C_1$-$C_5$ heteroalkyl. $R^{y2}$ and $R^{z2}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the pharmaceutical formulation comprises a compound that has a structure according to Formula (Iq):

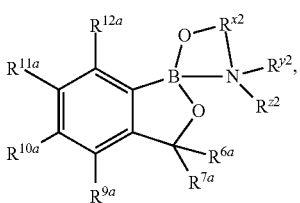

(Iq)

wherein B is boron. $R^{x2}$ is a member selected from substituted or unsubstituted $C_1$-$C_5$ alkyl and substituted or unsubstituted $C_1$-$C_5$ heteroalkyl. $R^{y2}$ and $R^{z2}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In another exemplary embodiment, at least one member selected from $R^{3a}$, $R^{4a}$, $R^{5a}$, $R^{6a}$, $R^{7a}$, $R^{8a}$, $R^{9a}$, $R^{10a}$, $R^{11a}$ and $R^{12a}$ is a member selected from nitro, cyano and halogen.

In an exemplary embodiment, the pharmaceutical formulation comprises a compound that has a structure which is a member selected from the following Formulae:

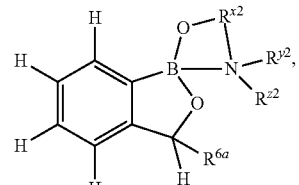

(Ir)

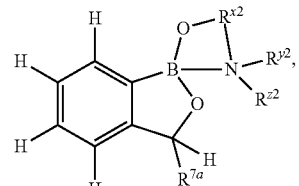

(Is)

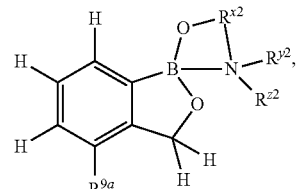

(It)

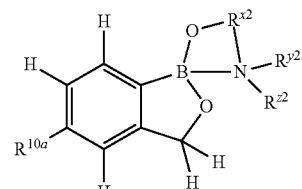

(Iu)

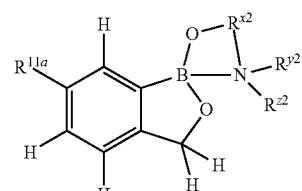

(Iv)

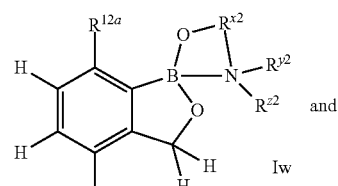

(Iw)

and Iw

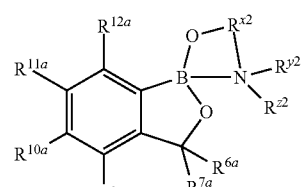

(Iz)

In an exemplary embodiment, the pharmaceutical formulation comprises a compound that has a formula according to Formulae (Ib)-(Ie) wherein at least one member selected from $R^{3a}$, $R^{4a}$, $R^{5a}$, $R^{6a}$, $R^{7a}$, $R^{8a}$, $R^{9a}$, $R^{10a}$, $R^{11a}$ and $R^{12a}$ is a member selected from nitro, cyano, fluro, chloro, bromo and cyanophenoxy. In an exemplary embodiment, the pharmaceutical formulation comprises a compound that has a structure which is a member selected from

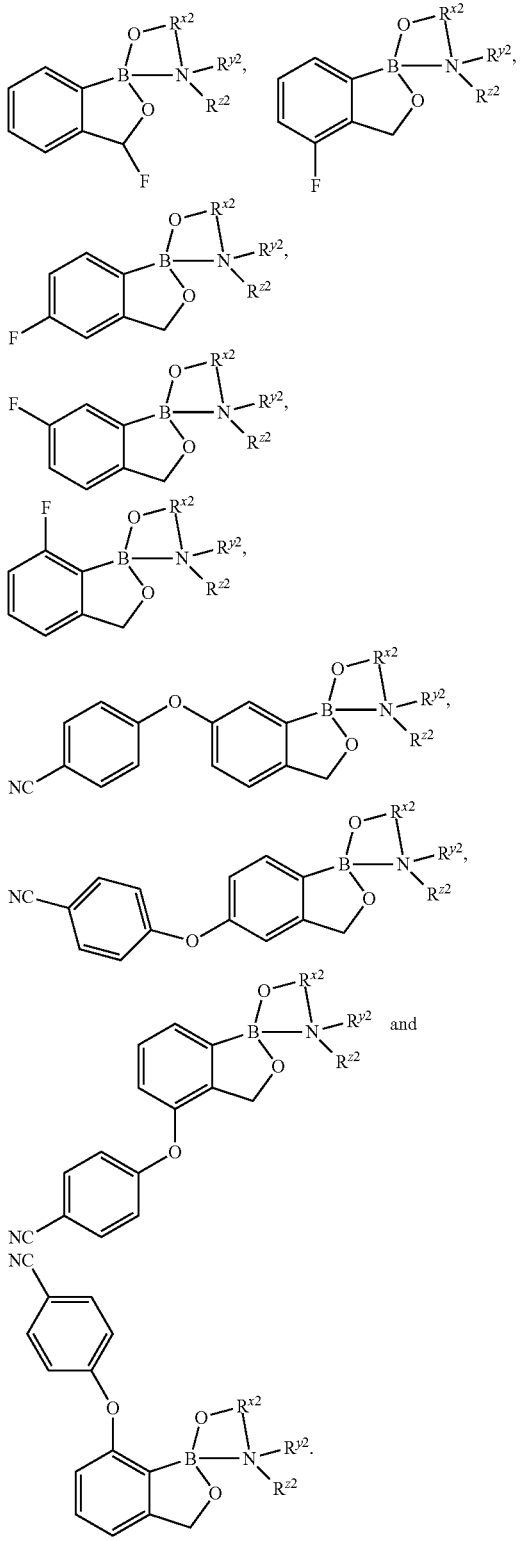

In an exemplary embodiment, the pharmaceutical formulation comprises a compound that has a structure that is a member selected from

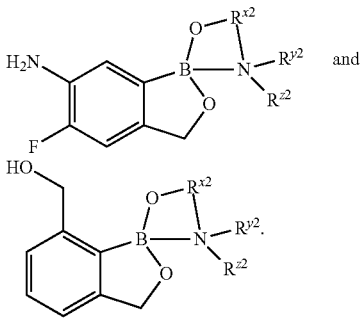

In another exemplary embodiment, there is a proviso that the pharmaceutical formulation cannot comprise a structure according to Formula (Iaa):

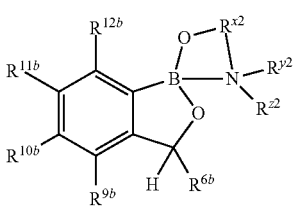

(Iaa)

wherein $R^{6b}$, $R^{9b}$, $R^{10b}$, $R^{11b}$ and $R^{12b}$ have the same substituent listings as described for Formulae (Ix) and (Iy) above.

The pharmaceutical formulations of the invention can take a variety of forms adapted to the chosen route of administration. Those skilled in the art will recognize various synthetic methodologies that may be employed to prepare non-toxic pharmaceutical formulations incorporating the compounds described herein. Those skilled in the art will recognize a wide variety of non-toxic pharmaceutically acceptable solvents that may be used to prepare solvates of the compounds of the invention, such as water, ethanol, propylene glycol, mineral oil, vegetable oil and dimethylsulfoxide (DMSO).

The compositions of the invention may be administered orally, topically, parenterally, by inhalation or spray or rectally in dosage unit formulations containing conventional non-toxic pharmaceutically acceptable carriers, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques.

The pharmaceutical formulations containing compounds of the invention are preferably in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical formulations, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical formulations of the invention may also be in the form of oil-in-water emulsions and water-in-oil emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth; naturally-occurring phosphatides, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical formulations may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The composition of the invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Alternatively, the compositions can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also added as a food or drink supplement for humans.

Dosage levels of the order of from about 5 mg to about 250 mg per kilogram of body weight per day and more preferably from about 25 mg to about 150 mg per kilogram of body weight per day, are useful in the treatment of the above-indicated conditions. The amount of active ingredient that may be combined with the carrier materials to produce a single dosage form will vary depending upon the condition being treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

Preferred compounds of the invention will have desirable pharmacological properties that include, but are not limited to, oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of laboratory animals that receive the compound intravenously.

Serum protein binding may be predicted from albumin binding assays. Such assays are described in a review by Oravcova, et al. (Journal of Chromatography B (1996) volume 677, pages 1-27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120-1127).

The amount of the composition required for use in treatment will vary not only with the particular compound selected but also with the route of administration, the nature of the condition being treated and the age and condition of the patient and will ultimately be at the discretion of the attendant physician or clinician.

In an exemplary embodiment, the pharmaceutical formulation excipient comprises ethanol and the pharmaceutical formulation compound is 1,3-dihydro-5-fluoro-1-hydroxy-2,1-benzoxaborole. In another exemplary embodiment, the pharmaceutical formulation excipient comprises propylene glycol and the pharmaceutical formulation compound is 1,3-dihydro-5-fluoro-1-hydroxy-2,1-benzoxaborole. In an exemplary embodiment the pharmaceutical formulation comprises: about propylene glycol:ethanol 1:4, with 1:10 wt/volume of 1,3-dihydro-5-fluoro-1-hydroxy-2,1-benzoxaborole. In an exemplary embodiment the pharmaceutical formulation comprises: about 70% ethanol; about 20% poly(vinyl methyl ether-alt-maleic acid monobutyl ester); about 10% 1,3-dihydro-5-fluoro-1-hydroxy-2,1-benzoxaborole. In an exemplary embodiment the pharmaceutical formulation comprises: about 56% ethanol; about 14% water; about 15% poly(2-hydroxyethyl methacrylate); about 5% dibutyl sebacate; about 10% 1,3-dihydro-5-fluoro-1-hydroxy-2,1-benzoxabocate. In an exemplary embodiment the pharmaceutical formulation comprises: about 55% ethanol; about 15% ethyl acetate; about 15% poly(vinyl acetate); about 5% dibutyl sebacate; about 10% 1,3-dihydro-5-fluoro-1-hydroxy-2,1-benzoxaborole. In another exemplary embodiment, 1,3-dihydro-5-fluoro-1-hydroxy-2,1-benzoxaborole is present in a pharmaceutical formulation in a concentration which is a member selected from 1%, 2.5%, 5%, 7.5%, 10% and 15% w/v. In another exemplary embodiment, the pharmaceutical formulation is a lacquer.

In an exemplary embodiment, the pharmaceutical formulation excipient comprises ethanol and the pharmaceutical formulation compound is 5-(4-cyanophenoxy)-1,3-dihydro-1-hydroxy-2,1-benzoxaborole. In another exemplary embodiment, the pharmaceutical formulation excipient comprises propylene glycol and the pharmaceutical formulation compound is 5-(4-cyanophenoxy)-1,3-dihydro-1-hydroxy-2,1-benzoxaborole. In an exemplary embodiment the pharmaceutical formulation comprises: about 20% propylene glycol; about 70% ethanol; about 10% 5-(4-cyanophenoxy)-1,3-dihydro-1-hydroxy-2,1-benzoxaborole. In an exemplary embodiment the pharmaceutical formulation comprises: about 70% ethanol; about 20% poly(vinyl methyl ether-alt-maleic acid monobutyl ester); about 10% 5-(4-cyanophenoxy)-1,3-dihydro-1-hydroxy-2,1-benzoxaborole. In an exemplary embodiment the pharmaceutical formulation comprises: about 56% ethanol; about 14% water; about 15% poly(2-hydroxyethyl methacrylate); about 5% dibutyl sebacate; about 10% 5-(4-cyanophenoxy)-1,3-dihydro-1-hydroxy-2,1-benzoxaborole. In an exemplary embodiment the pharmaceutical formulation comprises: about 55% ethanol; about 15% ethyl acetate; about 15% poly(vinyl acetate); about 5% dibutyl sebacate; about 10% 5-(4-cyanophenoxy)-1,3-dihydro-1-hydroxy-2,1-benzoxaborole. In another exemplary embodiment, 5-(4-cyanophenoxy)-1,3-dihydro-1-hydroxy-2,1-benzoxaborole is present in a pharmaceutical formulation in a concentration which is a member selected from 1%, 2.5%, 5%, 7.5%, 10% and 15% w/v. In another exemplary embodiment, the pharmaceutical formulation is a lacquer.

In an exemplary embodiment, the pharmaceutical formulation excipient comprises ethanol and the pharmaceutical formulation compound is a compound described herein. In another exemplary embodiment, the pharmaceutical formulation excipient comprises propylene glycol and the pharmaceutical formulation compound is a compound described herein. In an exemplary embodiment the pharmaceutical formulation comprises: about 20% propylene glycol; about 70% ethanol; about 10% of a compound described herein. In an exemplary embodiment the pharmaceutical formulation comprises: about 70% ethanol; about 20% poly(vinyl methyl ether-alt-maleic acid monobutyl ester); about 10% of a compound described herein. In an exemplary embodiment the pharmaceutical formulation comprises: about 56% ethanol; about 14% water; about 15% poly(2-hydroxyethyl methacrylate); about 5% dibutyl sebacate; about 10% of a compound described herein. In an exemplary embodiment the pharmaceutical formulation comprises: about 55% ethanol; about 15% ethyl acetate; about 15% poly(vinyl acetate); about 5% dibutyl sebacate; about 10% of a compound described herein. In another exemplary embodiment, a compound described herein is present in a pharmaceutical formulation in a concentration which is a member selected from 1%, 2.5%, 5%, 7.5%, 10% and 15% w/v. In another exemplary embodiment, the pharmaceutical formulation is a lacquer.

VII. a) Topical Formulations

In a preferred embodiment, the methods of the invention can be used employed through the topical application of the compounds described herein.

The compositions of the present invention comprises fluid or semi-solid vehicles that may include but are not limited to polymers, thickeners, buffers, neutralizers, chelating agents, preservatives, surfactants or emulsifiers, antioxidants, waxes or oils, emollients, sunscreens, and a solvent or mixed solvent system. The solvent or mixed solvent system is important to the formation because it is primarily responsible for dissolving the drug. The best solvent or mixed solvent systems are also capable of maintaining clinically relevant levels of the drug in solution despite the addition of a poor solvent to the formulation. The topical compositions useful in the subject invention can be made into a wide variety of product types. These include, but are not limited to, lotions, creams, gels, sticks, sprays, ointments, pastes, foams, mousses, and cleansers. These product types can comprise several types of carrier systems including, but not limited to particles, nanoparticles, and liposomes. If desired, disintegrating agents can be added, such as the cross-linked polyvinyl pyrrolidone, agar or alginic acid or a salt thereof such as sodium alginate. Techniques for formulation and administration can be found in Remington: The Science and Practice of Pharmacy, supra. The formulation can be selected to maximize delivery to a desired target site in the body.

Lotions, which are preparations that are to be applied to the skin, nail, hair, claw or hoof surface without friction, are typically liquid or semi-liquid preparations in which finely divided solid, waxy, or liquid are dispersed. Lotions will typically contain suspending agents to produce better dispersions as well as compounds useful for localizing and holding the active agent in contact with the skin, nail, hair, claw or hoof, e.g., methylcellulose, sodium carboxymethylcellulose, or the like.

Creams containing the active agent for delivery according to the present invention are viscous liquid or semisolid emulsions, either oil-in-water or water-in-oil. Cream bases are water-washable, and contain an oil phase, an emulsifier and an aqueous phase. The oil phase is generally comprised of petrolatum or a fatty alcohol, such as cetyl- or stearyl alcohol; the aqueous phase usually, although not necessarily, exceeds the oil phase in volume, and generally contains a humectant. The emulsifier in a cream formulation, as explained in Remington: The Science and Practice of Pharmacy, supra, is generally a nonionic, anionic, cationic or amphoteric surfactant.

Gel formulations can also be used in connection with the present invention. As will be appreciated by those working in the field of topical drug formulation, gels are semisolid. Single-phase gels contain organic macromolecules distributed substantially uniformly throughout the carrier liquid, which is typically aqueous, but also may be a solvent or solvent blend.

Ointments, which are semisolid preparations, are typically based on petrolatum or other petroleum derivatives. As will be appreciated by the ordinarily skilled artisan, the specific ointment base to be used is one that provides for optimum delivery for the active agent chosen for a given formulation, and, preferably, provides for other desired characteristics as well, e.g., emolliency or the like. As with other carriers or vehicles, an ointment base should be inert, stable, nonirritating and non-sensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, reference may be had to Remington: The Science and Practice of Pharmacy, supra, for further information.

Useful formulations of the invention also encompass sprays. Sprays generally provide the active agent in an aqueous and/or alcoholic solution which can be misted onto the skin, nail, hair, claw or hoof for delivery. Such sprays include those formulated to provide for concentration of the active agent solution at the site of administration following delivery, e.g., the spray solution can be primarily composed of alcohol or other like volatile liquid in which the drug or active agent can be dissolved. Upon delivery to the skin, nail, hair, claw or hoof, the carrier evaporates, leaving concentrated active agent at the site of administration.

The topical pharmaceutical compositions may also comprise suitable solid or gel phase carriers. Examples of such carriers include but are not limited to calcium carbonate, calcium phosphate, various sugars, starches, cellulose derivatives, gelatin, and polymers such as polyethylene glycols.

The topical pharmaceutical compositions may also comprise a suitable emulsifier which refers to an agent that enhances or facilitates mixing and suspending oil-in-water or water-in-oil. The emulsifying agent used herein may consist of a single emulsifying agent or may be a nonionic, anionic, cationic or amphoteric surfactant or blend of two or more such surfactants; preferred for use herein are nonionic or anionic emulsifiers. Such surface-active agents are described in "McCutcheon's Detergent and Emulsifiers," North American Edition, 1980 Annual published by the McCutcheon Division, MC Publishing Company, 175 Rock Road, Glen Rock, N.J. 07452, USA.

Preferred for use herein are high molecular weight alcohols such as cetearyl alcohol, cetyl alcohol, stearyl alcohol, emulsifying wax, glyceryl monostearate. Other examples are ethylene glycol distearate, sorbitan tristearate, propylene glycol monostearate, sorbitan monooleate, sorbitan monostearate (SPAN 60), diethylene glycol monolaurate, sorbitan monopalmitate, sucrose dioleate, sucrose stearate (CRODESTA F-160), polyoxyethylene lauryl ether (BRIJ 30), polyoxyethylene (2) stearyl ether (BRIJ 72), polyoxyethylene (21) stearyl ether (BRIJ 721), polyoxyethylene monostearate (Myrj 45), polyoxyethylene sorbitan monostearate (TWEEN 60), polyoxyethylene sorbitan monooleate (TWEEN 80), polyoxyethylene sorbitan monolaurate (TWEEN 20) and sodium oleate. Cholesterol and cholesterol derivatives may also be employed in externally used emulsions and promote w/o emulsions.

Especially suitable nonionic emulsifying agents are those with hydrophile-lipophile balances (HLB) of about 3 to 6 for w/o system and 8 to 18 for o/w system as determined by the method described by Paul L. Lindner in "Emulsions and Emulsion", edited by Kenneth Lissant, published by Dekker, New York, N.Y., 1974, pages 188-190. More preferred for use herein are one or more nonionic surfactants that produce a system having HLB of about 8 to about 18.

Examples of such nonionic emulsifiers include but are not limited to "BRIJ 72", the trade name for a polyoxyethylene (2) stearyl ether having an HLB of 4.9; "BRIJ 721", the trade name for a polyoxyethylene (21) stearyl ether having an HLB of 15.5, "Brij 30", the trade name for polyoxyethylene lauryl ether having an HLB of 9.7; "Polawax", the trade name for emulsifying wax having an HLB of 8.0; "Span 60", the trade name for sorbitan monostearate having an HLB of 4.7; "Crodesta F-160", the trade name for sucrose stearate" having an HLB of 14.5. All of these materials are available from Ruger Chemicals Inc.; Croda; ICI Americas, Inc.;

Spectrum Chemicals; and BASF. When the topical formulations of the present invention contain at least one emulsifying agent, each emulsifying agent is present in amount from about 0.5 to about 2.5 wt %, preferably 0.5 to 2.0%, more preferably 1.0% or 1.8%. Preferably the emulsifying agent comprises a mixture of steareth 21 (at about 1.8%) and steareth 2 (at about 1.0%).

The topical pharmaceutical compositions may also comprise suitable emollients. Emollients are materials used for the prevention or relief of dryness, as well as for the protection of the skin, nail, hair, claw or hoof. Useful emollients include, but are not limited to, cetyl alcohol, isopropyl myristate, stearyl alcohol, and the like. A wide variety of suitable emollients are known and can be used herein. See e.g., Sagarin, Cosmetics, Science and Technology, 2nd Edition, Vol. 1, pp. 32-43 (1972), and U.S. Pat. No. 4,919,934, to Deckner et al., issued Apr. 24, 1990, both of which are incorporated herein by reference in their entirety. These materials are available from Ruger Chemical Co, (Irvington, N.J.).

When the topical formulations of the present invention contain at least one emollient, each emollient is present in an amount from about 0.1 to 15%, preferably 0.1 to about 3.0, more preferably 0.5, 1.0, or 2.5 wt %. Preferably the emollient is a mixture of cetyl alcohol, isopropyl myristate and stearyl alcohol in a 1/5/2 ratio. The emollient may also be a mixture of cetyl alcohol and stearyl alcohol in a 1/2 ratio.

The topical pharmaceutical compositions may also comprise suitable antioxidants, substances known to inhibit oxidation. Antioxidants suitable for use in accordance with the present invention include, but are not limited to, butylated hydroxytoluene, ascorbic acid, sodium ascorbate, calcium ascorbate, ascorbic palmitate, butylated hydroxyanisole, 2,4,5-trihydroxybutyrophenone, 4-hydroxymethyl-2,6-di-tert-butylphenol, erythorbic acid, gum guaiac, propyl gallate, thiodipropionic acid, dilauryl thiodipropionate, tert-butylhydroquinone and tocopherols such as vitamin E, and the like, including pharmaceutically acceptable salts and esters of these compounds. Preferably, the antioxidant is butylated hydroxytoluene, butylated hydroxyanisole, propyl gallate, ascorbic acid, pharmaceutically acceptable salts or esters thereof, or mixtures thereof. Most preferably, the antioxidant is butylated hydroxytoluene. These materials are available from Ruger Chemical Co, (Irvington, N.J.).

When the topical formulations of the present invention contain at least one antioxidant, the total amount of antioxidant present is from about 0.001 to 0.5 wt %, preferably 0.05 to about 0.5 wt %, more preferably 0.1%.

The topical pharmaceutical compositions may also comprise suitable preservatives. Preservatives are compounds added to a pharmaceutical formulation to act as an anti-microbial agent. Among preservatives known in the art as being effective and acceptable in parenteral formulations are benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. See, e.g., Wallhausser, K.-H., Develop. Biol. Standard, 24:9-28 (1974) (S. Krager, Basel). Preferably, the preservative is selected from methylparaben, propylparaben and mixtures thereof.

These materials are available from Inolex Chemical Co (Philadelphia, Pa.) or Spectrum Chemicals.

When the topical formulations of the present invention contain at least one preservative, the total amount of preservative present is from about 0.01 to about 0.5 wt %, preferably from about 0.1 to 0.5%, more preferably from about 0.03 to about 0.15. Preferably the preservative is a mixture of methylparaben and proplybarben in a 5/1 ratio. When alcohol is used as a preservative, the amount is usually 15 to 20%.

The topical pharmaceutical compositions may also comprise suitable chelating agents to form complexes with metal cations that do not cross a lipid bilayer. Examples of suitable chelating agents include ethylene diamine tetraacetic acid (EDTA), ethylene glycol-bis(beta-aminoethyl ether)-N,N,N',N'-tetraacetic acid (EGTA) and 8-Amino-2-[(2-amino-5-methylphenoxy)methyl]-6-methoxyquinoline-N,N,N',N'-tetraacetic acid, tetrapotassium salt (QUIN-2). Preferably the chelating agents are EDTA and citric acid. These materials are available from Spectrum Chemicals.

When the topical formulations of the present invention contain at least one chelating agent, the total amount of chelating agent present is from about 0.005% to 2.0% by weight, preferably from about 0.05% to about 0.5 wt %, more preferably about 0.1% by weight.

The topical pharmaceutical compositions may also comprise suitable neutralizing agents used to adjust the pH of the formulation to within a pharmaceutically acceptable range. Examples of neutralizing agents include but are not limited to trolamine, tromethamine, sodium hydroxide, hydrochloric acid, citric acid, and acetic acid. Such materials are available from are available from Spectrum Chemicals (Gardena, Calif.).

When the topical formulations of the present invention contain at least one neutralizing agent, the total amount of neutralizing agent present is from about 0.1 wt to about 10 wt %, preferably 0.1 wt % to about 5.0 wt %, and more preferably about 1.0 wt %. The neutralizing agent is generally added in whatever amount is required to bring the formulation to the desired pH.

The topical pharmaceutical compositions may also comprise suitable viscosity increasing agents. These components are diffusible compounds capable of increasing the viscosity of a polymer-containing solution through the interaction of the agent with the polymer. CARBOPOL ULTREZ 10 may be used as a viscosity-increasing agent. These materials are available from Noveon Chemicals, Cleveland, Ohio.

When the topical formulations of the present invention contain at least one viscosity increasing agent, the total amount of viscosity increasing agent present is from about 0.25% to about 5.0% by weight, preferably from about 0.25% to about 1.0 wt %, and more preferably from about 0.4% to about 0.6% by weight.

The topical pharmaceutical compositions may also comprise suitable nail penetration enhancers. Examples of nail penetration enhancers include mercaptan compounds, sulfites and bisulfites, keratolytic agents and surfactants. Nail penetration enhancers suitable for use in the invention are described in greater detail in Malhotra et al., J. Pharm. Sci., 91:2, 312-323 (2002), which is incorporated herein by reference in its entirety.

The topical pharmaceutical compositions may also comprise one or more suitable solvents. The ability of any solid substance (solute) to dissolve in any liquid substance (solvent) is dependent upon the physical properties of the solute and the solvent. When solutes and solvents have similar physical properties the solubility of the solute in the solvent will be the greatest. This gives rise to the traditional understanding that "like dissolves like." Solvents can be characterized in one extreme as non-polar, lipophilic oils, while in the other extreme as polar hydrophilic solvents. Oily solvents dissolve other non-polar substances by Van der Wals interactions while water and other hydrophilic solvents dissolve polar substances by ionic, dipole, or hydrogen bonding interactions. All solvents can be listed along a continuum from the least polar, i.e. hydrocarbons such as decane, to the most polar solvent being water. A solute will have its greatest solubility in solvents having equivalent polarity. Thus, for drugs having minimal solubility in water, less polar solvents will provide improved solubility with the solvent having polarity nearly equivalent to the solute providing maximum solubility. Most drugs have intermediate polarity, and thus experience maximum solubility in solvents such as propylene glycol or ethanol, which are significantly less polar than water. If the drug has greater solubility in propylene glycol (for example 8% (w/w)) than in water (for example 0.1% (w/w)), then addition of water to propylene glycol should decrease the maximum amount of drug solubility for the solvent mixture compared with pure propylene glycol. Addition of a poor solvent to an excellent solvent will decrease the maximum solubility for the blend compared with the maximum solubility in the excellent solvent.

When compounds are incorporated into topical formulations the concentration of active ingredient in the formulation may be limited by the solubility of the active ingredient in the chosen solvent and/or carrier. Non-lipophilic drugs typically display very low solubility in pharmaceutically acceptable solvents and/or carriers. For example, the solubility of some compounds in the invention in water is less than 0.00025% wt/wt. The solubility of the same compounds in the invention can be less than about 2% wt/wt in either propylene glycol or isopropyl myristate. In one embodiment of the present invention, diethylene glycol monoethyl ether (DGME) is the solvent used to dissolve the compounds of the invention. The compounds in the invention useful in the present formulation are believed to have a solubility of from about 10% wt/wt to about 25% wt/wt in DGME. In another embodiment a DGME water cosolvent system is used to dissolve the compounds of the invention. The solvent capacity of DGME drops when water is added; however, the DGME/water cosolvent system can be designed to maintain the desired concentration of from about 0.1% to about 5% wt/wt active ingredient. Preferably the active ingredient is present from about 0.5% to about 3% wt/wt, and more preferably at about 1% wt/wt, in the as-applied topical formulations. Because DGME is less volatile than water, as the topical formulation evaporates upon application, the active agent becomes more soluble in the cream formulation. This increased solubility reduces the likelihood of reduced bioavailability caused by the drug precipitating on the surface of the skin, nail, hair, claw or hoof.

Liquid forms, such as lotions suitable for topical administration or suitable for cosmetic application, may include a suitable aqueous or nonaqueous vehicle with buffers, suspending and dispensing agents, thickeners, penetration enhancers, and the like. Solid forms such as creams or pastes or the like may include, for example, any of the following ingredients, water, oil, alcohol or grease as a substrate with surfactant, polymers such as polyethylene glycol, thickeners, solids and the like. Liquid or solid formulations may include enhanced delivery technologies such as liposomes, microsomes, microsponges and the like.

Additionally, the compounds can be delivered using a sustained-release system, such as semipermeable matrices of solid hydrophobic polymers containing the therapeutic agent. Various sustained-release materials have been established and are well known by those skilled in the art.

Topical treatment regimens according to the practice of this invention comprise applying the composition directly to the skin, nail, hair, claw or hoof at the application site, from one to several times daily.

Formulations of the present invention can be used to treat, ameliorate or prevent conditions or symptoms associated with bacterial infections, acne, inflammation and the like.

In an exemplary embodiment, the pharmaceutical formulation includes a simple solution. In an exemplary embodiment, the simple solution includes an alcohol. In an exemplary embodiment, the simple solution includes alcohol and water. In an exemplary embodiment, the alcohol is ethanol, ethylene glycol, propanol, polypropylene glycol, isopropanol or butanol. In another exemplary embodiment, the simple solution is a member selected from about 10% polypropylene glycol and about 90% ethanol; about 20% polypropylene glycol and about 80% ethanol; about 30% polypropylene glycol and about 70% ethanol; about 40% polypropylene glycol and about 60% ethanol; about 50% polypropylene glycol and about 50% ethanol; about 60% polypropylene glycol and about 40% ethanol; about 70% polypropylene glycol and about 30% ethanol; about 80% polypropylene glycol and about 20% ethanol; about 90% polypropylene glycol and about 10% ethanol.

In an exemplary embodiment, the pharmaceutical formulation is a lacquer. Please see Remington's, supra, for more information on the production of lacquers.

In an exemplary embodiment, the compound is present in said pharmaceutical formulation in a concentration of from about 0.5% to about 15%. In an exemplary embodiment, the compound is present in said pharmaceutical formulation in a concentration of from about 0.1% to about 12.5%. In an exemplary embodiment, the compound is present in said pharmaceutical formulation in a concentration of from about 1% to about 10%. In an exemplary embodiment, the compound is present in said pharmaceutical formulation in a concentration of from about 1% to about 5%. In an exemplary embodiment, the compound is present in said pharmaceutical formulation in a concentration of from about 0.5% to about 5%. In an exemplary embodiment, the compound is present in said pharmaceutical formulation in a concentration of from about 0.5% to about 7.5%. In an exemplary embodiment, the compound is present in said pharmaceutical formulation in a concentration of from about 5% to about 7.5%. In an exemplary embodiment, the compound is present in said pharmaceutical formulation in a concentration of from about 2% to about 8%. In an exemplary embodiment, the compound is present in said pharmaceutical formulation in a concentration of from about 4% to about 9%.

VII. b) Additional Active Agents

The following are examples of the cosmetic and pharmaceutical agents that can be added to the topical pharmaceutical formulations of the present invention. The following agents are known compounds and are readily available commercially.

Anti-inflammatory agents include, but are not limited to, bisabolol, mentholatum, dapsone, aloe, hydrocortisone, and the like.

Vitamins include, but are not limited to, Vitamin B, Vitamin E, Vitamin A, Vitamin D, and the like and vitamin derivatives such as tazarotene, calcipotriene, tretinoin, adapalene and the like.

Anti-aging agents include, but are not limited to, niacinamide, retinol and retinoid derivatives, AHA, Ascorbic acid, lipoic acid, coenzyme Q 10, beta hydroxy acids, salicylic acid, copper binding peptides, dimethylaminoethyl (DAEA), and the like.

Sunscreens and or sunburn relief agents include, but are not limited to, PABA, jojoba, aloe, padimate-O, methoxycinnamates, proxamine HCl, lidocaine and the like. Sunless tanning agents include, but are not limited to, dihydroxyacetone (DHA).

Psoriasis-treating agents and/or acne-treating agents include, but are not limited to, salicylic acid, benzoyl peroxide, coal tar, selenium sulfide, zinc oxide, pyrithione (zinc and/or sodium), tazarotene, calcipotriene, tretinoin, adapalene and the like.

Agents that are effective to control or modify keratinization, including without limitation: tretinoin, tazarotene, and adapalene.

The compositions comprising an compound/active agent of the invention, and optionally at least one of these additional agents, are to be administered topically. In a primary application, this leads to the compounds of the invention and any other active agent working upon and treating the skin, nail, hair, claw or hoof. Alternatively, any one of the topically applied active agents may also be delivered systemically by transdermal routes.

In such compositions an additional cosmetically or pharmaceutically effective agent, such as an anti-inflammatory agent, vitamin, anti-aging agent, sunscreen, and/or acne-treating agent, for example, is usually a minor component (from about 0.001% to about 20% by weight or preferably from about 0.01% to about 10% by weight) with the remainder being various vehicles or carriers and processing aids helpful for forming the desired dosing form.

VII. c) Testing

Preferred compounds for use in the present topical formulations will have certain pharmacological properties. Such properties include, but are not limited to, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcova et al. (1996, *J. Chromat.* B677: 1-27). Compound half-life is inversely proportional to the frequency of dosage of a compound. In vitro half-lives of compounds may be predicted from assays of microsomal half-life as described by Kuhnz and Gleschen (Drug Metabolism and Disposition, (1998) volume 26, pages 1120-1127).

Toxicity and therapeutic efficacy of such compounds can be determined by standard pharmaceutical procedures in cell cultures or experimental animals, e.g., for determining the LD50 (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch. 1, p. 1).

VII. d) Administration

For any compound used in the method of the invention, the therapeutically effective dose can be estimated initially from cell culture assays, as disclosed herein.

For example, a dose can be formulated in animal models to achieve a circulating concentration range that includes the $EC_{50}$ (effective dose for 50% increase) as determined in cell culture, i.e., the concentration of the test compound which achieves a half-maximal inhibition of bacterial cell growth. Such information can be used to more accurately determine useful doses in humans.

In general, the compounds prepared by the methods, and from the intermediates, described herein will be administered in a therapeutically or cosmetically effective amount by any of the accepted modes of administration for agents that serve similar utilities. It will be understood, however, that the specific dose level for any particular patient will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician. The drug can be administered from once or twice a day, or up to 3 or 4 times a day.

Dosage amount and interval can be adjusted individually to provide plasma levels of the active moiety that are sufficient to maintain bacterial cell growth inhibitory effects. Usual patient dosages for systemic administration range from 0.1 to 1000 mg/day, preferably, 1-500 mg/day, more preferably 10-200 mg/day, even more preferably 100-200 mg/day. Stated in terms of patient body surface areas, usual dosages range from 50-91 mg/m$^2$/day.

The amount of the compound in a formulation can vary within the full range employed by those skilled in the art. Typically, the formulation will contain, on a weight percent (wt %) basis, from about 0.01-10 wt % of the drug based on the total formulation, with the balance being one or more suitable pharmaceutical excipients. Preferably, the compound is present at a level of about 0.1-3.0 wt %, more preferably, about 1.0 wt %.

The invention is further illustrated by the Examples that follow. The Examples are not intended to define or limit the scope of the invention.

EXAMPLES

Proton NMR are recorded on Varian AS 300 spectrometer and chemical shifts are reported as δ (ppm) down field from tetramethylsilane. Mass spectra are determined on Micromass Quattro II.

Example 1

Preparation of 3 from 1

1.1 Reduction of Carboxylic Acid

To a solution of 1 (23.3 mmol) in anhydrous THF (70 mL) under nitrogen was added dropwise a BH$_3$THF solution (1.0 M, 55 mL, 55 mmol) at 0° C. and the reaction mixture was stirred overnight at room temperature. Then the mixture was cooled again with ice bath and MeOH (20 mL) was added dropwise to decompose excess BH$_3$. The resulting mixture was stirred until no bubble was released and then 10%

NaOH (10 mL) was added. The mixture was concentrated and the residue was mixed with water (200 mL) and extracted with EtOAc. The residue from rotary evaporation was purified by flash column chromatography over silica gel to give 20.7 mmol of 3.

1.2 Results

Exemplary compounds of structure 3 prepared by the method above are provided below.

1.2.a 2-Bromo-5-chlorobenzyl Alcohol $^1$H NMR (300 MHz, DMSO-$d_6$): δ 7.57 (d, J=8.7 Hz, 1H), 7.50-7.49 (m, 1H), 7.28-7.24 (m, 1H), 5.59 (t, J=6.0 Hz, 1H) and 4.46 (d, J=6.0 Hz, 2H) ppm.

1.2.b 2-Bromo-5-methoxybenzyl Alcohol $^1$H NMR (300 MHz, DMSO-$d_6$): δ 7.42 (d, J=8.7 Hz, 1H), 7.09 (d, J=2.4 Hz, 1H), 6.77 (dd, J=3 Hz, $J_2$=3 Hz, 1H), 5.43 (t, J=5.7 Hz, 1H), 4.44 (d, J=5.1 Hz, 2H), 3.76 (s, 3H).

Example 2

Preparation of 3 from 2

2.1. Reduction of Aldehyde

To a solution of 2 (Z=H, 10.7 mmol) in methanol (30 mL) was added sodium borohydride (5.40 mol), and the mixture was stirred at room temperature for 1 h. Water was added, and the mixture was extracted with ethyl acetate. The organic layer was washed with brine and dried on anhydrous sodium sulfate. The solvent was removed under reduced pressure to afford 9.9 mmol of 3.

2.2 Results

Exemplary compounds of structure 3 prepared by the method above are provided below.

2.2.a 2-Bromo-5-(4-cyanophenoxy)benzyl Alcohol $^1$H-NMR (300 MHz, CDCl$_3$) δ (ppm) 2.00 (br s, 1H), 4.75 (s, 2H), 6.88 (dd, J=8.5, 2.9 Hz, 1H), 7.02 (d, J=8.8 Hz, 1H), 7.26 (d, J=2.6 Hz, 1H), 7.56 (d, J=8.5 Hz, 1H), 7.62 (d, J=8.8 Hz, 2H).

2.2.b 2-Bromo-4-(4-cyanophenoxy)benzyl Alcohol $^1$H NMR (300 MHz, DMSO-$d_6$): δ 7.83 (d, 2H), 7.58 (d, 1H), 7.39 (d, 1H), 7.18 (dd, 1H), 7.11 (d, 2H), 5.48 (t, 1H) and 4.50 (d, 2H) ppm.

2.2.c 5-(4-Cyanophenoxy)-1-Indanol

M.p. 50-53° C. MS (ESI+): m/z=252 (M+1). HPLC: 99.7% purity at 254 nm and 99.0% at 220 nm. $^1$H NMR (300 MHz, DMSO-$d_6$): δ 7.80 (d, 2H), 7.37 (d, 1H), 7.04 (d, 2H), 6.98-6.93 (m, 2H), 5.27 (d, 1H), 5.03 (q, 1H), 2.95-2.85 (m, 1H), 2.75-2.64 (m, 1H), 2.39-2.29 (m, 1H) and 1.85-1.74 (m, 1H) ppm.

2.2.d 2-Bromo-5-(tert-butyldimethylsiloxy)benzyl Alcohol $^1$H-NMR (300 MHz, CDCl$_3$) δ (ppm) 0.20 (s, 6H), 0.98 (s, 9H), 4.67 (br s, 1H), 6.65 (dd, J=8.2, 2.6 Hz, 1H), 6.98 (d, J=2.9 Hz, 1H), 7.36 (d, J=8.8 Hz, 1H).

Additional examples of compounds which can be produced by this method include 2-bromo-4-(3-cyanophenoxy)benzyl alcohol; 2-bromo-4-(4-chlorophenoxy)benzyl alcohol; 2-bromo-4-phenoxybenzyl alcohol; 2-bromo-5-(3,4-dicyanophenoxy)benzyl alcohol; 2-(2-bromo-5-fluorophenyl)ethyl alcohol; 2-bromo-5-fluorobenzyl alcohol; and 1-bromo-2-naphthalenemethanol.

Example 3

Preparation of 4 from 3

3.1 Protective Alkylation

Compound 3 (20.7 mmol) was dissolved in CH$_2$Cl$_2$ (150 mL) and cooled to 0° C. with ice bath. To this solution under nitrogen were added in sequence N,N-diisopropyl ethyl amine (5.4 mL, 31.02 mmol, 1.5 eq) and chloromethyl methyl ether (2 mL, 25.85 mmol, 1.25 eq). The reaction mixture was stirred overnight at room temperature and washed with NaHCO$_3$-saturated water and then NaCl-saturated water. The residue after rotary evaporation was purified by flash column chromatography over silica gel to give 17.6 mmol of 4.

3.2 Results

Exemplary compounds of structure 4 prepared by the method above are provided below.

3.2.a 2-Bromo-5-chloro-1-(methoxymethoxymethyl)benzene $^1$H NMR (300 MHz, DMSO-$d_6$): δ 7.63 (d, J=8.7 Hz, 1H), 7.50 (dd, J=2.4 & 0.6 Hz, 1H), 7.32 (dd, J=8.4 & 2.4 Hz, 1H), 4.71 (s, 2H), 4.53 (s, 2H) and 3.30 (s, 3H) ppm.

3.2.b 2-Bromo-5-fluoro-1-[1-(methoxymethoxy)ethyl]benzene $^1$H-NMR (300.058 MHz, CDCl$_3$) δ ppm 1.43 (d, J=6.5 Hz, 3H), 3.38 (s, 3H), 4.55 (d, J=6.5 Hz, 1H), 4.63 (d, J=6.5 Hz, 1H), 5.07 (q, J=6.5 Hz, 1H), 6.85 (m, 1H), 7.25 (dd, J=9.7, 2.6 Hz, 1H), 7.46 (dd, J=8.8, 5.3 Hz, 1H).

3.2.c 2-Bromo-5-fluoro-1-[2-(methoxymethoxy)ethyl]benzene $^1$H-NMR (300.058 MHz, CDCl$_3$) δ ppm 3.04 (t, J=6.7 Hz, 2H), 3.31 (s, 3H), 3.77 (t, J=6.7 Hz, 2H), 4.62 (s, 2H), 6.82 (td, J=8.2, 3.2 Hz, 1H), 7.04 (dd, J=9.4, 2.9 Hz, 1H), 7.48 (dd, J=8.8, 5.3 Hz, 1H).

3.2.d 2-Bromo-4,5-difluoro-1-(methoxymethoxymethyl)benzene $^1$H-NMR (300.058 MHz, CDCl$_3$) δ ppm 3.42 (s, 3H), 4.57 (d, J=1.2 Hz, 2H), 4.76 (s, 2H), 7.3-7.5 (m, 2H).

3.2.e 2-Bromo-5-cyano-1-(methoxymethoxymethyl)benzene $^1$H-NMR (300.058 MHz, CDCl$_3$) δ ppm 3.43 (s, 3H), 4.65 (s, 2H), 4.80 (s, 2H), 7.43 (dd, J=8.2, 4.1 Hz, 1H), 7.66 (d, J=8.2 Hz, 1H), 7.82 (d, J=4.1 Hz, 1H).

3.2.f 2-Bromo-5-methoxy-1-(methoxymethoxymethyl) benzene $^1$H NMR (300 MHz, DMSO-d$_6$): δ 7.48 (dd, J$_1$=1.2 Hz, J$_2$=1.2 Hz, 1H), 7.05 (d, J=2.7 Hz, 1H), 6.83 (dd, J$_1$×3 Hz, J$_2$=3 Hz, 1H), 4.69 (d, J=1.2 Hz, 2H), 4.5 (s, 2H), 3.74 (d, J=1.5 Hz, 3H), 3.32 (d, J=2.1 Hz, 3H) ppm.

3.2.g 1-Benzyl-1-(2-bromophenyl)-1-(methoxymethoxy)ethane $^1$H NMR (300 MHz, DMSO-d$_6$): δ 7.70-7.67 (m, 1H), 7.25-7.09 (m, 6H), 6.96-6.93 (m, 2H), 4.61 (d, 1H), 4.48 (d, 1H), 3.36-3.26 (m, 2H), 3.22 (s, 3H) and 1.63 (s, 3H) ppm.

3.2.h 2-Bromo-6-fluoro-1-(methoxymethoxymethyl)benzene $^1$H-NMR (300 MHz, CDCl$_3$) δ (ppm) 3.43 (s, 3H), 4.74 (s, 2H), 4.76 (d, J=2.1 Hz, 2H), 7.05 (t, J=9.1 Hz, 1H), 7.18 (td, J=8.2, 5.9 Hz, 1H), 7.40 (d, J=8.2 Hz, 1H).

3.2.i 2-Bromo-4-(4-cyanophenoxy)-1-(methoxymethoxymethyl)benzene $^1$H NMR (300 MHz, DMSO-d$_6$): δ 7.84 (d, 2H), 7.56 (d, 1H), 7.44 (d, 1H), 7.19-7.12 (m, 3H), 4.69 (s, 2H), 4.56 (s, 2H) and 3.31 (s, 3H) ppm.

3.2.j 2-Bromo-5-(tert-butyldimethylsiloxy)-1-(methoxymethoxymethyl)benzene $^1$H-NMR (300 MHz, CDCl$_3$) δ (ppm) 0.19 (s, 6H), 0.98 (s, 9H), 3.43 (s, 3H), 4.59 (s, 2H), 4.75 (s, 2H), 6.64 (dd, J=8.5, 2.9 Hz, 1H), 6.98 (d, J=2.9 Hz, 1H), 7.36 (d, J=8.5 Hz, 1H).

3.2.k 2-Bromo-5-(2-cyanophenoxy)-1-(methoxymethoxymethyl)benzene $^1$H-NMR (300 MHz, CDCl$_3$) δ (ppm) 3.41 (s, 3H), 4.64 (s, 2H), 4.76 (s, 2H), 6.8-6.9 (m, 2H), 7.16 (td, J=7.6, 0.9 Hz, 1H), 7.28 (d, J=2.9 Hz, 1H), 7.49 (ddd, J=8.8, 7.6, 1.8 Hz, 1H), 7.56 (d, J=8.5 Hz, 1H), 7.67 (dd, J=7.9, 1.8 Hz, 1H).

3.2.l 2-Bromo-5-phenoxy-1-(methoxymethoxymethyl)benzene $^1$H-NMR (300 MHz, CDCl$_3$) δ (ppm) 3.40 (s, 3H), 4.62 (s, 2H), 4.74 (s, 2H), 6.80 (dd, J=8.8, 2.9 hz, 1H), 7.01 (d, J=8.5 Hz, 2H), 7.12 (t, J=7.9 Hz, 1H), 7.19 (d, J=2.9 hz, 1H), 7.35 (t, J=7.6 Hz, 2H), 7.48 (d, J=8.5 Hz, 1H).

Additional examples of compounds which can be produced by this method include 2-bromo-1-(methoxymethoxymethyl)benzene; 2-bromo-5-methyl-1-(methoxymethoxymethyl)benzene; 2-bromo-5-(methoxymethoxymethyl)-1-(methoxymethoxymethyl)benzene; 2-bromo-5-fluoro-1-(methoxymethoxymethyl)benzene; 1-bromo-2-(methoxymethoxymethyl)naphthalene; 2-bromo-4-fluoro-1-(methoxymethoxymethyl)benzene; 2-phenyl-1-(2-bromophenyl)-1-(methoxymethoxy)ethane; 2-bromo-5-(4-cyanophenoxy)-1-(methoxymethoxy methyl)benzene; 2-bromo-4-(3-cyanophenoxy)-1-(methoxymethoxymethyl)benzene; 2-bromo-4-(4-chloro-phenoxy)-1-(methoxymethoxymethyl)benzene; 2-bromo-4-phenoxy-1-(methoxymethoxymethyl)benzene; 2-bromo-5-(3,4-dicyanophenoxy)-1-(methoxymethoxymethyl)benzene.

Example 4

Preparation of I from 4 via 5

4.1 Metallation and Boronylation

To a solution of 4 (17.3 mmol) in anhydrous THF (80 mL) at −78° C. under nitrogen was added dropwise tert-BuLi or n-BuLi (11.7 mL) and the solution became brown colored. Then, B(OMe)$_3$ (1.93 mL, 17.3 mmol) was injected in one portion and the cooling bath was removed. The mixture was warmed gradually with stirring for 30 min and then stirred with a water bath for 2 h. After addition of 6N HCl (6 mL), the mixture was stirred overnight at room temperature and about 50% hydrolysis has happened as shown by TLC analysis. The solution was rotary evaporated and the residue was dissolved in MeOH (50 mL) and 6N HCl (4 mL). The solution was refluxed for 1 h and the hydrolysis was completed as indicated by TLC analysis. Rotary evaporation gave a residue which was dissolved in EtOAc, washed with water, dried and then evaporated. The crude product was purified by flash column chromatography over silica gel to provide a solid with 80% purity. The solid was further purified by washing with hexane to afford 7.2 mmol of I.

4.2 Results

Analytical data for exemplary compounds of structure I are provided below.

4.2.a 5-Chloro-1,3-dihydro-1-hydroxy-2,1-benzoxaborole 5-chlorobenzo[c][1,2]oxaborol-1(3H)-ol (C1)

M.p. 142-150° C. MS (ESI): m/z=169 (M+1, positive) and 167 (M−1, negative). HPLC (220 nm): 99% purity. $^1$H NMR (300 MHz, DMSO-d$_6$): δ 9.30 (s, 1H), 7.71 (d, J=7.8 Hz, 1H), 7.49 (s, 1H), 7.38 (d, J=7.8 Hz, 1H) and 4.96 (s, 2H) ppm.

4.2.b 1,3-Dihydro-1-hydroxy-2,1-benzoxaborole benzo[c][1,2]oxaborol-1(3H)-ol (C2)

M.p. 83-86° C. MS (ESI): m/z=135 (M+1, positive) and 133 (M−1, negative). HPLC (220 nm): 95.4% purity. $^1$H NMR (300 MHz, DMSO-d$_6$): δ 9.14 (s, 1H), 7.71 (d, J=7.2 Hz, 1H), 7.45 (t, J=7.5 Hz, 1H), 7.38 (d, J=7.5 Hz, 1H), 7.32 (t, J=7.1 Hz, 1H) and 4.97 (s, 2H) ppm.

4.2.c 5-chloro-3-methylbenzo[c][1,2]oxaborol-1(3H)-ol (C3)

$^1$H-NMR (300 MHz, DMSO-d$_6$) δ ppm 1.37 (d, J=6.4 Hz, 3H), 5.17 (q, J=6.4 Hz, 1H), 7.14 (m, 1H), 7.25 (dd, J=9.7, 2.3 Hz, 1H), 7.70 (dd, J=8.2, 5.9 Hz, 1H), 9.14 (s, 1H).

4.2.d 6-Fluoro-1-hydroxy-1, 2, 3, 4-tetrahydro-2,1-benzoxaborine 6-fluoro-3,4-dihydrobenzo[c][1,2]oxaborinin-1-ol (C4)

$^1$H-NMR (300 MHz, DMSO-d$_6$) δ ppm 2.86 (t, J=5.9 Hz, 2H), 4.04 (t, J=5.9 Hz, 2H), 7.0-7.1 (m, 2H), 7.69 (dd, J=8.2, 7.2 Hz, 1H), 8.47 (s, 1H).

4.2.e 5,6-Difluoro-1,3-dihydro-1-hydroxy-2,1-benzoxaborole 5,6-difluorobenzo[c][1,2]oxaborol-1(3H)-ol (C5)

$^1$H-NMR (300 MHz, DMSO-d$_6$) δ ppm 4.94 (s, 2H), 7.50 (dd, J=10.7, 6.8 Hz, 1H), 7.62 (dd, J=9.7, 8.2 Hz, 1H), 9.34 (s, 1H).

4.2.f 5-Cyano-1,3-dihydro-1-hydroxy-2,1-benzoxaborole 1-hydroxy-1,3-dihydrobenzo[c][1,2]oxaborole-5-carbonitrile (C6)

$^1$H-NMR (300 MHz, DMSO-d$_6$) δ ppm 5.03 (s, 2H), 7.76 (d, J 8.2 Hz, 1H), 7.89 (d, J=8.2 Hz, 1H), 7.90 (s, 1H), 9.53 (s, 1H).

4.2.g 1,3-Dihydro-1-hydroxy-5-methoxy-2,1-benzoxaborole 5-methoxybenzo[c][1,2]oxaborol-1(3H)-ol (C7)

M.p. 102-104° C. MS ESI: m/z=165.3 (M+1) and 162.9 (M−1). $^1$H NMR (300 MHz, DMSO-d$_6$): δ 8.95 (s, 1H), 7.60 (d, J=8.1 Hz, 1H), 6.94 (s, 1H), 6.88 (d, J=8.1 Hz, 1H), 4.91 (s, 2H), 3.77 (s, 3H) ppm.

4.2.h 1,3-Dihydro-1-hydroxy-5-methyl-2,1-benzoxaborole 5-methylbenzo[c][1,2]oxaborol-1(3H)-ol (C8)

M.p. 124-128° C. MS ESI: m/z=148.9 (M+1) and 146.9 (M−1). $^1$H NMR (300 MHz, DMSO-d$_6$): δ 9.05 (s, 1H), 7.58 (d, J=7.2 Hz, 1H), 7.18 (s, 1H), 7.13 (d, J=7.2 Hz, 2H), 4.91 (s, 2H), 2.33 (s, 3H) ppm.

4.2.i 1,3-Dihydro-1-hydroxy-5-hydroxymethyl-2,1-benzoxaborole 5-(hydroxymethyl)benzo[c][1,2]oxaborol-1(3H)-ol (C9)

MS: m/z=163 (M−1, ESI−). $^1$H NMR (300 MHz, DMSO-d$_6$): δ 9.08 (s, 1H), 7.64 (d, 1H), 7.33 (s, 1H), 7.27 (d, 1H), 5.23 (t, 1H), 4.96 (s, 2H), 4.53 (d, 2H) ppm.

4.2.j 1,3-Dihydro-5-fluoro-1-hydroxy-2,1-benzoxaborole 5-fluorobenzo[c][1,2]oxaborol-1(3H)-ol (C10)

M.p. 110-114° C. MS ESI: m/z=150.9 (M−1). $^1$H NMR (300 MHz, DMSO-d$_6$): δ 9.20 (s, 1H), 7.73 (dd, J$_1$=6 Hz, J$_2$=6 Hz, 1H), 7.21 (m, 1H), 7.14 (m, 1H), 4.95 (s, 2H) ppm.

4.2.k 1,3-Dihydro-2-oxa-1-cyclopenta[á]naphthalene naphtho[1,2-c][1,2]oxaborol-1(3H)-ol (C11)

M.P. 139-143° C. MS ESI: m/z=184.9 (M+1). $^1$H NMR (300 MHz, DMSO-d$_6$): δ 9.21 (s, 1H), 8.28 (dd, J$_1$=6.9 Hz, J$_2$=0.6 Hz, 1H), 7.99 (d, J=8.1 Hz, 1H), 7.95 (d, J=7.5 Hz, 1H), 7.59-7.47 (m, 3H), 5.09 (s, 2H) ppm.

4.2.m 1,3-Dihydro-6-fluoro-1-hydroxy-2,1-benzoxaborole 6-fluorobenzo[c][1,2]oxaborol-1(3H)-ol (C13)

M.p. 110-117.5° C. MS (ESI): m/z=151 (M−1, negative). HPLC (220 nm): 100% purity. $^1$H NMR (300 MHz, DMSO-d$_6$): δ 9.29 (s, 1H), 7.46-7.41 (m, 2H), 7.29 (td, 1H) and 4.95 (s, 2H) ppm.

4.2.n 3-Benzyl-1,3-dihydro-1-hydroxy-3-methyl-2,1-benzoxaborole 3-benzyl-3-methylbenzo[c][1,2]oxaborol-1(3H)-ol (C14)

MS (ESI): m/z=239 (M+1, positive). HPLC: 99.5% purity at 220 nm and 95.9% at 254 nm. $^1$H NMR (300 MHz, DMSO-d$_6$): δ 8.89 (s, 1H), 7.49-7.40 (m, 3H), 7.25-7.19 (m, 1H), 7.09-7.05 (m, 3H), 6.96-6.94 (m, 2H), 3.10 (d, 1H), 3.00 (d, 1H) and 1.44 (s, 3H) ppm.

4.2.o 3-Benzyl-1,3-dihydro-1-hydroxy-2,1-benzoxaborole 3-benzylbenzo[c][1,2]oxaborol-1(3H)-ol (C15)

MS (ESI+): m/z=225 (M+1). HPLC: 93.4% purity at 220 nm. $^1$H NMR (300 MHz, DMSO-d$_6$): δ 9.08 (s, 1H), 7.63 (dd, 1H), 7.43 (t, 1H), 7.35-7.14 (m, 7H), 5.38 (dd, 1H), 3.21 (dd, 1H) and 2.77 (dd, 1H) ppm.

4.2.p 1,3-Dihydro-4-fluoro-1-hydroxy-2,1-benzoxaborole 4-fluorobenzo[c][1,2]oxaborol-1(3H)-ol (C16)

$^1$H-NMR (300 MHz, DMSO-d$_6$) δ (ppm) 5.06 (s, 2H), 7.26 (ddd, J=9.7, 7.9, 0.6 Hz, 1H), 7.40 (td, J=8.2, 4.7 Hz, 1H), 7.55 (d, J=7.0 Hz, 1H), 9.41 (s, 1H).

4.2.q 5-(4-Cyanophenoxy)-1,3-dihydro-1-hydroxy-2,1-benzoxaborole 4-(1-hydroxy-1,3-dihydrobenzo[c][1,2]oxaborol-5-yloxy)benzonitrile (C17)

$^1$H-NMR (300 MHz, DMSO-d$_6$) δ ppm 4.95 (s, 2H), 7.08 (dd, J=7.9, 2.1 Hz, 1H), 7.14 (d, J=8.8 Hz, 1H), 7.15 (d, J=2.1 Hz, 1H), 7.78 (d, J=7.9 Hz, 1H), 7.85 (d, J=9.1 Hz, 2H), 9.22 (s, 1H).

4.2.r 6-(4-Cyanophenoxy)-1,3-dihydro-1-hydroxy-2,1-benzoxaborole 4-(1-hydroxy-1,3-dihydrobenzo[c][1,2]oxaborol-6-yloxy)benzonitrile (C18)

M.p. 148-151° C. MS: m/z=252 (M+1) (ESI+) and m/z=250 (M−1) (ESI−). HPLC: 100% purity at 254 nm and 98.7% at 220 nm. $^1$H NMR (300 MHz, DMSO-d$_6$): δ 9.26 (s, 1H), 7.82 (d, 2H), 7.50 (d, 1H), 7.39 (d, 1H), 7.26 (dd, 1H), 7.08 (d, 2H) and 4.99 (s, 2H) ppm.

4.2.s 6-(3-Cyanophenoxy)-1,3-dihydro-1-hydroxy-2,1-benzoxaborole 3-(1-hydroxy-1,3-dihydrobenzo[c][1,2]oxaborol-6-yloxy)benzonitrile (C19)

M.p. 146-149° C. MS: m/z=252 (M+1) (ESI+) and m/z=250 (M−1) (ESI−). HPLC: 100% purity at 254 nm and 97.9% at 220 nm. $^1$H NMR (300 MHz, DMSO-d$_6$): δ 9.21 (s, 1H), 7.60-7.54 (m, 2H), 7.50-7.45 (m, 2H), 7.34-7.30 (m, 2H), 7.23 (dd, 1H) and 4.98 (s, 2H) ppm.

4.2.t 6-(4-Chlorophenoxy)-1,3-dihydro-1-hydroxy-2,1-benzoxaborole 6-(4-chlorophenoxy)benzo[c][1,2]oxaborol-1(3H)-ol (C20)

M.p. 119-130° C. MS: m/z=261 (M+1) (ESI+) and m/z=259 (M−1) (ESI−). HPLC: 100% purity at 254 nm and 98.9% at 220 nm. $^1$H NMR (300 MHz, DMSO-d$_6$): δ 9.18 (s, 1H), 7.45-7.41 (m, 3H), 7.29 (d, 1H), 7.19 (dd, 1H), 7.01 (d, 2H) and 4.96 (s, 2H) ppm.

4.2.u 6-Phenoxy-1,3-dihydro-1-hydroxy-2,1-benzoxaborole 6-phenoxybenzo[c][1,2]oxaborol-1(3H)-ol (C21)

M.p. 95-99° C. MS: m/z=227 (M+1) (ESI+) and m/z=225 (M−1) (ESI−). HPLC: 100% purity at 254 nm and 98.4% at 220 nm. $^1$H NMR (300 MHz, DMSO-d$_6$): δ 9.17 (s, 1H), 7.43-7.35 (m, 3H), 7.28 (s, 1H), 7.19-7.09 (m, 2H), 6.99 (d, 2H) and 4.96 (s, 2H) ppm.

4.2.v 5-(4-Cyanobenzyloxy)-1,3-dihydro-1-hydroxy-2,1-benzoxaborole 4-((1-hydroxy-1,3-dihydrobenzo[c][1,2]oxaborol-5-yloxy)methyl)benzonitrile (C22)

$^1$H-NMR (300 MHz, DMSO-d$_6$) δ (ppm) 4.90 (s, 2H), 5.25 (s, 2H), 6.98 (dd, J=7.9, 2.1 Hz, 1H), 7.03 (d, J=1.8 Hz, 1H), 7.62 (d, J=7.9 Hz, 1H), 7.64 (d, J=8.5 Hz, 2H), 7.86 (d, J=8.5 Hz, 1H), 9.01 (s, 1H).

4.2.w 5-(2-Cyanophenoxy)-1,3-dihydro-1-hydroxy-2,1-benzoxaborole 2-(1-hydroxy-1,3-dihydrobenzo[c][1,2]oxaborol-5-yloxy)benzonitrile (C23)

$^1$H-NMR (300 MHz, DMSO-d$_6$) δ (ppm) 4.95 (s, 2H), 7.0-7.2 (m, 3H), 7.32 (td, J=7.6, 1.2 Hz, 1H), 7.68 (ddd, J=9.1, 7.6, 1.8 Hz, 1H), 7.77 (d, J=7.9 Hz, 1H), 7.91 (dd, J=7.9, 1.8 Hz, 1H).

4.2.x 5-Phenoxy-1,3-dihydro-1-hydroxy-2,1-benzoxaborole 5-phenoxybenzo[c][1,2]oxaborol-1(3H)-ol (C24)

$^1$H-NMR (300 MHz, DMSO-d$_6$) δ (ppm) 4.91 (s, 2H), 6.94 (s, 1H), 6.96 (d, J=8.8 Hz, 1H), 7.05 (d, J=7.6 Hz, 2H), 7.17 (t, J=7.3 Hz, 1H), 7.41 (t, J=7.3 Hz, 2H), 7.70 (d, J=8.5 Hz, 1H), 9.11 (s, 1H).

4.2.y 5-[4-(N,N-Diethylcarbamoyl)phenoxy]-1,3-dihydro-1-hydroxy-2,1-benzoxaborole N,N-diethyl-4-(1-hydroxy-1,3-dihydrobenzo[c][1,2]oxaborol-5-yloxy)benzamide (C25)

$^1$H-NMR (300 MHz, DMSO-d$_6$) δ (ppm) 1.08 (br s, 6H), 3.1-3.5 (m, 4H), 4.93 (s, 2H), 7.0-7.1 (m, 4H), 7.37 (d, J=8.5 Hz, 2H), 7.73 (d, J=7.9 Hz, 1H), 9.15 (s, 1H).

4.2.z 1,3-Dihydro-1-hydroxy-5-[4-(morpholinocarbonyl)phenoxy]-2,1-benzoxaborole (4-(1-hydroxy-1,3-dihydrobenzo[c][1,2]oxaborol-5-yloxy)phenyl)(morpholino)methanone (C26)

$^1$H-NMR (300 MHz, DMSO-d$_6$) δ (ppm) 3.3-3.7 (m, 8H), 4.93 (s, 2H), 7.0-7.1 (m, 4H), 7.44 (d, J=8.8 Hz, 2H), 7.73 (d, J=7.9 Hz, 1H), 9.16 (s, 1H).

4.2.aa 5-(3,4-Dicyanophenoxy)-1,3-dihydro-1-hydroxy-2,1-benzoxaborole 4-(1-hydroxy-1,3-dihydrobenzo[c][1,2]oxaborol-5-yloxy)phthalonitrile (C27)

$^1$H-NMR (300 MHz, DMSO-d$_6$) δ (ppm) 4.97 (s, 2H), 7.13 (dd, J=7.9, 2.1 Hz, 1H), 7.21 (d, J=1.5 Hz, 1H), 7.43 (dd, J=8.8, 2.6 Hz, 1H), 7.81 (d, J=7.9 Hz, 1H), 7.82 (d, J=2.6 Hz, 1H), 8.11 (d, J=8.5 Hz, 1H), 9.26 (s, 1H).

4.2.ab 6-Phenylthio-1,3-dihydro-1-hydroxy-2,1-benzoxaborole 6-(phenylthio)benzo[c][1,2]oxaborol-1(3H)-ol (C28)

M.p. 121-124° C. MS: m/z=243 (M+1) (ESI+) and m/z=241 (M−1) (ESI−). HPLC: 99.6% purity at 254 nm and 99.6% at 220 nm. $^1$H NMR (300 MHz, DMSO-d$_6$): δ 9.25 (s, 1H), 7.72 (dd, 1H), 7.48 (dd, 1H), 7.43 (dd, 1H), 7.37-7.31 (m, 2H), 7.29-7.23 (m, 3H), and 4.98 (s, 2H) ppm.

4.2.ac 6-(4-trifluoromethoxyphenoxy)-1,3-dihydro-1-hydroxy-2,1-benzoxaborole 6-(4-(trifluoromethoxy)phenoxy)benzo[c][1,2]oxaborol-1(3H)-ol (C29)

M.p. 97-101° C. MS: m/z=311 (M+1) (ESI+) and m/z=309 (M−1) (ESI−). HPLC: 100% purity at 254 nm and 100% at 220 nm. $^1$H NMR (300 MHz, DMSO-d$_6$): δ 9.20 (s, 1H), 7.45 (d, 1H), 7.37 (d, 2H), 7.33 (d, 1H), 7.21 (dd, 1H), 7.08 (d, 2H), and 4.97 (s, 2H) ppm.

4.2.ad 5-(N-Methyl-N-phenylsulfonylamino)-1,3-dihydro-1-hydroxy-2, 1-benzoxaborole N-(1-hydroxy-1,3-dihydrobenzo[c][1,2]oxaborol-5-yl)-N-methylbenzenesulfonamide (C30)

M.p. 85-95° C. MS: m/z=304 (M+1) (ESI+) and m/z=302 (M−1) (ESI−). HPLC: 96.6% purity at 254 nm and 89.8% at 220 nm. $^1$H NMR (300 MHz, DMSO-$d_6$): δ 9.23 (s, 1H), 7.72-7.63 (m, 2H), 7.56 (t, 2H), 7.50 (d, 2H), 7.16 (s, 1H), 7.03 (d, 1H), 4.91 (s, 2H) and 3.14 (s, 3H) ppm.

4.2.ae 6-(4-Methoxyphenoxy)-1,3-dihydro-1-hydroxy-2,1-benzoxaborole 6-(4-methoxyphenoxy)benzo[c][1,2]oxaborol-1(3H)-ol (C31)

M.p. 126-129° C. MS: m/z=257 (M+1) (ESI+) and m/z=255 (M−1) (ESI−). HPLC: 98.4% purity at 254 nm and 98.4% at 220 nm. $^1$H NMR (300 MHz, DMSO-$d_6$): δ 9.14 (s, 1H), 7.36 (d, 1H), 7.19 (s, 1H), 7.12 (d, 1H), 6.98 (d, 2H), 6.95 (d, 2H), 4.93 (s, 2H) and 3.73 (s, 3H) ppm.

4.2.af 6-(4-Methoxyphenylthio)-1,3-dihydro-1-hydroxy-2,1-benzoxaborole 6-(4-methoxyphenylthio)benzo[c][1,2]oxaborol-1(3H)-ol (C32)

M.p. 95-100° C. MS: m/z=272 (M+), 273 (M+1) (ESI+) and m/z=271 (M−1) (ESI−). HPLC: 100% purity at 254 nm and 99.2% at 220 nm. $^1$H NMR (300 MHz, DMSO-$d_6$): δ 9.20 (s, 1H), 7.51 (d, 1H), 7.39-7.28 (m, 4H), 6.98 (d, 2H), 4.93 (s, 2H) and 3.76 (s, 3H) ppm.

4.2.ag 6-(4-Methoxyphenylsulfonyl)-1,3-dihydro-1-hydroxy-2,1-benzoxaborole 6-(4-methoxyphenylsulfonyl)benzo[c][1,2]oxaborol-1(3H)-ol (C33)

M.p. 180-192° C. MS: m/z=305 (M+1) (ESI+) and m/z=303 (M−1) (ESI−). HPLC: 96.8% purity at 254 nm and 95.5% at 220 nm. $^1$H NMR (300 MHz, DMSO-$d_6$): δ 9.46 (s, 1H), 8.28 (s, 1H), 7.99 (d, 1H), 7.85 (d, 2H), 7.61 (d, 1H), 7.11 (d, 2H), 5.02 (s, 2H) and 3.80 (s, 3H) ppm.

4.2.ah 6-(4-Methoxyphenylsulfinyl)-1,3-dihydro-1-hydroxy-2,1-benzoxaborole 6-(4-methoxyphenylsulfinyl)benzo[c][1,2]oxaborol-1(3H)-ol (C34)

$^1$H NMR (300 MHz, DMSO-$d_6$): δ 9.37 (s, 1H), 8.02 (d, 1H), 7.71 (dd, 1H), 7.59 (d, 2H), 7.53 (d, 1H), 7.07 (d, 2H), 5.00 (s, 2H) and 3.76 (s, 3H) ppm.

4.2.ai 5-Trifluoromethyl-1,3-dihydro-1-hydroxy-2, 1-benzoxaborole 5-(trifluoromethyl)benzo[c][1,2]oxaborol-1(3H)-ol (C35)

M.p. 113-118° C. MS: m/z=203 (M+1) (ESI+) and m/z=201 (M−1) (ESI−). HPLC: 100% purity at 254 nm and 100% at 220 nm. $^1$H NMR (300 MHz, DMSO-$d_6$): δ 9.48 (s, 1H), 7.92 (d, 1H), 7.78 (s, 1H), 7.67 (d, 1H) and 5.06 (s, 2H) ppm.

4.2.aj 4-(4-Cyanophenoxy)-1,3-dihydro-1-hydroxy-2, 1-benzoxaborole 4-(1-hydroxy-1,3-dihydrobenzo[c][1,2]oxaborol-4-yloxy)benzonitrile (C36)

For coupling reaction between 4-fluorobenzonitrile and substituted phenol to give starting material 2, see Igarashi, S.; et al. Chemical & Pharmaceutical Bulletin (2000), 48(11), 1689-1697.

$^1$H-NMR (300 MHz, DMSO-$d_6$) □ (ppm) 4.84 (s, 2H), 7.08 (d, J=8.2 Hz, 2H), 7.18 (d, J=7.9 Hz, 1H), 7.45 (t, J=7.3 Hz, 1H), 7.63 (d, J=7.3 Hz, 1H), 7.82 (d, J=8.5 Hz, 2H).

4.2.ak 5-(3-Cyanophenoxy)-1,3-dihydro-1-hydroxy-2, 1-benzoxaborole 3-(1-hydroxy-1,3-dihydrobenzo[c][1,2]oxaborol-5-yloxy)benzonitrile (C37)

For coupling between 3-fluorobenzonitrile and substituted phenol to give starting material 2: Li, F. et al., *Organic Letters* (2003), 5(12), 2169-2171.

$^1$H-NMR (300 MHz, DMSO-$d_6$) □ (ppm) 4.93 (s, 2H), 7.0-7.1 (m, 2H), 7.3-7.4 (m, 1H), 7.5-7.7 (m, 3H), 7.75 (d, J=8.2 Hz, 1H).

4.2.al 5-(4-Carboxyphenoxy)-1,3 dihydro-1-hydroxy-2,1-benzoxaborole 4-(1-hydroxy-1,3-dihydrobenzo[c][1,2]oxaborol-5-yloxy)benzoic acid (C38)

To a solution of 5-(4-cyanophenoxy)-1-hydroxy-2,1-benzoxaborole obtained in C17 (430 mg, 1.71 mmol) in ethanol (10 mL) was added 6 mol/L sodium hydroxide (2 mL), and the mixture was refluxed for 3 hours. Hydrochloric acid (6 mol/L, 3 mL) was added, and the mixture was extracted with ethyl acetate. The organic layer was washed with brine and dried on anhydrous sodium sulfate. The solvent was removed under reduced pressure, and the residue was purified by silica gel column chromatography (ethyl acetate) followed by trituration with diisopropyl ether to give the target compound (37 mg, 8%).

$^1$H-NMR (300 MHz, DMSO-$d_6$) δ (ppm) 4.94 (s, 2H), 7.0-7.1 (m, 4H), 7.76 (d, J=7.9 Hz, 1H), 7.94 (d, J=8.8 Hz, 2H), 9.19 (s, 1H), 12.8 (br s, 1H).

4.2.am 1-Hydroxy-1, 3 dihydro-5-[4-(tetrazole-1-yl)phenoxy]-2,1-benzoxaborole 5-(4-(1H-tetrazole-5-yl)phenoxy)benzo[c][1,2]oxaborol-1(3H)-ol (C39)

A mixture of 5-(4-cyanophenoxy)-1-hydroxy-2,1-benzoxaborole (200 mg, 0.797 mmol), sodium azide (103 mg, 1.59 mmol), and ammonium chloride (85 mg, 1.6 mmol) in N,N-dimethylformamide (5 mL) was stirred at 80° C. for two days.

Water was added, and the mixture was extracted with ethyl acetate. The organic layer was washed with water and brine, and dried on anhydrous sodium sulfate. The solvent was removed under reduced pressure, and the residue was purified by silica gel column chromatography (ethyl acetate) followed by trituration with ethyl acetate to give the target compound (55 mg, 23%).

$^1$H-NMR (300 MHz, DMSO-d$_6$) δ (ppm) 4.95 (s, 2H), 7.0-7.1 (m, 2H), 7.23 (d, J=8.8 Hz, 2H), 7.76 (d, J=7.9 Hz, 1H), 8.05 (d, J=8.5 Hz, 2H), 9.18 (br s, 1H).

Example 5

Preparation of I from 2 via 6

5.1 Catalytic Boronylation, Reduction and Cyclization

A mixture of 2 (10.0 mmol), bis(pinacolato)diboron (2.79 g, 11.0 mmol), PdCl$_2$(dppf) (250 mg, 3 mol %), and potassium acetate (2.94 g, 30.0 mmol) in 1,4-dioxane (40 mL) was stirred at 80° C. for overnight. Water was added, and the mixture was extracted with ethyl acetate. The organic layer was washed with brine and dried on anhydrous sodium sulfate. The solvent was removed under reduced pressure. The crude product was dissolved in tetrahydrofuran (80 mL), then sodium periodate (5.56 g, 26.0 mmol) was added. After stirring at room temperature for 30 min, 2N HCl (10 mL) was added, and the mixture was stirred at room temperature for overnight. Water was added, and the mixture was extracted with ethyl acetate. The organic layer was washed with brine and dried on anhydrous sodium sulfate. The solvent was removed under reduced pressure, and the residue was treated with ether to afford 6.3 mmol of the corresponding boronic acid. To the solution of the obtained boronic acid (0.595 mmol) in methanol (5 mL) was added sodium borohydride (11 mg, 0.30 mmol), and the mixture was stirred at room temperature for 1 h. Water was added, and the mixture was extracted with ethyl acetate. The organic layer was washed with brine and dried on anhydrous sodium sulfate. The solvent was removed under reduced pressure, and the residue was purified by silica gel column chromatography to give 0.217 mmol of I.

5.2 Results

Analytical data for exemplary compounds of structure I are provided below.

5.2.a
1,3-Dihydro-5-fluoro-1-hydroxy-2,1-benzoxaborole (C10)

Analytical data for this compound is listed in 4.2.j.

Example 6

Preparation of I from 3

6.1 One-Pot Boronylation and Cyclization

To a solution of 3 (4.88 mmol) and triisopropyl borate (1.35 mL, 5.86 mmol) in tetrahydrofuran (10 mL) was added n-butyllithium (1.6 mol/L in hexanes; 6.7 mL, 10.7 mmol) dropwise over 15 min at −78° C. under nitrogen atmosphere, and the mixture was stirred for 2 h while allowing to warm to room temperature. The reaction was quenched with 2N HCl, and extracted with ethyl acetate. The organic layer was washed with brine and dried on anhydrous sodium sulfate. The solvent was removed under reduced pressure, and the residue was purified by silica gel column chromatography and treated with pentane to give 0.41 mmol of I.

6.2 Results

Analytical data for exemplary compounds of structure I are provided below.

6.2.a
1,3-Dihydro-5-fluoro-1-hydroxy-2,1-benzoxaborole (C10)

Analytical data for this compound is listed in 4.2.j.

Example 7

Preparation of I from 3

7.1 One-Pot Boronylation and Cyclization with Distillation

To a solution of 3 (4.88 mmol) in toluene (20 mL) was added triisopropyl borate (2.2 mL, 9.8 mmol), and the mixture was heated at reflux for 1 h. The solvent, the generated isopropyl alcohol and excess triisopropyl borate were removed under reduced pressure. The residue was dissolved in tetrahydrofuran (10 mL) and cooled to −78° C. n-Butyllithium (3.2 mL, 5.1 mmol) was added dropwise over 10 min, and the mixture was stirred for 1 h while allowing to warm to room temperature. The reaction was quenched with 2N HCl, and extracted with ethyl acetate. The organic layer was washed with brine and dried on anhydrous sodium sulfate. The solvent was removed under reduced pressure, and the residue was purified by silica gel column chromatography to give 1.54 mmol of I.

7.2 Results

Analytical data for exemplary compounds of structure I are provided below.

7.2.a
1,3-Dihydro-5-fluoro-1-hydroxy-2,1-benzoxaborole (C10)

Analytical data for this compound is listed in 4.2.j.

Example 8

Preparation of 8 from 7

8.1 Bromination

To a solution of 7 (49.5 mmol) in carbon tetrachloride (200 mL) were added N-bromosuccinimide (8.81 g, 49.5 mmol) and N,N-azoisobutylonitrile (414 mg, 5 mol %), and the mixture was heated at reflux for 3 h. Water was added, and the mixture was extracted with chloroform. The organic layer was washed with brine and dried on anhydrous sodium sulfate. The solvent was removed under reduced pressure to give the crude methyl-brominated intermediate 8.

Example 9

Preparation of 3 from 8

9.1 Hydroxylation

To crude 8 (49.5 mmol) were added dimethylformamide (150 mL) and sodium acetate (20.5 g, 250 mmol), and the mixture was stirred at 80° C. for overnight. Water was added, and the mixture was extracted with ether. The organic layer was washed with water and brine, and dried on anhydrous sodium sulfate. The solvent was removed under reduced pressure. To the residue was added methanol (150 mL) and 1N sodium hydroxide (50 mL), and the mixture was stirred at room temperature for 1 h. The reaction mixture was concentrated to about a third of volume under reduced pressure. Water and hydrochloric acid were added, and the mixture was extracted with ethyl acetate. The organic layer was washed with water and brine, and dried on anhydrous sodium sulfate. The solvent was removed under reduced pressure, and the residue was purified by silica gel column chromatography followed by trituration with dichloromethane to give 21.8 mmol of 3.

9.2 Results

Exemplary compounds of structure 3 prepared by the method above are provided below.

9.2.a 2-Bromo-5-cyanobenzyl Alcohol $^1$H-NMR (300 MHz, DMSO-$d_6$) δ ppm 4.51 (d, J=5.9 Hz, 2H), 5.67 (t, J=5.6 Hz, 1H), 7.67 (dd, J=8.2, 2.0 Hz, 1H), 7.80 (s, J=8.2 Hz, 1H), 7.83 (d, J=2.0 Hz, 1H).

Additional examples of compounds which can be produced by this method include 2-bromo-5-(4-cyanophenoxy) benzyl alcohol.

Example 10

Preparation of 9 from 2

10.1 Reaction

A mixture of 2 (20.0 mmol), (methoxymethyl)triphenylphosphonium chloride (8.49 g, 24.0 mmol), and potassium tert-butoxide (2.83 g, 24.0 mol) in N,N-dimethylformamide (50 mL) was stirred at room temperature for overnight. The reaction was quenched with 6 N HCl, and the mixture was extracted with ethyl acetate. The organic layer was washed with water (×2) and brine, and dried on anhydrous sodium sulfate. The solvent was removed under reduced. To the residue were added tetrahydrofuran (60 mL) and 6 N HCl, and the mixture was heated at reflux for 8 h. Water was added, and the mixture was extracted with ether. The organic layer was washed with brine and dried on anhydrous sodium sulfate. The solvent was removed under reduced pressure to afford 16.6 mmol of 9.

Example 11

Preparation Method of Step 13

11.1 Reaction

A solution of I in an appropriate alcohol solvent ($R^1$—OH) was refluxed under nitrogen atmosphere and then distilled to remove the alcohol to give the corresponding ester.

Example 12

Preparation of Ib from Ia 12.1 Reaction

To a solution of Ia in toluene was added amino alcohol and the participated solid was collected to give Ib.

12.2 Results (500 mg, 3.3 mmol) was dissolved in toluene (37 mL) at 80° C. and ethanolamine (0.20 mL, 3.3 mmol) was added. The mixture was cooled to room temperature, then ice bath, and filtered to give C40 as a white powder (600.5 mg, 94%).

12.2a Ethanolamine adduct of 1,3-Dihydro-5-fluoro-1-hydroxy-2,1-benzoxaborole (C40)

$^1$H-NMR (300 MHz, DMSO-$d_6$) δ (ppm) 2.88 (t, J=6.2 Hz, 2H), 3.75 (t, J=6.3 Hz, 2H), 4.66 (s, 2H), 5.77 (br, 2H), 6.85-6.91 (m, 2H), 7.31 (td, J=7.2, 1.2 Hz, 1H).

Example 13

Formulations

Compounds of the present invention can be administered to a patient using a therapeutically effective amount of a compound described herein in any one of the following three lacquer formulations and one solvent formulation. The lacquer formulation provides good durability while the solvent formulation provides good ease of use. These compounds can also be applied using a spray formulation, paint-on lacquer, drops, or other.
1. 1:4 propylene glycol:ethanol; 1:10 wt/vol compound of invention;
2. 1:4 poly(vinyl methyl ether-alt-maleic acid monobutyl ester:ethanol; 1:10 wt/vol compound of the invention;
3. 56% ethanol; 14% water; 15% poly(2-hydroxyethyl methacrylate); 5% dibutyl sebacate; 10% compound of the invention;
4. 55% ethanol; 15% ethyl acetate; 15% poly(vinyl acetate); 5% dibutyl sebacate; 10% compound of the invention.

The preparation of these formulations is well known in the art and is found in references such as *Remington: The Science and Practice of Pharmacy*, supra.

Example 14

Antifungal MIC Testing

All MIC testing followed the National Committee for Clinical Laboratory Standards (NCCLS) guidelines for antimicrobial testing of yeasts (M27-A2 NCCLS) and filamentous fungi (Pfaller et al., NCCLS publication M38-A—Reference Method for Broth Dilution Antifungal Susceptibility Testing of Filamentous Fungi; Approved Standard. Wayne, Pa.: NCCLS; 2002 (Vol. 22, No. 16) except the *Malassezia* species which was incubated in a urea broth (Nakamura et al., *Antimicrobial Agents And Chemotherapy*, 2000, 44(8) p. 2185-2186). Results of the MIC testing is provided in FIG. 1.

Example 15

Keratin Assay

Many antifungal agents strongly bind to keratin which not only reduces their antifungal potency but also may restrict their penetration into the nail. The affinities of the compounds for keratin powder was determined by a method described in Tatsumi, *Antimicrobial Agents and Chemotherapy*, 46(12):3797-3801 (2002).

A comparison of MIC data for several compounds of the invention against *T. rubrum*, with and without the presence of 5% keratin, is provided in FIG. 1.

Example 16

(C10) Antifungal Spectrum of Activity (C10) is a novel compound in development for use as a topical antifungal treatment. The purpose of this study was to determine the minimum inhibitory concentration (MIC) for (C10) against 19 test strains of fungi including: *Aspergillus fumigatus* (*A. fumigatus*), *Candida Albicans* (*C. albicans*, both fluconazole sensitive and resistant strains), *Candida glabrata* (*C. glabrata*), *Candida krusei* (*C. krusei*), *Cryptococcus neoformans* (*C. neoformans*), *Candida parapsilosis* (*C. parapsilosis*), *Candida tropicalis* (*C. tropicalis*), *Epidermophyton floccosum* (*E. floccosum*), *Fusarium solani* (*F. solani*), *Malassezia furfur* (*M. furfur*), *Malassezia pachydermatis* (*M. pachydermatis*), *Malassezia sympodialis* (*M. sympodialis*), *Microsporum audouinii* (*M. audouinii*), *Microsporum canis* (*M. canis*), *Microsporum gypseum* (*M. gypseum*), *Trichophyton mentagrophytes* (*T. mentagrophytes*), *Trichophyton rubrum* (*T. rubrum*), *Trichophyton tonsurans* (*T. tonsurans*). Fungal growth was evaluated after exposure to different concentrations of (C10). In addition, the MIC for (C10) against *T. rubrum* in the presence of 5% keratin powder and the minimum fungicidal concentration (MFC) for (C10) against *T. rubrum* and *T. mentagrophytes* were also determined. Ciclopirox and/or terbinafine and/or fluconazole and/or itraconazole were used as comparators and tested in a similar manner. These studies were conducted at NAEJA Pharmaceutical, Inc.

Materials and Methods (C10) was obtained from Anacor Pharmaceuticals, Inc. (Palo Alto, Calif., USA). ATCC strains were obtained from ATCC (Manassas, Va., USA). Ciclopirox-olamine was obtained from Sigma-Aldrich Co. (St. Louis, Mo., USA). Terbinafine, fluconazole and itraconazole were synthesized at NAEJA Pharmaceutical Inc. (Edmonton, AB, Canada), experimental procedures and analytical data for these standards are stored in NAEJA archives.

All MIC testing followed the National Committee for Clinical Laboratory Standards (NCCLS) guidelines for antimicrobial testing of yeasts and filamentous fungi (Pfaller et al., 2002) except the *Malassezia* species which were incubated in a urea broth (Nakamura et al., 2000). The microbroth dilution method was used to test the in vitro activity of (C10) against 19 test strains of fungi. Briefly, compounds were dissolved in DMSO and diluted in sterile water to give a working stock. Two-fold serial dilutions of the working stock were prepared in 96-well plates and media was added. Media was RPMI, RPMI+MOPS, modified RPMI, or modified Urea broth. The plates were inoculated with the fungal suspensions to give a final inoculum size of $0.5$-$2.5 \times 10^3$ cells/mL for yeasts or $0.4$-$5 \times 10^4$ CFU/mL for filamentous fungi and then incubated for 24-168 h at 35° C. The final concentration of DMSO did not exceed 5%. The MIC was defined as the lowest concentration that resulted in over 90% reduction of growth, as compared to a drug-free control. The MFC was defined as the lowest concentration that killed over 90% of the fungi, as compared to a drug-free control.

Results and Conclusions

The results for the MIC of (C10) and reference compounds against 19 strains of fungi are shown in FIG. 2. The results for the MFC of C10 against 2 strains of fungi are shown in Table 2. (C10) had MIC values ranging from 0.25-2 μg/mL against all fungi tested. Addition of 5% keratin powder to the media did not effect the MIC against *T. rubrum*. (C10) had fungicidal activity against *T. rubrum* and *T. mentagrophytes* with MFC values of 8 and 16 μg/mL, respectively. Reference compounds had MIC values in the range defined by NCCLS.

Example 17

The Solubility, Stability and Log P Determination of Compounds of the Present Invention by LC/MS/MS The solubility, room temperature stability and Log P of C10 was determined by the following methodology.

Reagents and Standards:

Ethanol: 200 proof ACS Grade (EM Science, Gibbstown, N.J., USA); Octanol: Octyl alcohol (EM Science, Gibbstown, N.J., USA); Acetonitrile: HPLC Grade (Burdick & Jackson, Muskegon, Mich., USA); Ammonium Acetate: lot 3272X49621 (Mallinckrodt, Phillipsburg, N.J., USA); C10: lot A032-103 (Anacor Pharmaceuticals, Palo Alto, Calif., USA); p-Nitrophenol (PNP): lot OGNO1 (TCI America, Portland, Oreg., USA); Water: Deionized water (from Millipore systems, Billerica, Mass., USA)

Solubility

N-Octanol and water were mutually pre-saturated by vigorously stirring a mixture of both solvents for up to 12 h and the mixture was allowed to separate. Solubility in each solvent was determined by adding 10 μL of 20, 40, 200, 1000 and 5000 μg/mL of C10 in DMSO to the pre-saturated n-octanol or water. After the sample was vortexed for 10 sec, the sample was centrifuged for 10 min at ca. 3000 rpm. A visual inspection was made to determine if the sample was clear or if a pellet had formed on the bottom of the tube.

Log P

C10 (10 μL of 5000μ/mL) at 2× the final concentration was added to 0.5 mL pre-saturated n-octanol and mixed. An equal volume (0.5 mL) of pre-saturated water was added, vortex mixed and then mixed on a rotating shaker for one hour and 24 h in triplicate at ca. 25° C. The organic and aqueous layers were separated by centrifugation for 5 min at ca. 2000 rpm. Twenty five L of the octanol (top) layer were removed and placed in a pre-labeled tube. Twenty five L of the aqueous layer (bottom) were removed, taking care to avoid octanol contamination, and placed in a pro-labeled tube.

Stability at Room Temperature

C10 (10 µL of 5000 µg/mL) was added both to 0.5 mL n-octanol and 0.5 mL water in triplicate. Samples were mixed. At 0 h and 24 h samples were stored at ca. −20° C. Twenty five L of sample was used for analysis.

Extraction Procedure C10

For the octanol sample, 25 µL of ethanol, 25 µL of water and 300 µL of acetonitrile containing the internal standard was added. For the water sample, 25 µL of ethanol, 25 µL of octanol and 300 µL of acetonitrile containing the internal standard [60 mL of acetonitrile add 6 µL of PNP (1000 µg/mL)] was added. For the calibrators 25 µL of octanol, 25 µL of water and 300 µL of acetonitrile containing the internal standard was added. The sample was vortexed for 10 seconds. Two hundred µL of the organic layer were transferred into a clean deactivated autosampler vial.

Calculations

A 1/concentration weighted linear regression was used for the quantitation of C10. All integration were performed with peak areas using Analyst version 1.3, Applied Biosystems. For C10, peak area ratios analyte to internal standard PNP were used for all quantitation.

The partition coefficient (P) was calculated according to the equation detailed below:

$$P = [\text{Sample concentration}]_{octanol} / [\text{Sample concentration}]_{water}$$

$$\text{Log } P = \log_{10}(\text{partition coefficient})$$

Results:

As shown in Table 17A the solubility of C10 in both octanol and water is very good over the concentration range tested.

TABLE 17A

Solubility of C10 in water and octanol

| Targeted Conc (µg/mL) | Water Visual | Octanol Visual |
|---|---|---|
| 0.800 | Clear | Clear |
| 4.00 | Clear | Clear |
| 20.0 | Clear | Clear |
| 100 | Clear | Clear |

Table 17B shows the results of the log P determination after 1 h and 24 h for C10. The mean log P after 1 h was 1.97 (n=3). After 24 h the concentrations in both the octanol and water layer remained the same. The mean log P after 24 h was 1.93 (n=3).

TABLE 17B

Log P of C10

| Sample | Conc. in Water (µg/mL) | Conc. in Octanol (µg/mL) | Log P |
|---|---|---|---|
| 1 h-1 | 1.26 | 108 | 1.93 |
| 1 h-2 | 1.21 | 103 | 1.93 |
| 1 h-3 | 1.05 | 115 | 2.04 |
| 24 h-1 | 1.27 | 104 | 1.91 |
| 24 h-2 | 1.17 | 109 | 1.97 |
| 24 h-3 | 1.28 | 99.0 | 1.89 |

A stability study for C10 was initiated at room temperature over 24 h without continuous mixing. Table 17C shows that C10 in pure water and octanol is stable over 24 h.

TABLE 17C

Water and Octanol stability for C10 at room temperature after 24 h.

| Sample | Mean (µg/mL) | SD | Percent Remaining 24 h versus 0 g |
|---|---|---|---|
| Water-0 h | 82.5 | 3.72 | 115 |
| Water-24 h | 95.0 | 21.4 | |
| Octanol-0 h | 115 | 3.06 | 93 |
| Octanol-24 h | 107 | 6.11 | |

Example 18

Determination of Penetration of C10 into the Human Nail

Two nail penetration studies were performed based on the protocol in Hui et al., *Journal of Pharmaceutical Sciences*, 91(1): 189-195 (2002) ("Hui protocol"). The purpose of this study was to determine and compare the penetration and distribution of C10 in vehicle into the human nail plate in vitro relative to 8% ciclopirox w/w in commercial lacquer (Penlac®).

Materials and Methods

Test Article and Dosage Formulation

8% ciclopirox w/w in commercial lacquer was manufactured by Dermick (Berwyn, Pa.). The radiochemical purity and specific activity of the chemical was determined as >95% and 12.5 mCi/mmol, respectively.

The study was composed of two groups. The compositions (weight %) of the dosage formulations are as follows:

Active radiolabeled compound in four groups.

| Groups* | Dosing (×14 days) | Test Chemical (%) | Radioactivity (per 10 µL) |
|---|---|---|---|
| A (C10) | qd | 10 | 0.19 µCi |
| C (Ciclopirox) | qd | 8 | 0.22 µCi |

*A = C10 group, C = Ciclopiriox group

Human Nails

Healthy human finger nail plates were collected from adult human cadavers and stored in a closed container at 0-4° C. Before the experiment, the nail plates were gently washed with normal saline to remove any contamination, then re-hydrated by placing them for three hours on a cloth wetted with normal saline. The nail samples were randomly selected into four groups.

Dosing and Surface Washing Procedures

Dose Preparation:

Radioactivity of each group is approximately 0.19±0.01 and 0.22±0.03 µCi/10 µL solutions respectively, for $^{14}$C—C10 (group A), and $^{14}$C-ciclopirox (group C).

Experiment Procedure:

| Study Day | Group A | | | Group C | | |
|---|---|---|---|---|---|---|
| | wash | dose | sample | wash | dose | sample |
| 1 | | D | | | D | |
| 2 | W | D | | W | D | |
| 3 | W | D | C | W | D | C |
| 4 | W | D | | W | D | |
| 5 | W | D | | W | D | |

-continued

| Study | Group A | | | Group C | | |
|---|---|---|---|---|---|---|
| Day | wash | dose | sample | wash | dose | sample |
| 6 | W | D | C | W | D | C |
| 7 | W | D |  | W | D |  |
| 8 | W | D |  | W | D |  |
| 9 | W | D | C | W | D | C |
| 10 | W | D |  | W | D |  |
| 11 | W | D |  | W | D |  |
| 12 | W | D | C | W | D | C |
| 13 | W | D |  | W | D |  |
| 14 | W | D |  | W | D |  |
| 15 | W |  | C, N | W |  | C, N |

W = once per day before dosing (9~10 AM).
D = once per day (9~10 AM).
C = changing/sampling cotton ball after surface washing before topical dosing.
N = Nail sampling.

Washing Procedure

Surface washing was started in morning 10 min prior to next dosing, the surface of the nail was washed with cotton tips in a cycle, as follows:
  a tip wetted with absolute ethanol, then
  a tip wetted with 50% IVORY liquid soap, then
  a tip wetted with distilled water, then
  a final tip wetted with distilled water.

The washing samples from each cycle of each nail were pooled and collected by breaking off the cotton tip into scintillation glass vials. Aliquots of 3.0 mL methanol were added into each vial to extract test material. The radioactivity of each sample was measured in a liquid scintillation counter.

Incubation System

A Teflon one-chamber diffusion cell (PermeGear, Inc., Hellertown, Pa.) was used to hold each nail. To approximate physiological conditions, a small cotton ball wetted with 0.1 mL normal saline was placed in the chamber to serve as a nail bed and provide moisture for the nail plate. Every 3 days, 0.1 mL normal saline was injected through the inlet into the chamber to keep the cotton ball wet. The nail plate was placed on a ledge inside the receptor (1.0 cm in diameter and 0.5 cm high). The ventral (inner) surface of the nail was placed face down and rested on the wet cotton ball. The cells were placed on a platform in a large glass holding tank filled with saturated sodium phosphate solution to keep the cells at a constant humidity of 40%.

Sampling Instrument

The nail sampling instrument had two parts, a nail sample stage and a drill.

The nail sampling stage consists of a copper nail holder, three adjustments, and a nail powder capture. Three adjustments allow movement in vertical direction. The first coarse adjustment (on the top) was for changing the copper cell and taking powder samples from the capture. The other two adjustments (lower) were for sampling process. The second coarse adjustment allowed movement of 25 mm and the fine adjustment provides movement of 0.20 mm. The nail powder capture was located between the copper cell and the cutter. The inner shape of the capture was inverted funnel and the end of funnel connects to a vacuum. By placing a circle filter paper inside of the funnel, the nail powder samples were captured on the filter paper during the sampling process.

Sampling Procedure

After completion of the incubation phase, the nail plate was transferred from the diffusion cell to a clean copper nail holder for sampling process. The nail plate was inverted so that the ventral (nail bed) surface now faced up and the dorsal (outer) dosed surfaced faced down. The copper nail holder has an opening as it sits on top of the stage. When the sampling process initiated, the coarse adjustment was adjusted to move the position of the stage until the nail plate was just touching the tip of the cutter. Then the drill was turned on and the fine adjustment was turned to push the stage closer to the drill, removing a nail core sample. After the above process, approximate 0.40-0.50 mm in depth and 7.9 mm in diameter nail pulverized samples were harvested from the center of the ventral (nail bed) surface of the nail.

The powdered nail samples were collected into a glass scintillation vial and weighted. Aliquots of 5.0 mL Packard soluene-350 (Packard Instrument Company, Meriden, Conn.) was added to the scintillation vial to dissolve the powder. The upper part, the intermediate and dorsal layers of the center of the nail, including the area of application of the dose was cut in the same diameter as the sampled area and was then placed into a glass scintillation vial with 5.0 mL packard soluene-350. The rest of the nail was also placed in a glass scintillation vial with 5.0 mL packard soluene-350.

The amount of nail sample removed was measured by the difference in weight of the nail plate before and after drilling, and collecting the core of powder.

Radioactivity Measurement

All radioactivity measurements were conducted with a Model 1500 Liquid Scintillation Counter (Packard Instrument Company, Downer Grove, Ill.). The counter was audited for accuracy using sealed samples of quenched and unquenched standards as detailed by the instrument manual. The $^{14}C$ counting efficiency is equal to or greater than 95%. All nail samples pre-treated with packard soluene-350 were incubated at 40° C. for 48 hours followed by the addition of 10 mL scintillation cocktail (HIONIC-FLUOR, Packard Instrument Company, Meriden, Conn.). Other samples (standard dose, surface washing, and bedding material) were mixed directly with Universal ES scintillation cocktail (ICN Biomedicals, Costa Mesa, Calif.). Background control and test samples were counted for 3 minutes each for radioactivity.

Data Analysis

All sample counts (expressed as dpm) were transcribed by hand to a computerized spreadsheet (Microsoft Excel). The individual and mean (+S.D.) amount of test chemical equivalent in nail, bedding material, and wash samples are presented as dpm, µCi, percent administered dose, and mg equivalent at each time point. The concentration of $^{14}C$-labeled test chemicals were calculated from the value based on the specific activity of each [$^{14}C$]-test chemical. The information of concentration of non-labeled test chemical in the topical formulation was obtained from the manufactures. Total concentration of test chemical equivalent is the sum of the concentration of $^{14}C$-labeled test chemical and the concentration of non-labeled test chemical. The value of total amount of test chemical equivalent in each nail sample was calculated from those values based on radioactivity of the sample and the ratio of total mg test chemical equivalent and radioactivity of the test chemical. The data was further normalized by dividing with the weight of the sample. Statistical significant of nail samples from every two groups was analyzed by student t-test.

Results

Characteristics of Nail Samples

For both groups (Group A group and Group C) the thickness of whole nail plate, the depth of the ventral surface core sample removed by cutter, the percentage of the whole nail thickness, and the actual weight of powdered nail sample were collected. No statistical difference is found between two groups (P>0.05).

Weight Normalized C10 and Ciclopirox Equivalent in Nail

FIG. 3 shows summarized normalized drug equivalents in each part (layer) of nail samples. After weight normalization, the concentration of C10 equivalent in dorsal/intermediate center, ventral/intermediate center, and remainder nail samples was significantly higher than that of ciclopirox equivalent (p≤0.002).

C10 and Ciclopirox Equivalent in Cotton Ball Nail Supporting Bed

FIG. 4 shows summarized C10 and ciclopirox equivalent in supporting bed cotton ball samples. Similar to weight normalized C10 equivalent in the nail plate samples, absolute amount of C10 equivalent per cotton ball sample in group A (after 14 day dosing) was significantly higher than that of ciclopirox in group C (p≤0.004). The difference of these two test chemicals was 250 times.

Mass Balance of Radioactivity of [$^{14}$C]-C10 and [$^{14}$C]-Ciclopirox after 14-Day Treatment Table 5 shows summarized radioactive recovery from washing, nail samples, and supporting bed cotton ball samples. Cumulative radioactivity recoveries of carbon-14 were 88±9.21, and 89±1.56 percent of applied dose in group A, and group C, respectively. 88% of the radiolabeled material was accounted for.

Conclusion

In this study, penetration rate of [$^{14}$C]-C10 in Anacor topical formulation and [$^{14}$C]-ciclopirox (8% w/w in commercial lacquer) into human nail with four different dosing and washing methods was studied.

Results show that much more amount of [$^{14}$C]-C10 penetrating into the deeper parts of the nail when compared with [$^{14}$C]-ciclopirox. Tables 3 and 4 show that the amount of [$^{14}$C]-C10 equivalent in ventral/intermediate center of the nail layer and cotton ball supporting bed in the group A was statistically higher (p≤0.002) than group C after a 14-day dosing period.

Example 19

Determination of Penetration of C10 into the Human Nail

The aim of the current study was to assess and compare the perungual absorption of C10 in a simple vehicle using MedPharm's TurChub® model (see http://www.medpharm.co.uk; specificaly http://www.medpharm.co.uk/downloads/Skin%20and%20nail%2dec%202003.pdf viewed Feb. 14, 2006). in a full scale experiment. Six replicates involving C10 were conducted and Formulations Y (8% ciclopirox w/w in commercial lacquer) and Z (Loceryl, 5% amorolfine w/v in commercial lacquer) were used as the reference formulations.

The following materials were used in these experiments. These materials were used without any modifications.

A dose of 40 µL/cm$^2$ of the test compound C10 in 50:50 propylene glycol:ethyl acetate was applied to a full thickness nail sample each day over a total duration of five days. Both the reference formulations were also applied at the same dose.

TurChub® Zone of Inhibition Experiment

Placebo, test item C10 in vehicle and the reference formulations Y and Z were tested for their inhibition of *Trichophyton rubrum* (*T. rubrum*) growth after penetration through a full thickness human nail using a zone of inhibition measurement.

Formulation Efficacy Testing

FIGS. 5-9 show the results obtained from the TurChub zone of inhibition assays. It can be observed that C10 is a potent antifungal agent, which can penetrate through a full thickness nail to elicit its effect against the target organism *T. rubrum*. No zones of inhibition were observed with reference formulations Y and Z or with the placebo for C10. The experiment using C10 was repeated for a second time to confirm the result and it can be observed from FIGS. 6 and 7 that C10 shows zones of inhibition of 100%, 67%, 46%, 57%, 38% and 71% in the first experiment and 74%, 86%, 100%, 82%, 100% and 84% in the second experiment. The measurement was taken from the nail to the first point of growth observed.

From the results obtained using MedPharm's TurChub zone of inhibition assay as a test system, the test item C10 was found to be a powerful antifungal agent and demonstrated superior results vs. the commercial reference formulations Y and Z. From these experiments it appears that the compound is permeating through a full thickness nail barrier to exhibit the antifungal activity.

Example 20

Determination of Penetration of C10 into the Human Nail: Dose Response

The optimal dose-response range for penetration into the human nail was determined to be between 1% and 15%. The experiments to determine the optimal dose-response was conducted as follows.

Tests at different test compound concentrations were conducted on nails derived from the same cadaver. Cadaver nails were hydrated overnight, cut into 4 equally sized squares and placed onto individual poloxomer supports. Test articles were formulated in a lacquer at 1%, 2.5%, 5%, 7.5%, 10% and 15% w/v. A 40 µL/cm$^2$ dose is applied to the center of the nail piece and the nails are left for 24 hrs. Nails are removed from the poloxomer support. Poloxomer support is analyzed for quantity of compound using LC/MS/MS.

Example 21

Preparation of Pyridinyloxaboroles

21a. Metallation and Boronylation

To a solution of 3-bromo-4-hydroxymethylpyridine (10.7 mmol) and B(OMe)$_3$ (2.73 mL, 11.9 mmol) in anhydrous THF (20 mL) at −78° C. under nitrogen was added dropwise n-BuLi (13.6 mL, 21.8 mmol). The cooling bath was then removed. The mixture was warmed gradually with stirring for 30 min and then stirred with a water bath for 2 h. Brine was then added and the pH adjusted to 7 using 6N HCl. The mixture was washed with THF (×2) and the aqueous layer (containing product) was evaporated to dryness. The residue was washed with THF and the product was extracted into ethanol (×2). Ethanol was removed in vacuo, water was added to the residue and removed in vacuo. Toluene was added and removed in vacuo. The resulting residue was triturated with diethyl ether and the product was collected by filtration to afford C12.

21b. 7-Hydroxy-2,1-oxaborolano[5,4-c]pyridine [[1,2]oxaborolo[3,4-c]pyridin-1(3H)-ol] (C12)

$^1$H-NMR (300 MHz, DMSO-$d_6$): δ ppm 5.00 (s, 2H), 7.45 (d, J=5.0 Hz, 1H), 8.57 (d, J=5.3 Hz, 1H), 8.91 (s, 1H), 9.57 (s, 1H). ESI-MS m/z 134 (M-H)$^-$, $C_6H_6BNO_2$=135.

Example 22

Cyclic Borinic Esters

Additional compounds can be produced by the methods described herein. By choosing the appropriate starting material such as 1 or 3, Examples 1-7 can be used to formulate the following compounds. Where available, melting point characterization is provided for these compounds.

22. Results

Analytical data for exemplary compounds of structure I are provided below.

22a Ethyl 2-(1-hydroxy-1,3-dihydrobenzo[c][1,2] oxaborol-5-yloxy)acetate (C41)

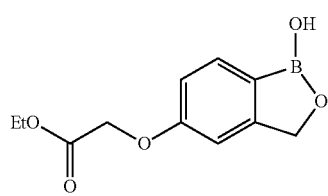 [SMILES: O=C(O)COc1ccc2c(c1)COB2O]

M.P. 134-137° C. Exemplary starting material: ethyl 2-(4-bromo-3-(hydroxymethyl)phenoxy)acetate.

22b 2-(1-hydroxy-1,3-dihydrobenzo[c][1,2]oxaborol-5-yloxy)acetic acid (C42)

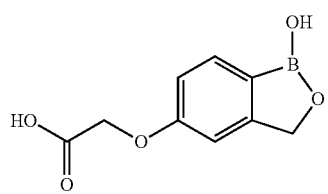

M.P. 163-166° C. Exemplary starting material: ethyl 2-(4-bromo-3-(hydroxymethyl)phenoxy)acetate. The title compound is obtained after saponification of the corresponding ester.

22c 6-(thiophen-2-ylthio)benzo[c][1,2]oxaborol-1 (3H)-ol (C43)

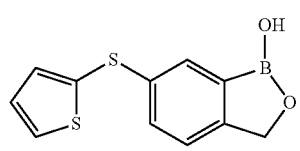 [SMILES: OB1OCc2ccc(Sc3cccs3)cc21]

M.P. 99-104° C. Exemplary starting material: (2-bromo-4-(thiophen-2-ylthio)phenyl)methanol.

22d 6-(4-fluorophenylthio)benzo[c][1,2]oxaborol-1 (3H)-ol (C44)

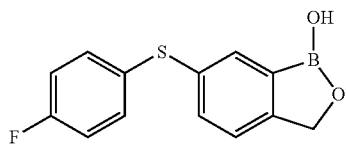 [SMILES: OB1OCc2ccc(Sc3ccc(F)cc3)cc21]

M.P. 135-138° C. Exemplary starting material: (2-bromo-4-(4-fluorophenylthio)phenyl)methanol.

22e 1-(3-((1-hydroxy-1,3-dihydrobenzo[c][1,2]oxaborol-5-yloxy)methyl)phenyl)pentan-1-one (C45)

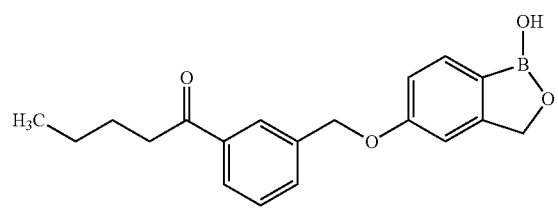 [SMILES: CCCCC(=O)c1cccc(COc2ccc3c(c2)COB3O)c1]

M.P. 96-98° C. Exemplary starting material: 1-(3-((4-bromo-3-(hydroxymethyl)phenoxy)methyl)phenyl)pentan-1-one.

22f 2-(1-hydroxy-1,3-dihydrobenzo[c][1,2]oxaborol-5-yloxy)-1-(piperidin-1-yl)ethanone (C46)

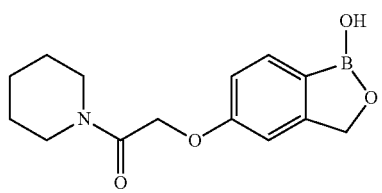 [SMILES: O=C(COc1ccc2c(c1)COB2O)N1CCCCC1]

M.P. 158-163° C. Exemplary starting material: 2-(4-bromo-3-(hydroxymethyl)phenoxy)-1-(piperidin-1-yl)ethanone.

22g 2-(1-hydroxy-1,3-dihydrobenzo[c][1,2]oxaborol-5-yloxy)-1-(4-(pyrimidin-2-yl)piperazin-1-yl) ethanone (C47)

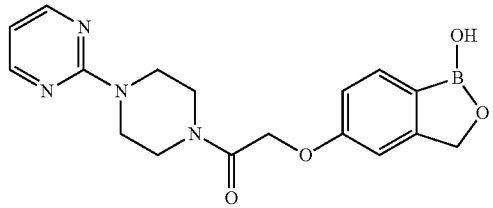 [SMILES: O=C(COc1ccc2c(c1)COB2O)N1CCN(c2ncccn2)CC1]

M.P. 190-195° C. Exemplary starting material: 2-(4-bromo-3-(hydroxymethyl)phenoxy)-1-(4-(pyrimidin-2-yl)piperazin-1-yl)ethanone.

22h 6-(4-(pyridin-2-yl)piperazin-1-yl)benzo[c][1,2]oxaborol-1(3H)-ol (C48)

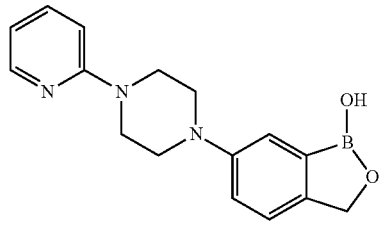 [SMILES: OB1OCc2ccc(N3CCN(c4ccccn4)CC3)cc21]

M.P. 135-138° C. Exemplary starting material: (2-bromo-4-(4-(pyridin-2-yl)piperazin-1-yl)phenyl)methanol.

22i 6-nitrobenzo[c][1,2]oxaborol-1(3H)-ol (C49)

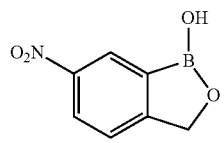

M.P. 163-171° C. Exemplary starting material: benzo[c][1,2]oxaborol-1(3H)-ol. See JACS 82, 2172, 1960 for preparation.

22j 6-aminobenzo[c][1,2]oxaborol-1(3H)-ol (C50)

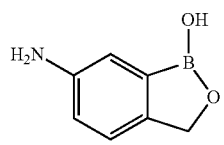

M.P. 145-148° C. Exemplary starting material: 6-nitrobenzo[c][1,2]oxaborol-1(3H)-ol.

22k 6-(dimethylamino)benzo[c][1,2]oxaborol-(3H)-ol (C51)

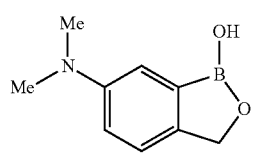 [SMILES: CN(C)c1ccc2c(c1)B(O)OC2]

M.P. 120-123° C. Exemplary starting material: 6-aminobenzo[c][1,2]oxaborol-1(3H)-ol.

22l N-(1-hydroxy-1,3-dihydrobenzo[c][1,2]oxaborol-6-yl)benzamide (C52)

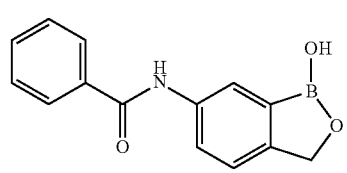 [SMILES: O=C(Nc1ccc2c(c1)B(O)OC2)c1ccccc1]

M.P. 186-193° C. Exemplary starting material: 6-aminobenzo[c][1,2]oxaborol-1(3H)-ol.

22m 6-(4-phenylpiperazin-1-yl)benzo[c][1,2]oxaborol-1(3H)-ol (C53)

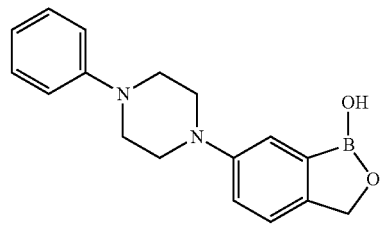 [SMILES: OB1OCc2ccc(N3CCN(c4ccccc4)CC3)cc21]

M.P. 159-161° C. Exemplary starting material: (2-bromo-4-(4-phenylpiperazin-1-yl)phenyl)methanol.

22o 6-(1H-indol-1-yl)benzo[c][1,2]oxaborol-1(3H)-ol (C55)

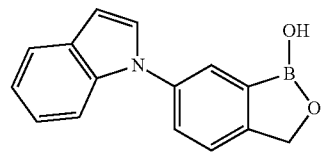 [SMILES: OB1OCc2ccc(-n3ccc4ccccc43)cc21]

M.P. 135-140° C. Exemplary starting material: (2-bromo-4-(1H-indol-1-yl)phenyl)methanol.

22p 6-morpholinobenzo[c][1,2]oxaborol-1(3H)-ol (C56)

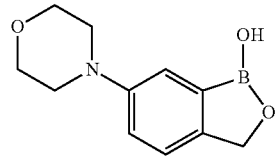 [SMILES: OB1OCc2ccc(N3CCOCC3)cc21]

M.P. 128-132° C. Exemplary starting material: (2-bromo-4-morpholinophenyl)methanol.

22q 6-(1-hydroxy-1,3-dihydrobenzo[c][1,2]oxa-
borol-5-yloxy)nicotinonitrile (C57)

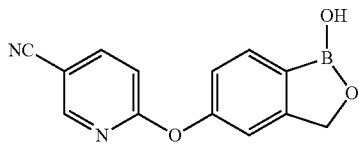 [SMILES: N#Cc1ccc(Oc2ccc3c(c2)COB3O)nc1]

M.P. 193-198° C. Exemplary starting material: 6-(4-bromo-3-(hydroxymethyl)phenoxy)nicotinonitrile.

22r 5-fluoro-6-nitrobenzo[c][1,2]oxaborol-1(3H)-ol
(C58)

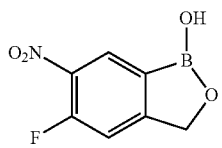

M.P. 162-167° C. Exemplary starting material: 5-fluorobenzo[c][1,2]oxaborol-1(3H)-ol.

22s 5-bromo-6-(hydroxymethyl)benzo[c][1,2]oxa-
borol-1(3H)-ol (C59)

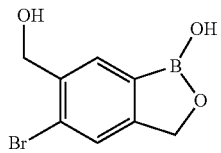

M.P.>257° C. Exemplary starting material: (2,5-dibromo-4-(methoxymethyl)phenyl)methanol.

22t 3, 7-dihydro-1,5-dihydroxy-1H,3H-Benzo[2-c:
4, 5-c']bis[1,2]oxaborole (C60)

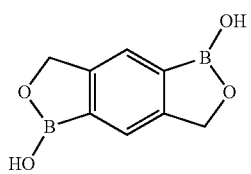 [SMILES: OB1OCc2cc3c(cc21)COB3O]

M.P.>250° C. Exemplary starting material: (2,5-dibromo-1,4-phenylene)dimethanol.

22u 1-(1-hydroxy-1,3-dihydrobenzo[c][1,2]oxa-
borol-6-yl)-3-phenylurea (C61)

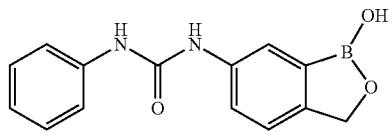 [SMILES: O=C(Nc1ccccc1)Nc1ccc2c(c1)B(O)OC2]

M.P. 213-215° C. Exemplary starting material: 6-aminobenzo[c][1,2]oxaborol-1(3H)-ol.

22v N-(1-hydroxy-1,3-dihydrobenzo[c][1,2]oxa-
borol-6-yl)benzenesulfonamide (C62)

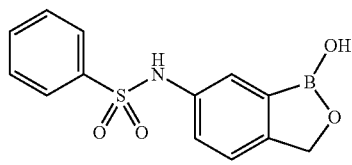 [SMILES: O=S(=O)(Nc1ccc2c(c1)B(O)OC2)c1ccccc1]

M.P. 175-184° C. Exemplary starting material: 6-aminobenzo[c][1,2]oxaborol-1(3H)-ol.

22w N-(1-hydroxy-1,3-dihydrobenzo[c][1,2]oxa-
borol-6-yl)acetamide (C63)

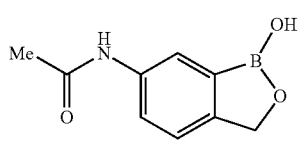

M.P. 176-185° C. Exemplary starting material: 6-aminobenzo[c][1,2]oxaborol-1(3H)-ol.

22x
7-(hydroxymethyl)benzo[c][1,2]oxaborol-1(3H)-ol
(C64)

M.P. 241-250° C. Exemplary starting material: (2-bromo-1,3-phenylene)dimethanol.

22y 7-methylbenzo[c][1,2]oxaborol-1(3H)-ol (C65)

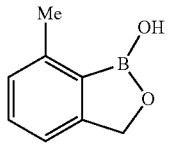 [SMILES: Cc1cccc2c1B(O)OC2]

M.P. 107-111° C. Exemplary starting material: (2-bromo-3-methylphenyl)methanol.

22z 6-(3-(phenylthio)-1H-indol-1-yl)benzo[c][1,2]oxaborol-1(3H)-ol (C66)

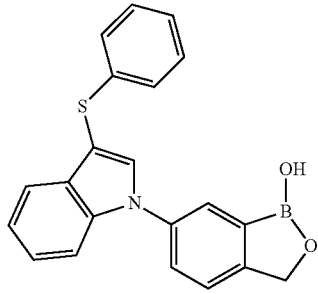 [SMILES: OB1OCc2ccc(-n3cc(Sc4ccccc4)c4ccccc43)cc21]

M.P. 159-163° C. Exemplary starting material: (2-bromo-4-(3-(phenylthio)-1H-indol-1-yl)phenyl)methanol.

22aa 3-(1-(1-hydroxy-1,3-dihydrobenzo[c][1,2]oxaborol-6-yl)-1H-indol-3-ylthio)propanenitrile (C67)

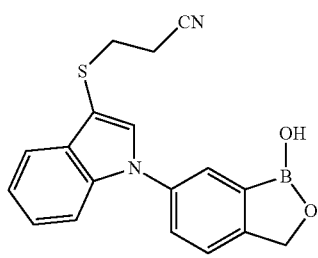 [SMILES: N#CCCSc1cn(-c2ccc3c(c2)B(O)OC3)c2ccccc12]

M.P. 135-141° C. Exemplary starting material: 3-(1-(3-bromo-4-(hydroxymethyl)phenyl)-1H-indol-3-ylthio)propanenitrile.

22bb 6-(5-methoxy-1H-indol-1-yl)benzo[c][1,2]oxaborol-1(3H)-ol (C68)

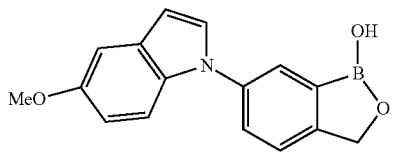 [SMILES: COc1ccc2c(ccn2-c2ccc3c(c2)B(O)OC3)c1]

M.P. 120-124° C. Exemplary starting material: (2-bromo-4-(5-methoxy-1H-indol-1-yl)phenyl)methanol.

22cc 5,6-methylenedioxybenzo[c][1,2]oxaborol-1(3H)-ol. (C69)

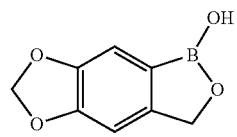 [SMILES: OB1OCc2cc3c(cc21)OCO3]

M.P. 185-189° C. Exemplary starting material: (6-bromobenzo[d][1,3]dioxol-5-yl)methanol.

22dd 6-amino-5-fluorobenzo[c][1,2]oxaborol-1(3H)-ol (C70)

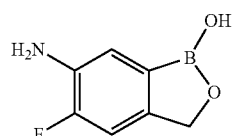

M.P. 142-145° C. Exemplary starting material: 6-nitro-5-fluorobenzo[c][1,2]oxaborol-1(3H)-ol.

22ee 6-(benzylamino)-5-fluorobenzo[c][1,2]oxaborol-1(3H)-ol (C71)

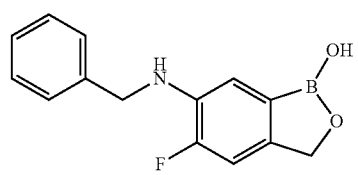 [SMILES: OB1OCc2cc(F)c(NCc3ccccc3)cc21]

M.P. 159-164° C. Exemplary starting material: 6-amino-5-fluorobenzo[c][1,2]oxaborol-1(3H)-ol.

22ff 6-(5-methoxy-3-(phenylthio)-1H-indol-1-yl)benzo[c][1,2]oxaborol-1(3H)-ol (C72)

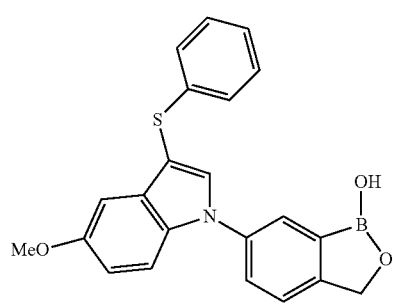 [SMILES: COc1ccc2c(c1)c(Sc1ccccc1)cn2-c1ccc2c(c1)B(O)OC2]

M.P. 135-141° C. Exemplary starting material: (2-bromo-4-(5-methoxy-3-(phenylthio)-1H-indol-1-yl)phenyl)methanol.

22gg 3-(1-(1-hydroxy-1,3-dihydrobenzo[c][1,2]oxaborol-6-yl)-5-methoxy-1H-indol-3-ylthio)propanenitrile (C73)

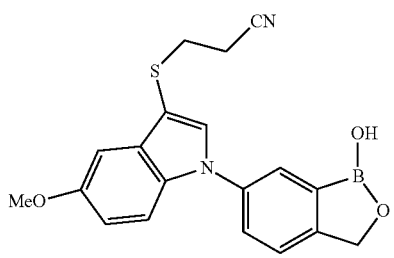 [SMILES: COc1ccc2c(c1)c(SCCC#N)cn2-c1ccc2c(c1)B(O)OC2]

M.P. 149-154° C. Exemplary starting material: 3-(1-(3-bromo-4-(hydroxymethyl)phenyl)-5-methoxy-1H-indol-3-ylthio)propanenitrile.

22hh 4-(1-hydroxy-1,3-dihydrobenzo[c][1,2]oxaborol-7-yloxy)benzonitrile (C74)

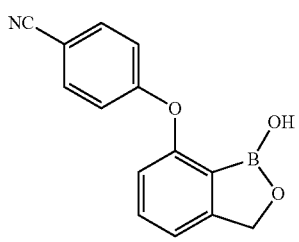 [SMILES: N#Cc1ccc(Oc2cccc3c2B(O)OC3)cc1]

M.P. 148-153° C. Exemplary starting material: 4-(2-bromo-3-(hydroxymethyl)phenoxy)benzonitrile.

22ii 6-(5-chloro-1H-indol-1-yl)benzo[c][1,2]oxaborol-1(3H)-ol (C75)

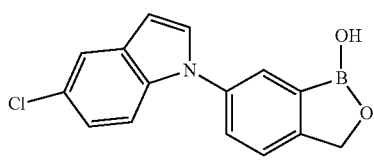 [SMILES: OB1OCc2ccc(-n3ccc4cc(Cl)ccc43)cc21]

M.P. 149-154° C. Exemplary starting material: (2-bromo-4-(5-chloro-1H-indol-1-yl)phenyl)methanol.

22jj 3-(5-chloro-1-(1-hydroxy-1,3-dihydrobenzo[c][1,2]oxaborol-6-yl)-1H-indol-3-ylthio)propanenitrile (C76)

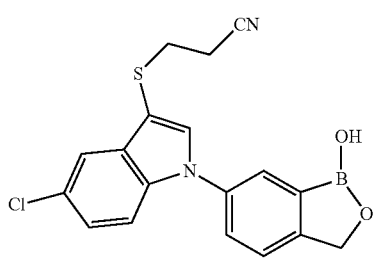 [SMILES: N#CCCSc1cn(-c2ccc3c(c2)B(O)OC3)c2ccc(Cl)cc12]

M.P.>225° C. Exemplary starting material: 3-(1-(3-bromo-4-(hydroxymethyl)phenyl)-5-chloro-1H-indol-3-ylthio)propanenitrile.

22kk 6-(benzylamino)benzo[c][1,2]oxaborol-1(3H)-ol (C77)

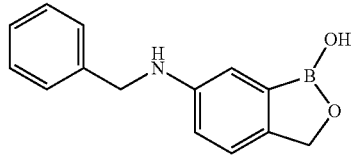 [SMILES: OB1OCc2ccc(NCc3ccccc3)cc21]

M.P. 126-133° C. Exemplary starting material: 6-aminobenzo[c][1,2]oxaborol-1(3H)-ol.

22ll 6-(dibenzylamino)benzo[c][1,2]oxaborol-1(3H)-ol (C78)

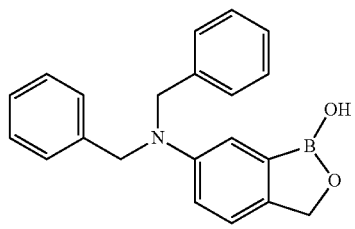 [SMILES: OB1OCc2ccc(N(Cc3ccccc3)Cc3ccccc3)cc21]

M.P. 115-123° C. Exemplary starting material: 6-aminobenzo[c][1,2]oxaborol-1(3H)-ol.

22 mm 7-(4-(1H-tetrazol-5-yl)phenoxy)benzo[c][1,2]oxaborol-1(3H)-ol (C79)

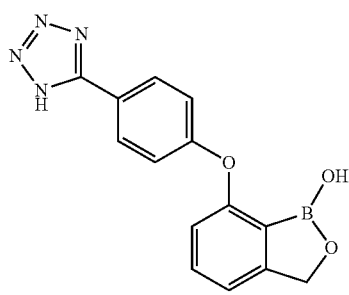 [SMILES: OB1OCc2cccc(Oc3ccc(-c4nnn[nH]4)cc3)c21]

M.P. decomposition at 215° C. Exemplary starting material: 4-(1-hydroxy-1,3-dihydrobenzo[c][1,2]oxaborol-7-yloxy)benzonitrile.

22nn 6-(5-chloro-3-(phenylthio)-1H-indol-1-yl)benzo[c][1,2]oxaborol-1(3H)-ol (C80)

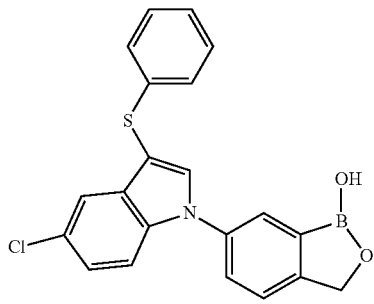 [SMILES: OB1OCc2ccc(-n3cc(Sc4ccccc4)c4cc(Cl)ccc43)cc21]

M.P. 145-151° C. Exemplary starting material: (2-bromo-4-(5-chloro-3-(phenylthio)-1H-indol-1-yl)phenyl)methanol.

22pp 6-(4-(pyrimidin-2-yl)piperazin-1-yl)benzo[c][1,2]oxaborol-1(3H)-ol (C82)

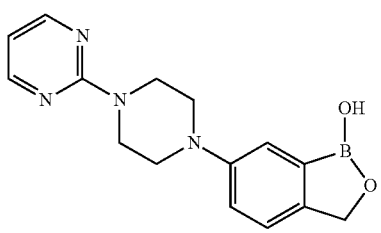 [SMILES: OB1OCc2ccc(N3CCN(c4ncccn4)CC3)cc21]

M.P. NA ° C. Exemplary starting material: (2-bromo-4-(4-(pyrimidin-2-yl)piperazin-1-yl)phenyl)methanol.

22qq 7-(benzyloxy)benzo[c][1,2]oxaborol-1(3H)-ol (C83)

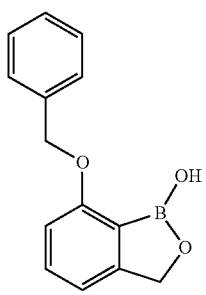 [SMILES: OB1OCc2cccc(OCc3ccccc3)c21]

M.P. NA ° C. Exemplary starting material: (3-(benzyloxy)-2-bromophenyl)methanol.

22rr 4-(1-hydroxy-1,3-dihydrobenzo[c][1,2]oxaborol-6-ylthio)pyridinium chloride (C84)

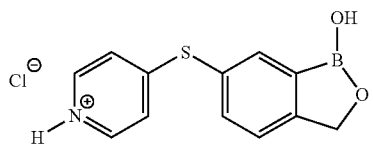 [SMILES: [Cl-] ; OB1OCc2ccc(Sc3cc[nH+]cc3)cc21]

M.P. NA ° C. Exemplary starting material: (2-bromo-4-(pyridin-4-ylthio)phenyl)methanol.

22ss 6-(pyridin-2-ylthio)benzo[c][1,2]oxaborol-1(3H)-ol (C85)

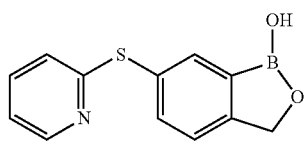 [SMILES: OB1OCc2ccc(Sc3ccccn3)cc21]

M.P. NA ° C. Exemplary starting material: (2-bromo-4-(pyridin-2-ylthio)phenyl)methanol.

22tt 7-fluorobenzo[c][1,2]oxaborol-1(3H)-ol (C86)

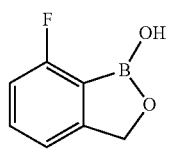

M.P. 120-124° C. Exemplary starting material: (2-bromo-3-fluorophenyl)methanol.

22uu 6-(4-(trifluoromethyl)phenoxy)benzo[c][1,2]oxaborol-1(3H)-ol (C87)

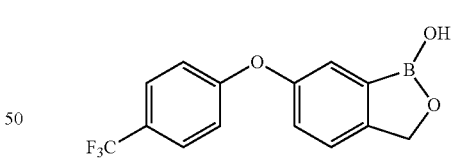

M.P. 98-105° C. Exemplary starting material: (2-bromo-4-(4-(trifluoromethyl)phenoxy)phenyl)methanol.

22vv 6-(4-chlorophenylthio)benzo[c][1,2]oxaborol-1(3H)-ol (C88)

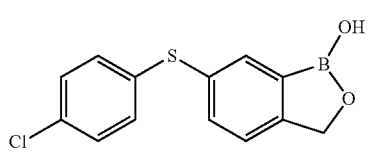 [SMILES: OB1OCc2ccc(Sc3ccc(Cl)cc3)cc21]

M.P. 157-161° C. Exemplary starting material: (2-bromo-4-(4-chlorophenylthio)phenyl)methanol.

22ww 6-(4-chlorophenylsulfinyl)benzo[c][1,2]oxaborol-1(3H)-ol (C89)

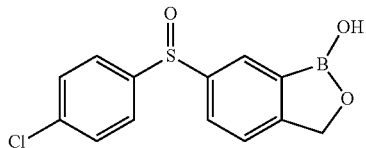 [SMILES: O=S(c1ccc(Cl)cc1)c1ccc2c(c1)B(O)OC2]

M.P. 154-161° C. Exemplary starting material: 6-(4-chlorophenylthio)benzo[c][1,2]oxaborol-1(3H)-ol.

22xx 6-(4-chlorophenylsulfonyl)benzo[c][1,2]oxaborol-1(3H)-ol (C90)

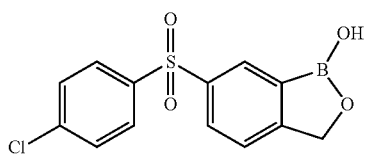 [SMILES: O=S(=O)(c1ccc(Cl)cc1)c1ccc2c(c1)B(O)OC2]

M.P. 157-163° C. Exemplary starting material: 6-(4-chlorophenylthio)benzo[c][1,2]oxaborol-1(3H)-ol.

22yy N-(1-hydroxy-1,3-dihydrobenzo[c][1,2]oxaborol-5-yl)-N-(phenylsulfonyl)benzenesulfonamide (C91)

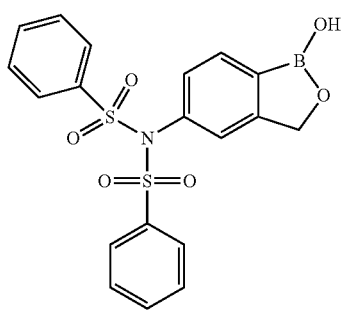 [SMILES: O=S(=O)(c1ccccc1)N(c1ccc2c(c1)COB2O)S(=O)(=O)c1ccccc1]

M.P. 142-152° C. Exemplary starting material: N-(4-bromo-3-(hydroxymethyl)phenyl)-N-(phenylsulfonyl)benzenesulfonamide.

22zz 6-(4-(trifluoromethyl)phenylthio)benzo[c][1,2]oxaborol-1(3H)-ol (C92)

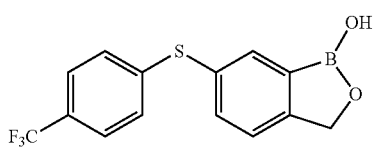 [SMILES: OB1OCc2ccc(Sc3ccc(C(F)(F)F)cc3)cc21]

M.P. 111-113° C. Exemplary starting material: (2-bromo-4-(4-(trifluoromethyl)phenylthio)phenyl)methanol.

22aaa 6-(4-(trifluoromethyl)phenylsulfinyl)benzo[c][1,2]oxaborol-1(3H)-ol (C93)

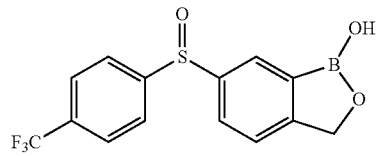 [SMILES: O=S(c1ccc(C(F)(F)F)cc1)c1ccc2c(c1)B(O)OC2]

M.P. 79-88° C. Exemplary starting material: 6-(4-(trifluoromethyl)phenylthio)benzo[c][1,2]oxaborol-1(3H)-ol.

22bbb 6-(4-(methylthio)phenylthio)benzo[c][1,2]oxaborol-1(3H)-ol (C94)

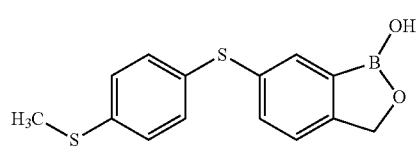 [SMILES: CSc1ccc(Sc2ccc3c(c2)B(O)OC3)cc1]

M.P. 117-120° C. Exemplary starting material: (2-bromo-4-(4-(methylthio)phenylthio)phenyl)methanol.

22ccc 6-(p-tolylthio)benzo[c][1,2]oxaborol-1(3H)-ol (C95)

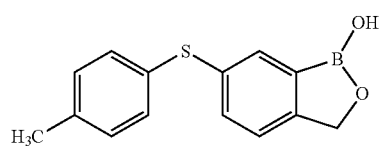

M.P. 139-144° C. Exemplary starting material: (2-bromo-4-(p-tolylthio)phenyl)methanol.

22ddd 3-((1-hydroxy-1,3-dihydrobenzo[c][1,2]oxaborol-5-yloxy)methyl)benzonitrile (C96)

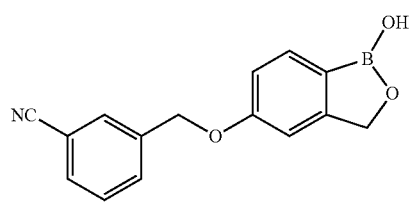 [SMILES: N#Cc1cccc(COc2ccc3c(c2)COB3O)c1]

M.P. 147-150° C. Exemplary starting material: 3-((4-bromo-3-(hydroxymethyl)phenoxy)methyl)benzonitrile.

Example 23

Alternative Preparation of 4 from 3

A 22.0 L 3-neck flask was equipped with a stir motor, N₂ inlet, addition funnel, heating mantle, and condenser. The flask was charged with 3500 g (17.1 mol) of 2-bromo-5-fluorobenzyl alcohol followed by the addition of 3556 g of tetrahydrofuran and 16.4 g (0.17 mol) of methanesulfonic acid. Next, 400 g (4.7 mol) of 3,4-dihydro-2H-pyran was added at 10° C. This step is exothermic so no additional charges should be made until exotherm subsides. The temperature was increased to 27° C., stirred for 15 min and then charged with 400 g (4.7 mol) of 3,4-dihydro-2H-pyran at 24° C. Again the temperature increased (24° C. to 38° C.). The mixture was stirred for 15 min. Once the exotherm subsided, the flask was again charged with 400 g (4.7 mol) of 3,4-dihydro-2H-pyran at 35° C. The temperature again increased to 47° C. over a 20 min period. Once the exotherm subsided, the mixture was stirred for 15 min. Finally the remaining 400 g (4.7 mol) of 3,4-dihydro-2H-pyran was added at 44° C. The temperature increased to 51° C. After stirring for one hour, a sample was removed to check for removal of starting material. Upon reaction completion, contents were cooled to 20±5° C.

Example 24

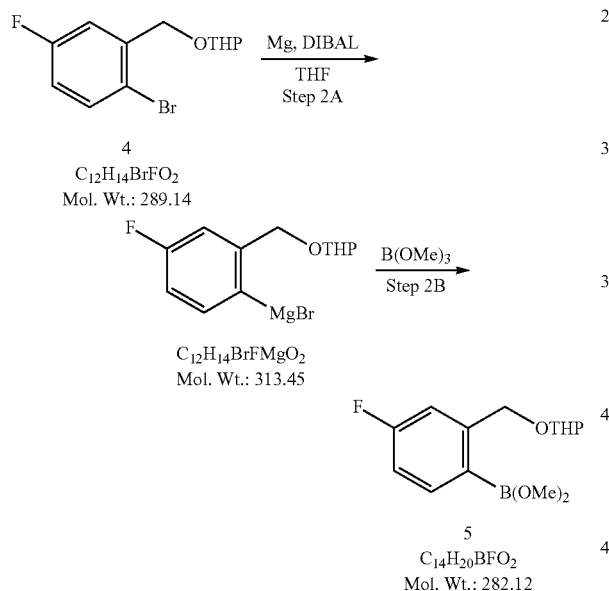

4
$C_{12}H_{14}BrFO_2$
Mol. Wt.: 289.14

$C_{12}H_{14}BrFMgO_2$
Mol. Wt.: 313.45

5
$C_{14}H_{20}BFO_2$
Mol. Wt.: 282.12

Alternative Preparation of 5 from 4

To a 22.0 L 3-neck flask equipped with a stir motor, $N_2$ inlet, addition funnel, cooling bath, and condenser was charged 436 g (17.96 mol) of magnesium turnings. 5334 g of tetrahydrofuran was then added followed by 291 g (0.51 mol) of diisobutylaluminum hydride (DIBAL) (25% wt) in toluene. The mixture was stirred for 60 min at 20±5° C. Some gas evolution was seen. Next, 260-430 g ~3-5% (by weight if solution of 4 was dropped to drums) of 4 in THF was added. The mixture was stirred for 15-30 min at which time a slight exotherm should be seen (ΔT=10-15° C.). Once the exotherm was observed, the reaction mixture was cooled to 5±5° C. To this mixture, the remaining 8.22-8.39 kg of 4 in THF was added at a rate such that the temperature was kept below 30° C. (t=3 h). The reaction was stirred at 20-25° C. for 30 min, at which time an aliquot was removed, quench with 3 N HCl (10 mL), and analyzed.

Upon completion, the contents were cooled to −25±5° C. A solution of trimethylborate in THF was prepared by mixing 2665 g (25.7 mol) of trimethyl borate and 6666 g of tetrahydrofuran. This solution can be prepared in a drum with stirring.

Next, the 9331 g of trimethyl borate in THF was added at a rate such that the temperature was kept between −35 and −20° C. (t=2.5 h). The mixture became very thick so THF was added. After stirring at −25±5° C. for 10 min, 50 mL aliquot was removed, quenched with 25 mL of 3N HCl, and submitted for CoR. Stirring continued at −25±5° C. for 1 h, and then the mixture was allowed to warm to ambient temperature, where it was stirred for at least 12 h. Pull two samples (one at 6 h and the other at 12 h).
Results:
$^1$H-NMR (300 MHz, DMSO-$d_6$) δ (ppm) 1.45-1.75 (m, 6H), 3.53 (s, 6H), 3.45 (m, 1H), 3.75 (m, 1H), 4.69 (t, J=3 Hz, 1H), 4.97 (d, J=14.1 Hz, 1H), 5.14 (d, J=14.1 Hz, 1H), 7.03 ((td, J=8.4, 2.7 Hz, 1H), 7.24 (dd, J=10.8, 2.1 Hz, 1H), 7.89 (t, J=7.8 Hz, 1H), 8.76 (s, 1H).

Example 25

Alternative Preparation of I from 5

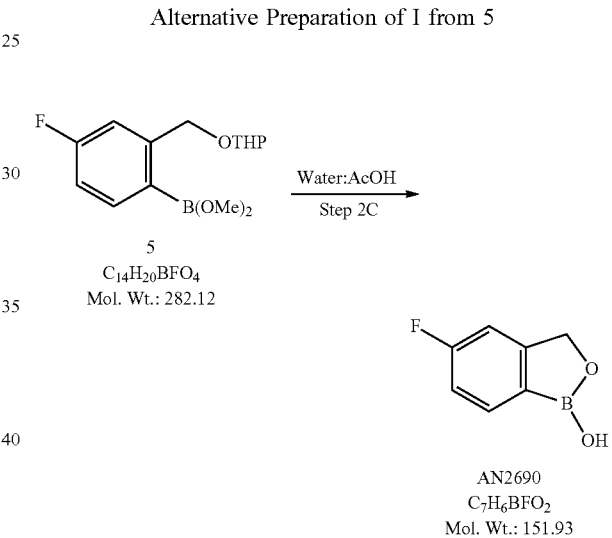

5
$C_{14}H_{20}BFO_4$
Mol. Wt.: 282.12

AN2690
$C_7H_6BFO_2$
Mol. Wt.: 151.93

To the reaction mixture above was added 5.3 kg of USP water. After stirring for 30 min, the mixture was charged 5.3 kg of acetic acid. Gas evolution was seen. After stirring for 30 min, an aliquot was removed for analysis. Mixture was then heated to reflux for 36-48 hours. During the reflux period, 12-13 L of THF were removed.

When the reaction was complete, the contents were cooled by the reactor to ≤40° C. by setting jacket and by charging 10.5 kg of USP water. THF was removed until distillate did not remain. Contents of the reactor were transferred to Rosenmund filter dryer and allowed to cool to 20±5° C. Reactor was rinsed with water, filtered, and then washed again with 10.5 kg of USP water. The flask was charged with 10.5 kg of 10% ACN in water (v/v) and agitated for 1 h. After filtering, the cake was washed with 10.5 kg of 10% ACN in water (v/v), and then charged with 10.5 kg 10% ACN in water (v/v). The contents were agitated for 1 h. The contents were subsequently washed with 10.5 kg of USP water, charged with 7.0 L of 5% Methyl t-Butyl Ether (MTBE)/Heptane (v/v), agitated for 1 h, filtered, charged with 7.0 L of 5% MTBE/Heptanes (v/v) and again agitated for 1 h. After filtering, the contents were charged

Example 26

Alternative Preparation of C10-Intermediate

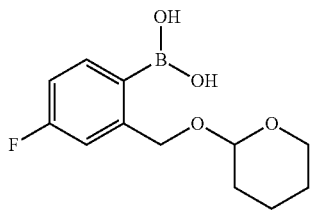 [SMILES: OB(O)c1ccc(F)cc1COC1CCCCO1]

[[4-Fluoro-2-[(tetrahydro-2H-pyran-2-yl)oxy]
methyl]phenyl]boronic acid

2-Bromo-5-fluorobenzyl alcohol (5 g, 24.4 mmol) was dissolved in dichloromethane (100 mL). To this solution was added 3,4-dihydro-2H-pyran (3.2 mL, 36.6 mmol) and (1S)-(+)-10-camphorsulfonic acid (117 mg, 0.5 mmol) and stirred at RT under nitrogen for 4 h. Saturated sodium bicarbonate was added to quench the reaction. It was extracted using dichloromethane and the organic layer was washed with brine and dried over sodium sulfate, then concentrated in vacuo to give [1-bromo-4-fluoro-6-[(tetrahydro-2H-pyran-2-yl)oxy]methyl]benzene as a colorless oil (7 g, 100%).

[1-Bromo-4-fluoro-6-[(tetrahydro-2H-pyran-2-yl)oxy]methyl]benzene (1.8 g, 6.2 mmol) was dissolved in THF and cooled to −78° C. under nitrogen. To this solution was added n-butyllithium (1.6M in hexane)(6.2 mL, 9.3 mmol) dropwise, then added triisopropyl borate (2.2 mL, 9.3 mmol). The mixture was slowly warmed to RT and stirred for 3 h. Water was added to quench the reaction. It was then extracted using ethyl acetate, washed with brine, dried over sodium sulfate and concentrated in vacuo. After column chromatography (silica gel; hexane:ethyl acetate=4:1 to 2:1) purification, [[4-Fluoro-2-[(tetrahydro-2H-pyran-2-yl)oxy]methyl]phenyl]boronic acid was obtained as a white solid (1.1 g, 70%).

Results:
$^1$H-NMR (300 MHz, DMSO-$d_6$) δ (ppm) 1.45-1.74 (m, 6H), 3.44 (m, 1H), 3.75 (m, 1H), 4.58 (d, J=13.2 Hz, 1H), 4.64 (t, J=3 Hz, 1H), 4.79 (d, J=13.2 Hz, 1H), 7.03 (td, J=8.4, 2.7 Hz, 1H), 7.13 (dd, J=10.8, 2.7 Hz, 1H), 7.50 (t, J=6.9 Hz, 1H).

Example 27

Alternative Preparation of C10-Intermediate

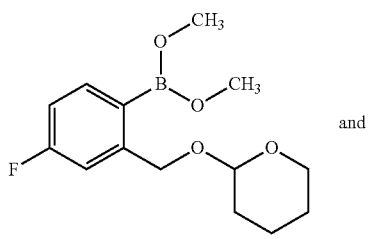

and

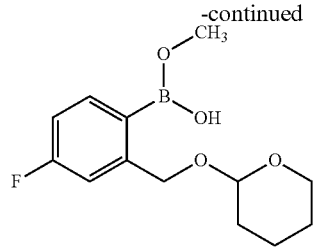

[[4-Fluoro-2-[(tetrahydro-2H-pyran-2-yl)oxy]
methyl]phenyl]boronic acid dimethyl ester

[[4-Fluoro-6-[(tetrahydro-2H-pyran-2-yl)oxy]methyl]phenyl]boronic acid (100 mg) was dissolved in dry methanol, the solution was distilled repeatedly to remove water. The resulting residue was immediately characterized by NMR and was found to be a mixture containing dimethyl ester and monomethyl ester.

[[4-Fluoro-2-[(tetrahydro-2H-pyran-2-yl)oxy]
methyl]phenyl]boronic acid dimethyl ester $^1$H-NMR (300 MHz, DMSO-$d_6$) δ (ppm) 1.45-1.75 (m, 6H), 3.43 (s, 6H), 3.45 (m, 1H), 3.75 (m, 1H), 4.69 (t, J=3 Hz, 1H), 4.97 (d, J=14.1 Hz, 1H), 5.14 (d, J=14.1 Hz, 1H), 7.03 ((td, J=8.4, 2.7 Hz, 1H), 7.24 (dd, J=10.8, 2.1 Hz, 1H), 7.89 (t, J=7.8 Hz, 1H).

[[4-Fluoro-6-[(tetrahydro-2H-pyran-2-yl)oxy]
methyl]phenyl]boronic acid monomethyl ester $^1$H-NMR (300 MHz, DMSO-$d_6$) δ (ppm) 1.45-1.75 (m, 6H), 3.53 (s, 6H), 3.45 (m, 1H), 3.75 (m, 1H), 4.69 (t, J=3 Hz, 1H), 4.97 (d, J=14.1 Hz, 1H), 5.14 (d, J=14.1 Hz, 1H), 7.03 ((td, J=8.4, 2.7 Hz, 1H), 7.24 (dd, J=10.8, 2.1 Hz, 1H), 7.89 (t, J=7.8 Hz, 1H), 8.76 (s, 1H).

Example 28

Alternative Preparation of C10-Intermediate

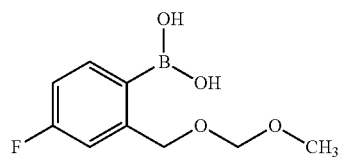

[(4-Fluoro-2-methoxoxymethoxyethyl)phenyl]boronic
acid

[1-Bromo-4-fluoro-6-methoxymethoxymethyl]benzene (525 mg, 2 mmol) was dissolved in THF and cooled to −78° C. under nitrogen. To this solution was added n-butyllithium (1.6M in hexane)(1.5 mL, 2.4 mmol) dropwise, then added triisopropyl borate (0.7 mL, 2.4 mmol). The mixture was slowly warmed to RT and stirred for 3 h. Water was added to quench the reaction. It was then extracted using ethyl acetate, washed with brine, dried over sodium sulfate and concentrated in vacuo. After recrystallization from hexane:

ethyl acetate=4:1 [(4-Fluoro-2-methoxymethoxymethyl)phenyl]boronic acid was obtained as a white solid (340 mg, 75%).

$^1$H-NMR (300 MHz, DMSO-$d_6$) δ (ppm) 3.28 (s, 3H), 4.70 (s, 2H), 5.02 (s, 2H), 7.04 (td, J=9.0, 3.0 Hz, 1H), 7.23 (dd, J=11.1, 2.4 Hz, 1H), 7.90 (t, J=7.8 Hz, 1H).

Example 29

Alternative Preparation of C17-Intermediate

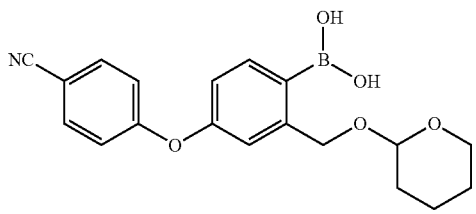 [SMILES: N#Cc1ccc(Oc2ccc(B(O)O)c(COC3CCCCO3)c2)cc1]

[[4-[4-cyanophenoxy]-2-[(tetrahydro-2H-pyran-2-yl)oxy]methyl]phenyl]boronic acid 2-Bromo-5-(4-cyanophenoxy)benzyl alcohol (10.4 g, 34.2 mmol) was dissolved in dichloromethane (110 mL). To this solution was added 3,4-dihydro-2H-pyran (9.2 mL, 101 mmol) and (1S)-(+)-10-camphorsulfonic acid (156 mg, 0.67 mmol) and stirred at RT under nitrogen for 3 h. Methanesulfonic acid (50 μL, 0.77 mmol) was then added and reaction was stirred overnight. Saturated sodium bicarbonate was added to quench the reaction. It was extracted using ethyl acetate and the organic layer was washed with brine and dried over sodium sulfate, then concentrated in vacuo to give [1-bromo-4-(4-cyanophenoxy)-6-[(tetrahydro-2H-pyran-2-yl)oxy]methyl]benzene as a colorless oil (13.3 g quant.).

[1-Bromo-4-(4-cyanophenoxy)-6-[(tetrahydro-2H-pyran-2-yl)oxy]methyl]benzene (13.3 g, 34.2 mmol) was dissolved in THF (100 mL), triisopropyl borate (8.5 mL, 37 mmol) was added and the reaction was cooled to −78° C. under nitrogen. To this solution was added n-butyllithium (1.6M in hexane)(22 mL, 35.2 mmol) dropwise. The mixture was slowly warmed to RT and stirred overnight. THF was removed in vacuo and the residue was dissolved in ethyl acetate. It was then washed with water, brine, dried over sodium sulfate and concentrated in vacuo. After column chromatography (silica gel; hexane:ethyl acetate 2:1) purification of a portion of crude, [[4-(4-cyanophenoxy)-6-[(tetrahydro-2H-pyran-2-yl)oxy]methyl]phenyl]boronic acid was obtained as a clear oil (500 mg, 4%).

$^1$H-NMR (300 MHz, DMSO-$d_6$+$D_2O$) δ (ppm) 1.35-1.75 (m, 6H), 3.40 (m, 1H), 3.73 (m, 1H), 4.58 (d, J=13.2 Hz, 1H), 4.59 (s, 1H), 4.77 (d, J=12.7 Hz, 1H), 6.99 (dd, J=8.1, 2.2 Hz, 1H), 7.05 (m, 3H), 7.54 (d, J=7.9 Hz, 1H), 7.81 (d, J=8.8 Hz, 2H).

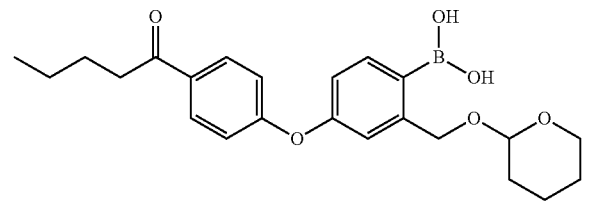 [SMILES: CCCCC(=O)c1ccc(Oc2ccc(B(O)O)c(COC3CCCCO3)c2)cc1]

Also isolated was [[4-(4-pentanoylphenoxy)-6-[(tetrahydro-2H-pyran-2-yl)oxy]methyl]phenyl]boronic acid as a clear oil (500 mg, 4%). $^1$H-NMR (300 MHz, DMSO-$d_6$+$D_2O$) δ (ppm)), 0.85 (t, J=7.5 Hz, 3H), 1.20-1.75 (m, 10H), 2.93 (t, J=7.0 Hz, 2H), 3.42 (m, 1H), 3.70 (m, 1H), 4.58 (d, J=12.8 Hz, 1H), 4.60 (s, 1H), 4.78 (d, J=13.2 Hz, 1H), 6.94 (d, J=8.4 Hz, 1H), 7.03 (d, J=8.4 Hz, 2H), 7.04 (s, 1H), 7.54 (d, J=8.4 Hz, 1H), 7.96 (d, J=8.4 Hz, 2H).

Example 30

Alternative Preparation of C17-Intermediate

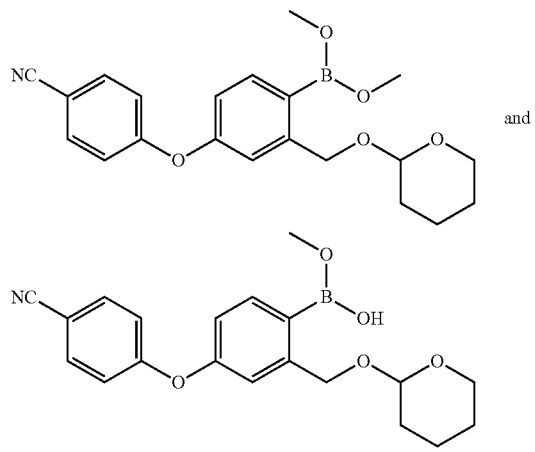

[[4-[4-cyanophenoxy]-2-[(tetrahydro-2H-pyran-2-yl)oxy]methyl]phenyl]boronic acid dimethyl ester Using the same method as in C10 Example IIE, a mixture of mono- and dimethyl esters of [[4-(4-cyanophenoxy)-2-[(tetrahydro-2H-pyran-2-yl)oxy]methyl]phenyl]boronic acid were synthesized.

$^1$H-NMR (300 MHz, DMSO-$d_6$) δ (ppm) 1.35-1.80 (m, 6H), 3.40-3.50 (m, 7H), 3.60-3.70 (m, 1H), 4.43 (d, J=12.7 Hz, 1H), 4.60-4.80 (m, 2H), 6.95-7.15 (m, 4H), 7.38 (d, J=8.4 Hz, 1H), 7.80-7.90 (m, 2H).

[[4-[4-cyanophenoxy]-6-[(tetrahydro-2H-pyran-2-yl)oxy]methyl]phenyl]boronic acid monomethyl ester $^1$H-NMR (300 MHz, DMSO-$d_6$) δ (ppm) 1.35-1.80 (m, 6H), 3.40-3.50 (m, 1H), 3.55 (s, 3H), 3.60-3.70 (m, 1H), 4.55 (d, J=12.8 Hz, 1H), 4.60-4.80 (m, 2H), 6.95-7.15 (m, 4H), 7.53 (d, J=7.9 Hz, 1H), 7.80-7.90 (m, 2H), 8.77 (s, 1H).

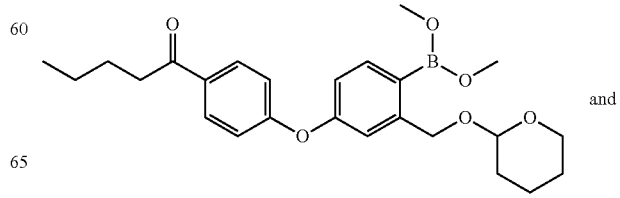

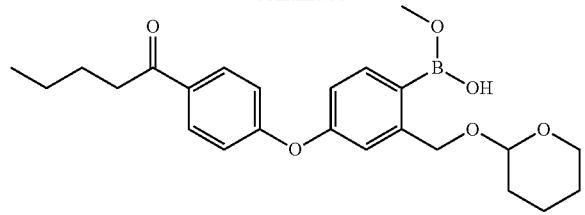

Using the same method as above, a mixture of mono- and dimethyl esters of [[4-(4-pentanoylphenoxy)-2-[(tetrahydro-2H-pyran-2-yl)oxy]methyl]phenyl]boronic acid were synthesized.

[[4-(4-pentanoylphenoxy)-2-[(tetrahydro-2H-pyran-2-yl)oxy]methyl]phenyl]boronic acid dimethyl ester $^1$H-NMR (300 MHz, DMSO-$d_6$) δ (ppm) 0.87 (t, J=7.3 Hz, 3H), 1.25-1.80 (m, 10H), 2.94 (t, J=7.3 Hz, 2H), 3.40-3.50 (m, 7H), 3.60-3.70 (m, 1H), 4.43 (d, J=12.8 Hz, 1H), 4.60-4.80 (m, 2H), 6.90-7.10 (m, 4H), 7.36 (d, J=7.9 Hz, 1H), 7.95-8.05 (m, 2H).

[[4-(4-pentanoylphenoxy)-6-[(tetrahydro-2H-pyran-2-yl)oxy]methyl]phenyl]boronic acid monomethyl ester $^1$H-NMR (300 MHz, DMSO-$d_6$) δ (ppm) 0.87 (t, J=7.3 Hz, 3H), 1.25-1.80 (m, 10H), 2.94 (t, J=7.3 Hz, 2H), 3.40-3.50 (m, 1H), 3.55 (s, 3H), 3.60-3.70 (m, 1H), 4.55 (d, J=12.8 Hz, 1H), 4.60-4.80 (m, 2H), 6.95-7.15 (m, 4H), 7.52 (d, J=7.9 Hz, 1H), 7.95-8.05 (m, 2H), 8.75 (s, 1H).

Example 31

Alternative Preparation of C10-Intermediate

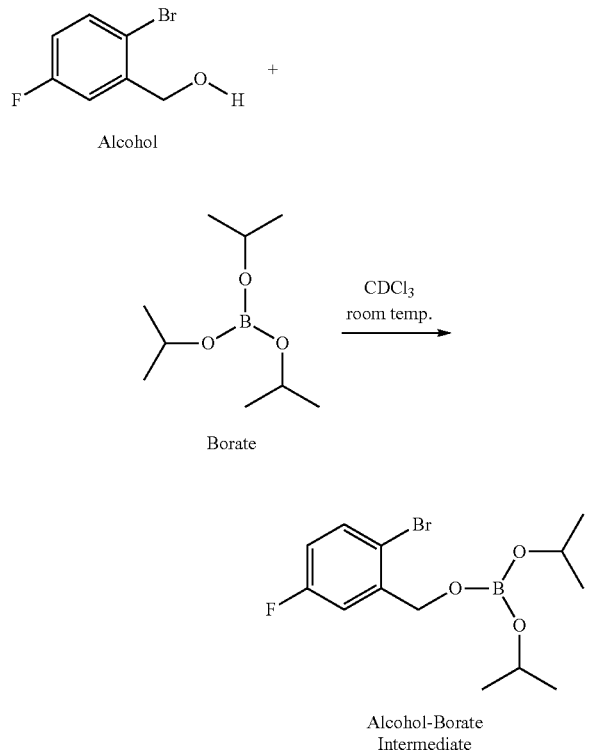

To a pre-recorded NMR tube containing a solution of 2-bromo-5-fluorobenzyl alcohol (16 mg, 0.078 mmol) in CDCl$_3$ (0.75 mL) was injected triisopropyl borate (0.036 mL, 2 eq, 0.156 mmol) and the solution was sonicated briefly for 30 second at room temperature. $^1$H NMR determination indicated there were 74.3 mol % of the desired alcohol-borate intermediate, 19.3 mol % of an unknown intermediate and 6.3 mol % of unreacted alcohol.

Results:

$^1$H NMR (CDCl$_3$, 300 MHz) of (2-bromo-5-fluorobenzyl) diisopropyl borate: δ=7.45 (dd, J=8.7 Hz, J=5.1 Hz, 1H), 7.20 (dd, J=9.6 Hz, J=2.7 Hz, 1H), 6.84 (td, $J_t$=8.1 Hz, $J_d$=3.3 Hz, 1H), 4.84 (s, 2H), 4.44 (septet, J=6.0 Hz, 2H), 1.18 (d, J=6.0 Hz, 12H) ppm. $^1$H NMR (CDCl$_3$, 300 MHz) of an unknown intermediate: δ=7.47-7.42 (1H overlap with product peaks), 7.16 (dd, 1H, partially overlap with product peak), 6.91-6.81 (1H, overlap with product peak), 4.94 (s, 2H), and other unknown peaks due to overlapping. $^1$H NMR (CDCl$_3$, 300 MHz) of 2-bromo-5-fluorobenzyl alcohol pre-recorded before mixing: δ=7.48 (dd, J=9.0 Hz, J=5.4 Hz, 1H, overlap with product peaks after mixing with triisopropyl borate), 7.26 (dd, J=9.3 Hz, J=3.3 Hz, 1H, intensity decreased but resolved after mixing), 6.88 (td, $J_t$=8.3 Hz, $J_d$=3.0 Hz, 1H, overlap with product peaks after mixing), 4.71 (s, 2H, CH$_2$ intensity decreased but resolved after mixing), 2.04 (s, 1H, OH disappeared after mixing with triisopropyl borate) ppm.

Example 32

Alternative Preparation of C17-Intermediate

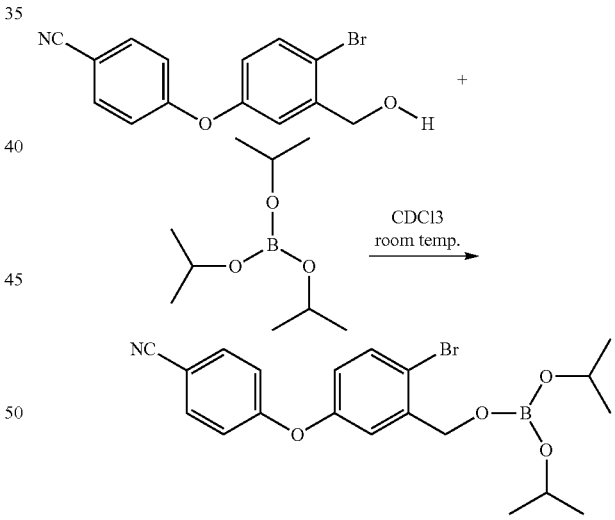

The procedure described in Example II I was followed for $^1$H NMR characterization of the current alcohol-borate intermediate. $^1$H NMR determination indicated there were 72.7 mol % of the desired alcohol-borate intermediate [2-bromo-5-(4-cyanophenoxy)benzyl]diisopropyl borate, 20.7 mol % of an unknown intermediate and 6.5 mol % of unreacted alcohol. $^1$H NMR (CDCl$_3$, 300 MHz) of [2-bromo-5-(4-cyanophenoxy)benzyl]diisopropyl borate: δ=7.61 (d, J=9.0 Hz, 2H), 7.52 (d, J=8.4 Hz, 1H), 7.15 (d, J=3.0 Hz, 1H), 7.03 (d, J=8.7 Hz, 2H), 6.84 (dd, J=8.7 Hz, J=3.0 Hz, 1H), 4.85 (s, 2H), 4.35 (septet, J=6.1 Hz, 2H), 1.11 (d, J=6.1 Hz, 12H) ppm.

Example 33

Alternative Preparation

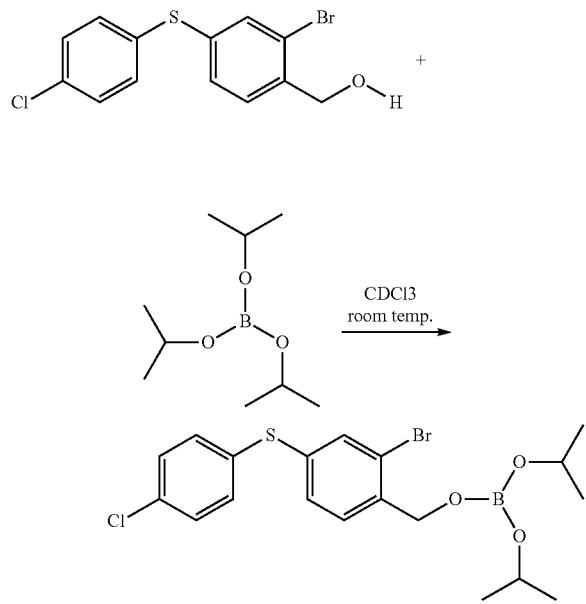

The procedure described in Example II I was followed for ¹H NMR characterization of the current alcohol-borate intermediate. ¹H NMR determination indicated there were 73.5 mol % of the desired alcohol-borate intermediate [2-bromo-4-(4-chlorophenylthio)benzyl]diisopropyl borate, 20.2 mol % of an unknown intermediate and 6.2 mol % of unreacted alcohol. ¹H NMR (CDCl₃, 300 MHz) of [2-bromo-4-(4-chlorophenylthio)benzyl]diisopropyl borate: δ=7.48 (d, J=1.8 Hz, 1H), 7.40 (d, J=8.3 Hz, 1H), 7.27 (s, 4H), 7.25 (dd, J=8.3 Hz, J=1.8 Hz, 1H), 4.86 (s, 2H), 4.42 (septet, J=6.3 Hz, 2H), 1.16 (d, J=6.3 Hz, 12H) ppm.

Example 34

C10-Adenosine Complex

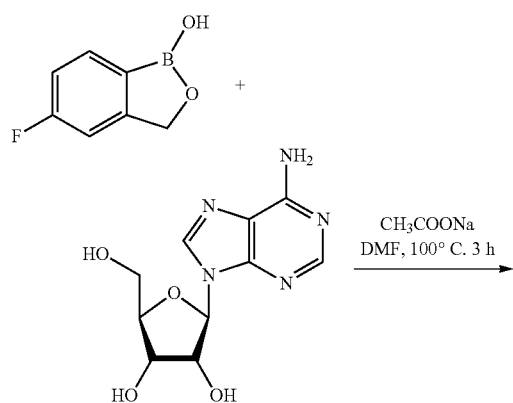

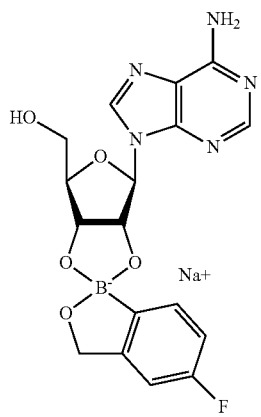

A mixture of 1,3-dihydro-5-fluoro-1-hydroxy-2,1-benzoxaborole (C10, 0.76 g, 5 mmol), adenosine (1.34 g, 5 mmol) and sodium acetate (0.41 g, 5 mmol) in dry DMF (100 mL) was stirred at 100° C. for 3 h under nitrogen atmosphere. The homogeneous solution was rotary evaporated at 50° C. under high vacuum. The residue was mixed with methylene chloride, sonicated and filtered under nitrogen atmosphere to give the desired complex as white solid that was pumped overnight (2.2 g, yield 100%). ¹H NMR indicated there were 5.7 mol % of unreacted adenosine, 5.5 mol % of unreacted C10, and the reaction conversion was more than 94%. ¹H NMR (DMSO-d₆, 300 MHz): δ=8.33 (s, 1H), 8.12 (s, 1H), 7.35-7.14 (broad m, 1H), 7.29 (s, 2H), 6.80 (broad m, 1H), 6.73 (d, J=9.9 Hz, 1H), 5.99 (broad d, J=2.1 Hz, 1H), 5.10 (very broad s, 1H), 4.71 (dd, J=5.7 Hz, J=3.9 Hz, 1H), 4.51 (s, 2H), 4.42 (dd, J=6.3 Hz, J=3.9 Hz, 1H), 4.07 (broad s, 1H), 3.64 (dd, J=12 Hz, J=3.6 Hz, 1H) and 3.52 (dd, J=12 Hz, J=5.1 Hz, 1H) ppm; M.p: started soften at 115° C. due to residue solvents, remained as soften solid and started decomposing at 230° C.; HPLC: 91.8% at 220 nm (adenosine was 5.3%); MS: m/z=423 (M−, ESI−), 392 (M-CH₂OH, ESI+).

Example 35

C17-Adenosine Complex

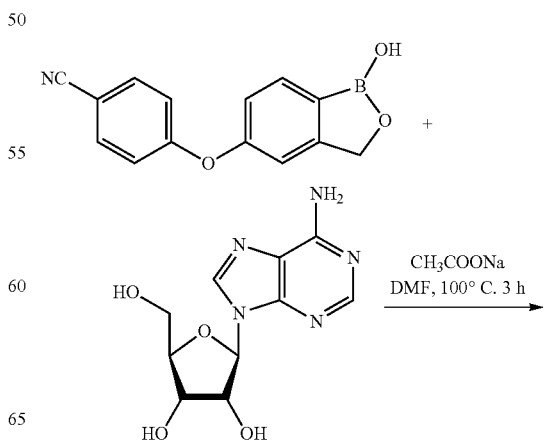

221

-continued

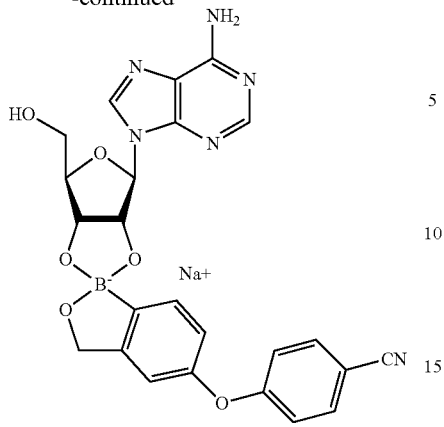

The procedure described above was adapted for the preparation of the title complex by replacing (C10) with 5-(4-cyanophenoxy)-1,3-dihydro-1-hydroxy-2,1-benzoxaborole (C17, 1.25 g, 5 mmol). White solid product (2.7 g, yield 100%) was obtained after pumping overnight. $^1$H NMR indicated there were 3.5 mol % of unreacted adenosine, 3.5 mol % of unreacted C17, and the reaction conversion was more than 96%. $^1$H NMR (DMSO-d$_6$, 300 MHz): δ=8.35 (s, 1H), 8.13 (s, 1H), 7.76 (d, J=8.7 Hz, 2H), 7.45-7.36 (broad m, 1H), 7.29 (s, 2H), 7.00 (d, J=8.7 Hz, 2H), 6.81 (broad m, 1H), 6.73 (s, 1H), 6.01 (broad s, 1H), 5.10 (very broad s, 1H), 4.73 (dd, J=6.0 Hz, J=3.9 Hz, 1H), 4.54 (s, 2H), 4.45 (dd, J=6.0 Hz, J=3.9 Hz, 1H), 4.09 (broad s, 1H), 3.65 (dd, J=12 Hz, J=3.3 Hz, 1H) and 3.54 (dd, J=12 Hz, J=4.8 Hz, 1H) ppm; M.p: started soften at 120° C. due to residue solvents, remained as soften solid and started decomposing at 230° C.; HPLC: 92.1% at 220 nm (adenosine was 3.8%).

Example 36

C28-Adenosine Complex

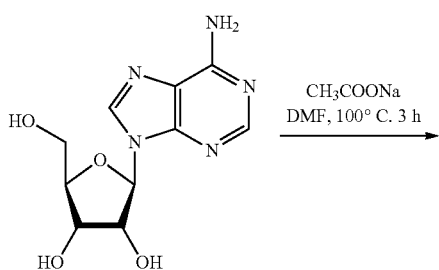

222

-continued

The procedure for the synthesis of C10-adenosine complex was adapted for the preparation of the title complex by replacing (C10) with 6-phenylthio-1,3-dihydro-1-hydroxy-2,1-benzoxaborole (C28, 1.21 g, 5 mmol). White solid product (2.8 g, yield 100%) was obtained after pumping overnight. $^1$H NMR indicated there was 5 mol % of unreacted C28, and the reaction conversion was 95%. $^1$H NMR (DMSO-d$_6$, 300 MHz): δ=8.29 (s, 1H), 8.13 (s, 1H), 7.53 (broad s, 1H), 7.29 (s, 2H), 7.32-7.04 (m, 7H), 6.05-5.96 (broad m, 1H), 5.15 (very broad s, 1H), 4.73-4.70 (m, 1H), 4.58 (s, 2H), 4.46 (broad s, 1H), 4.12-4.03 (broad m, 1H), 3.63 (dd, J=11.7 Hz, J=3.3 Hz, 1H) and 3.52 (dd, J=11.7 Hz, J=4.8 Hz, 1H) ppm; M.p: started soften at 110° C. due to residue solvents, remained as soften solid and started decomposing at 238° C. HPLC: 91.3% at 220 nm (adenosine was 3.8%).

Example 37

C2-Adenosine Complex

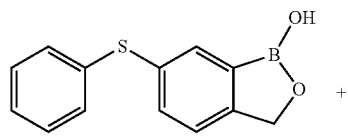

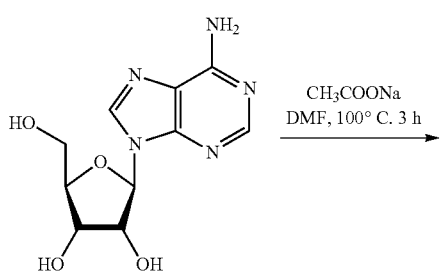

-continued

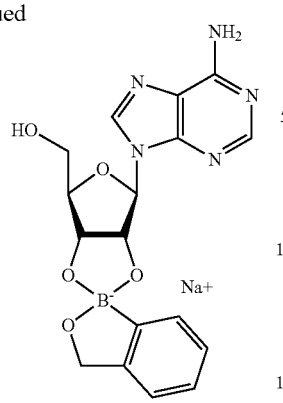

The procedure for the synthesis of C10-adenosine complex was adapted for the preparation of the title complex by replacing (C10) with 1,3-dihydro-1-hydroxy-2,1-benzoxaborole (C2, 0.67 g, 5 mmol). Cream solid product (2.18 g, yield 100%) was obtained after pumping overnight. $^1$H NMR indicated there was 4.5 mol % of unreacted C2, and the reaction conversion was more than 94%. $^1$H NMR (DMSO-d$_6$, 300 MHz): δ=8.33 (s, 1H), 8.13 (s, 1H), 7.42-7.20 (broad m, 1H), 7.30 (s, 2H), 7.03-6.94 (m, 3H), 6.02 (d, J=3.6 Hz, 1H), 5.25 (very broad s, 1H), 4.73 (dd, J=5.7 Hz, J=4.2 Hz, 1H), 4.56 (s, 2H), 4.46 (dd, J=6.0 Hz, J=3.9 Hz, 1H), 4.10 (broad q, J=3.3 Hz, 1H), 3.66 (dd, J=12 Hz, J=2.7 Hz, 1H) and 3.52 (dd, J=11.7 Hz, J=4.8 Hz, 1H) ppm; M.p: started soften at 115° C. due to residue solvents, remained as soften solid and started decomposing at 233° C. HPLC: 91.6% at 220 nm (adenosine was 5.9%).

Example 38

Synthesis of Methyl β-D-ribofuranoside

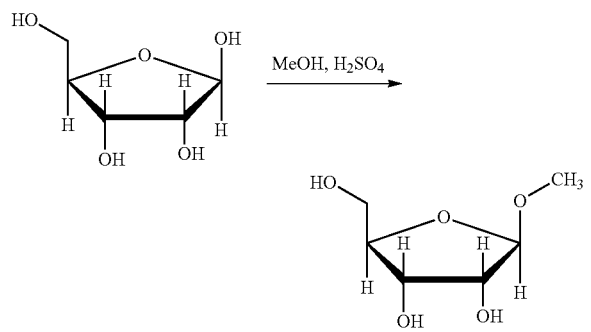

5 g of D-Ribose was dissolved in 100 mL of methanol and cooled to 0° C. 0.5 mL of concentrated sulfuric acid was added and the solution was stored at −20° C. for 48 hrs. Solution was neutralized by passage through a bed of sodium carbonate and evaporated under vacuum to a viscous oil. Crude material was purified on a silica column eluting with 10% methanol in ethyl acetate to yield 2.1 grams of methyl j-D-ribofuranoside.

$^1$H NMR 300 MHz (DMSO-d$_6$) δ 4.97-4.99 (d, J=4.8 Hz, 1H), 4.76-4.79 (d, J=6.6 Hz, 1H), 4.57-4.62 (m, 2H), 3.76-3.80 (m, 1H), 3.72-3.74 (m, 1H), 3.66-3.71 (m, 1H), 3.44-3.50 (m, 1H), 3.26-3.34 (m, 1H), 3.19 (s, 3H)

Example 39

General Procedure for Complex Formation

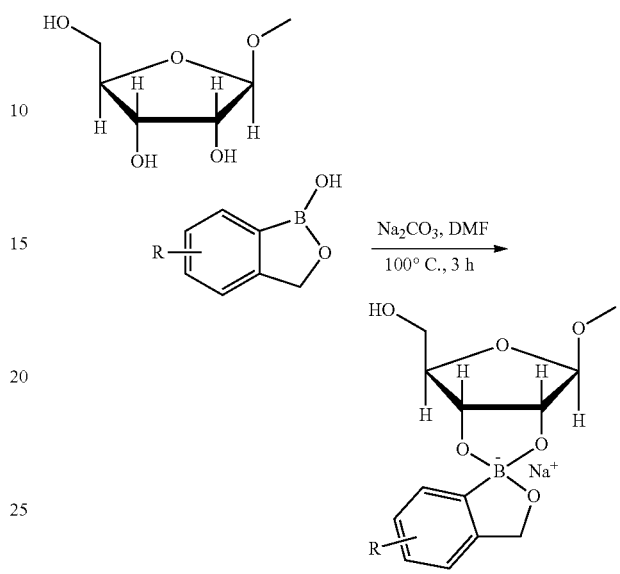

300 mg of methyl β-D-ribofuranoside was dissolved in 20 ml of dimethylformamide. To this solution was added 1 eq of boronic ester and 0.5 eq of finely powdered sodium carbonate. Reaction mixture was heated to 100° C. and stirred for 3 hours then stripped of solvent under vacuum. Residue was co-evaporated 2 times with ethyl acetate then sonicated in dichloromethane and filtered to yield an off-white solid.

C10-Methylribose Complex

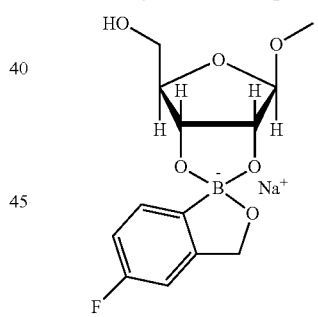

$^1$H NMR 300 MHz (DMSO-d$_6$) δ 7.28 (bs, 1H), 6.68-6.77 (m, 2H), 4.71 (s, 1H), 4.52-4.55 (m, 3H), 4.26-4.28 (d, J=5.1 Hz, 1H), 4.17-4.19 (d, J=5.7 Hz, 1H), 3.95-4.00 (t, J=6.8 Hz, 1H), 3.31-3.36 (m, 2H), 3.19 (s, 3H).

C17-Methylribose Complex

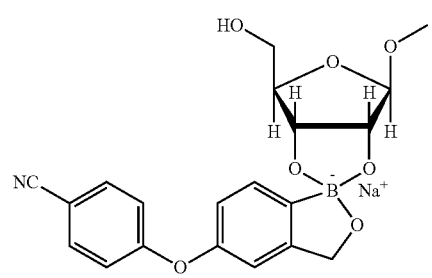

¹H NMR 300 MHz (DMSO-d₆) δ 7.73-7.76 (d, J=6.9 Hz, 2H), 7.38-7.41 (d, J=7.8 Hz, 1H), 6.96-6.99 (d, J=6.9 Hz, 2H), 6.72-6.75 (d, J=7.5 Hz, 1H), 6.68 (s, 1H), 4.70 (s, 1H), 4.49-4.51 (m, 3H), 4.23-4.25 (d, J=5.4 Hz, 1H), 4.14-4.16 (d, J=5.4 Hz, 1H), 3.95-3.98 (m, 1H), 3.22-3.26 (t, J=6.0, 1H), 3.19 (s, 3H), 3.13-3.14 (d, J=2.1, 1H).

C2-Methylribose Complex

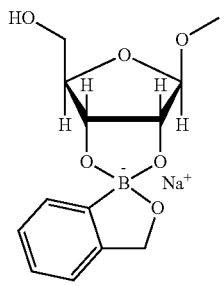

¹H NMR 300 MHz (DMSO-d₆) δ 7.31 (bs, 1H), 6.87-6.95 (m, 3H), 4.70 (s, 1H), 4.46-4.50 (m, 3H), 4.20-4.22 (d, J=5.7, 1H), 4.12-4.14 (d, J=6.0 Hz, 1H), 3.94-3.99 (t, J=7.8 Hz, 1H), 3.30-3.34 (m, 2H), 3.19 (s, 3H)

C28-Methylribose Complex

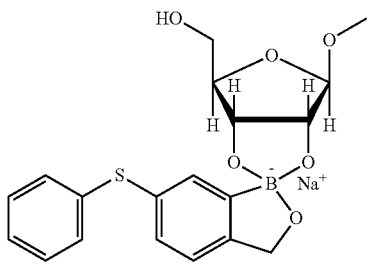

¹H NMR 300 MHz (DMSO-d₆) δ 7.48 (bs, 1H), 7.21-7.26 (m, 2H), 7.05-7.12 (m, 4H), 6.98-7.01 (d, J=7.8 Hz, 1H), 4.65 (s, 1H), 4.47-4.58 (m, 3H), 4.22-4.24 (d, J=5.7 Hz, 1H), 4.13-4.15 (d, J=6.0 Hz, 1H), 3.89-3.93 (t, J=6.6 Hz, 1H), 3.28-3.32 (t, J=6.5, 1H), 3.13-3.16 (m, 4H).

Example 40

Mechanism of Action

The purpose of this study is to determine the mechanism of action (MOA) of C10 in the model fungi *Saccharomyces cerevisiae*.

40.1 Methods

The haploid *Saccharomyces cerevisiae* strain ATCC 201388 was used in the selection of C10 resistant mutants. Spontaneous and EMS-induced resistant mutants were isolated from YPD agar plates containing 4×, 8×, 16×MIC of C10. All minimal inhibitory concentrations (MIC) were determined using NCCLS protocol M27 with the exception of using YPD or synthetic defined media. All yeast and molecular genetic manipulations were essentially performed as described by Guthrie C., et al., *Methods in Enzymology*, 350: Part B, (2002).

40.2 Results and Conclusions

A total of 11 C10 resistant mutants were isolated from *S. cerevisiae*, all mutants were dominant and showed an 8 to 64-fold increase in the MIC to C10. Further characterization of these mutants showed that they were not resistant to several known antifungals including amphotericin B, cerulenin, itraconazole, aculeacin A, terbinafine, tunicamycin, ciclopirox, cyclohexamide and nikkomycin Z. All 11 mutations in the C10 resistant mutants were mapped to 9 amino acid residues in the editing domain of CDC60, the essential cytoplasmic leucyl-tRNA synthetase, one of 40 aminoacyl-tRNA synthetases in *S. cerevisiae*. Furthermore, *S. cerevisiae* strains bearing multiple copies of CDC60 on a 2 μM plasmid were eight times more resistant to C10. The combination of mutant and over-expression data predicts that CDC60 is the target for C10. The fact that all mutations were present in the editing domain of CDC60 indicates that C10 inhibits CDC60 via a novel mechanism.

The lack of a genomic sequence or any genetic tools for *Trichophyton* spp. makes it difficult to study the mechanism of action of C10 in either *Trichophyton* species, therefore, the model fungi *Saccharomyces cerevisiae* was used.

40.3 Materials and Methods 40.3a Chemicals, Strains and Plasmids

C10 (5-fluoro-1,3-dihydro-1-hydroxy-2,1-benzoxaborole, was obtained from Anacor Pharmaceuticals, Inc. (Palo Alto, Calif., USA). All *S. cerevisiae* strains and plasmids were obtained from ATCC (Manassas, Va., USA). The haploid *Saccharomyces cerevisiae* strain ATCC201388 (MATa his3Δ1 leu2Δ0 met5Δ0 ura3Δ0) was used for generating mutants, while ATCC 200901 (MATα leu2Δ0 lys2Δ0 ura3Δ0) was used to mate with C10 resistant mutants to determine genetic dominance of the mutation. The yeast-*E. coli* shuttle plasmid pRS315 (Sikorski R S et al., *Genetics* 122: 19-27, (1989)), which has CEN6, leu2, ampR genes, and is a low copy plasmid in yeast was used in the construction of the genomic library. In the over-expression experiment, the shuttle vector pRS425 (Christianson T W et al., *Gene* 110(1):119-22 (1992)), which has the leu2 and ampR genes, and is a high copy plasmid in yeast, was used.

40.3b Isolation of Spontaneous Resistant Mutants

The haploid *S. cerevisiae* strain ATCC201388 was grown overnight in YPD broth (BD, NJ USA) at 30° C. and 1 mL of cells was plated out onto YPD agar plates (YPD broth+ 1.5% Bacto-agar, BD, NJ USA) containing either 1.6, 3.2 or 6.4 μg/mL C10 (equivalent to 4×, 8×, 16×MIC of C10). Resistant mutants appeared after 2 d incubation at 30° C. Frequency of resistance was determined by dividing the number of resistant mutants by the total number of cells plated as determined by plating dilutions of the overnight culture on YPD plates.

40.3c EMS (Ethylmethane Sulfonate) Mutagenesis

A 2.5 mL of the overnight culture, which was grown in YPD media, was centrifuged at 700×g for 5 minutes. The cell pellet was resuspended in 10 mL 50 mM potassium phosphate buffer, pH 7.0. The cell suspension was centrifuged again and the cell pellet was resuspended in phosphate buffer to obtain a cell density of 5×10⁷ cells/mL as determined by counting the cells using a Petroff Hausser Counting Chamber (Horsham, Pa. USA). The cell suspension was shaken with 300 μL of EMS (Alfa Aesar, Ward Hill, Mass., USA) for 30 min. at 30° C. The mutagenesis was stopped by adding 10% (w/v) sodium thiosulfate (Sigma-Aldrich, St. Louis, Mo., USA), and the cells were pelleted by centrifugation at 700×g for 5 min. and resuspended in 1 mL sterile H₂O. This was repeated once more before the cells were plated on YPD agar plates containing 1.6 μg/mL of C10.

40.3d Determination of MICs

The minimal inhibitory concentration (MIC) was essentially performed following the NCCLS guidelines outlined in the M27 protocol with the exception of using YPD or synthetic defined media (SDM).

40.3e Yeast Mating Experiment

The haploid mutants derived from *S. cerevisiae* ATCC201388 were mixed with *S. cerevisiae* ATCC 200901, and were incubated on YPD agar plates at 30° C. for 4 h. The cell mixture was streaked out on synthetic defined media agar (BD, NJ USA) without the amino acids lysine and methionine, which are selective for diploids.

40.3f Construction of Plasmid Genomic DNA Library

Genomic DNA from mutant strains was isolated using the DNeasy tissue kit from Qiagen (Valencia, Calif., USA). Genomic DNA fragments of 4-10 kb were generated by partial digestion with Mbo I from Fermantas (Hanover, Md., USA), followed by purification using the Wizard®SV gel and PCR Clean-Up system (Promega, Madison Wis. USA). The purified DNA fragments were ligated into pRS315 digested with BamH I (Fermantas, Hanover Md. USA) using T4 DNA ligase (Fermantas, Hanover Md. USA). The ligation mixture was dialyzed against water using the VSWP 0025 filters (Millipore, Billerica, Mass., USA) before it was electroporated into *Escherichia coli E. cloni* SUPREME cells (Lucigen, Middleton, Wis., USA) following the protocol of the manufacturer. Transformants were plated out on LB plates with 200 µg/ml carbinicillin and incubated overnight at 37° C. The transformants were pooled and the plasmid DNA was isolated using Qiagen miniprep kit (Valencia, Calif., USA). The plasmid library was transformed into *S. cerevisiae* (Gietz, R D et al., *Methods in Enzymology* 305: 87-96 (2002)).

40.3g Sequencing

All sequencing was performed by Sequetech Corporation (Mountain View, Calif. USA).

40.3g(1) Mapping Mutations

To further map the mutations to specific domains in CDC60, the following three pairs of primers were used 5' gcgaaaagaaacctaacgcatattc 3' and 5'ctatcgtgatccatacaagctt-gac 3', 5' cgatagacaatccggtgaaggtgttac 3' and 5' catc-ccaaggcaatctggtacctaacc 3', and 5' gaaaaatacttagttgagtctt-tatca 3' and 5' caccatgaggcatcttgaaatattctc 3'.

40.3h Cloning and Over-Expressing Wild Type CDC60 in *S. cerevisiae*

A 4.0 kb BamH I-Sal I DNA fragment containing the entire CDC60 open reading frame (ORF) and 700 bp of upstream sequence was amplified using KOD DNA polymerase, *S. cerevisiae* genomic DNA (Novagen, Madison, Wis., USA), and the primers GAG GGA TCC GGT TAG TTT TAG TTC GCG AGT GAC CTG and GAG GTC GAC GAT TTC TGG TTG CTG TTT ATT GAT CTT (Operon, Alameda, Calif., USA). This DNA fragment was then cloned into the 2 µM multi-copy plasmid pRS425, and transformed into *S. cerevisiae* ATCC201388 (Gietz, R D et al., *Methods in Enzymology* 305: 87-96 (2002)).

40.4 Results and Discussions 40.4a Isolation of Resistant Mutants

From 5×10⁹ cells, 600 spontaneous C10 resistant mutants were isolated, which makes the frequency of resistance $1.2 \times 10^{-7}$ at 4×MIC. Similar frequencies of resistance were obtained for 8× and 16×MIC. We also used EMS to isolate C10 resistance mutants. Use of EMS increased the mutagenic frequency by 4,000 fold. The MICs of 8 spontaneous mutants and 3 EMS generated mutants were tested. All the mutants showed an 8 to 64-fold increase in resistance to C10 (Table 1).

TABLE 1

MICs of Spontaneous and EMS induced C10 mutants

| S. cerevisiae Haploid Strains | MIC (µg/mL) | |
|---|---|---|
| | Cerulenin | C10 |
| ATCC201388 | 1 | 0.5 |
| (A) | 0.5 | 4 |
| (B) | 0.5 | 16 |
| (C) | 0.5 | 16 |
| (D) | 0.5 | 32 |
| (E) | 0.5 | 16 |
| (F) | 0.5 | 32 |
| (G) | 0.5 | 32 |
| (H) | 0.5 | 32 |
| (I) | 1 | 32 |
| (J) | 1 | 32 |
| (K) | 1 | 32 |

40.4b C10 Resistant Mutations do not Confer Resistance to Other Antifungals

To further characterize these resistant mutants, three C10 resistant mutants were tested against various antifungal agents with known mechanisms of action. The C10 resistant mutants did not show any resistance to these compounds (Table 2), which suggests that C10 acts very differently from these antifungal agents.

TABLE 2

C10 mutants are not resistant to other antifungals

| Antifungal Agents | MIC (µg/mL) | | | |
|---|---|---|---|---|
| | ATCC201388 | (C) | (G) | (H) |
| C10 | 0.5 | 16 | 16 | 16 |
| Amphotericin B | 0.125 | 0.125 | 0.125 | 0.125 |
| Cyclohexamide | <0.06 | <0.06 | <0.06 | <0.06 |
| Cerulenin | 0.5 | 0.5 | 0.5 | 0.5 |
| Itraconazole | 0.125 | 0.125 | 0.125 | 0.125 |
| Aculeacin A | 4 | 4 | 4 | 4 |
| Cicloprirox | 0.5 | 0.5 | 0.5 | 0.5 |
| Terbinafine | 4 | 4 | 4 | 4 |
| Nikkomycin Z | 64 | 64 | 64 | 64 |
| Tunicamycin | 8 | 8 | 8 | 8 |

40.4c Resistance to C10 is Dominant

In order to identify the gene that gives rise to C10 resistance, it was first determined whether the mutation was either dominant or recessive. The parental *S. cerevisiae* strain and three mutants were selected and mated with *S. cerevisiae* ATCC 200901. The MIC of the diploids generated from the C10 mutants were found to be 64-fold greater than the diploid generated from the parental strain (Table 3), which suggests that the mutations are dominant, and therefore, plasmid libraries were constructed from these three haploid C10 resistant mutants.

TABLE 3

C10 mutants are dominant

| Diploid (mutant strain/ATCC200901) | MIC (µg/mL) C10 |
|---|---|
| ATCC201388/ATCC200901 | 0.5 |
| (C)/ATCC200901 | 32 |
| (G)/ATCC200901 | 32 |
| (H)/ATCC200901 | 32 |

40.4d the CDC60 Gene Confers Resistance to C10

Plasmid libraries from the three mutants were transformed into S. cerevisiae ATCC201388 and selected on SDM minus leucine agar with 1 µg/mL of C10. Plasmid DNA was isolated from C10 resistant transformants and electroporated into E. coli 10G cells. The plasmid DNAs from the resulting E. coli carbenicillin resistant transformants were then transformed into S. cerevisiae ATCC201388 to confirm that the plasmids bore the gene for C10 resistance. One plasmid from each library that conferred C10 resistance was sequenced and analyzed using a BLASTN search against the S. cerevisiae genome database (http://seq.yeastgenome.org/cgi-bin/nph-blast2sgd). The CDC60 gene was the only open reading frame identified in the cloned inserts from two plasmids derived from two of the plasmid libraries. Two genes were revealed, CDC60 and PET20, in the cloned insert from the remaining plasmid library. This suggests that these C10 resistant mutations are located in the CDC60 gene, which encodes for the cytoplasmic leucyl-tRNA synthetase. CDC60 (leucyl tRNA synthetase) is one of 20 essential aminoacyl-tRNA synthetases (ARS) that attach amino acids to the 2' or 3' end of tRNAs.

40.4e C10 Resistance Mutations Reside in the Editing Domain of CDC60

DNA sequence analysis of the plasmids derived from the three mutants showed that there was a single amino acid substitution in CDC60 from each of the three mutants (Table 4). An additional eight mutants were analyzed by amplifying CDC60 by colony PCR and transforming the resulting product into S. cerevisiae ATCC201388. All transformants were resistant to C10 and subsequent sequence analysis showed that all of them contained a single amino acid change within the editing domain of CDC60 (Table 4). The function of the ARS is to charge the correct tRNA with the correct amino acid. In leucyl-tRNA synthetases the active site for the editing mechanism is located in a separate domain, which is called the connective polypeptide 1 (CP1), from the synthetic active site (Schmidt E. et al, Biochemistry 34(35): 11204-10 (1995)). All of the amino acid substitutions from 11 mutants were located in this CP1 domain, demonstrating a link between the editing function of the enzyme and inhibitory activity of C10.

40.4f Over-Expression of Wild Type CDC60 in S. cerevisiae

Since all 11 C10 resistant mutants have single amino acid substitutions in the editing domain of leucyl-tRNA synthetase (Table 4), it strongly suggests that CDC60 is the target for C10. If leucyl-tRNA synthetase is the target, increasing the copies of CDC60 should increase resistance to C10. To test this hypothesis, the wild type CDC60 gene was cloned onto a multi-copy plasmid pRS425, and transformed into S. cerevisiae ATCC201388. As shown in Table 5, the MIC for this strain is eight times higher than the same strain bearing pRS425.

TABLE 4

Amino acid (AA) substitutions in C10 resistant mutants

| Resistant mutants | AA substitution in CDC60 |
|---|---|
| (H) | T314M |
| (G) | L315V |
| (K) | T319I |
| (C) | C326F |
| (E) | C326R |
| (D) | G405V |
| (A) | N415D |

TABLE 4-continued

Amino acid (AA) substitutions in C10 resistant mutants

| Resistant mutants | AA substitution in CDC60 |
|---|---|
| (I) | S416L |
| (J) | D487N |
| (F) | D487G |
| (B) | R316I |

TABLE 5

CDC60 overexpression increases C10 resistance

| | MIC (µg/mL) | |
|---|---|---|
| Compound | pRS425 Plasmid control | CDC60 on pRS425 (20 copies) |
| Fluconazole | 2 | 2 |
| 1 | 0.125 | 1 |

Example 41

Experiments to isolate mutant leucyl tRNA transferase molecules that were also resistant to C10.

The haploid wild type Saccharomyces cerevisiae strain ATCC 201388 (MATa his3Δ1 leu2Δ 0 met5Δ 0 ura3Δ 0) was used for selection of clones showing resistance to C10.

Mutations in the leucyl tRNA transferase were isolated in two ways. In one set of experiments, EMS was used as a chemical mutagenic agent. 2.5 mL of an overnight culture was washed 2× with 50 mM potassium phosphate buffer, pH 7.0, and resuspended in 10 mL of the buffer to reach approximately $5 \times 10^7$ cells/ml. 300 µL EMS (Alfa Aesar, Ward Hill, Mass.) was added to the cells, which were then incubated for 30 min at 30° C. with shaking. The mutagenesis process was halted with the addition of 10% (w/v) sodium thiosulfate (Sigma-Aldrich, St. Louis, Mo., USA). At the end of the mutagenesis cycle, the cells were washed 2× with water and then plated out on YPD agar plates containing C10.

In the second method, spontaneous mutant clones were isolated from YPD plates containing large concentrations of C10. Wild type haploid S. cerevisiae strain ATCC201388 (MATa his3Δ1 leu2Δ 0 met5Δ 0 ura3Δ 0) was grown overnight in Difco YPD broth (1% yeast extract, 2% Bacto Peptone, 2% glucose) at 30° C. to reach ~$1.0 \times 10^8$ cells/ml. Cells were concentrated 10× in YPD broth, and 100 µL was plated out onto each of 30 YPD agar (Difco YPD broth+ 1.5% Bacto agar) plates containing 1.6, 3.2, 6.4 µg/ml C10 (equivalent to 4×, 8×, and 16× minimal inhibitory concentration of C10). Resistant mutants appeared after 2 days of incubation at 30° C. Frequency of resistance was determined by counting the number of the mutants, and the total number of cells.

The minimal inhibitory concentration (MIC) test was performed using NCCLS protocol. Yeast mating experiment was conducted following the procedure in Methods in Enzymology by Guthrie, C etc.

The genomic plasmid library for each clone was constructed using the yeast-E. coli shuttle vector pRS315 and transformed into S. cerevisiae ATCC201388. Transformants were selected on synthetic defined media with 0.2 ug/ml C10 minus leucine. All sequencing work was done by Sequeteq. Blast search was performed using Saccharomyces genome database. Yeast Transformation was carried out using LiAc/

PEG method. Over-expression of CDC60 construct was made by using *S. cerevisiae* genomic DNA, and two primers 5'GAGGGATCCGGTTAGT TTTAGTTCGCGAGTGACC TG 3', 5'GAGGTCGACGATTTCTGGTTGCT GTTTATT-GATCTT 3'.

A total of 23 C10 resistant mutants were isolated from *S. cerevisiae*. All mutants were dominant and had 8-64 fold increased resistance to C10 over wildtype in the minimal inhibitory concentration test. Further characterization of these mutants showed that they were not cross resistant to any anti-fungal agents with known mechanism of action.

Determination of Dominance/Recessiveness

In order to identify the resistant gene in mutant strain, we first determined whether the mutation is dominant or recessive. The mutant was mated with a wild type strain with opposite mating type to make mutant diploid. There were two sets of genes in the resulting mutant diploid cells, one from resistant mutant, and the other one from the C10-sensitive wild type. If the mutant diploid was resistant to C10, the muted gene was dominant. To map the mutation, we constructed a plasmid library from the mutant strain, and transformed the library into the C10-sensitive wild type strain to select for the resistant phenotype. If the mutant diploid was sensitive to C10, the muted gene would be identified as recessive. A12, F4, H4 was mated with a wild type strain, respectively, as control; the parental strain was also mated with the same strain. Minimal inhibitory concentrations of both wild type diploid and 3 mutant diploids are shown in Table 3. Compared to wild type diploid, all 3 mutant diploids were resistant to C10, indicating that the resistant mutation in these 3 mutants is dominant.

Genetic Mapping of Mutation

All the mutations in the 23 isolated C10 resistant mutants were mapped to 11 residues in the editing domain of CDC60, the cytoplasmic leucyl-tRNA synthetase.

To identify the mutation in the resistant mutant, we constructed 3 plasmid genomic libraries from mutant A12, F4 and H4, respectively. Plasmids with random genomic DNA fragment insert, size from 4-10 kb, were transformed back into parental wild type strain. Transformants with plasmids carrying resistant genes were selected on SDM-leu agar plates with addition of C10. Plasmids were then isolated and sent for sequencing. Nucleotide sequence of the insert was BLAST searched against *S. cerevisiae* genome database, and the results revealed that there was a single ORF present in the insert of both plasmids isolated from F4 and H4 plasmid library. This ORF was identified as CDC60, the cytoplasmic leucyl tRNA synthetase, one of the 20 essential cytoplasmic aminoacyl-tRNA synthetases in *S. cerevisiae* (there are 20 more in mitochondrial). In addition to CDC60, there was a second ORF pet20 present in the plasmid isolated from A12 plasmid library, which encoded the protein required for respiratory growth and stability of the mitochondrial genome. To confirm that the CDC60 from these 3 mutants conferred resistance to C10, we re-transformed the 3 plasmids back to parental wild type strain. Compared to the control transformation of the plasmid without CDC60, ones with CDC60 from A12, F4, H4 gave >1,000 more resistant colonies on YPD agar containing C10, confirming that CDC60 from the 3 mutant strains contributed to C10 resistance.

Sequence in CDC60 from Each of the Mutants Contains Single Amino Acid Substitution In order to identify whether there were any amino acid substitutions, the whole ORF of CDC60 from resistant plasmids A12, F4, and H4 was sequenced. Comparing the sequence with wild type CDC60 showed that there was a single amino acid substitution in each of the 3 CDC60 (Table 4). In addition, sequence analysis of CDC60 from the rest of 20 resistant mutants showed that each contains a single amino acid change within CDC60. DNA PCR fragments containing each mutation were transform back into wild type strain. These transformations conferred resistance, indicating that the resistance of all the mutants was due to the single amino acid substitution in CDC60.

CDC60 (leucyl tRNA synthetase) is one of the aminoacyl-tRNA synthetases (ARS) that belong to a family of essential enzymes that attach amino acids to the 2', or 3' end of tRNAs, the charged tRNAs are then used in protein synthesis. The aminoacylation of tRNA is a two-step reaction: a) activation of amino acids with ATP by forming aminoacyl adenylates and b) transferring of the aminoacyl residue from the aminoacyl adenylate to the cognate tRNA substrate. The accuracy of aminoacylation depends on both the specific recognition of amino acids during their activations (coarse sieve) and the pre- or post transferring editing (fine sieve). Some of the ARS have evolved editing mechanism that specifically hydrolyzes structurally close related misactivated amino acids. Leucyl tRNA synthetase is one of such enzymes that can discriminate leucine from isoleucine, and valine. The region that carries out this editing function is called connective polypeptide 1 (CP1), it's a large insertion that interrupts the active site between the third and fourth b strands of the Rossman fold. All of the 11 amino acid substitutions from 23 mutants were located in this CP1 region, suggesting that there might be a link between the editing function of the enzyme and inhibition activity of C10.

Example 42

Assay for Determining that C10 Inhibits the Editing Domain of tRNA Synthetase in a Bacteria This example sets forth a representative assay for determining whether a particular compound inhibits the editing domain of an ARS in a bacterium.

The [$^3$H]-isoleucine mischarged tRNAleu was synthesized by incubating 1 µM of *Saccharomyces cerevisiae* editing defective Cdc60p (C326F) in 500 µL of 50 mM Tris-HCl (pH 8.0), 60 mM MgCl$_2$, 4 mM ATP, 1 mM DTT, 0.02% (w/v) BSA, 4 mg/mL crude *E. coli* tRNA tRNA (Roche), 0.1 mM isoleucine and 5 mCi L-[4,5-3H]isoleucine (100 Ci/mmole, GE Healthcare) and 20% (v/v) DMSO for 1 hour at 30° C. The reaction was stopped by adding 10 µL of 10% (v/v) acetic acid followed by two acidic phenol (Sigma) extractions. The mischarged tRNA in the top aqueous phase was removed and precipitated by adding two volumes of 96% (v/v) ethanol and incubating at −20° C. for 30 minutes. The precipitate was pelleted by centrifugation at 13,200×g for 30 minutes and the mischarged tRNA pellet was washed twice with 70% (v/v) ethanol and then resuspended in 50 mM potassium phosphate buffer pH 5.2.

The reaction was terminated after 2 hours incubation at 30° C. by the addition of acetic acid to 0.17% (v/v). The isoleucylated crude tRNA$^{Leu}$ was purified by extracting twice with acidic phenol-chloroform extractions (pH 4.3), followed by ethanol precipitation. The tRNA pellet was washed twice with 70% ethanol, dried and then resuspended in 50 mM potassium phosphate (pH 5.0) and stored at −20° C. An aliquot was precipitated with 10% (w/v) TCA to quantify ile-tRNA$^{Leu}$.

Post-transfer editing hydrolysis assays were carried out at 30° C. in 50 mM Hepes (pH 8), 10 mM MgCl$_2$, 30 mM KCl, with ³H-isoleucine-tRNA crude (~0.3 µCi/mL). Each reaction was initiated by addition of the 150 nM enzyme. At each time point three 20 µL aliquots of the reaction mixture was added to 200 µL of 10% (w/v) TCA in a Millipore filter plate and precipitated for 20 minutes at 4° C. The precipitate was filtered and washed three times with 200 µL of 5% (w/v) TCA, then dried and 20 µL Supermix scintillation cocktail was added. The Millipore filter plates were counted in the MicroBeta Trilux. The $IC_{50}$ was determined by the amount of inhibitor that inhibited 50% activity, 100% post-transfer editing was calculated by taking the activity of the no enzyme control from the wild-type enzyme activity.

Compare the minimal inhibitory concentration (MIC) of a tolC Escherichia coli strain bearing a pUC derived plasmid with and without an leuS gene insert.

If the MIC of the strain bearing the extra copies of leuS is greater than 2-fold more than the control strain then pour LB agar plates with four times the concentration of the MIC of the compound.

Plate $1 \times 10^{10}$ E. coli on ten plates containing 4×MIC of the compound. Incubate for 1-2 days at 37° C. and pick ten colonies and restreak on 4×MIC LB agar plates to confirm resistance.

Take one large colony from each of the ten E. coli resistant mutants and resuspend in 50 µL of PCR buffer.

Amplify the editing domain of CDC60 using a proof-reading PCR enzyme and the following primers, ggcaccgtg-gacgtacgacaacatcgc and gggaaacaccccagtcgcgcaggcgg.

Purify the 980 bp PCR product using either Qiagen or Promega PCR cleanup kits.

Sequence amplify the mutant DNA and compared it to wild-type. If the mutant DNA bears mutations in the editing domain the inhibitor affects leucyl-tRNA synthetase via the editing domain.

Example 43

Assay for Determining that C10 Inhibits the Editing Domain of tRNA Synthetase in a Fungi This example details an exemplary assay for determining whether a selected compound inhibits the editing domain of an ARS in a fungus.

The [³H]-isoleucine mischarged tRNAleu was synthesized by incubating 1 µM of Saccharomyces cerevisiae editing defective Cdc60p (C326F) in 500 µL of 50 mM Tris-HCl (pH 8.0), 60 mM $MgCl_2$, 4 mM ATP, 1 mM DTT, 0.02% (w/v) BSA, 16 µM brewer's yeast tRNA (Roche), 0.1 mM isoleucine and 5 mCi L-[4,5-3H]isoleucine (100 Ci/mmole, GE Healthcare) and 20% (v/v) DMSO for 1 hour at 30° C. The reaction was stopped by adding 10 µL of 10% (v/v) acetic acid followed by two acidic phenol (Sigma) extractions. The mischarged tRNA in the top aqueous phase was removed and precipitated by adding two volumes of 96% (v/v) ethanol and incubating at −20° C. for 30 minutes. The precipitate was pelleted by centrifugation at 13,200×g for 30 minutes and the mischarged tRNA pellet was washed twice with 70% (v/v) ethanol and then resuspended in 50 mM potassium phosphate buffer pH 5.2.

The reaction was terminated after 2 hours incubation at 30° C. by the addition of acetic acid to 0.17% (v/v). The isoleucylated crude $tRNA^{Leu}$ was purified by extracting twice with acidic phenol-chloroform extractions (pH 4.3), followed by ethanol precipitation. The tRNA pellet was washed twice with 70% ethanol, dried and then resuspended in 50 mM potassium phosphate (pH 5.0) and stored at −20° C. An aliquot was precipitated with 10% (w/v) TCA to quantify ile-$tRNA^{Leu}$.

Post-transfer editing hydrolysis assays were carried out at 25° C. in 50 mM Hepes (pH 7.5), 10 mM $MgCl_2$, 30 mM KCl, with ³H-isoleucine-tRNA crude (~0.3 µCi/mL). Each reaction was initiated by addition of the 150 nM enzyme. At each time point three 20 µL aliquots of the reaction mixture was added to 200 µL of 10% (w/v) TCA in a Millipore filter plate and precipitated for 20 min. at 4° C. The precipitate was filtered and washed three times with 200 µL of 5% (w/v) TCA, then dried and 20 µL Supermix scintillation cocktail was added. The Millipore filter plates were counted in the MicroBeta Trilux. The $IC_{50}$ was determined by the amount of inhibitor that inhibited 50% activity, 100% activity was calculated by taking the activity of the no enzyme control from the wild-type enzyme post-transfer editing activity.

Example 44

Equilibrium Dialysis

Equilibrium dialysis experiments were performed in 1×AARS buffer containing 50 mM Hepes-KOH (pH 8.0), 30 mM $MgCl_2$ and 30 mM KCl. Experiments were performed using 5k MWCO DispoEquilibrium Dialyzer apparatus (Harvard Apparatus, Holliston, Mass.). On one side of the dialysis membrane (side A), [methylene-¹⁴C]C10, 2.04 GBq/mmol (Amersham) was added at concentrations ranging from 1 to 200 µM in 20 µL. On the opposite side of the membrane (side B), 3 µM recombinant Cdc60p (Saccharomyces cerevisiae cytoplasmic LeuRS) and 10 mM AMP (adenosine 5'-monophosphate, Sigma) was added in 20 µL. Samples were incubated at room temperature (21° C.) while shaking for 4.5 hrs to establish C10 equilibrium across the membrane. At equilibrium, C10 on each side of the dialysis membrane was quantified by scintillation counting using a Wallac MicroBeta Trilux model 1450 liquid scintillation counter. The amount of C10 bound to Cdc60p was determined by subtracting $[C10]A$ from $[C10]_B$.

PPi Exchange Assay

The PPi exchange assay was performed in 1×AARS buffer containing 50 mM Hepes-KOH (pH 8.0), 30 mM $MgCl_2$ and 30 mM KCl supplemented with 2 mM ATP and [³²P] PPi ($10^5$ cpm/µmol), 2 mM leucine and 7 nM recombinant Cdc60p. Experiments were also performed in the presence or absence of C10 (1 µM) and tRNA (16 µM). After a 20 minute incubation at 30° C., reactions were initiated by the addition of ATP. At various time intervals, 45 µL of reaction mixture was added to 100 µL of 2% perchloric acid and 0.1 M $Na_4P_2O_7$ to quench the reaction. Radioactive ATP was then absorbed to activated charcoal by the addition of 30 µL of a 5% suspension of acid-washed Norit A. This mixture was filtered though GF/C glass filters and washed 2× with 200 µL of distilled water then 1× with 200 µL of 95% ethanol. Filters were dried and scintillation counted using a Wallac MicroBeta Trilux model 1450 liquid scintillation counter.

Synthesis of Tritiated Mischarged $tRNA_{leu}$

The [³H]-isoleucine mischarged tRNAleu was synthesized by incubating 1 µM of Saccharomyces cerevisiae editing defective Cdc60p (C326F) in 500 µL of 50 mM Tris-HCl (pH 8.0), 60 mM $MgCl_2$, 4 mM ATP, 1 mM DTT, 0.02% (w/v) BSA, 1 µM brewer's yeast tRNA (Roche), 0.1 mM isoleucine and 5 mCi L-[4,5-3H]isoleucine (100 Ci/mmole, GE Healthcare) and 20% (v/v) DMSO for 1 hour at 30° C. The reaction was stopped by adding 10 µL of 10%

(v/v) acetic acid followed by two acidic phenol (Sigma) extractions. The mischarged tRNA in the top aqueous phase was removed and precipitated by adding two volumes of 96% (v/v) ethanol and incubating at −20° C. for 30 minutes. The precipitate was pelleted by centrifugation at 13,200×g for 30 minutes and the mischarged tRNA pellet was washed twice with 70% (v/v) ethanol and then resuspended in 50 mM potassium phosphate buffer pH 5.2.

Post-Transfer Editing Assay

The [$^3$H]-isoleucine mischarged tRNAleu substrate, 40 nM, was added to 50 mM Hepes-KOH pH 8.0, 30 mM KCl, 30 mM $MgCl_2$, 0.02% (w/v) BSA, 1 mM DTT, 2.4 nM S. cerevisiae Cdc60p at 30° C. to start the reaction and 20 µL aliquots, taken at set time points, were added to ice cold 200 µL 10% (w/v) trichloroacetic acid (TCA). The TCA precipitates were washed twice with 200 µl ice cold 5% (w/v) TCA and filtered through a Multiscreen HTS HA filter (Millipore). Optiphase (Perkin Elmer) scintillation cocktail was added to the filters and the TCA precipitate was counted in a Wallac MicroBeta Trilux model 1450 liquid scintillation counter.

Example 45

Assay for Determining that Compounds Inhibit ARS Synthesis Activity

Aminoacylation assays were performed to determine the rate of net leucine/tRNA$^{Leu}$ synthesis by leucyl tRNA synthetase. Experiments were performed in 500 ul reaction mixtures containing 1×AARS buffer (50 mM Hepes-KOH (pH 8.0), 30 mM $MgCl_2$ and 30 mM KCl) supplemented with 20 uM [14C]-leucine (PerkinElmer, 11.32 GBq/mmol.), 16 uM crude yeast tRNA, 0.02% BSA, 1 mM dithiothreitol, 2 nM recombinant yeast LeuRS (CDC60) and 2 mM ATP. Reactions were performed at 30 deg Celsius. At time zero reactions were started by the addition of ATP. At various time intervals, 20 ul aliquots were added to 150 ul of 10% trichloroacetic acid (TCA) within a single well of a 96-well nitrocellulose membrane filterplate (Millipore Multiscreen HTS, MSHAN4B50). Each well was then washed 3× with 100 ul of 5% TCA. Filterplates were then dried under a heat lamp and the precipitated [14C]-leucine/tRNA$^{Leu}$ complexes were quantified by liquid scintillation counting using a Wallac MicroBeta Trilux model 1450 liquid scintillation counter. The inhibitory effects of boron-containing compounds, was determined by addition of up to a 100 uM of the compound in the reaction mixture for 20 minutes prior to the addition of ATP.

Example 46

Test Article and Dosage Formulation

C10 (5-fluoro-1,3-dihydro-1-hydroxy-2,1-benzoxaborole), 5-fluoro-1,3-dihydro-1-phenyl-2,1-benzoxaborole, C1 (5-chloro-1,3-dihydro-1-hydroxy-2,1-benzoxaborole), and 5-fluoro-1,3-dihydro-1-(3-hydroxymethylphenyl)-2,1-benzoxaborole were obtained from Anacor Pharmaceuticals, Inc. (Palo Alto, Calif.). [$^{14}$C]-C10 was synthesized by Amersham Biosciences UK Limited (Buckinghamshire HP& 9NA, UK) radiochemical purity and specific activity of >99.3% and 55 mCi/mmol, respectively.

Penlac™ nail lacquer (ciclopirox 8% topical solution) was manufactured by Dermik (Berwyn, Pa.). [$^{14}$C]-Ciclopirox (pyridinone-6-($^{14}$C)-ciclopirox) was synthesized by PerkinElmer Life and Analytical Sciences (Boston, Mass.). The radiochemical purity and specific activity of the chemical was >95% and 12.5 mCi/mmol, respectively.

Experiment 1: Screening Four Oxaborole Compounds

C10, 5-fluoro-1,3-dihydro-1-phenyl-2,1-benzoxaborole, C1, and 5-fluoro-1,3-dihydro-1-(3-hydroxymethylphenyl)-2,1-benzoxaborole, formulated at 10% w/v in ethanol, were tested. A single aliquot (10 µl) of each formulation was dosed to the top of human nail plates using the nail penetration procedure described below, and allowed to stand for 3-days. The dosed area was washed, and then the cotton ball bed supporting the nail and the nail samples were collected at the end of the incubation period, stored at 4° C. and analyzed for drug using LC/MS/MS.

Experiment 2: Effect of Vehicle on C10 Nail Penetration

The following formulations, all containing 10% C10 were tested. Formulation A: 70% ethanol, 20% poly (vinyl methyl ether alt maleic acid monobutyl ester (v/v); Formulation B: 6% ethanol, 14% water, 15% poly (2-hydroxyethyl methacrylate), 5% dibutyl sebacate (v/v); Formulation C: 55% ethanol, 15% ethyl acetate, 15% poly (vinyl acetate), 5% dibutyl sebacate (v/v); Formulation D: 20% propylene glycol, 70% ethanol (v/v). Using the nail penetration procedure described below, aliquots (10 µL) of the dose formulations were applied to human nail plates once per day for 14 days with a daily wash before dosing. The cotton ball bed supporting the nail was collected from each cell chamber and replaced with a new one at day 5, 10, and 15 after the first dose. The nail samples were collected at the end of the 14-day dose period, stored at 4° C. and analyzed for drug by LC/MS/MS.

Experiment 3: Penetration of C10 Following a 14-Day Multiple Dose Treatment

Two test articles, C10, 10% in propylene glycol and ethanol (1:4, v/v) and ciclopirox, 8% in Penlac™ nail lacquer were compared for their penetration rate into and through the human nail plate. Trace amounts of carbon-14 radiolabelled C10 and ciclopirox were added to their respective formulations the day before the first dose. Using the nail penetration procedure described below, aliquots (10 µl) of the dose formulations were applied to human nail plates once per day for 14 days with a washing before each dose. The cotton ball bed supporting the nail was collected from each cell chamber and replaced with a new one every 72 hours after the first dose (days 3, 6, 9, 12, and 15). The nail samples were collected at the 14-day dose period. The radioactivity of all samples was analyzed and compared.

Nail Penetration Procedure

Details of the nail incubation have been previously described[9, 10]. Briefly, a healthy finger nail plate was mounted in a one-chamber diffusion cell (FIG. 1, Permegear, Inc., Hellertown, Pa.) with the nail surface (top center) open to the air and the inner surface in contact with a small cotton ball acting as a supporting nail bed. The supporting cotton ball under the nail was wetted by normal saline providing moisture for the nail plate, and the degree of hydration was monitored and controlled during the experiment. The incubation period started 24 hours prior to the first dose, and ended 24 hours after the final dose. Aliquots (10 µL) were applied to the surface of the nail plate once daily.

Dosed surface area washing was conducted at the end of incubation period (for single dose study), or each morning before dosing starting on the second day (multiple dose study). The dosed surface area of the nail was washed with cotton tips in a cycle, as follows: two times with ethanol, then with 50% Ivory® liquid soap (Procter & Gamble, Cincinnati, Ohio), then two times with distilled water. The washing samples from each cycle were pooled and the radioactivity was measured. After completion of the dosing and the incubation phase, the nail plate was transferred to a cutting holder for sampling. Under the controlled humidity and temperature, we did not observe any abnormal situations such as the nail plate color change, hydration changes, or fungal growth during the 14-day dosing period. The nail plate was secured in position so that the outer dorsal-dosed surface faced the holder. The cutting holder was moved to bring the plate surface just barely in contact with the cutter tip. The drill was then started and a fine adjustment moved the stage toward the cutter tip, removing a powder sample from the nail. In this way, a hole approximately 0.3-0.4 mm in depth and 7.9 mm in diameter was drilled in each nail, enabling the harvest of powder sample from the center of each nail's ventral surface. These samples are referred to as samples taken from the "ventral/intermediate nail plate center". Then the nail outside the dosing area (and also the sampling area) was cut away and saved as the "remainder nail plate". The layer above the powder sampling area was also saved as "the dorsal/intermediate center". All the nail plate samples were individually collected into a glass scintillation vial and weighed.

Quantitative Analysis of Oxaboroles

LC/MS/MS (API3000, Applied Biosystems, Foster City, Calif.) was used to quantitate the amounts of non-radiolabeled oxaboroles, C10, 5-fluoro-1,3-dihydro-1-phenyl-2,1-benzoxaborole, C1, and 5-fluoro-1,3-dihydro-1-(3-hydroxymethylphenyl)-2,1-benzoxaborole in samples from the nail penetration studies. For the cotton ball analysis eleven calibration standards were prepared fresh in normal saline. A volume of 100 µL of each standard was spiked onto a fresh cotton ball with final calibration standard concentrations of 0, 2.5, 5, 10, 20, 40, 80, 160, 320, 640, 1280, and 2560 µg/mL. Acetonitrile (Burdick & Jackson, Muskegon, Mich.) containing the internal standard p-nitrophenol (PNP) was added to all cotton balls. The cotton ball samples and any residual solvent were transferred to centrifuge filter tubes. After centrifugation, the filtrate from the cotton ball samples was transferred to autosampler vials and analyzed by LC/MS/MS. For the ciclopirox samples, the filtrate was first derivatized with dimethylsulfate according to a previously described method before analysis by LC/MS/MS (Myoung and Choi, 2003). Samples with calculated concentrations above the highest calibration standard were diluted 10- or 20-fold with acetonitrile containing internal standard p-Nitrophenol (TCI America, Portland, Oreg.). For the nail analysis, two separate calibration curves were prepared, one for nail powder analysis and one for top of the nail analysis. Each curve contained eleven calibration standards. Standards were first prepared in dimethylsulfoxide. A volume of 10 µL of each standard was spiked onto keratin powder (6.5 mg for nail powder curve and 17 mg for top of the nail curve). Nail samples were digested with 1N NaOH overnight at 45° C. The next morning, before extraction with methylenechloride, the pH of the samples was adjusted to pH 3. After extraction, the organic layer was transferred and evaporated. Samples were reconstituted in acetonitrile and analyzed by LC/MS/MS using an Eclipse XDB-C18 5 µm, 2.1×50 mm column (Agilent, Wilmington, Del.) and a gradient mobile phase from 5 mM ammonium acetate and acetonitrile.

Radioactivity Measurement

All radioactivity measurements were conducted with a Model 1500 Liquid Scintillation Counter (Packard Instrument Company, Downer Grove, Ill.). The counter was audited for accuracy using sealed samples of quenched and unquenched standards as detailed by the instrument manual. The $^{14}C$ counting efficiency is equal to or greater than 95%. All nail samples pre-treated with Packard soluene-350 were incubated at 40° C. for 48 hours followed by the addition of 10 mL scintillation cocktail (HIONIC-FLUOR, Packard Instrument Company, Meriden, Conn.). Other samples (standard dose, surface washing, and bedding material) were mixed directly with Universal ES scintillation cocktail (ICN Biomedicals, Costa Mesa, Calif.). Background control and test samples were counted for radioactivity for 3 minutes each.

Calculations and Data Analysis

Quantitation of non-radioactive compounds was based on peak area ratios of compound to internal standard. The method of regression for the calibration curves was selected based on the best fit. Linear and quadratic regression was used with 1/x or 1/x squared weighting. All integrations were performed using Analyst version 1.3 (Applied Biosystems, Foster City, Calif.). The concentrations of compound in the cotton balls were converted to absolute amounts by taking the sample volume of 100 µl into account. The amount of compound in the nail powder and top of the nail were adjusted for their respective weights and reported in µg/mg.

The individual and mean (±S.E.) amount of test chemical equivalent in nail, bedding material, and wash samples are presented as dpm, µCi, percent administered dose, and mg equivalent at each time point. The concentration of $^{14}C$-labeled test chemicals were calculated from the value based on the specific activity of each [$^{14}C$]-labeled test chemical. The information of concentration of non-labeled test chemical in the topical formulation was obtained from the manufacturers. The total concentration of test chemical equivalent is the sum of the concentration of $^{14}C$-labeled test chemical and the concentration of non-labeled test chemical. The value of the total amount of test chemical equivalent in each nail sample was calculated from those values based on the radioactivity of the sample and the ratio of total mg test chemical equivalent and radioactivity of the test chemical. The data was further normalized by dividing by the weight of the sample. Statistical significant of nail samples from every two groups was analyzed by student t-test.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating a human having onychomycosis of a toenail caused by *Trichophyton rubrum* or *Trichophyton mentagrophytes*, the method comprising:
    topically administering to the toenail a pharmaceutical composition comprising an amount of 1,3-dihydro-5-fluoro-1-hydroxy-2,1-benzoxaborole or a pharmaceutically acceptable salt thereof, effective to inhibit an aminoacyl tRNA synthetase in the *Trichophyton rubrum* or *Trichophyton mentagrophytes*.

2. The method of claim 1, wherein the pharmaceutical composition is in the form of a solution comprising 5% w/w of 1,3-dihydro-5-fluoro-1-hydroxy-2,1-benzoxaborole or a pharmaceutically acceptable salt thereof.

3. The method of claim 1, wherein the pharmaceutical composition further comprises ethanol and propylene glycol.

4. The method of claim 1, wherein the aminoacyl tRNA synthetase is leucyl tRNA synthetase.

5. The method of claim 4, wherein the pharmaceutical composition is in the form of a solution comprising 5% w/w of 1,3-dihydro-5-fluoro-1-hydroxy-2,1-benzoxaborole or a pharmaceutically acceptable salt thereof.

6. The method of claim 5, wherein the pharmaceutical composition further comprises ethanol and propylene glycol.

7. The method of claim 1, wherein the administering of the pharmaceutical composition occurs once a day.

8. The method of claim 6, wherein the administering of the pharmaceutical composition occurs once a day.

9. The method of claim 1, wherein the method inhibits an aminoacyl tRNA synthetase in *Trichophyton rubrum*.

10. The method of claim 1, wherein the method inhibits an aminoacyl tRNA synthetase in *Trichophyton mentagrophytes*.

11. The method of claim 6, wherein the method inhibits leucyl tRNA synthetase in *Trichophyton rubrum*.

12. The method of claim 6, wherein the method inhibits leucyl tRNA synthetase in *Trichophyton mentagrophytes*.

* * * * *

(12) INTER PARTES REVIEW CERTIFICATE (2012th)
United States Patent  (10) Number:  US 9,566,290 K1
Baker et al.  (45) Certificate Issued:  Apr. 8, 2021

(54) BORON-CONTAINING SMALL MOLECULES

(71) Applicants: Stephen J. Baker; Tsutomu Akama; Vincent S. Hernandez; Karin M. Hold; Kirk Maples; Jacob J. Plattner; Virginia Sanders; Yong-Kang Zhang; Gregory T. Fieldson; James J. Leyden

(72) Inventors: Stephen J. Baker; Tsutomu Akama; Vincent S. Hernandez; Karin M. Hold; Kirk Maples; Jacob J. Plattner; Virginia Sanders; Yong-Kang Zhang; Gregory T. Fieldson; James J. Leyden

(73) Assignee: ANACOR PHARMACEUTICALS, INC.

Trial Numbers:

IPR2018-00170 filed Nov. 21, 2017
IPR2018-01360 filed Jul. 10, 2018

Inter Partes Review Certificate for:

Patent No.: 9,566,290
Issued: Feb. 14, 2017
Appl. No.: 15/134,286
Filed: Apr. 20, 2016

The results of IPR2018-00170 joined with IPR2018-01360 are reflected in this inter partes review certificate under 35 U.S.C. 318(b).

INTER PARTES REVIEW CERTIFICATE
U.S. Patent 9,566,290 K1
Trial No. IPR2018-00170
Certificate Issued Apr. 8, 2021

AS A RESULT OF THE INTER PARTES REVIEW PROCEEDING, IT HAS BEEN DETERMINED THAT:

Claims 1-12 are cancelled.

\* \* \* \* \*

SEQUENCE LISTING

<160> NUMBER OF SEQ ID NOS: 68

<210> SEQ ID NO 1
<211> LENGTH: 258
<212> TYPE: PRT

<213> ORGANISM: Saccharomyces cerevisiae

<400> SEQUENCE: 1

Thr Pro Gln Glu Tyr Ile Gly Val Lys Ile Glu Ala Leu Glu Phe Ala
1               5                   10                  15

Asp Asp Ala Ala Lys Ile Ile Asp Ser Ser Ser Asp Leu Asp Lys Ser
            20                  25                  30

Lys Lys Phe Tyr Phe Val Ala Ala Thr Leu Arg Pro Glu Thr Met Tyr
        35                  40                  45

Gly Gln Thr Cys Cys Phe Val Ser Pro Thr Ile Glu Tyr Gly Ile Phe
    50                  55                  60

Asp Ala Gly Asp Ser Tyr Phe Ile Thr Thr Glu Arg Ala Phe Lys Asn
65                  70                  75                  80

Met Ser Tyr Gln Lys Leu Thr Pro Lys Arg Gly Phe Tyr Lys Pro Ile
                85                  90                  95

Val Thr Val Pro Gly Lys Ala Phe Ile Gly Thr Lys Ile His Ala Pro
            100                 105                 110

Gln Ser Val Tyr Pro Glu Leu Arg Ile Leu Pro Met Glu Thr Val Ile
        115                 120                 125

Ala Thr Lys Gly Thr Gly Val Val Thr Cys Val Pro Ser Asn Ser Pro
    130                 135                 140

Asp Asp Tyr Ile Thr Thr Lys Asp Leu Leu His Lys Pro Glu Tyr Tyr
145                 150                 155                 160

Gly Ile Lys Pro Glu Trp Ile Asp His Glu Ile Val Pro Ile Met His
                165                 170                 175

Thr Glu Lys Tyr Gly Asp Leu Thr Ala Lys Ala Ile Val Glu Glu Lys
            180                 185                 190

Lys Ile Gln Ser Pro Lys Asp Lys Asn Leu Leu Ala Glu Ala Lys Lys
        195                 200                 205

Ile Ala Tyr Lys Glu Asp Tyr Tyr Thr Gly Thr Met Ile Tyr Gly Pro
    210                 215                 220

Tyr Lys Gly Glu Lys Val Glu Gln Ala Lys Asn Lys Val Lys Ala Asp
225                 230                 235                 240

Met Ile Ala Ala Gly Glu Ala Phe Val Tyr Asn Glu Pro Glu Ser Gln
                245                 250                 255

Asp Pro

<210> SEQ ID NO 2
<211> LENGTH: 280
<212> TYPE: PRT
<213> ORGANISM: Saccharomyces cerevisiae

<400> SEQUENCE: 2

Met Thr Pro Gln Glu Tyr Ile Gly Val Lys Ile Glu Ala Leu Glu Phe
1               5                   10                  15

Ala Asp Asp Ala Ala Lys Ile Ile Asp Ser Ser Ser Asp Leu Asp Lys
            20                  25                  30

Ser Lys Lys Phe Tyr Phe Val Ala Ala Thr Leu Arg Pro Glu Thr Met
        35                  40                  45

Tyr Gly Gln Thr Cys Cys Phe Val Ser Pro Thr Ile Glu Tyr Gly Ile
    50                  55                  60

Phe Asp Ala Gly Asp Ser Tyr Phe Ile Thr Thr Glu Arg Ala Phe Lys
65                  70                  75                  80

Asn Met Ser Tyr Gln Lys Leu Thr Pro Lys Arg Gly Phe Tyr Lys Pro
                85                  90                  95

```
Ile Val Thr Val Pro Gly Lys Ala Phe Ile Gly Thr Lys Ile His Ala
            100                 105                 110

Pro Gln Ser Val Tyr Pro Glu Leu Arg Ile Leu Pro Met Glu Thr Val
            115                 120                 125

Ile Ala Thr Lys Gly Thr Gly Val Val Thr Cys Val Pro Ser Asn Ser
130                 135                 140

Pro Asp Asp Tyr Ile Thr Thr Lys Asp Leu Leu His Lys Pro Glu Tyr
145                 150                 155                 160

Tyr Gly Ile Lys Pro Glu Trp Ile Asp His Glu Ile Val Pro Ile Met
            165                 170                 175

His Thr Glu Lys Tyr Gly Asp Leu Thr Ala Lys Ala Ile Val Glu Glu
            180                 185                 190

Lys Lys Ile Gln Ser Pro Lys Asp Lys Asn Leu Leu Ala Glu Ala Lys
            195                 200                 205

Lys Ile Ala Tyr Lys Glu Asp Tyr Tyr Thr Gly Thr Met Ile Tyr Gly
            210                 215                 220

Pro Tyr Lys Gly Glu Lys Val Glu Gln Ala Lys Asn Lys Val Lys Ala
225                 230                 235                 240

Asp Met Ile Ala Ala Gly Glu Ala Phe Val Tyr Asn Glu Pro Glu Ser
            245                 250                 255

Gln Asp Pro Gln Asp Pro Asn Ser Ser Ser Val Asp Lys Leu Ala Ala
            260                 265                 270

Ala Leu Glu His His His His His
            275                 280

<210> SEQ ID NO 3
<211> LENGTH: 185
<212> TYPE: PRT
<213> ORGANISM: Escherichia coli

<400> SEQUENCE: 3

Glu Gly Val Glu Ile Thr Phe Asn Val Asn Asp Tyr Asp Asn Thr Leu
1               5                   10                  15

Thr Val Tyr Thr Thr Arg Pro Asp Thr Phe Met Gly Cys Thr Tyr Leu
            20                  25                  30

Ala Val Ala Ala Gly His Pro Leu Ala Gln Lys Ala Ala Glu Asn Asn
            35                  40                  45

Pro Glu Leu Ala Ala Phe Ile Asp Glu Cys Arg Asn Thr Lys Val Ala
            50                  55                  60

Glu Ala Glu Met Ala Thr Met Glu Lys Lys Gly Val Asp Thr Gly Phe
65                  70                  75                  80

Lys Ala Val His Pro Leu Thr Gly Glu Glu Ile Pro Val Trp Ala Ala
            85                  90                  95

Asn Phe Val Leu Met Glu Tyr Gly Thr Gly Ala Val Met Ala Val Pro
            100                 105                 110

Gly His Asp Gln Arg Asp Tyr Glu Phe Ala Ser Lys Tyr Gly Leu Asn
            115                 120                 125

Ile Lys Pro Val Ile Leu Ala Ala Asp Gly Ser Glu Pro Asp Leu Ser
            130                 135                 140

Gln Gln Ala Leu Thr Glu Lys Gly Val Leu Phe Asn Ser Gly Glu Phe
145                 150                 155                 160

Asn Gly Leu Asp His Glu Ala Ala Phe Asn Ala Ile Ala Asp Lys Leu
            165                 170                 175

Thr Ala Met Gly Val Gly Glu Arg Lys
```

```
              180             185

<210> SEQ ID NO 4
<211> LENGTH: 185
<212> TYPE: PRT
<213> ORGANISM: Propionibacterium acnes

<400> SEQUENCE: 4

Glu Gly Ala Tyr Val Asp Phe Thr Ile Asp Gly His Lys Glu Pro Val
1               5                   10                  15

Arg Val Phe Thr Thr Arg Pro Asp Thr Leu Tyr Gly Ala Thr Phe Met
            20                  25                  30

Val Val Ala Pro Asp Ser Ala Leu Ala Gln Glu Ile Val Ser Asp Glu
        35                  40                  45

Ala Arg Pro Ala Phe Glu Thr Tyr Leu Asp Glu Val Lys Lys Lys Ser
    50                  55                  60

Glu Ile Glu Arg Gln Ala Thr Asp His Glu Lys Thr Gly Val Pro Leu
65                  70                  75                  80

Gly Val Glu Ala Thr Asn Pro Val Asn Gly Ala Lys Val Pro Val Trp
                85                  90                  95

Ala Gly Asp Tyr Val Leu Ala Asp Tyr Gly Thr Gly Ala Val Met Ala
            100                 105                 110

Val Pro Ala His Asp Gln Arg Asp Leu Asp Phe Ala Arg Thr Tyr Gly
        115                 120                 125

Ile Asp Val Ile Pro Val Ile Asp Thr Gly Glu Ala Asp Pro Arg Glu
130                 135                 140

Ser Gly Val Ala Thr Thr Gly Asp Gly Val Tyr Gln Asn Ser Gly Phe
145                 150                 155                 160

Leu Asn Gly Ile Ala Thr Lys Ala Glu Ala Ile Ala Lys Met Cys Glu
                165                 170                 175

Phe Leu Asp Glu Lys Gly Ile Gly Glu
            180                 185

<210> SEQ ID NO 5
<211> LENGTH: 194
<212> TYPE: PRT
<213> ORGANISM: Pseudomonas aeruginosa

<400> SEQUENCE: 5

Gly Met Glu Ile Gly Phe Pro Tyr Asp Gln Ala Ser Ile Gly His Ala
1               5                   10                  15

Gly Gln Leu Lys Val Phe Thr Thr Arg Pro Asp Thr Leu Met Gly Ala
            20                  25                  30

Thr Tyr Val Ala Val Ala Ala Glu His Pro Leu Ala Thr Gln Ala Ala
        35                  40                  45

Gln Asn Asp Pro Gln Leu Gln Ala Phe Ile Asp Glu Cys Lys Arg Gly
    50                  55                  60

Gly Val Ala Glu Ala Asp Ile Ala Thr Gln Glu Lys Lys Gly Met Ala
65                  70                  75                  80

Thr Ser Leu Phe Val Glu His Pro Leu Thr Gly Asp Lys Leu Pro Val
                85                  90                  95

Trp Val Ala Asn Tyr Val Leu Met Asn Tyr Gly Glu Gly Ala Val Met
            100                 105                 110

Ala Val Pro Gly His Asp Glu Arg Asp Phe Glu Phe Ala Asn Lys Tyr
        115                 120                 125

Gly Leu Pro Ile Arg Gln Val Ile Ala Lys Val Glu Gly Asp Asp Asp
```

```
            130                 135                 140
Phe Glu Ser Ser Val Trp Lys Glu Trp Tyr Gly Ala Lys Asp Glu Ser
145                 150                 155                 160

Val Leu Thr Val Asn Ser Gly Lys Tyr Asp Asn Leu Gly Tyr Gln Ala
                165                 170                 175

Ala Phe Asp Ala Ile Gly Ala Asp Leu Glu Ala Lys Gly Leu Gly Gln
            180                 185                 190

Ala Arg

<210> SEQ ID NO 6
<211> LENGTH: 183
<212> TYPE: PRT
<213> ORGANISM: Bacillus anthracis

<400> SEQUENCE: 6

Glu Gly Ala Glu Val His Phe Asn Ile Asp Gly Thr Asp Glu Lys Phe
1               5                   10                  15

Thr Val Phe Thr Thr Arg Pro Asp Thr Leu Phe Gly Ala Ser Tyr Cys
                20                  25                  30

Val Leu Ala Pro Glu His Ala Leu Val Ala Asp Ile Thr Thr Ala Asp
            35                  40                  45

Gln Lys Glu Ala Val Glu Ala Tyr Ile Asn Ser Val Lys Met Lys Ser
    50                  55                  60

Asp Leu Glu Arg Thr Glu Leu Ala Lys Glu Lys Thr Gly Val Phe Thr
65                  70                  75                  80

Gly Ala Tyr Ala Val Asn Pro Val Asn Gly Glu Lys Leu Pro Ile Trp
                85                  90                  95

Ile Ala Asp Tyr Val Leu Ala Thr Tyr Gly Thr Gly Ala Val Met Ala
            100                 105                 110

Val Pro Ala His Asp Glu Arg Asp Tyr Glu Phe Ala Ser Thr Phe Asn
        115                 120                 125

Leu Pro Met Lys Glu Val Val Lys Gly Gly Asp Ile Thr Lys Glu Ala
    130                 135                 140

Tyr Thr Gly Asp Gly Ala His Val Asn Ser Ala Phe Leu Asp Gly Leu
145                 150                 155                 160

Asn Lys Glu Glu Ala Ile Ala Lys Met Ile Glu Trp Leu Glu Val Thr
                165                 170                 175

Ser Ala Gly Asn Gln Lys Val
            180

<210> SEQ ID NO 7
<211> LENGTH: 183
<212> TYPE: PRT
<213> ORGANISM: Staphylococcus aureus

<400> SEQUENCE: 7

Glu Gly Ala Lys Val Thr Phe Lys Ile Glu Gln Ser Asp Gln Asn Ile
1               5                   10                  15

Glu Val Phe Thr Thr Arg Pro Asp Thr Ile Tyr Gly Thr Ser Phe Leu
                20                  25                  30

Val Leu Ser Pro Glu His Pro Leu Val Asn Glu Ile Thr Thr Ser Asp
            35                  40                  45

Lys Glu Gln Glu Val Lys Leu Tyr Gln Asn Glu Ala Ser Lys Lys Ser
    50                  55                  60

Asp Leu Glu Arg Thr Asp Leu Ala Lys Glu Lys Thr Gly Val Phe Thr
65                  70                  75                  80
```

```
Gly Thr Phe Ala Ile Asn Pro Leu Ser Gly Asp Lys Leu Pro Ile Trp
                85                  90                  95

Ile Ala Asp Tyr Val Leu Ser Thr Tyr Gly Thr Gly Ala Val Met Ala
            100                 105                 110

Val Pro Gly His Asp Glu Arg Asp His Glu Phe Ala Thr Lys Phe Asn
        115                 120                 125

Leu Pro Ile Ile Glu Val Ile Glu Gly Gly Glu Val Gln Lys Tyr Ala
    130                 135                 140

Tyr Thr Gly Glu Gly Lys His Ile Asn Ser Gly Glu Leu Asp Gly Leu
145                 150                 155                 160

Glu Asn Glu Ala Ala Ile Ser Lys Ala Ile Glu Leu Leu Glu Ser Lys
                165                 170                 175

Gly Ala Gly Glu Lys Lys Val
            180

<210> SEQ ID NO 8
<211> LENGTH: 182
<212> TYPE: PRT
<213> ORGANISM: Streptococcus pyogens

<400> SEQUENCE: 8

Gly Ala Asn Val Thr Phe Lys Val Lys Asp Thr Asp Lys Asn Phe Thr
1               5                   10                  15

Val Phe Thr Thr Arg Pro Asp Thr Leu Phe Gly Ala Thr Tyr Ala Val
            20                  25                  30

Leu Ala Pro Glu His Ala Leu Val Asp Ala Ile Thr Thr Ala Asp Gln
        35                  40                  45

Ala Glu Ala Val Ala Asp Tyr Lys Arg Gln Ala Ser Leu Lys Ser Asp
    50                  55                  60

Leu Ala Arg Thr Asp Leu Ala Lys Glu Lys Thr Gly Val Trp Thr Gly
65                  70                  75                  80

Ser Tyr Ala Ile Asn Pro Val Asn Gly Lys Glu Ile Pro Val Trp Ile
                85                  90                  95

Ala Asp Tyr Val Leu Ala Ser Tyr Gly Thr Gly Ala Ile Met Ala Val
            100                 105                 110

Pro Ala His Asp Glu Arg Asp Trp Glu Phe Ala Lys Gln Phe Asn Leu
        115                 120                 125

Asp Ile Ile Pro Val Leu Glu Gly Gly Asn Val Glu Glu Ala Ala Phe
    130                 135                 140

Thr Glu Asp Gly Leu His Ile Asn Ser Gly Phe Leu Asp Gly Leu Asp
145                 150                 155                 160

Lys Ala Ser Ala Ile Ala Lys Met Val Glu Trp Leu Glu Ala Glu Gly
                165                 170                 175

Val Gly Asn Glu Lys Val
            180

<210> SEQ ID NO 9
<211> LENGTH: 187
<212> TYPE: PRT
<213> ORGANISM: Thermus thermophilus

<400> SEQUENCE: 9

Glu Gly Ala Glu Ile Leu Phe Pro Val Glu Gly Lys Glu Val Arg Ile
1               5                   10                  15

Pro Val Phe Thr Thr Arg Pro Asp Thr Leu Phe Gly Ala Thr Phe Leu
            20                  25                  30
```

```
Val Leu Ala Pro Glu His Pro Leu Thr Leu Glu Leu Ala Ala Pro Glu
            35                  40                  45

Lys Arg Glu Glu Val Leu Ala Tyr Val Glu Ala Ala Lys Arg Lys Thr
 50                  55                  60

Glu Ile Glu Arg Gln Ala Glu Gly Arg Glu Lys Thr Gly Val Phe Leu
 65                  70                  75                  80

Gly Ala Tyr Ala Leu Asn Pro Ala Thr Gly Glu Arg Ile Pro Ile Trp
                85                  90                  95

Thr Ala Asp Tyr Val Leu Phe Gly Tyr Gly Thr Gly Ala Ile Met Ala
            100                 105                 110

Val Pro Ala His Asp Gln Arg Asp Tyr Glu Phe Ala Arg Lys Phe Gly
            115                 120                 125

Leu Pro Ile Lys Lys Val Ile Glu Arg Pro Gly Glu Pro Leu Pro Glu
130                 135                 140

Pro Leu Glu Arg Ala Tyr Glu Glu Pro Gly Ile Met Val Asn Ser Gly
145                 150                 155                 160

Pro Phe Asp Gly Thr Glu Ser Glu Glu Gly Lys Arg Lys Val Ile Ala
                165                 170                 175

Trp Leu Glu Glu Lys Gly Leu Gly Lys Gly Arg
            180                 185

<210> SEQ ID NO 10
<211> LENGTH: 186
<212> TYPE: PRT
<213> ORGANISM: Mycobacterium tuberculosis

<400> SEQUENCE: 10

Phe Glu Val Asp Ile Glu Val Phe Thr Thr Arg Pro Asp Thr Leu Phe
1               5                   10                  15

Gly Ala Thr Tyr Leu Val Leu Ala Pro Glu His Asp Leu Val Asp Glu
                20                  25                  30

Leu Val Ala Ala Ser Trp Pro Ala Gly Val Asn Pro Leu Trp Thr Tyr
            35                  40                  45

Gly Gly Gly Thr Pro Gly Glu Ala Ile Ala Ala Tyr Arg Arg Ala Met
 50                  55                  60

Ala Ala Lys Ser Asp Leu Glu Arg Gln Glu Ser Arg Glu Lys Thr Gly
 65                  70                  75                  80

Val Phe Val Gly Ser Tyr Ala Ile Asn Pro Ala Asn Gly Glu Pro Val
                85                  90                  95

Pro Ile Phe Ile Ala Asp Tyr Val Leu Ala Gly Tyr Gly Thr Gly Ala
            100                 105                 110

Ile Met Ala Val Pro Gly His Asp Gln Arg Asp Trp Asp Phe Ala Arg
            115                 120                 125

Ala Phe Gly Leu Pro Ile Val Glu Val Ile Ala Gly Gly Asn Ile Ser
130                 135                 140

Glu Ser Ala Tyr Thr Gly Asp Gly Ile Leu Val Asn Ser Asp Tyr Leu
145                 150                 155                 160

Asn Gly Met Ser Val Pro Ala Ala Lys Arg Ala Ile Val Asp Arg Leu
                165                 170                 175

Glu Ser Ala Gly Arg Gly Arg Ala Arg Ile
            180                 185

<210> SEQ ID NO 11
<211> LENGTH: 251
<212> TYPE: PRT
```

<213> ORGANISM: Candida albicans

<400> SEQUENCE: 11

Tyr Val Gly Ile Lys Ile Arg Leu Thr Asp Val Ala Pro Gln Ala Gln
1               5                   10                  15

Glu Leu Phe Lys Lys Glu Ser Leu Asp Val Lys Glu Asn Lys Val Tyr
            20                  25                  30

Leu Val Ala Ala Thr Leu Arg Pro Glu Thr Met Tyr Gly Gln Thr Cys
        35                  40                  45

Cys Phe Val Ser Pro Lys Ile Asp Tyr Gly Val Phe Asp Ala Gly Asn
    50                  55                  60

Gly Asp Tyr Phe Ile Thr Thr Glu Arg Ala Phe Lys Asn Met Ser Phe
65                  70                  75                  80

Gln Asn Leu Thr Pro Lys Arg Gly Tyr Tyr Lys Pro Leu Phe Thr Ile
                85                  90                  95

Asn Gly Lys Thr Leu Ile Gly Ser Arg Ile Asp Ala Pro Tyr Ala Val
            100                 105                 110

Asn Lys Asn Leu Arg Val Leu Pro Met Glu Thr Val Leu Ala Thr Lys
        115                 120                 125

Gly Thr Gly Val Val Thr Cys Val Pro Ser Asp Ser Pro Asp Asp Phe
130                 135                 140

Val Thr Thr Arg Asp Leu Ala Asn Lys Pro Glu Tyr Tyr Gly Ile Glu
145                 150                 155                 160

Lys Asp Trp Val Gln Thr Asp Ile Val Pro Ile Val His Thr Glu Lys
                165                 170                 175

Tyr Gly Asp Lys Cys Ala Glu Phe Leu Val Asn Asp Leu Lys Ile Gln
            180                 185                 190

Ser Pro Lys Asp Ser Val Gln Leu Ala Asn Ala Lys Glu Leu Ala Tyr
        195                 200                 205

Lys Glu Gly Phe Tyr Asn Gly Thr Met Leu Ile Gly Lys Tyr Lys Gly
    210                 215                 220

Asp Lys Val Glu Asp Ala Lys Pro Lys Val Lys Gln Asp Leu Ile Asp
225                 230                 235                 240

Glu Gly Leu Ala Phe Val Tyr Asn Glu Pro Glu
                245                 250

<210> SEQ ID NO 12
<211> LENGTH: 256
<212> TYPE: PRT
<213> ORGANISM: Aspergillus fumigatus

<400> SEQUENCE: 12

Tyr Thr Ala Met Lys Leu Gln Val Lys Glu Trp Ala Pro Glu Ile Ala
1               5                   10                  15

Glu Leu Val Lys Gly Lys Ile Glu Asp Asp Ala Lys Val Tyr Phe Val
            20                  25                  30

Pro Ala Thr Leu Arg Pro Glu Thr Met Tyr Gly Gln Thr Cys Cys Phe
        35                  40                  45

Leu Gly Pro Lys Ile Lys Tyr Gly Ile Phe Arg Val Lys Glu Lys Glu
    50                  55                  60

Tyr Tyr Ile Val Thr Lys Arg Ala Ala Trp Asn Met Ala Phe Gln Gly
65                  70                  75                  80

Ile Phe Phe Asp Ser Glu His Phe Pro Lys Thr Gln Asp Glu Leu Pro
                85                  90                  95

Leu Val Leu Glu Ala Pro Gly Ser Ala Phe Val Gly Thr Leu Val Asn

```
            100                 105                 110
Ala Pro Leu Ser Phe His Thr Glu Gly Val Arg Ile Leu Pro Met Glu
            115                 120                 125

Gly Val Ser Ala Thr Lys Gly Thr Gly Val Val Thr Ser Val Pro Ser
130                 135                 140

Asp Ser Pro Asp Asp Tyr Ala Thr Leu Val Asp Leu Ala Lys Lys Pro
145                 150                 155                 160

Glu Tyr Tyr Gly Ile Lys Lys Glu Trp Ala Glu Leu Glu Ile Phe Pro
                    165                 170                 175

Leu Ile Glu Thr Pro Thr Tyr Gly Asn Leu Thr Ala Pro Thr Leu Val
                180                 185                 190

Lys Lys Leu Lys Ile Asn Ser Pro Lys Asp Val Asn Gln Leu Ala Gln
            195                 200                 205

Ala Lys Glu Leu Ala Tyr Gly Glu Ala Tyr Tyr Lys Gly Thr Met Leu
        210                 215                 220

Val Gly Glu Phe Lys Gly Glu Pro Val Ser Ala Ala Lys Glu Lys Ile
225                 230                 235                 240

Arg Lys Ser Leu Tyr Glu Ser Gly Asp Ala Phe Pro Phe Ala Asp Pro
                245                 250                 255

<210> SEQ ID NO 13
<211> LENGTH: 256
<212> TYPE: PRT
<213> ORGANISM: Trichophyton rubrum

<400> SEQUENCE: 13

Tyr Thr Ala Met Lys Leu Lys Val Lys Glu Trp Ser Pro Lys Ala Lys
1               5                   10                  15

Glu Ile Ile Gln Gly Lys Ile Glu Lys Asp Ala Asn Val Tyr Phe Val
                20                  25                  30

Pro Ala Thr Leu Arg Pro Glu Thr Met Tyr Gly Gln Thr Cys Cys Phe
            35                  40                  45

Val Gly Pro Ala Ile Ser Tyr Gly Ile Phe Lys Val Lys Glu Lys Glu
    50                  55                  60

Tyr Tyr Val Val Thr Lys Arg Ala Ala Trp Asn Met Ala Phe Gln Gly
65                  70                  75                  80

Ile Phe Phe Asp Val Asn Asn Leu Pro Lys Ser Gln Asp Glu Leu Pro
                85                  90                  95

Pro Val Val Glu Ala Pro Gly Ser Ala Leu Ile Gly Thr Leu Val Asn
            100                 105                 110

Ala Pro Leu Ser Phe His Lys Glu Gly Val Arg Ile Leu Pro Met Glu
            115                 120                 125

Thr Val Ser Ala Asn Lys Gly Thr Gly Val Val Ser Cys Val Pro Ser
        130                 135                 140

Asp Ser Pro Asp Asp Phe Ala Thr Ile Ser Asp Leu Ala Lys Lys Ala
145                 150                 155                 160

Asp Tyr Tyr Gly Ile Gln Lys Glu Trp Ala Glu Leu Glu Ile His Pro
                165                 170                 175

Leu Ile Glu Thr Pro Thr Tyr Gly Asn Leu Thr Ala Pro Ala Leu Val
                180                 185                 190

Lys Gln Leu Lys Ile Asn Ser Pro Lys Asp Thr Val Gln Leu Ala Gln
            195                 200                 205

Ala Lys Asp Leu Ala Tyr Thr Glu Gly Phe Tyr Lys Gly Lys Met Leu
        210                 215                 220
```

-continued

Val Gly Glu Phe Lys Gly Glu Pro Val Gln Thr Ala Lys Glu Lys Val
225                 230                 235                 240

Arg Asn Ser Leu Ile Lys Ser Gly Asp Ala Phe Pro Phe Ala Asp Pro
                245                 250                 255

<210> SEQ ID NO 14
<211> LENGTH: 253
<212> TYPE: PRT
<213> ORGANISM: Homo sapiens

<400> SEQUENCE: 14

Val Gly Pro Gln Glu Tyr Thr Leu Leu Lys Leu Lys Val Leu Glu Pro
1               5                   10                  15

Tyr Pro Ser Lys Leu Ser Gly Leu Lys Gly Lys Asn Ile Phe Leu Val
                20                  25                  30

Ala Ala Thr Leu Arg Pro Glu Thr Met Phe Gly Gln Thr Asn Cys Trp
            35                  40                  45

Val Arg Pro Asp Met Lys Tyr Ile Gly Phe Glu Thr Val Asn Gly Asp
50                  55                  60

Ile Phe Ile Cys Thr Gln Lys Ala Ala Arg Asn Met Ser Tyr Gln Gly
65                  70                  75                  80

Phe Thr Lys Asp Asn Gly Val Val Pro Val Val Lys Glu Leu Met Gly
                85                  90                  95

Glu Glu Ile Leu Gly Ala Ser Leu Ser Ala Pro Leu Thr Ser Tyr Lys
            100                 105                 110

Val Ile Tyr Val Leu Pro Met Leu Thr Ile Lys Glu Asp Lys Gly Thr
        115                 120                 125

Gly Val Val Thr Ser Val Pro Ser Asp Ser Pro Asp Asp Ile Ala Ala
130                 135                 140

Leu Arg Asp Leu Lys Lys Lys Gln Ala Leu Arg Ala Lys Tyr Gly Ile
145                 150                 155                 160

Arg Asp Asp Met Val Leu Pro Phe Glu Pro Val Pro Val Ile Glu Ile
                165                 170                 175

Pro Gly Phe Gly Asn Leu Ser Ala Val Thr Ile Cys Asp Glu Leu Lys
            180                 185                 190

Ile Gln Ser Gln Asn Asp Arg Glu Lys Leu Ala Glu Ala Lys Glu Lys
        195                 200                 205

Ile Tyr Leu Lys Gly Phe Tyr Glu Gly Ile Met Leu Val Asp Gly Phe
210                 215                 220

Lys Gly Gln Lys Val Gln Asp Val Lys Lys Thr Ile Gln Lys Lys Met
225                 230                 235                 240

Ile Asp Ala Gly Asp Ala Leu Ile Tyr Met Glu Pro Glu
                245                 250

<210> SEQ ID NO 15
<211> LENGTH: 259
<212> TYPE: PRT
<213> ORGANISM: Trypanosoma brucei

<400> SEQUENCE: 15

Tyr Thr Val Val Lys Leu Lys Val Lys Asn Pro Leu Glu Gln Pro Ala
1               5                   10                  15

Leu Ala Pro Phe Ser Glu Ile Ile Gly Asn Arg Ser Val Ile Leu Pro
                20                  25                  30

Gly Ala Thr Leu Arg Pro Glu Thr Val Ile Gly Gln Thr Asn Cys Trp
            35                  40                  45

Val Ser Pro Asn Phe Ser Tyr Met Ala Tyr Ser Ile Leu Asn Gly Thr
 50                  55                  60

Gly Glu Glu Glu Ile Tyr Ile Met Thr Ser Arg Ala Ala Arg Asn Leu
 65                  70                  75                  80

Ala Tyr Gln Asn Phe Thr Val Asn Gly Lys Thr Gly Val Asp Pro Ser
                 85                  90                  95

Pro Leu Phe Glu Val Asp Gly Ala Lys Leu Ile Gly Leu Pro Leu Ser
            100                 105                 110

Ala Pro Leu Cys Pro Tyr Asp Thr Ile Tyr Thr Leu Pro Met Gln Ser
            115                 120                 125

Ile Ile Glu Thr Lys Gly Thr Gly Val Val Met Ser Val Pro Ala Asp
130                 135                 140

Ser Pro Asp Asp Tyr Ile Asn Tyr Val Gln Leu Val Asn Lys Pro Asp
145                 150                 155                 160

Tyr Arg Ala Lys Leu Gly Leu Lys Asp Glu Trp Val Ala Asn Lys Ile
                165                 170                 175

Val Ser Leu Ile Glu Val Pro Gly Glu Met Gly Arg Glu Ser Ala Lys
            180                 185                 190

Tyr Met Cys Glu Lys Leu Lys Ile Asn Gly Pro Asn Ala Thr Asp Leu
            195                 200                 205

Leu Glu Glu Ala Lys Lys Val Ile Tyr Gln Ala Gly Phe Tyr Gln Gly
210                 215                 220

Val Met Ile Ala Gly Pro Phe Ala Gly Glu Lys Val Ser Ala Ala Lys
225                 230                 235                 240

Val Lys Thr Val Lys Leu Leu Glu Glu Gln Asn Ala Ala Ile Arg Tyr
                245                 250                 255

Tyr Glu Pro

<210> SEQ ID NO 16
<211> LENGTH: 85
<212> TYPE: DNA
<213> ORGANISM: Saccharomyces cerevisiae

<400> SEQUENCE: 16
gggagtttgg ccgagtggtt taaggcgtca gatttaggct ctgatatctt cggatgcaag    60
ggttcgaatc ccttagctct cacca                                         85

<210> SEQ ID NO 17
<211> LENGTH: 74
<212> TYPE: DNA
<213> ORGANISM: Saccharomyces cerevisiae

<400> SEQUENCE: 17
gaaactataa ttcaattggt tagaatagta ttttgataag gtacaaatat aggttcaatc    60
cctgttagtt tcat                                                     74

<210> SEQ ID NO 18
<211> LENGTH: 85
<212> TYPE: DNA
<213> ORGANISM: Saccharomyces cerevisiae
<220> FEATURE:
<221> NAME/KEY: modified_base
<222> LOCATION: (10)..(10)
<223> OTHER INFORMATION: m2g
<220> FEATURE:
<221> NAME/KEY: modified_base
<222> LOCATION: (12)..(12)
<223> OTHER INFORMATION: ac4c
<220> FEATURE:

```
<221> NAME/KEY: modified_base
<222> LOCATION: (17)..(17)
<223> OTHER INFORMATION: gm
<220> FEATURE:
<221> NAME/KEY: modified_base
<222> LOCATION: (27)..(27)
<223> OTHER INFORMATION: m22g
<220> FEATURE:
<221> NAME/KEY: modified_base
<222> LOCATION: (33)..(33)
<223> OTHER INFORMATION: p
<220> FEATURE:
<221> NAME/KEY: modified_base
<222> LOCATION: (35)..(35)
<223> OTHER INFORMATION: m5c
<220> FEATURE:
<221> NAME/KEY: modified_base
<222> LOCATION: (38)..(38)
<223> OTHER INFORMATION: m1g
<220> FEATURE:
<221> NAME/KEY: modified_base
<222> LOCATION: (40)..(40)
<223> OTHER INFORMATION: p
<220> FEATURE:
<221> NAME/KEY: modified_base
<222> LOCATION: (57)..(57)
<223> OTHER INFORMATION: m5c
<220> FEATURE:
<221> NAME/KEY: modified_base
<222> LOCATION: (64)..(64)
<223> OTHER INFORMATION: p

<400> SEQUENCE: 18
gguuguuugg ccgagcggdc daaggcgccu gauucaagcu cagguaucgu aagaugcaag    60
agtucgaauc ucuuagcaac cacca                                          85

<210> SEQ ID NO 19
<211> LENGTH: 87
<212> TYPE: DNA
<213> ORGANISM: Haloferax volcanii
<220> FEATURE:
<221> NAME/KEY: modified_base
<222> LOCATION: (15)..(15)
<223> OTHER INFORMATION: fa7d7G
<220> FEATURE:
<221> NAME/KEY: modified_base
<222> LOCATION: (28)..(28)
<223> OTHER INFORMATION: m22G
<220> FEATURE:
<221> NAME/KEY: modified_base
<222> LOCATION: (39)..(39)
<223> OTHER INFORMATION: m1G
<220> FEATURE:
<221> NAME/KEY: modified_base
<222> LOCATION: (41)..(41)
<223> OTHER INFORMATION: p
<220> FEATURE:
<221> NAME/KEY: modified_base
<222> LOCATION: (59)..(59)
<223> OTHER INFORMATION: m5C
<220> FEATURE:
<221> NAME/KEY: modified_base
<222> LOCATION: (65)..(65)
<223> OTHER INFORMATION: m1p
<220> FEATURE:
<221> NAME/KEY: modified_base
<222> LOCATION: (66)..(66)
<223> OTHER INFORMATION: p
<220> FEATURE:
<221> NAME/KEY: modified_base
<222> LOCATION: (67)..(67)
<223> OTHER INFORMATION: Cm
<220> FEATURE:
<221> NAME/KEY: modified_base
<222> LOCATION: (68)..(68)
<223> OTHER INFORMATION: m1i
```

<400> SEQUENCE: 19

```
gcgaggguag cuaagucagg aaaaagcggc ggacucaaga uccgcucccg uagggguccg    60
uggguucaaa ucccucccu cgcacca                                         87
```

<210> SEQ ID NO 20
<211> LENGTH: 87
<212> TYPE: DNA
<213> ORGANISM: Phage T4
<220> FEATURE:
<221> NAME/KEY: modified_base
<222> LOCATION: (8)..(8)
<223> OTHER INFORMATION: s4U
<220> FEATURE:
<221> NAME/KEY: modified_base
<222> LOCATION: (16)..(16)
<223> OTHER INFORMATION: d
<220> FEATURE:
<221> NAME/KEY: modified_base
<222> LOCATION: (18)..(18)
<223> OTHER INFORMATION: m2g
<220> FEATURE:
<221> NAME/KEY: modified_base
<222> LOCATION: (20)..(20)
<223> OTHER INFORMATION: d
<220> FEATURE:
<221> NAME/KEY: modified_base
<222> LOCATION: (35)..(35)
<223> OTHER INFORMATION: unidentified methylated uridine
<220> FEATURE:
<221> NAME/KEY: modified_base
<222> LOCATION: (38)..(38)
<223> OTHER INFORMATION: ms2i6A
<220> FEATURE:
<221> NAME/KEY: modified_base
<222> LOCATION: (40)..(40)
<223> OTHER INFORMATION: p
<220> FEATURE:
<221> NAME/KEY: modified_base
<222> LOCATION: (66)..(66)
<223> OTHER INFORMATION: p

<400> SEQUENCE: 20

```
gcgagaaugg ucaaauuggu aaaggcacag cacuuaaaau gcugcggaau gauuuccuug    60
ugggtucgag ucccacuucu cgcacca                                        87
```

<210> SEQ ID NO 21
<211> LENGTH: 85
<212> TYPE: DNA
<213> ORGANISM: Phage T5
<220> FEATURE:
<221> NAME/KEY: modified_base
<222> LOCATION: (17)..(17)
<223> OTHER INFORMATION: d
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (20)..(20)
<223> OTHER INFORMATION: d
<220> FEATURE:
<221> NAME/KEY: modified_base
<222> LOCATION: (38)..(38)
<223> OTHER INFORMATION: m6a
<220> FEATURE:
<221> NAME/KEY: modified_base
<222> LOCATION: (40)..(40)
<223> OTHER INFORMATION: p
<220> FEATURE:
<221> NAME/KEY: modified_base
<222> LOCATION: (64)..(64)

<223> OTHER INFORMATION: p

<400> SEQUENCE: 21
ggggcuaugc uggaacuggu agacaauacg gccuuagauu ccguagcuua aaugcguggg    60
agtucgaguc ucccuagccc cacca                                         85

<210> SEQ ID NO 22
<211> LENGTH: 87
<212> TYPE: DNA
<213> ORGANISM: Bacillus subtilis
<220> FEATURE:
<221> NAME/KEY: modified_base
<222> LOCATION: (17)..(17)
<223> OTHER INFORMATION: d
<220> FEATURE:
<221> NAME/KEY: modified_base
<222> LOCATION: (20)..(20)
<223> OTHER INFORMATION: d
<220> FEATURE:
<221> NAME/KEY: modified_base
<222> LOCATION: (38)..(38)
<223> OTHER INFORMATION: m1g
<220> FEATURE:
<221> NAME/KEY: modified_base
<222> LOCATION: (40)..(40)
<223> OTHER INFORMATION: p
<220> FEATURE:
<221> NAME/KEY: modified_base
<222> LOCATION: (66)..(66)
<223> OTHER INFORMATION: p
<220> FEATURE:
<221> NAME/KEY: modified_base
<222> LOCATION: (69)..(69)
<223> OTHER INFORMATION: m1a

<400> SEQUENCE: 22
gcgggugugc gggaauuggu agaccggcua gauucaggau cuagggucuu uauggaccug    60
agggtucaag ucccuucacc cgcacca                                       87

<210> SEQ ID NO 23
<211> LENGTH: 87
<212> TYPE: DNA
<213> ORGANISM: Escherichia coli
<220> FEATURE:
<221> NAME/KEY: modified_base
<222> LOCATION: (8)..(8)
<223> OTHER INFORMATION: s4U
<220> FEATURE:
<221> NAME/KEY: modified_base
<222> LOCATION: (16)..(16)
<223> OTHER INFORMATION: d
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (20)..(20)
<223> OTHER INFORMATION: d
<220> FEATURE:
<221> NAME/KEY: modified_base
<222> LOCATION: (33)..(33)
<223> OTHER INFORMATION: p
<220> FEATURE:
<221> NAME/KEY: modified_base
<222> LOCATION: (35)..(35)
<223> OTHER INFORMATION: unidentified methylated adenosine
<220> FEATURE:
<221> NAME/KEY: modified_base
<222> LOCATION: (38)..(38)
<223> OTHER INFORMATION: ms2i6a
<220> FEATURE:
<221> NAME/KEY: modified_base -continued

```
<222> LOCATION: (40)..(40)
<223> OTHER INFORMATION: p
<220> FEATURE:
<221> NAME/KEY: modified_base
<222> LOCATION: (66)..(66)
<223> OTHER INFORMATION: p

<400> SEQUENCE: 23
gcccggaugg uggaaucggu agacacaagg gauuaaaaau cccucggcgu ucgcgcugug    60 cgggucaag ucccgcuccg gguacca                                         87

<210> SEQ ID NO 24
<211> LENGTH: 87
<212> TYPE: DNA
<213> ORGANISM: Salmonella typhi
<220> FEATURE:
<221> NAME/KEY: modified_base
<222> LOCATION: (16)..(16)
<223> OTHER INFORMATION: d
<220> FEATURE:
<221> NAME/KEY: modified_base
<222> LOCATION: (17)..(17)
<223> OTHER INFORMATION: d
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (20)..(20)
<223> OTHER INFORMATION: d
<220> FEATURE:
<221> NAME/KEY: modified_base
<222> LOCATION: (38)..(38)
<223> OTHER INFORMATION: unidentified methylated guanosine
<220> FEATURE:
<221> NAME/KEY: modified_base
<222> LOCATION: (39)..(39)
<223> OTHER INFORMATION: p
<220> FEATURE:
<221> NAME/KEY: modified_base
<222> LOCATION: (41)..(41)
<223> OTHER INFORMATION: p
<220> FEATURE:
<221> NAME/KEY: modified_base
<222> LOCATION: (66)..(66)
<223> OTHER INFORMATION: p

<400> SEQUENCE: 24
gcgaaggugg cggaauuggu agacgcgcua gcuucaggug uuaguguccu uacggacgug    60 ggggucaag uccccccccu cgcacca                                         87

<210> SEQ ID NO 25
<211> LENGTH: 85
<212> TYPE: DNA
<213> ORGANISM: Rhodospirillum rubrum
<220> FEATURE:
<221> NAME/KEY: modified_base
<222> LOCATION: (16)..(16)
<223> OTHER INFORMATION: d
<220> FEATURE:
<221> NAME/KEY: modified_base
<222> LOCATION: (19)..(19)
<223> OTHER INFORMATION: d
<220> FEATURE:
<221> NAME/KEY: modified_base
<222> LOCATION: (36)..(36)
<223> OTHER INFORMATION: unidentified methylated adenosine
<220> FEATURE:
<221> NAME/KEY: modified_base
<222> LOCATION: (38)..(38)
<223> OTHER INFORMATION: p
<220> FEATURE:
```

```
<221> NAME/KEY: modified_base
<222> LOCATION: (64)..(64)
<223> OTHER INFORMATION: p

<400> SEQUENCE: 25
gccuuuguag cggaauggua acgcggcaga cucaaaaucu gcuuugguaa cccagguggu    60
agtucgacuc uccccaaagg cacca                                         85

<210> SEQ ID NO 26
<211> LENGTH: 87
<212> TYPE: DNA
<213> ORGANISM: Anacystis nidulans
<220> FEATURE:
<221> NAME/KEY: modified_base
<222> LOCATION: (17)..(17)
<223> OTHER INFORMATION: d
<220> FEATURE:
<221> NAME/KEY: modified_base
<222> LOCATION: (20)..(20)
<223> OTHER INFORMATION: d
<220> FEATURE:
<221> NAME/KEY: modified_base
<222> LOCATION: (38)..(38)
<223> OTHER INFORMATION: unidentified methylated adenosine
<220> FEATURE:
<221> NAME/KEY: modified_base
<222> LOCATION: (40)..(40)
<223> OTHER INFORMATION: p
<220> FEATURE:
<221> NAME/KEY: modified_base
<222> LOCATION: (66)..(66)
<223> OTHER INFORMATION: p

<400> SEQUENCE: 26
gggcaagugg cggaauuggu agacgcagca gacucaaaau cugccgcuag cgauagugug    60
ugggtucgag ucccaccuug cccacca                                       87

<210> SEQ ID NO 27
<211> LENGTH: 87
<212> TYPE: DNA
<213> ORGANISM: Anacystis nidulans
<220> FEATURE:
<221> NAME/KEY: modified_base
<222> LOCATION: (17)..(17)
<223> OTHER INFORMATION: d
<220> FEATURE:
<221> NAME/KEY: modified_base
<222> LOCATION: (20)..(20)
<223> OTHER INFORMATION: d
<220> FEATURE:
<221> NAME/KEY: modified_base
<222> LOCATION: (38)..(38)
<223> OTHER INFORMATION: m1g
<220> FEATURE:
<221> NAME/KEY: modified_base
<222> LOCATION: (39)..(39)
<223> OTHER INFORMATION: p
<220> FEATURE:
<221> NAME/KEY: modified_base
<222> LOCATION: (40)..(40)
<223> OTHER INFORMATION: p
<220> FEATURE:
<221> NAME/KEY: modified_base
<222> LOCATION: (66)..(66)
<223> OTHER INFORMATION: p

<400> SEQUENCE: 27
gcggaacugg cggaauuggu agacgcgcua gauucagguu cuaguggutu cacgacuguc    60
cgggtucaag ucccggguuc cgcacca                                       87
```

```
<210> SEQ ID NO 28
<211> LENGTH: 86
<212> TYPE: DNA
<213> ORGANISM: Bacillus stearothermophilus
<220> FEATURE:
<221> NAME/KEY: modified_base
<222> LOCATION: (8)..(8)
<223> OTHER INFORMATION: s4u
<220> FEATURE:
<221> NAME/KEY: modified_base
<222> LOCATION: (17)..(17)
<223> OTHER INFORMATION: d
<220> FEATURE:
<221> NAME/KEY: modified_base
<222> LOCATION: (23)..(23)
<223> OTHER INFORMATION: m1a
<220> FEATURE:
<221> NAME/KEY: modified_base
<222> LOCATION: (35)..(35)
<223> OTHER INFORMATION: cm
<220> FEATURE:
<221> NAME/KEY: modified_base
<222> LOCATION: (38)..(38)
<223> OTHER INFORMATION: ms2i6a
<220> FEATURE:
<221> NAME/KEY: modified_base
<222> LOCATION: (40)..(40)
<223> OTHER INFORMATION: p
<220> FEATURE:
<221> NAME/KEY: modified_base
<222> LOCATION: (65)..(65)
<223> OTHER INFORMATION: p

<400> SEQUENCE: 28
gccgaugugg cggaauuggc agacgcgcac gacucaaaau cgugugggcu uugcccgugu      60
gggtucgacu cccaccaucg gcacca                                          86

<210> SEQ ID NO 29
<211> LENGTH: 84
<212> TYPE: DNA
<213> ORGANISM: Glycine max
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (19)..(19)
<223> OTHER INFORMATION: d
<220> FEATURE:
<221> NAME/KEY: modified_base
<222> LOCATION: (34)..(34)
<223> OTHER INFORMATION: cm
<220> FEATURE:
<221> NAME/KEY: modified_base
<222> LOCATION: (37)..(37)
<223> OTHER INFORMATION: unidentified methylated adenosine
<220> FEATURE:
<221> NAME/KEY: modified_base
<222> LOCATION: (39)..(39)
<223> OTHER INFORMATION: p
<220> FEATURE:
<221> NAME/KEY: modified_base
<222> LOCATION: (63)..(63)
<223> OTHER INFORMATION: p

<400> SEQUENCE: 29
gccuuggugg ugaaauggua gccacgcgag acucaaaauc ucgugcuaca gagcguggag      60
gtucgagucc ucuucaaggc acca                                            84

<210> SEQ ID NO 30
<211> LENGTH: 88
<212> TYPE: DNA
```

```
<213> ORGANISM: Glycine max
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (20)..(20)
<223> OTHER INFORMATION: d
<220> FEATURE:
<221> NAME/KEY: modified_base
<222> LOCATION: (27)..(27)
<223> OTHER INFORMATION: p
<220> FEATURE:
<221> NAME/KEY: modified_base
<222> LOCATION: (35)..(35)
<223> OTHER INFORMATION: um
<220> FEATURE:
<221> NAME/KEY: modified_base
<222> LOCATION: (38)..(38)
<223> OTHER INFORMATION: unidentified methylated adenosine
<220> FEATURE:
<221> NAME/KEY: modified_base
<222> LOCATION: (40)..(40)
<223> OTHER INFORMATION: p
<220> FEATURE:
<221> NAME/KEY: modified_base
<222> LOCATION: (67)..(67)
<223> OTHER INFORMATION: p

<400> SEQUENCE: 30
ggggauaugg cgaaauuggu agacgcuacg gacuuaaaau ccgucgacuu aagaaaucau    60 gagggucaa gucccucuau ccccacca                                         88

<210> SEQ ID NO 31
<211> LENGTH: 83
<212> TYPE: DNA
<213> ORGANISM: Glycine max
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (20)..(20)
<223> OTHER INFORMATION: d
<220> FEATURE:
<221> NAME/KEY: modified_base
<222> LOCATION: (37)..(37)
<223> OTHER INFORMATION: m7g
<220> FEATURE:
<221> NAME/KEY: modified_base
<222> LOCATION: (38)..(38)
<223> OTHER INFORMATION: m1g
<220> FEATURE:
<221> NAME/KEY: modified_base
<222> LOCATION: (62)..(62)
<223> OTHER INFORMATION: p

<400> SEQUENCE: 31
gccgcuaugg ugaaauuggu agacacgcug cucuuaggaa gcagugcuag agcaucucgg    60
tucgaguccg aguagcggca cca                                             83

<210> SEQ ID NO 32
<211> LENGTH: 85
<212> TYPE: DNA
<213> ORGANISM: Phaseolus vulgaris
<220> FEATURE:
<221> NAME/KEY: modified_base
<222> LOCATION: (18)..(18)
<223> OTHER INFORMATION: gm
<220> FEATURE:
<221> NAME/KEY: modified_base
```

```
<222> LOCATION: (20)..(20)
<223> OTHER INFORMATION: d
<220> FEATURE:
<221> NAME/KEY: modified_base
<222> LOCATION: (35)..(35)
<223> OTHER INFORMATION: cm
<220> FEATURE:
<221> NAME/KEY: modified_base
<222> LOCATION: (38)..(38)
<223> OTHER INFORMATION: unidentified methylated adenosine
<220> FEATURE:
<221> NAME/KEY: modified_base
<222> LOCATION: (64)..(64)
<223> OTHER INFORMATION: p

<400> SEQUENCE: 32
ggcuugaugg ugaaauuggu agacacgcga gacucaaaau cucgugcuaa agagcgugga      60 ggucgaguc cucuucaagu cacca                                            85

<210> SEQ ID NO 33
<211> LENGTH: 88
<212> TYPE: DNA
<213> ORGANISM: Phaseolus vulgaris
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (20)..(20)
<223> OTHER INFORMATION: d
<220> FEATURE:
<221> NAME/KEY: modified_base
<222> LOCATION: (27)..(27)
<223> OTHER INFORMATION: p
<220> FEATURE:
<221> NAME/KEY: modified_base
<222> LOCATION: (35)..(35)
<223> OTHER INFORMATION: unidentified methylated uridine
<220> FEATURE:
<221> NAME/KEY: modified_base
<222> LOCATION: (38)..(38)
<223> OTHER INFORMATION: unidentified methylated adenosine
<220> FEATURE:
<221> NAME/KEY: modified_base
<222> LOCATION: (40)..(40)
<223> OTHER INFORMATION: p
<220> FEATURE:
<221> NAME/KEY: modified_base
<222> LOCATION: (67)..(67)
<223> OTHER INFORMATION: p

<400> SEQUENCE: 33
ggggauaugg cgaaauuggu agacgcuacg gacuuaaaau ccgucgacuu aauaaaucau      60 gagggucaa gucccucuau ccccacca                                         88

<210> SEQ ID NO 34
<211> LENGTH: 83
<212> TYPE: DNA
<213> ORGANISM: Phaseolus vulgaris
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (20)..(20)
<223> OTHER INFORMATION: d
<220> FEATURE:
<221> NAME/KEY: modified_base
<222> LOCATION: (37)..(37)
<223> OTHER INFORMATION: m7g
<220> FEATURE:
```

<221> NAME/KEY: modified_base
<222> LOCATION: (38)..(38)
<223> OTHER INFORMATION: m1g
<220> FEATURE:
<221> NAME/KEY: modified_base
<222> LOCATION: (62)..(62)
<223> OTHER INFORMATION: p

<400> SEQUENCE: 34
gccgcuaugg ugaaauuggu agacacgcug cucuuaggaa gcagugcuag agcaucucgg    60
tucgaguccg aguagcggca cca                                          83

<210> SEQ ID NO 35
<211> LENGTH: 83
<212> TYPE: DNA
<213> ORGANISM: Spinacia oleracea
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (20)..(20)
<223> OTHER INFORMATION: d
<220> FEATURE:
<221> NAME/KEY: modified_base
<222> LOCATION: (37)..(37)
<223> OTHER INFORMATION: m7g
<220> FEATURE:
<221> NAME/KEY: modified_base
<222> LOCATION: (38)..(38)
<223> OTHER INFORMATION: m1g
<220> FEATURE:
<221> NAME/KEY: modified_base
<222> LOCATION: (62)..(62)
<223> OTHER INFORMATION: p

<400> SEQUENCE: 35
gccgcuaugg ugaaauuggu agacacgcug cucuuaggaa gcagugcgag agcaucucgg    60
tucgaguccg aguagcggca cca                                          83

<210> SEQ ID NO 36
<211> LENGTH: 85
<212> TYPE: DNA
<213> ORGANISM: Neurospora crassa
<220> FEATURE:
<221> NAME/KEY: modified_base
<222> LOCATION: (16)..(16)
<223> OTHER INFORMATION: d
<220> FEATURE:
<221> NAME/KEY: modified_base
<222> LOCATION: (19)..(19)
<223> OTHER INFORMATION: d
<220> FEATURE:
<221> NAME/KEY: modified_base
<222> LOCATION: (34)..(34)
<223> OTHER INFORMATION: unidentified methylated uridine
<220> FEATURE:
<221> NAME/KEY: modified_base
<222> LOCATION: (64)..(64)
<223> OTHER INFORMATION: p

<400> SEQUENCE: 36
auccgaguga uggaauggua gacauaacau gcuuaaaaca ugugggcuuc aagcugugaa    60
ggtucaaguc cuucuucgga uacca                                        85

<210> SEQ ID NO 37
<211> LENGTH: 87
<212> TYPE: DNA
<213> ORGANISM: Neurospora crassa

```
<220> FEATURE:
<221> NAME/KEY: modified_base
<222> LOCATION: (16)..(16)
<223> OTHER INFORMATION: d
<220> FEATURE:
<221> NAME/KEY: modified_base
<222> LOCATION: (20)..(20)
<223> OTHER INFORMATION: d
<220> FEATURE:
<221> NAME/KEY: modified_base
<222> LOCATION: (33)..(33)
<223> OTHER INFORMATION: p
<220> FEATURE:
<221> NAME/KEY: modified_base
<222> LOCATION: (38)..(38)
<223> OTHER INFORMATION: m1g
<220> FEATURE:
<221> NAME/KEY: modified_base
<222> LOCATION: (66)..(66)
<223> OTHER INFORMATION: p

<400> SEQUENCE: 37
auaggugugc uggaauuggu agacagguuc cguuuaggcc ggaaugguuu aaaaacugua      60
caagtucaag ucuugucauc uauacca                                         87

<210> SEQ ID NO 38
<211> LENGTH: 85
<212> TYPE: DNA
<213> ORGANISM: Saccharomyces cerevisiae
<220> FEATURE:
<221> NAME/KEY: modified_base
<222> LOCATION: (16)..(16)
<223> OTHER INFORMATION: d
<220> FEATURE:
<221> NAME/KEY: modified_base
<222> LOCATION: (20)..(20)
<223> OTHER INFORMATION: d
<220> FEATURE:
<221> NAME/KEY: modified_base
<222> LOCATION: (27)..(27)
<223> OTHER INFORMATION: m22g
<220> FEATURE:
<221> NAME/KEY: modified_base
<222> LOCATION: (32)..(32)
<223> OTHER INFORMATION: p
<220> FEATURE:
<221> NAME/KEY: modified_base
<222> LOCATION: (35)..(35)
<223> OTHER INFORMATION: cmnm5U
<220> FEATURE:
<221> NAME/KEY: modified_base
<222> LOCATION: (38)..(38)
<223> OTHER INFORMATION: m1g
<220> FEATURE:
<221> NAME/KEY: modified_base
<222> LOCATION: (40)..(40)
<223> OTHER INFORMATION: p
<220> FEATURE:
<221> NAME/KEY: modified_base
<222> LOCATION: (64)..(64)
<223> OTHER INFORMATION: p

<400> SEQUENCE: 38
gcuauuuugg uggaauuggu agacacgaua cucuuaagau guauuacuuu acaguaugaa      60
ggtucaaguc cuuuaaauag cacca                                           85

<210> SEQ ID NO 39
<211> LENGTH: 86
<212> TYPE: DNA
<213> ORGANISM: Solanum tuberosum
<220> FEATURE:
<221> NAME/KEY: modified_base
<222> LOCATION: (12)..(12)
```

```
<223> OTHER INFORMATION: ac4c
<220> FEATURE:
<221> NAME/KEY: modified_base
<222> LOCATION: (16)..(16)
<223> OTHER INFORMATION: d
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (19)..(19)
<223> OTHER INFORMATION: d
<220> FEATURE:
<221> NAME/KEY: modified_base
<222> LOCATION: (21)..(21)
<223> OTHER INFORMATION: acp3u  3-(3-amino-3-carboxy-propyl)uridine
<220> FEATURE:
<221> NAME/KEY: modified_base
<222> LOCATION: (27)..(27)
<223> OTHER INFORMATION: m22g
<220> FEATURE:
<221> NAME/KEY: modified_base
<222> LOCATION: (35)..(35)
<223> OTHER INFORMATION: unidentified methylated adenosine
<220> FEATURE:
<221> NAME/KEY: modified_base
<222> LOCATION: (37)..(37)
<223> OTHER INFORMATION: m1g
<220> FEATURE:
<221> NAME/KEY: modified_base
<222> LOCATION: (39)..(39)
<223> OTHER INFORMATION: p
<220> FEATURE:
<221> NAME/KEY: modified_base
<222> LOCATION: (44)..(44)
<223> OTHER INFORMATION: um
<220> FEATURE:
<221> NAME/KEY: modified_base
<222> LOCATION: (58)..(58)
<223> OTHER INFORMATION: m5c
<220> FEATURE:
<221> NAME/KEY: modified_base
<222> LOCATION: (65)..(65)
<223> OTHER INFORMATION: p
<220> FEATURE:
<221> NAME/KEY: modified_base
<222> LOCATION: (68)..(68)
<223> OTHER INFORMATION: m1A

<400> SEQUENCE: 39
gucaggaugg ccgagugguc uaaggcgcca gacuaaguuc uggucuucgu aagagggcgu    60
gggtucaaau cccacuucug acacca                                        86

<210> SEQ ID NO 40
<211> LENGTH: 86
<212> TYPE: DNA
<213> ORGANISM: Phaseolus vulgaris
<220> FEATURE:
<221> NAME/KEY: modified_base
<222> LOCATION: (10)..(10)
<223> OTHER INFORMATION: m2g
<220> FEATURE:
<221> NAME/KEY: modified_base
<222> LOCATION: (12)..(12)
<223> OTHER INFORMATION: ac4c
<220> FEATURE:
<221> NAME/KEY: modified_base
<222> LOCATION: (16)..(16)
<223> OTHER INFORMATION: d
<220> FEATURE:
<221> NAME/KEY: modified_base
<222> LOCATION: (17)..(17)
<223> OTHER INFORMATION: gm
<220> FEATURE:
<221> NAME/KEY: modified_base
```

```
<222> LOCATION: (19)..(19)
<223> OTHER INFORMATION: d
<220> FEATURE:
<221> NAME/KEY: modified_base
<222> LOCATION: (21)..(21)
<223> OTHER INFORMATION: acp3u
<220> FEATURE:
<221> NAME/KEY: modified_base
<222> LOCATION: (27)..(27)
<223> OTHER INFORMATION: m22g
<220> FEATURE:
<221> NAME/KEY: modified_base
<222> LOCATION: (35)..(35)
<223> OTHER INFORMATION: unidentified methylated adenosin
<220> FEATURE:
<221> NAME/KEY: modified_base
<222> LOCATION: (37)..(37)
<223> OTHER INFORMATION: m1g
<220> FEATURE:
<221> NAME/KEY: modified_base
<222> LOCATION: (38)..(38)
<223> OTHER INFORMATION: p
<220> FEATURE:
<221> NAME/KEY: modified_base
<222> LOCATION: (39)..(39)
<223> OTHER INFORMATION: p
<220> FEATURE:
<221> NAME/KEY: modified_base
<222> LOCATION: (44)..(44)
<223> OTHER INFORMATION: um
<220> FEATURE:
<221> NAME/KEY: modified_base
<222> LOCATION: (58)..(58)
<223> OTHER INFORMATION: m5c
<220> FEATURE:
<221> NAME/KEY: modified_base
<222> LOCATION: (65)..(65)
<223> OTHER INFORMATION: p
<220> FEATURE:
<221> NAME/KEY: modified_base
<222> LOCATION: (68)..(68)
<223> OTHER INFORMATION: m1a

<400> SEQUENCE: 40
gucaggaugg ccgaguggus uaaggcgcca gacuaaguuc uggucuucga gagagggcgu      60
gggtucaaau cccacuucug acacca                                          86

<210> SEQ ID NO 41
<211> LENGTH: 86
<212> TYPE: DNA
<213> ORGANISM: Phaseolus vulgaris
<220> FEATURE:
<221> NAME/KEY: modified_base
<222> LOCATION: (10)..(10)
<223> OTHER INFORMATION: m2g
<220> FEATURE:
<221> NAME/KEY: modified_base
<222> LOCATION: (12)..(12)
<223> OTHER INFORMATION: ac4c
<220> FEATURE:
<221> NAME/KEY: modified_base
<222> LOCATION: (16)..(16)
<223> OTHER INFORMATION: d
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (19)..(19)
<223> OTHER INFORMATION: d
<220> FEATURE:
<221> NAME/KEY: modified_base
<222> LOCATION: (21)..(21)
<223> OTHER INFORMATION: acp3u
<220> FEATURE:
```

<221> NAME/KEY: modified_base
<222> LOCATION: (27)..(27)
<223> OTHER INFORMATION: m22g
<220> FEATURE:
<221> NAME/KEY: modified_base
<222> LOCATION: (35)..(35)
<223> OTHER INFORMATION: unidentified methylated adenosine
<220> FEATURE:
<221> NAME/KEY: modified_base
<222> LOCATION: (37)..(37)
<223> OTHER INFORMATION: m1g
<220> FEATURE:
<221> NAME/KEY: modified_base
<222> LOCATION: (38)..(38)
<223> OTHER INFORMATION: p
<220> FEATURE:
<221> NAME/KEY: modified_base
<222> LOCATION: (39)..(39)
<223> OTHER INFORMATION: p
<220> FEATURE:
<221> NAME/KEY: modified_base
<222> LOCATION: (44)..(44)
<223> OTHER INFORMATION: um
<220> FEATURE:
<221> NAME/KEY: modified_base
<222> LOCATION: (58)..(58)
<223> OTHER INFORMATION: m5c
<220> FEATURE:
<221> NAME/KEY: modified_base
<222> LOCATION: (65)..(65)
<223> OTHER INFORMATION: p
<220> FEATURE:
<221> NAME/KEY: modified_base
<222> LOCATION: (68)..(68)
<223> OTHER INFORMATION: m1a

<400> SEQUENCE: 41
gucaggaugg ccgagugguc uaaggcgcca gacuaaguuc uggucuucga aagagggcgu    60
gggtucaaau cccacuucug acacca                                        86

<210> SEQ ID NO 42
<211> LENGTH: 82
<212> TYPE: DNA
<213> ORGANISM: Phaseolus vulgaris
<220> FEATURE:
<221> NAME/KEY: modified_base
<222> LOCATION: (10)..(10)
<223> OTHER INFORMATION: m2g
<220> FEATURE:
<221> NAME/KEY: modified_base
<222> LOCATION: (12)..(12)
<223> OTHER INFORMATION: ac4c
<220> FEATURE:
<221> NAME/KEY: modified_base
<222> LOCATION: (16)..(16)
<223> OTHER INFORMATION: d
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (19)..(19)
<223> OTHER INFORMATION: d
<220> FEATURE:
<221> NAME/KEY: modified_base
<222> LOCATION: (21)..(21)
<223> OTHER INFORMATION: acp3u
<220> FEATURE:
<221> NAME/KEY: modified_base
<222> LOCATION: (27)..(27)
<223> OTHER INFORMATION: m22g
<220> FEATURE:
<221> NAME/KEY: modified_base
<222> LOCATION: (33)..(33)
<223> OTHER INFORMATION: p

```
<220> FEATURE:
<221> NAME/KEY: modified_base
<222> LOCATION: (35)..(35)
<223> OTHER INFORMATION: unidentified methylated adenosine
<220> FEATURE:
<221> NAME/KEY: modified_base
<222> LOCATION: (37)..(37)
<223> OTHER INFORMATION: m1g
<220> FEATURE:
<221> NAME/KEY: modified_base
<222> LOCATION: (39)..(39)
<223> OTHER INFORMATION: p
<220> FEATURE:
<221> NAME/KEY: modified_base
<222> LOCATION: (44)..(44)
<223> OTHER INFORMATION: um
<220> FEATURE:
<221> NAME/KEY: modified_base
<222> LOCATION: (51)..(51)
<223> OTHER INFORMATION: unidentified methylated guanosine
<220> FEATURE:
<221> NAME/KEY: modified_base
<222> LOCATION: (54)..(54)
<223> OTHER INFORMATION: m5c
<220> FEATURE:
<221> NAME/KEY: modified_base
<222> LOCATION: (61)..(61)
<223> OTHER INFORMATION: p
<220> FEATURE:
<221> NAME/KEY: modified_base
<222> LOCATION: (64)..(64)
<223> OTHER INFORMATION: m1a

<400> SEQUENCE: 42
gauaguuugg ccgagugguc uaaggcgcca gauuaggcuc ugguccgaaa gggcgugggu      60
ucaaauccca cagcugucac ca                                              82

<210> SEQ ID NO 43
<211> LENGTH: 85
<212> TYPE: DNA
<213> ORGANISM: Phaseolus vulgaris
<220> FEATURE:
<221> NAME/KEY: modified_base
<222> LOCATION: (12)..(12)
<223> OTHER INFORMATION: ac4c
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (19)..(19)
<223> OTHER INFORMATION: d
<220> FEATURE:
<221> NAME/KEY: modified_base
<222> LOCATION: (20)..(20)
<223> OTHER INFORMATION: d
<220> FEATURE:
<221> NAME/KEY: modified_base
<222> LOCATION: (26)..(26)
<223> OTHER INFORMATION: m22g
<220> FEATURE:
<221> NAME/KEY: modified_base
<222> LOCATION: (34)..(34)
<223> OTHER INFORMATION: unidentified methylated adenosine
<220> FEATURE:
<221> NAME/KEY: modified_base
<222> LOCATION: (36)..(36)
<223> OTHER INFORMATION: m1g
<220> FEATURE:
<221> NAME/KEY: modified_base
<222> LOCATION: (38)..(38)
<223> OTHER INFORMATION: p
<220> FEATURE:
<221> NAME/KEY: modified_base
<222> LOCATION: (43)..(43)
```

<223> OTHER INFORMATION: um
<220> FEATURE:
<221> NAME/KEY: modified_base
<222> LOCATION: (57)..(57)
<223> OTHER INFORMATION: m5c
<220> FEATURE:
<221> NAME/KEY: modified_base
<222> LOCATION: (64)..(64)
<223> OTHER INFORMATION: p
<220> FEATURE:
<221> NAME/KEY: modified_base
<222> LOCATION: (67)..(67)
<223> OTHER INFORMATION: m1a

<400> SEQUENCE: 43
gcugguuugg ccgagagguu aaggcggaag acuaagaucu ucugcaguca acugcgcaug      60
ggtucgaacc ccauagccag cacca                                           85

<210> SEQ ID NO 44
<211> LENGTH: 73
<212> TYPE: DNA
<213> ORGANISM: Rattus norvegicus
<220> FEATURE:
<221> NAME/KEY: modified_base
<222> LOCATION: (8)..(8)
<223> OTHER INFORMATION: m1a
<220> FEATURE:
<221> NAME/KEY: modified_base
<222> LOCATION: (9)..(9)
<223> OTHER INFORMATION: m2g
<220> FEATURE:
<221> NAME/KEY: modified_base
<222> LOCATION: (18)..(18)
<223> OTHER INFORMATION: d
<220> FEATURE:
<221> NAME/KEY: modified_base
<222> LOCATION: (25)..(25)
<223> OTHER INFORMATION: p
<220> FEATURE:
<221> NAME/KEY: modified_base
<222> LOCATION: (35)..(35)
<223> OTHER INFORMATION: m1g
<220> FEATURE:
<221> NAME/KEY: modified_base
<222> LOCATION: (46)..(46)
<223> OTHER INFORMATION: m5c

<400> SEQUENCE: 44
cuuuuauagg auagaaguaa uccauugguc uuaggaacca aaaaccuugg ugcaacucca      60
aauaaaagua cca                                                        73

<210> SEQ ID NO 45
<211> LENGTH: 85
<212> TYPE: DNA
<213> ORGANISM: Candida albicans
<220> FEATURE:
<221> NAME/KEY: modified_base
<222> LOCATION: (12)..(12)
<223> OTHER INFORMATION: ac4c
<220> FEATURE:
<221> NAME/KEY: modified_base
<222> LOCATION: (16)..(16)
<223> OTHER INFORMATION: d
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (19)..(19)
<223> OTHER INFORMATION: d
<220> FEATURE:
<221> NAME/KEY: modified_base

```
<222> LOCATION: (20)..(20)
<223> OTHER INFORMATION: d
<220> FEATURE:
<221> NAME/KEY: modified_base
<222> LOCATION: (26)..(26)
<223> OTHER INFORMATION: m22g
<220> FEATURE:
<221> NAME/KEY: modified_base
<222> LOCATION: (37)..(37)
<223> OTHER INFORMATION: m1g
<220> FEATURE:
<221> NAME/KEY: modified_base
<222> LOCATION: (38)..(38)
<223> OTHER INFORMATION: p
<220> FEATURE:
<221> NAME/KEY: modified_base
<222> LOCATION: (39)..(39)
<223> OTHER INFORMATION: p
<220> FEATURE:
<221> NAME/KEY: modified_base
<222> LOCATION: (57)..(57)
<223> OTHER INFORMATION: m5c
<220> FEATURE:
<221> NAME/KEY: modified_base
<222> LOCATION: (64)..(64)
<223> OTHER INFORMATION: p
<220> FEATURE:
<221> NAME/KEY: modified_base
<222> LOCATION: (67)..(67)
<223> OTHER INFORMATION: m1a

<400> SEQUENCE: 45
gauacgaugg ccgagugguu aaggcgaagg augcagguuc cuuugggcau ugcccgcgca      60
ggtucgaacc cugcucgugu cgcca                                           85

<210> SEQ ID NO 46
<211> LENGTH: 85
<212> TYPE: DNA
<213> ORGANISM: Saccharomyces cerevisiae
<220> FEATURE:
<221> NAME/KEY: modified_base
<222> LOCATION: (10)..(10)
<223> OTHER INFORMATION: m2g
<220> FEATURE:
<221> NAME/KEY: modified_base
<222> LOCATION: (12)..(12)
<223> OTHER INFORMATION: ac4c
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (19)..(19)
<223> OTHER INFORMATION: d
<220> FEATURE:
<221> NAME/KEY: modified_base
<222> LOCATION: (21)..(21)
<223> OTHER INFORMATION: d
<220> FEATURE:
<221> NAME/KEY: modified_base
<222> LOCATION: (27)..(27)
<223> OTHER INFORMATION: m22g
<220> FEATURE:
<221> NAME/KEY: modified_base
<222> LOCATION: (33)..(33)
<223> OTHER INFORMATION: p
<220> FEATURE:
<221> NAME/KEY: modified_base
<222> LOCATION: (35)..(35)
<223> OTHER INFORMATION: m5c
<220> FEATURE:
<221> NAME/KEY: modified_base
<222> LOCATION: (38)..(38)
<223> OTHER INFORMATION: m1g
<220> FEATURE:
```

<220> FEATURE:
<221> NAME/KEY: modified_base
<222> LOCATION: (40)..(40)
<223> OTHER INFORMATION: p
<220> FEATURE:
<221> NAME/KEY: modified_base
<222> LOCATION: (57)..(57)
<223> OTHER INFORMATION: m5c
<220> FEATURE:
<221> NAME/KEY: modified_base
<222> LOCATION: (64)..(64)
<223> OTHER INFORMATION: p

<400> SEQUENCE: 46
gguuguuugg ccgagcgguc uaaggcgccu gauucaagcu cagguaucgu aagaugcaag    60
agtucgaauc ucuuagcaac cacca                                         85

<210> SEQ ID NO 47
<211> LENGTH: 85
<212> TYPE: DNA
<213> ORGANISM: Saccharomyces cerevisiae
<220> FEATURE:
<221> NAME/KEY: modified_base
<222> LOCATION: (10)..(10)
<223> OTHER INFORMATION: m2g
<220> FEATURE:
<221> NAME/KEY: modified_base
<222> LOCATION: (12)..(12)
<223> OTHER INFORMATION: ac4c
<220> FEATURE:
<221> NAME/KEY: modified_base
<222> LOCATION: (16)..(16)
<223> OTHER INFORMATION: d
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (19)..(19)
<223> OTHER INFORMATION: d
<220> FEATURE:
<221> NAME/KEY: modified_base
<222> LOCATION: (20)..(20)
<223> OTHER INFORMATION: d
<220> FEATURE:
<221> NAME/KEY: modified_base
<222> LOCATION: (21)..(21)
<223> OTHER INFORMATION: d
<220> FEATURE:
<221> NAME/KEY: modified_base
<222> LOCATION: (27)..(27)
<223> OTHER INFORMATION: m22g
<220> FEATURE:
<221> NAME/KEY: modified_base
<222> LOCATION: (28)..(28)
<223> OTHER INFORMATION: p
<220> FEATURE:
<221> NAME/KEY: modified_base
<222> LOCATION: (33)..(33)
<223> OTHER INFORMATION: p
<220> FEATURE:
<221> NAME/KEY: modified_base
<222> LOCATION: (38)..(38)
<223> OTHER INFORMATION: m1g
<220> FEATURE:
<221> NAME/KEY: modified_base
<222> LOCATION: (40)..(40)
<223> OTHER INFORMATION: p
<220> FEATURE:
<221> NAME/KEY: modified_base
<222> LOCATION: (57)..(57)
<223> OTHER INFORMATION: m5c
<220> FEATURE:
<221> NAME/KEY: modified_base
<222> LOCATION: (64)..(64)
<223> OTHER INFORMATION: p

```
<220> FEATURE:
<221> NAME/KEY: modified_base
<222> LOCATION: (67)..(67)
<223> OTHER INFORMATION: m1a

<400> SEQUENCE: 47
gggaguuugg ccgaguggpuu uaaggcguca gauuuaggcu cugauaucuu cggaugcaag      60 ggucgaauc ccuuagcucu cacca                                             85

<210> SEQ ID NO 48
<211> LENGTH: 85
<212> TYPE: DNA
<213> ORGANISM: Candida cylindracea
<220> FEATURE:
<221> NAME/KEY: modified_base
<222> LOCATION: (12)..(12)
<223> OTHER INFORMATION: ac4c
<220> FEATURE:
<221> NAME/KEY: modified_base
<222> LOCATION: (16)..(16)
<223> OTHER INFORMATION: d
<220> FEATURE:
<221> NAME/KEY: modified_base
<222> LOCATION: (19)..(19)
<223> OTHER INFORMATION: d
<220> FEATURE:
<221> NAME/KEY: modified_base
<222> LOCATION: (21)..(21)
<223> OTHER INFORMATION: d
<220> FEATURE:
<221> NAME/KEY: modified_base
<222> LOCATION: (27)..(27)
<223> OTHER INFORMATION: m22g
<220> FEATURE:
<221> NAME/KEY: modified_base
<222> LOCATION: (35)..(35)
<223> OTHER INFORMATION: i
<220> FEATURE:
<221> NAME/KEY: modified_base
<222> LOCATION: (38)..(38)
<223> OTHER INFORMATION: m1g
<220> FEATURE:
<221> NAME/KEY: modified_base
<222> LOCATION: (39)..(39)
<223> OTHER INFORMATION: p
<220> FEATURE:
<221> NAME/KEY: modified_base
<222> LOCATION: (57)..(57)
<223> OTHER INFORMATION: m5c
<220> FEATURE:
<221> NAME/KEY: modified_base
<222> LOCATION: (64)..(64)
<223> OTHER INFORMATION: p
<220> FEATURE:
<221> NAME/KEY: modified_base
<222> LOCATION: (67)..(67)
<223> OTHER INFORMATION: m1a

<400> SEQUENCE: 48
ggcucucugg ccgagugguc uaaggcgcua ggguaagguc cuagucucuu cggaggcgcg      60 agucgaacc ucgcgggagu cacca                                             85

<210> SEQ ID NO 49
<211> LENGTH: 86
<212> TYPE: DNA
<213> ORGANISM: Phaseolus vulgaris
<220> FEATURE:
<221> NAME/KEY: modified_base
<222> LOCATION: (10)..(10)
<223> OTHER INFORMATION: m2g
<220> FEATURE:
<221> NAME/KEY: modified_base
<222> LOCATION: (12)..(12)
```

```
<223> OTHER INFORMATION: ac4c
<220> FEATURE:
<221> NAME/KEY: modified_base
<222> LOCATION: (16)..(16)
<223> OTHER INFORMATION: d
<220> FEATURE:
<221> NAME/KEY: modified_base
<222> LOCATION: (19)..(19)
<223> OTHER INFORMATION: d
<220> FEATURE:
<221> NAME/KEY: modified_base
<222> LOCATION: (21)..(21)
<223> OTHER INFORMATION: acp3u
<220> FEATURE:
<221> NAME/KEY: modified_base
<222> LOCATION: (27)..(27)
<223> OTHER INFORMATION: m22g
<220> FEATURE:
<221> NAME/KEY: modified_base
<222> LOCATION: (35)..(35)
<223> OTHER INFORMATION: unidentified methylated adenosine
<220> FEATURE:
<221> NAME/KEY: modified_base
<222> LOCATION: (37)..(37)
<223> OTHER INFORMATION: m1g
<220> FEATURE:
<221> NAME/KEY: modified_base
<222> LOCATION: (38)..(38)
<223> OTHER INFORMATION: p
<220> FEATURE:
<221> NAME/KEY: modified_base
<222> LOCATION: (39)..(39)
<223> OTHER INFORMATION: p
<220> FEATURE:
<221> NAME/KEY: modified_base
<222> LOCATION: (44)..(44)
<223> OTHER INFORMATION: um
<220> FEATURE:
<221> NAME/KEY: modified_base
<222> LOCATION: (58)..(58)
<223> OTHER INFORMATION: m5c
<220> FEATURE:
<221> NAME/KEY: modified_base
<222> LOCATION: (65)..(65)
<223> OTHER INFORMATION: p
<220> FEATURE:
<221> NAME/KEY: modified_base
<222> LOCATION: (68)..(68)
<223> OTHER INFORMATION: m1a

<400> SEQUENCE: 49
gucaggaugg ccgagugguc uaaggcgcca gacuaaguuc uggucuucga gagagggcgu      60
gggtucaaau cccacuucug acacca                                          86

<210> SEQ ID NO 50
<211> LENGTH: 86
<212> TYPE: DNA
<213> ORGANISM: Phaseolus vulgaris
<220> FEATURE:
<221> NAME/KEY: modified_base
<222> LOCATION: (10)..(10)
<223> OTHER INFORMATION: m2g
<220> FEATURE:
<221> NAME/KEY: modified_base
<222> LOCATION: (12)..(12)
<223> OTHER INFORMATION: ac4c
<220> FEATURE:
<221> NAME/KEY: modified_base
<222> LOCATION: (16)..(16)
<223> OTHER INFORMATION: d
<220> FEATURE:
<221> NAME/KEY: modified_base
<222> LOCATION: (19)..(19)
<223> OTHER INFORMATION: d
<220> FEATURE:
<221> NAME/KEY: modified_base
```

```
<222> LOCATION: (21)..(21)
<223> OTHER INFORMATION: acp3u
<220> FEATURE:
<221> NAME/KEY: modified_base
<222> LOCATION: (27)..(27)
<223> OTHER INFORMATION: m22g
<220> FEATURE:
<221> NAME/KEY: modified_base
<222> LOCATION: (35)..(35)
<223> OTHER INFORMATION: unidentified methylated adenosine
<220> FEATURE:
<221> NAME/KEY: modified_base
<222> LOCATION: (37)..(37)
<223> OTHER INFORMATION: m1g
<220> FEATURE:
<221> NAME/KEY: modified_base
<222> LOCATION: (38)..(38)
<223> OTHER INFORMATION: p
<220> FEATURE:
<221> NAME/KEY: modified_base
<222> LOCATION: (39)..(39)
<223> OTHER INFORMATION: p
<220> FEATURE:
<221> NAME/KEY: modified_base
<222> LOCATION: (44)..(44)
<223> OTHER INFORMATION: um
<220> FEATURE:
<221> NAME/KEY: modified_base
<222> LOCATION: (58)..(58)
<223> OTHER INFORMATION: m5c
<220> FEATURE:
<221> NAME/KEY: modified_base
<222> LOCATION: (65)..(65)
<223> OTHER INFORMATION: p
<220> FEATURE:
<221> NAME/KEY: modified_base
<222> LOCATION: (68)..(68)
<223> OTHER INFORMATION: m1a

<400> SEQUENCE: 50
gucaggaugg ccgagugguc uaaggcgcca gacuaaguuc uggucuucga aagagggcgu      60
gggtucaaau cccacuucug acacca                                          86

<210> SEQ ID NO 51
<211> LENGTH: 82
<212> TYPE: DNA
<213> ORGANISM: Phaseolus vulgaris
<220> FEATURE:
<221> NAME/KEY: modified_base
<222> LOCATION: (10)..(10)
<223> OTHER INFORMATION: m2g
<220> FEATURE:
<221> NAME/KEY: modified_base
<222> LOCATION: (12)..(12)
<223> OTHER INFORMATION: ac4c
<220> FEATURE:
<221> NAME/KEY: modified_base
<222> LOCATION: (16)..(16)
<223> OTHER INFORMATION: d
<220> FEATURE:
<221> NAME/KEY: modified_base
<222> LOCATION: (19)..(19)
<223> OTHER INFORMATION: d
<220> FEATURE:
<221> NAME/KEY: modified_base
<222> LOCATION: (21)..(21)
<223> OTHER INFORMATION: acp3u
<220> FEATURE:
<221> NAME/KEY: modified_base
<222> LOCATION: (27)..(27)
<223> OTHER INFORMATION: m22g
<220> FEATURE:
<221> NAME/KEY: modified_base
<222> LOCATION: (33)..(33)
<223> OTHER INFORMATION: p
<220> FEATURE:
```

```
<221> NAME/KEY: modified_base
<222> LOCATION: (35)..(35)
<223> OTHER INFORMATION: unidentified methylated adenosin
<220> FEATURE:
<221> NAME/KEY: modified_base
<222> LOCATION: (37)..(37)
<223> OTHER INFORMATION: m1g
<220> FEATURE:
<221> NAME/KEY: modified_base
<222> LOCATION: (39)..(39)
<223> OTHER INFORMATION: p
<220> FEATURE:
<221> NAME/KEY: modified_base
<222> LOCATION: (44)..(44)
<223> OTHER INFORMATION: um
<220> FEATURE:
<221> NAME/KEY: modified_base
<222> LOCATION: (51)..(51)
<223> OTHER INFORMATION: unidentified methylated guanosine
<220> FEATURE:
<221> NAME/KEY: modified_base
<222> LOCATION: (54)..(54)
<223> OTHER INFORMATION: m5c
<220> FEATURE:
<221> NAME/KEY: modified_base
<222> LOCATION: (61)..(61)
<223> OTHER INFORMATION: p
<220> FEATURE:
<221> NAME/KEY: modified_base
<222> LOCATION: (64)..(64)
<223> OTHER INFORMATION: m1a

<400> SEQUENCE: 51
gauaguuugg ccgagugguc uaaggcgcca gauuaggcuc ugguccgaaa gggcgugggu      60
ucaaauccca cagcugucac ca                                              82

<210> SEQ ID NO 52
<211> LENGTH: 85
<212> TYPE: DNA
<213> ORGANISM: Phaseolus vulgaris
<220> FEATURE:
<221> NAME/KEY: modified_base
<222> LOCATION: (12)..(12)
<223> OTHER INFORMATION: ac4c
<220> FEATURE:
<221> NAME/KEY: modified_base
<222> LOCATION: (19)..(19)
<223> OTHER INFORMATION: d
<220> FEATURE:
<221> NAME/KEY: modified_base
<222> LOCATION: (20)..(20)
<223> OTHER INFORMATION: d
<220> FEATURE:
<221> NAME/KEY: modified_base
<222> LOCATION: (26)..(26)
<223> OTHER INFORMATION: m22g
<220> FEATURE:
<221> NAME/KEY: modified_base
<222> LOCATION: (34)..(34)
<223> OTHER INFORMATION: unidentified methylated adenosine
<220> FEATURE:
<221> NAME/KEY: modified_base
<222> LOCATION: (36)..(36)
<223> OTHER INFORMATION: m1g
<220> FEATURE:
<221> NAME/KEY: modified_base
<222> LOCATION: (38)..(38)
<223> OTHER INFORMATION: p
<220> FEATURE:
<221> NAME/KEY: modified_base
<222> LOCATION: (43)..(43)
<223> OTHER INFORMATION: um
<220> FEATURE:
<221> NAME/KEY: modified_base
<222> LOCATION: (57)..(57)
<223> OTHER INFORMATION: m5c
```

<220> FEATURE:
<221> NAME/KEY: modified_base
<222> LOCATION: (64)..(64)
<223> OTHER INFORMATION: p
<220> FEATURE:
<221> NAME/KEY: modified_base
<222> LOCATION: (67)..(67)
<223> OTHER INFORMATION: m1a

<400> SEQUENCE: 52
gcugguuugg ccgagagguu aaggcggaag acuaagaucu ucugcaguca acugcgcaug    60
ggtucgaacc ccauagccag cacca                                         85

<210> SEQ ID NO 53
<211> LENGTH: 86
<212> TYPE: DNA
<213> ORGANISM: Solanum tuberosum
<220> FEATURE:
<221> NAME/KEY: modified_base
<222> LOCATION: (12)..(12)
<223> OTHER INFORMATION: ac4c
<220> FEATURE:
<221> NAME/KEY: modified_base
<222> LOCATION: (16)..(16)
<223> OTHER INFORMATION: d
<220> FEATURE:
<221> NAME/KEY: modified_base
<222> LOCATION: (19)..(19)
<223> OTHER INFORMATION: d
<220> FEATURE:
<221> NAME/KEY: modified_base
<222> LOCATION: (21)..(21)
<223> OTHER INFORMATION: acp3u
<220> FEATURE:
<221> NAME/KEY: modified_base
<222> LOCATION: (27)..(27)
<223> OTHER INFORMATION: m22g
<220> FEATURE:
<221> NAME/KEY: modified_base
<222> LOCATION: (35)..(35)
<223> OTHER INFORMATION: unidentified methylated adenosine
<220> FEATURE:
<221> NAME/KEY: modified_base
<222> LOCATION: (37)..(37)
<223> OTHER INFORMATION: m1g
<220> FEATURE:
<221> NAME/KEY: modified_base
<222> LOCATION: (39)..(39)
<223> OTHER INFORMATION: p
<220> FEATURE:
<221> NAME/KEY: modified_base
<222> LOCATION: (44)..(44)
<223> OTHER INFORMATION: um
<220> FEATURE:
<221> NAME/KEY: modified_base
<222> LOCATION: (58)..(58)
<223> OTHER INFORMATION: m5c
<220> FEATURE:
<221> NAME/KEY: modified_base
<222> LOCATION: (65)..(65)
<223> OTHER INFORMATION: p
<220> FEATURE:
<221> NAME/KEY: modified_base
<222> LOCATION: (68)..(68)
<223> OTHER INFORMATION: m1a

<400> SEQUENCE: 53
gucaggaugg ccgagugguc uaaggcgcca gacuaaguuc uggucuucgu aagagggcgu    60
gggtucaaau cccacuucug acacca                                        86

<210> SEQ ID NO 54
<211> LENGTH: 87
<212> TYPE: DNA

```
<213> ORGANISM: Cucumis sativus
<220> FEATURE:
<221> NAME/KEY: modified_base
<222> LOCATION: (10)..(10)
<223> OTHER INFORMATION: m2g
<220> FEATURE:
<221> NAME/KEY: modified_base
<222> LOCATION: (12)..(12)
<223> OTHER INFORMATION: m5c
<220> FEATURE:
<221> NAME/KEY: modified_base
<222> LOCATION: (16)..(16)
<223> OTHER INFORMATION: d
<220> FEATURE:
<221> NAME/KEY: modified_base
<222> LOCATION: (19)..(19)
<223> OTHER INFORMATION: d
<220> FEATURE:
<221> NAME/KEY: modified_base
<222> LOCATION: (21)..(21)
<223> OTHER INFORMATION: acp3u
<220> FEATURE:
<221> NAME/KEY: modified_base
<222> LOCATION: (27)..(27)
<223> OTHER INFORMATION: m22g
<220> FEATURE:
<221> NAME/KEY: modified_base
<222> LOCATION: (35)..(35)
<223> OTHER INFORMATION: unidentified methylated uridine
<220> FEATURE:
<221> NAME/KEY: modified_base
<222> LOCATION: (38)..(38)
<223> OTHER INFORMATION: m1g
<220> FEATURE:
<221> NAME/KEY: modified_base
<222> LOCATION: (39)..(39)
<223> OTHER INFORMATION: p
<220> FEATURE:
<221> NAME/KEY: modified_base
<222> LOCATION: (40)..(40)
<223> OTHER INFORMATION: p
<220> FEATURE:
<221> NAME/KEY: modified_base
<222> LOCATION: (45)..(45)
<223> OTHER INFORMATION: um
<220> FEATURE:
<221> NAME/KEY: modified_base
<222> LOCATION: (59)..(59)
<223> OTHER INFORMATION: m5c
<220> FEATURE:
<221> NAME/KEY: modified_base
<222> LOCATION: (66)..(66)
<223> OTHER INFORMATION: p
<220> FEATURE:
<221> NAME/KEY: modified_base
<222> LOCATION: (69)..(69)
<223> OTHER INFORMATION: m1a

<400> SEQUENCE: 54
gucaggaugg ccgagugguc uaaggcgcca gacuuaaguu cugguccucu aaggagggcg      60
ugggtucaaa ucccacuucu gacacca                                         87

<210> SEQ ID NO 55
<211> LENGTH: 85
<212> TYPE: DNA
<213> ORGANISM: Caenorhabditis elegans
<220> FEATURE:
<221> NAME/KEY: modified_base
<222> LOCATION: (12)..(12)
<223> OTHER INFORMATION: ac4c
<220> FEATURE:
<221> NAME/KEY: modified_base
<222> LOCATION: (19)..(19)
<223> OTHER INFORMATION: d
<220> FEATURE:
<221> NAME/KEY: modified_base
```

<222> LOCATION: (35)..(35)
<223> OTHER INFORMATION: i

<400> SEQUENCE: 55
ggagagaugg ccgagcgguc uaaggcgcug guuuaaggca ccagucccuu cgggggcgug 60
ggtucgaauc ccacucucuu cacca 85

<210> SEQ ID NO 56
<211> LENGTH: 89
<212> TYPE: DNA
<213> ORGANISM: Mycoplasma capricolum
<220> FEATURE:
<221> NAME/KEY: modified_base
<222> LOCATION: (8)..(8)
<223> OTHER INFORMATION: unidentified methylated uridine
<220> FEATURE:
<221> NAME/KEY: modified_base
<222> LOCATION: (20)..(20)
<223> OTHER INFORMATION: d
<220> FEATURE:
<221> NAME/KEY: modified_base
<222> LOCATION: (23)..(23)
<223> OTHER INFORMATION: m1a
<220> FEATURE:
<221> NAME/KEY: modified_base
<222> LOCATION: (35)..(35)
<223> OTHER INFORMATION: cmnm5Um (5-carboxymethylaminomethyl-2'
O-methyluridine)
<220> FEATURE:
<221> NAME/KEY: modified_base
<222> LOCATION: (38)..(38)
<223> OTHER INFORMATION: m6a
<220> FEATURE:
<221> NAME/KEY: modified_base
<222> LOCATION: (40)..(40)
<223> OTHER INFORMATION: p
<220> FEATURE:
<221> NAME/KEY: modified_base
<222> LOCATION: (68)..(68)
<223> OTHER INFORMATION: p

<400> SEQUENCE: 56
ccccaagugg cggaauaggu agacgcauug gacuuaaaau ccaacgggcu uaauauccug 60
ugccgguuca aguccggccu uggggacca 89

<210> SEQ ID NO 57
<211> LENGTH: 85
<212> TYPE: DNA
<213> ORGANISM: Mycoplasma capricolum
<220> FEATURE:
<221> NAME/KEY: modified_base
<222> LOCATION: (17)..(17)
<223> OTHER INFORMATION: d
<220> FEATURE:
<221> NAME/KEY: modified_base
<222> LOCATION: (23)..(23)
<223> OTHER INFORMATION: m1a
<220> FEATURE:
<221> NAME/KEY: modified_base
<222> LOCATION: (35)..(35)
<223> OTHER INFORMATION: cm
<220> FEATURE:
<221> NAME/KEY: modified_base
<222> LOCATION: (38)..(38)
<223> OTHER INFORMATION: m6a
<220> FEATURE:
<221> NAME/KEY: modified_base
<222> LOCATION: (40)..(40)
<223> OTHER INFORMATION: p
<220> FEATURE:
<221> NAME/KEY: modified_base
<222> LOCATION: (64)..(64)
<223> OTHER INFORMATION: p

<400> SEQUENCE: 57
gccuuuuugg cggaauuggc agacgcauua gacucaaaau cuaacgaaga aauucguauc    60
gguucgaauc cgauaaaggg cacca    85

<210> SEQ ID NO 58
<211> LENGTH: 86
<212> TYPE: DNA
<213> ORGANISM: Haloferax volcanii
<220> FEATURE:
<221> NAME/KEY: modified_base
<222> LOCATION: (15)..(15)
<223> OTHER INFORMATION: fa7d7g
<220> FEATURE:
<221> NAME/KEY: modified_base
<222> LOCATION: (27)..(27)
<223> OTHER INFORMATION: m22g
<220> FEATURE:
<221> NAME/KEY: modified_base
<222> LOCATION: (35)..(35)
<223> OTHER INFORMATION: mo5u
<220> FEATURE:
<221> NAME/KEY: modified_base
<222> LOCATION: (38)..(38)
<223> OTHER INFORMATION: m1g
<220> FEATURE:
<221> NAME/KEY: modified_base
<222> LOCATION: (58)..(58)
<223> OTHER INFORMATION: m5c
<220> FEATURE:
<221> NAME/KEY: modified_base
<222> LOCATION: (64)..(64)
<223> OTHER INFORMATION: m1p
<220> FEATURE:
<221> NAME/KEY: modified_base
<222> LOCATION: (65)..(65)
<223> OTHER INFORMATION: p
<220> FEATURE:
<221> NAME/KEY: modified_base
<222> LOCATION: (66)..(66)
<223> OTHER INFORMATION: cm

<400> SEQUENCE: 58
gcgcggguag ccaaguggcc aaaggcgcag cgcuuaggac gcuguggugu agaccuucgc    60
agguucgaac ccugucccgc gcacca    86

<210> SEQ ID NO 59
<211> LENGTH: 88
<212> TYPE: DNA
<213> ORGANISM: Haloferax volcanii
<220> FEATURE:
<221> NAME/KEY: modified_base
<222> LOCATION: (15)..(15)
<223> OTHER INFORMATION: fa7d7g
<220> FEATURE:
<221> NAME/KEY: modified_base
<222> LOCATION: (27)..(27)
<223> OTHER INFORMATION: m22g
<220> FEATURE:
<221> NAME/KEY: modified_base
<222> LOCATION: (35)..(35)
<223> OTHER INFORMATION: mo5u
<220> FEATURE:
<221> NAME/KEY: modified_base
<222> LOCATION: (38)..(38)
<223> OTHER INFORMATION: m1g
<220> FEATURE:
<221> NAME/KEY: modified_base
<222> LOCATION: (58)..(58)
<223> OTHER INFORMATION: m5c
<220> FEATURE:
<221> NAME/KEY: modified_base
<222> LOCATION: (64)..(64)

<223> OTHER INFORMATION: m1p
<220> FEATURE:
<221> NAME/KEY: modified_base
<222> LOCATION: (65)..(65)
<223> OTHER INFORMATION: p
<220> FEATURE:
<221> NAME/KEY: modified_base
<222> LOCATION: (66)..(66)
<223> OTHER INFORMATION: cm

<400> SEQUENCE: 59 gcggggugg cugagccagg ccaaaagcgg cggacuuaag auccgcuccc guaggguuc        60 gcgaguucga aucucguccc ccgcacca                                        88

<210> SEQ ID NO 60
<211> LENGTH: 88
<212> TYPE: DNA
<213> ORGANISM: Haloferax volcanii
<220> FEATURE:
<221> NAME/KEY: modified_base
<222> LOCATION: (15)..(15)
<223> OTHER INFORMATION: fa7d7g
<220> FEATURE:
<221> NAME/KEY: modified_base
<222> LOCATION: (29)..(29)
<223> OTHER INFORMATION: m22g
<220> FEATURE:
<221> NAME/KEY: modified_base
<222> LOCATION: (40)..(40)
<223> OTHER INFORMATION: m1g
<220> FEATURE:
<221> NAME/KEY: modified_base
<222> LOCATION: (42)..(42)
<223> OTHER INFORMATION: m5c
<220> FEATURE:
<221> NAME/KEY: modified_base
<222> LOCATION: (60)..(60)
<223> OTHER INFORMATION: m5c
<220> FEATURE:
<221> NAME/KEY: modified_base
<222> LOCATION: (66)..(66)
<223> OTHER INFORMATION: m1p
<220> FEATURE:
<221> NAME/KEY: modified_base
<222> LOCATION: (67)..(67)
<223> OTHER INFORMATION: p
<220> FEATURE:
<221> NAME/KEY: modified_base
<222> LOCATION: (68)..(68)
<223> OTHER INFORMATION: cm
<220> FEATURE:
<221> NAME/KEY: modified_base
<222> LOCATION: (69)..(69)
<223> OTHER INFORMATION: m1i

<400> SEQUENCE: 60 gcgugggudag ccaagccagg ccaacggcgc agcguugagg gcgcuguccu guagaggucc     60
gccgguucaa auccggcccc acgcacca                                        88

<210> SEQ ID NO 61
<211> LENGTH: 88
<212> TYPE: DNA
<213> ORGANISM: Haloferax volcanii
<220> FEATURE:
<221> NAME/KEY: modified_base
<222> LOCATION: (15)..(15)
<223> OTHER INFORMATION: fa7d7g
<220> FEATURE:
<221> NAME/KEY: modified_base
<222> LOCATION: (29)..(29)
<223> OTHER INFORMATION: m22g
<220> FEATURE:
<221> NAME/KEY: modified_base
<222> LOCATION: (40)..(40)
<223> OTHER INFORMATION: m1g
<220> FEATURE:
<221> NAME/KEY: modified_base
<222> LOCATION: (60)..(60)
<223> OTHER INFORMATION: m5c
<220> FEATURE:
<221> NAME/KEY: modified_base
<222> LOCATION: (66)..(66)
<223> OTHER INFORMATION: m1p
<220> FEATURE:
<221> NAME/KEY: modified_base
<222> LOCATION: (67)..(67)
<223> OTHER INFORMATION: p
<220> FEATURE:
<221> NAME/KEY: modified_base
<222> LOCATION: (68)..(68)
<223> OTHER INFORMATION: cm
<220> FEATURE:
<221> NAME/KEY: modified_base
<222> LOCATION: (69)..(69)
<223> OTHER INFORMATION: m1i

<400> SEQUENCE: 61
gcagggauag ccaagucugg ccaacggcgc agcguucagg gcgcugucuc auaggaguac    60
gcagguucaa auccugcucc cugcacca                                      88

<210> SEQ ID NO 62
<211> LENGTH: 87
<212> TYPE: DNA
<213> ORGANISM: Haloferax volcanii
<220> FEATURE:
<221> NAME/KEY: modified_base
<222> LOCATION: (15)..(15)
<223> OTHER INFORMATION: fa7d7g
<220> FEATURE:
<221> NAME/KEY: modified_base
<222> LOCATION: (28)..(28)
<223> OTHER INFORMATION: m22g
<220> FEATURE:
<221> NAME/KEY: modified_base
<222> LOCATION: (39)..(39)
<223> OTHER INFORMATION: m1g
<220> FEATURE:
<221> NAME/KEY: modified_base
<222> LOCATION: (41)..(41)
<223> OTHER INFORMATION: p
<220> FEATURE:
<221> NAME/KEY: modified_base
<222> LOCATION: (59)..(59)
<223> OTHER INFORMATION: m5c
<220> FEATURE:
<221> NAME/KEY: modified_base
<222> LOCATION: (65)..(65)
<223> OTHER INFORMATION: m1p
<220> FEATURE:
<221> NAME/KEY: modified_base
<222> LOCATION: (66)..(66)
<223> OTHER INFORMATION: p
<220> FEATURE:
<221> NAME/KEY: modified_base
<222> LOCATION: (67)..(67)
<223> OTHER INFORMATION: cm
<220> FEATURE:
<221> NAME/KEY: modified_base
<222> LOCATION: (68)..(68)
<223> OTHER INFORMATION: m1i

<400> SEQUENCE: 62
gcgaggguag cuaagucagg aaaaagcggc ggacucaaga uccgcucccg uagggguccg    60 ugngguucaaa ucccucccu cgcacca                                       87

<210> SEQ ID NO 63

```
<211> LENGTH: 87
<212> TYPE: DNA
<213> ORGANISM: Escherichia coli
<220> FEATURE:
<221> NAME/KEY: modified_base
<222> LOCATION: (16)..(16)
<223> OTHER INFORMATION: p
<220> FEATURE:
<221> NAME/KEY: modified_base
<222> LOCATION: (17)..(17)
<223> OTHER INFORMATION: p
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (20)..(20)
<223> OTHER INFORMATION: d
<220> FEATURE:
<221> NAME/KEY: modified_base
<222> LOCATION: (38)..(38)
<223> OTHER INFORMATION: unidentified methylated guanosine
<220> FEATURE:
<221> NAME/KEY: modified_base
<222> LOCATION: (39)..(39)
<223> OTHER INFORMATION: p
<220> FEATURE:
<221> NAME/KEY: modified_base
<222> LOCATION: (41)..(41)
<223> OTHER INFORMATION: p
<220> FEATURE:
<221> NAME/KEY: modified_base
<222> LOCATION: (66)..(66)
<223> OTHER INFORMATION: p

<400> SEQUENCE: 63
gcgaaggugg cggaauuggu agacgcgcua gcuucaggug uuaguguccu uacggacgug        60
ggggtucaag ucccccccu cgcacca                                            87

<210> SEQ ID NO 64
<211> LENGTH: 87
<212> TYPE: DNA
<213> ORGANISM: Escherichia coli
<220> FEATURE:
<221> NAME/KEY: modified_base
<222> LOCATION: (16)..(16)
<223> OTHER INFORMATION: d
<220> FEATURE:
<221> NAME/KEY: modified_base
<222> LOCATION: (17)..(17)
<223> OTHER INFORMATION: d
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (20)..(20)
<223> OTHER INFORMATION: d
<220> FEATURE:
<221> NAME/KEY: modified_base
<222> LOCATION: (38)..(38)
<223> OTHER INFORMATION: unidentified methylated guanosine
<220> FEATURE:
<221> NAME/KEY: modified_base
<222> LOCATION: (39)..(39)
<223> OTHER INFORMATION: p
<220> FEATURE:
<221> NAME/KEY: modified_base
<222> LOCATION: (66)..(66)
<223> OTHER INFORMATION: p

<400> SEQUENCE: 64
gccgaggugg uggaauuggu agacacgcua ccuugaggug guagugccca auagggcuua        60
```

```
cgggucaag ucccguccuc gguacca                                           87
```

<210> SEQ ID NO 65
<211> LENGTH: 87
<212> TYPE: DNA
<213> ORGANISM: Saccharomyces cerevisiae
<220> FEATURE:
<221> NAME/KEY: modified_base
<222> LOCATION: (10)..(10)
<223> OTHER INFORMATION: m2g
<220> FEATURE:
<221> NAME/KEY: modified_base
<222> LOCATION: (12)..(12)
<223> OTHER INFORMATION: ac4c
<220> FEATURE:
<221> NAME/KEY: modified_base
<222> LOCATION: (16)..(16)
<223> OTHER INFORMATION: d
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (19)..(19)
<223> OTHER INFORMATION: d
<220> FEATURE:
<221> NAME/KEY: modified_base
<222> LOCATION: (21)..(21)
<223> OTHER INFORMATION: d
<220> FEATURE:
<221> NAME/KEY: modified_base
<222> LOCATION: (27)..(27)
<223> OTHER INFORMATION: m22g
<220> FEATURE:
<221> NAME/KEY: modified_base
<222> LOCATION: (33)..(33)
<223> OTHER INFORMATION: cm
<220> FEATURE:
<221> NAME/KEY: modified_base
<222> LOCATION: (38)..(38)
<223> OTHER INFORMATION: m1g
<220> FEATURE:
<221> NAME/KEY: modified_base
<222> LOCATION: (40)..(40)
<223> OTHER INFORMATION: p
<220> FEATURE:
<221> NAME/KEY: modified_base
<222> LOCATION: (59)..(59)
<223> OTHER INFORMATION: m5c
<220> FEATURE:
<221> NAME/KEY: modified_base
<222> LOCATION: (66)..(66)
<223> OTHER INFORMATION: p
<220> FEATURE:
<221> NAME/KEY: modified_base
<222> LOCATION: (69)..(69)
<223> OTHER INFORMATION: m1a

<400> SEQUENCE: 65

```
ggaggguugg ccgagugguc uaaggcggca gacuuaagau cuguuggacg guugccgcg      60 cgagucgaa ccucgcaucc uucacca                                          87
```

<210> SEQ ID NO 66
<211> LENGTH: 85
<212> TYPE: DNA
<213> ORGANISM: Torulopsis utilis
<220> FEATURE:
<221> NAME/KEY: modified_base
<222> LOCATION: (10)..(10)
<223> OTHER INFORMATION: m2g
<220> FEATURE:
<221> NAME/KEY: modified_base
<222> LOCATION: (12)..(12)

```
<223> OTHER INFORMATION: ac4c
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (19)..(19)
<223> OTHER INFORMATION: d
<220> FEATURE:
<221> NAME/KEY: modified_base
<222> LOCATION: (20)..(20)
<223> OTHER INFORMATION: d
<220> FEATURE:
<221> NAME/KEY: modified_base
<222> LOCATION: (27)..(27)
<223> OTHER INFORMATION: m22g
<220> FEATURE:
<221> NAME/KEY: modified_base
<222> LOCATION: (33)..(33)
<223> OTHER INFORMATION: cm
<220> FEATURE:
<221> NAME/KEY: modified_base
<222> LOCATION: (35)..(35)
<223> OTHER INFORMATION: cm
<220> FEATURE:
<221> NAME/KEY: modified_base
<222> LOCATION: (38)..(38)
<223> OTHER INFORMATION: m1g
<220> FEATURE:
<221> NAME/KEY: modified_base
<222> LOCATION: (40)..(40)
<223> OTHER INFORMATION: p
<220> FEATURE:
<221> NAME/KEY: modified_base
<222> LOCATION: (57)..(57)
<223> OTHER INFORMATION: m5c
<220> FEATURE:
<221> NAME/KEY: modified_base
<222> LOCATION: (64)..(64)
<223> OTHER INFORMATION: p
<220> FEATURE:
<221> NAME/KEY: modified_base
<222> LOCATION: (67)..(67)
<223> OTHER INFORMATION: m1a

<400> SEQUENCE: 66
ggaucuuugg ccgagcgguu uaaggcgcuc gacucaagau cgaguaucgu aagaugcaug    60 agucgaauc ucauaggauc cacca                                          85

<210> SEQ ID NO 67
<211> LENGTH: 85
<212> TYPE: DNA
<213> ORGANISM: Candida cylindracea
<220> FEATURE:
<221> NAME/KEY: modified_base
<222> LOCATION: (10)..(10)
<223> OTHER INFORMATION: m2g
<220> FEATURE:
<221> NAME/KEY: modified_base
<222> LOCATION: (12)..(12)
<223> OTHER INFORMATION: ac4c
<220> FEATURE:
<221> NAME/KEY: modified_base
<222> LOCATION: (16)..(16)
<223> OTHER INFORMATION: d
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (19)..(19)
<223> OTHER INFORMATION: d
<220> FEATURE:
<221> NAME/KEY: modified_base
```

```
<222> LOCATION: (21)..(21)
<223> OTHER INFORMATION: d
<220> FEATURE:
<221> NAME/KEY: modified_base
<222> LOCATION: (27)..(27)
<223> OTHER INFORMATION: m22g
<220> FEATURE:
<221> NAME/KEY: modified_base
<222> LOCATION: (33)..(33)
<223> OTHER INFORMATION: cm
<220> FEATURE:
<221> NAME/KEY: modified_base
<222> LOCATION: (35)..(35)
<223> OTHER INFORMATION: cm
<220> FEATURE:
<221> NAME/KEY: modified_base
<222> LOCATION: (38)..(38)
<223> OTHER INFORMATION: m1g
<220> FEATURE:
<221> NAME/KEY: modified_base
<222> LOCATION: (40)..(40)
<223> OTHER INFORMATION: p
<220> FEATURE:
<221> NAME/KEY: modified_base
<222> LOCATION: (45)..(45)
<223> OTHER INFORMATION: um
<220> FEATURE:
<221> NAME/KEY: modified_base
<222> LOCATION: (57)..(57)
<223> OTHER INFORMATION: m5c
<220> FEATURE:
<221> NAME/KEY: modified_base
<222> LOCATION: (64)..(64)
<223> OTHER INFORMATION: p
<220> FEATURE:
<221> NAME/KEY: modified_base
<222> LOCATION: (67)..(67)
<223> OTHER INFORMATION: m1a

<400> SEQUENCE: 67
ggccguuugg ccgagugguc uaaggcgucu gacucaagau cagaucucgu aagaggcgug    60
ugtucgaacc acacagcggu cacca                                         85

<210> SEQ ID NO 68
<211> LENGTH: 85
<212> TYPE: DNA
<213> ORGANISM: Candida cylindracea
<220> FEATURE:
<221> NAME/KEY: modified_base
<222> LOCATION: (12)..(12)
<223> OTHER INFORMATION: ac4c
<220> FEATURE:
<221> NAME/KEY: modified_base
<222> LOCATION: (16)..(16)
<223> OTHER INFORMATION: d
<220> FEATURE:
<221> NAME/KEY: modified_base
<222> LOCATION: (19)..(19)
<223> OTHER INFORMATION: d
<220> FEATURE:
<221> NAME/KEY: modified_base
<222> LOCATION: (21)..(21)
<223> OTHER INFORMATION: d
<220> FEATURE:
<221> NAME/KEY: modified_base
<222> LOCATION: (27)..(27)
<223> OTHER INFORMATION: m22g
<220> FEATURE:
<221> NAME/KEY: modified_base
<222> LOCATION: (33)..(33)
<223> OTHER INFORMATION: p
<220> FEATURE:
<221> NAME/KEY: modified_base
<222> LOCATION: (35)..(35)
<223> OTHER INFORMATION: i
<220> FEATURE:
```

```
<221> NAME/KEY: modified_base
<222> LOCATION: (38)..(38)
<223> OTHER INFORMATION: m1g
<220> FEATURE:
<221> NAME/KEY: modified_base
<222> LOCATION: (39)..(39)
<223> OTHER INFORMATION: p
<220> FEATURE:
<221> NAME/KEY: modified_base
<222> LOCATION: (57)..(57)
<223> OTHER INFORMATION: m5c
<220> FEATURE:
<221> NAME/KEY: modified_base
<222> LOCATION: (64)..(64)
<223> OTHER INFORMATION: p
<220> FEATURE:
<221> NAME/KEY: modified_base
<222> LOCATION: (67)..(67)
<223> OTHER INFORMATION: m1a

<400> SEQUENCE: 68
gguucucugg ccgagugguc uaaggcgcau gguuaagguc caugucucuu cggaggcgcg      60
agtucgaacc ucgcgggaau cacca                                           85
```